(12) United States Patent
Andrez et al.

(10) Patent No.: US 10,526,285 B2
(45) Date of Patent: Jan. 7, 2020

(54) THERAPEUTIC COMPOUNDS AND METHODS OF USE THEREOF

(71) Applicants: GENENTECH, INC., South San Francisco, CA (US); XENON PHARMACEUTICALS INC., Burnaby (CA)

(72) Inventors: Jean-Christophe Andrez, Burnaby (CA); Philippe Bergeron, South San Francisco, CA (US); Paul Robert Bichler, Burnaby (CA); Sultan Chowdhury, Burnaby (CA); Christoph Martin Dehnhardt, Burnaby (CA); Thilo Focken, Burnaby (CA); Wei Gong, Burnaby (CA); Michael Edward Grimwood, Burnaby (CA); Abid Hasan, Burnaby (CA); Ivan William Hemeon, Burnaby (CA); Qi Jia, Burnaby (CA); Brian Salvatore Safina, South San Francisco, CA (US); Shaoyi Sun, Burnaby (CA); Michael Scott Wilson, Burnaby (CA); Alla Yurevna Zenova, Burnaby (CA)

(73) Assignees: GENENTECH, INC., South San Francisco, CA (US); XENON PHARMACEUTICALS INC., Burnaby, BC (CA)

(*) Notice: Subject to any disclaimer, the term of this patent is extended or adjusted under 35 U.S.C. 154(b) by 0 days.

(21) Appl. No.: 16/150,070

(22) Filed: Oct. 2, 2018

(65) Prior Publication Data
US 2019/0031607 A1 Jan. 31, 2019

Related U.S. Application Data

(62) Division of application No. 15/988,956, filed on May 24, 2018, now Pat. No. 10,125,098, which is a division of application No. 15/321,335, filed as application No. PCT/US2015/039413 on Jul. 7, 2015, now Pat. No. 10,005,724.

(60) Provisional application No. 62/021,587, filed on Jul. 7, 2014.

(51) Int. Cl.
| | |
|---|---|
| C07D 207/16 | (2006.01) |
| C07D 403/12 | (2006.01) |
| C07D 413/14 | (2006.01) |
| C07D 221/22 | (2006.01) |
| C07D 401/12 | (2006.01) |

(Continued)

(52) U.S. Cl.
CPC .......... *C07D 207/16* (2013.01); *C07C 235/42* (2013.01); *C07C 235/52* (2013.01); *C07C 235/54* (2013.01); *C07D 205/04* (2013.01); *C07D 207/08* (2013.01); *C07D 207/10* (2013.01); *C07D 207/22* (2013.01); *C07D 209/02* (2013.01); *C07D 209/52* (2013.01); *C07D 209/54* (2013.01); *C07D 211/20* (2013.01); *C07D 211/38* (2013.01); *C07D 211/60* (2013.01); *C07D 213/69* (2013.01); *C07D 221/22* (2013.01); *C07D 231/06* (2013.01); *C07D 263/04* (2013.01); *C07D 263/26* (2013.01); *C07D 265/30* (2013.01); *C07D 277/06* (2013.01); *C07D 305/08* (2013.01); *C07D 401/10* (2013.01); *C07D 401/12* (2013.01); *C07D 401/14* (2013.01); *C07D 403/04* (2013.01);

(Continued)

(58) Field of Classification Search
None
See application file for complete search history.

(56) References Cited

U.S. PATENT DOCUMENTS

| | | | |
|---|---|---|---|
| 3,705,185 A | 12/1972 | Moore et al. | |
| 5,171,748 A | 12/1992 | Roberts et al. | |

(Continued)

FOREIGN PATENT DOCUMENTS

| | | |
|---|---|---|
| CN | 101466665 A | 6/2009 |
| CN | 101643458 A | 2/2010 |

(Continued)

OTHER PUBLICATIONS

Amaya, et al., "The voltage-gated sodium channel Na(v)1.9 is an effector of peripheral inflammatory pain hypersensitivity", J. Neurosci 26 (50), 12852-12860 (2006).

(Continued)

*Primary Examiner* — Heidi Reese
(74) *Attorney, Agent, or Firm* — Viksnins Harris Padys Malen LLP

(57) ABSTRACT

The invention provides compounds having the general Formula (I);

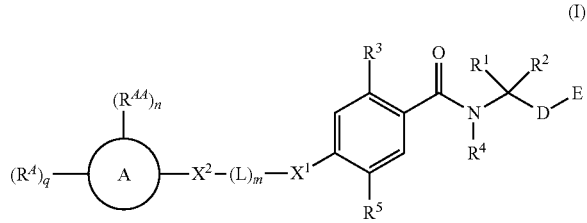

and pharmaceutically acceptable salts thereof; wherein the variables $R^4$, $R^{AA}$, subscript n, subscript q, ring A, $X^2$, L, subscript m, $X^1$, $R^1$, $R^2$, $R^3$, $R^4$, $R^5$, D and E have the meaning as described herein, and compositions containing such compounds and methods for using such compounds and compositions.

17 Claims, No Drawings

(51) Int. Cl.

| | | |
|---|---|---|
| *C07D 413/12* | (2006.01) | |
| *C07C 235/52* | (2006.01) | |
| *C07D 205/04* | (2006.01) | |
| *C07D 277/06* | (2006.01) | |
| *C07D 209/02* | (2006.01) | |
| *C07D 305/08* | (2006.01) | |
| *C07D 401/14* | (2006.01) | |
| *C07D 231/06* | (2006.01) | |
| *C07D 403/04* | (2006.01) | |
| *C07D 403/14* | (2006.01) | |
| *C07D 409/06* | (2006.01) | |
| *C07D 417/12* | (2006.01) | |
| *C07D 451/02* | (2006.01) | |
| *C07D 263/04* | (2006.01) | |
| *C07D 263/26* | (2006.01) | |
| *C07C 235/42* | (2006.01) | |
| *C07C 235/54* | (2006.01) | |
| *C07D 265/30* | (2006.01) | |
| *C07D 207/08* | (2006.01) | |
| *C07D 207/10* | (2006.01) | |
| *C07D 207/22* | (2006.01) | |
| *C07D 209/52* | (2006.01) | |
| *C07D 209/54* | (2006.01) | |
| *C07D 211/20* | (2006.01) | |
| *C07D 211/38* | (2006.01) | |
| *C07D 211/60* | (2006.01) | |
| *C07D 213/69* | (2006.01) | |
| *C07D 401/10* | (2006.01) | |
| *C07D 405/10* | (2006.01) | |
| *C07D 471/08* | (2006.01) | |

(52) U.S. Cl.
CPC ......... *C07D 403/12* (2013.01); *C07D 403/14* (2013.01); *C07D 405/10* (2013.01); *C07D 409/06* (2013.01); *C07D 413/12* (2013.01); *C07D 413/14* (2013.01); *C07D 417/12* (2013.01); *C07D 451/02* (2013.01); *C07D 471/08* (2013.01); *C07C 2601/02* (2017.05); *C07C 2601/04* (2017.05); *C07C 2603/74* (2017.05)

(56) References Cited

U.S. PATENT DOCUMENTS

| | | | |
|---|---|---|---|
| 5,573,653 | A | 11/1996 | Bandlish |
| 5,580,982 | A | 12/1996 | O'Malley et al. |
| 5,753,653 | A | 5/1998 | Bender et al. |
| 6,096,771 | A | 8/2000 | Kojima et al. |
| 7,262,304 | B2 | 8/2007 | Ueno et al. |
| 7,291,638 | B2 | 11/2007 | Lee et al. |
| 7,858,639 | B2 | 12/2010 | Sun et al. |
| 8,153,814 | B2 | 4/2012 | Beaudoin et al. |
| 8,193,194 | B2 | 6/2012 | Martinborough et al. |
| 8,642,660 | B2 | 2/2014 | Goldfarb |
| 8,889,741 | B2 | 11/2014 | Shinozuka et al. |
| 8,933,236 | B2 | 1/2015 | Chowdhury et al. |
| 8,952,169 | B2 | 2/2015 | Andrez et al. |
| 9,102,621 | B2 | 8/2015 | Brown et al. |
| 10,005,724 | B2 | 6/2018 | Andrez et al. |
| 10,125,098 | B2 | 11/2018 | Andrez et al. |
| 2006/0069093 | A1 | 3/2006 | Scarborough et al. |
| 2007/0088015 | A1 | 4/2007 | Silva et al. |
| 2008/0161303 | A1 | 7/2008 | Zhang et al. |
| 2008/0312286 | A1 | 12/2008 | Pinkerton et al. |
| 2009/0012103 | A1 | 1/2009 | Abelman et al. |
| 2010/0179137 | A1 | 7/2010 | Kamikubo et al. |
| 2010/0197655 | A1 | 8/2010 | Beaudoin et al. |
| 2010/0286110 | A1 | 11/2010 | Fyfe et al. |
| 2011/0092703 | A1 | 4/2011 | Sakuma et al. |
| 2012/0004714 | A1 | 1/2012 | Kleve et al. |
| 2012/0010182 | A1 | 1/2012 | Brown et al. |
| 2012/0010183 | A1 | 1/2012 | Bell et al. |
| 2012/0010207 | A1 | 1/2012 | Bell et al. |
| 2012/0196869 | A1 | 8/2012 | Hadida Ruah et al. |
| 2013/0324525 | A1 | 12/2013 | Abelman et al. |
| 2013/0338111 | A1 | 12/2013 | Beaudoin et al. |
| 2014/0213616 | A1 | 7/2014 | Hadida-Ruah et al. |
| 2014/0296266 | A1 | 10/2014 | Hu et al. |
| 2015/0252038 | A1 | 9/2015 | Andrez et al. |
| 2015/0291514 | A1 | 10/2015 | Brown et al. |

FOREIGN PATENT DOCUMENTS

| | | |
|---|---|---|
| EP | 0179619 B1 | 9/1990 |
| EP | 0516392 A2 | 12/1992 |
| EP | 2184278 A1 | 5/2010 |
| JP | 2014118368 A | 6/2014 |
| WO | 1990008128 A1 | 7/1990 |
| WO | 2000039077 A2 | 7/2000 |
| WO | 2003059882 A1 | 7/2003 |
| WO | 2004014913 A2 | 2/2004 |
| WO | 2004052869 A1 | 6/2004 |
| WO | 2004092145 A1 | 10/2004 |
| WO | 2005013914 A2 | 2/2005 |
| WO | 2005032488 A2 | 4/2005 |
| WO | 2006015158 A1 | 2/2006 |
| WO | 2006020830 A2 | 2/2006 |
| WO | 2006020830 A3 | 2/2006 |
| WO | 2006039212 A2 | 4/2006 |
| WO | 2006121097 A1 | 11/2006 |
| WO | 2006122800 A1 | 11/2006 |
| WO | 2007030582 A3 | 3/2007 |
| WO | 2007045572 A1 | 4/2007 |
| WO | 2007062078 A2 | 5/2007 |
| WO | 2007067994 A1 | 6/2007 |
| WO | 2007120647 A2 | 10/2007 |
| WO | 2008094602 A2 | 8/2008 |
| WO | 2008097991 A1 | 8/2008 |
| WO | 2008118758 A1 | 10/2008 |
| WO | 2009010784 A1 | 1/2009 |
| WO | 2009012242 A3 | 1/2009 |
| WO | 2009157399 A1 | 12/2009 |
| WO | 2010022055 A2 | 2/2010 |
| WO | 2010079443 A1 | 7/2010 |
| WO | 2011014462 A1 | 2/2011 |
| WO | 2011016234 A1 | 2/2011 |
| WO | 2011037192 A1 | 2/2011 |
| WO | 2011059042 A1 | 5/2011 |
| WO | 2011063001 A1 | 5/2011 |
| WO | 2011088201 A1 | 7/2011 |
| WO | 2011100433 A1 | 8/2011 |
| WO | 2011153588 A1 | 12/2011 |
| WO | 2012004664 A2 | 1/2012 |
| WO | 2012004706 A2 | 1/2012 |
| WO | 2012004706 A3 | 1/2012 |
| WO | 2012004714 A2 | 1/2012 |
| WO | 2012007836 A1 | 1/2012 |
| WO | 2012007861 A1 | 1/2012 |
| WO | 2012007868 A2 | 1/2012 |
| WO | 2012007869 A2 | 1/2012 |
| WO | 2012007877 A2 | 1/2012 |
| WO | 2012007883 A1 | 1/2012 |
| WO | 2012035023 A1 | 3/2012 |
| WO | 2012039657 A1 | 3/2012 |
| WO | 2012085650 A1 | 6/2012 |
| WO | 2012095781 A1 | 7/2012 |
| WO | 2013025883 A1 | 2/2013 |
| WO | 2013056232 A1 | 4/2013 |
| WO | 2013063459 A1 | 5/2013 |
| WO | 2013064983 A1 | 5/2013 |
| WO | 2013064984 A1 | 5/2013 |
| WO | 2013072758 A1 | 5/2013 |
| WO | 2013086229 A1 | 6/2013 |
| WO | 2013088315 A1 | 6/2013 |
| WO | 2013102826 A1 | 7/2013 |
| WO | 2013118805 A1 | 8/2013 |
| WO | 2013118854 A1 | 8/2013 |
| WO | 2013122897 A1 | 8/2013 |

(56) References Cited

FOREIGN PATENT DOCUMENTS

| | | | |
|---|---|---|---|
| WO | 2013134518 A1 | 9/2013 | |
| WO | 2013146969 A1 | 10/2013 | |
| WO | 2013177224 A1 | 11/2013 | |
| WO | 2014008458 A2 | 1/2014 | |
| WO | 2014014050 A1 | 1/2014 | |
| WO | 2014066490 A1 | 5/2014 | |
| WO | 2014066491 A1 | 5/2014 | |
| WO | 2014096941 A1 | 6/2014 | |
| WO | 2014144545 A2 | 9/2014 | |
| WO | 2014151472 A1 | 9/2014 | |
| WO | 2014153037 A1 | 9/2014 | |
| WO | 2015051043 A1 | 4/2015 | |
| WO | 2015078374 A1 | 6/2015 | |

OTHER PUBLICATIONS

Arcangeli, et al., "Targeting Ion Channels in Cancer: A Novel Frontier in AntineoplasticTherapy", Current Medicinal Chemistry 16, 66-93 (2009).
Bach, et al., "A novel series of piperazinyl-pyridine ureas as antagonists of the purinergic P2712 receptor", Bioorganic & Medicinal Chemistry Letters 21, 2877-2881 (2011).
Banks, et al., "The Reaction of N-Aikylhydroxamic Acids with Sulphinyl Chlorides", J. Chem. Soc. Perkin Trans. II, 1211-1216 (1986).
Bean, et al., "Lidocaine Block of Cardiac Sodium Channels", J. Gen. Physiol. 81, 613-642 (1983).
Binder, et al., "Disease Mechanisms in Neuropathic Itch", Nature Clinical Practice Neurology 4(6), 329-337 (2008).
Black, et al., "Changes in the expression of tetrodotoxin-sensitive sodium channels within dorsal root ganglia neurons in inflammatory pain", Pain 108 (3), 237-247 (2004).
Blair, et al., "Roles of tetrodotoxin (TIX)-sensitive Na+ current, TIX-resistant Na+ current, and Ca2+ current in the action potentials of nociceptive sensory neurons", J. Neurosci 22, 10277-10290 (2002).
Brackenbury, et al., "Activity-dependent regulation of voltage-gated Na+ channel expression in Mat-LyLu rat prostate cancer cell line", J. Physiol 573.2, 343-356 (2006).
Braga, et al., "Making crystals from crystals: a green route to crystal engineering and polymorphism", Chern Commun J Roy Soc Chern, 3635-3645 (2005).
Caldwell, et al., "Sodium channel Na(v)1.6 is localized at nodes of ranvier, dendrites, and synapses", Proc. Nail. Acad. Sci. 97(10), 5616-5620 (2000).
CAS Registry, Nos. 1027529-26-5, 1027209-51-3 and 1026292-79-4, 1 page (2015).
CAS Registry, RN 1163247-96-8, 1 page (Jul. 15, 2009).
Catron, et al., "Preparation of 4-[4-[2-phenylcclohexen-1-en-1-yl)methyl]piperazin-1-ui]-N-(phenylsulfonyl) 13 benzamides and 4-[4-[2-phenylcyclohexen-1-en-1-yl)methyl]piperazin-1-71]-N-(3-pyridylsulfonlyl) benzamides", CAPLUS 2012:637301, 156:638098, 2 pages (2012).
Catterall, "From ionic currents to molecular mechanisms: the structure and function of voltage-gated sodium channels", Neuron 26 (1), 13-25 (2000).
Catterall, "Molecular mechanisms of gating and drug block of sodium channels", Novartis Foundation Symposium 241, 206-225 (2002).
Catterall, "Structural biology: A 3D view of sodium channels", Nature, vol. 409, 988-990 (2001).
Cestele, et al., "Molecular mechanisms of neurotoxin action on voltage-gated sodium channels", Biochimie vol. 82 (9-1 0), 883-892 (2000).
Chan, et al., "Rh(II)-Catalyzed Intermolecular Oxidative Sulfamidalion of Aldehydes: A Mild Efficient Synthesis of N-Sulfonylcarboxamides", J. Am. Chern. Soc., 129, 14106-14107 (2007).
Chemical Abstract Service, STN Registry Database No. 891026-77-0 [entered STN: Jul. 9, 2006].
Chemical Abstract Service, STN Registry Database No. 892698-09-8 [entered STN: Jul. 14, 2006].
Chemical Abstracts_4, XP002744146, Database accession No. 1294599-14-6 Abstract, (May 15, 2011).
Chemical Abstracts_1, XP002744143, Database accession No. 1321299-48-2 Abstract (Aug. 22, 2011).
Chemical Abstracts_10, XP002744152, Database accession No. 1288553-28-5 Abstract (May 1, 2011).
Chemical Abstracts_11, XP002744153, Database accession No. 1278399-39-5 Abstract (Apr. 11, 2011).
Chemical Abstracts_12, XP002744154, Database accession No. 1297052-59-5 Abstract (May 19, 2011).
Chemical Abstracts_13, XP002744155, Database accession No. 1277490-84-2 Abstract (Apr. 10, 2011).
Chemical Abstracts_2, XP002744144, Database accession No. 1320435-32-2 Abstract (Aug. 22, 2011).
Chemical Abstracts_3, XP002744145, Database accession No. 1319619-74-3 Abstract (Aug. 18, 2011).
Chemical Abstracts_5, XP002744147, Database accession No. 1051238-85-7 Abstract (Sep. 21, 2008).
Chemical Abstracts_6, XP002744148, Database accession No. 1051172-94-1 Abstract (Sep. 21, 2008).
Chemical Abstracts_7, XP002744149, Database accession No. 1301192-24-4 (May 26, 2011).
Chemical Abstracts_8, XP002744150, Database accession No. 1299653-84-3 Abstract (May 24, 2011).
Chemical Abstracts_9, XP002744151, Database accession No. 299214-10-0 (May 24, 2011).
Chioni, et al., "A novel adhesion molecule in human breast cancer cell lines: Voltage-gated Na+ channel β1 subunit", Int'l J. Biochem. Cell Biol. 41, 1216-1227 (2009).
Chung, et al., "Sodium channels and neuropathic pain", Novartis Foundation Symposium 261, 19-31 (2004).
Clare, et al., "Voltage-gated sodium channels as therapeutic targets", Drug Discovery Today 5(11), 506-520 (2000).
Cox, et al., "An SCN9A channelopathy causes congenital inability to experience pain", Nature 444, 894-898 (2006).
Daeniker, et al., "234. Uber bicyclische Sulfonamide", Helvetica Chimica ACTA, vol. 45 (6), 1972-1981 (1962). [English Translation.].
Database Reaxys, XP002692384, Accession No. XRN: 6729065, 6731122, 1 page, (D. Bertoia et al., Base 24 promoted ring-opening reactions of 2-p-lolyl-5,6-dihydro-1, 4,3-oxathiazine 4,4-dioxides, Gazella Chimica Ilaliana, vol. 118 (6), 435-440 (1988).
Deng, et al., "Dynamic 1-15 Receptor-Based Pharmacophore Model Development and Its Application in Designing Novel HIV-1 Integrase Inhibitors", Journal of Medicinal Chemistry. vol. 48. No. 5, 1496-1505 (2005), Supporting Information, S1-S14. XP055285519. DOI: 10.1021jjm049410e (2005).
Devor, et al., "Na+ ChannelImmunolocalization in Peripheral Mammalian Axons and Changes following Nerve Injury and Neuroma Formation", J. Neurosci. 13 (5), 1976-1992 (1993).
Dib-Hajj, et al., "Genetics and Molecular Pathophysiology of NaV1.7-related Pain Syndromes", Advances in Genetics 63,85-110 (2008).
Dib-Hajj, et al., "NaN, a novel voltage-gated Na channel, is expressed preferentially in peripheral sensory neurons and down-regulated after axotomy", Proc. Natl. Acad. Sci. 95 (15), 8963-8968 (1998).
Dib-Hajj, et al., "The Na(V)1.7 sodium channel: from molecule to man", Nature Reviews Neuroscience 14, 49-62 (2013).
Dickore, "Synthese und reaktionen von 1.3.4-oxathiazolin-3-dioxyden", Justus Liebigs Annalen Der Chemie, vol. 671, 135-146, XP055053742, Compounds IVa, IVb, IVd, V, VI (1964). [English Translation.].
Diss, et al., "A potential novel marker for human prostate cancer: voltage-gated sodium channel expression in vivo", Prostate Cancer and Prostatic Diseases 8, 266-273 (2005).
Diss, et al., "Expression profiles of voltage-gated sodium channel a-subunit genes in rat and human prostate cancer cell lines", The Prostate 48, 165-178 (2001).
Diss, et al., "Identification and characterization of the promoter region of the NaV1.7 voltage-gated sodium channel gene (SCN9A)", Mol. Cell. Neurosci. 37, 537-547 (2008).

(56) References Cited

OTHER PUBLICATIONS

Dong, et al., "Small interfering RNA-mediated selective knockdown of Na(V)1.8 tetrodotoxin-resistant sodium channel reverses mechanical allodynia in neuropathic rats", Neuroscience 146, 812-821 (2007).
Tanelian, et al., "Neuropathic pain can be relieved by drugs that are use-dependent sodium channel blockers: lidocaine, carbamazepine and mexileline", Anesthesiology, 74(5), 949-951 (1991).
Termin, et al., "Recent Advances in Voltage-Gated Sodium Channel Blockers: Therapeutic Potential as Drug Targets in the CNS", Annual Reports in Medicinal Chemistry 43, 43-60 (2008).
Thornton, et al., "Quinazoline antifolate thymidylate synthase inhibitors: difluoro-substituted benzene ring analogs", J Med Chem 35, 2321-2327 (1992).
Toledo-Aral, et al., "Identification of PN1, a predominant voltage-dependent sodium channel expressed principally in peripheral neurons", Proc. Nail. Acad. Sci. 94 (4), 1527-1532 (1997).
Villamil, et al., "Efficacy of lidocaine in the treatment of pruritus in patients with chronic chlolestatic liver disease", Am. J. Med, 118, 1160-1163 (2005).
Vippagunta, et al., "Crystal Solids", Adv Drug Del Rev vol. 48, 3-26 (2001).
Wallace, et al., "Efficacy of oral mexileline for neuropathic pain with allodynia: a double-blind, placebo-controlled, crossover study", Reg. Anesth. Pain Med. 25 (5), 459-467 (2000).
Wolff, "Burger's Medicinal Chemistry and Drug Discovery", Fifth Edition, vol. 1: Principles and Practice, 975-977 (1995).
Wood, et al., "Voltage-gated sodium channels and pain pathways", J. Neurobiol. 61(1 ), 55-71 (2004).
Xiao, et al., "C-fiber spontaneous discharge evoked by chronic inflammation is suppressed by a long-term infusion of lidocaine yielding nanogram per milliliter plasma levels", Pain, 137,218-228 (2008).
Yang, et al., "Mutations in SCN9A, encoding a sodium channel alpha subunit, in patients with primary erythermalgia", J. Med_ Genet_ 41 (3), 171-174 (2004).
Yu, et al., "Reduced sodium current in GABAergic interneurons in a mouse model of severe myoclonic epilepsy in infancy", Nat Neurosci 9, 1142-1149 (2006).
Yu, et al., "Sodium Channel β4. a New Disulfide-Linked Auxiliary Subunit with Similarity to β2", J. Neurosci. 23(20), 7577-7585 (2003).
Yu, et al., "The VGL-chanome: a protein superfamily specialized for electrical signaling and ionic homeostasis", Sci. STKE 253, re15, 17 pages (2004).
Zhao, et al., "Voltage-gated sodium channel expression in rat and human epidermal keratinocytes: evidence for a role in pain", Pain, 139, 90-105 (2008).
Zuliani, et al., "Sodium channel blockers for neuropathic pain", Expert Opinion Ther Patents 20(6), 755-779 (2010).
England, et al., "Isoform-selective voltage-gated Na(+) channel modulators as next-generation analgesics", Future Med Chern 2 (5), 775-790 (2010).
Estacion, et al., "A sodium channel gene SCN9A polymorphism that increases nociceptor excitability", Ann Neurol 66 (6), 862-866 (2009).
Federal Register, vol. 76(27), 7162-7175, Slide 1, 64-67 (2011).
File Caplus, Registry No. 1333872-40-4, entered STN: Sep. 29, 2011.
Fishman, et al., "Intravenous lidocaine for treatment-resistant pruritus", American J. of Medicine 102, 584-585 (1997).
Fraser, et al., "Voltage-gated sodium channel expression and potentiation of human breast cancer metastasis", Clin. Cancer Res. 11(15), 5381-5389 (2005).
Goldberg, et al., "Loss-of-function mutations in the Nav1.7 gene underlie congenital indifference to pain in multiple human populations", Clin. Genet. 71, 311-319 (2007).
Goldin, et al., "Nomenclature of Voltage-Gated Sodium Channels", Neuron vol. 28, 365-368 (2000).

Gould, et al., "Development of inflammatory hypersensitivity and augmentation of sodium channels in rat dorsal root ganglia", Brain Res. 824 (2), 296-299 (1999).
Hains, et al., "Upregulation of sodium channel Nav1.3 and functional involvement in neuronal hyperexcitability associated with central neuropathic pain after spinal cord injury", J. Neurosci. 23 (26), 8881-8892 (2003).
Hayes, et al., "Na(V)1.7 Paint Control: A Novel Target", Neurosurgery 73, N16 (2013).
Ikoma, et al., "Neuronal sensitization for histamine-induced itch in lesional skin of patients with atopic dermatitis", Arch. Dermatol. 139, 1445-1458 (2003).
Ikoma, et al., "The neurobiology of itch", Nature Reviews Neuroscience 7, 535-547 (2006).
Ikuma, et al., "Preparation of 3-substituted proline derivatives as FXIa inhibitors", CA159:371450 (2013).
Kis-Toth, et al., "Voltage-gated sodium channel NaV1.7 maintains the membrane potential and regulates the 45 activation and chemokine-induced migration of a monocyte-derived dendritic cell subset", J. Immunology 187, 1273-1280 (2011).
Klugbauer, et al., "Structure and functional expression of a new member of the tetrodotoxin-sensitive voltage-activated sodium channel family from human neuroendocrine cells", EMBO J. 14 (6), 1084-1090 (1995).
Kuo, et al., "Application of CoMFA and CoMSIA 3D-QSAR and Docking Studies in Optimization of Mercaptobenzenesulfonamides as HIV-1 Integrase Inhibitors", Journal of Medicinal Chemistry. American Chemical Society. US. vol. 47. No. 2, 385-399 (2003).
Kutt, et al., "A Comprehensive Self-Consistent Spectrophotometric Acidity Scale of Neutral Bronsted Acids in Acetonitrile", J. Org. Chern. 71, 2829-2838 (2006).
Lai, et al. "Inhibition of neuropathic pain by decreased expression of the tetrodotoxin-resistant sodium channel, NaV1.8", Pain 95 (1-2), 143-152 (2002).
Lai, et al. "The role of voltage-gated sodium channels in neuropathic pain", Current Opinion in Neurobiology 13, 291-297 (2003).
Lamoureux, et al., "Use of the adamantane structure in medicinal chemistry", Curr Med Chem 17(26), 2967-2978 (2010).
Lee, et al. "A monoclonal antibody that targets a NaV1.7 channel voltage sensor for pain and itch relief", Cell 157(6), 1393-1404 (2014).
Leeman, et al., "Preparation of 4-benzimidazolylmethoxy-3-halophenylmethoxybenzoates and analogs as tRNA synthetase inhibitors", CA 133:35021 (2000).
Li, et al., "Recent advances in the structure-activity relationship study of small-molecule sodium channel blockers with analgesic effects", Acta Pharmaceutica Sinica, vol. 44, (2), 101-108 (2009). [English Translation.].
Liu, et al., "Mutations in cardiac sodium channels: clinical implications", Am. J. Pharmacogenomics 3(3), 173-179 (2003).
Mao, et al., "Systemic lidocaine for neuropathic pain relief", Pain 87, 7-17 (2000).
Massah, et al., "Synthesis. in vitro antibacterial and carbonic anyydrase II inhibitory activities of N-acylsulfonamides 2 using silica sulfuric acid as an efficient catalyst under both solvent-free and heterogeneous conditions", Bioorganic & Medicinal Chemistry 16, 5465-5472 (2008).
Meisler, et al., "Sodium channel gene family: epilepsy mutations, gene interactions and modifier effects", The Journal of Physiology 588.11, 1841-1848 (2010).
Morinville, et al., "Distribution of the voltage-gated sodium channel NaV1.7 in the rat: expression in the autonomic and endocrine systems", J. Comparative Neurology 504, 680-689 (2007).
Oaklander, et al., "Intractable post-herpetic itch and cutaneous deafferentation after facial singles", Pain 96,9-12 (2002).
Patani, et al., "Bioisosterism: A Rational Approach in Drug Design", Chem Rev 96, 3147-3176 (1996).
Patent Cooperation Treaty, International Searching Authority, Search Report and Written Opinion for PCT/US2015/039413, 18 pages, dated Oct. 5, 2015.
Priest, et al., "Contribution of the tetrodotoxin-resistant voltage-gated sodium channel NaV1.9 to sensory transmission and nociceptive behavior", Proc Nail Acad Sci 102 (26) 9382-9387 (2005).

(56) References Cited

OTHER PUBLICATIONS

Priest, "Future potential and status of selective sodium channel blockers for the treatment of pain", Current Opinion in Drug Discovery and Development, 12(5), 682-692 (2009).

Prodrug, Dictionary 1-2, Internet (2002).

Pubchem, Compound Summary for CID 14280666, N-(1,2-benzoxazol-3-yl) methanesulfonamide, https://pubchem.ncbi.nim.nih.gov/summary/summary.cgi?cid=14280666, 3 pages (2007).

Raymond, et al., "Expression of alternatively spliced sodium channel alpha-subunit genes. Unique splicing patterns are observed in dorsal root ganglia", J. Bioi. Chern. 279(44), 46234-46241 (2004).

Reimann, et al., "Pain perception is altered by a nucleotide polymorphism in SCN9A", Proc. Nail. Acad. Sci. 107, 5148-5153 (2010).

Roberts, et al., "Molybdenum-Mediated Carbonylaiton of Aryl Halides with Nucleophiles Using Microwave Irradiation", Organic Letters, vol. 12 (19), 4280-4283 (2010).

Roberts, et al., "Novel Aryl and Heteroaryl Acyl Sulfamide Synthesis via Microwave-Assisted Palladium-Catalyzed Carbonylation", Organic Letters, vol. 12 (6), 1264-1267 (2010).

Ruan, et al., "Sodium channel mutations and arrhythmias", Nature Reviews Cardiology, 6, 337-348 (2009).

Rugiero, et al., "Selective Expression of a Persistent Tetrodotoxin-Resistant Na+ Current and NaV1.9 Subunit in Myenteric Sensory Neurons", J. Neurosci 23 (7), 2715-2725 (2003).

Sakuma, et al., "Preparation of piperazine", CA150:260220 (2009).

Sangameswaran, et al., "A novel tetrodotoxin-sensitive, voltage-gated sodium channel expressed in rat and human dorsal root ganglia", J. Bioi. Chern. 272 (23), 14805-14809 (1997).

Sato, et al., "The voltage-sensitive sodium channel is a bell-shaped molecule with several cavities", Nature 409, 1047-1051 (2001).

Schmelz, et al., "Itch and pain", Neuroscience and Biobehaviorial Reviews, 34, 171-176 (2010).

Seddon, "Pseudopolymorph: A Polemic", Crystal Growth and Design vol. 4(6), 1087 (2004).

Silos-Santiago, "Drugs in Clinical Development for Neuropathic Pain", presented at First World Conference Abdominal and Pelvic Pain, Amsterdam, pp. 1-23 (Jun. 6, 2013).

Smith, et al., "Sodium channel protein expression enhances the invasiveness of rat and human prostate cancer cells", FEBS Letters, 423, 19-24 (1998).

Tamaoka, "Paramyotonia congenita and skeletal sodium channelopathy", Intern. Med. 42 (9), 769-770 (2003).

THERAPEUTIC COMPOUNDS AND METHODS OF USE THEREOF

RELATED APPLICATIONS

This application is a divisional of Ser. No. 15/988,956 filed 24 May 2018, which is a divisional of Ser. No. 15/321,335 filed 22 Dec. 2016, which is a national stage application of PCT/US2015/039413 filed on 7 Jul. 2015, which claims priority to U.S. Provisional Application No. 62/021,587 filed on 7 Jul. 2014. The entire contents of the foregoing are incorporated herein by reference.

The present invention relates to organic compounds useful for therapy in a mammal, and in particular to inhibitors of sodium channel (e.g., NaV1.7) that are useful for treating sodium channel-mediated diseases or conditions, such as pain, as well as other diseases and conditions associated with the modulation of sodium channels.

Voltage-gated sodium channels are transmembrane proteins that initiate action potentials in nerve, muscle and other electrically excitable cells, and are a necessary component of normal sensation, emotions, thoughts and movements (Catterall, W. A., Nature (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., Neuron (2000), Vol. 28, pp. 365-368). Electrophysiological recording, biochemical purification, and molecular cloning have identified ten different sodium channel alpha subunits and four beta subunits (Yu, F. H., et al., Sci. STKE (2004), 253; and Yu, F. H., et al., Neurosci. (2003), 20:7577-85).

The sodium channel family of proteins has been extensively studied and shown to be involved in a number of vital body functions. Research in this area has identified variants of the alpha subunits that result in major changes in channel function and activities, which can ultimately lead to major pathophysiological conditions. The members of this family of proteins are denoted NaV1.1 to NaV1.9.

NaV1.7 is a tetrodotoxin-sensitive voltage-gated sodium channel encoded by the gene SCN9A. Human NaV1.7 was first cloned from neuroendocrine cells (Klugbauer, N., et al., 1995 EMBO J., 14 (6): 1084-90) and rat NaV1.7 was cloned from a pheochromocytoma PC12 cell line (Toledo-Aral, J. J., et al., Proc. Natl. Acad. Sci. USA (1997), 94:1527-1532) and from rat dorsal root ganglia (Sangameswaran, L., et al., (1997), J. Biol. Chem., 272 (23): 14805-9). NaV1.7 is expressed primarily in the peripheral nervous system, especially nociceptors and olfactory neurons and sympathetic neurons. The inhibition, or blocking, of NaV1.7 has been shown to result in analgesic activity. Knockout of NaV1.7 expression in a subset of sensory neurons that are predominantly nociceptive results in resistance to inflammatory pain (Nassar, et al., op. cit.). Likewise, loss of function mutations in humans results in congenital indifference to pain (CIP), in which the individuals are resistant to both inflammatory and neuropathic pain (Cox, J. J., et al., Nature (2006); 444:894-898; Goldberg, Y. P., et al., Clin. Genet. (2007); 71:311-319). Conversely, gain of function mutations in NaV1.7 have been established in two human heritable pain conditions, primary erythromelalgia and familial rectal pain, (Yang, Y., et al., J. Med. Genet. (2004), 41(3):171-4). In addition, a single nucleotide polymorphism (R1150W) that has very subtle effects on the time- and voltage-dependence of channel gating has large effects on pain perception (Estacion, M., et al., 2009. Ann Neurol 66: 862-6; Reimann, F., et al., Proc Natl Acad Sci USA (2010), 107: 5148-53). About 10% of the patients with a variety of pain conditions have the allele conferring greater sensitivity to pain and thus might be more likely to respond to block of NaV1.7. Because NaV1.7 is expressed in both sensory and sympathetic neurons, one might expect that enhanced pain perception would be accompanied by cardiovascular abnormalities such as hypertension, but no correlation has been reported. Thus, both the CIP mutations and SNP analysis suggest that human pain responses are more sensitive to changes in NaV1.7 currents than are perturbations of autonomic function.

Sodium channel blockers have been shown to be useful in the treatment of pain, (see, e.g., Wood, J. N., et al., J. Neurobiol. (2004), 61(1), 55-71. Genetic and functional studies have provided evidence to support that activity of NaV1.7 as a major contributor to pain signalling in mammals. (See Hajj, et al. Nature Reviews Neuroscience; 2013, vol 14, 49-62; and Lee, et al. Cell; 2014, vol 157; 1-12). Presently, there are a limited number of effective sodium channel blockers for the treatment of pain with a minimum of adverse side effects which are currently in the clinic. Thus there remains a need for selective voltage-gated sodium channel modulators (e.g., modulators of NaV1.7) that can provide a greater therapeutic index for treatment.

SUMMARY OF THE INVENTION

In one aspect the present invention provides novel compounds having sodium channel blocking activity that are useful for the treatment of pain. In a first embodiment (Embodiment 1; abbreviated as "E1") the invention provides for a compound of Formula (I);

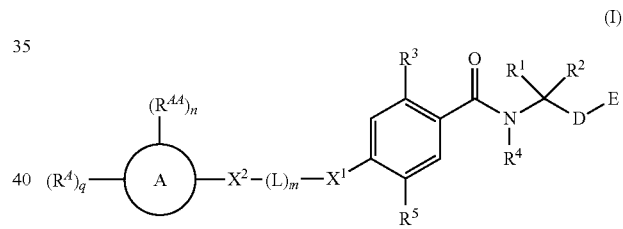

or a pharmaceutically acceptable salt thereof; wherein:
D is absent or is —CH$_2$—;
E is tetrazolyl, —C(=O)OR$^0$, or —C(=O)NR$^{oa}$R$^{ob}$,
R$^o$ is hydrogen or C$_{1-6}$ alkyl; R$^{oa}$ is hydrogen or C$_{1-6}$ alkyl;
R$^{ob}$ is hydrogen, hydroxyl, or C$_{1-6}$ alkyl;
R$^1$ and R$^2$ are each independently selected from the group consisting of hydrogen, —CN, —F, —Cl, —Br, —I, C$_{1-8}$ alkyl, C$_{1-8}$ haloalkyl, C$_{1-8}$ heteroalkyl, C$_{3-8}$ cycloalkyl-C$_{1-6}$ alkyl, C$_{2-7}$ heterocycloalkyl-C$_{1-6}$ alkyl, C$_{3-8}$ cycloalkyl, and C$_{2-7}$ heterocycloalkyl, wherein said R$^1$ and R$^2$ substituents are independently optionally substituted with 1-3 R$^{1/2}$ substituents selected from the group consisting of F, Cl, Br, I, —CN, —OH, —NH$_2$, —NO$_2$, carboxy, C$_{1-6}$ alkyl, C$_{1-8}$ haloalkyl, C$_{1-8}$ alkoxy, C$_{1-8}$ alkylthio, C$_{1-8}$ alkylamino and C$_{1-8}$ dialkylamino;
or R$^1$ and R$^2$ are combined to form a 3- to 7-membered carbocycle or heterocycle ring comprising 1 to 2 heteroatoms selected from N, O and S, and wherein said carbocycle or heterocycle ring are optionally substituted with 1 to 3 R$^{1/2}$ substituents selected from the group consisting of F, Cl, Br, I, —CN, —OH, —NH$_2$, —NO$_2$, =CH—R$^{1/2a}$, C$_{1-6}$ alkyl, C$_{1-8}$ haloalkyl, C$_{1-8}$ alkoxy, C$_{1-8}$ alkylthio, C$_{1-8}$alkylamino and C$_{1-8}$ dialkylamino, wherein said R$^{1/2a}$ is H or C$_{1-8}$ alkyl;
or R$^1$ and R$^4$ are combined to form a 3- to 7-membered heterocycle ring comprising 1 to 2 heteroatoms selected from N, O and S, wherein said heterocycle ring is optionally substituted with 1 to 3 $R^{1/4}$ substituents selected from the group consisting of F, Cl, Br, I, —CN, —OH, —NH$_2$, —NO$_2$, =CH—R$^{1/4a}$, C$_{1-6}$ alkyl, C$_{1-8}$ haloalkyl, C$_{1-8}$ alkoxy, C$_{1-8}$ alkylthio, C$_{1-8}$ alkylamino and C$_{1-8}$ dialkylamino, wherein said R$^{1/4a}$ is H or C$_{1-8}$ alkyl; and R$^2$ is selected from the group consisting of hydrogen, —CN, —F, —Cl, —Br, —I, C$_{1-8}$ alkyl, C$_{1-8}$ haloalkyl and C$_{1-8}$ heteroalkyl;

R$^3$ is selected from the group consisting of hydrogen, F, Cl, Br, I, —CN, C$_{1-8}$ alkyl and C$_{1-8}$ haloalkyl;

R$^4$ is selected from the group consisting of hydrogen, C$_{1-4}$ alkyl and C$_{1-4}$ haloalkyl; or R$^1$ and R$^4$ are combined to form a 3- to 7-membered heterocycle ring as described above;

R$^5$ is selected from the group consisting of F, Cl, Br, I, —CN, C$_{1-8}$ alkyl, C$_{1-8}$ haloalkyl, C$_{1-8}$ alkoxy, C$_{3-8}$ cycloalkyl and C$_{2-7}$ heterocyclyl, wherein said C$_{3-8}$ cycloalkyl and C$_{2-7}$ heterocyclyl is optionally substituted with 1-3 substituents selected from F, Cl, Br, I, —OH, —NH$_2$, —NH(C$_{1-4}$ alkyl)-, —N(C$_{1-4}$ dialkyl)-, and C$_{1-4}$ alkyl substituted with 1-3 substituents selected from F, Cl, Br, I, —OH, —NH$_2$, —NH(C$_{1-4}$ alkyl)- and —N(C$_{1-4}$ dialkyl)-;

L is C$_{1-6}$ alkylene, wherein L is optionally substituted with from 1 to 3 substituents selected from the group consisting of C$_{1-4}$ alkyl, C$_{1-4}$ alkoxy, halo, oxo (=O), and C$_{1-4}$ haloalkyl, and wherein any two substituents attached to the same atom on L are optionally combined to form a 3- to 5-membered carbocyclic ring;

the subscript m represents the integer 0 or 1;

X$^1$ and X$^2$ are each independently selected from the group consisting of absent, —S—, —O— and —N(R$^X$)— wherein R$^x$ is H, C$_{1-8}$ alkyl, C$_{1-8}$ haloalkyl, and wherein if the subscript m is 0 then one of X$^1$ or X$^2$ is absent;

the ring "A" in is selected from the group consisting of:

(i) C$_{2-11}$ heterocycle comprising a nitrogen atom and further optionally comprising 1-2 heteroatoms selected from N, O and S; wherein R$^{AA}$ is independently selected from the group consisting of C$_{1-8}$ alkyl, C$_{1-8}$ haloalkyl, C$_{1-8}$ heteroalkyl, F, Cl, Br, I, —CN, —(X$^{RAA}$)$_{0-1}$NR$^{AA1}$R$^{AA2}$, —(X$^{RAA}$)$_{0-1}$OR$^{AA1}$, —(X$^{RAA}$)$_{0-1}$SR$^{AA1}$, —(X$^{RAA}$)$_{0-1}$N(R$^{AA1}$)C(=O) OR$^{AA3}$, —(X$^{RAA}$)$_{0-1}$OC(=O)N(R$^{AA1}$)(R$^{AA2}$), —(X$^{RAA}$)$_{0-1}$N(R$^{AA1}$)C(=O)N(R$^{AA1}$)(R$^{AA2}$), —(X$^{RAA}$)$_{0-1}$C(=O)N(R$^{AA1}$)(R$^{AA2}$), —(X$^{RAA}$)$_{0-1}$N(R$^{AA1}$)C(=O)R$^{AA2}$, —(X$^{RAA}$)$_{0-1}$C(=O)OR$^{AA1}$, —(X$^{RAA}$)$_{0-1}$OC(=O)R$^{AA1}$, —(X$^{RAA}$)$_{0-1}$S(O)$_{1-2}$R$^{AA3}$, —(X$^{RAA}$)$_{0-1}$S(O)$_{1-2}$N(R$^{AA1}$)(R$^{AA2}$), —(X$^{RAA}$)$_{0-1}$N(R$^{AA1}$)S(O)$_{1-2}$N(R$^{AA1}$)(R$^{AA2}$), —(X$^{RAA}$)$_{0-1}$N(R$^{AA1}$)S(O)$_{1-2}$(R$^{AA3}$), and —C(=O)R$^{AA1}$; wherein X$^{RAA}$ is selected from the group consisting of absent, C$_{1-4}$ alkylene, C$_{1-4}$ heteroalkylene, C$_{2-4}$ alkenylene and C$_{2-4}$ alkynylene; X$^{RAA}$ is optionally substituted with 1 to 3 substituents selected from the group consisting of C$_{1-4}$ alkyl, C$_{1-4}$ haloalkyl, C$_{1-4}$ heteroalkyl and oxo (=O); R$^{AA1}$ and R$^{AA2}$ are each independently selected from the group consisting of hydrogen, C$_{1-8}$ alkyl, C$_{2-8}$ alkenyl and C$_{1-8}$ haloalkyl; R$^{AA3}$ is selected from the group consisting of C$_{1-8}$ alkyl, C$_{2-8}$ alkenyl and C$_{1-8}$ haloalkyl; wherein R$^{AA}$ substituent is optionally substituted with from 1 to 5 R$^{RAA}$ substituents selected from, F, Cl, Br, I, —NH$_2$, —OH, —CN, —NO$_2$, =O, C$_{1-4}$ alkyl, C$_{1-4}$ haloalkyl, C$_{1-4}$ alkoxy, C$_{1-4}$ alkylamino and C$_{1-4}$ dialkylamino;

n is an integer from 0 to 5;

R$^A$ is selected from the group consisting of —(C=O) OR$^{A1}$, (C$_{6-10}$ aryl)$_{1-2}$-(X$^{RA}$)—, (5- to 10-membered heteroaryl)$_{1-2}$-(X$^{RA}$)—, (C$_{3-12}$ cycloalkyl)$_{1-2}$-(X$^{RA}$)—, and (C$_{2-11}$ heterocyclyl)$_{1-2}$-(X$^{RA}$)—, wherein said C$_{6-10}$ aryl, 5- to 10 membered heteroaryl, C$_{3-12}$ cycloalkyl and C$_{2-11}$ heterocyclyl of R$^A$ is independently optionally substituted with from 1 to 5 R$^{RA}$ substituents selected from the group consisting of F, Cl, Br, I, —NH$_2$, —OH, —CN, —NO$_2$, =O, C$_{1-4}$ alkyl, C$_{1-4}$ haloalkyl, C$_{1-4}$ alkoxy, C$_{1-4}$ alkylamino, C$_{1-4}$ dialkylamino, —N(R$^{A1}$)C(=O)OR$^{A3}$, —OC(=O)N(R$^{A1}$)(R$^{A2}$), —N(R$^{A1}$)C(=O)N(R$^{A1}$)(R$^{A2}$), —C(=O)N(R$^{A1}$)(R$^{A2}$), —N(R$^{A1}$)C(=O)R$^{A2}$, —C(=O)OR$^{A1}$, —C(=O)OR$^{A1}$, —OC(=O)R$^{A1}$, —S(O)$_{1-2}$R$^{A3}$, —S(O)$_{1-2}$N(R$^{A1}$)(R$^{A2}$), —N(R$^{A1}$)S(O)$_{1-2}$N(R$^{A1}$)(R$^{A2}$), —N(R$^{A1}$)S(O)$_{1-2}$(R$^{A3}$), —C(=O)R$^{A1}$, C$_{3-6}$ cycloalkyl, C$_{3-6}$ cycloalkoxy, C$_{2-5}$ heterocyclyl, C$_{2-5}$ heterocyclyloxy, 5- to 6 membered heteroaryl and phenyl, wherein the R$^{RA}$ substituent is optionally substituted with 1 to 5 R$^{RAi}$ substituents selected from, F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino; X$^{RA}$ is selected from the group consisting of absent, —O—, —S—, —N(H)—, —N(C$_{1-4}$ alkyl)-, —S(O)$_{1-2}$—, —S(O)$_{1-2}$N(H)—, —C(C=O)N(H)—, —C(C=O)N(C$_{1-4}$ alkyl)-, —OC(C=O)N(H)—, —N(H)C(C=O)N(H)—, —N(H)S(O)$_{1-2}$N(H)—, —C(=O)—, C$_{1-4}$ alkylene, C$_{1-4}$ heteroalkylene, C$_{2-4}$ alkenylene and C$_{2-4}$ alkynylene; wherein X$^{RA}$ is optionally substituted with 1 to 3 substituents selected from the group consisting of C$_{1-4}$ alkyl, C$_{1-4}$ haloalkyl, C$_{1-4}$ heteroalkyl and oxo (=O); R$^{A1}$ and R$^{A2}$ are each independently selected from the group consisting of hydrogen, C$_{1-8}$ alkyl, C$_{2-8}$ alkenyl, C$_{1-8}$ haloalkyl, C$_{3-8}$ cycloalkyl, phenyl, benzyl, 5- to 6-membered heteroaryl and C$_{2-7}$ heterocyclyl; R$^{A3}$ is selected from the group consisting of C$_{1-8}$ alkyl, C$_{2-8}$ alkenyl, C$_{1-8}$ haloalkyl, C$_{3-8}$ cycloalkyl, phenyl, benzyl, 5- to 6-membered heteroaryl and C$_{2-7}$ heterocyclyl; and q is an integer from 0 to 1;

(ii) C$_{3-12}$ membered carbocycle; wherein

R$^A$ is selected from the group consisting of C$_{1-8}$ alkyl, C$_{1-8}$ alkoxy, C$_{1-8}$ alkylamino, C$_{1-8}$ dialkylamino, C$_{1-8}$ haloalkyl, F, Cl, Br, I, —OH, —CN, —NO$_2$, =O, —(X$^{RA}$)$_{0-1}$NR$^A$R$^{A2}$, —(X$^{RA}$)$_{0-1}$OR$^{A1}$, —(X$^{RA}$)$_{0-1}$SR$^{A1}$, —(X$^{RA}$)$_{0-1}$N(R$^{A1}$)C(=O)OR$^{A3}$, —(X$^{RA}$)$_{0-1}$OC(=O)N(R$^{A1}$)(R$^{A2}$), —(X$^{RA}$)$_{0-1}$N(R$^{A1}$)C(=O)N(R$^{A1}$)(R$^{A2}$), —(X$^{RA}$)$_{0-1}$C(=O)N(R$^{A1}$)(R$^{A2}$), —(X$^{RA}$)$_{0-1}$N(R$^{A1}$)C(=O)R$^{A2}$, —(X$^{RA}$)$_{0-1}$C(=O)OR$^{A1}$, —(X$^{RA}$)$_{0-1}$OC(=O)R$^{A1}$, —(X$^{RA}$)$_{0-1}$S(O)$_{1-2}$R$^{A3}$, —(X$^{RA}$)$_{0-1}$S(O)$_{1-2}$N(R$^{A1}$)(R$^{A2}$), —(X$^{RA}$)$_{0-1}$N(R$^{A1}$)S(O)$_{1-2}$N(R$^{A1}$)(R$^{A2}$), —(X$^{RA}$)$_{0-1}$N(R$^{A1}$)S(O)$_{1-2}$(R$^{A3}$), —C(=O)R$^{A1}$, C$_{3-6}$ cycloalkyl, C$_{2-5}$ heterocyclyl, 5- to 10 membered heteroaryl and phenyl; wherein X$^{RA}$ is selected from the group consisting of C$_{1-4}$ alkylene, C$_{1-4}$ heteroalkylene, C$_{2-4}$ alkenylene and C$_{2-4}$ alkynylene; wherein R$^{A1}$ and R$^{A2}$ are independently selected from the group consisting of hydrogen, C$_{1-8}$ alkyl, C$_{2-8}$ alkenyl, C$_{1-8}$ haloalkyl, C$_{3-8}$ cycloalkyl, phenyl, benzyl, 5- to 6 membered heteroaryl and C$_{2-7}$ heterocyclyl; R$^{A3}$ is selected from the group consisting of C$_{1-8}$ alkyl, C$_{1-8}$ haloalkyl, C$_{3-8}$ cycloalkyl, phenyl, benzyl, 5- to 6-membered heteroaryl and C$_{2-7}$ heterocyclyl; wherein R$^A$ substituent is optionally substituted with from 1 to 5 R$^{RA}$ substituents selected from, F, Cl, Br, I, —NH$_2$, —OH, —CN, —NO$_2$, =O, C$_{1-4}$ alkyl, C$_{1-4}$ haloalkyl, C$_{1-4}$ alkoxy, C$_{1-4}$ alkylamino and C$_{1-4}$ dialkylamino;

n is the integer 0; and q is the integer 0 to 6;

(iii) phenyl substituted at the 2-position, the 3,4-positions, the 2,4-positions, or the 3,5-positions with groups independently selected from $R^A$, wherein each $R^A$ is selected from the group consisting of $C_{1-8}$ alkyl, $C_{1-8}$ alkoxy, $C_{1-8}$ alkylamino, $C_{1-8}$ dialkylamino, $C_{1-8}$ haloalkyl, F, Cl, Br, I, —OH, —CN, —NO$_2$, =O, —(X$^{RA}$)$_{0-1}$NR$^{A1}$R$^{A2}$, —(X$^{RA}$)$_{0-1}$OR$^{A1}$, —(X$^{RA}$)$_{0-1}$SR$^{A1}$, —(X$^{RA}$)$_{0-1}$N(R$^{A1}$)C(=O)OR$^{A3}$, —(X$^{RA}$)$_{0-1}$OC(=O)N(R$^{A1}$)(R$^{A2}$), —(X$^{RA}$)$_{0-1}$N(R$^{A1}$)C(=O)N(R$^{A1}$)(R$^{A2}$), —(X$^{RA}$)$_{0-1}$C(=O)N(R$^{A1}$)(R$^{A2}$), —(X$^{RA}$)$_{0-1}$N(R$^{A1}$)C(=O)R$^{A2}$, —(X$^{RA}$)$_{0-1}$C(=O)OR$^{A1}$, —(X$^{RA}$)$_{0-1}$OC(=O)R$^{A1}$, —(X$^{RA}$)$_{0-1}$S(O)$_{1-2}$R$^{A3}$, —(X$^{RA}$)$_{0-1}$S(O)$_{1-2}$N(R$^{A1}$)(R$^{A2}$), —(X$^{RA}$)$_{0-1}$N(R$^{A1}$)S(O)$_{1-2}$N(R$^{A1}$)(R$^{A2}$), —(X$^{RA}$)$_{0-1}$N(R$^{A1}$)S(O)$_{1-2}$(R$^{A3}$), —C(=O)R$^{A1}$, $C_{3-6}$ cycloalkyl, $C_{3-6}$ cycloalkoxy, $C_{2-5}$ heterocyclyl, $C_{2-5}$ heterocycloalkoxy, 5- to 10 membered heteroaryl and phenyl; wherein X$^{RA}$ is selected from the group consisting of $C_{1-4}$ alkylene, $C_{1-4}$ heteroalkylene, $C_{2-4}$ alkenylene and $C_{2-4}$ alkynylene; wherein R$^{A1}$ and R$^{A2}$ are independently selected from the group consisting of hydrogen, $C_{1-8}$ alkyl, $C_{2-8}$ alkenyl, $C_{1-8}$ haloalkyl, $C_{3-8}$ cycloalkyl, phenyl, benzyl, 5- to 6-membered heteroaryl and $C_{2-7}$ heterocyclyl; R$^{A3}$ is selected from the group consisting of $C_{1-8}$ alkyl, $C_{1-8}$ haloalkyl, $C_{3-8}$ cycloalkyl, phenyl, benzyl, 5- to 6-membered heteroaryl and $C_{2-7}$ heterocyclyl; wherein R$^A$ substituent is optionally substituted with from 1 to 5 R$^{RA}$ substituents selected from, F, Cl, Br, I, —NH$_2$, —OH, —CN, —NO$_2$, =O, $C_{1-4}$ alkyl, $C_{1-4}$ haloalkyl, $C_{1-4}$ alkoxy, $C_{1-4}$ alkylamino, $C_{1-4}$ dialkylamino, $C_{2-5}$ heterocyclyloxy, and $C_{2-7}$ heterocyclyl that is optionally substituted with one or more substituents independently selected from, F, Cl, Br, I, —NH$_2$, —OH, —CN, —NO$_2$, =O, $C_{1-4}$ alkyl, $C_{1-4}$ haloalkyl, $C_{1-4}$ alkoxy, and $C_{1-4}$ alkoxycarbonyl;

(iv) naphthyl; and (v) 5- to 10-membered heteroaryl comprising 1- to 3-nitrogen atoms and optionally further comprising 1- to 2-heteroatoms selected from O and S; wherein in (iv) and (v)

$R^A$ is selected from the group consisting of $C_{1-8}$ alkyl, $C_{1-8}$ alkoxy, $C_{1-8}$ alkylamino, $C_{1-8}$ dialkylamino, $C_{1-8}$ haloalkyl, F, Cl, Br, I, —OH, —CN, —NO$_2$, =O, —(X$^{RA}$)$_{0-1}$NR$^{A1}$R$^{A2}$, —(X$^{RA}$)$_{0-1}$OR$^{A1}$, —(X$^{RA}$)$_{0-1}$SR$^{A1}$, —(X$^{RA}$)$_{0-1}$N(R$^{A1}$)C(=O)OR$^{A3}$, —(X$^{RA}$)$_{0-1}$OC(=O)N(R$^{A1}$)(R$^{A2}$), —(X$^{RA}$)$_{0-1}$N(R$^{A1}$)C(=O)N(R$^{A1}$)(R$^{A2}$), —(X$^{RA}$)$_{0-1}$C(=O)N(R$^{A1}$)(R$^{A2}$), —(X$^{RA}$)$_{0-1}$N(R$^{A1}$)C(=O)R$^{A2}$, —(X$^{RA}$)$_{0-1}$C(=O)OR$^{A1}$, —(X$^{RA}$)$_{0-1}$OC(=O)R$^{A1}$, —(X$^{RA}$)$_{0-1}$S(O)$_{1-2}$R$^{A3}$, —(X$^{RA}$)$_{0-1}$S(O)$_{1-2}$N(R$^{A1}$)(R$^{A2}$), —(X$^{RA}$)$_{0-1}$N(R$^{A1}$)S(O)$_{1-2}$N(R$^{A1}$)(R$^{A2}$), —(X$^{RA}$)$_{0-1}$N(R$^{A1}$)S(O)$_{1-2}$(R$^{A3}$), —C(=O)R$^{A1}$, $C_{3-6}$ cycloalkyl, $C_{2-5}$ heterocyclyl, 5- to 10 membered heteroaryl and phenyl; wherein X$^{RA}$ is selected from the group consisting of $C_{1-4}$ alkylene, $C_{1-4}$ heteroalkylene, $C_{2-4}$ alkenylene and $C_{2-4}$ alkynylene; wherein R$^{A1}$ and R$^{A2}$ are independently selected from the group consisting of hydrogen, $C_{1-8}$ alkyl, $C_{2-8}$ alkenyl, $C_{1-8}$ haloalkyl, $C_{3-8}$ cycloalkyl, phenyl, benzyl, 5- to 6 membered heteroaryl and $C_{2-7}$ heterocyclyl; R$^{A3}$ is selected from the group consisting of $C_{1-8}$ alkyl, $C_{1-8}$ haloalkyl, $C_{3-8}$ cycloalkyl, phenyl, benzyl, 5- to 6-membered heteroaryl and $C_{2-7}$ heterocyclyl; wherein R$^A$ substituent is optionally substituted with from 1 to 5 R$^{RA}$ substituents selected from, F, Cl, Br, I, —NH$_2$, —OH, —CN, —NO$_2$, =O, $C_{1-4}$ alkyl, $C_{1-4}$ haloalkyl, $C_{1-4}$ alkoxy, $C_{1-4}$ alkylamino, $C_{1-4}$ dialkylamino and $C_{2-5}$ heterocyclyloxy;

n is the integer 0; and
q is an integer from 0 to 4.

Further embodiments (E2-E52) of the first embodiment of compounds of the invention are described below.

E2 The compound of E1 which is a compound of Formula (II):

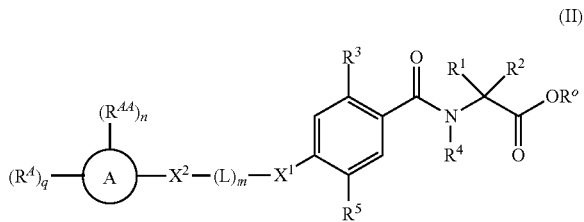

or a pharmaceutically acceptable salt thereof; wherein:

$R^o$ is hydrogen or $C_{1-6}$ alkyl;

$R^1$ and $R^2$ are each independently selected from the group consisting of hydrogen, —CN, —F, —Cl, —Br, —I, $C_{1-8}$ alkyl, $C_{1-8}$ haloalkyl, $C_{1-8}$ heteroalkyl, $C_{3-8}$ cycloalkyl-$C_{1-6}$ alkyl, $C_{2-7}$ heterocycloalkyl-$C_{1-6}$ alkyl, wherein said $R^1$ and $R^2$ substituents are independently optionally substituted with 1-3 $R^{1/2}$ substituents selected from the group consisting of F, Cl, Br, I, —CN, —OH, —NH$_2$, —NO$_2$, $C_{1-6}$ alkyl, $C_{1-8}$ haloalkyl, $C_{1-8}$ alkoxy, $C_{1-8}$ alkylthio, $C_{1-8}$ alkylamino and $C_{1-8}$ dialkylamino;

or $R^1$ and $R^2$ are combined to form a 3- to 7-membered carbocycle or heterocycle ring comprising 1 to 2 heteroatoms selected from N, O and S, and wherein said carbocycle or heterocycle ring are optionally substituted with 1 to 3 $R^{1/2}$ substituents selected from the group consisting of F, Cl, Br, I, —CN, —OH, —NH$_2$, —NO$_2$, $C_{1-6}$ alkyl, $C_{1-8}$ haloalkyl, $C_{1-8}$ alkoxy, $C_{1-8}$ alkylthio, $C_{1-8}$ alkylamino and $C_{1-8}$ dialkylamino;

or $R^1$ and $R^4$ are combined to form a 3- to 7-membered heterocycle ring comprising 1 to 2 heteroatoms selected from N, O and S, wherein said heterocycle ring is optionally substituted with 1 to 3 $R^{1/4}$ substituents selected from the group consisting of F, Cl, Br, I, —CN, —OH, —NH$_2$, —NO$_2$, $C_{1-6}$ alkyl, $C_{1-8}$ haloalkyl, $C_{1-8}$ alkoxy, $C_{1-8}$ alkylthio, $C_{1-8}$ alkylamino and $C_{1-8}$ dialkylamino; and $R^2$ is selected from the group consisting of hydrogen, —CN, —F, —Cl, —Br, —I, $C_{1-8}$ alkyl, $C_{1-8}$ haloalkyl and $C_{1-8}$ heteroalkyl;

$R^3$ is selected from the group consisting of hydrogen, F, Cl, Br, I, —CN, $C_{1-8}$ alkyl and $C_{1-8}$ haloalkyl;

$R^4$ is selected from the group consisting of hydrogen, $C_{1-4}$ alkyl and $C_{1-4}$ haloalkyl; or $R^1$ and $R^4$ are combined to form a 3- to 7-membered heterocycle ring as described above;

$R^5$ is selected from the group consisting of F, Cl, Br, I, —CN, $C_{1-8}$ alkyl, $C_{1-8}$ haloalkyl, $C_{1-8}$ alkoxy, $C_{3-8}$ cycloalkyl and $C_{2-7}$ heterocyclyl, wherein said $C_{3-8}$ cycloalkyl and $C_{2-7}$ heterocyclyl is optionally substituted with 1-3 substituents selected from F, Cl, Br, I, —OH, —NH$_2$, —NH($C_{1-4}$ alkyl)-, —N($C_{1-4}$ dialkyl)-, and $C_{1-4}$ alkyl substituted with 1-3 substituents selected from F, Cl, Br, I, —OH, —NH$_2$, —NH($C_{1-4}$ alkyl)- and —N($C_{1-4}$ dialkyl)-;

L is $C_{1-6}$ alkylene, wherein L is optionally substituted with from 1 to 3 substituents selected from the group consisting of $C_{1-4}$ alkyl, $C_{1-4}$ alkoxy, halo, oxo (=O), and $C_{1-4}$ haloalkyl, and wherein any two substituents attached to the same atom on L are optionally combined to form a 3- to 5-membered carbocyclic ring;

the subscript m represents the integer 0 or 1;

$X^1$ and $X^2$ are each independently selected from the group consisting of absent, —S—, —O— and —N(R$^X$)— wherein $R^x$ is H, $C_{1-8}$ alkyl, $C_{1-8}$ haloalkyl, and wherein if the subscript m is 0 then one of $X^1$ or $X^2$ is absent;

the ring "A" in is selected from the group consisting of:

(i) $C_{2-11}$ heterocycle comprising a nitrogen atom and further optionally comprising 1-2 heteroatoms selected from N, O and S; wherein $R^{AA}$ is independently selected from the group consisting of $C_{1-8}$ alkyl, $C_{1-8}$ haloalkyl, $C_{1-8}$ heteroalkyl, F, Cl, Br, I, —CN, —$(X^{RAA})_{0-1}NR^{AA1}R^{AA2}$, —$(X^{RAA})_{0-1}OR^{AA1}$, —$(X^{RAA})_{0-1}SR^{AA1}$, —$(X^{RAA})_{0-1}N(R^{AA1})C(\!\!=\!\!O)OR^{AA3}$, —$(X^{RAA})_{0-1}OC(\!\!=\!\!O)N(R^{AA1})(R^{AA2})$, —$(X^{RAA})_{0-1}N(R^{AA1})C(\!\!=\!\!O)N(R^{AA1})(R^{AA2})$, —$(X^{RAA})_{0-1}C(\!\!=\!\!O)N(R^{AA1})(R^{AA2})$, —$(X^{RAA})_{0-1}N(R^{AA1})C(\!\!=\!\!O)R^{AA2}$, —$(X^{RAA})_{0-1}C(\!\!=\!\!O)OR^{AA1}$, —$(X^{RAA})_{0-1}OC(\!\!=\!\!O)R^{AA1}$, —$(X^{RAA})_{0-1}S(O)_{1-2}R^{AA3}$, —$(X^{RAA})_{0-1}S(O)_{1-2}N(R^{AA1})(R^{AA2})$, —$(X^{RAA})_{0-1}N(R^{AA1})S(O)_{1-2}N(R^{AA1})(R^{AA2})$, —$(X^{RAA})_{0-1}N(R^{AA1})S(O)_{1-2}(R^{AA3})$, and —$C(\!\!=\!\!O)R^{AA1}$; wherein $X^{RAA}$ is selected from the group consisting of absent, $C_{1-4}$ alkylene, $C_{1-4}$ heteroalkylene, $C_{2-4}$ alkenylene and $C_{2-4}$ alkynylene; $X^{RAA}$ is optionally substituted with 1 to 3 substituents selected from the group consisting of $C_{1-4}$ alkyl, $C_{1-4}$ haloalkyl, $C_{1-4}$ heteroalkyl and oxo ($=\!\!O$); $R^{AA1}$ and $R^{AA2}$ are each independently selected from the group consisting of hydrogen, $C_{1-8}$ alkyl, $C_{2-8}$ alkenyl and $C_{1-8}$ haloalkyl; $R^{AA3}$ is selected from the group consisting of $C_{1-8}$ alkyl, $C_{2-8}$ alkenyl and $C_{1-8}$ haloalkyl; wherein $R^{AA}$ substituent is optionally substituted with from 1 to 5 $R^{RAA}$ substituents selected from, F, Cl, Br, I, —NH$_2$, —OH, —CN, —NO$_2$, $=\!\!O$, $C_{1-4}$ alkyl, $C_{1-4}$ haloalkyl, $C_{1-4}$ alkoxy, $C_{1-4}$ alkylamino and $C_{1-4}$ dialkylamino;

n is an integer from 0 to 5;

$R^A$ is selected from the group consisting of —$(C\!\!=\!\!O)OR^{A1}$, $(C_{6-10}\text{ aryl})_{1-2}\text{-}(X^{RA})$—, (5- to 10-membered heteroaryl)$_{1-2}$-$(X^{RA})$—, $(C_{3-12}\text{ cycloalkyl})_{1-2}$-$(X^{RA})$—, and $(C_{2-11}\text{ heterocyclyl})_{1-2}$-$(X^{RA})$—, wherein said $C_{6-10}$ aryl, 5- to 10 membered heteroaryl, $C_{3-12}$ cycloalkyl and $C_{2-11}$ heterocyclyl of $R^A$ is independently optionally substituted with from 1 to 5 $R^{RA}$ substituents selected from the group consisting of F, Cl, Br, I, —NH$_2$, —OH, —CN, —NO$_2$, $=\!\!O$, $C_{1-4}$ alkyl, $C_{1-4}$ haloalkyl, $C_{1-4}$ alkoxy, $C_{1-4}$ alkylamino, $C_{1-4}$ dialkylamino, —N($R^{A1}$)C($=\!\!O$)OR$^{A3}$, —OC($=\!\!O$)N($R^{A1}$)($R^{A2}$), —N($R^{A1}$)C($=\!\!O$)N($R^{A1}$)($R^{A2}$), —C($=\!\!O$)N($R^{A1}$)($R^{A2}$), —N($R^{A1}$)C($=\!\!O$)R$^{A2}$, —C($=\!\!O$)OR$^{A1}$, —C($=\!\!O$)OR$^{A1}$, —OC($=\!\!O$)R$^{A1}$, —S(O)$_{1-2}$R$^{A3}$, —S(O)$_{1-2}$N($R^{A1}$)($R^{A2}$), —N($R^{A1}$)S(O)$_{1-2}$N($R^{A1}$)($R^{A2}$), —N($R^{A1}$)S(O)$_{1-2}$($R^{A3}$), —C($=\!\!O$)R$^{A1}$, $C_{3-6}$ cycloalkyl, $C_{3-6}$ cycloalkoxy, $C_{2-5}$ heterocyclyl, $C_{2-5}$ heterocyclyloxy, 5- to 6 membered heteroaryl and phenyl, wherein the $R^{RA}$ substituent is optionally substituted with 1 to 5 $R^{RAi}$ substituents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; $X^{RA}$ is selected from the group consisting of absent, —O—, —S—, —N(H)—, —N($C_{1-4}$ alkyl)-, —S(O)$_{1-2}$—, —S(O)$_{1-2}$N(H)—, —C(C$=\!\!O$)N(H)—, —C(C$=\!\!O$)N($C_{1-4}$ alkyl)-, —OC(C$=\!\!O$)N(H)—, —N(H)C(C$=\!\!O$)N(H)—, —N(H)S(O)$_{1-2}$N(H)—, —C($=\!\!O$)—, $C_{1-4}$ alkylene, $C_{1-4}$ heteroalkylene, $C_{2-4}$ alkenylene and $C_{2-4}$ alkynylene; wherein $X^{RA}$ is optionally substituted with 1 to 3 substituents selected from the group consisting of $C_{1-4}$ alkyl, $C_{1-4}$ haloalkyl, $C_{1-4}$ heteroalkyl and oxo ($=\!\!O$); $R^{A1}$ and $R^{A2}$ are each independently selected from the group consisting of hydrogen, $C_{1-8}$ alkyl, $C_{2-8}$ alkenyl, $C_{1-8}$ haloalkyl, $C_{3-8}$ cycloalkyl, phenyl, benzyl, 5- to 6-membered heteroaryl and $C_{2-7}$ heterocyclyl; $R^{A3}$ is selected from the group consisting of $C_{1-8}$ alkyl, $C_{2-8}$ alkenyl, $C_{1-8}$ haloalkyl, $C_{3-8}$ cycloalkyl, phenyl, benzyl, 5- to 6-membered heteroaryl and $C_{2-7}$ heterocyclyl; and q is an integer from 0 to 1;

(ii) $C_{3-12}$ membered carbocycle; wherein $R^A$ is selected from the group consisting of $C_{1-8}$ alkyl, $C_{1-8}$ alkoxy, $C_{1-8}$ alkylamino, $C_{1-8}$ dialkylamino, $C_{1-8}$ haloalkyl, F, Cl, Br, I, —OH, —CN, —NO$_2$, $=\!\!O$, —$(X^{RA})_{0-1}NR^{A1}R^{A2}$, —$(X^{RA})_{0-1}OR^{A1}$, —$(X^{RA})_{0-1}SR^{A1}$, —$(X^{RA})_{0-1}N(R^{A1})C(\!\!=\!\!O)OR^{A3}$, —$(X^{RA})_{0-1}OC(\!\!=\!\!O)N(R^{A1})(R^{A2})$, —$(X^{RA})_{0-1}N(R^{A1})C(\!\!=\!\!O)N(R^{A1})(R^{A2})$, —$(X^{RA})_{0-1}C(\!\!=\!\!O)N(R^{A1})(R^{A2})$, —$(X^{RA})_{0-1}N(R^{A1})C(\!\!=\!\!O)R^{A2}$, —$(X^{RA})_{0-1}C(\!\!=\!\!O)OR^{A1}$, —$(X^{RA})_{0-1}OC(\!\!=\!\!O)R^{A1}$, —$(X^{RA})_{0-1}S(O)_{1-2}R^{A3}$, —$(X^{RA})_{0-1}S(O)_{1-2}N(R^{A1})(R^{A2})$, —$(X^{RA})_{0-1}N(R^{A1})S(O)_{1-2}N(R^{A1})(R^{A2})$, —$(X^{RA})_{0-1}N(R^{A1})S(O)_{1-2}(R^{A3})$, —$C(\!\!=\!\!O)R^{A1}$, $C_{3-6}$ cycloalkyl, $C_{2-5}$ heterocyclyl, 5- to 10 membered heteroaryl and phenyl; wherein $X^{RA}$ is selected from the group consisting of $C_{1-4}$ alkylene, $C_{1-4}$ heteroalkylene, $C_{2-4}$ alkenylene and $C_{2-4}$ alkynylene; wherein $R^{A1}$ and $R^{A2}$ are independently selected from the group consisting of hydrogen, $C_{1-8}$ alkyl, $C_{2-8}$ alkenyl, $C_{1-8}$ haloalkyl, $C_{3-8}$ cycloalkyl, phenyl, benzyl, 5- to 6 membered heteroaryl and $C_{2-7}$ heterocyclyl; $R^{A3}$ is selected from the group consisting of $C_{1-8}$ alkyl, $C_{1-8}$ haloalkyl, $C_{3-8}$ cycloalkyl, phenyl, benzyl, 5- to 6-membered heteroaryl and $C_{2-7}$ heterocyclyl; wherein $R^A$ substituent is optionally substituted with from 1 to 5 $R^{RA}$ substituents selected from, F, Cl, Br, I, —NH$_2$, —OH, —CN, —NO$_2$, $=\!\!O$, $C_{1-4}$ alkyl, $C_{1-4}$ haloalkyl, $C_{1-4}$ alkoxy, $C_{1-4}$ alkylamino and $C_{1-4}$ dialkylamino;

n is the integer 0; and q is the integer 0 to 6;

(iii) phenyl substituted at the 2-position, the 3,4-positions, the 2,4-positions, or the 3,5-positions with groups independently selected from $R^A$, wherein each $R^A$ is selected from the group consisting of $C_{1-8}$ alkyl, $C_{1-8}$ alkoxy, $C_{1-8}$ alkylamino, $C_{1-8}$ dialkylamino, $C_{1-8}$ haloalkyl, F, Cl, Br, I, —OH, —CN, —NO$_2$, $=\!\!O$, —$(X^{RA})_{0-1}NR^{A1}R^{A2}$, —$(X^{RA})_{0-1}OR^{A1}$, —$(X^{RA})_{0-1}SR^{A1}$, —$(X^{RA})_{0-1}N(R^{A1})C(\!\!=\!\!O)OR^{A3}$, —$(X^{RA})_{0-1}OC(\!\!=\!\!O)N(R^{A1})(R^{A2})$, —$(X^{RA})_{0-1}N(R^{A1})C(\!\!=\!\!O)N(R^{A1})(R^{A2})$, —$(X^{RA})_{0-1}C(\!\!=\!\!O)N(R^{A1})(R^{A2})$, —$(X^{RA})_{0-1}N(R^{A1})C(\!\!=\!\!O)R^{A2}$, —$(X^{RA})_{0-1}C(\!\!=\!\!O)OR^{A1}$, —$(X^{RA})_{0-1}OC(\!\!=\!\!O)R^{A1}$, —$(X^{RA})_{0-1}S(O)_{1-2}R^{A3}$, —$(X^{RA})_{0-1}S(O)_{1-2}N(R^{A1})(R^{A2})$, —$(X^{RA})_{0-1}N(R^{A1})S(O)_{1-2}N(R^{A1})(R^{A2})$, —$(X^{RA})_{0-1}N(R^{A1})S(O)_{1-2}(R^{A3})$, —$C(\!\!=\!\!O)R^{A1}$, $C_{3-6}$ cycloalkyl, $C_{3-6}$ cycloalkoxy, $C_{2-5}$ heterocyclyl, $C_{2-5}$ heterocycloalkoxy, 5- to 10 membered heteroaryl and phenyl; wherein $X^{RA}$ is selected from the group consisting of $C_{1-4}$ alkylene, $C_{1-4}$ heteroalkylene, $C_{2-4}$ alkenylene and $C_{2-4}$ alkynylene; wherein $R^{A1}$ and $R^{A2}$ are independently selected from the group consisting of hydrogen, $C_{1-8}$ alkyl, $C_{2-8}$ alkenyl, $C_{1-8}$ haloalkyl, $C_{3-8}$ cycloalkyl, phenyl, benzyl, 5- to 6-membered heteroaryl and $C_{2-7}$ heterocyclyl; $R^{A3}$ is selected from the group consisting of $C_{1-8}$ alkyl, $C_{1-8}$ haloalkyl, $C_{3-8}$ cycloalkyl, phenyl, benzyl, 5- to 6-membered heteroaryl and $C_{2-7}$ heterocyclyl; wherein $R^A$ substituent is optionally substituted with from 1 to 5 $R^{RA}$ substituents selected from, F, Cl, Br, I, —NH$_2$, —OH, —CN, —NO$_2$, $=\!\!O$, $C_{1-4}$ alkyl, $C_{1-4}$ haloalkyl, $C_{1-4}$ alkoxy, $C_{1-4}$ alkylamino, $C_{1-4}$ dialkylamino, $C_{2-5}$ heterocyclyloxy, and $C_{2-7}$ heterocyclyl that is optionally substituted with one or more substituents independently selected from, F, Cl, Br, I, —NH$_2$, —OH, —CN, —NO$_2$, =O, C$_{1-4}$ alkyl, C$_{1-4}$ haloalkyl, C$_{1-4}$ alkoxy, and C$_{1-4}$ alkoxycarbonyl;

(iv) naphthyl; and (v) 5- to 10-membered heteroaryl comprising 1- to 3-nitrogen atoms and optionally further comprising 1- to 2-heteroatoms selected from O and S; wherein in (iv) and (v)

R$^A$ is selected from the group consisting of C$_{1-8}$ alkyl, C$_{1-8}$ alkoxy, C$_{1-8}$ alkylamino, C$_{1-8}$ dialkylamino, C$_{1-8}$ haloalkyl, F, Cl, Br, I, —OH, —CN, —NO$_2$, =O, —(X$^{RA}$)$_{0-1}$NR$^{A1}$R$^{A2}$, —(X$^{RA}$)$_{0-1}$OR$^{A1}$, —(X$^{RA}$)$_{0-1}$SR$^{A1}$, —(X$^{RA}$)$_{0-1}$N(R$^{A1}$)C(=O)OR$^{A3}$, —(X$^{RA}$)$_{0-1}$OC(=O)N(R$^{A1}$)(R$^{A2}$), —(X$^{RA}$)$_{0-1}$N(R$^{A1}$)C(=O)N(R$^{A1}$)(R$^{A2}$), —(X$^{RA}$)$_{0-1}$C(=O)N(R$^{A1}$)(R$^{A2}$), —(X$^{RA}$)$_{0-1}$N(R$^{A1}$)C(=O)R$^{A2}$, —(X$^{RA}$)$_{0-1}$C(=O)OR$^{A1}$, —(X$^{RA}$)$_{0-1}$OC(=O)R$^{A1}$, —(X$^{RA}$)$_{0-1}$S(O)$_{1-2}$R$^{A3}$, —(X$^{RA}$)$_{0-1}$S(O)$_{1-2}$N(R$^{A1}$)(R$^{A2}$), —(X$^{RA}$)$_{0-1}$N(R$^{A1}$)S(O)$_{1-2}$N(R$^{A1}$)(R$^{A2}$), —(X$^{RA}$)$_{0-1}$N(R$^{A1}$)S(O)$_{1-2}$(R$^{A3}$), —C(=O)R$^{A1}$, C$_{3-6}$ cycloalkyl, C$_{2-5}$ heterocyclyl, 5- to 10 membered heteroaryl and phenyl; wherein X$^{RA}$ is selected from the group consisting of C$_{1-4}$ alkylene, C$_{1-4}$ heteroalkylene, C$_{2-4}$ alkenylene and C$_{2-4}$ alkynylene; wherein R$^{A1}$ and R$^{A2}$ are independently selected from the group consisting of hydrogen, C$_{1-8}$ alkyl, C$_{2-8}$ alkenyl, C$_{1-8}$ haloalkyl, C$_{3-8}$ cycloalkyl, phenyl, benzyl, 5- to 6 membered heteroaryl and C$_{2-7}$ heterocyclyl; R$^{A3}$ is selected from the group consisting of C$_{1-8}$ alkyl, C$_{1-8}$ haloalkyl, C$_{3-8}$ cycloalkyl, phenyl, benzyl, 5- to 6-membered heteroaryl and C$_{2-7}$ heterocyclyl; wherein R$^A$ substituent is optionally substituted with from 1 to 5 R$^{RA}$ substituents selected from, F, Cl, Br, I, —NH$_2$, —OH, —CN, —NO$_2$, =O, C$_{1-4}$ alkyl, C$_{1-4}$ haloalkyl, C$_{1-4}$ alkoxy, C$_{1-4}$ alkylamino, C$_{1-4}$ dialkylamino and C$_{2-5}$ heterocyclyloxy;

n is the integer 0; and q is an integer from 0 to 4.

E3 The compound of E1 or E2, wherein R$^o$ is hydrogen.

E4 The compound of E1 or E2, wherein R$^o$ is C$_{1-6}$ alkyl.

E5 The compound of E1 or E2, wherein R$^o$ is methyl, ethyl, propyl, isopropyl, butyl, sec-butyl or tert-butyl.

E6 The compound of E1 or E2, wherein R$^o$ is ethyl, propyl, isopropyl, butyl, sec-butyl or tert-butyl.

E7 The compound of E1 or E2, wherein R$^o$ is methyl.

E8 The compound of any one of E1-E7, wherein R$^1$ and R$^2$ are each independently selected from the group consisting of hydrogen, C$_{1-8}$ alkyl, C$_{1-8}$ haloalkyl and C$_{1-8}$ heteroalkyl.

E9 The compound of any one of E1-E7, wherein R$^1$ and R$^2$ are each independently selected from the group consisting of hydrogen, methyl, trifluoromethyl, ethyl, propyl, butyl, sec-butyl, tert-butyl, methoxymethyl and methoxyethyl.

E10 The compound of any one of E1-E9, wherein R$^2$ is hydrogen.

E11 The compound of any one of E8-E10, wherein R$^1$ is other than hydrogen and is in the (R)-configuration.

E12 The compound of any one of E8-E10, wherein R$^1$ is other than hydrogen and is in the (S)-configuration.

E13 The compound of any one of E1-E7, wherein R$^1$ and R$^2$ are combined to form a 3- to 7-membered carbocycle or heterocycle ring comprising 1 to 2 heteroatoms selected from N, O and S, and wherein said carbocycle or heterocycle ring are optionally substituted.

E14 The compound of any one of E1-E7, wherein R$^1$ and R$^2$ are combined to form a cyclopropyl, cyclobutyl, cyclopentyl, cyclohexyl, azetidinyl, pyrrolidinyl or piperidinyl ring, and is optionally substituted.

E15 The compound of any one of E1-E7, wherein R$^1$ and R$^4$ are combined to form a 3- to 7-membered heterocycle ring comprising 1 to 2 heteroatoms selected from N, O and S, wherein said heterocycle ring is optionally substituted.

E16 The compound of any one of E1-E7, wherein R$^1$ and R$^4$ are combined to form an optionally substituted ring selected from the group consisting of azetidine, pyrrolidine, piperidine, homopiperidine, oxazolidine, thiazolidine, imidazolidine, morpholine, homomorpholine, thiomorpholine, piperazine, and homopiperidine.

E17 The compound of any one of E1-E7, E15, and E16, wherein R$^{1/4}$ substituent is selected from the group consisting of F, Cl, Br, I, —CN, —OH, —NH$_2$, C$_{1-6}$ alkyl and C$_{1-8}$ haloalkyl.

E18 The compound of any one of E1-E7 and E17, wherein a compound of Formula I has the subformulae I-a:

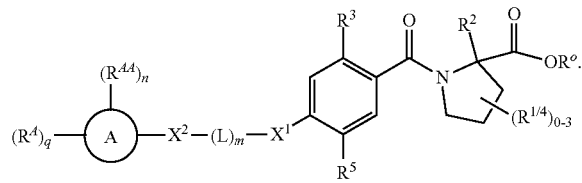

(I-a)

E19 The compound of any one of E1-E7, wherein in a compound of Formula I, R$^2$ is hydrogen and said compound has the subformula selected from the group consisting of:

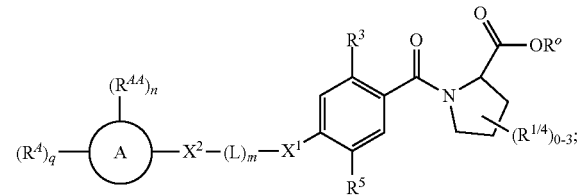

(I-ai)

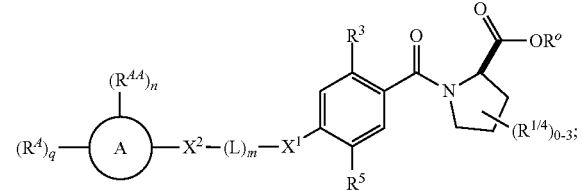

(I-aii)

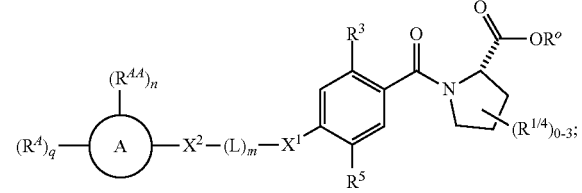

(I-aiii)

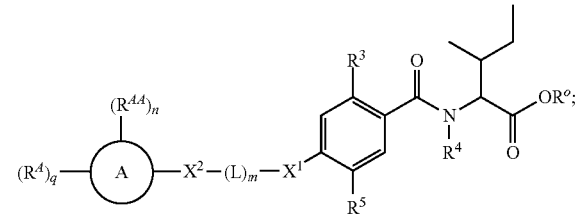

(I-bi)

-continued (I-bii)

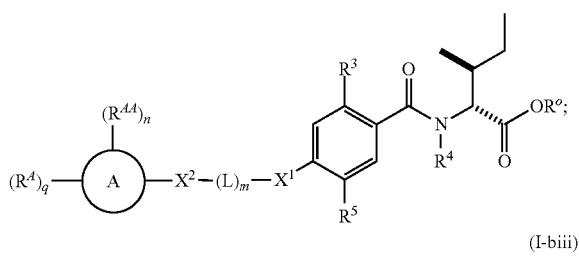

(I-biii)

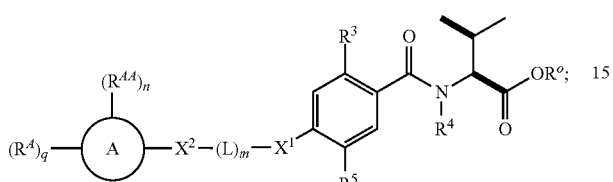

(I-ci)

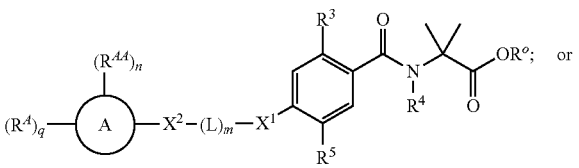

(I-di)

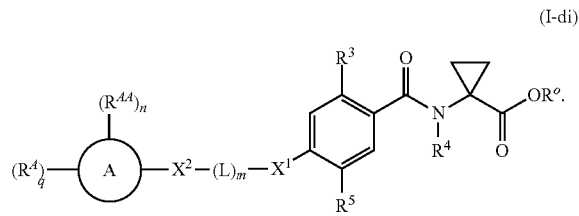

E20 The compound of any one of E1-E19, wherein $R^3$ is F or Cl; and $R^5$ is selected from the group consisting of F, Cl, $C_{1-4}$ alkyl, $C_{1-4}$ alkoxy, and $C_{3-8}$ cycloalkyl.

E21 The compound of any one of E1-E19, wherein $R^3$ is F or Cl and $R^5$ is selected from the group consisting of F, Cl, cyclopropyl, cyclobutyl and cyclopentyl.

E22 The compound of any one of E1-E21, wherein $X^1$ is —O— or —N(H)—; $X^2$ is absent; the subscript m is 1; and -(L)- is an optionally substituted $C_{1-4}$ alkylene.

E23 The compound of any one of E1-E21, wherein $X^1$ is —O— or —N(H)—; $X^2$ is absent; the subscript m is 1; and -(L)- is selected from the group consisting of —CH$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$— or —CH$_2$CH$_2$CH$_2$CH$_2$—.

E24 The compound of any one of E1-E23, wherein $X^1$ is —O—; the subscript m is 1 and -(L)- is —CH$_2$—, —C(H)(CH$_3$)—, or —CH$_2$—CH$_2$—.

E25 The compound of any one of E1-E21, wherein $X^1$ is absent; $X^2$ is —O— or —N(H)—; the subscript m is 1; and -(L)- is selected from the group consisting of —C(H)$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$— or —CH$_2$CH$_2$CH$_2$CH$_2$—.

E26 The compound of any one of E1-E21, wherein $X^1$ and $X^2$ are absent; the subscript m is 1; and -(L)- is selected from the group consisting of —C(H)$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$— or —CH$_2$CH$_2$CH$_2$CH$_2$—.

E27 The compound of any one of E1-E21, wherein $X^1$ and $X^2$ are absent; the subscript m is 1; and -(L)- is selected from the group consisting of —C(H)$_2$—, —C(=O)—, —C(H)(CH$_3$)— and —CH$_2$—CH$_2$.

E28 The compound of any one of E1-E21, wherein m is 0; $X^1$ is selected from —O—, and —N(H)—; and $X^2$ is absent.

E29 The compound of any one of E1-E28, wherein in Formula I the ring "A" is (i) $C_{2-11}$ heterocycle and is selected from the group consisting of azetidine, pyrrolidine, piperidine, morpholine, homopiperazine, piperazine and 8-azabicyclo[3.2.1]octane, and is optionally substituted.

E30 The compound of any one of E1-E28, wherein the group

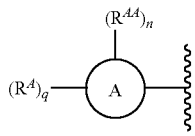

in Formula I is selected from the group consisting of:

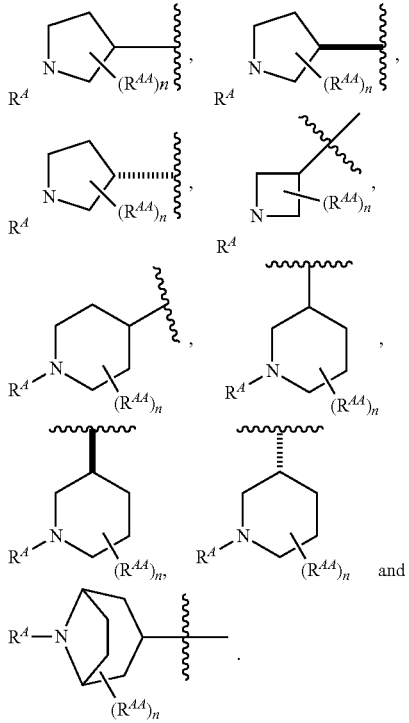

and

E31 The compound of any one of E1-E28, wherein the group

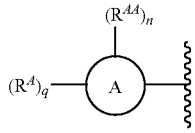

in Formula I is selected from the group consisting of:

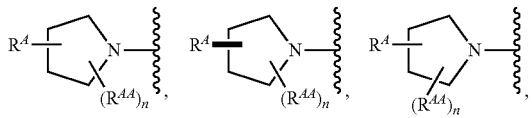

-continued

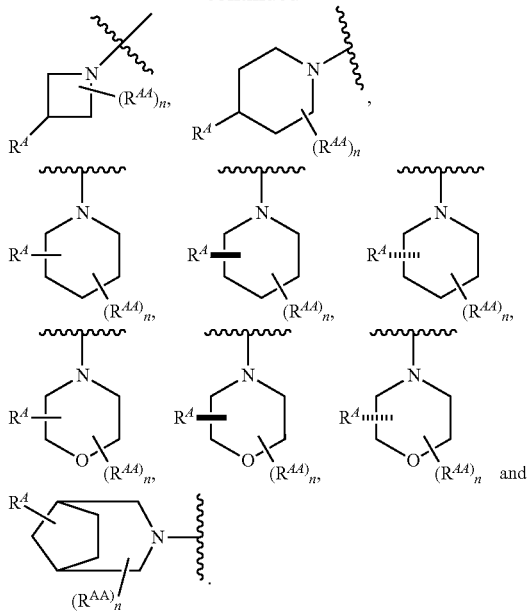

E32 The compound of any one of E1-E31, wherein each $R^{AA}$ is independently selected from the group consisting of methyl, trifluoromethyl, ethyl, F, Cl, Br, and I.

E33 The compound of any one of E1-E32, wherein each $R^A$ is independently selected from the group consisting of (phenyl)$_{1-2}$-$(X^{RA})$—, (5-6 membered heteroaryl)$_{1-2}$-$(X^{RA})$, wherein said phenyl or said 5-6 membered heteroaryl is optionally substituted with from 1 to 5 substituents selected from, F, Cl, Br, —NH$_2$, —OH, —CN, —NO$_2$, C$_{1-4}$ alkyl, C$_{1-4}$ haloalkyl, C$_{1-4}$ alkoxy, C$_{1-4}$ alkylamino, C$_{1-4}$ dialkylamino, phenyl, C$_{1-4}$ alkanoyl, C$_{1-4}$ alkyl-OC(=O)— and C$_{3-6}$ cycloalkyl; and wherein $X^{RA}$ is selected from the group consisting of absent, —O—, —S—, —N(H)—, —N(C$_{1-4}$ alkyl)-, C$_{1-4}$ alkylene, C$_{1-4}$ heteroalkylene, C$_{2-4}$ alkenylene and C$_{2-4}$ alkynylene; and wherein $X^{RA}$ is optionally substituted with 1 to 3 substituents selected from the group consisting of C$_{1-4}$ alkyl, C$_{1-4}$ haloalkyl, and C$_{1-4}$ heteroalkyl.

E34 The compound of E33, wherein $R^A$ is (phenyl)—$(X^{RA})$— or (5-6 membered heteroaryl)-$(X^{RA})$—.

E35 The compound of E34, wherein each $R^A$ is independently selected from the group consisting

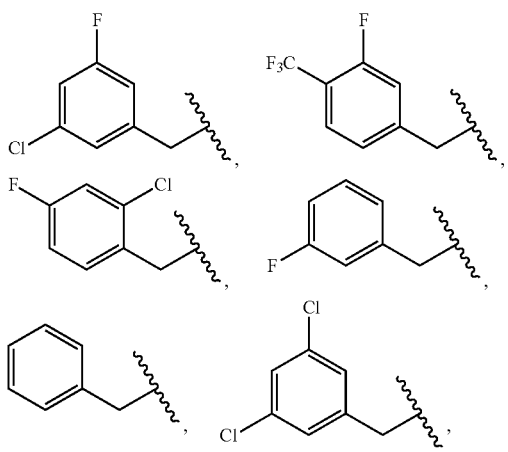

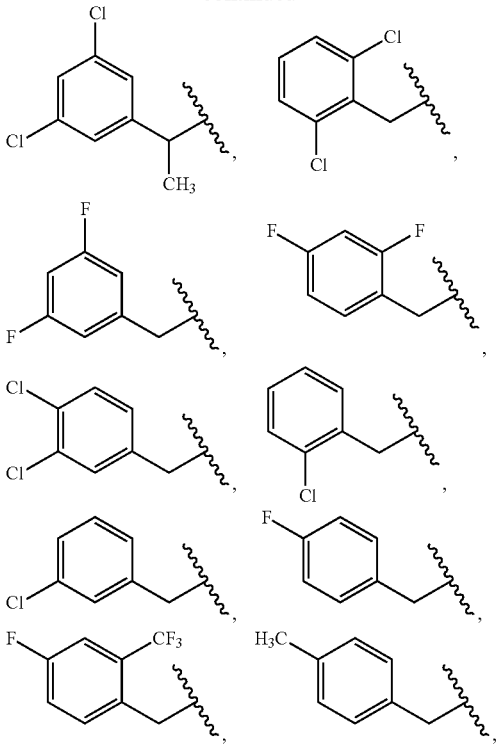

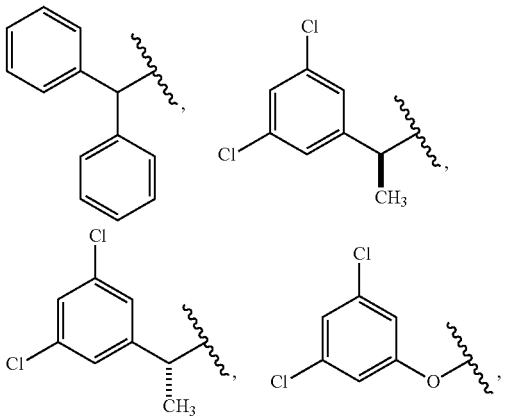

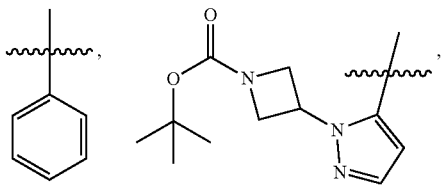

E36 The compound of any of of E1-E28, wherein the group

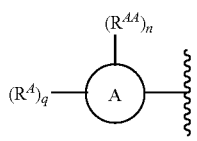

in Formula I is selected from the group consisting of:

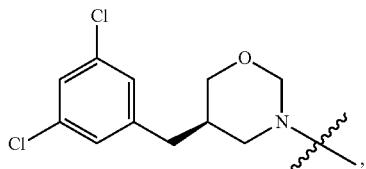

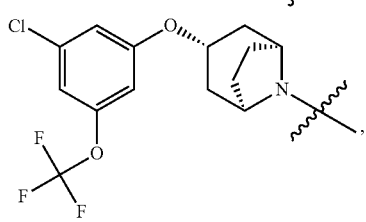

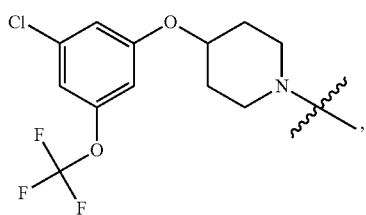

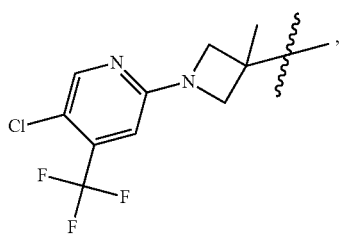

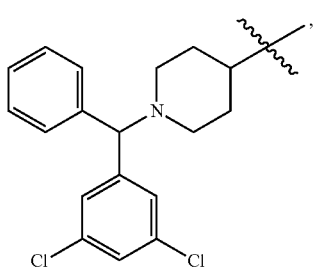

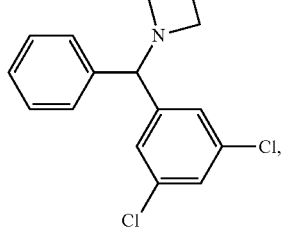

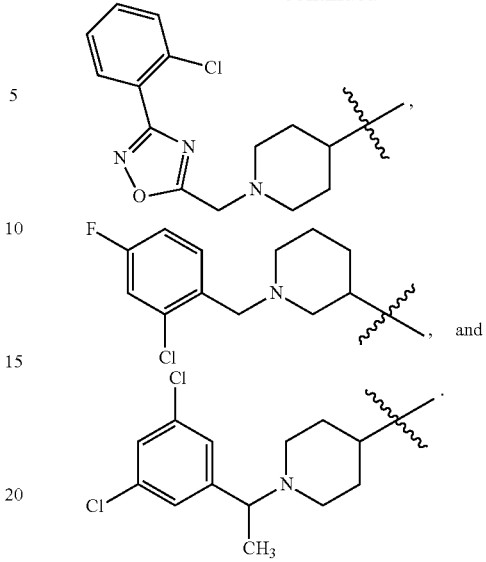

E37 The compound of any one of E1-E28, wherein in Formula I the ring "A" is (ii) $C_{3-12}$ carbocycle selected from the group consisting of cyclopropane, cyclobutane, cyclopentane, cyclohexane, cycloheptane, adamantane, cubane, bicyclo[2.1.1]hexane, bicyclo[2.2.2]octane, bicyclo[4.1.1]octane, bicyclo[3.1.1]heptane, bicyclo[2.2.1]heptane, bicyclo[3.2.1]octane, bicyclo[3.3.1]nonane, bicyclo[3.1.0]hexane, tetrahydronaphthyl, spiro[2,5]octane, norpinane, spiro[3.5]nonanyl, norbornanyl, spiro[4.5]decane, bicyclo[4.1.0]heptane and spiro[5.5]undecanyl, and is optionally substituted.

E38 The compound of E37, wherein each $R^A$ is independently selected from the group consisting of $C_{1-8}$ alkyl, $C_{1-8}$ alkoxy, $C_{1-8}$ alkylamino, $C_{1-8}$ dialkylamino, $C_{1-8}$ haloalkyl, F, Cl, Br, I, —OH, —CN, —NO$_2$, =O, —$(X^{RA})_{0-1}$NR$^{A1}$R$^{A2}$, —$(X^{RA})_{0-1}$OR$^{A1}$, —$(X^{RA})_{0-1}$SR$^{A1}$, —$(X^{RA})_{0-1}$C(=O)N(R$^{A1}$)(R$^{A2}$) and —$(X^{RA})_{0-1}$C(=O)OR$^{A1}$.

E39 The compound of E38, wherein each $R^A$ is independently selected from the group consisting of, fluoro, methyl, cyano, and trifluoromethyl.

E40 The compound of any one of E1-E28, wherein the group

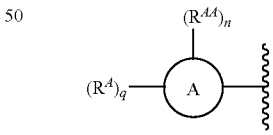

in Formula I is selected from the group consisting of:

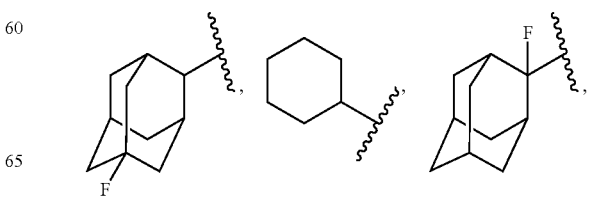

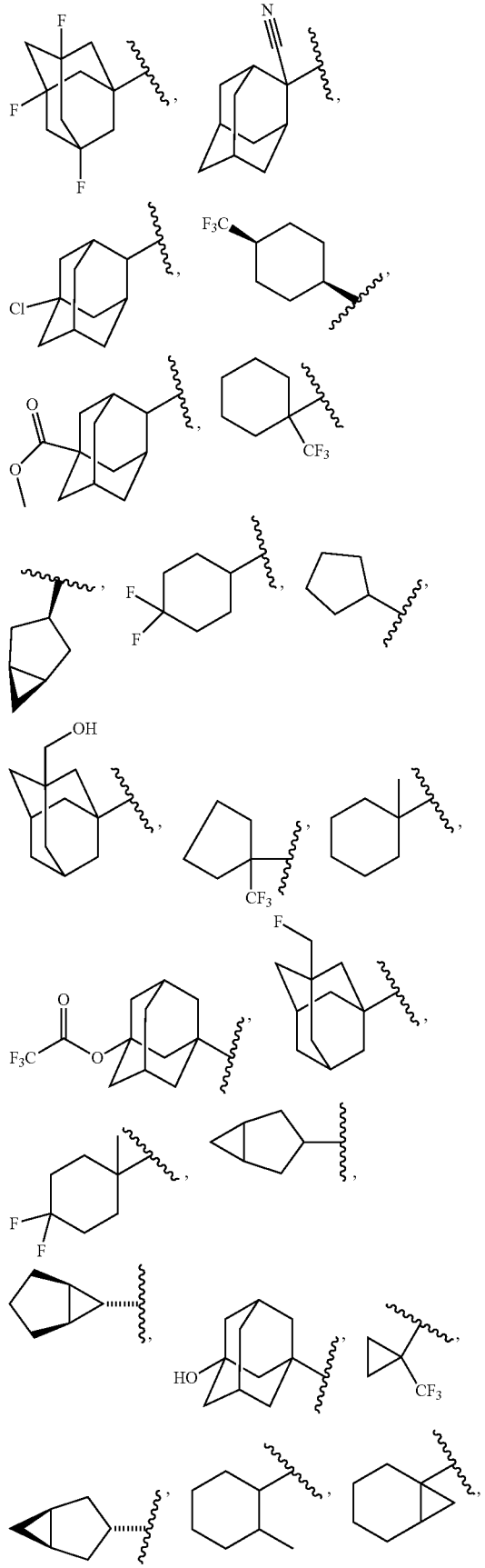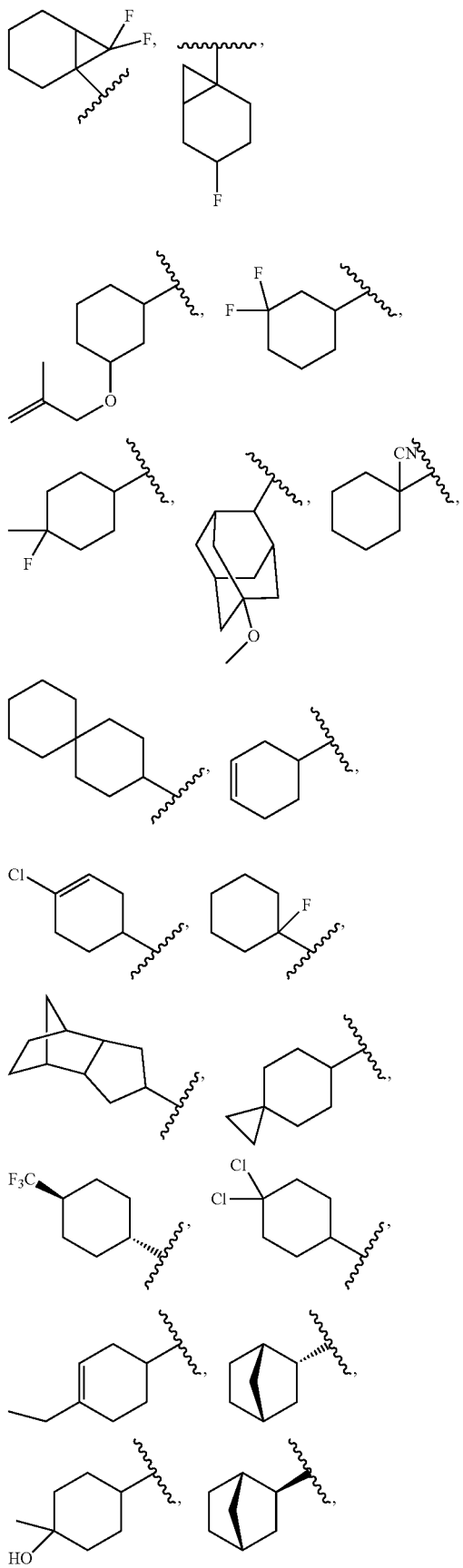

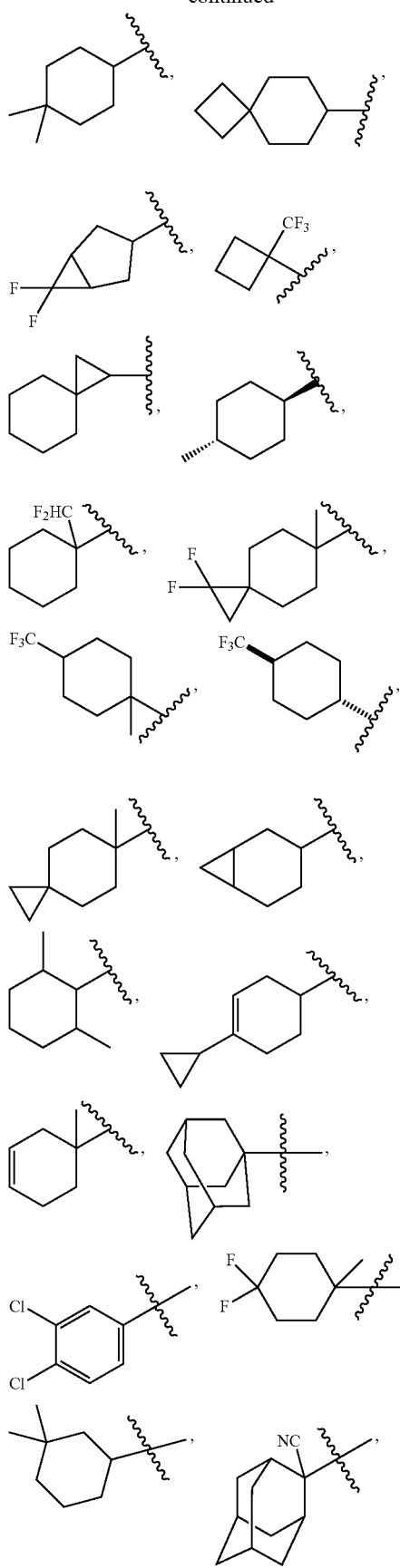
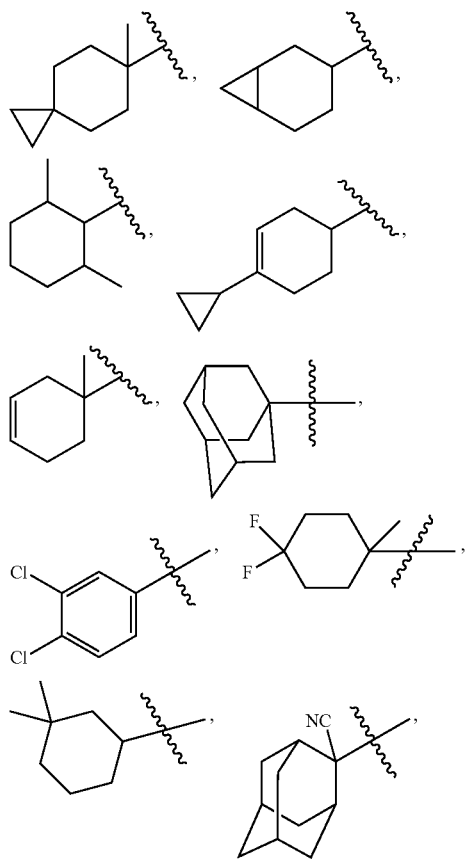
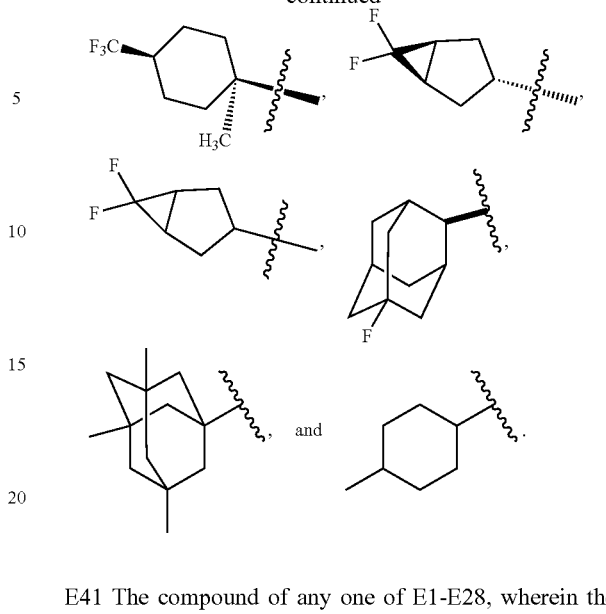
E41 The compound of any one of E1-E28, wherein the group
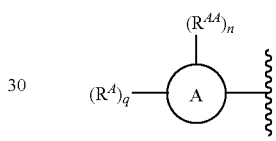
in Formula I is selected from the group consisting of:
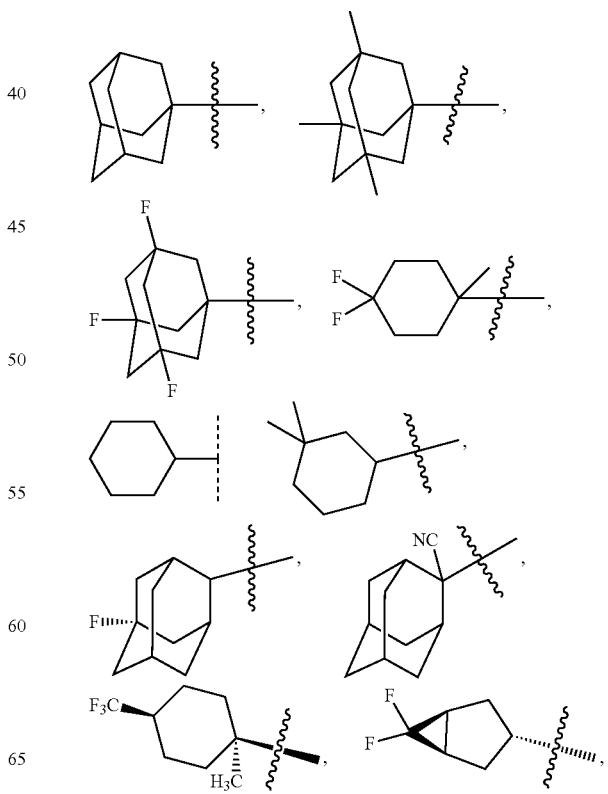

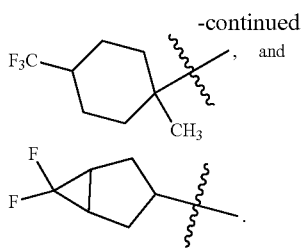

E42 The compound of any one of E1-E28, wherein the group

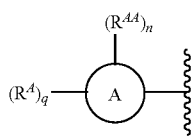

in Formula I is selected from the group consisting of:

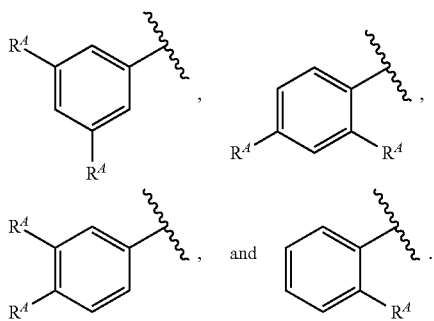

E43 The compound of E42 wherein each $R^A$ is independently selected from the group consisting of $C_{1-8}$ alkyl, $C_{1-8}$ haloalkyl, F, Cl, Br, I, —OH, —CN, —$(X^{RA})_{0-1}NR^{A1}R^{A2}$, —$(X^{RA})_{0-1}OR^{A1}$, —$(X^{RA})_{0-1}SR^{A1}$, —C(=O)$R^{A1}$, $C_{3-6}$ cycloalkyl, $C_{2-5}$ heterocyclyl, 5- to 10 membered heteroaryl and phenyl, wherein $R^A$ is further optionally substituted.

E44 The compound of any one of E1-E28, wherein the group

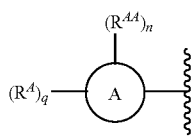

in Formula I is selected from the group consisting of:

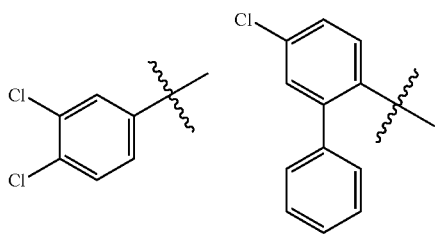

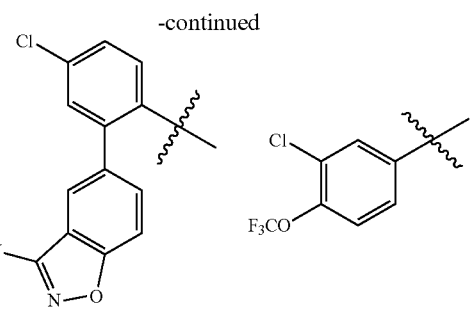

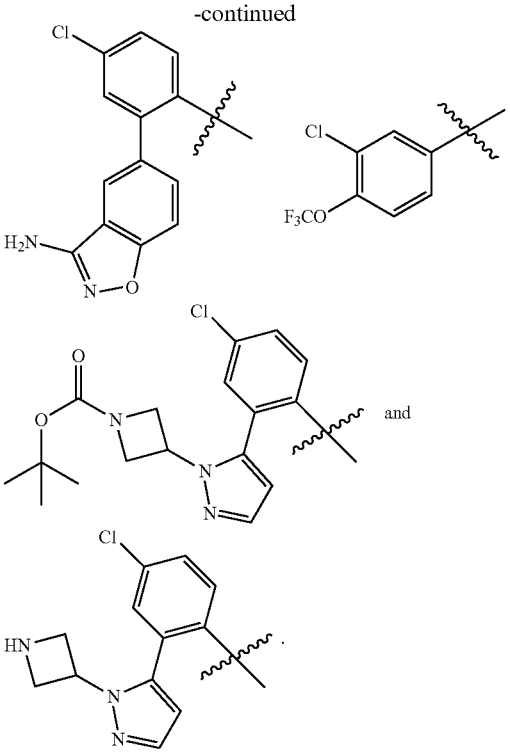

E45 The compound of any one of E1-E28, wherein in Formula I the ring "A" is (iv) naphthyl; or (v) 5- to 10-membered heteroaryl selected from the group consisting of pyridine, pyrimidine, pyridazine and pyrazine, and wherein (iv) and (v) are optionally substituted with from 1 to 3 $R^A$ group selected from the group consisting of $C_{1-8}$ alkyl, $C_{1-8}$ haloalkyl, F, Cl, Br, I, —OH, —CN, —$(X^{RA})_{0-1}$ $NR^{A1}R^{A2}$, —$(X^{RA})_{0-1}OR^{A1}$, —$(X^{RA})_{0-1}SR^{A1}$, —C(=O) $R^{A1}$, $C_{3-6}$ cycloalkyl, $C_{2-5}$ heterocyclyl, 5- to 10 membered heteroaryl and phenyl, and wherein $R^A$ is further optionally substituted.

E46 The compound of any one of E1-E28, wherein the group

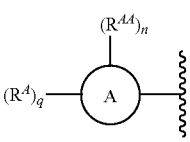

in Formula I is selected from the group consisting of:

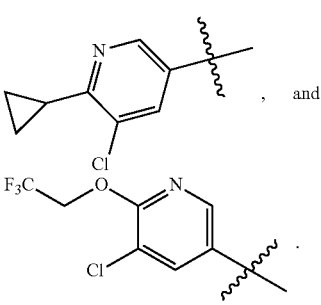

E47 The compound of any one of E1-E28, wherein the group
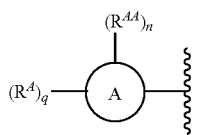
in Formula I is selected from the group consisting of:
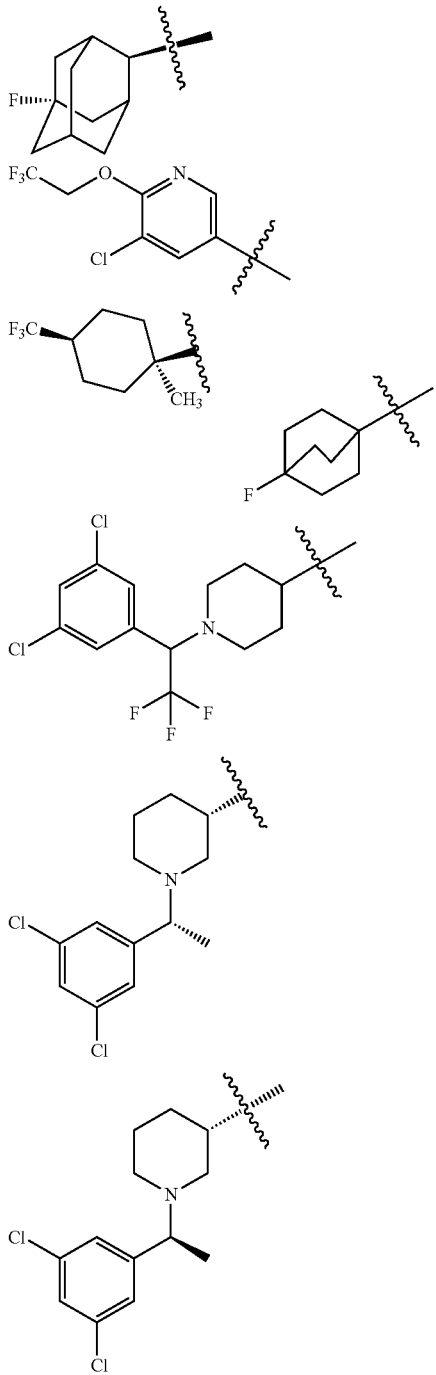
-continued
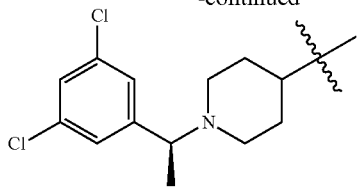
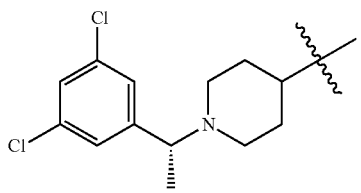
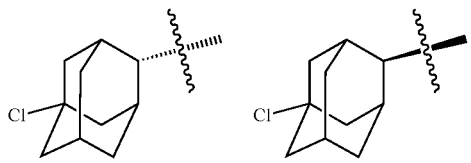
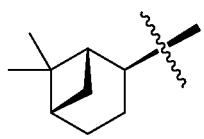
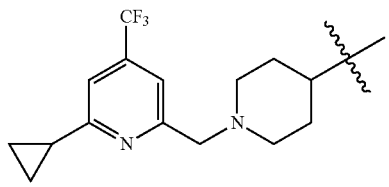
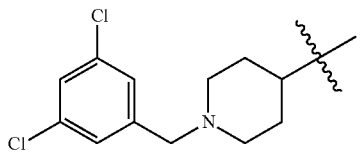
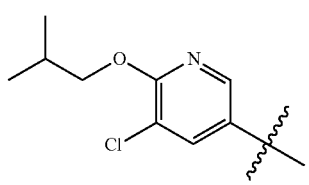
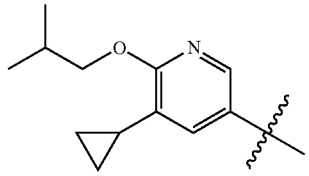
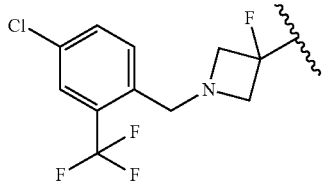

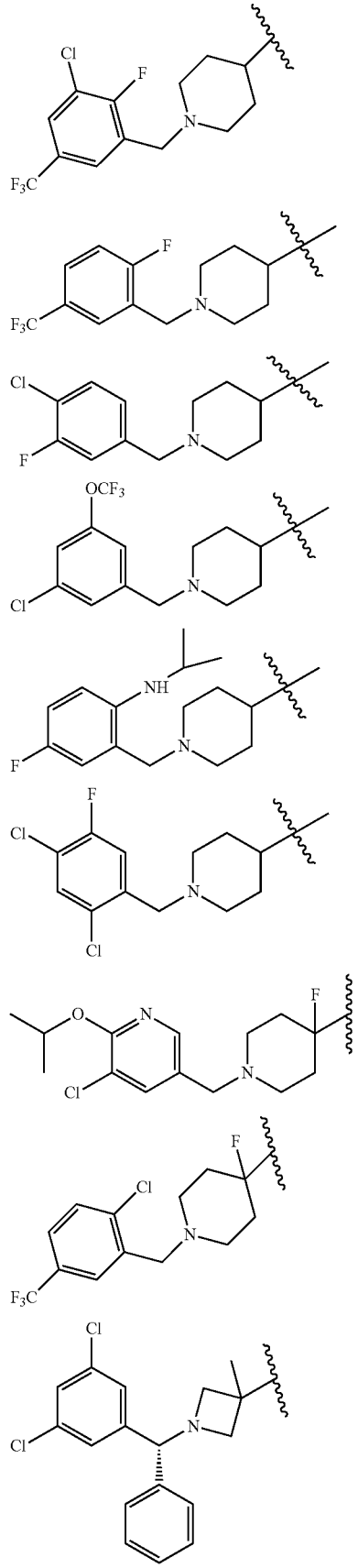
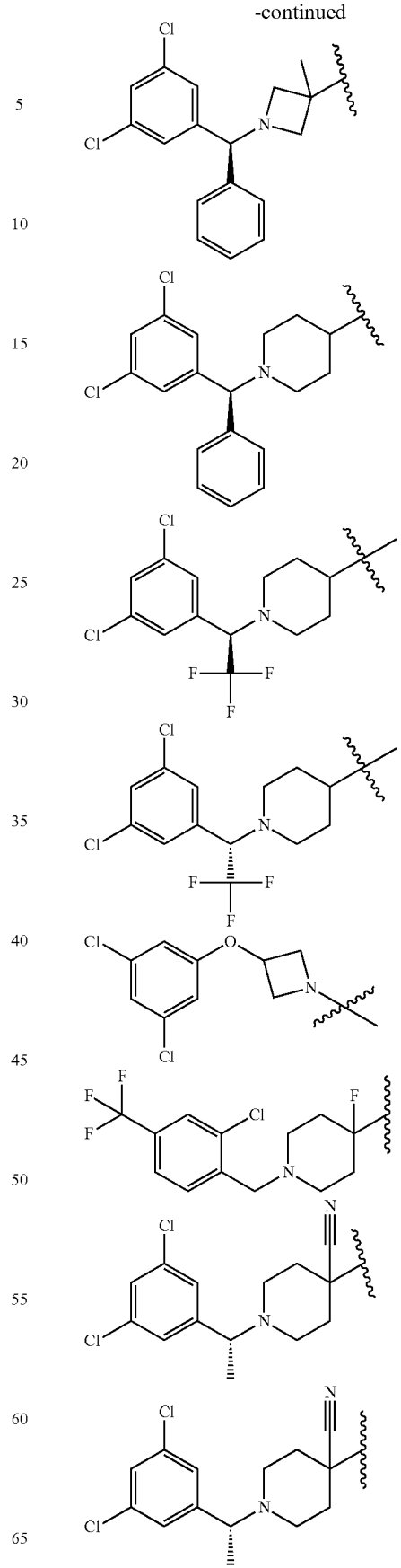

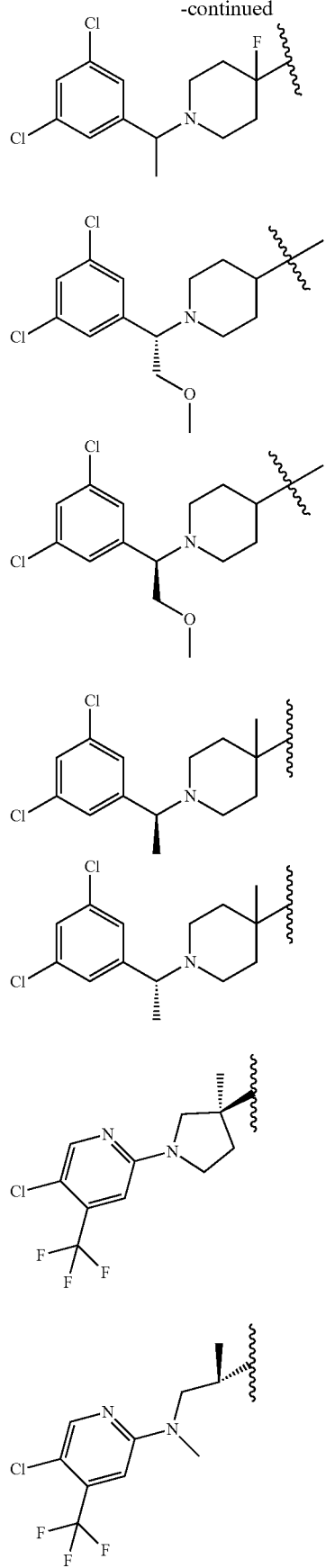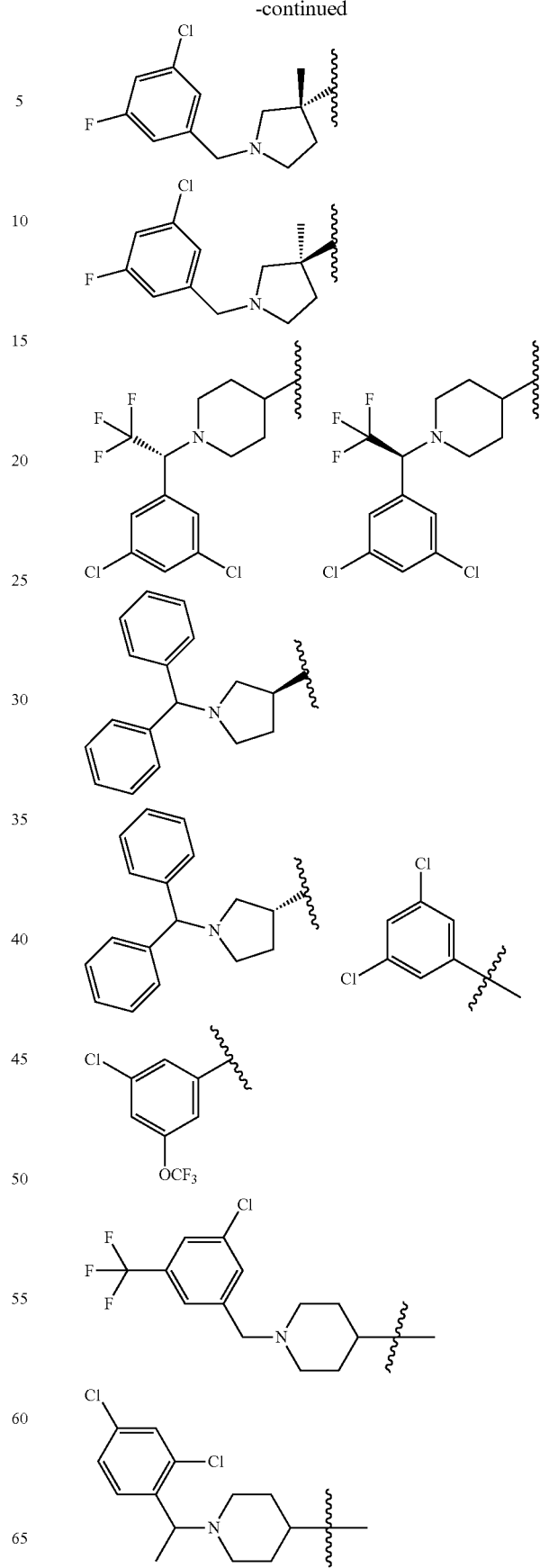

-continued
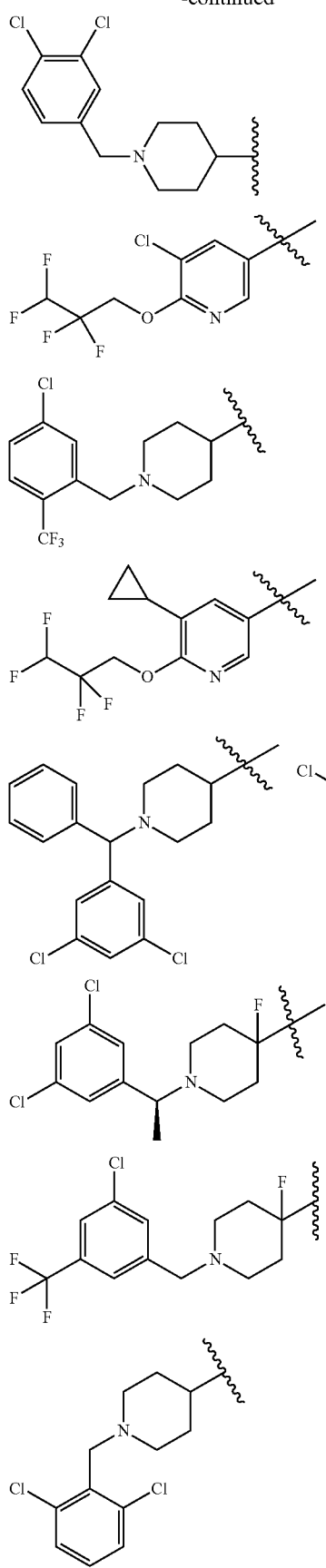
-continued
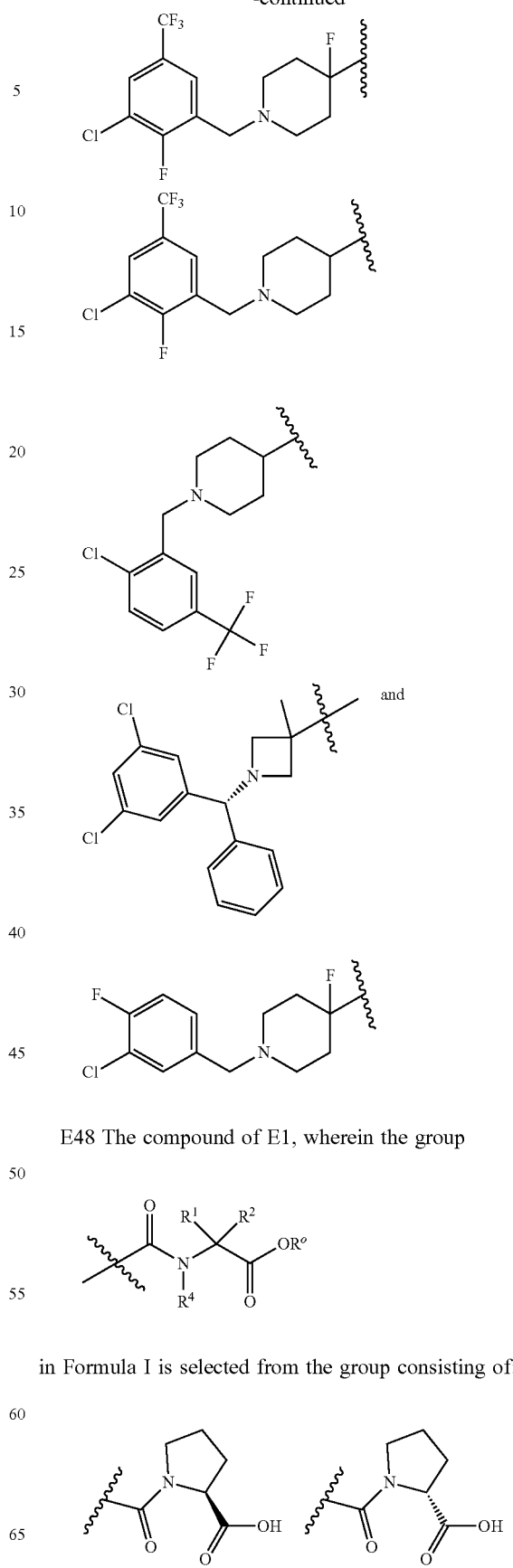
E48 The compound of E1, wherein the group
in Formula I is selected from the group consisting of:

31
-continued
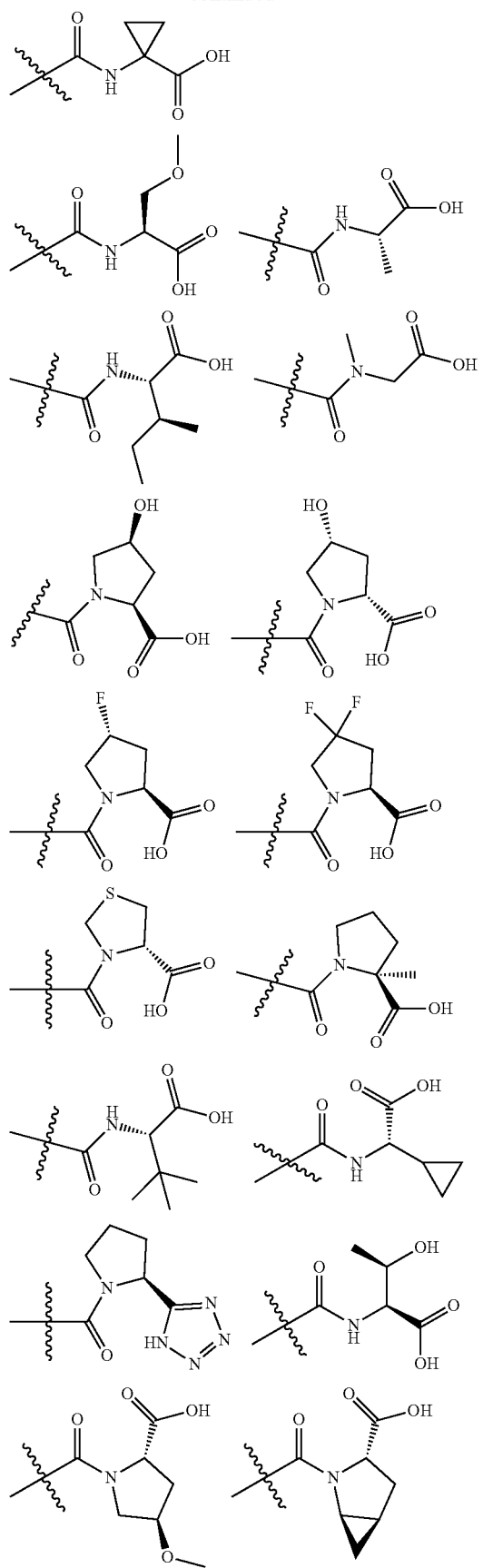
32
-continued
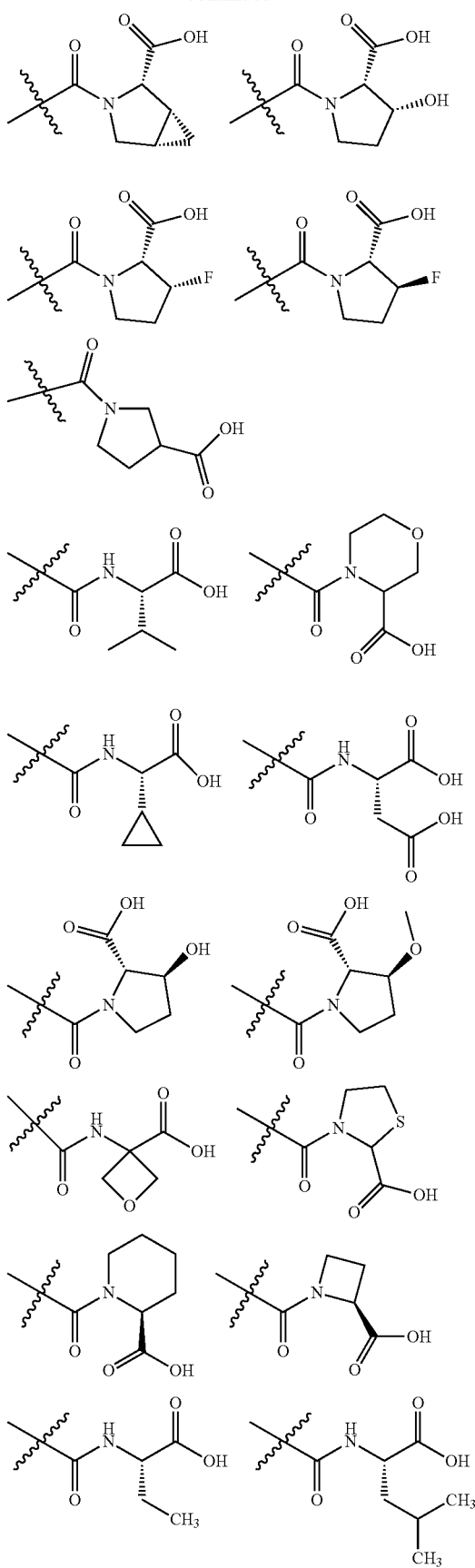

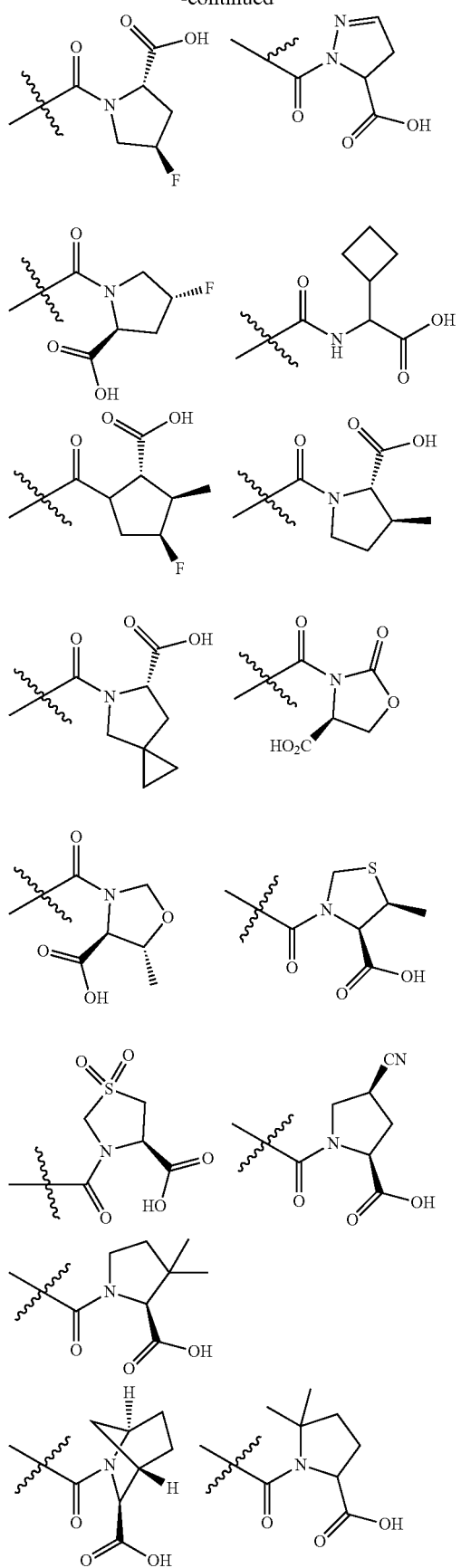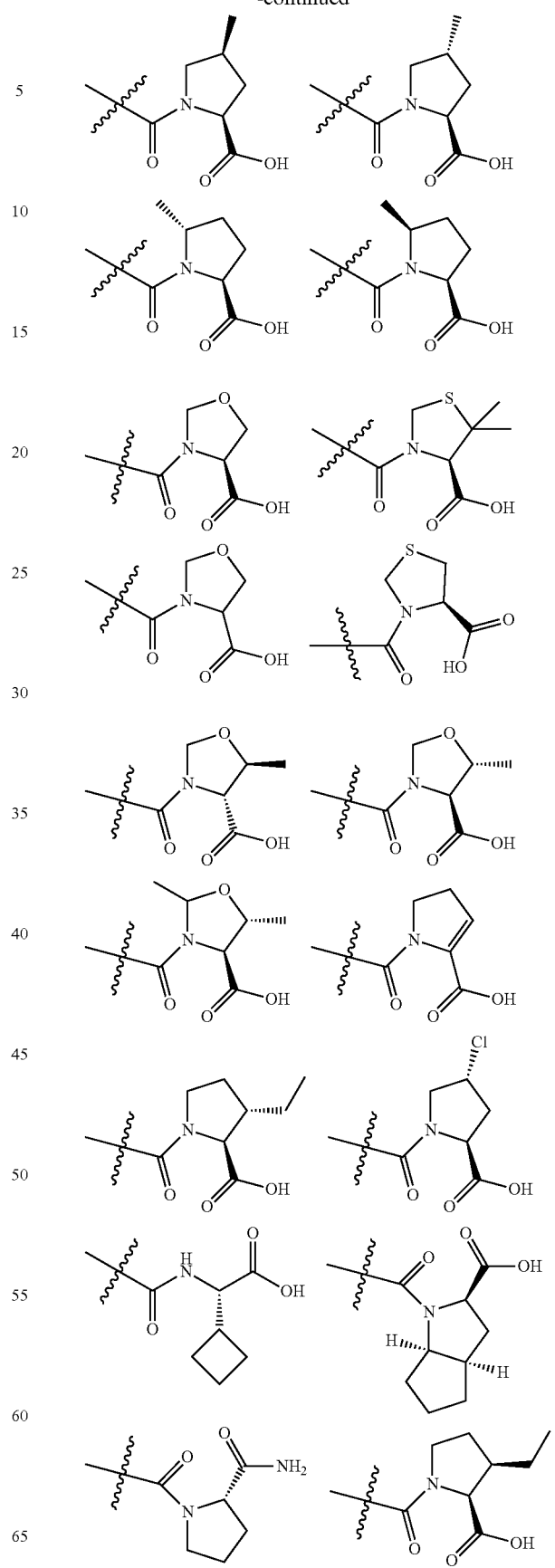

-continued

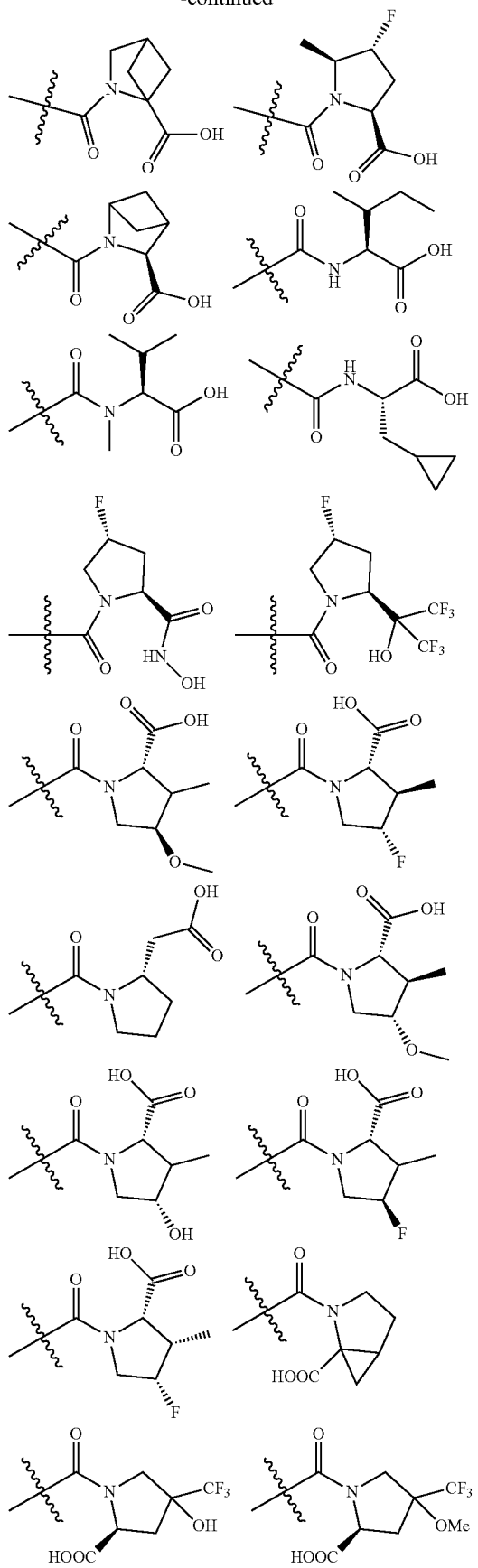
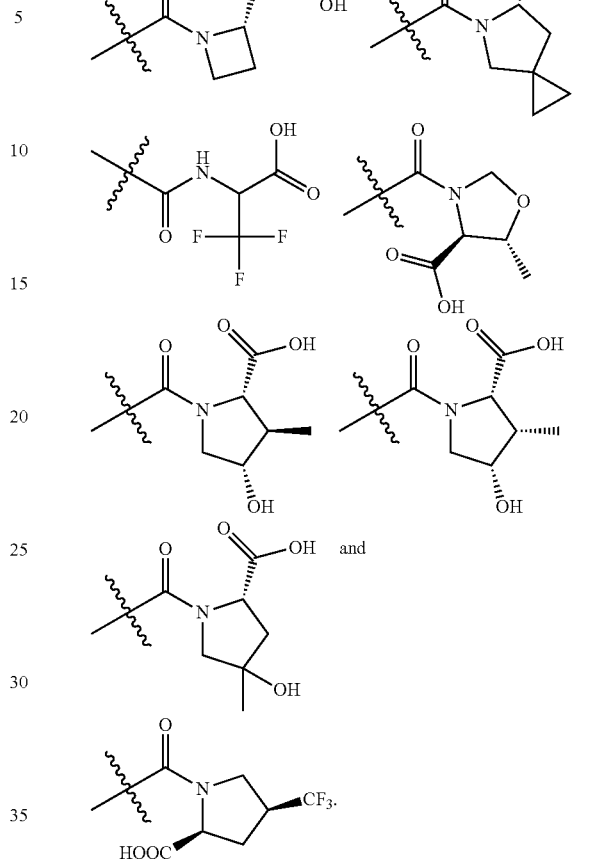

E49 A compound as described in E1 or E2, or a pharmaceutically acceptable salt thereof, wherein:

$R^o$ is hydrogen or $C_{1-6}$ alkyl;

$R^1$ and $R^2$ are each independently selected from the group consisting of hydrogen and $C_{1-8}$ alkyl;

or $R^1$ and $R^2$ are combined to form a 3- to 7-membered;

or $R^1$ and $R^4$ are combined to form a 3- to 7-membered heterocycle ring comprising 1 to 2 heteroatoms selected from N, O and S wherein said heterocycle ring is optionally substituted with 1 to 3 $R^{1A}$ substituents selected from the group consisting off and —OH; and $R^2$ is hydrogen;

$R^3$ is selected from the group consisting of hydrogen and F;

$R^4$ is selected from the group consisting of hydrogen or $C_{1-4}$ alkyl; or $R^1$ and $R^4$ are combined to form a 3- to 7-membered heterocycle ring as described above;

$R^5$ is selected from the group consisting of F, Cl, $C_{1-8}$ alkyl, and $C_{3-8}$ cycloalkyl;

L is $C_{1-6}$ alkylene;

the subscript m represents the integer 0 or 1;

$X^1$ and $X^2$ are each independently selected from the group consisting of absent and —O—, and wherein if the subscript m is 0 then one of $X^1$ or $X^2$ is absent;

the ring "A" in is selected from the group consisting of:

(i) $C_{2-11}$ heterocycle comprising a nitrogen atom and further optionally comprising 1-2 heteroatoms selected from N, O and S; wherein $R^{AA}$ is independently selected from the group consisting of $C_{1-8}$ alkyl, $C_{1-8}$ haloalkyl, $C_{1-8}$ heteroalkyl, F, Cl, Br and I;

n is an integer from 0 to 5;

$R^A$ is selected from the group consisting of $(C_{6-10}$ aryl$)_{1-2}$-$(X^{RA})$—, and (5- to 10-membered heteroaryl$)_{1-2}$-$(X^{RA})$—, wherein said $C_{6-10}$ aryl, 5- to 10 membered heteroaryl $R^A$ is independently optionally substituted with from 1 to 5 $R^{RA}$ substituents selected from the group consisting of F, Cl, $C_{1-4}$ haloalkyl, $C_{1-4}$ alkoxy and phenyl, wherein the $R^{RA}$ substituent is optionally substituted with 1 to 5 $R^{RAi}$ substituents selected from F and Cl; $X^{RA}$ is selected from the group consisting of absent, —O—, —S—, —N(H)—, —N($C_{1-4}$ alkyl)-, —S(O)$_2$—, —C(=O)—, $C_{1-4}$ alkylene; and q is an integer from 0 to 1;

(ii) $C_{3-12}$ membered carbocycle; wherein $R^A$ is selected from the group consisting of $C_{1-8}$ alkyl, $C_{1-8}$ haloalkyl, F, and —CN;

n is the integer 0; and q is the integer 0 to 6;

(iii) phenyl substituted at the 2-position, the 3,4-positions, the 2,4-positions, or the 3,5-positions with groups independently selected from $R^A$, wherein each $R^A$ is selected from the group consisting of Cl, —OR$^{A1}$, 5- to 10 membered heteroaryl and phenyl; $R^{A1}$ is $C_{1-8}$ haloalkyl; wherein each $R^A$ substituent is optionally substituted with from 1 to 5 $R^{RA}$ substituents selected from, —NH$_2$, and $C_{2-7}$ heterocyclyl that is optionally substituted with one or more $C_{1-4}$ alkoxycarbonyl;

and (v) 5- to 10-membered heteroaryl comprising 1- to 3-nitrogen atoms and optionally further comprising 1- to 2-heteroatoms selected from O and S; wherein (v)

$R^A$ is selected from the group consisting of Cl, —OR$^{A1}$, and $C_{3-6}$ cycloalkyl; wherein $R^{A1}$ is $C_{1-8}$ haloalkyl;

n is the integer 0; and q is an integer from 0 to 4.

E50. A compound as described in any one of E1, E3-E17, and E20-E49 wherein D is absent.

E51. A compound as described in any one of E1, E3-E17, and E20-E49 wherein D is —CH$_2$—.

E52. A compound as described in any one of claims E1, E3-E17, and E20-E51 wherein E is tetrazolyl.

E53. A compound as described in any one of E1, E3-E17, and E20-E51 wherein E is —C(=O)OR$^o$.

E54. A compound as described in any one of E1, E3-E17, and E20-E51 wherein E is —C(=O)NR$^{oa}$R$^{ob}$.

E55. A compound as described in E54 wherein R$^{oa}$ is hydrogen and R$^{ob}$ is hydrogen or hydroxyl.

E56. A compound as described in any one of wherein D is absent and E is —C(=O)OR$^o$.

E57 A compound selected from the group consisting of

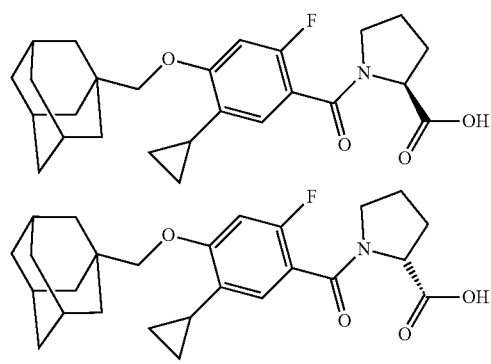

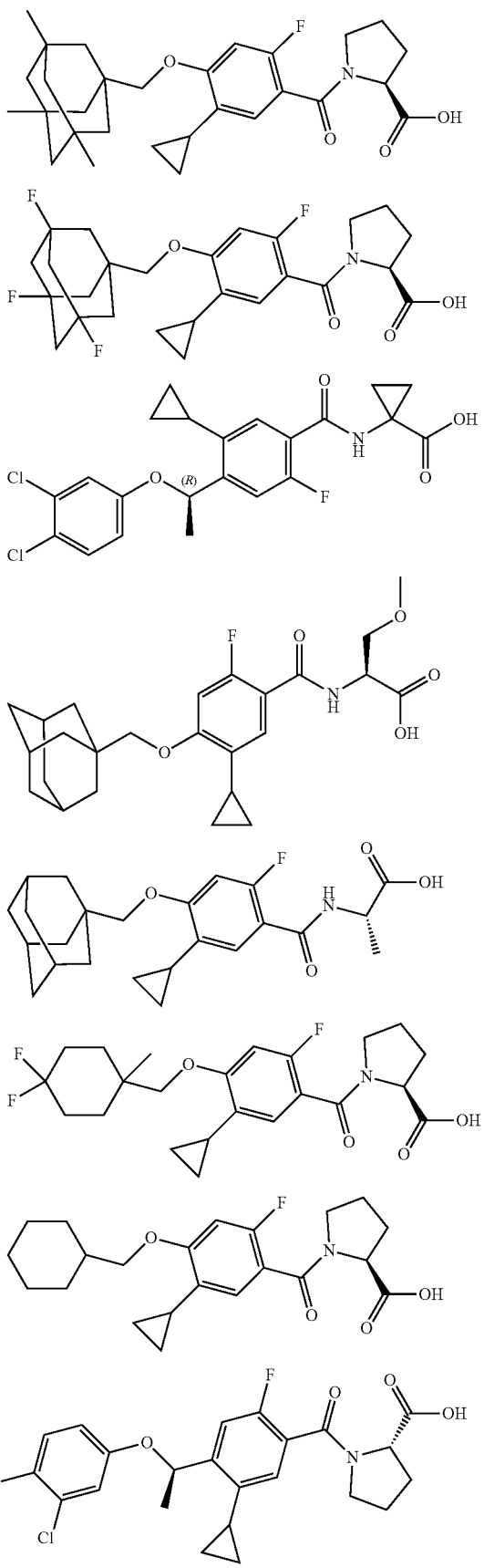

39
-continued
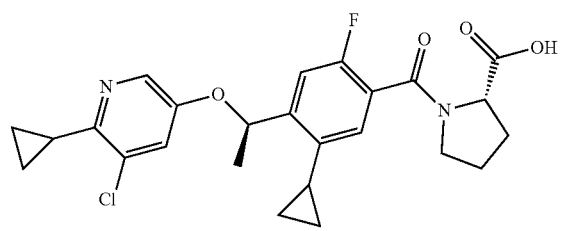
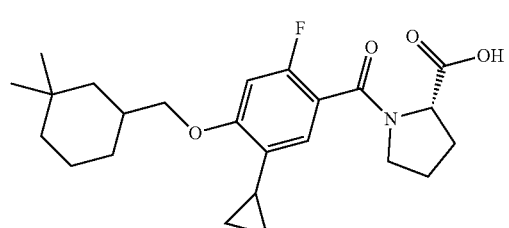
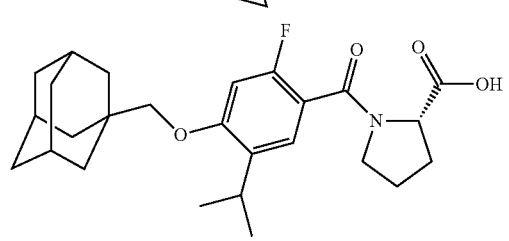
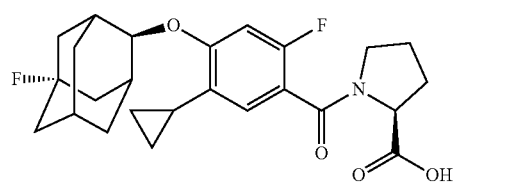
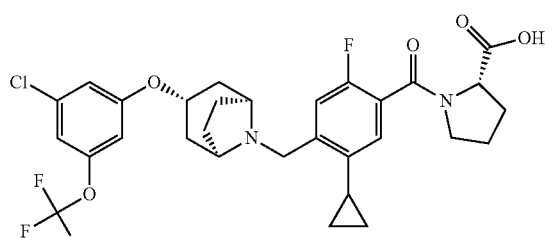
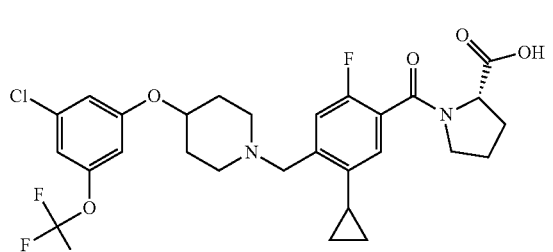
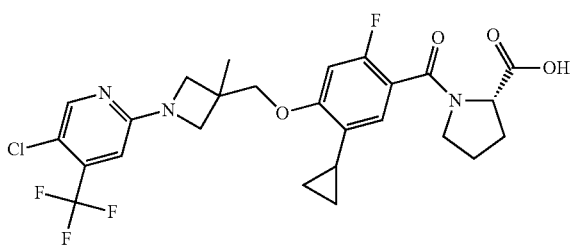
40
-continued
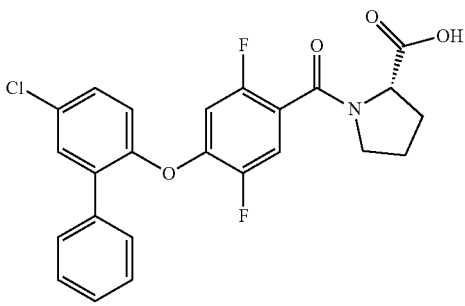
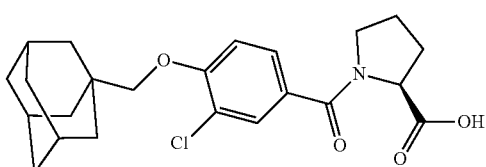
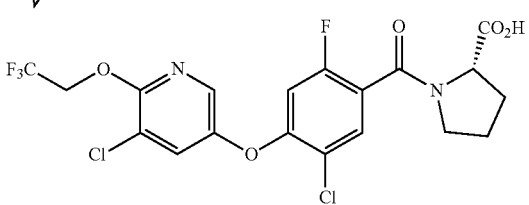
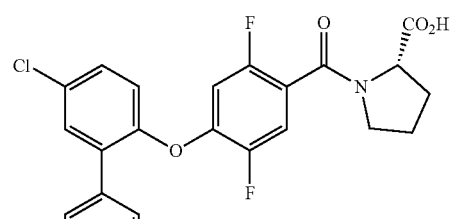
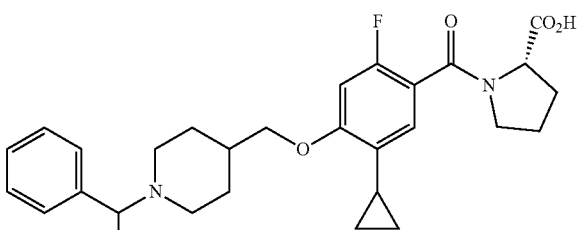
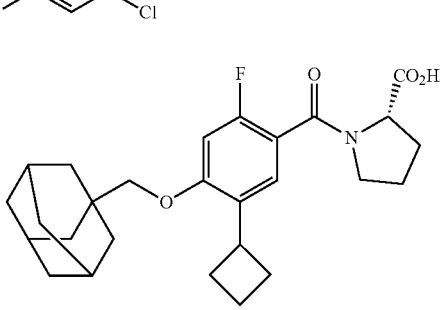

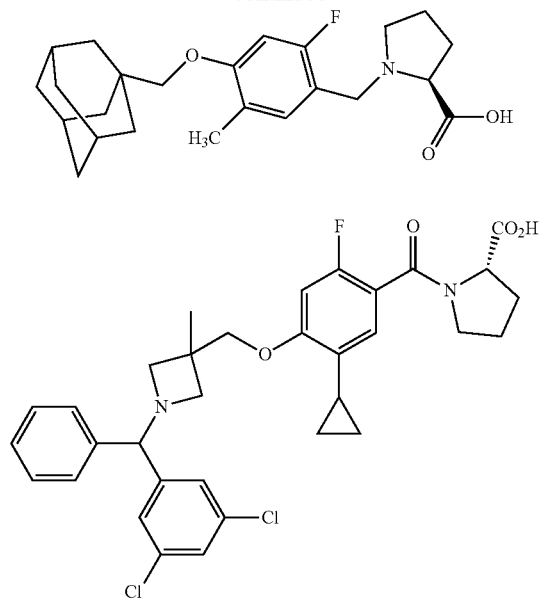
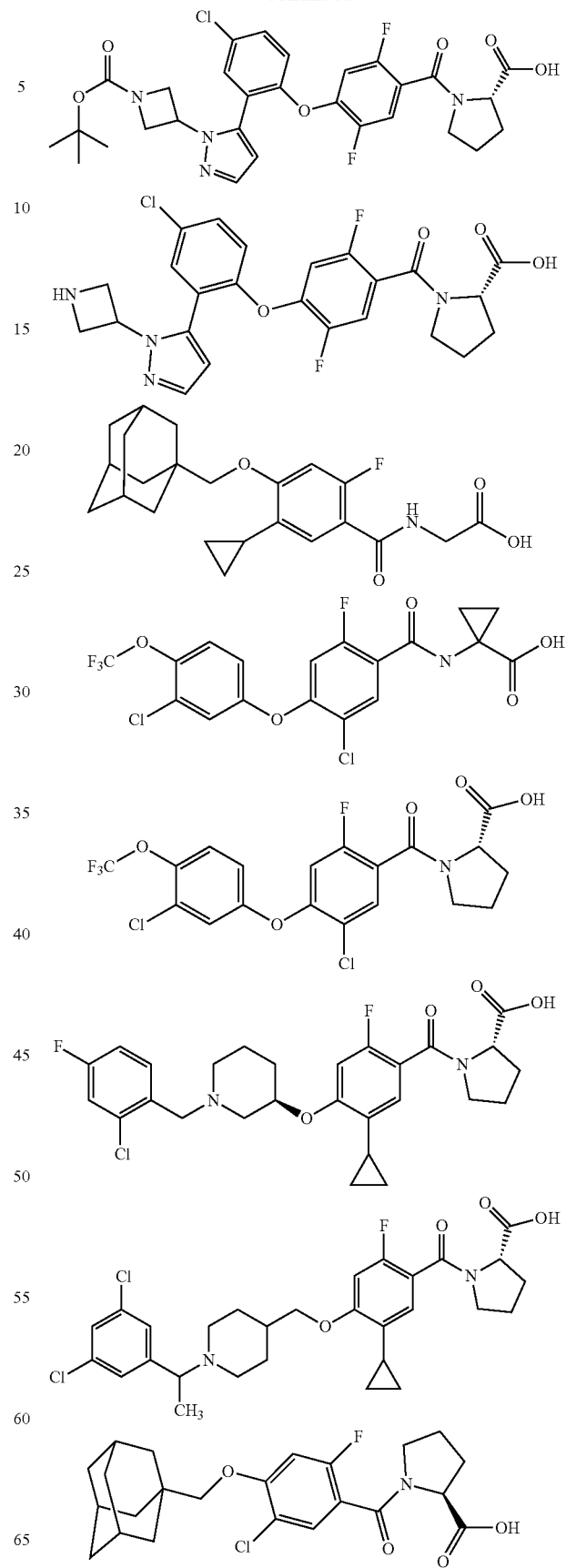

-continued
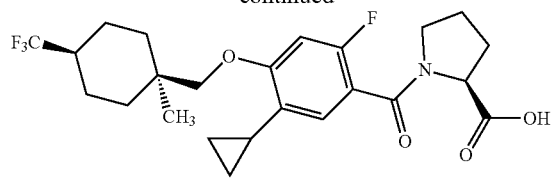
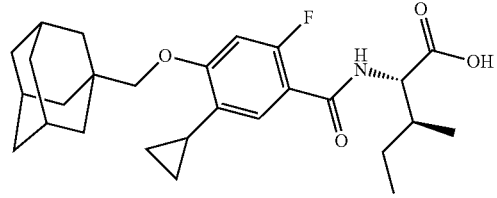
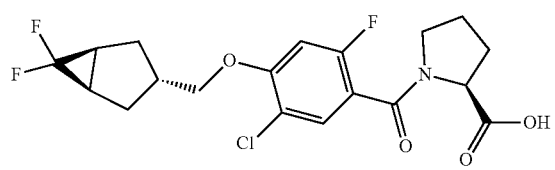
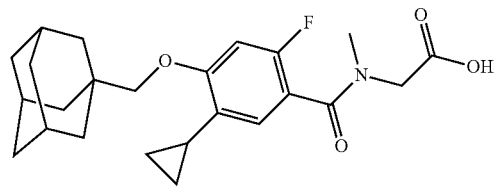
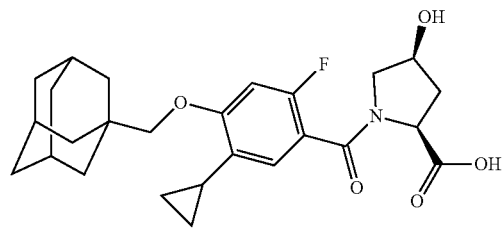
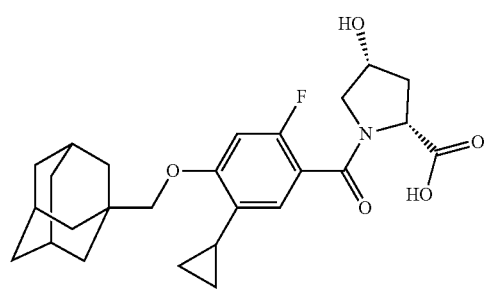
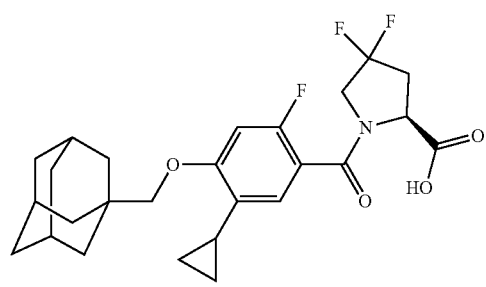
-continued
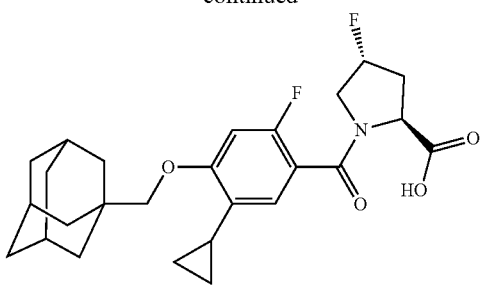
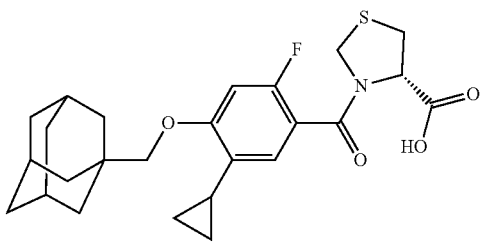
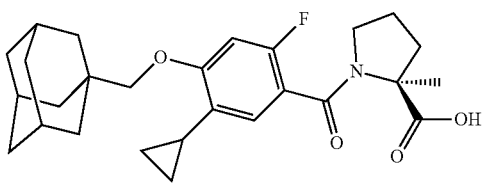
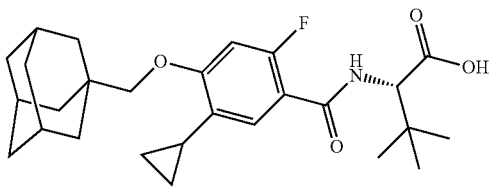
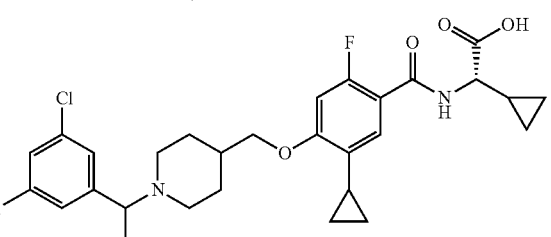
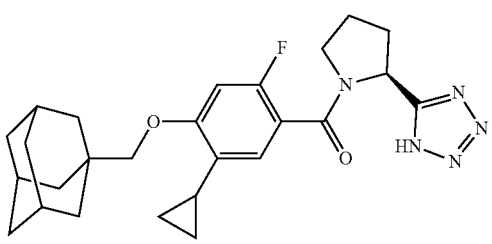
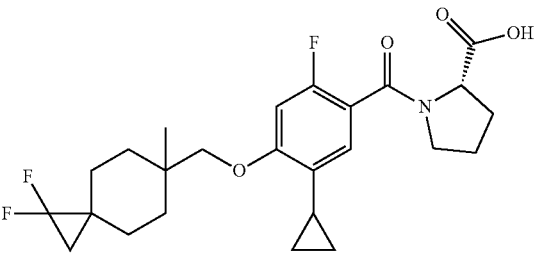

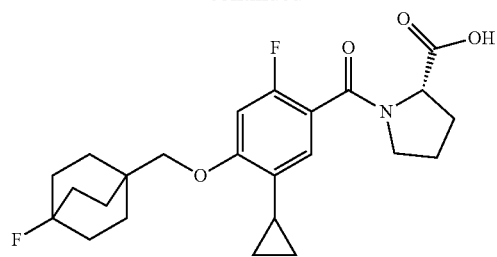
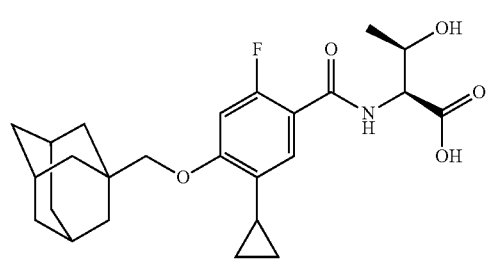
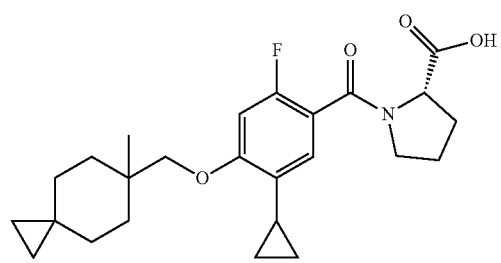
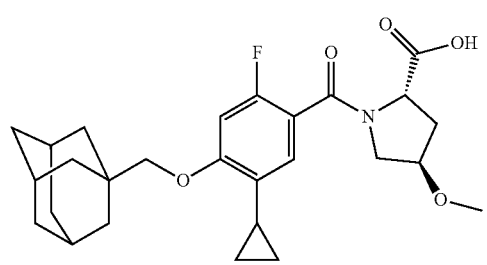
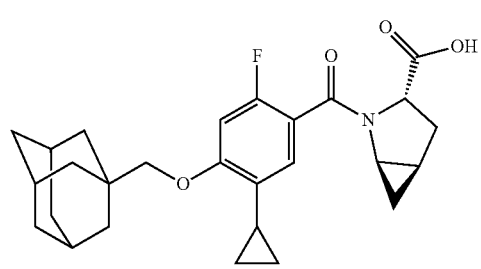
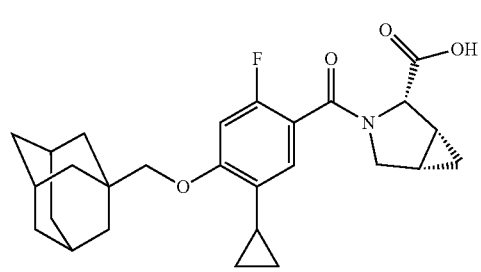
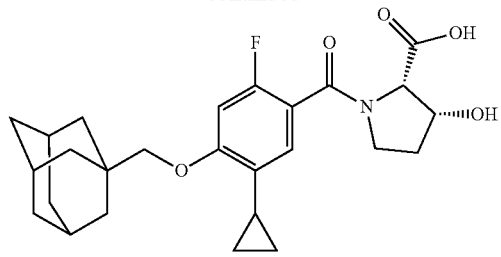
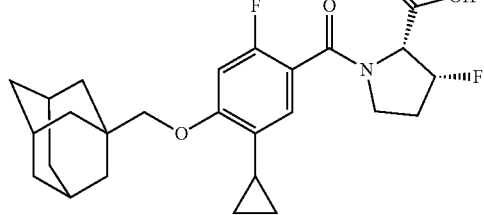
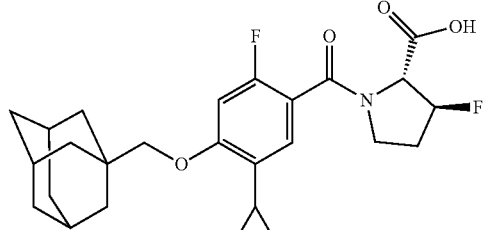
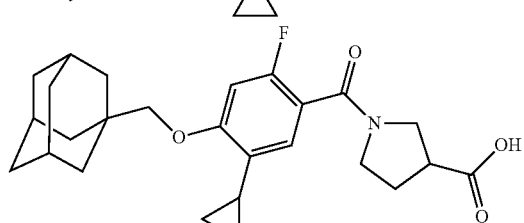
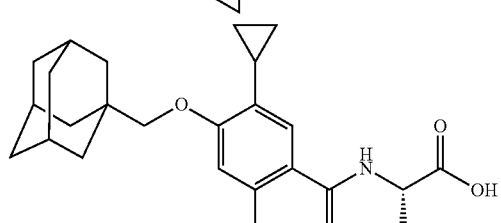

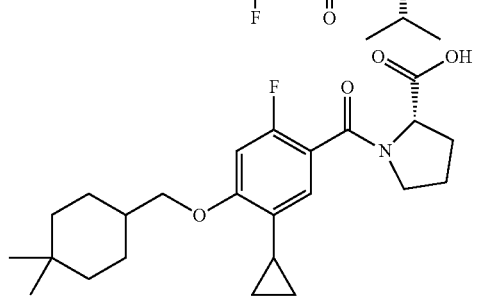

47
-continued
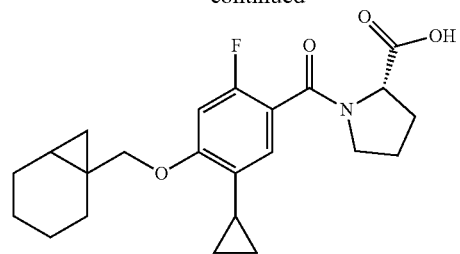
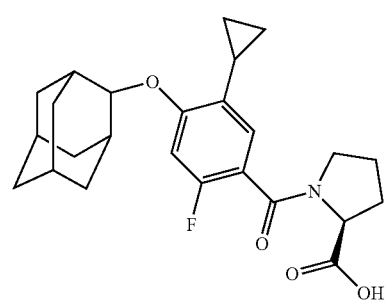
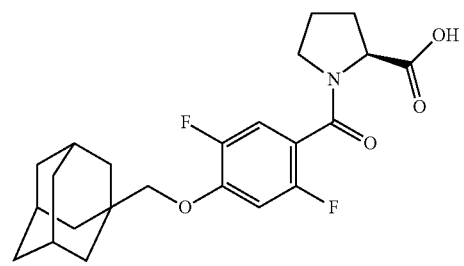
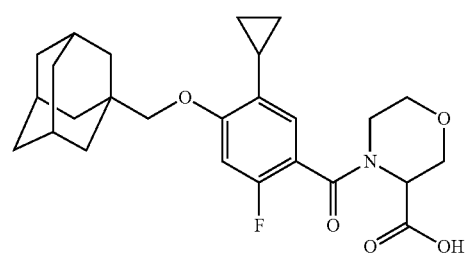
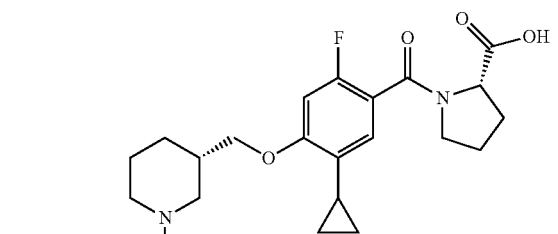
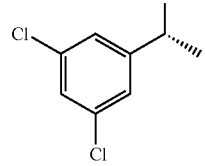
48
-continued
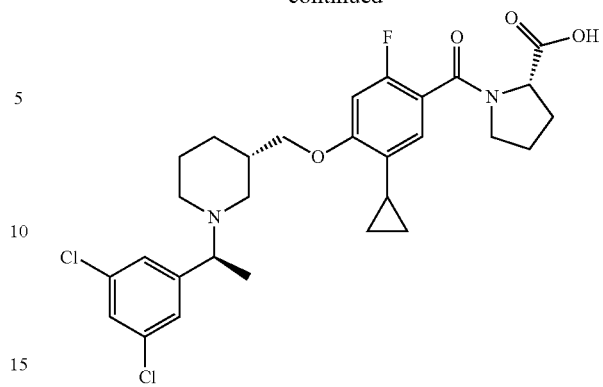
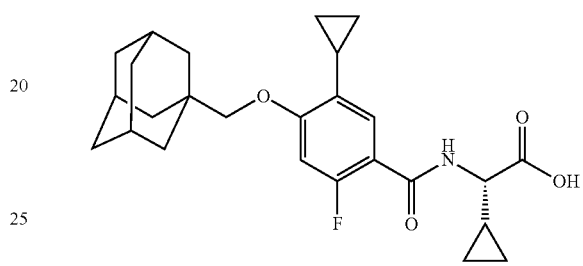
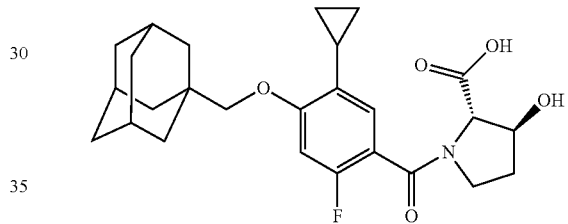
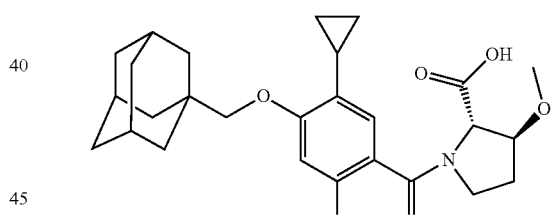
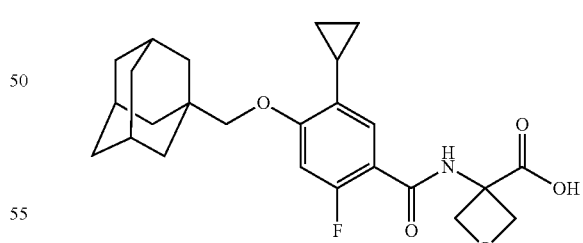
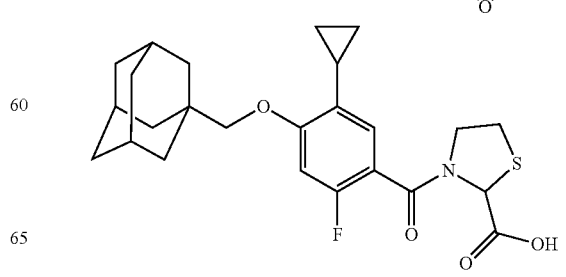

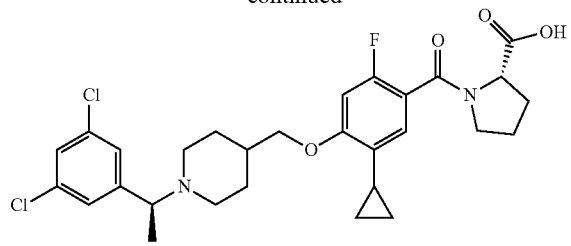
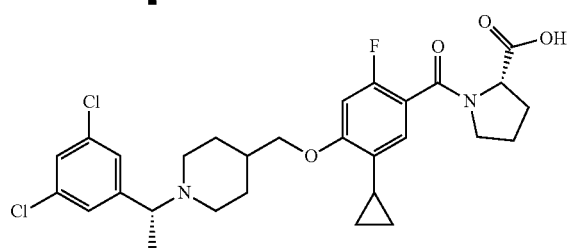
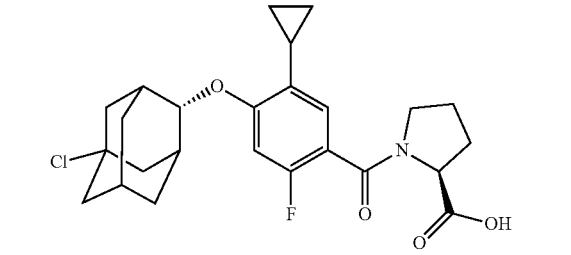
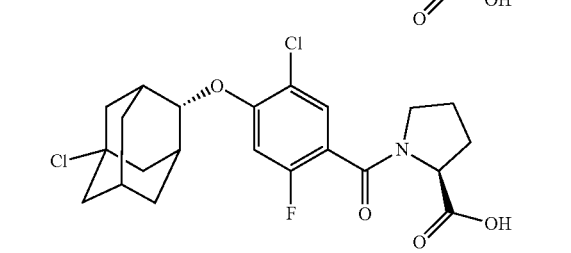
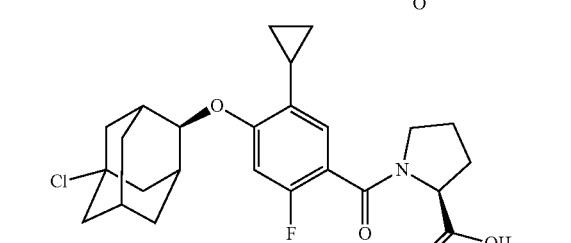
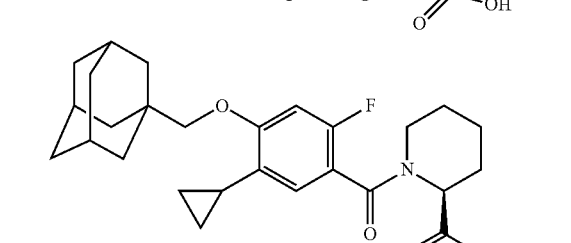
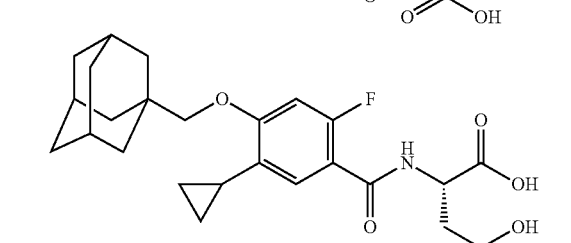

-continued
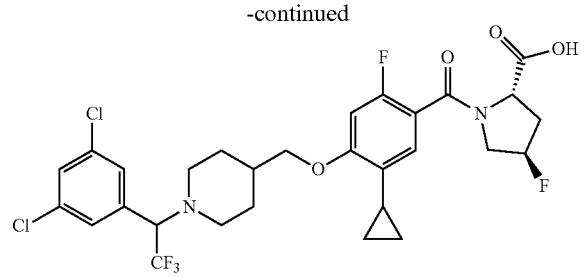
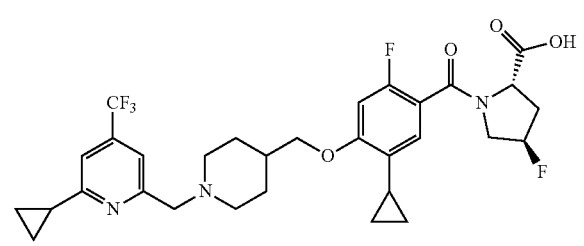
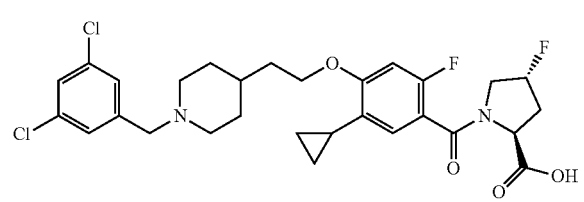
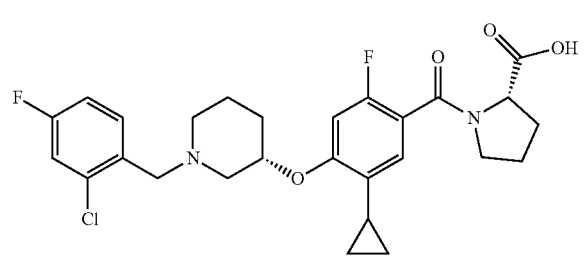
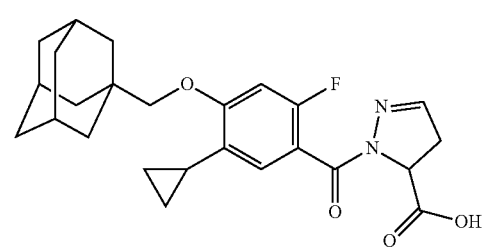
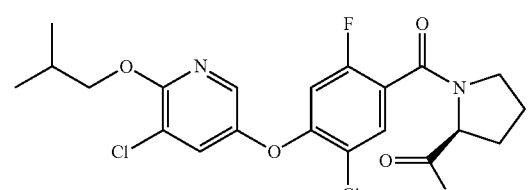
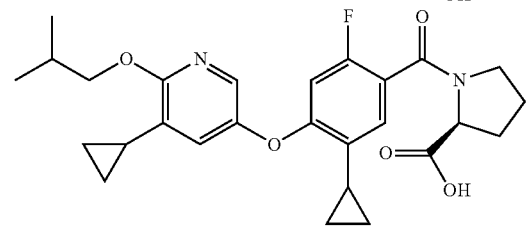
-continued
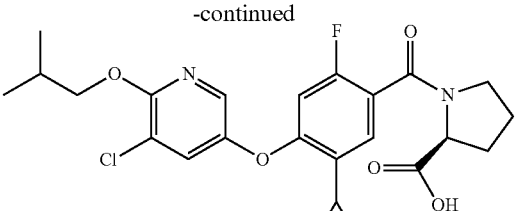
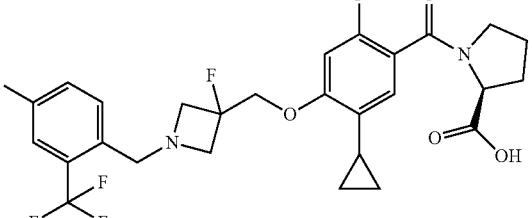
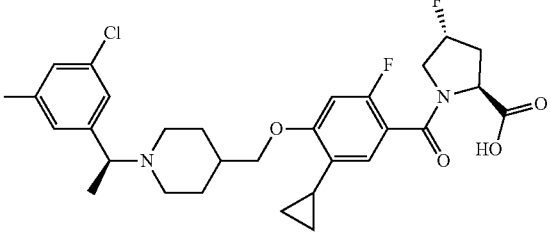
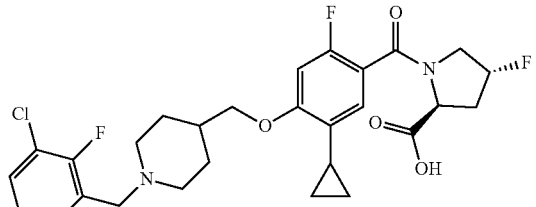
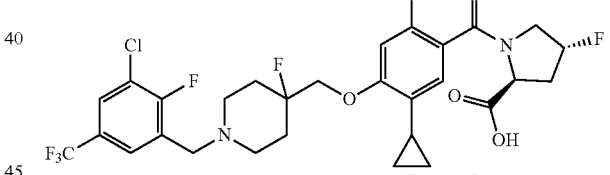
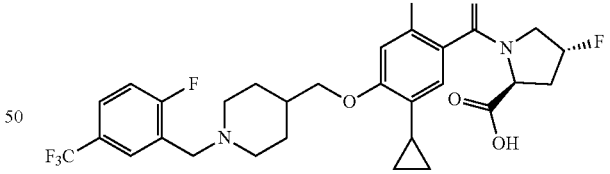
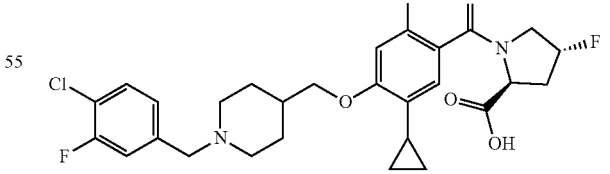
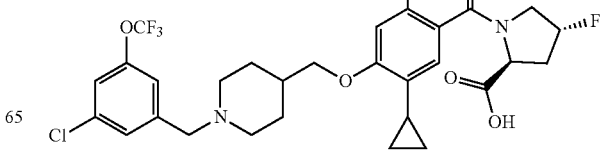

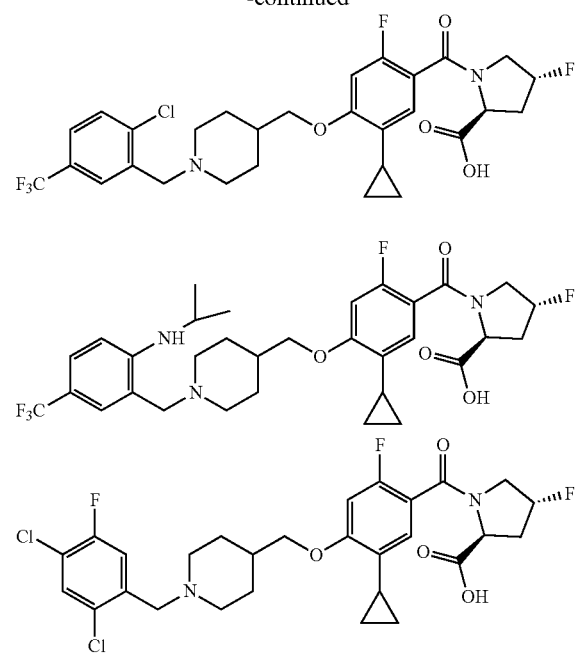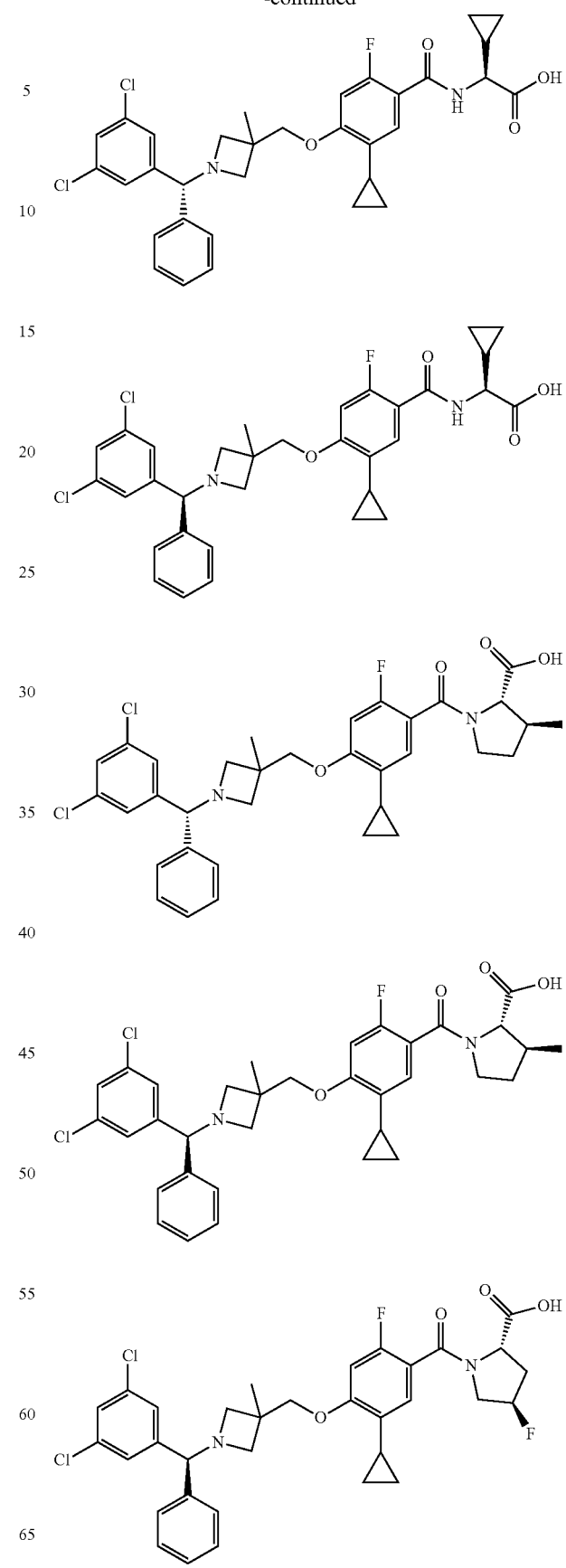

55
-continued
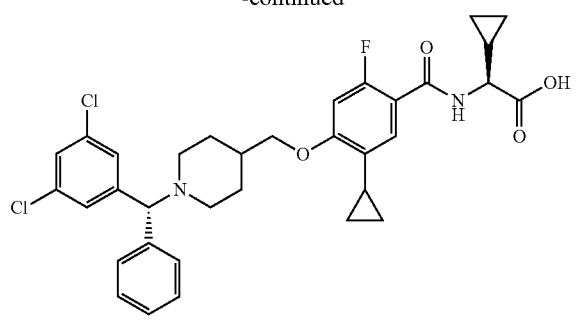
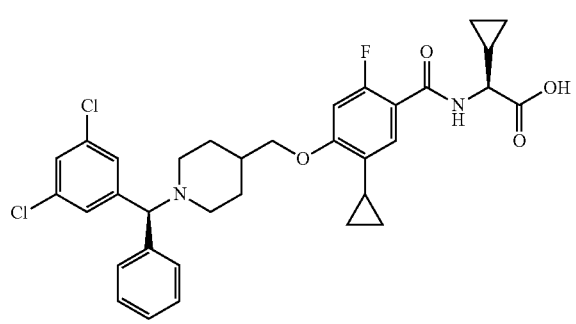
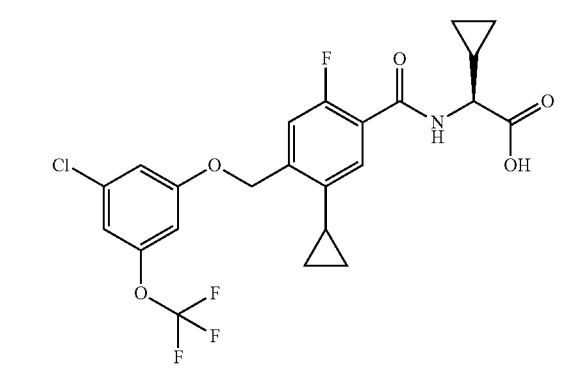
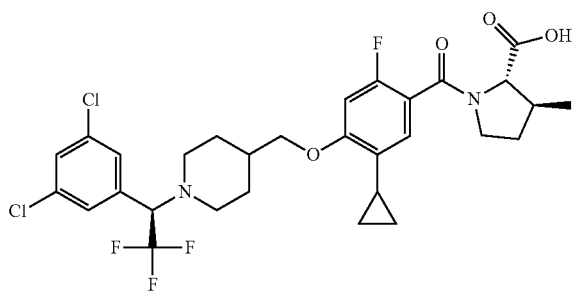 [SMILES: C[C@H]1CCN(C(=O)c2cc(C3CC3)c(OCC3CCN([C@H](c4cc(Cl)cc(Cl)c4)C(F)(F)F)CC3)cc2F)[C@@H]1C(=O)O]
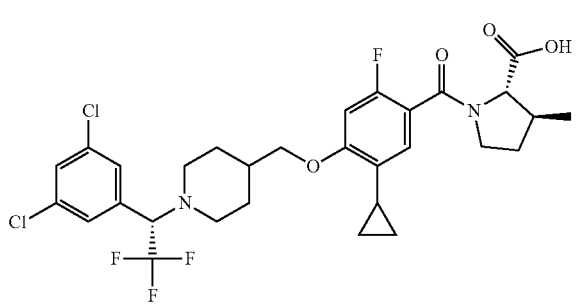
56
-continued
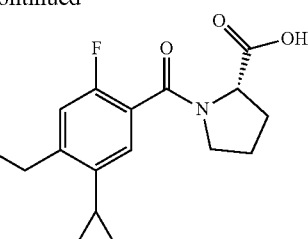
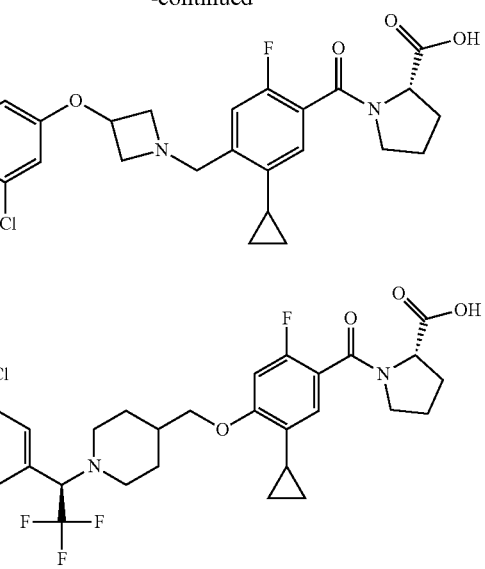
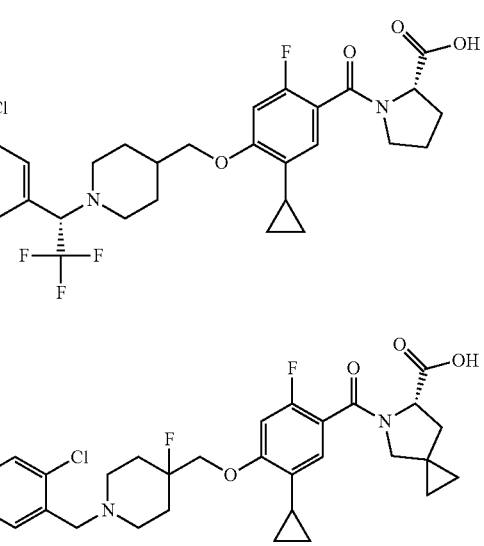
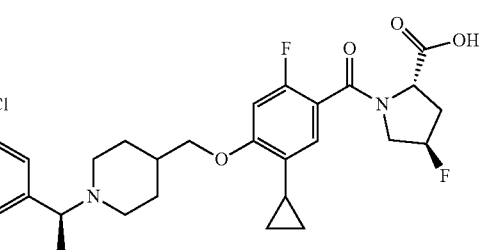
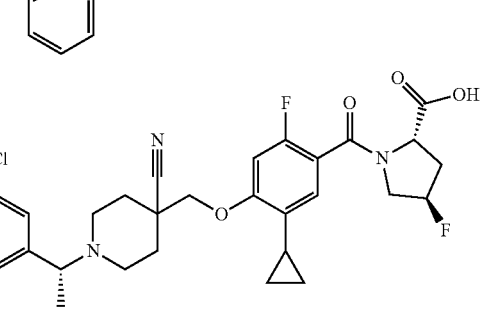

-continued
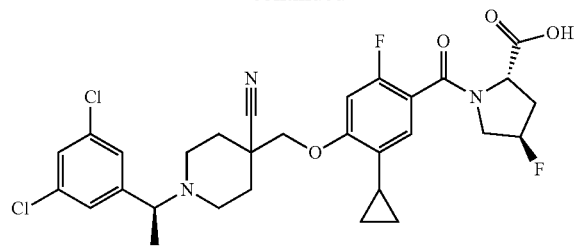
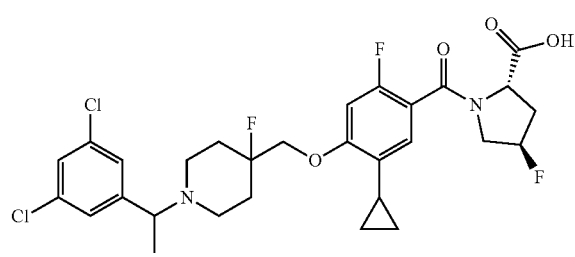
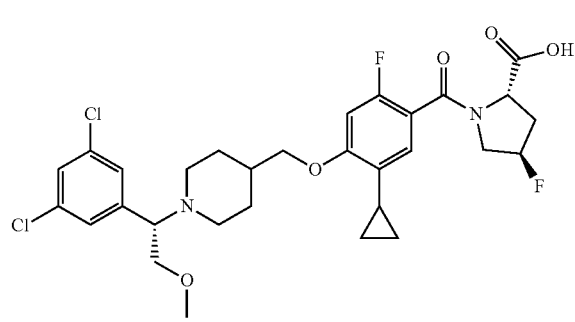
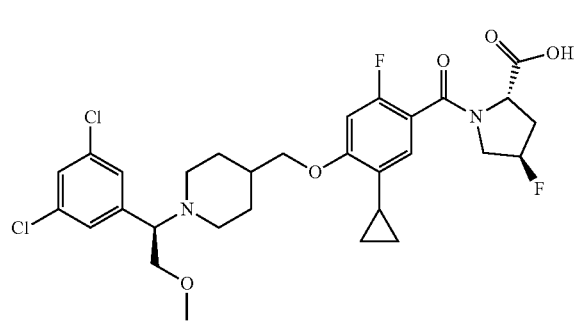
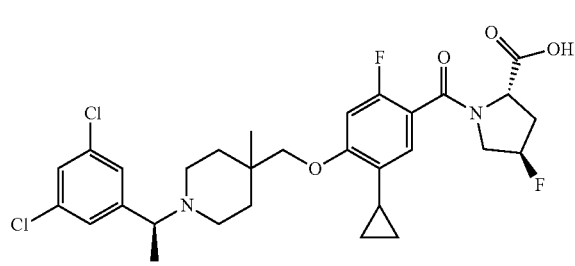
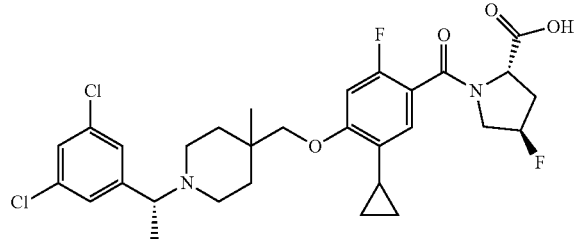
-continued
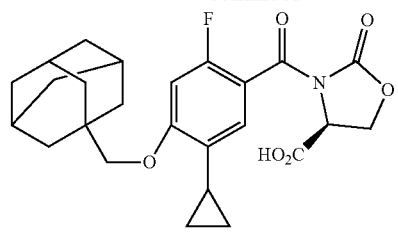
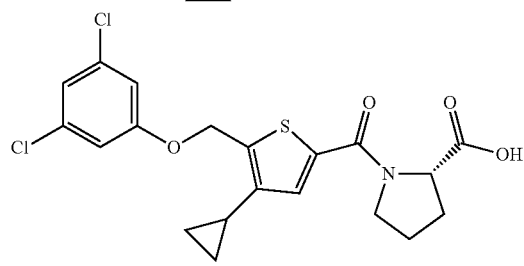
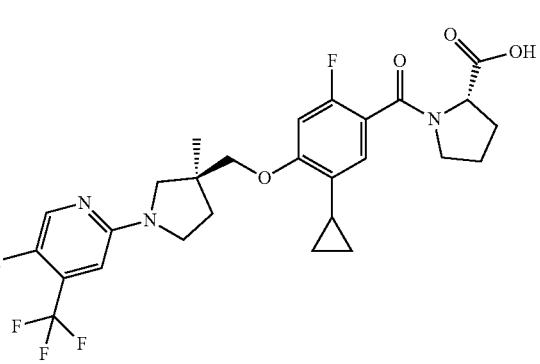
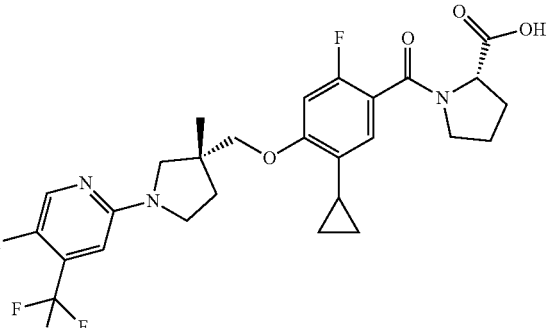
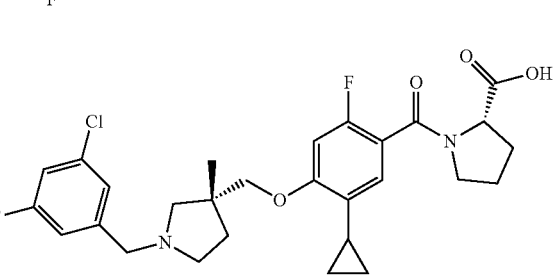
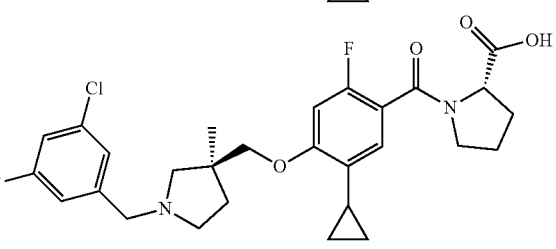

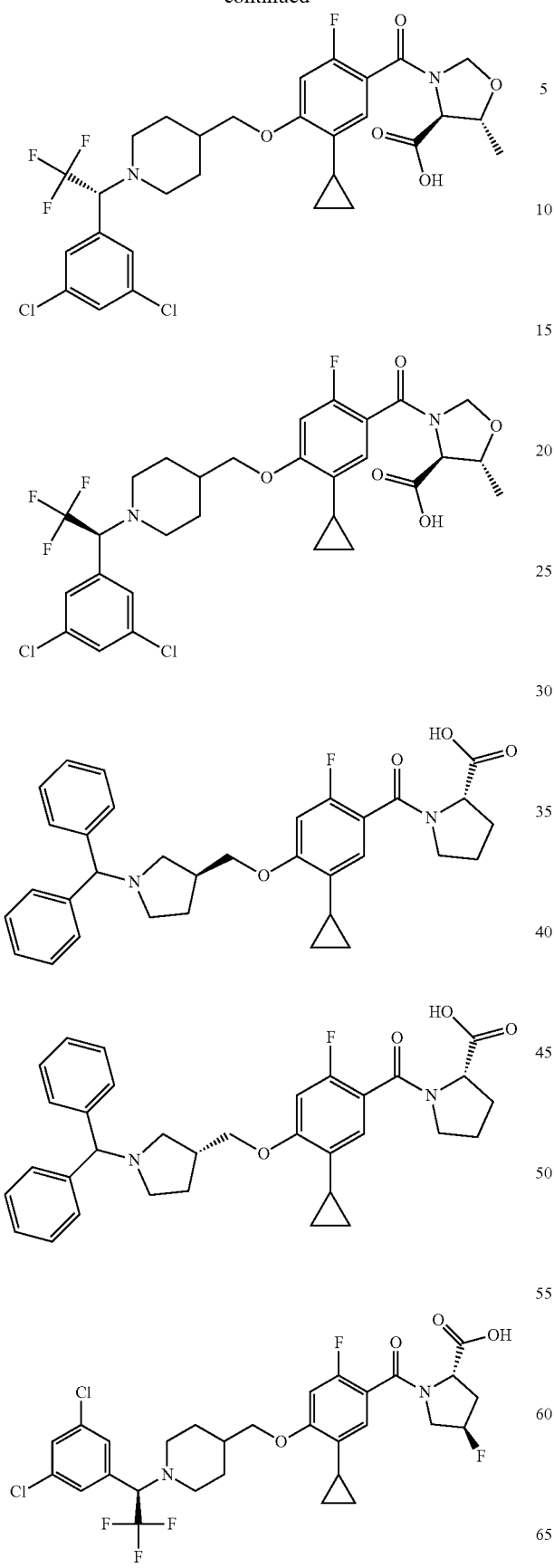
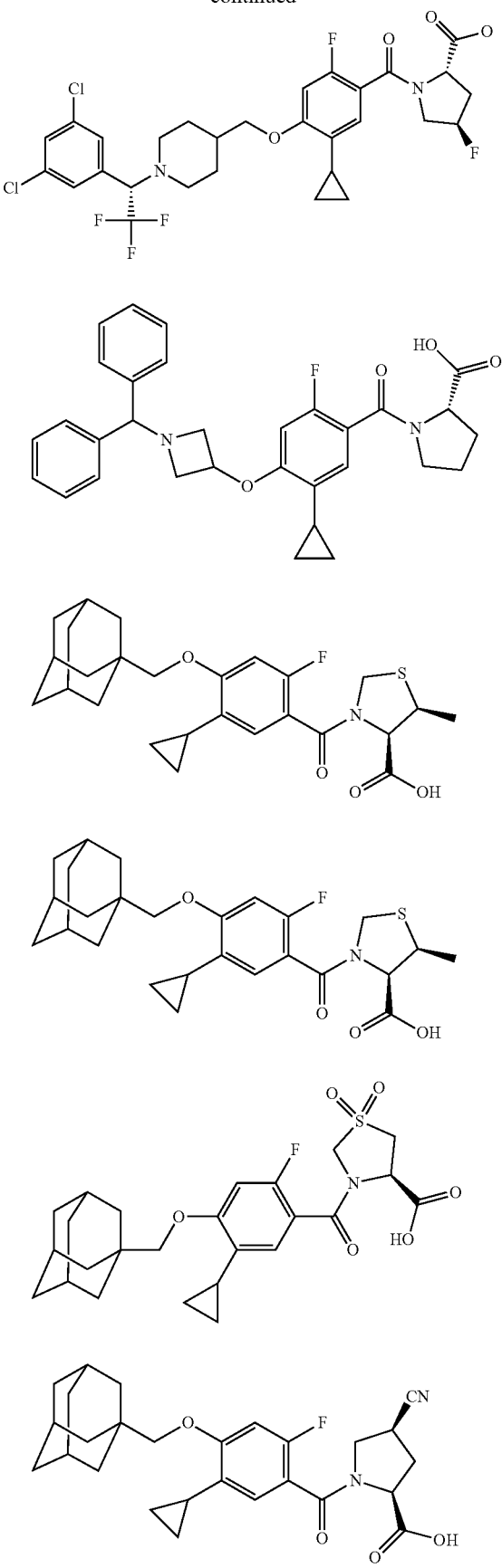

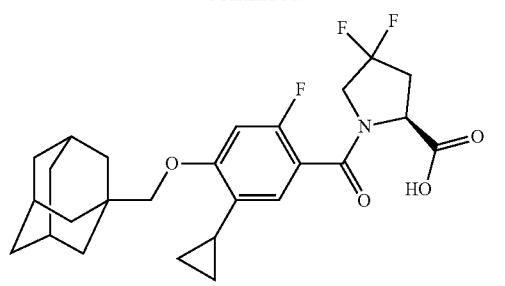
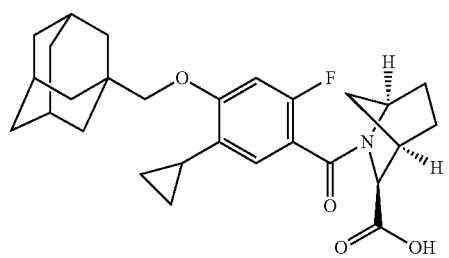
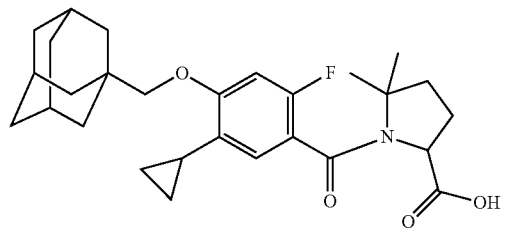
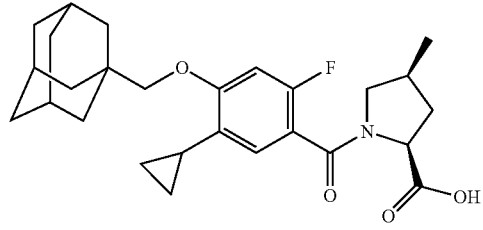
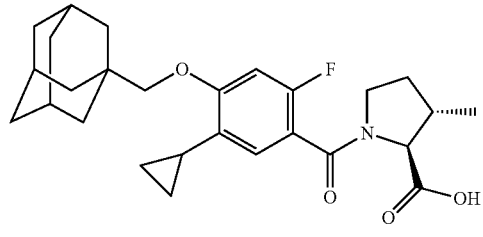
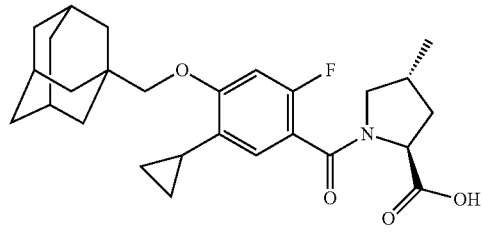
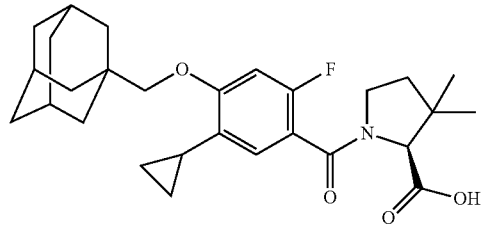
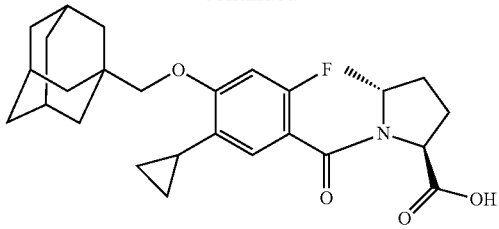
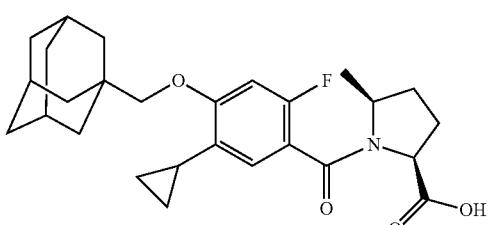
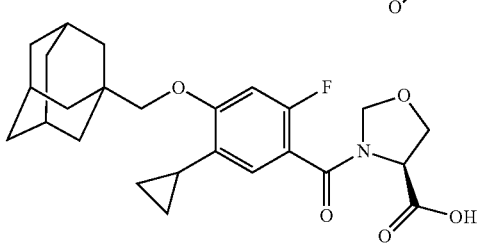
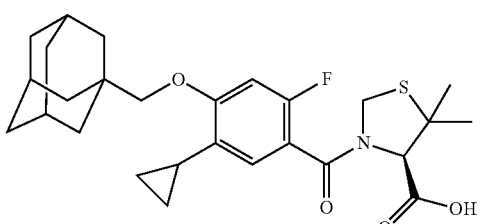
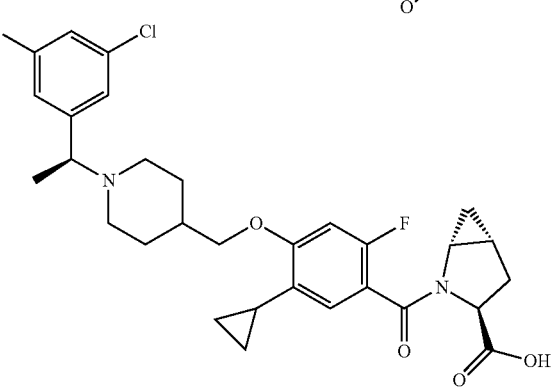
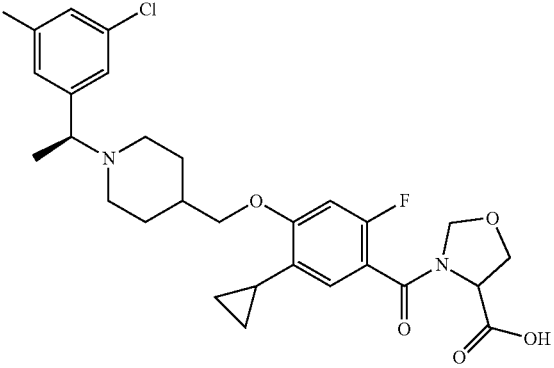

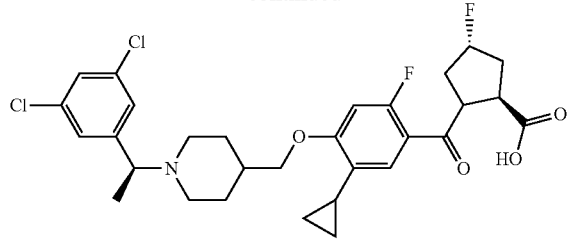
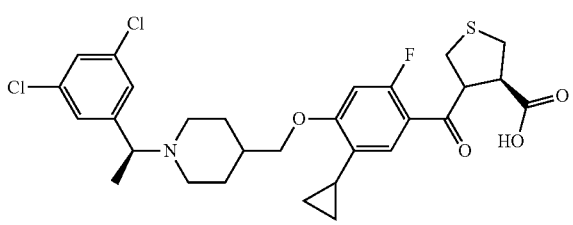
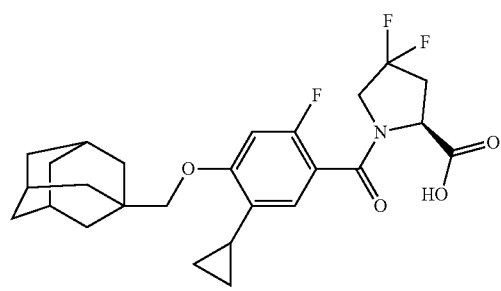
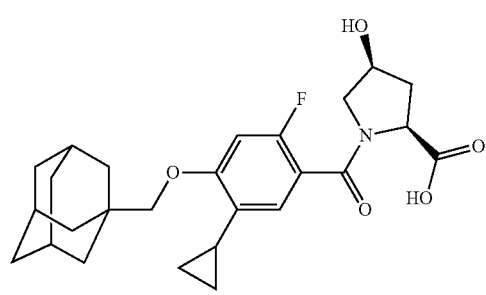
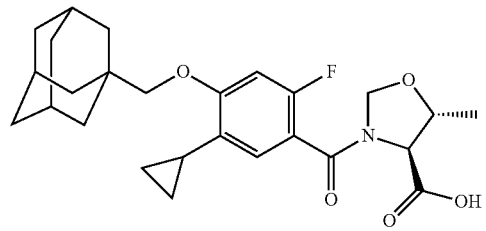
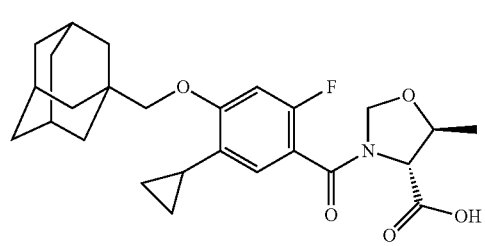
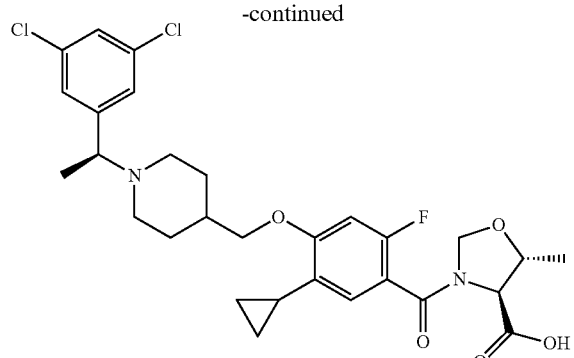
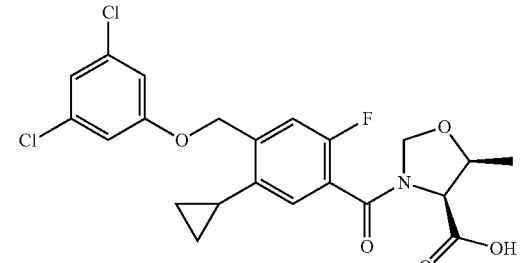
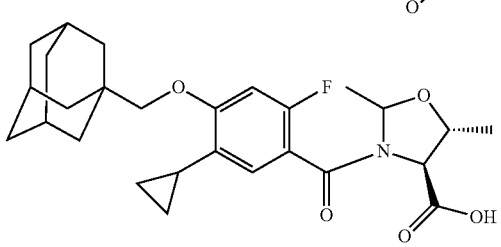
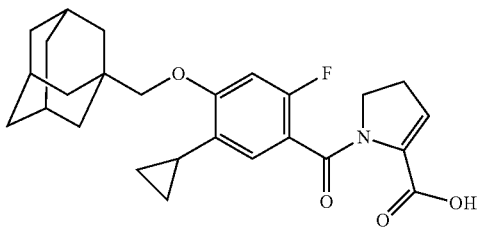
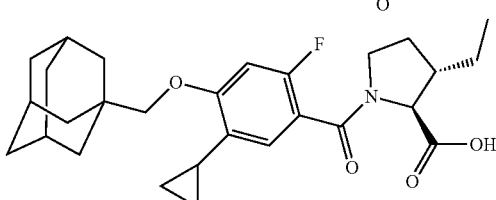
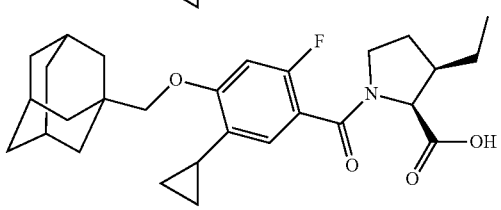
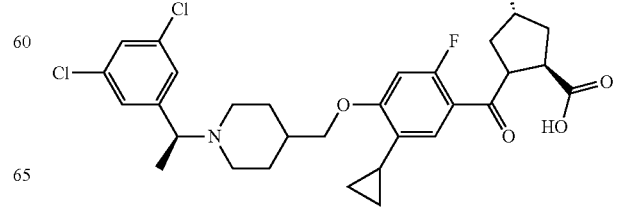

US 10,526,285 B2
65
-continued
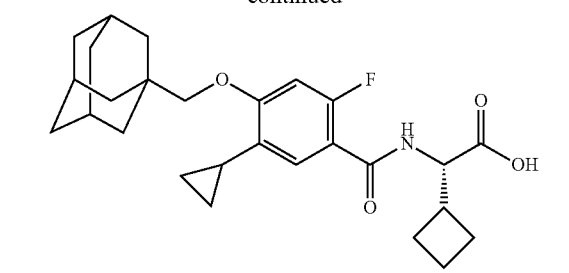
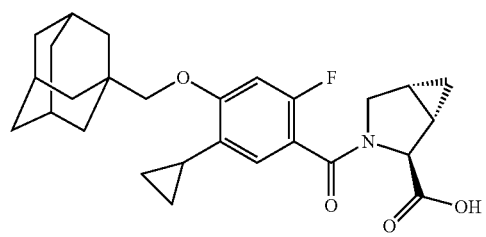
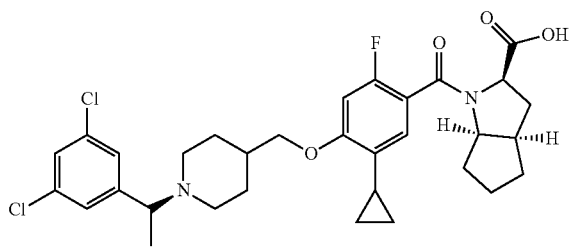
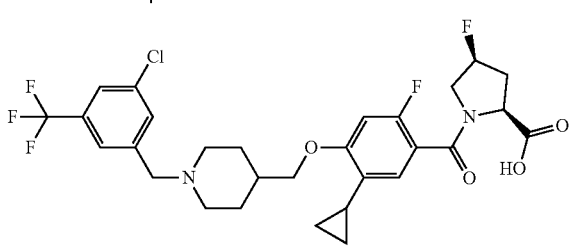
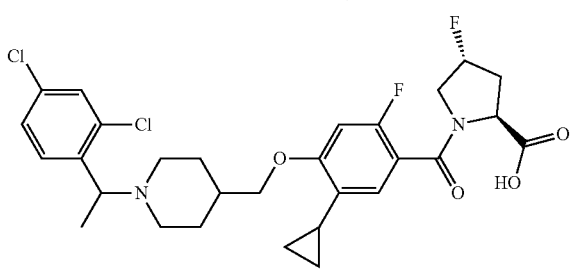
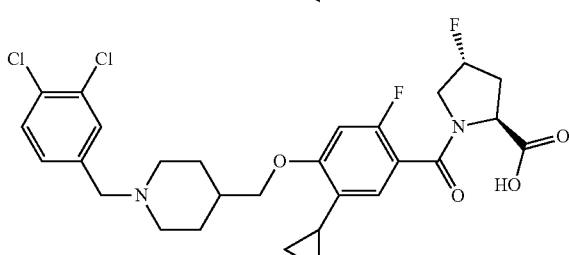
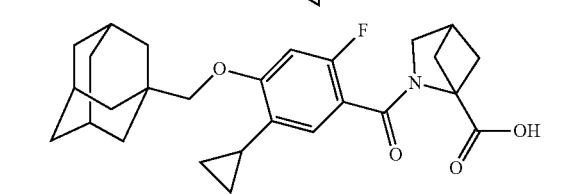
66
-continued
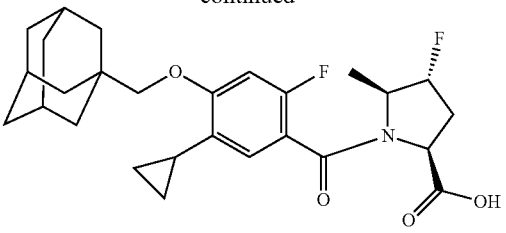
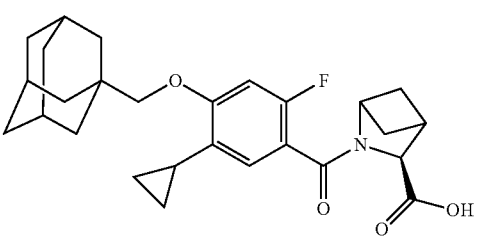
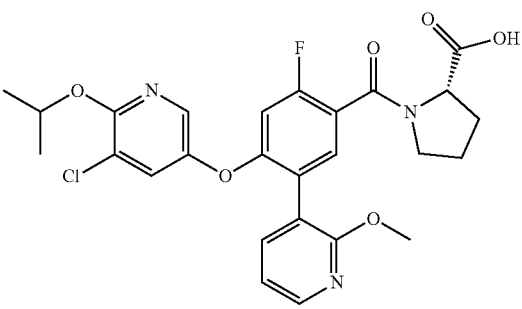
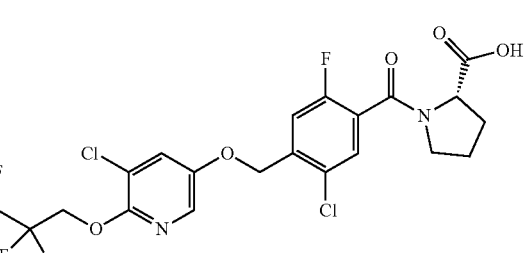
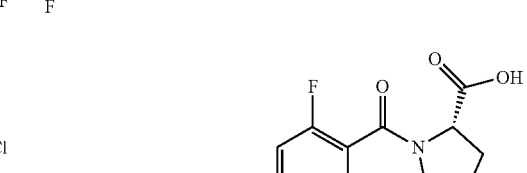
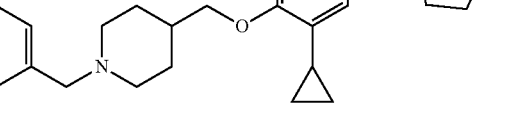
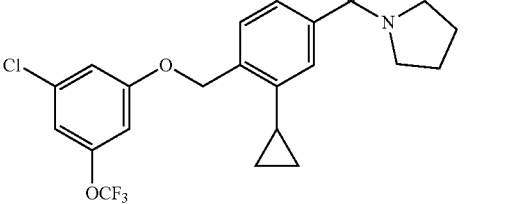

-continued
67
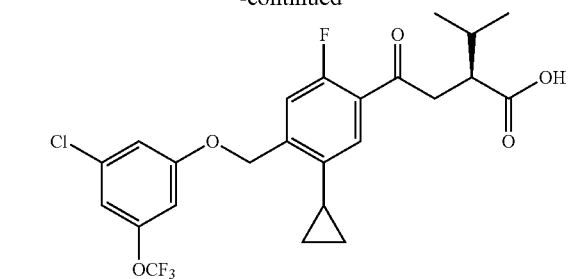
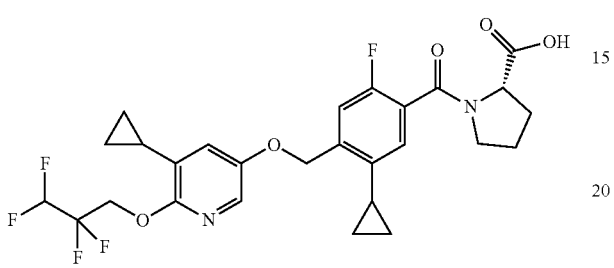
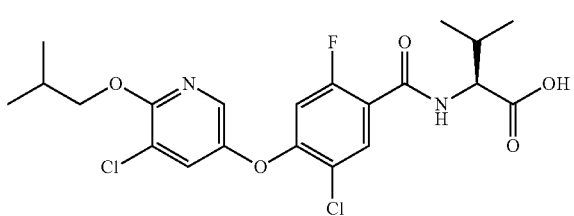
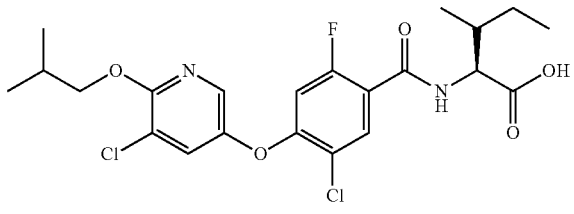
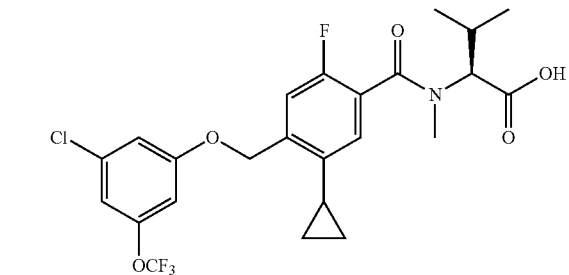
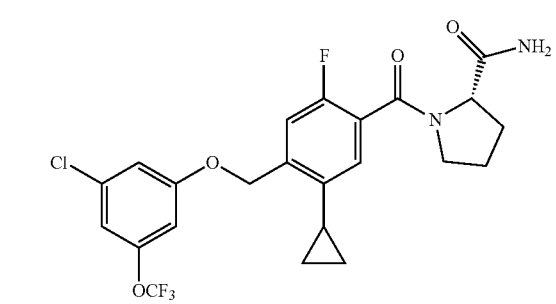
-continued
68
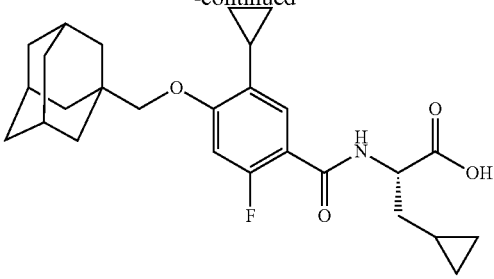
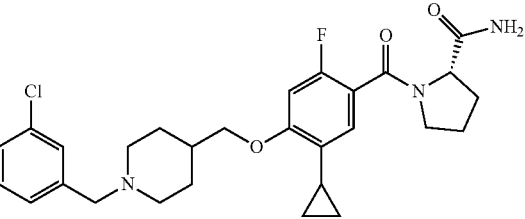
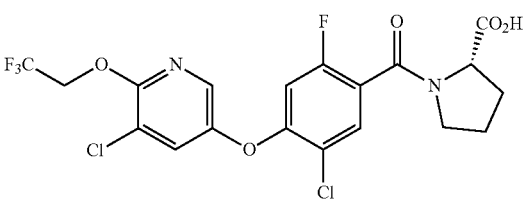
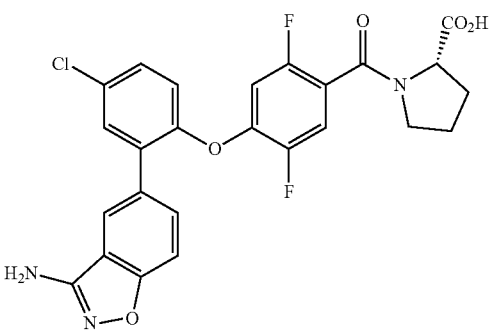
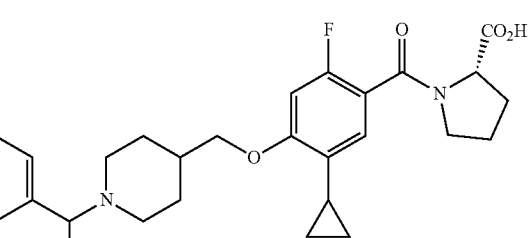
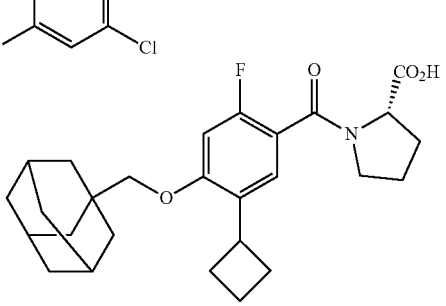

69
-continued
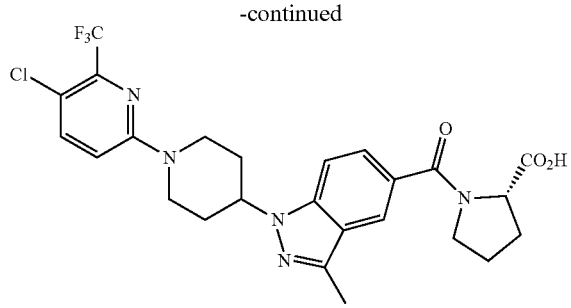
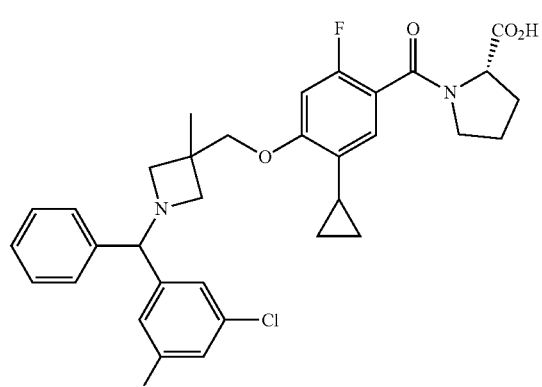
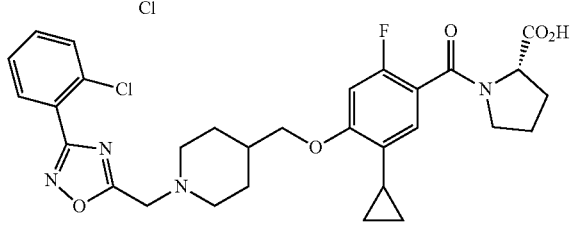
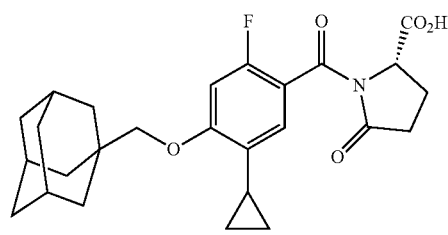
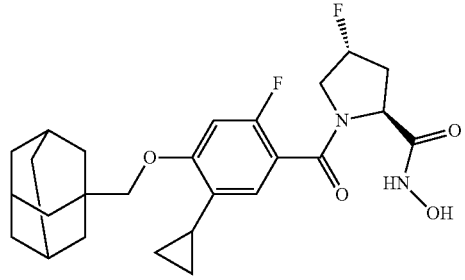
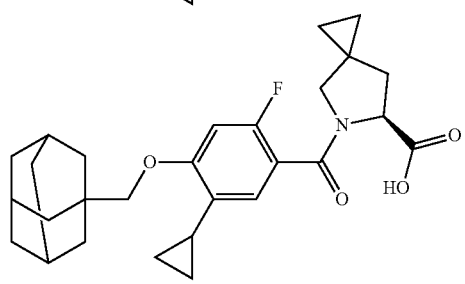
70
-continued
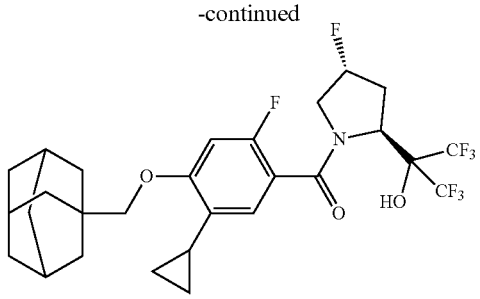
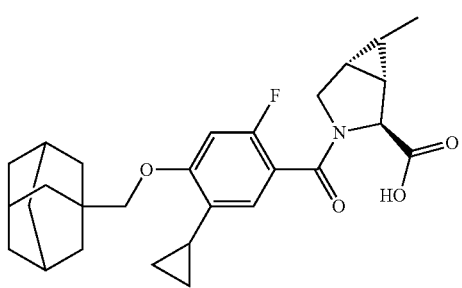
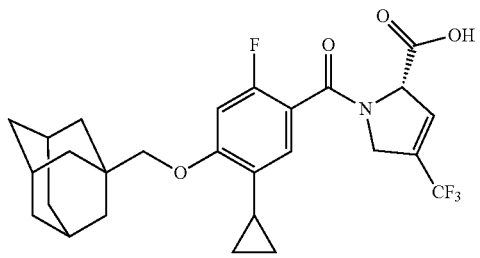
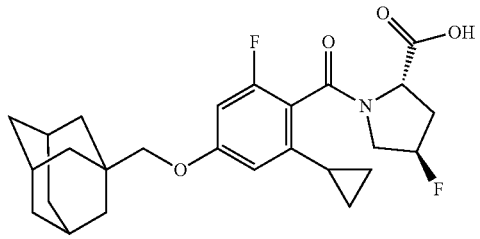
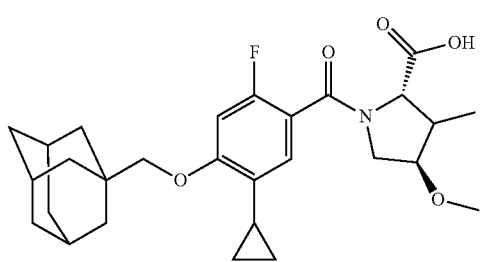
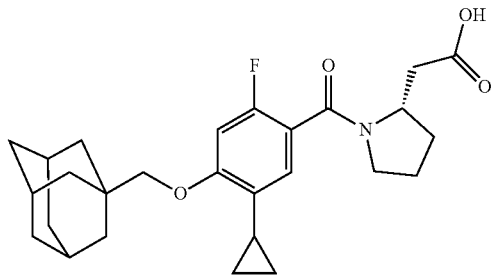

71
-continued
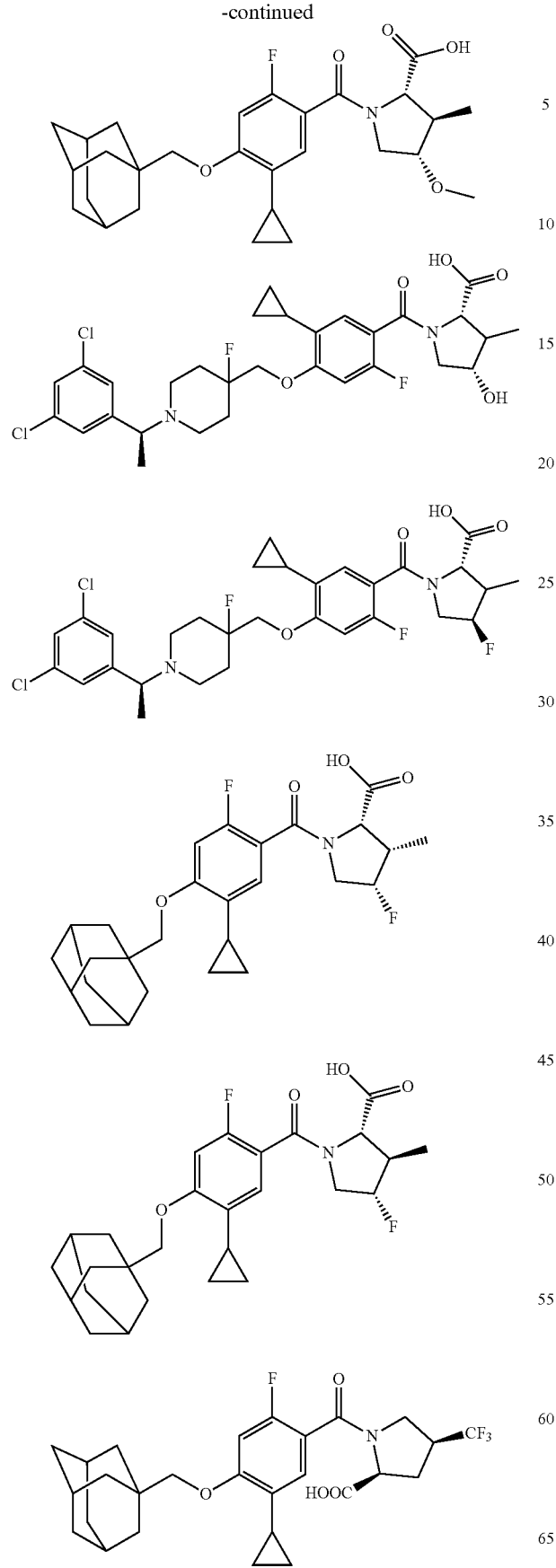
72
-continued
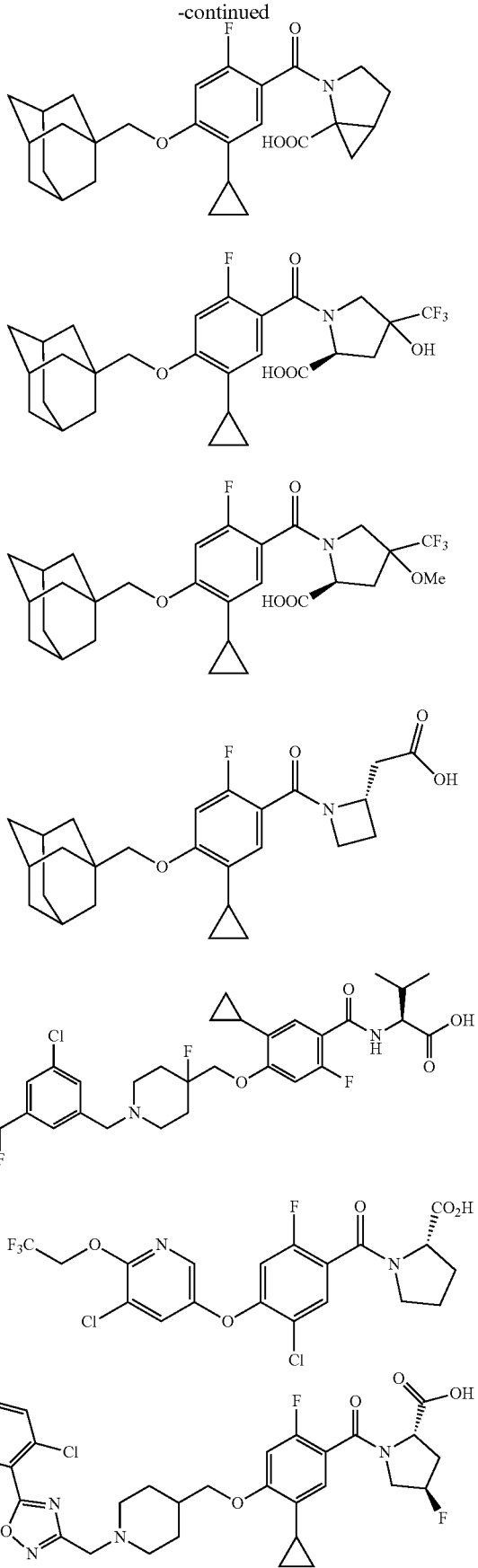

73
-continued
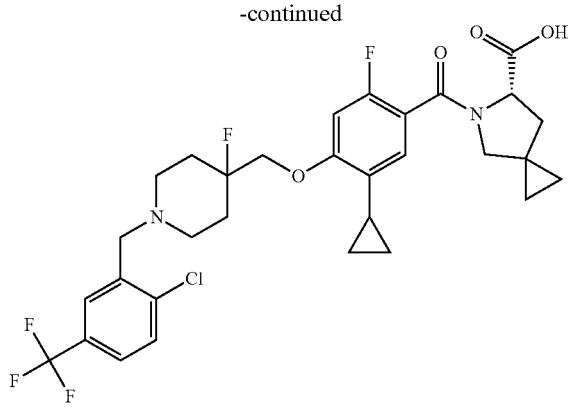
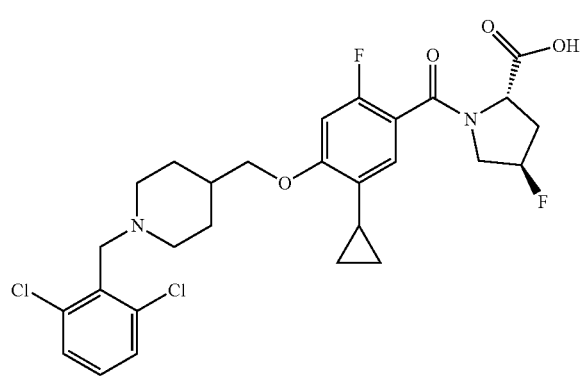
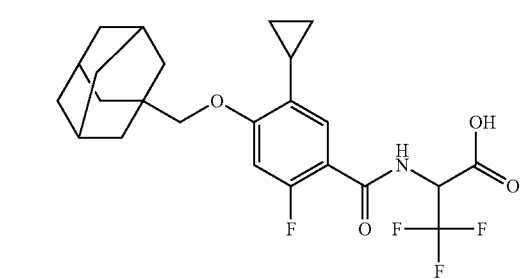
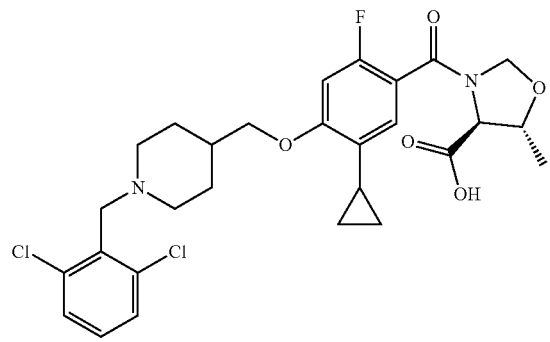
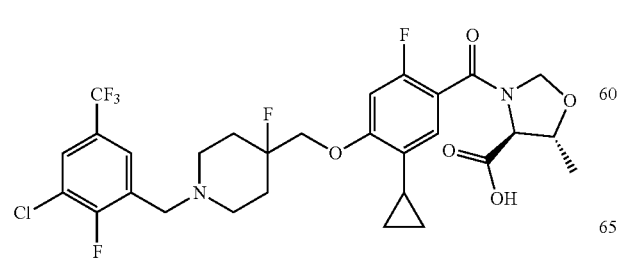
74
-continued
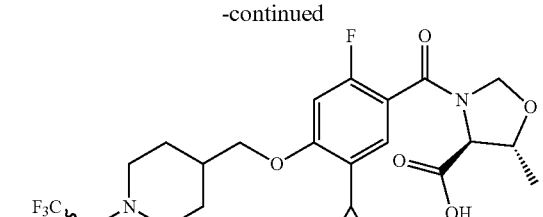
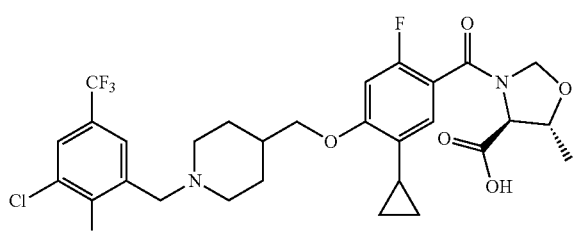
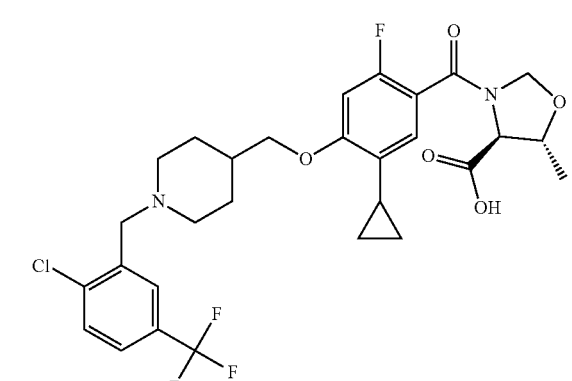
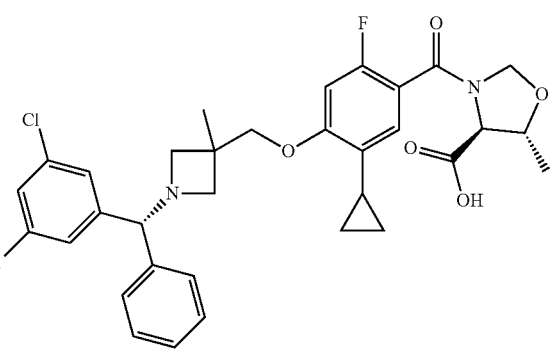
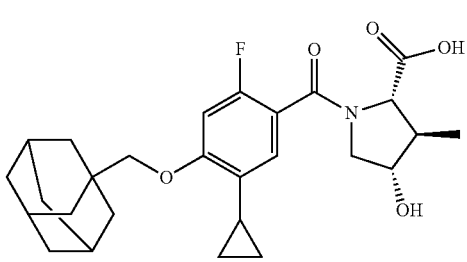

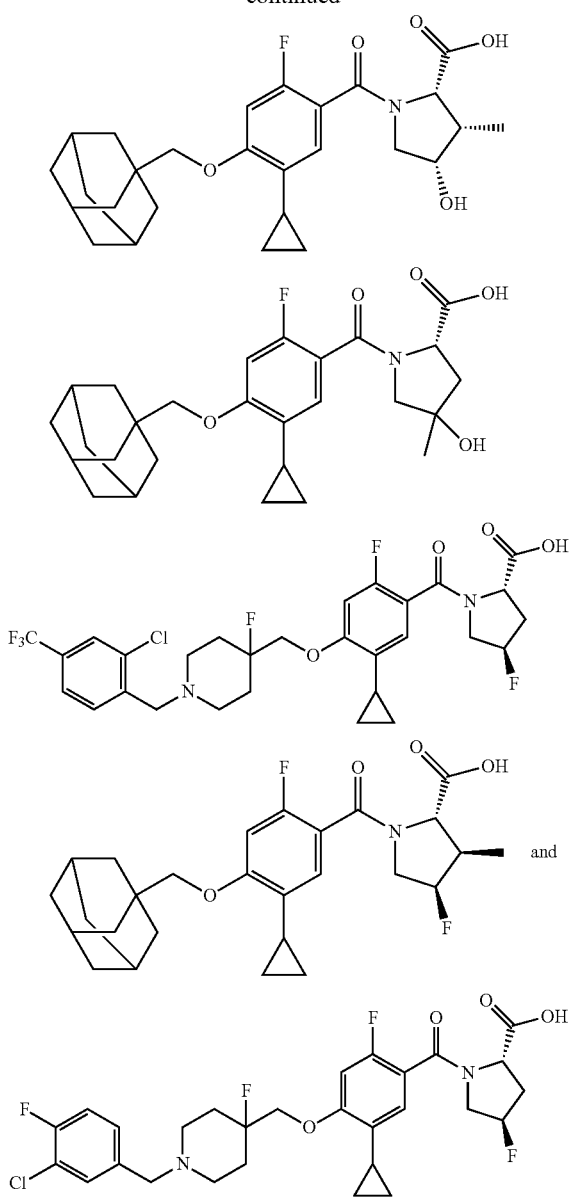
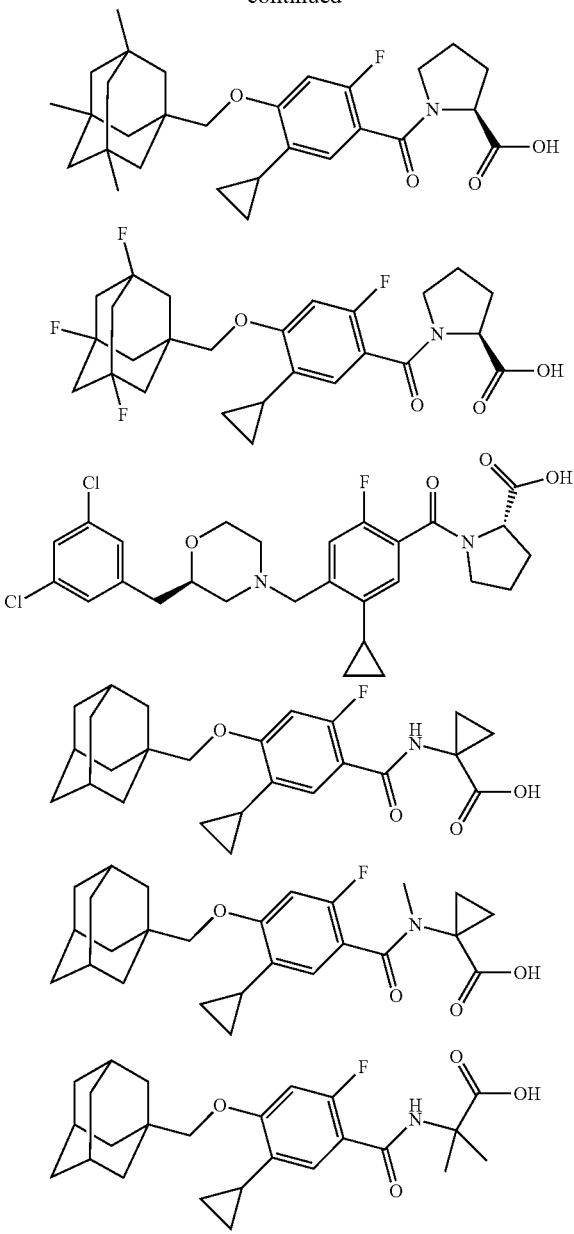
and salts thereof.
E58 A compound selected from the group consisting of:
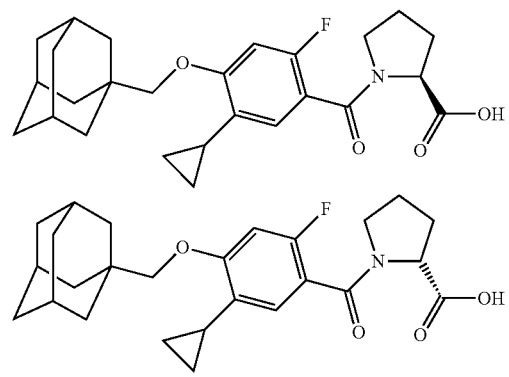
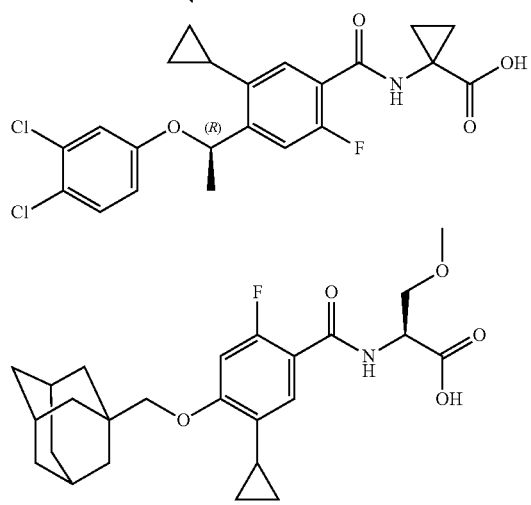

77
-continued
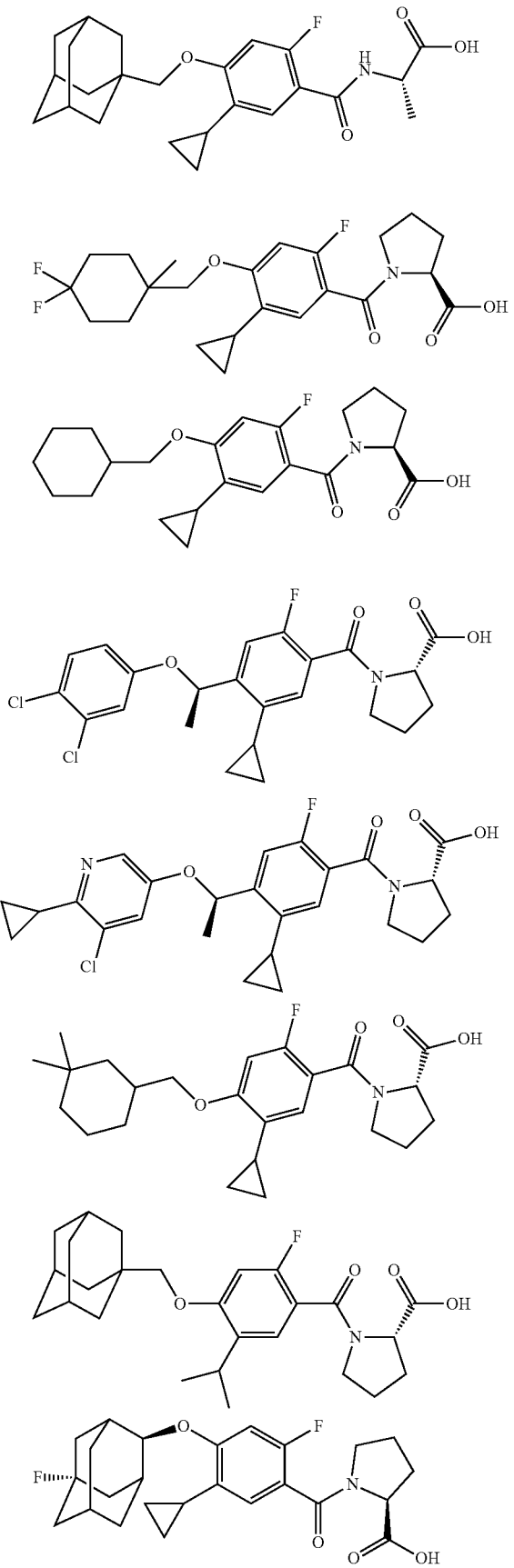
78
-continued
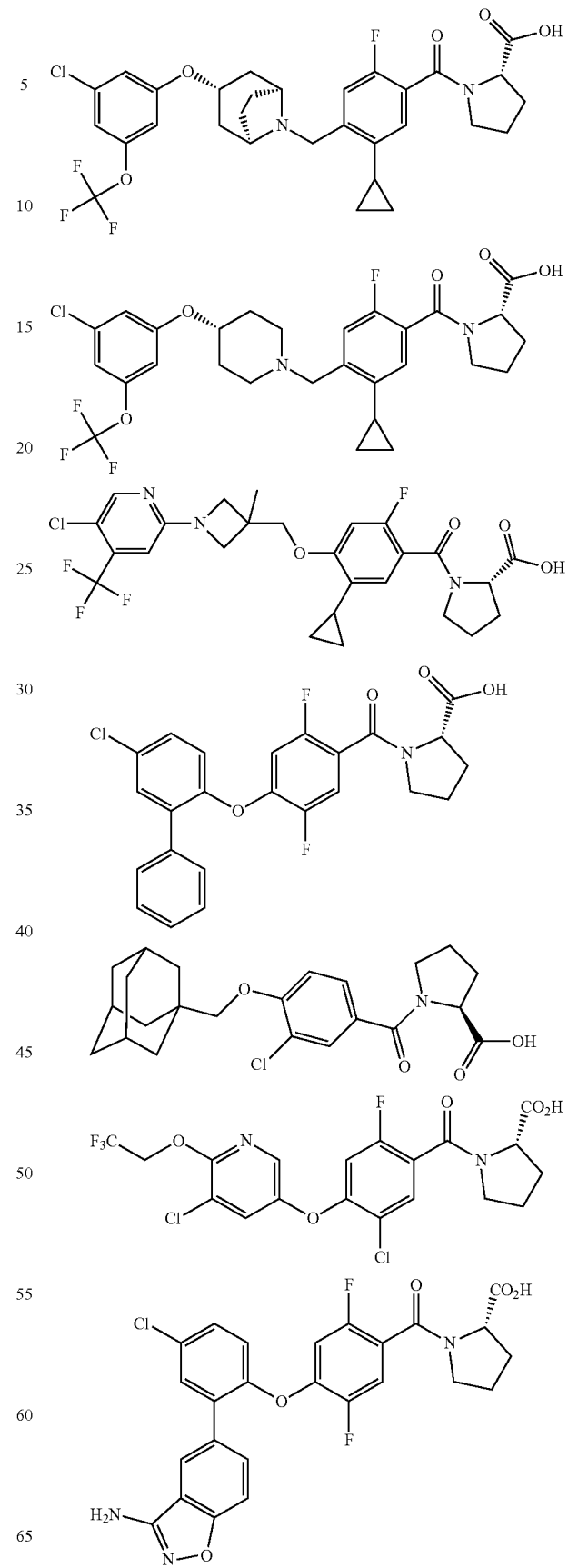

79
-continued
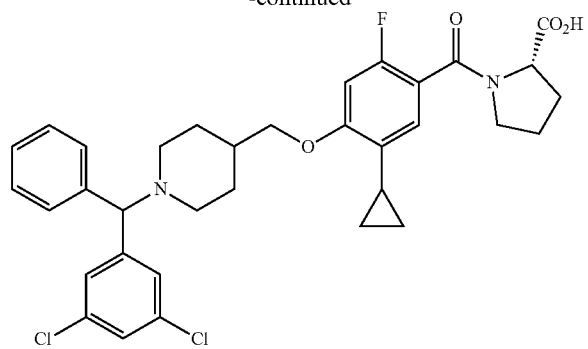
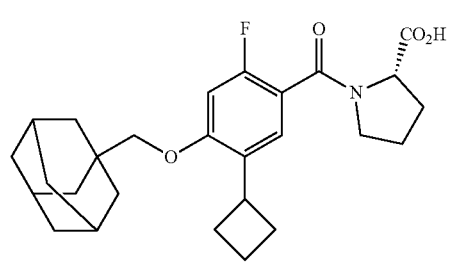
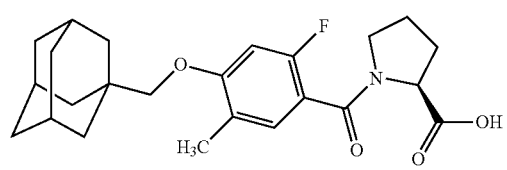
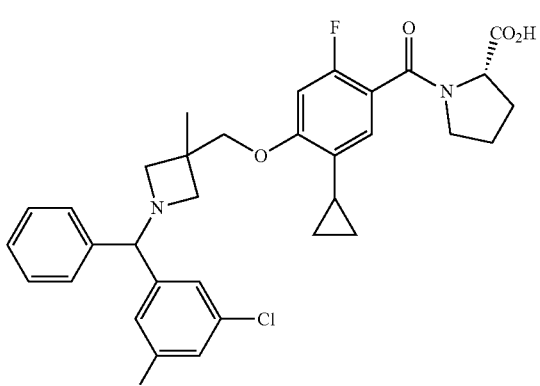
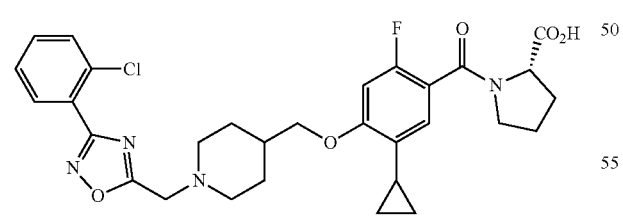
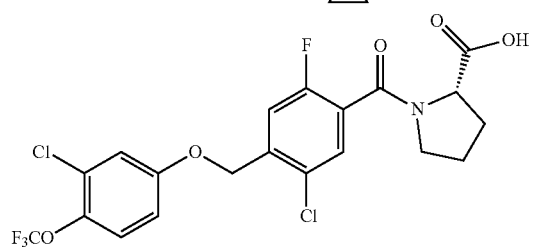
80
-continued
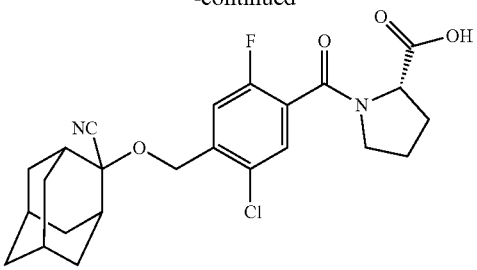
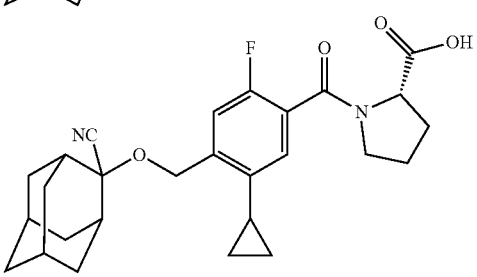
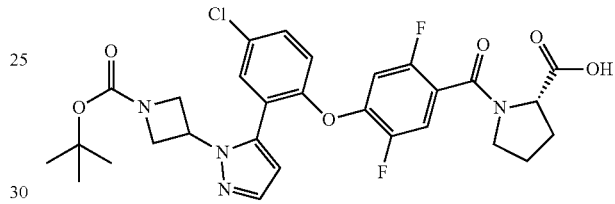
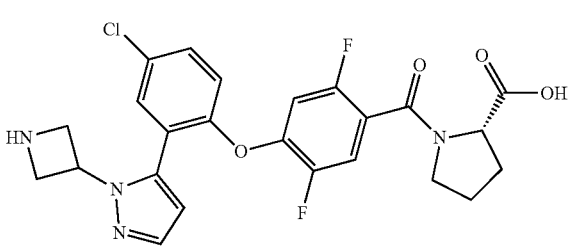
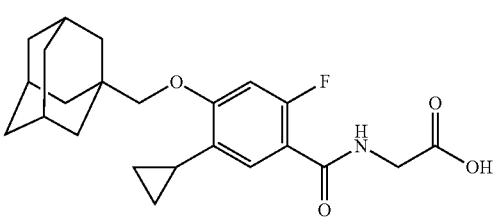
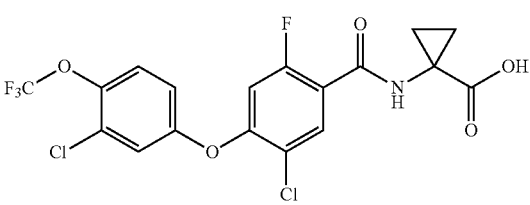
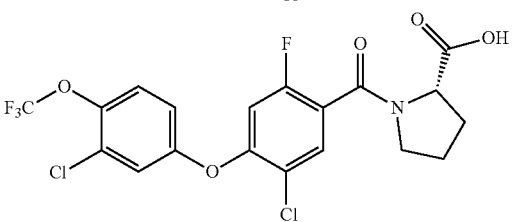

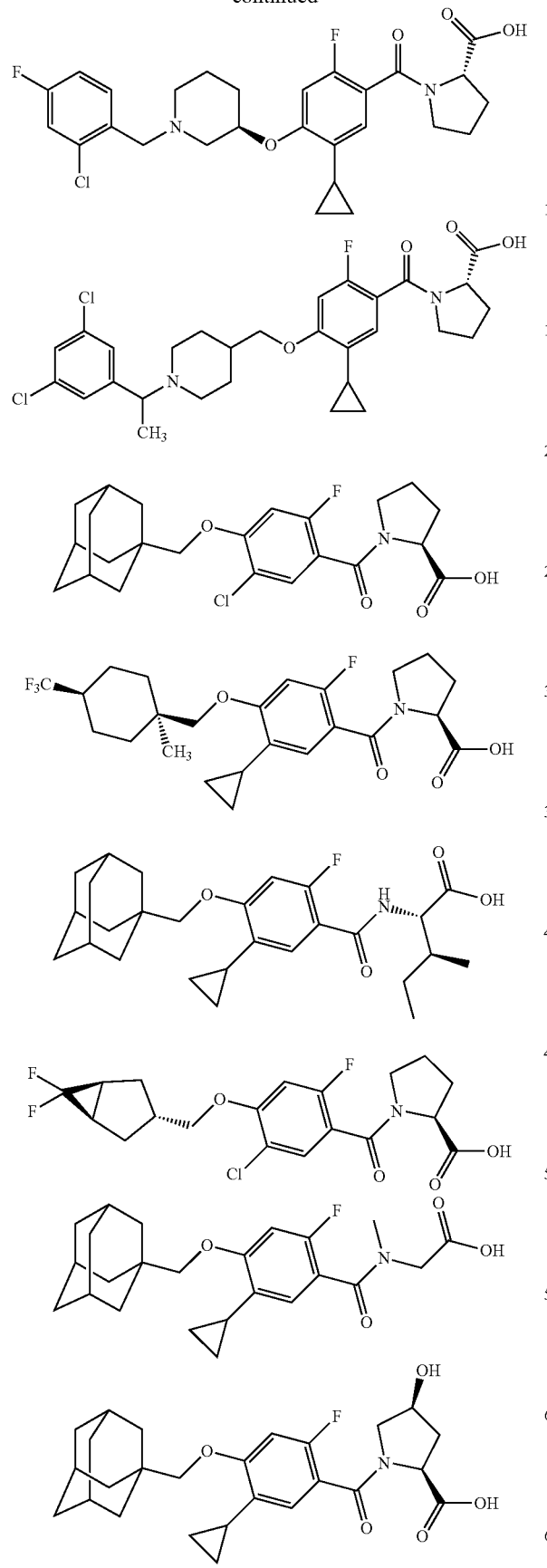
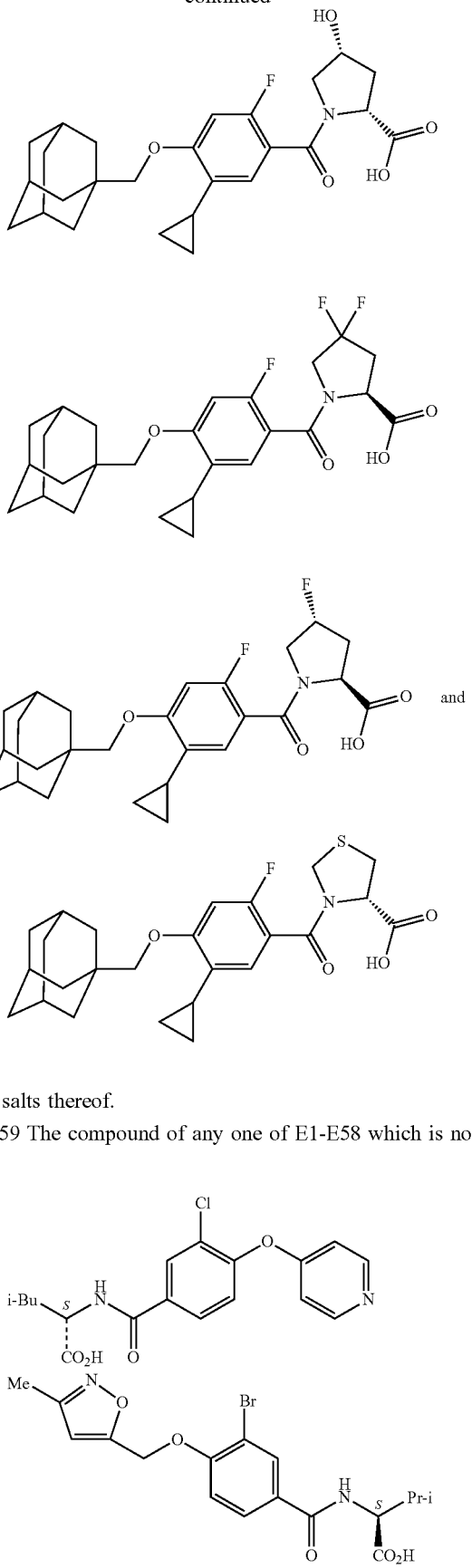
and salts thereof.
E59 The compound of any one of E1-E58 which is not:
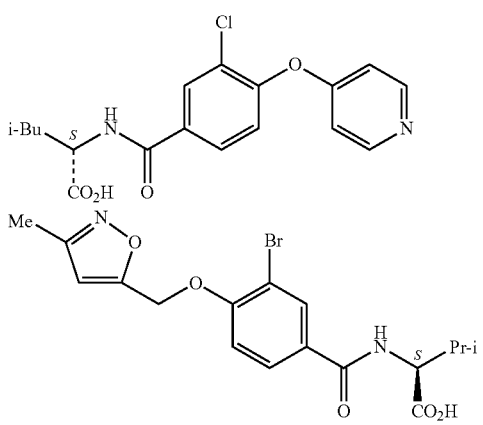

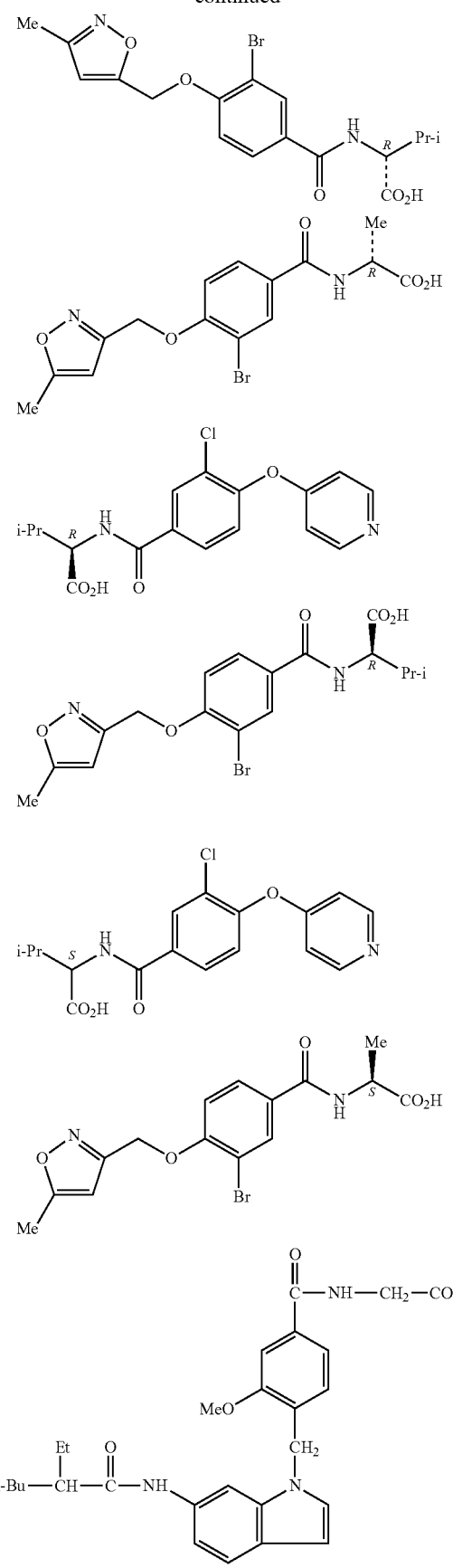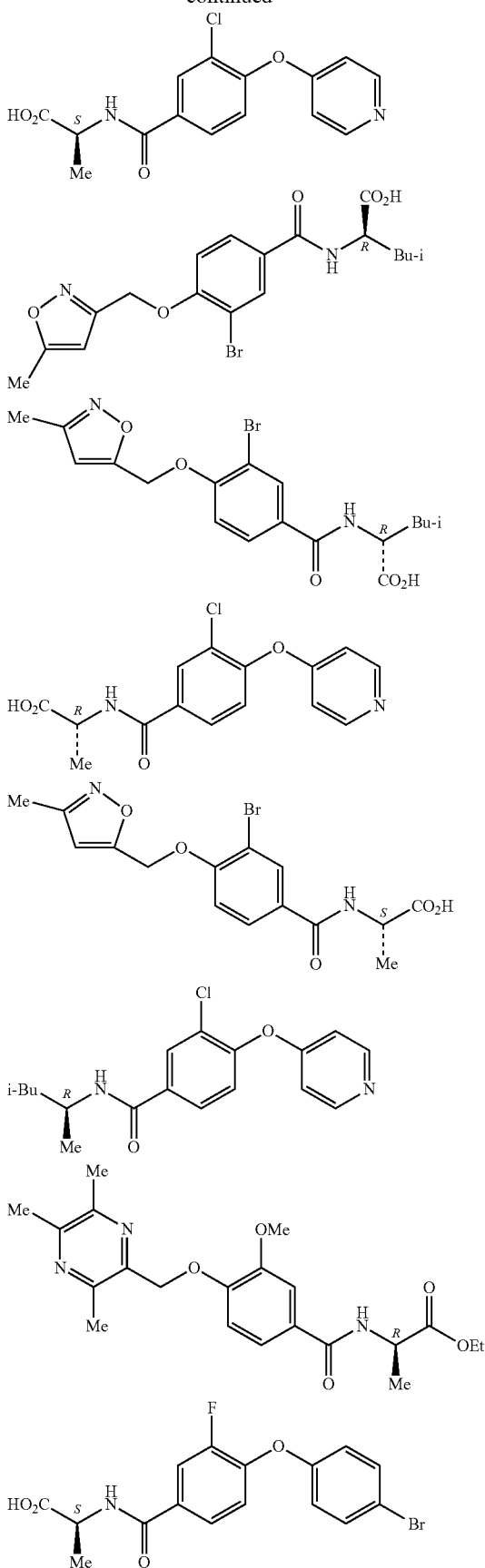

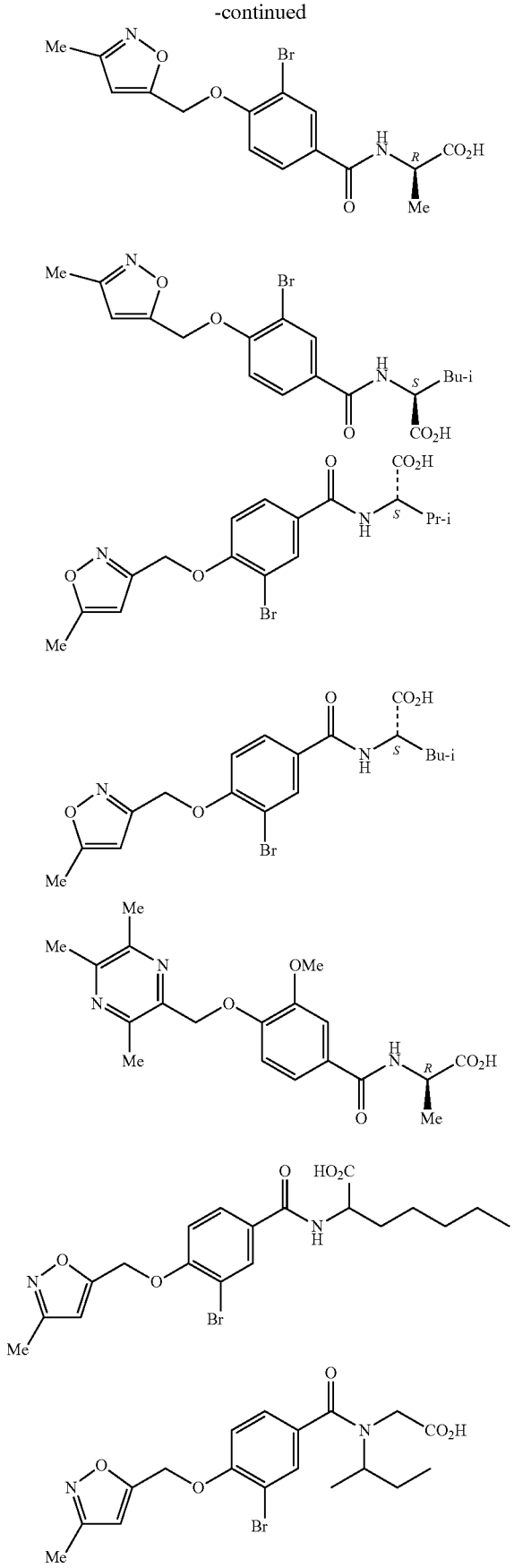
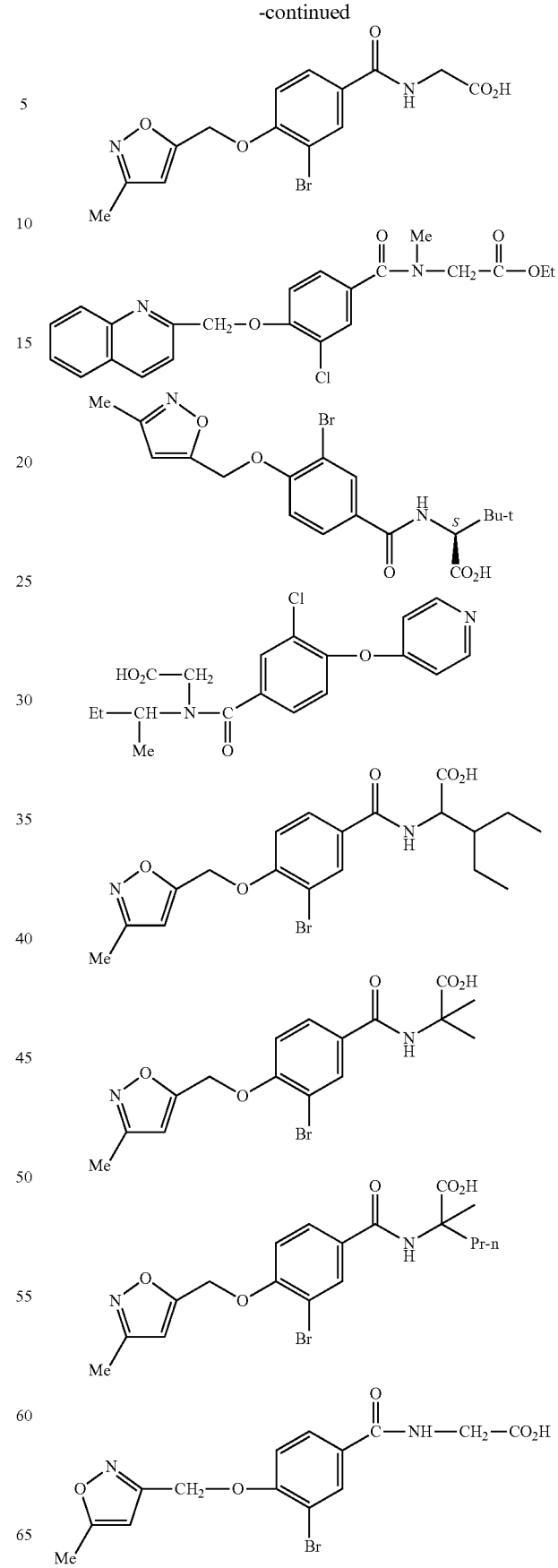

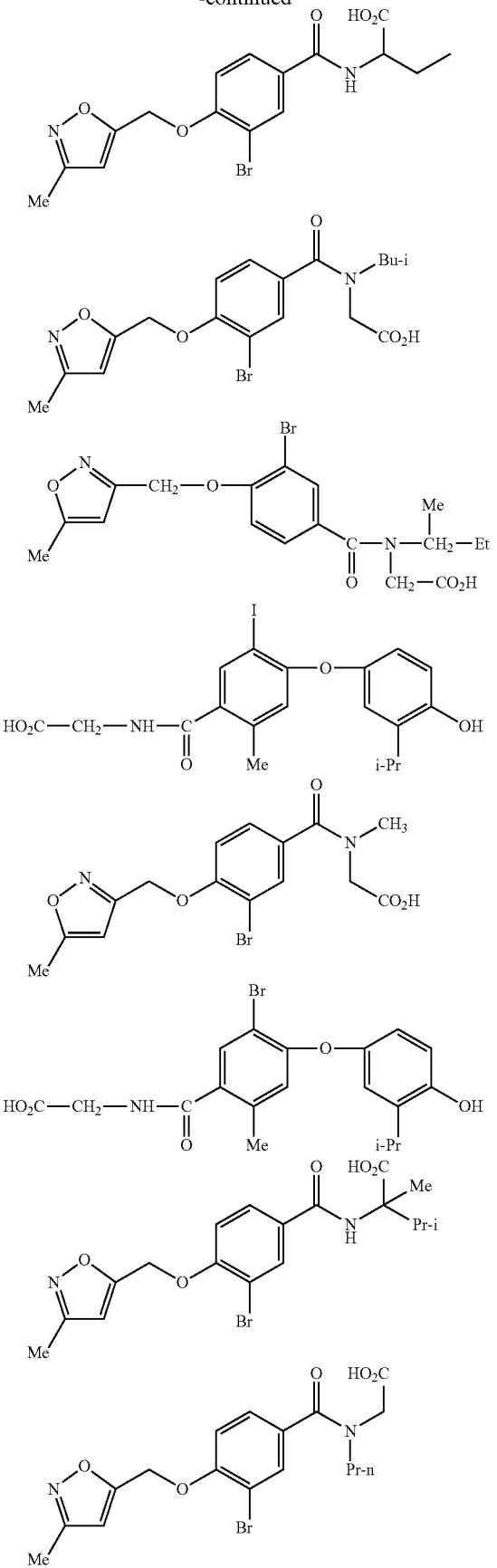
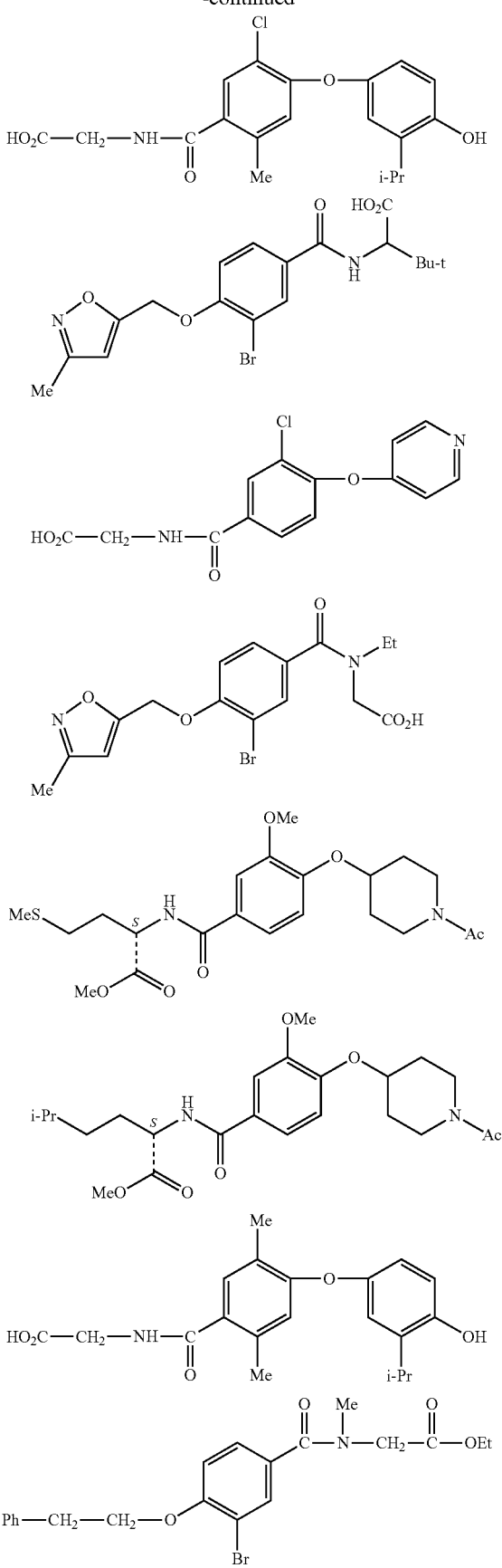

-continued
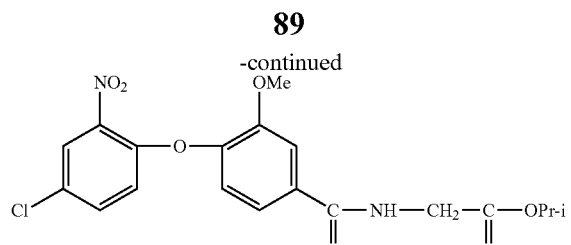
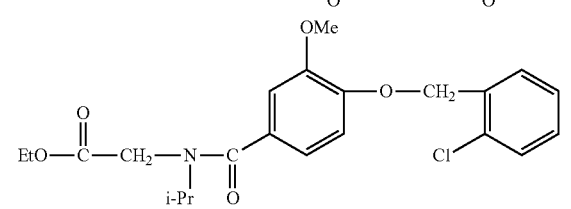
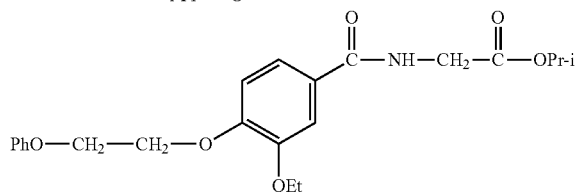
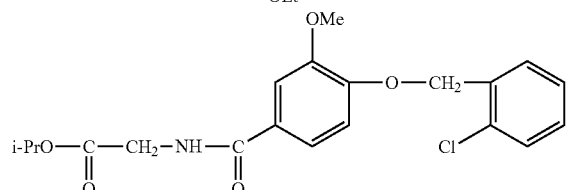
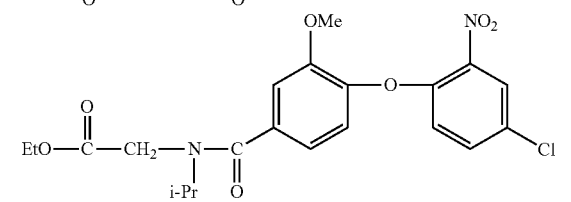
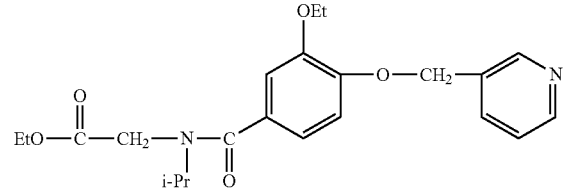
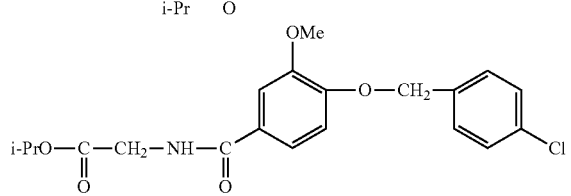
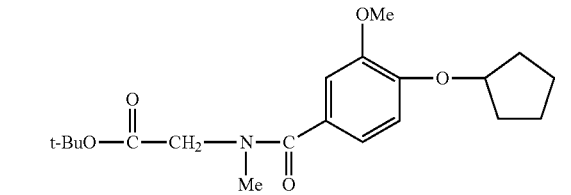
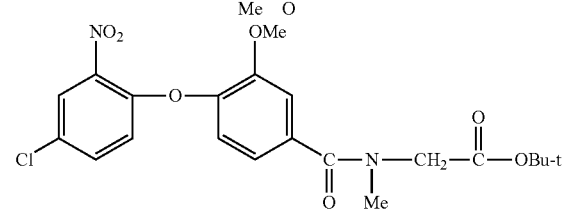
-continued
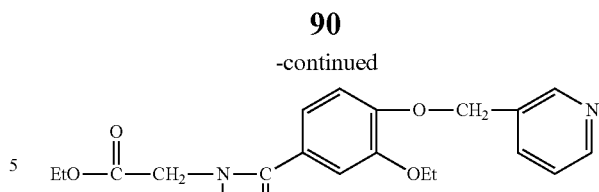
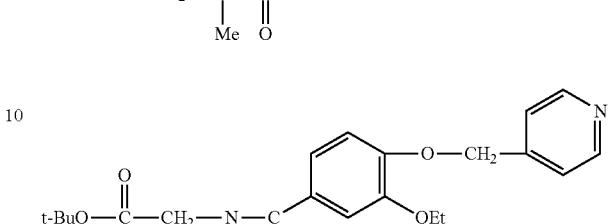
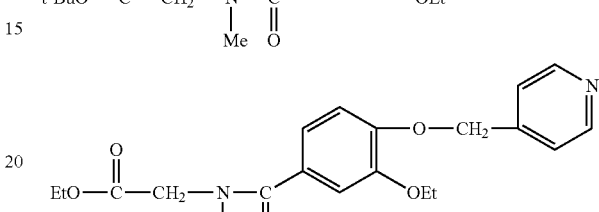
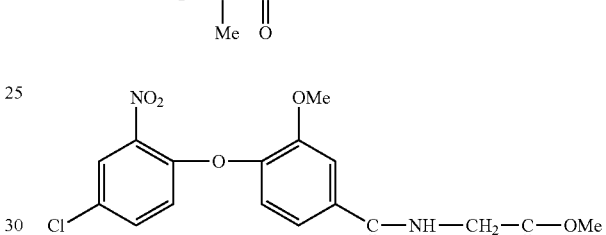
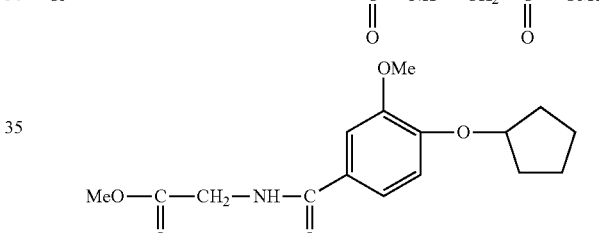
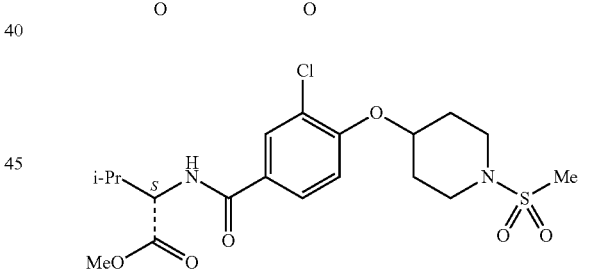
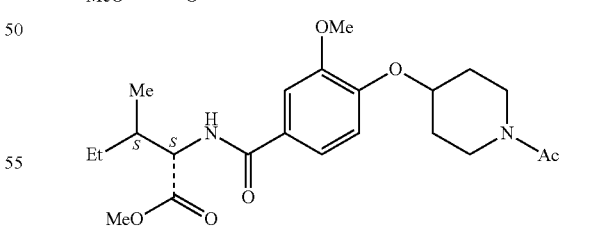
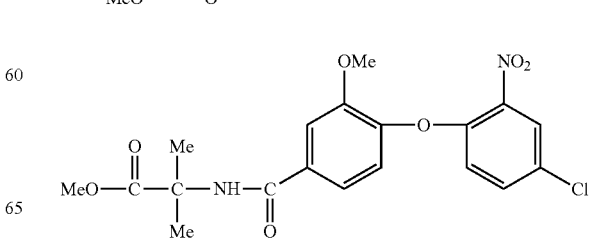

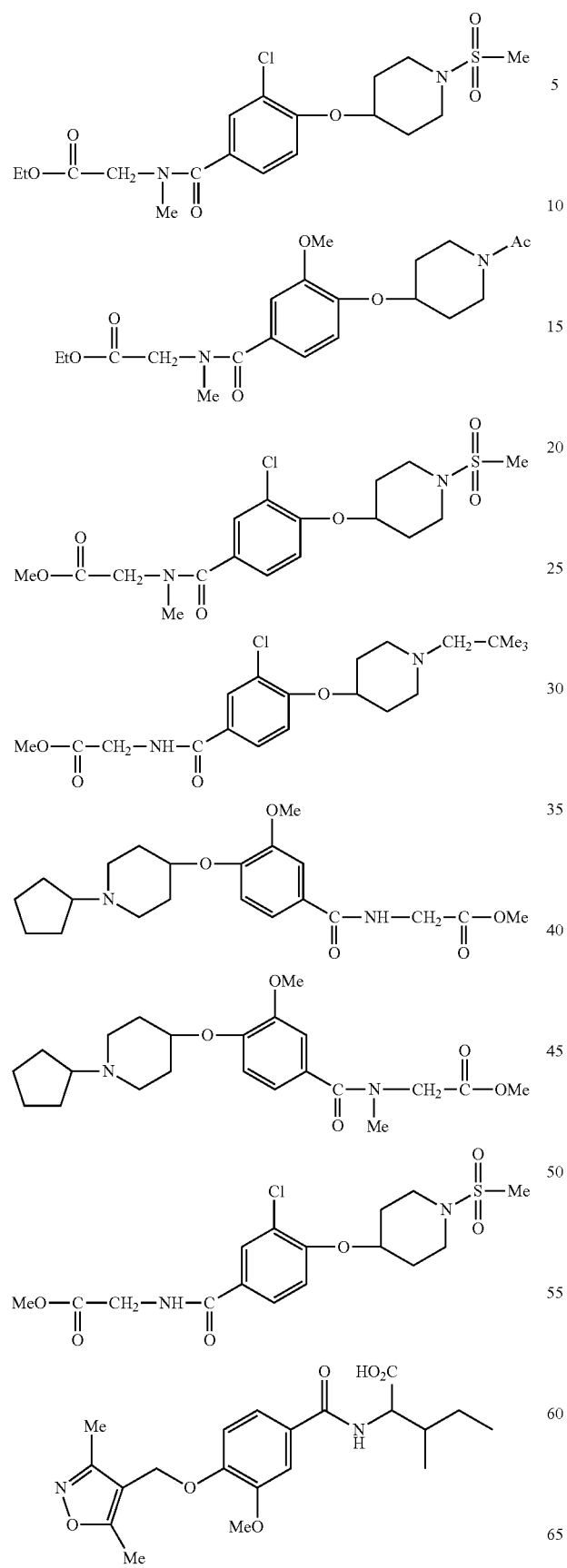
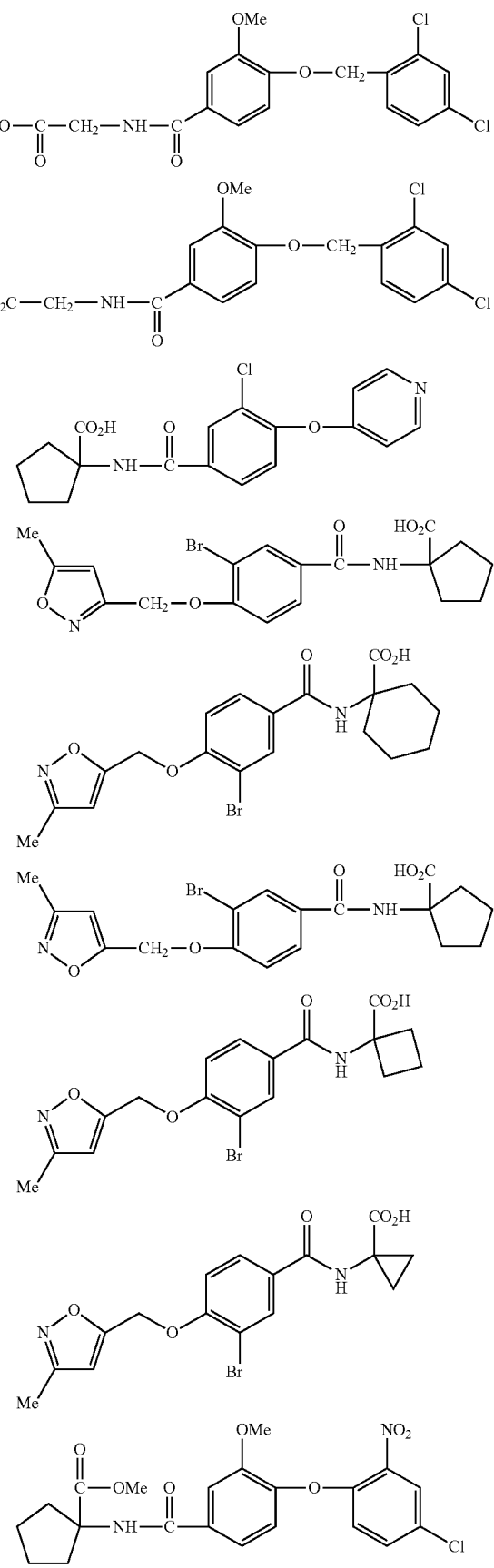

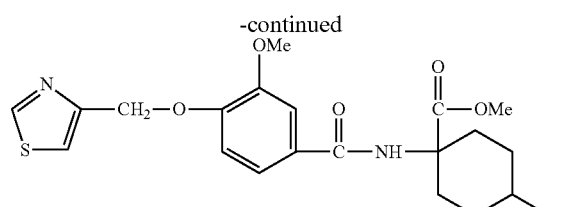
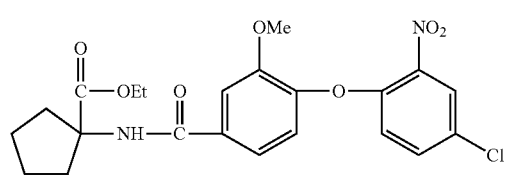
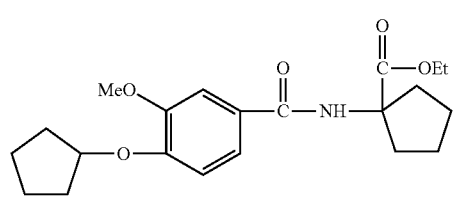
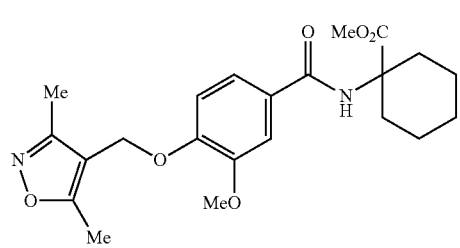
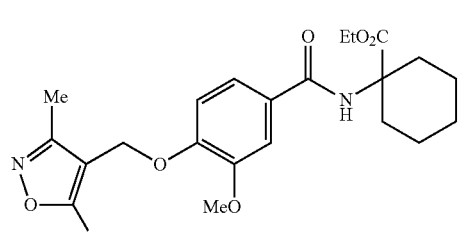
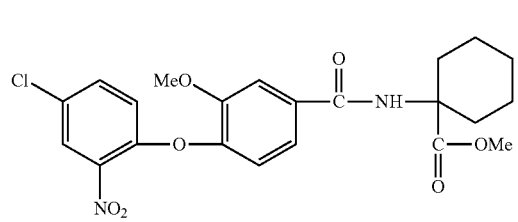
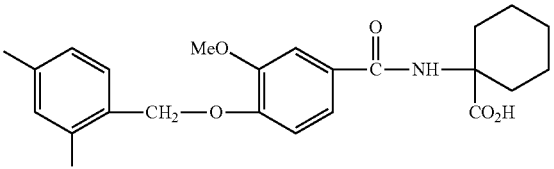
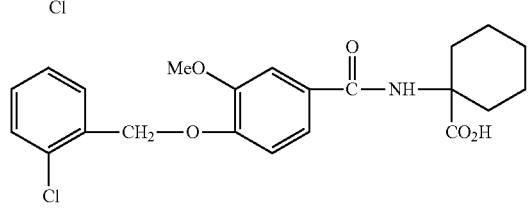
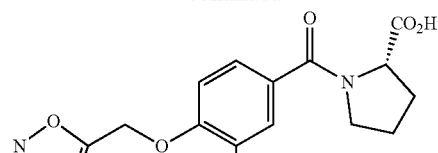
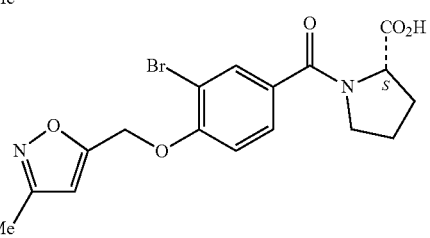
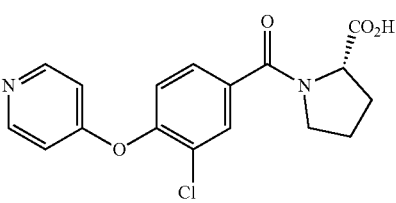
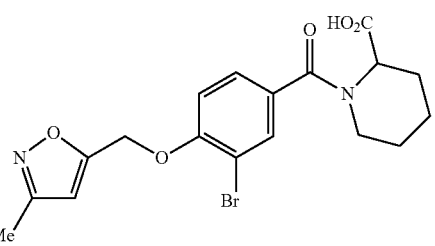
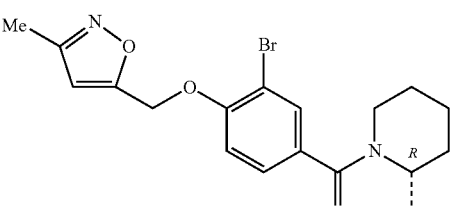
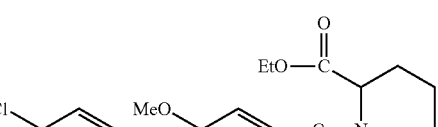
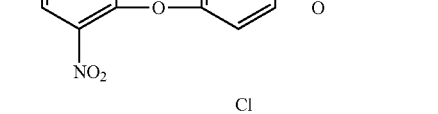
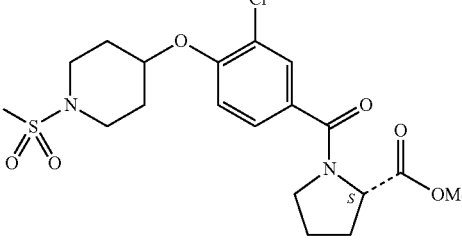
or

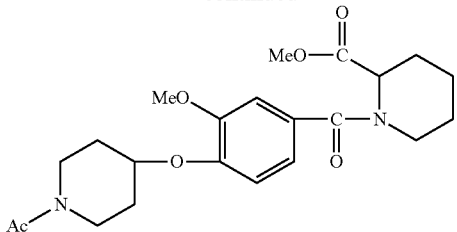

or a pharmaceutically acceptable salt thereof.

In another aspect the present invention provides for a pharmaceutical composition comprising a compound of formula I or a pharmaceutically acceptable salt thereof as described in any one of E1-E51, and a pharmaceutically acceptable excipient.

In another aspect the present invention provides for a method of treating a disease or condition in a mammal selected from the group consisting of pain, depression, cardiovascular diseases, respiratory diseases, and psychiatric diseases, and combinations thereof, wherein the method comprises administering to the mammal in need thereof a therapeutically effective amount of a compound of formula I, or a pharmaceutically acceptable salt thereof as described in any one of E1-E51. In another aspect of the present invention said disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect of the present invention said disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method of treating pain in a mammal by the inhibition of ion flux through a voltage-dependent sodium channel in the mammal, wherein the method comprises administering to the mammal in need thereof a therapeutically effective amount of a compound of formula I, or a pharmaceutically acceptable salt thereof as described in any one of E1-E59.

In another aspect the present invention provides for a method of decreasing ion flux through a voltage-dependent sodium channel in a cell in a mammal, wherein the method comprises contacting the cell with a compound of formula I, or a pharmaceutically acceptable salt thereof as described in any one of E1-E59.

In another aspect the present invention provides for a method of treating pruritus in a mammal, wherein the method comprises administering to the mammal in need thereof a therapeutically effective amount of a compound of formula I, or a pharmaceutically acceptable salt thereof as described in any one of E1-E59.

In another aspect the present invention provides for a method of treating cancer in a mammal, wherein the method comprises administering to the mammal in need thereof a therapeutically effective amount a compound of formula I, or a pharmaceutically acceptable salt thereof as described in any one of E1-E59.

In another aspect the present invention provides for a method of treating, but not preventing, pain in a mammal, wherein the method comprises administering to the mammal in need thereof a therapeutically effective amount of a compound of formula I, or a pharmaceutically acceptable salt thereof as described in any one of E1-E59. In another aspect of the present invention the pain is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect the present invention the pain is associated with a disease or condition selected from the group consisting of HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method for the treatment or prophylaxis of pain, depression, cardiovascular disease, respiratory disease, or psychiatric disease, or a combinations thereof, in an animal which method comprises administering an effective amount of a compound of formula I, or a pharmaceutically acceptable salt thereof as described in any one of E1-E59.

In another aspect the present invention provides for a compound of formula I, or a pharmaceutically acceptable salt thereof as described in any one of E1-E59 for the use as a medicament for the treatment of diseases and disorders selected from the group consisting of pain, depression, cardiovascular diseases, respiratory diseases, and psychiatric diseases, or a combination thereof.

In another aspect the present invention provides for the use of a compound of formula I, or a pharmaceutically acceptable salt thereof as described in any one of E1-E59 for the manufacture of a medicament for the treatment of diseases and disorders selected from the group consisting of pain, depression, cardiovascular diseases, respiratory diseases, and psychiatric diseases, or a combination thereof.

DETAILED DESCRIPTION OF THE INVENTION

In another aspect the present invention provides a compound as described in the Examples hereinbelow, or a free-base or a salt thereof.

In another aspect the present invention provides for the invention as described herein.

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH=N($CH_3$)—$CH_3$. Up to two heteroatoms can be consecutive, such as, for example, —$CH_2$—NH—O$CH_3$ and —$CH_2$—O—Si($CH_3$)$_3$.

The term "alkylene" by itself or as part of another substituent means a divalent radical derived from an alkane (including branched alkane), as exemplified by —$CH_2CH_2CH_2CH_2$— and —CH($CH_2$)$CH_2CH_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)C $H_2$—O—$CH_2$— and —S—$CH_2$—C≡C—. For heteroalkylene groups, heteroatoms can also occupy either or both of the chain termini (e.g., alkyleneoxy, alkylenedi-oxy, alkyleneamino, alkylenediamino, and the like). The term "heteroalkylene" is also meant to include mono and poly-halogenated variants.

The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. The term "(halo)alkyl" is meant to include both a "alkyl" and "haloalkyl" substituent. Additionally, the term "haloalkyl," is meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1, 2, 3, 4-tetrahydronaphthyl, anthracenyl, and the like.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. In one embodiment the term carbocycle includes a $C_{3-12}$ carbocycle. In one embodiment the term carbocycle includes a $C_{3-8}$ carbocycle. In one embodiment the term carbocycle includes a $C_{3-6}$ carbocycle. In one embodiment the term carbocycle includes a $C_{3-5}$ carbocycle. Non-limiting examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, bicyclo[2.2.1]heptane, pinane, adamantane, norborene, spirocyclic $C_{5-12}$ alkane, and 1-cyclohex-3-enyl.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

The term "heterocyclyl," "heterocycloalkyl," or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one.

The term "heterocyclyloxy" as used herein refers to a group (heterocyclyl)-O—, wherein the term heterocyclyl has the meaning defined herein.

The term "alkoxycarbonyl" as used herein refers to a group (alkyl)-O—C(=O)—, wherein the term alkyl has the meaning defined herein.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl, carbocycle, and heterocyclyl) can be a variety of groups including, but not limited to, -halogen, —OR', —NR'R'', —SR', —SiR'R''R''', —OC(O)R', —C(O)R', —CO$_2$R', —CONR'R'', —OC(O)NR'R'', —NR''C(O)R', —NR'''C(O)NR'R'', —NR''C(O)$_2$R', —NHC(NH$_2$)=N H, —NR'C(NH$_2$)=NH, —NHC(NH$_2$)=NR', —NR'''C(NR'R'')=N—CN, —NR'''C(NR'R'')=NOR', —NHC(NH$_2$)=NR', —S(O)R', —S(O)$_2$R', —S(O)$_2$NR'R'', —NR'S(O)$_2$R'', —NR'''S(O)$_2$NR'R'', —CN, —NO$_2$, —(CH$_2$)$_{1-4}$—OR', —(CH$_2$)$_{1-4}$—NR'R'', —(CH$_2$)$_{1-4}$—SR', —(CH$_2$)$_{1-4}$—SiR'R''R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R'', in a number ranging from zero to (2m'+1), where m' is the total number of carbon atoms in such radical. R', R'' and R''' each independently refer groups including, for example, hydrogen, unsubstituted C$_{1-6}$ alkyl, unsubstituted heteroalkyl, unsubstituted aryl, aryl substituted with 1-3 halogens, unsubstituted C$_{1-6}$ alkyl, C$_{1-6}$ alkoxy or C$_{1-6}$ alkylthio groups, or unsubstituted aryl-C$_{1-4}$ alkyl groups, unsubstituted heteroaryl, substituted heteroaryl, among others. When R' and R'' are attached to the same nitrogen atom, they can be combined with the nitrogen atom to form a 3-, 4-, 5-, 6-, or 7-membered ring. For example, —NR'R'' is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above.

Similarly, substituents for the aryl and heteroaryl groups are varied and are generally selected from the group including, but not limited to halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'C(O)NR''R''', —NHC(NH$_2$)=NH, —NR'C(NH$_2$)=NH, —NHC(NH$_2$)=NR', —S(O)R', —S(O)$_2$R', —S(O)$_2$NR'R'', —NR'S(O)$_2$R'', —N$_3$, perfluoro-C$_{1-4}$ alkoxy, and perfluoro-C$_{1-4}$alkyl, —(CH$_2$)$_{1-4}$—OR', —(CH$_2$)$_{1-4}$—NR'R'', —(CH$_2$)$_{1-4}$—SR', —(CH$_2$)$_{1-4}$—SiR'R''R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R'', in a number ranging from zero to the total number of open valences on the aromatic ring system; and where R', R'' and R''' are independently selected from hydrogen, C$_{1-6}$ alkyl, C$_{3-6}$ carbocycle, C$_{2-6}$ alkenyl, C$_{2-6}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., —(CH$_2$)$_{1-4}$—NR'R''), the alkylene linker includes halo variants as well. For example, the linker "—(CH$_2$)$_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "⁓" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethyl silyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alphaaminoacyl-alpha-aminoacyl, where each alpha-aminoacyl group is independently selected from the naturally occurring L-amino acids, P(O)(OH)$_2$, —P(O)(O(C$_{1-6}$)alkyl)$_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}$C or $^{3}$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}$H ("D"), $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^{3}$H or $^{14}$C) are useful in compound and/or substrate tissue distribution assays. Tritiated ($^{3}$H) and carbon-14 ($^{14}$C) isotopes are useful for their ease of preparation and detectability. Further substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

A. Compounds

In one aspect the present invention provides for compounds of Formula I and its embodiments as described hereinbove.

In another embodiment, the compound is selected from compounds of formula I as described in the Examples herein and salts thereof.

Synthesis of Compounds

Compounds of formula (I) may be prepared by the process illustrated in Schemes 1 and 2. Compounds of formula (I), wherein X$^1$ is O, S, or NH, may be prepared by the process illustrated in Scheme 1.

Scheme 1
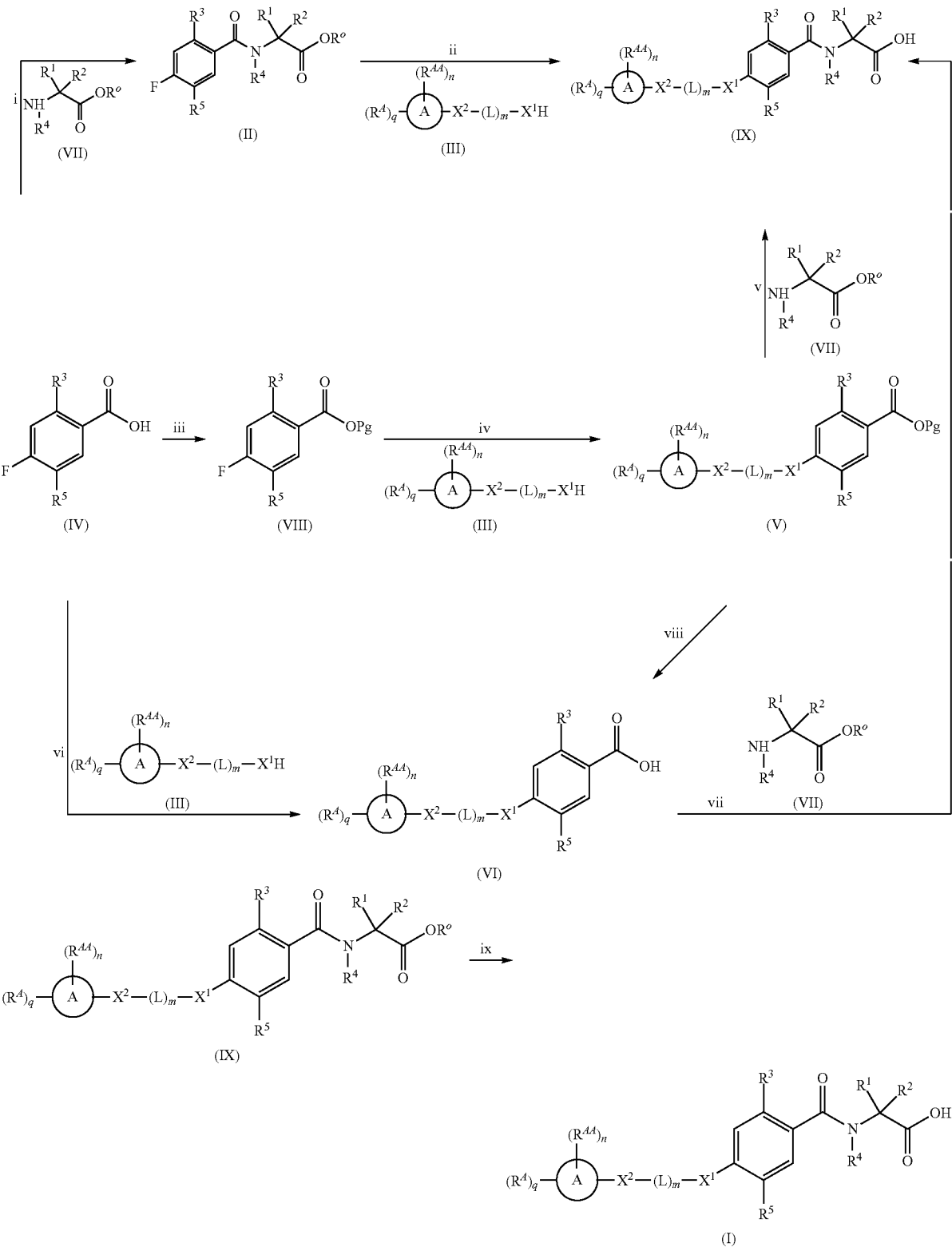
Compounds of formula (I) can be made according to step (ix) from compounds of formula (IX) by treatment with an acid (when R is t-butyl) such as trifluoroacetic acid, hydrogen chloride or by basic hydrolysis under a condition in the presence of a base such as lithium hydroxide, sodium hydroxide.

Compounds of formula (IX) can be made from compounds of formula (II) by displacement with formula (III) and a base (reaction step ii in Scheme 1). Suitable conditions include potassium tert-butoxide in DMSO, NaH in DMF or $K_2CO_3$ in DMF. Formula (II) can be made according to step (i) amide formation conditions by activation of the acid group of formula (IV) with reagents such as oxalyl chloride, carbonyl di-imidazole (CDI), propylphosphonic anhydride, a uronium based amide coupling reagent or a carbodiimide reagent followed by displacement with a formula (VII).

Alternatively, compounds of formula (IX) can be made from compounds of formula (IV) by reversing steps (i) and (ii) as described in Scheme 1. Illustrative conditions for steps vi and vii are as previously described in steps (ii) and (i), respectively.

Compounds of formula (IX) can also be made from compounds of formula (V) according to step (v) by displacement of the ester (when OPg is a suitable ester leaving group) with compounds of formula (VII) and a suitable base such as potassium tert-butoxide, NaH or DBU.

Compounds of formula (IX) can also be made from compounds of formula (V) by a two steps sequence (see steps viii and vii in Scheme 1). Compounds of formula (V) can be made from compounds of formula (VIII) according to step (iv) via a nucleophilic substitution reaction using compounds of formula (III) and a base as described in step ii. Compounds of formula (VIII) can be made from compounds of formula (IV) according to step (iii) using protecting group methodology as described in references such as 'Greene's Protective Groups in Organic Synthesis'. When Pg is tolyl, illustrative conditions comprise thionyl chloride or carbonyldiimidazole with para-cresol. When Pg is tert-butyl, illustrative conditions comprise di-tert butyl dicarbonate and 4-dimethylaminopyridine in tert-butanol.

Compounds of formula (I), wherein $R^5$ is Ar, heteroaryl, $C_{1-8}$ alkyl, $C_{1-8}$ haloalkyl, $C_{1-8}$ alkoxy, $C_{3-10}$ cycloalkyl or $C_{2-9}$ heterocycloalkyl can be prepared from compounds of formula (V) in Scheme 2 by a sequence illustrative in scheme 1 (step v or steps viii and vii).

Compounds of formula (V) can be prepared by palladium-catalyzed coupling of a compound of formula ($R_5M$) according to step (ii) from compounds of formula (XI) as described in Scheme 2, which can be prepared under similar conditions as illustrated in Scheme 1 (step iii and step iv), wherein X is a halide, such as Cl, Br or I. Conveniently the coupling is effective with a boronic acid or ester of formula ($R_5M$). The coupling reaction can be carried out with a variety of palladium catalysts such as palladium acetate or tetrakistriphenylphosphine palladium (0) in various solvents and in the presence of bases such as sodium and potassium carbonate, cesium fluoride or potassium phosphate.

Scheme 3

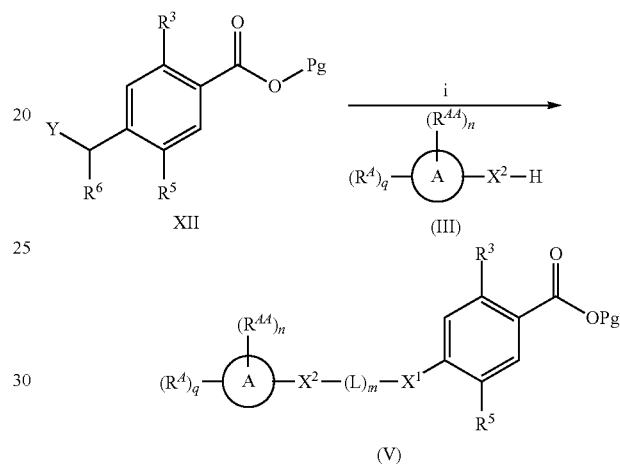

Compounds of formula (I), wherein the moiety $—X^2-(L)_m-X^1—$ is $OCHR^6$, $SCHR^6$, or $NR^7CHR^6$ may be prepared from compounds of formula (V), either $R^6$ and/or $R^7$ is H, or alkyl substitutions. Compounds of formula (V) can be prepared from compounds of formula (XII) under either basic or acidic conditions by the process illustrated in Scheme 3, Y is a halide, mesylate, tosylate or 2,2,2-trichloroacetimidate.

Scheme 2

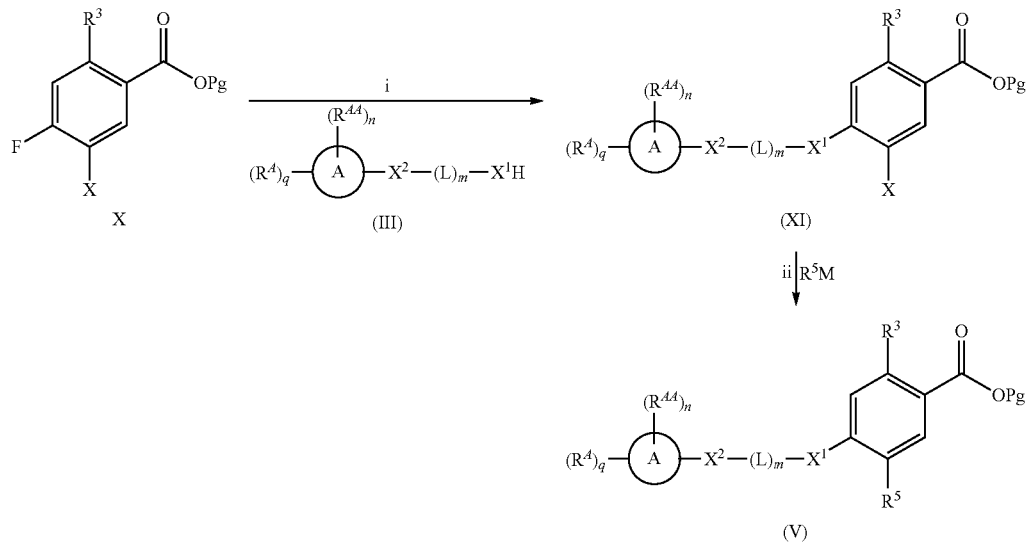

B. Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier, diluent or excipient. The compositions of the invention can be used to selectively inhibit NaV1.7 in patients (e.g, humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of formula I or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NaV1.7 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philidelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In one aspect of topical applications, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

Aqueous suspensions of a compound of the invention (e.g., compound of formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 g/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

C. Indications and Methods of Treatment

The compounds of the invention modulate, preferably inhibit, ion flux through a voltage-dependent sodium channel in a mammal, (e.g, a human). Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards by inhibiting the voltage-dependent activity of the sodium channel, and/or reduce or prevent sodium ion flux across a cell membrane by preventing sodium channel activity such as ion flux.

Accordingly, the compounds of the invention are sodium channel blockers and are therefore useful for treating diseases and conditions in mammals, for example humans, and other organisms, including all those diseases and conditions which are the result of aberrant voltage-dependent sodium channel biological activity or which may be ameliorated by modulation of voltage-dependent sodium channel biological activity. In particular, the compounds of the invention, i.e., the compounds of formula (I) and embodiments and (or stereoisomers, geometric isomers, tautomers, solvates, metabolites, isotopes, pharmaceutically acceptable salts, or prodrugs thereof), are useful for treating diseases and conditions in mammals, for example humans, which are the result of aberrant voltage-dependent NaV1.7 biological activity or which may be ameliorated by the modulation, preferably the inhibition, of NaV1.7 biological activity. In certain aspects, the compounds of the invention selectively inhibit NaV1.7 over NaV1.5.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

In one aspect, the present invention relates to compounds, pharmaceutical compositions and methods of using the compounds and pharmaceutical compositions for the treatment of sodium channel-mediated diseases in mammals, preferably humans and preferably diseases and conditions related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, for example a human, in need of such treatment an effective amount of a sodium channel blocker modulating, especially inhibiting, agent.

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g., opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, chronic regional pain syndrome (CRPS), reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Furthermore, sodium channel blockers have clinical uses in addition to pain. The present invention therefore also relates to compounds, pharmaceutical compositions and methods of using the compounds and pharmaceutical compositions for the treatment of diseases or conditions such as cancer and pruritus (itch).

Pruritus, commonly known as itch, is a common dermatological condition. While the exact causes of pruritus are complex and incompletely understood, there has long been evidence that itch involves sensory neurons, especially C fibers, similar to those that mediate pain (Schmelz, M., et al., J. Neurosci. (1997), 17: 8003-8). In particular, it is believed that sodium influx through voltage-gated sodium channels is essential for the propagation of itch sensation from the skin. Transmission of the itch impulses results in the unpleasant sensation that elicits the desire or reflex to scratch.

Multiple causes and electrical pathways for eliciting itch are known. In humans, pruritis can be elicited by histamine or PAR-2 agonists such as mucunain that activate distinct populations of C fibers (Namer, B., et al., J. Neurophysiol. (2008), 100: 2062-9). A variety of neurotrophic peptides are known to mediate itch in animal models (Wang, H., and Yosipovitch, G., International Journal of Dermatology (2010), 49: 1-11). Itch can also be elicited by opioids, evidence of distinct pharmacology from that of pain responses.

There exists a complex interaction between itch and pain responses that arises in part from the overlapping sensory input from the skin (Ikoma, A., et al., Arch. Dermatol. (2003), 139: 1475-8) and also from the diverse etiology of both pain and pruritis. Pain responses can exacerbate itching by enhancing central sensitization or lead to inhibition of painful scratching. Particularly severe forms of chronic itch occur when pain responses are absent, as in the case of post-herpetic itch (Oaklander, A. L., et al., Pain (2002), 96: 9-12).

The compounds of the invention can also be useful for treating pruritus. The rationale for treating itch with inhibitors of voltage-gated sodium channels, especially NaV1.7, is as follows:

The propagation of electrical activity in the C fibers that sense pruritinergic stimulants requires sodium entry through voltage-gated sodium channels.

NaV1.7 is expressed in the C fibers and kerotinocytes in human skin (Zhao, P., et al., Pain (2008), 139: 90-105).

A gain of function mutation of NaV1.7 (L858F) that causes erythromelalgia also causes chronic itch (Li, Y., et al., Clinical and Experimental Dermatology (2009), 34: e313-e4).

Chronic itch can be alleviated with treatment by sodium channel blockers, such as the local anesthetic lidocaine (Oaklander, A. L., et al., Pain (2002), 96: 9-12; Villamil, A. G., et al., The American Journal of Medicine (2005), 118: 1160-3). In these reports, lidocaine was effective when administered either intravenously or topically (a Lidoderm patch). Lidocaine can have multiple activities at the plasma concentrations achieved when administered systemically, but when administered topically, the plasma concentrations are only about 1 µM (Center for Drug Evaluation and Research NDA 20-612). At these concentrations, lidocaine is selective for sodium channel block and inhibits spontaneous electrical activity in C fibers and pain responses in animal models (Xiao, W. H., and Bennett, G. J. Pain (2008), 137: 218-28). The types of itch or skin irritation, include, but are not limited to:

psoriatic pruritus, itch due to hemodyalisis, aguagenic pruritus, and itching caused by skin disorders (e.g., contact dermatitis), systemic disorders, neuropathy, psychogenic factors or a mixture thereof;

itch caused by allergic reactions, insect bites, hypersensitivity (e.g., dry skin, acne, eczema, psoriasis), inflammatory conditions or injury;

itch associated with vulvar vestibulitis; and skin irritation or inflammatory effect from administration of another therapeutic such as, for example, antibiotics, antivirals and antihistamines.

The compounds of the invention are also useful in treating certain cancers, such as hormone sensitive cancers, such as prostate cancer (adenocarcinoma), breast cancer, ovarian cancer, testicular cancer and thyroid neoplasia, in a mammal, preferably a human. The voltage gated sodium channels have been demonstrated to be expressed in prostate and breast cancer cells. Up-regulation of neonatal NaV1.5 occurs as an integral part of the metastatic process in human breast cancer and could serve both as a novel marker of the metastatic phenotype and a therapeutic target (Clin. Cancer Res. (2005), August 1; 11(15): 5381-9). Functional expression of voltage-gated sodium channel alpha-subunits, specifically NaV1.7, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (Prostate Cancer Prostatic Dis., 2005; 8(3):266-73). See also Diss, J. K. J., et al., Mol. Cell. Neurosci. (2008), 37:537-547 and Kis-Toth, K., et al., The Journal of Immunology (2011), 187:1273-1280.

In consideration of the above, in one embodiment, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

In another embodiment of the invention is a method of treating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of acute pain, chronic pain, neuropathic pain, inflammatory pain, visceral pain, cancer pain, chemotherapy pain, trauma pain, surgical pain, post surgical pain, childbirth pain, labor pain, neurogenic bladder, ulcerative colitis, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tachy arrhythmias, atrial fibrillation and ventricular fibrillation.

Another embodiment of the invention is a method of treating, but not preventing, pain in a mammal, wherein the method comprises administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is a method wherein the pain is selected from the group consisting of neuropathic pain, inflammatory pain, visceral pain, cancer pain, chemotherapy pain, trauma pain, surgical pain, post surgical pain, childbirth pain, labor pain, dental pain, chronic pain, persistent pain, peripherally mediated pain, centrally mediated pain, chronic headache, migraine headache, sinus headache, tension headache, phantom limb pain, peripheral nerve injury, trigeminal neuralgia, post herpetic neuralgia, eudynia, familial erythromelalgia, primary erythromelalgia, familial rectal pain or fibromyalgia, and combinations thereof.

Another embodiment of this embodiment is a method wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy arrhythmias, atrial fibrillation and ventricular fibrillation.

Another embodiment of the invention is the method of treating pain in a mammal, preferably a human, by the inhibition of ion flux through a voltage dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating pruritus in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Another embodiment of the invention is the method of selectively inhibiting a first voltage-gated sodium channel over a second voltage-gated sodium channel in a mammal, wherein the method comprises administering to the mammal an inhibitory amount of a compound of formula (I), or an embodiment of a compound of formula (I).

Another embodiment of the invention is the method of selectively inhibiting NaV1.7 in a mammal or a mammalian cell as compared to NaV1.5, wherein the method comprises administering to the mammal in need thereof an inhibitory amount of a compound of formula (I) or an embodiment of an embodiment thereof.

For each of the above embodiments described related to treating diseases and conditions in a mammal, the present invention also contemplates relatedly a compound of formula I or an embodiment thereof for the use as a medicament in the treatment of such diseases and conditions.

For each of the above embodiments described related to treating diseases and conditions in a mammal, the present invention also contemplates relatedly the use of a compound of formula I or an embodiment thereof for the manufacture of a medicament for the treatment of such diseases and conditions.

Another embodiment of the invention is a method of using the compounds of formula (I) as standards or controls in in vitro or in vivo assays in determining the efficacy of test compounds in modulating voltage-dependent sodium channels.

In another embodiment of the invention, the compounds of formula (I) are isotopically-labeled by having one or more atoms therein replaced by an atom having a different atomic mass or mass number. Such isotopically-labeled (i.e., radio-labelled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the sodium channels, or binding affinity to pharmacologically important site of action on the sodium channels, particularly NaV1.7. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Testing Compounds

The assessment of the compounds of the invention in mediating, especially inhibiting, the sodium channel ion flux can be determined using the assays described hereinbelow. Alternatively, the assessment of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, Pain (2000), 87:7-17). Allometric scaling of the doses effective in these rat models, translates into doses similar to those shown to be efficacious in humans (Tanelian, D. L. and Brose, W. G., Anesthesiology (1991), 74(5):949-951). Furthermore, Lidoderm®, lidocaine applied in the form of a dermal patch, is currently an FDA approved treatment for post-herpetic neuralgia (Devers, A. and Glaler, B. S., Clin. J. Pain (2000), 16(3):205-8).

The present invention readily affords many different means for identification of sodium channel modulating agents that are useful as therapeutic agents. Identification of modulators of sodium channel can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., J. General Physiology (1983), 83:613-642, and Leuwer, M., et al., Br. J. Pharmacol (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive 22[Na] and 14[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Life Technologies, or Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

Modulating agents so identified are then tested in a variety of in vivo models so as to determine if they alleviate pain, especially chronic pain or other conditions such as cancer and pruritus (itch) with minimal adverse events. The assays described below in the Biological Assays Section are useful in assessing the biological activity of the instant compounds.

Typically, the efficacy of a compound of the invention is expressed by its IC50 value ("Inhibitory Concentration—50%"), which is the measure of the amount of compound required to achieve 50% inhibition of the activity of the target sodium channel over a specific time period. For example, representative compounds of the present invention have demonstrated IC50's ranging from less than 100 nanomolar to less than 10 micromolar in the patch voltage clamp NaV1.7 electrophysiology assay described herein.

In another aspect of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting NaV1.1, NaV1.2, NaV1.3, NaV1.4, NaV1.5, NaV1.6, NaV1.7, NaV1.8, or NaV1.9 activity, preferably NaV1.7 activity, in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, or NaV1.9 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention (or stereoisomers, geometric isomers, tautomers, solvates, metabolites, isotopes, pharmaceutically acceptable salts, or prodrugs thereof) and/or the pharmaceutical compositions described herein which comprise a pharmaceutically acceptable excipient and one or more compounds of the invention, can be used in the preparation of a medicament for the treatment of sodium channel-mediated disease or condition in a mammal.

E. Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, desipramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuprorion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinc) analgesics;
alpha-2-delta ligands;
prostaglandin E2 subtype antagonists;
leukotriene B4 antagonists;
5-lipoxygenase inhibitors; and
5-HT3 antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated CDCl$_3$, d$_6$-DMSO, CH$_3$OD or d$_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

ABBREVIATIONS

DMF N,N-Dimethylformamide
DMSO Dimethyl sulfoxide
HPLC High Pressure Liquid Chromatography
LCMS Liquid Chromatography Mass Spectrometry
RT Retention time

EXAMPLES

Example 1

Synthesis of (S)-1-(4-(adamantan-1-ylmethoxy)-5-cyclopropyl-2-fluorobenzoyl)pyrrolidine-2-carboxylic Acid

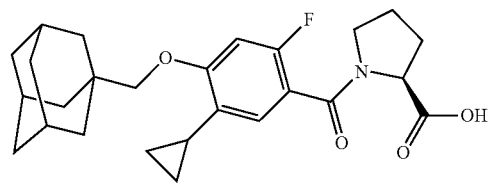 [SMILES: O=C(O)[C@@H]1CCCN1C(=O)c1cc(C2CC2)c(OCC23CC4CC(CC(C4)C2)C3)cc1F]

Step 1. Preparation of (S)-tert-butyl 1-(4-(adamantan-1-ylmethoxy)-5-cyclopropyl-2-fluorobenzoyl)pyrrolidine-2-carboxylate

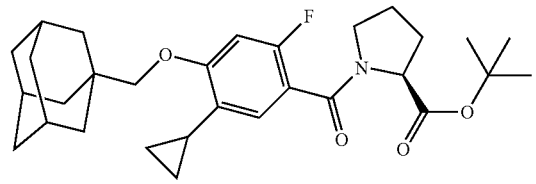 [SMILES: CC(C)(C)OC(=O)[C@@H]1CCCN1C(=O)c1cc(C2CC2)c(OCC23CC4CC(CC(C4)C2)C3)cc1F]

To a stirred solution of 4-(adamantan-1-ylmethoxy)-5-cyclopropyl-2-fluorobenzoic acid (0.35 g, 1.00 mmol) in acetonitrile (20 mL) was added O-(benzotriazol-1-yl)-N,N,N',N'-tetramethyluronium tetrafluoroborate (TBTU) (0.64 g, 2.00 mmol), hydroxybenzotriazole (HOBt) (0.20 g, 1.50 mmol) and N,N-diisopropylethylamine (1.0 mL, 5.74 mL). After 10 minutes, (S)-tert-butyl pyrrolidine-2-carboxylate hydrochloride (0.30 g, 1.44 mmol) was added and stirring was continued at ambient temperature for 20 hours. Diluted with ethyl acetate (200 mL), and washed with saturated sodium bicarbonate solution (20 mL×3), water and brine; dried over anhydrous sodium sulfate and concentrated in vacuo. Purification of the residue by column chromatography (10% ethyl acetate in hexanes) to provide the title compound as a colorless foam (0.34 g, 68%): $^1$H NMR (300 MHz, CDCl$_3$) δ 6.92 (d, J=8.1 Hz, 1H), 6.47 (d, J=11.7 Hz, 1H), 4.49-4.43 (m, 1H), 3.54-3.33 (m, 4H), 2.30-2.21 (m, 1H), 2.05-1.63 (m, 17H), 1.45 (s, 9H), 0.89-0.78 (m, 4H), 0.62-0.51 (m, 2H).

Step 2. Preparation of (S)-1-(4-(adamantan-1-yl-methoxy)-5-cyclopropyl-2-fluorobenzoyl)pyrrolidine-2-carboxylic Acid

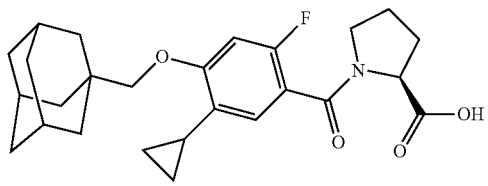 [SMILES: O=C(O)[C@@H]1CCCN1C(=O)c1cc(C2CC2)c(OCC23CC4CC(CC(C4)C2)C3)cc1F]

To a solution of (S)-tert-butyl 1-(4-(adamantan-1-yl-methoxy)-5-cyclopropyl-2-fluorobenzoyl)-pyrrolidine-2-carboxylate (0.34 g, 0.68 mmol) in dichloromethane (10 mL) was added trifluoroacetic acid (5 mL). The mixture was stirred at ambient temperature for 4 hours and then concentrated in vacuo. The residue was washed with hexanes to provide the title compound as colorless solid (0.28 g, 92%): $^1$H NMR (300 MHz, CDCl$_3$) δ 6.95 (d, J=8.1 Hz, 1H), 6.51 (d, J=12.0 Hz, 1H), 4.75-4.69 (m, 1H), 3.55-3.37 (m, 4H), 2.55-2.40 (m, 1H), 2.19-1.64 (m, 17H), 0.96-0.80 (m, 4H), 0.65-0.58 (m, 2H); MS (ES+) m/z 442.1 (M+1).

Example 2

Synthesis of (R)-1-(4-(adamantan-1-ylmethoxy)-5-cyclopropyl-2-fluorobenzoyl)pyrrolidine-2-carboxylic Acid

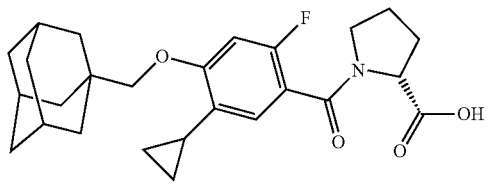

Following the procedure as described in Example 1, and making variation as required to replace (S)-tert-butyl pyrrolidine-2-carboxylate hydrochloride with (R)-tert-butyl pyrrolidine-2-carboxylate hydrochloride, the title compound was obtained as an colorless solid (0.26 g, 58% in 2 steps): $^1$H NMR (300 MHz, CDCl$_3$) δ 6.95 (d, J=8.1 Hz, 1H), 6.51 (d, J=12.0 Hz, 1H), 4.75-4.69 (m, 1H), 3.55-3.37 (m, 4H), 2.55-2.40 (m, 1H), 2.19-1.64 (m, 17H), 0.96-0.80 (m, 4H), 0.65-0.58 (m, 2H); MS (ES+) m/z 442.1 (M+1).

Example 3

Synthesis of (S)-1-(5-cyclopropyl-2-fluoro-4-((3,5,7-trimethyladamantan-1-yl)methoxy)benzoyl)pyrrolidine-2-carboxylic Acid

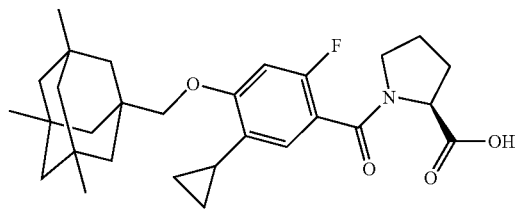 [SMILES: CC12CC3(C)CC(C)(C1)CC(COc1cc(F)c(C(=O)N4CCC[C@H]4C(=O)O)cc1C1CC1)(C2)C3]

Step 1. Preparation of (S)-tert-butyl 1-(5-cyclopropyl-2-fluoro-4-((3,5,7-trimethyladamantan-1-yl)methoxy)benzoyl)pyrrolidine-2-carboxylate

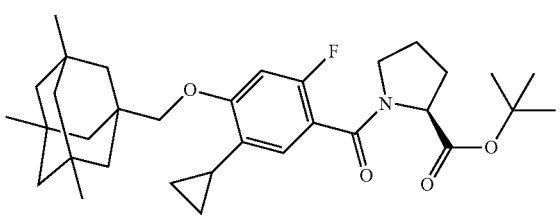 [SMILES: CC12CC3(C)CC(C)(C1)CC(COc1cc(F)c(C(=O)N4CCC[C@H]4C(=O)OC(C)(C)C)cc1C1CC1)(C2)C3]

Following the procedure as described in Example 1 step 1, and making variation as required to replace 4-(adamantan-1-ylmethoxy)-5-cyclopropyl-2-fluorobenzoic acid with 5-cyclopropyl-2-fluoro-4-((3,5,7-trimethyladamantan-1-yl)methoxy)benzoic acid, the title compound was obtained as an colorless foam (0.49 g, 90%): $^1$H NMR (300 MHz, CDCl$_3$) δ 6.90 (d, J=7.8 Hz, 1H), 6.44 (d, J=11.7 Hz, 1H), 4.46-4.40 (m, 1H), 3.72-3.30 (m, 4H), 2.29-2.15 (m, 1H), 2.01-1.75 (m, 4H), 1.43 (s, 6H), 1.23 (s, 3H), 1.19 (s, 6H), 1.05 (s, 6H), 0.86-0.77 (m, 11H), 0.59-0.50 (m, 2H).

Step 2. Preparation of (S)-1-(5-cyclopropyl-2-fluoro-4-((3,5,7-trimethyladamantan-1-yl)methoxy)benzoyl)pyrrolidine-2-carboxylic Acid

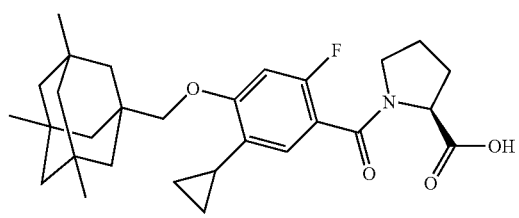 [SMILES: CC12CC3(C)CC(C)(C1)CC(COc1cc(F)c(C(=O)N4CCC[C@H]4C(=O)O)cc1C1CC1)(C2)C3]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-cyclopropyl-2-fluoro-4-((3,5,7-trimethyladamantan-1-yl)methoxy)benzoyl)pyrrolidine-2-carboxylate, the title compound was obtained as an colorless solid (0.40 g, 82%):

¹H NMR (300 MHz, CDCl₃) δ 6.95 (d, J=7.8 Hz, 1H), 6.50 (d, J=12.0 Hz, 1H), 4.75-4.69 (m, 1H), 3.58-3.36 (m, 4H), 2.55-2.41 (m, 1H), 2.21-1.80 (m, 4H), 1.23 (s, 6H), 1.09 (s, 6H), 0.94-0.80 (m, 11H), 0.65-0.58 (m, 2H); MS (ES+) m/z 484.2 (M+1).

Example 4

Synthesis of (5)-1-(5-cyclopropyl-2-fluoro-4-((3,5,7-trifluoroadamantan-1-yl)methoxy)benzoyl)pyrrolidine-2-carboxylic Acid

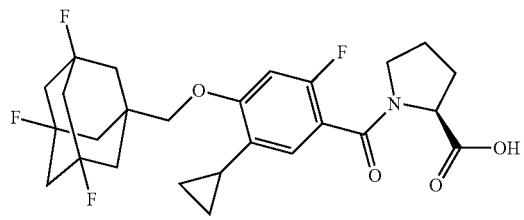 [SMILES: O=C(O)[C@@H]1CCCN1C(=O)c1cc(C2CC2)c(OCC23CC4(F)CC(F)(CC(F)(C4)C2)C3)cc1F]

Step 1. Preparation of (S)-tert-butyl 1-(5-cyclopropyl-2-fluoro-4-((3,5,7-trifluoroadamantan-1-yl)methoxy)benzoyl)pyrrolidine-2-carboxylate

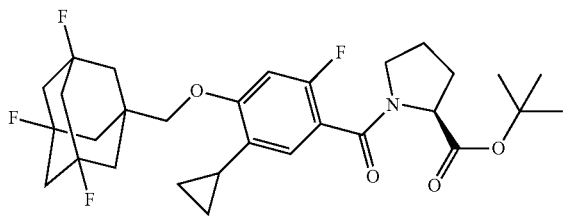 [SMILES: CC(C)(C)OC(=O)[C@@H]1CCCN1C(=O)c1cc(C2CC2)c(OCC23CC4(F)CC(F)(CC(F)(C4)C2)C3)cc1F]

Following the procedure as described in Example 1 step 1, and making variation as required to replace 4-(adamantan-1-ylmethoxy)-5-cyclopropyl-2-fluorobenzoic acid with 5-cyclopropyl-2-fluoro-4-((3,5,7-trifluoroadamantan-1-yl)methoxy)benzoic acid, the title compound was obtained as an colorless foam (0.26 g, 47%): ¹H NMR (300 MHz, CDCl₃) δ 6.96 (d, J=7.8 Hz, 1H), 6.46 (d, J=11.1 Hz, 1H), 4.48-4.41 (m, 1H), 3.78-3.69 (m, 2H), 3.56-3.43 (m, 1H), 3.39-3.30 (m, 1H), 2.30-1.88 (m, 11H), 1.80 (s, 6H), 1.44 (s, 9H), 0.90-0.78 (m, 2H), 0.59-0.52 (m, 2H).

Step 2. (S)-1-(5-cyclopropyl-2-fluoro-4-((3,5,7-trifluoroadamantan-1-yl)methoxy)benzoyl)-pyrrolidine-2-carboxylic Acid

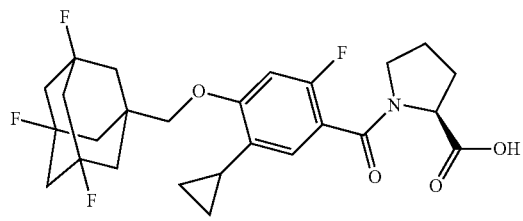 [SMILES: O=C(O)[C@@H]1CCCN1C(=O)c1cc(C2CC2)c(OCC23CC4(F)CC(F)(CC(F)(C4)C2)C3)cc1F]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-cyclopropyl-2-fluoro-4-((3,5,7-trifluoroadamantan-1-yl)methoxy)benzoyl)pyrrolidine-2-carboxylate, the title compound was obtained as an colorless solid (0.21 g, 90%): ¹H NMR (300 MHz, CDCl₃) δ 7.00 (d, J=7.8 Hz, 1H), 6.50 (d, J=11.4 Hz, 1H), 4.73-4.65 (m, 1H), 3.79 (s, 2H), 3.54-3.38 (m, 2H), 2.44-1.69 (m, 17H), 0.95-0.80 (m, 2H), 0.65-0.57 (m, 2H); MS (ES+) m/z 496.1 (M+1).

Example 5

Synthesis of (S)-1-(5-cyclopropyl-4-(((R)-2-(3,5-dichlorobenzyl)morpholino)methyl)-2-fluorobenzoyl)pyrrolidine-2-carboxylic Acid Trifluoroacetic Acid Salt

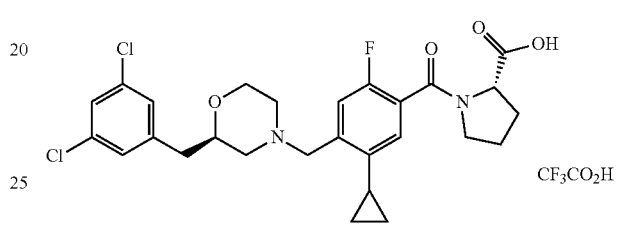

Step 1. Preparation of (R)-1-chloro-3-(3,5-dichlorophenyl)propan-2-ol

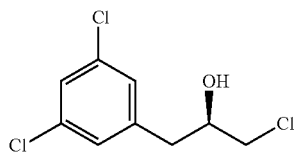 [SMILES: O[C@@H](CCl)Cc1cc(Cl)cc(Cl)c1]

A 250 mL flask was charged with magnesium turnings (1.90 g, 78.00 mmol) and heated via heat gun under hi-vac. The flask was cooled to ambient temperature and flushed with argon before freshly distilled diethyl ether (9 mL) and 1,2-dibromoethane (2 drops) were added. The flask was equipped with a condenser before a solution of 1-bromo-3,5-dichlorobenzene (17.64 g, 78.00 mmol) in diethyl ether (84 mL) was added dropwise so as to maintain a gentle reflux. The cloudy solution was stirred for 1 hour at ambient temperature. After cooling to 0° C., copper iodide (1.49 g, 7.80 mmol) was added. After 10 minutes stirring, a solution of (R)-epichlorohydrin (5.1 mL, 65.00 mmol) in diethyl ether (84 mL) was added dropwise. The resulting solution was slowly warmed to ambient temperature and stirred for 18 hours. The reaction mixture was cooled to 0° C., quenched with saturated aqueous ammonium chloride solution (60 mL), and then poured into water (250 mL). The biphasic mixture was stirred until all solids dissolved. The organic layer was separated and the aqueous layer was extracted with ethyl acetate (3×100 mL). The combined organics were washed with brine (150 mL); dried over anhydrous sodium sulfate, filtered and concentrated. The residue was purified using flash chromatography (0% to 10% ethyl acetate in hexanes) to yield the title compound as a colorless oil (12.93 g, 69%): ¹H NMR (300 MHz, CDCl₃) δ 7.27-7.24 (m, 1H), 7.18-7.12 (m, 2H), 4.09-3.98 (m, 1H), 3.62 (dd, J=3.9, 11.2 Hz, 1H), 3.49 (dd, J=6.3, 11.2 Hz, 1H), 2.87-2.79 (m, 2H), 2.22 (br s, 1H).

Step 2. Preparation of (R)-2-(3,5-dichlorobenzyl)morpholine

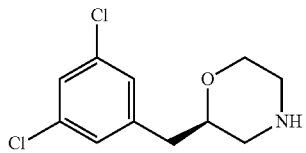 [SMILES: Clc1cc(Cl)cc(C[C@@H]2CNCCO2)c1]

To a solution of sodium hydroxide (12.96 g, 324.0 mmol) in water (26 mL) was added a solution of (R)-1-chloro-3-(3,5-dichlorophenyl)propan-2-ol (12.93 g, 54.0 mmol) in methanol (56 mL). After 5 min, 2-aminoethyl hydrogen sulfate (30.49 g, 215.6 mmol) was added in six portions. The resulting suspension was heated at 40° C. for 3.5 hours. Toluene (130 mL) and sodium hydroxide (12.96 g, 324.0 mmol) were added. The reaction mixture was stirred at 65° C. for 18 hours. After cooling to ambient temperature, the toluene layer was isolated and washed with water (200 mL). The combined aqueous layers were diluted with water (200 mL) and extracted with toluene (200 mL×2). The combined organics were washed with water (150 mL) and brine (100 mL); dried over sodium sulfate, and concentrated. The residue was purified using flash chromatography [0% to 100% (85:14:1 dichloromethane/ethanol/ammonium hydroxide) in dichloromethane] to yield the title compound as a colorless oil (6.98 g, 53%): MS (ES+) m/z 246.1, 248.1 (M+1).

Step 3. Preparation of tert-butyl 5-cyclopropyl-2-fluoro-4-(iodomethyl)benzoate

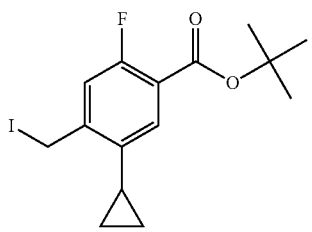 [SMILES: CC(C)(C)OC(=O)c1cc(C2CC2)c(CI)cc1F]

To a suspension of polymer bound triphenylphosphine (2.60 g, 7.80 mmol) in dichloromethane (60 mL) was added imidazole (0.53 g, 7.80 mmol) followed by iodine (2.00 g, 7.80 mmol). After 5 minutes, tert-butyl 5-cyclopropyl-2-fluoro-4-(hydroxymethyl)benzoate (1.60 g, 6.00 mmol) was added. Stirring was continued at ambient temperature for 18 hours, the reaction mixture was filtered and the filtrate was washed with saturated aqueous sodium bisulfate solution (50 mL), and water (50 mL). The organic layer was dried over sodium sulfate, and concentrated. The residue was dissolved in ethyl acetate (100 mL) and washed with saturated aqueous sodium bisulfate solution (20 mL), 1.0N hydrochloric acid solution (20 mL), and brine (20 mL). The organic layer was dried over sodium sulfate, and concentrated to yield the title compound as a yellow solid (2.14 g, 94%): $^1$H NMR (300 MHz, CDCl$_3$) δ 7.50 (d, J=7.3 Hz, 1H), 7.05 (d, J=10.9 Hz, 1H), 4.58 (m, 2H), 1.97-1.84 (m, 1H), 1.58 (s, 9H), 1.08-0.99 (m, 2H), 0.78-0.70 (m, 2H).

Step 4. Preparation of (R)-tert-butyl 5-cyclopropyl-4-((2-(3,5-dichlorobenzyl)morpholino)-methyl)-2-fluorobenzoate

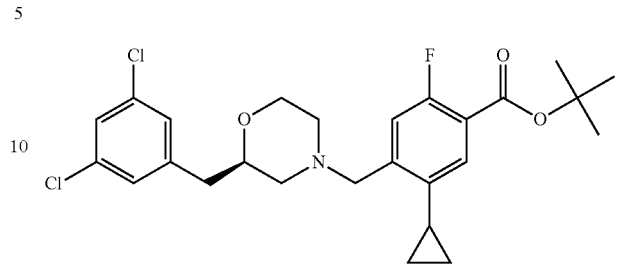

To a microwave vial was added tert-butyl 5-cyclopropyl-2-fluoro-4-(iodomethyl)benzoate (0.14 g, 0.37 mmol), (R)-2-(3,5-dichlorobenzyl)morpholine (0.18 g, 0.75 mmol), potassium phosphate (0.16 g, 0.75 mmol) and N,N-dimethyl formamide (8 mL). The reaction mixture was heated in the microwave reactor at 80° C. for 2 hours, cooled to ambient temperature and diluted with water (200 mL) and ethyl acetate (100 mL). The organic layer was separated and the aqueous layer was extracted with ethyl acetate (50 mL×3). The combined organics were concentrated and the residue was purified by flash chromatography (0% to 10% ethyl acetate in hexanes) to yield the title compound (0.18 g, 98%): MS (ES+) m/z 494.2, 496.2 (M+1).

Step 5. Preparation of (R)-5-cyclopropyl-4-((2-(3,5-dichlorobenzyl)morpholino)methyl)-2-fluorobenzoic Acid Hydrochloride

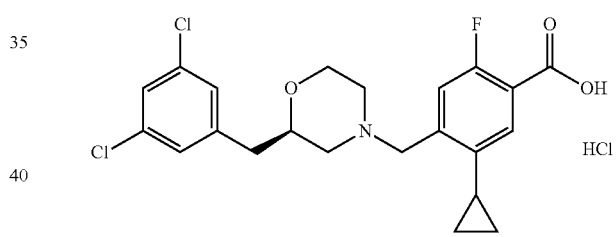

A solution of (R)-tert-butyl 5-cyclopropyl-4-((2-(3,5-dichlorobenzyl)morpholino)-methyl)-2-fluorobenzoate (0.18 g, 0.36 mmol) and concentrated hydrochloric acid (0.8 mL, 9.46 mmol) in 1,4-dioxane (4 mL) was stirred at ambient temperature for 18 hours. The reaction mixture was diluted with toluene (10 mL) and concentrated in vacuo. The residue was dried to yield the title compound as a white solid (0.08 g, 49%): MS (ES+) m/z 437.9, 439.9 (M+1); MS (ES-) m/z 436.0, 438.0 (M-1).

Step 6. Preparation of (S)-tert-butyl 1-(5-cyclopropyl-4-(((R)-2-(3,5-dichlorobenzyl)morpholino)-methyl)-2-fluorobenzoyl)pyrrolidine-2-carboxylate

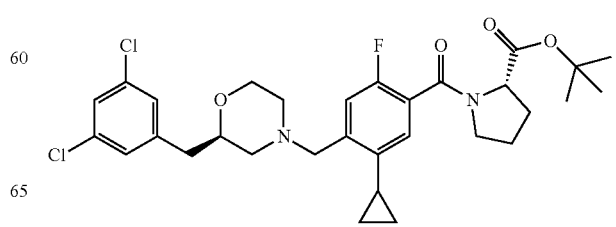

Following the procedure as described in Example 1 step 1, and making variation as required to replace 4-(adamantan-1-ylmethoxy)-5-cyclopropyl-2-fluorobenzoic acid with (R)-5-cyclopropyl-4-((2-(3,5-dichlorobenzyl)morpholino)methyl)-2-fluorobenzoic acid hydrochloride, the title compound was obtained as a white solid (0.09 g, 80%): MS (ES+) m/z 591.2, 593.2 (M+1).

Step 7. Preparation of (S)-1-(5-cyclopropyl-4-(((R)-2-(3,5-dichlorobenzyl)morpholino)methyl)-2-fluorobenzoyl)pyrrolidine-2-carboxylic Acid Trifluoroacetic Acid Salt

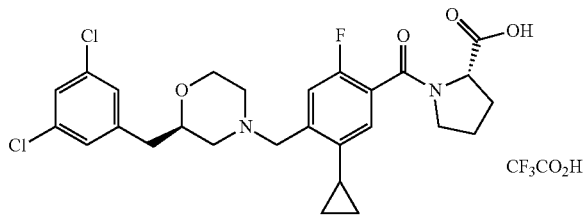

To a solution of (S)-tert-butyl 1-(5-cyclopropyl-4-(((R)-2-(3,5-dichlorobenzyl)morpholino) methyl)-2-fluorobenzoyl)pyrrolidine-2-carboxylate (0.09 g, 0.15 mmol) in dichloromethane (2 mL) was added trifluoroacetic acid (2 mL). The reaction mixture was stirred at ambient temperature for 18 hours, and concentrated in vacuo. The residue was dissolved in ethyl acetate (20 mL) and washed with saturated ammonium chloride solution (10 mL×2). The organic layer was dried over anhydrous sodium sulfate and concentrated in vacuo. The residue was purified by reverse-phase preparative HPLC to yield the title compound as a colorless solid (0.06 g, 69%): $^1$H NMR (300 MHz, DMSO-$d_6$) δ 7.49-7.38 (m, 2H), 7.30 (d, J=1.8 Hz, 2H) 6.99 (d, J=6.8 Hz, 0.7H), 6.90 (d, J=6.8 Hz, 0.3H), 4.58-4.52 (m, 2H), 4.37 (dd, J=4.3, 8.7 Hz, 1H), 4.12-3.94 (m, 2H), 3.94-3.80 (m, 1H), 3.77-3.60 (m, 1H), 3.39-3.08 (m, 4H), 3.03-2.69 (m, 3H), 2.34-2.18 (m, 1H), 2.18-2.05 (m, 1H), 2.00-1.74 (m, 3H), 1.07-0.92 (m, 2H), 0.78-0.56 (m, 2H); MS (ES+) m/z 535.1, 537.1 (M+1), (ES−) m/z 533.2, 535.2 (M−1).

Example 6

Synthesis of 1-(4-(adamantan-1-ylmethoxy)-5-cyclopropyl-2-fluorobenzamido)-cyclopropanecarboxylic Acid

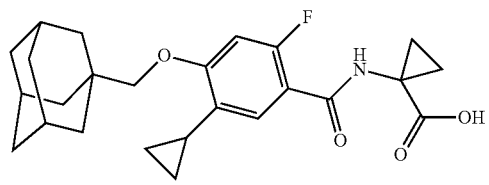 [SMILES: O=C(NC1(C(=O)O)CC1)c1cc(C2CC2)c(OCC23CC4CC(CC(C4)C2)C3)cc1F]

Step 1. Preparation of ethyl 1-(4-(adamantan-1-ylmethoxy)-5-cyclopropyl-2-fluorobenzamido)-cyclopropanecarboxylate

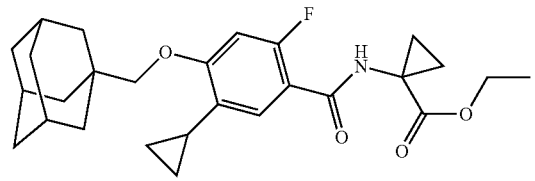 [SMILES: CCOC(=O)C1(NC(=O)c2cc(C3CC3)c(OCC34CC5CC(CC(C5)C3)C4)cc2F)CC1]

Following the procedure as described in Example 1 step 1, and making variation as required to replace (S)-tert-butyl pyrrolidine-2-carboxylate hydrochloride with ethyl 1-aminocyclopropanecarboxylate hydrochloride, the title compound was obtained as an colorless foam (0.88 g, 96%): $^1$H NMR (300 MHz, CDCl$_3$) δ 7.59 (d, J=9.3 Hz, 1H), 7.08 (d, J=14.1 Hz, 1H), 6.48 (d, J=14.4 Hz, 1H), 4.12 (q, J=7.2 Hz, 2H), 3.50 (s, 2H), 2.11-1.97 (m, 4H), 1.79-1.58 (m, 14H), 1.25-1.16 (m, 5H), 0.92-0.84 (m, 2H), 0.68-0.62 (m, 2H).

Step 2. Preparation of 1-(4-(adamantan-1-ylmethoxy)-5-cyclopropyl-2-fluorobenzamido)cyclopropanecarboxylic Acid

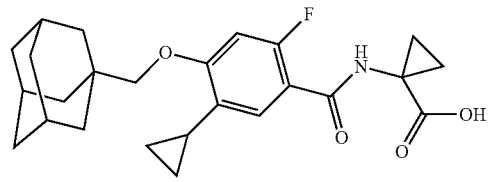 [SMILES: O=C(NC1(C(=O)O)CC1)c1cc(C2CC2)c(OCC23CC4CC(CC(C4)C2)C3)cc1F]

To a solution of ethyl 1-(4-(adamantan-1-ylmethoxy)-5-cyclopropyl-2-fluorobenzamido)cyclopropanecarboxylate (0.23 g, 0.50 mmol) in tetrahydrofuran (20 mL) and water (4 mL) was added lithium hydroxide (0.06 g, 2.50 mmol). The reaction mixture was stirred at ambient temperature for 50 hours, and then concentrated in vacuo to remove most of volatiles. The residue was acidified to pH~1 with 5% hydrochloric acid solution; the solid was collected by filtration and washed with hexanes to give the title compound as a colorless solid (0.20 g, 93%): $^1$H NMR (300 MHz, DMSO-$d_6$) δ 8.44 (d, J=5.4 Hz, 1H), 7.16 (d, J=8.7 Hz, 1H), 6.84 (d, J=13.2 Hz, 1H), 3.61 (s, 2H), 2.02-1.93 (m, 4H), 1.76-1.62 (m, 12H), 1.28-1.13 (m, 5H), 0.94-0.86 (m, 2H), 0.63-0.57 (m, 2H); MS (ES+) m/z 428.2 (M+1).

Example 7

Synthesis of 1-(4-(adamantan-1-ylmethoxy)-5-cyclopropyl-2-fluoro-N-methylbenzamido)-cyclopropanecarboxylic Acid

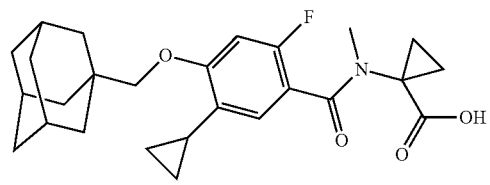 [SMILES: CN(C(=O)c1cc(C2CC2)c(OCC23CC4CC(CC(C4)C2)C3)cc1F)C1(C(=O)O)CC1]

Step 1. Preparation of ethyl 1-(4-(adamantan-1-ylmethoxy)-5-cyclopropyl-2-fluoro-N-methylbenzamido)cyclopropanecarboxylate

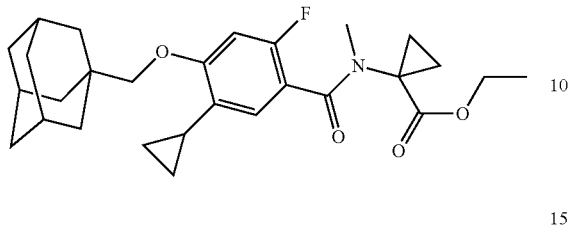

To a solution of ethyl 1-(4-(adamantan-1-ylmethoxy)-5-cyclopropyl-2-fluorobenzamido)-cyclopropanecarboxylate (0.28 g, 0.61 mmol) in N,N-dimethyl formamide (20 mL) was added cesium carbonate (0.80 g, 2.45 mmol) and iodomethane (0.15 mL, 2.40 mmol). The reaction mixture was stirred at ambient for 50 hours, diluted with ethyl acetate (200 mL), and washed with water and brine; dried over anhydrous sodium sulfate and concentrated in vacuo. Purification of the residue by column chromatography (10% ethyl acetate in hexanes) afforded the title compound as a colorless solid (0.24 g, 83%): $^1$H NMR (300 MHz, CDCl$_3$) δ 6.91 (d, J=7.8 Hz, 0.5H), 6.73 (d, J=7.8 Hz, 0.5H), 6.50-6.42 (m, 1H), 4.22-4.04 (m, 2H), 3.46 (s, 2H), 3.11 (s, 1.5H), 2.92 (s, 1.5H), 2.08-1.94 (m, 4H), 1.82-1.55 (m, 13H), 1.32-1.18 (m, 5H), 1.10-0.95 (m, 1H), 0.90-0.79 (m, 2H), 0.63-0.44 (m, 2H).

Step 2. Preparation of 1-(4-(adamantan-1-ylmethoxy)-5-cyclopropyl-2-fluoro-N-methylbenzamido)cyclopropanecarboxylic Acid

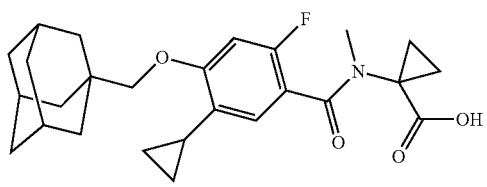 [SMILES: CN(C(=O)c1cc(C2CC2)c(OCC23CC4CC(CC(C4)C2)C3)cc1F)C1(C(=O)O)CC1]

To a solution of ethyl 1-(4-(adamantan-1-ylmethoxy)-5-cyclopropyl-2-fluoro-N-methylbenzamido)cyclopropanecarboxylate (0.24 g, 0.51 mmol) in tetrahydrofuran (20 mL) and water (4 mL) was added lithium hydroxide (0.10 g, 4.16 mmol). The reaction mixture was heated at 70° C. for 20 hours, and then concentrated in vacuo to remove most of volatiles. The residue was acidified to pH~1 with 10% hydrochloric acid solution; the solid was collected by filtration and washed with hexanes to give the title compound as a colorless solid (0.21 g, 93%): $^1$H NMR (300 MHz, CDCl$_3$) δ 11.65 (br s, 1H), 6.99 (d, J=7.8 Hz, 0.6H), 6.81 (d, J=7.8 Hz, 0.4H), 6.53-6.42 (m, 1H), 3.47 (s, 2H), 3.13 (s, 1H), 2.96 (s, 2H), 2.01 (br s, 4H), 1.79-1.62 (m, 12H), 1.42-1.08 (m, 4H), 0.91-0.82 (m, 2H), 0.65-0.43 (m, 2H); MS (ES+) m/z 442.1 (M+1).

Example 8

Synthesis of 2-(4-(adamantan-1-ylmethoxy)-5-cyclopropyl-2-fluorobenzamido)-2-methylpropanoic Acid

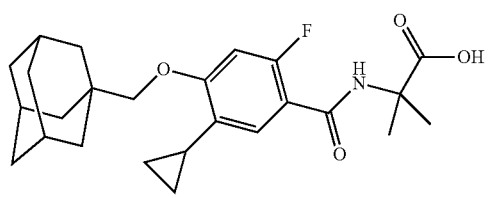 [SMILES: CC(C)(NC(=O)c1cc(C2CC2)c(OCC23CC4CC(CC(C4)C2)C3)cc1F)C(=O)O]

Step 1. Preparation of methyl 2-(4-(adamantan-1-ylmethoxy)-5-cyclopropyl-2-fluorobenzamido)-2-methylpropanoate

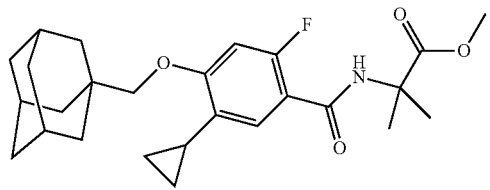 [SMILES: COC(=O)C(C)(C)NC(=O)c1cc(C2CC2)c(OCC23CC4CC(CC(C4)C2)C3)cc1F]

Following the procedure as described in Example 1 step 1, and making variation as required to replace (S)-tert-butyl pyrrolidine-2-carboxylate hydrochloride with methyl 2-amino-2-methylpropanoate hydrochloride, the title compound was obtained as an colorless foam (0.34 g, 76%): $^1$H NMR (300 MHz, CDCl$_3$) δ 7.53 (d, J=9.3 Hz, 1H), 7.15 (d, J=14.7 Hz, 1H), 6.47 (d, J=14.1 Hz, 1H), 3.71 (s, 3H), 3.48 (s, 2H), 2.03 (br s, 4H), 1.76-1.58 (m, 18H), 0.88-0.80 (m, 2H), 0.66-0.59 (m, 2H).

Step 2. Preparation of 2-(4-(adamantan-1-ylmethoxy)-5-cyclopropyl-2-fluorobenzamido)-2-methylpropanoic Acid

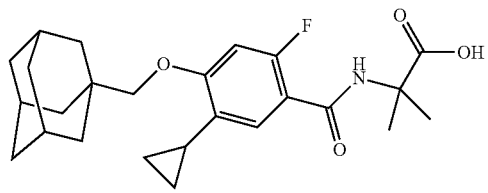 [SMILES: CC(C)(NC(=O)c1cc(C2CC2)c(OCC23CC4CC(CC(C4)C2)C3)cc1F)C(=O)O]

Following the procedure as described in Example 6 step 2, and making variation as required to replace ethyl 1-(4-(adamantan-1-ylmethoxy)-5-cyclopropyl-2-fluorobenzamido)-cyclopropanecarboxylate with methyl 2-(4-(adamantan-1-ylmethoxy)-5-cyclopropyl-2-fluorobenzamido)-2-methylpropanoate, the title compound was obtained as an colorless foam (0.23 g, 98%): $^1$H NMR (300 MHz, CDCl$_3$) δ 7.55 (d, J=9.3 Hz, 1H), 7.13 (d, J=15.3 Hz, 1H), 6.48 (d, J=15.6 Hz, 1H), 3.50 (s, 2H), 2.01 (br s, 4H), 1.78-1.59 (m, 18H), 0.92-0.84 (m, 2H), 0.68-0.61 (m, 2H); MS (ES+) m/z 430.1 (M+1).

Example 9

Synthesis of (R)-1-(5-cyclopropyl-4-(1-(3,4-dichlorophenoxy)ethyl)-2-fluorobenzamido)cyclopropanecarboxylic Acid

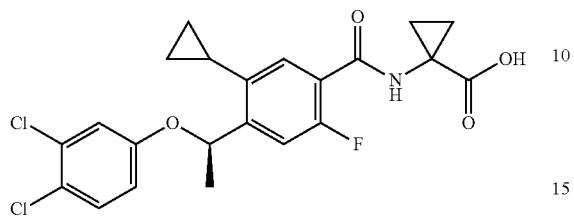

Step 1. Preparation of (R)-ethyl 1-(5-cyclopropyl-4-(1-(3,4-dichlorophenoxy)ethyl)-2-fluorobenzamido)cyclopropanecarboxylate

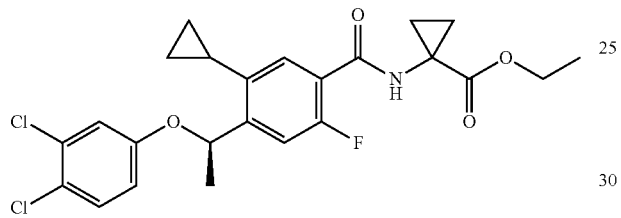

Following the procedure as described in Example 1 step 1, and making variations as required to replace 4-(adamantan-1-ylmethoxy)-5-cyclopropyl-2-fluorobenzoic acid with (R)-5-cyclopropyl-4-(1-(3,4-dichlorophenoxy)ethyl)-2-fluorobenzoic acid and to replace (S)-tert-butyl pyrrolidine-2-carboxylate hydrochloride with ethyl 1-aminocyclopropanecarboxylate hydrochloride, the title compound was obtained as an colorless foam (0.17 g, 70%): $^1$H NMR (300 MHz, CDCl$_3$) δ 772 (d, J=7.5 Hz, 1H), 7.21-7.06 (m, 3H), 6.86-6.83 (m, 1H), 6.63-6.55 (m, 1H), 5.69 (q, J=6.9 Hz, 1H), 4.10 (q, J=9.0 Hz, 2H), 1.90-1.79 (m, 1H), 1.65-1.58 (m, 5H), 1.26-1.14 (m, 5H), 1.10-0.93 (m, 2H), 0.90-0.82 (m, 1H), 0.77-0.68 (m, 1H).

Step 2. Preparation of (R)-1-(5-cyclopropyl-4-(1-(3,4-dichlorophenoxy)ethyl)-2-fluorobenzamido)cyclopropanecarboxylic Acid

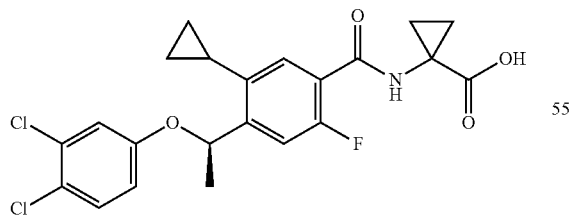

Following the procedure as described in Example 6 step 2, and making variation as required to replace ethyl 1-(4-(adamantan-1-ylmethoxy)-5-cyclopropyl-2-fluorobenzamido)-cyclopropanecarboxylate with (R)-ethyl 1-(5-cyclopropyl-4-(1-(3,4-dichlorophenoxy)ethyl)-2-fluorobenzamido)cyclopropanecarboxylate, the title compound was obtained as an colorless solid (0.11 g, 69%): $^1$H NMR (300 MHz, DMSO-d$_6$) δ 12.45 (br s, 1H), 8.69 (s, 1H), 744 (d, J=8.7 Hz, 1H), 7.17-7.09 (m, 3H), 6.89-6.83 (m, 1H), 5.93 (q, J=12.3 Hz, 1H), 2.14-2.03 (m, 1H), 1.55 (d, J=6.3 Hz, 3H), 1.33-1.27 (m, 2H), 1.17-0.90 (m, 4H), 0.78-0.61 (m, 2H); MS (ES−) m/z 450.0, 452.0 (M−1).

Example 10

Synthesis of (S)-2-(4-(adamantan-1-ylmethoxy)-5-cyclopropyl-2-fluorobenzamido)-3-methoxypropanoic Acid

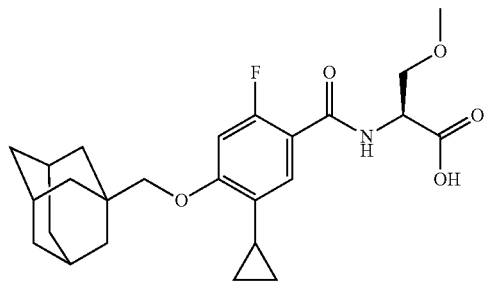 [SMILES: COC[C@H](NC(=O)c1cc(C2CC2)c(OCC23CC4CC(CC(C4)C2)C3)cc1F)C(=O)O]

Step 1. Preparation of (S)-methyl 2-(4-(adamantan-1-ylmethoxy)-5-cyclopropyl-2-fluorobenzamido)-3-methoxypropanoate

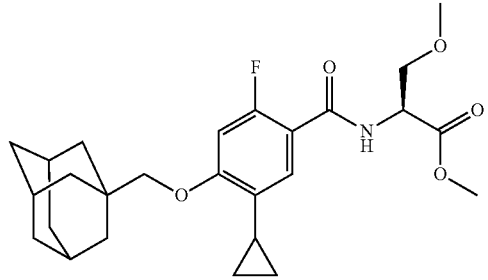 [SMILES: COC[C@H](NC(=O)c1cc(C2CC2)c(OCC23CC4CC(CC(C4)C2)C3)cc1F)C(=O)OC]

Following the procedure as described in Example 1 step 1, and making variation as required to replace (S)-tert-butyl pyrrolidine-2-carboxylate hydrochloride with (S)-methyl 2-amino-3-methoxypropanoate hydrochloride (0.04 g, 0.24 mmol) (prepared as described in *Tetrahedron: Asymmetry* 1998, 9, 3841), the title compound was obtained as an colorless solid (0.08 g, 87%): MS (ES+) m/z 460.2 (M+1).

Step 2. Preparation of (S)-2-(4-(adamantan-1-ylmethoxy)-5-cyclopropyl-2-fluorobenzamido)-3-methoxypropanoic Acid

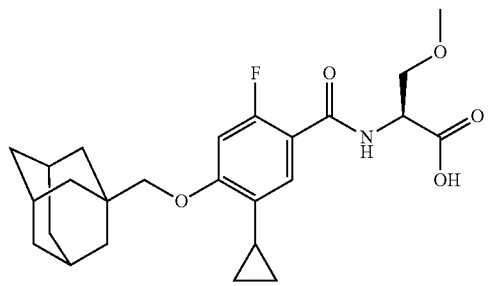 [SMILES: COC[C@H](NC(=O)c1cc(C2CC2)c(OCC23CC4CC(CC(C4)C2)C3)cc1F)C(=O)O]

To a solution of (S)-methyl 2-(4-(adamantan-1-yl-methoxy)-5-cyclopropyl-2-fluorobenzamido)-3-methoxy-propanoate (0.08 g, 0.17 mmol) in tetrahydrofuran (1.8 mL) was added 0.2M lithium hydroxide solution (0.88 mL, 0.17 mmol). After stirring at ambient temperature for 1 hour, the reaction mixture was diluted with diethyl ether (20 mL). The aqueous layer was isolated and extracted with diethyl ether (20 mL×2). The aqueous layer was acidified to pH~1 with 5% aqueous hydrochloric acid solution and extracted with ethyl acetate (50 mL×3). The combined organic extracts were dried over anhydrous sodium sulfate, and concentrated. The residue was purified by flash chromatography [0% to 40% ethyl acetate in hexanes (with 0.1% formic acid as additive)] to yield the title compound as a colorless solid (0.05 g, 67%): $^1$H NMR (300 MHz, CDCl$_3$) δ 7.59 (d, J=9.1 Hz, 2H) 7.49 (dd, J=7.1, 13.8 Hz, 1H), 6.52 (d, J=14.1 Hz, 1H), 4.93-4.88 (m, 1H), 3.97 (dd, J=3.4, 9.6 Hz, 1H), 3.75 (dd, J=3.7, 9.6 Hz, 1H), 3.53 (s, 2H), 3.41 (s, 3H), 2.09-1.98 (m, 4H), 1.82-1.64 (m, 12H), 0.96-0.85 (m, 2H), 0.71-0.64 (m, 2H); MS (ES+) m/z 446.2 (M+1), (ES−) m/z 444.3 (M−1).

Example 11

Synthesis of (S)-2-(4-(adamantan-1-ylmethoxy)-5-cyclopropyl-2-fluorobenzamido)propanoic Acid

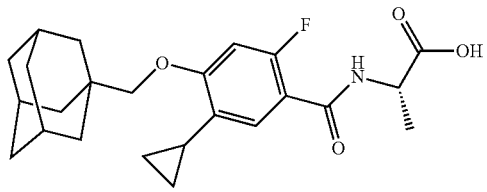 [SMILES: C[C@H](NC(=O)c1cc(C2CC2)c(OCC23CC4CC(CC(C4)C2)C3)cc1F)C(=O)O]

Step 1. Preparation of (S)-methyl 2-(4-(adamantan-1-ylmethoxy)-5-cyclopropyl-2-fluorobenzamido) propanoate

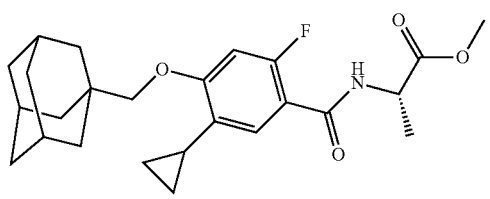 [SMILES: COC(=O)[C@H](C)NC(=O)c1cc(C2CC2)c(OCC23CC4CC(CC(C4)C2)C3)cc1F]

Following the procedure as described in Example 1 step 1, and making variation as required to replace (S)-tert-butyl pyrrolidine-2-carboxylate hydrochloride with (S)-methyl 2-aminopropanoate hydrochloride, the title compound was obtained as an colorless foam (0.70 g, 81%): $^1$H NMR (300 MHz, CDCl$_3$) δ 7.57 (d, J=9.0 Hz, 1H), 7.22-7.14 (m, 1H), 6.50 (d, J=14.1 Hz, 1H), 4.82-4.70 (m, 1H), 3.76 (s, 3H), 3.51 (s, 2H), 2.08-1.98 (m, 4H), 1.80-1.64 (m, 12H), 1.48 (d, J=7.2 Hz, 3H), 0.93-0.85 (m, 2H), 0.68-0.62 (m, 2H).

Step 2. Preparation of (S)-2-(4-(adamantan-1-yl-methoxy)-5-cyclopropyl-2-fluorobenzamido)propanoic Acid

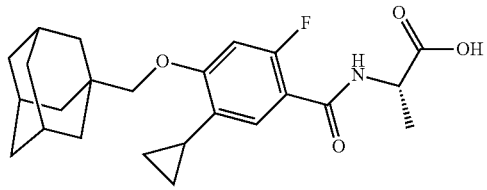 [SMILES: C[C@H](NC(=O)c1cc(C2CC2)c(OCC23CC4CC(CC(C4)C2)C3)cc1F)C(=O)O]

To a solution of (S)-methyl 2-(4-(adamantan-1-yl-methoxy)-5-cyclopropyl-2-fluorobenzamido)propanoate (0.35 g, 0.81 mmol) in tetrahydrofuran (20 mL) and water (4 mL) was added lithium hydroxide (0.03 g, 1.25 mmol). The reaction mixture was stirred at ambient for 20 hours, and then concentrated in vacuo to remove most of volatiles. The residue was acidified to pH~1 with 5% hydrochloric acid aqueous solution; the solid was collected by filtration and washed with hexanes to give the title compound as a colorless solid (0.28 g, 83%): $^1$H NMR (300 MHz, CDCl$_3$) δ 7.56 (d, J=9.0 Hz, 1H), 7.19-7.11 (m, 1H), 6.50 (d, J=14.4 Hz, 1H), 4.78-4.69 (m, 1H), 3.51 (s, 2H), 2.02 (br s, 4H), 1.79-1.64 (m, 12H), 1.54 (d, J=7.2 Hz, 3H), 0.93-0.85 (m, 2H), 0.68-0.62 (m, 2H); MS (ES+) m/z 416.1 (M+1).

Example 12

Synthesis of (S)-1-(5-cyclopropyl-4-((4,4-difluoro-1-methylcyclohexyl)methoxy)-2-fluorobenzoyl)pyr-rolidine-2-carboxylic Acid

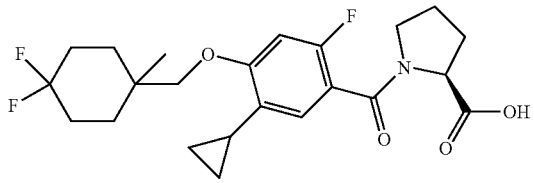 [SMILES: CC1(COc2cc(F)c(C(=O)N3CCC[C@H]3C(=O)O)cc2C2CC2)CCC(F)(F)CC1]

Step 1. Preparation of (S)-tert-butyl 1-(5-cyclopropyl-4-((4,4-difluoro-1-methylcyclohexyl)methoxy)-2-fluorobenzoyl)pyrrolidine-2-carboxylate

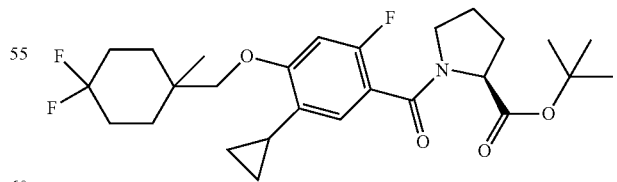

Following the procedure as described in Example 1 step 1, and making variation as required to replace 4-(adamantan-1-ylmethoxy)-5-cyclopropyl-2-fluorobenzoic acid with 5-cyclopropyl-4-((4,4-difluoro-1-methylcyclohexyl) methoxy)-2-fluorobenzoic acid, the title compound was obtained as a colorless oil (0.47 g, 93%): $^1$H NMR (300

MHz, CDCl$_3$) δ 7.04-6.88 (m, 1H), 6.57-6.43 (m, 1H), 4.54-4.18 (m, 1H), 3.82-3.34 (m, 4H), 2.36-2.19 (m, 1H), 2.08-1.72 (m, 10H), 1.67-1.60 (m, 2H), 1.54-1.11 (m, 12H), 0.92-0.81 (m, 2H), 0.65-0.54 (m, 2H); MS (ES+) m/z 496.3 (M+1).

Step 2. Preparation of (S)-1-(5-cyclopropyl-4-((4,4-difluoro-1-methylcyclohexyl)methoxy)-2-fluorobenzoyl)pyrrolidine-2-carboxylic Acid

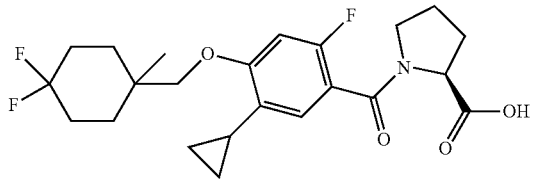 [SMILES: CC1(COc2cc(F)c(C(=O)N3CCC[C@H]3C(=O)O)cc2C2CC2)CCC(F)(F)CC1]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-cyclopropyl-4-((4,4-difluoro-1-methylcyclohexyl)methoxy)-2-fluorobenzoyl)pyrrolidine-2-carboxylate, the title compound was obtained as a colorless solid (0.22 g, 54%): $^1$H NMR (300 MHz, CDCl$_3$) δ 7.05-6.97 (m, 1H), 6.59-6.50 (m, 1H), 4.80-4.69 (m, 1H), 3.71 (s, 2H), 3.57-3.38 (m, 2H), 2.56-2.41 (m, 1H), 2.26-2.09 (m, 1H), 2.07-1.74 (m, 9H), 1.67-1.55 (m, 2H), 1.16 (s, 3H), 0.96-0.86 (m, 2H), 0.67-0.57 (m, 2H); MS (ES+) m/z 440.2 (M+1).

Example 13

Synthesis of (S)-1-(4-(cyclohexylmethoxy)-5-cyclopropyl-2-fluorobenzoyl)pyrrolidine-2-carboxylic Acid

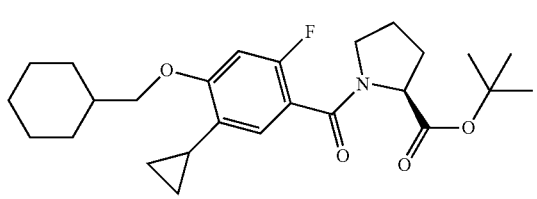 [SMILES: CC(C)(C)OC(=O)[C@@H]1CCCN1C(=O)c1cc(C2CC2)c(OCC2CCCCC2)cc1F]

Step 1. Preparation of (S)-tert-butyl 1-(4-(cyclohexylmethoxy)-5-cyclopropyl-2-fluorobenzoyl)pyrrolidine-2-carboxylate

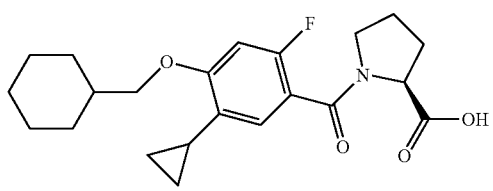 [SMILES: O=C(O)[C@@H]1CCCN1C(=O)c1cc(C2CC2)c(OCC2CCCCC2)cc1F]

Following the procedure as described in Example 1 step 1, and making variation as required to replace 4-(adamantan-1-ylmethoxy)-5-cyclopropyl-2-fluorobenzoic acid with 4-(cyclohexylmethoxy)-5-cyclopropyl-2-fluorobenzoic acid, the title compound was obtained as a colorless oil (0.36 g, 79%): $^1$H NMR (300 MHz, CDCl$_3$) δ 6.96-6.82 (m, 1H), 6.56-6.44 (m, 1H), 4.54-4.19 (m, 1H), 3.83-3.34 (m, 4H), 2.35-2.18 (m, 1H), 2.11-1.65 (m, 10H), 1.53-0.99 (m, 14H), 0.93-0.79 (m, 2H), 0.67-0.52 (m, 2H); MS (ES+) m/z 446.2 (M+1).

Step 2. Preparation of (S)-1-(4-(cyclohexylmethoxy)-5-cyclopropyl-2-fluorobenzoyl)pyrrolidine-2-carboxylic Acid Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-(cyclohexylmethoxy)-5-cyclopropyl-2-fluorobenzoyl)pyrrolidine-2-carboxylate, the title compound was obtained as a colorless solid (0.20 g, 65%): $^1$H NMR (300 MHz, CDCl$_3$) δ 6.98-6.91 (m, 1H), 6.58-6.49 (m, 1H), 4.77-4.70 (m, 1H), 3.82-3.73 (m, 2H), 3.59-3.37 (m, 2H), 2.57-2.43 (m, 1H), 2.25-1.67 (m, 10H), 1.41-1.04 (m, 5H), 0.98-0.81 (m, 2H), 0.71-0.55 (m, 2H); MS (ES−) m/z 388.2 (M−1).

Example 14

Synthesis of (S)-1-(5-cyclopropyl-4-((R)-1-(3,4-dichlorophenoxy)ethyl)-2-fluorobenzoyl)pyrrolidine-2-carboxylic Acid Step 1. Preparation of (S)-tert-butyl 1-(5-cyclopropyl-4-((R)-1-(3,4-dichlorophenoxy)ethyl)-2-fluorobenzoyl)pyrrolidine-2-carboxylate

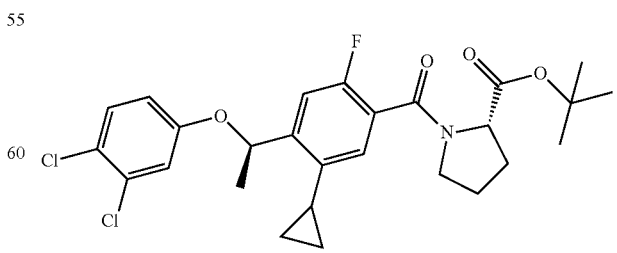

Following the procedure as described in Example 1 step 1, and making variation as required to replace 4-(adamantan-1-ylmethoxy)-5-cyclopropyl-2-fluorobenzoic acid with (R)-

5-cyclopropyl-4-(1-(3,4-dichlorophenoxy)ethyl)-2-fluorobenzoic acid, the title compound was obtained as a colorless oil (0.29 g, 91%): MS (ES+) m/z 522.1, 524.1 (M+1).

Step 2. Preparation of (S)-1-(5-cyclopropyl-4-((R)-1-(3,4-dichlorophenoxy)ethyl)-2-fluorobenzoyl)pyrrolidine-2-carboxylic Acid

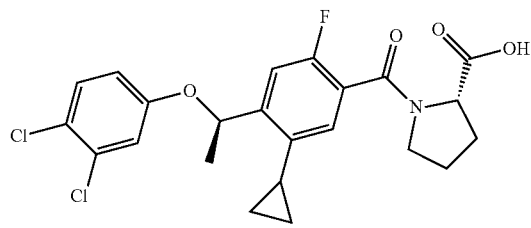 [SMILES: C[C@@H](Oc1ccc(Cl)c(Cl)c1)c1cc(F)c(C(=O)N2CCC[C@H]2C(=O)O)cc1C1CC1]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-cyclopropyl-4-((R)-1-(3,4-dichlorophenoxy)ethyl)-2-fluorobenzoyl)pyrrolidine-2-carboxylate, the title compound was obtained as a colorless solid (0.08 g, 30%): $^1$H NMR (300 MHz, CDCl$_3$) δ 7.26-7.21 (m, 1H), 7.18-7.10 (m, 2H), 6.93-6.87 (m, 1H), 6.67-6.56 (m, 1H), 5.81-5.66 (m, 1H), 4.81-4.68 (m, 1H), 3.55-3.35 (m, 2H), 2.52-2.37 (m, 1H), 2.30-1.80 (m, 4H), 1.67-1.58 (m, 3H), 1.15-0.97 (m, 2H), 0.92-0.67 (m, 2H); MS (ES−) m/z 464.0, 466.0 (M−1).

Example 15

Synthesis of (S)-1-(4-((R)-1-((5-chloro-6-cyclopropylpyridin-3-yl)oxy)ethyl)-5-cyclopropyl-2-fluorobenzoyl)pyrrolidine-2-carboxylic Acid

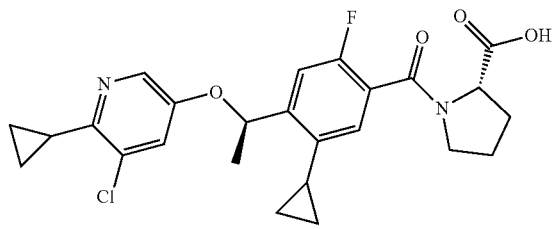 [SMILES: C[C@@H](Oc1cnc(C2CC2)c(Cl)c1)c1cc(F)c(C(=O)N2CCC[C@H]2C(=O)O)cc1C1CC1]

Step 1. Preparation of (S)-tert-butyl 1-(4-((R)-1-((5-chloro-6-cyclopropylpyridin-3-yl)oxy)ethyl)-5-cyclopropyl-2-fluorobenzoyl)pyrrolidine-2-carboxylate

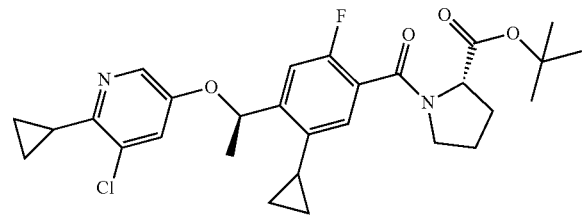 [SMILES: C[C@@H](Oc1cnc(C2CC2)c(Cl)c1)c1cc(F)c(C(=O)N2CCC[C@H]2C(=O)OC(C)(C)C)cc1C1CC1]

Following the procedure as described in Example 1 step 1, and making variation as required to replace 4-(adamantan-1-ylmethoxy)-5-cyclopropyl-2-fluorobenzoic acid with (R)-4-(1-((5-chloro-6-cyclopropylpyridin-3-yl)oxy)ethyl)-5-cyclopropyl-2-fluorobenzoic acid, the title compound was obtained as a colorless oil (0.42 g, 85%): MS (ES+) m/z 529.2, 531.2 (M+1).

Step 2. Preparation of (S)-1-(4-((R)-1-((5-chloro-6-cyclopropylpyridin-3-yl)oxy)ethyl)-5-cyclopropyl-2-fluorobenzoyl)pyrrolidine-2-carboxylic Acid

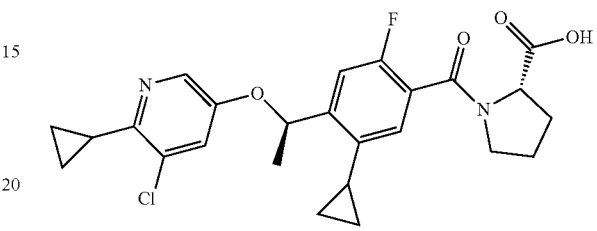

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-((R)-1-((5-chloro-6-cyclopropylpyridin-3-yl)oxy)ethyl)-5-cyclopropyl-2-fluorobenzoyl)pyrrolidine-2-carboxylate, the title compound was obtained as a colorless solid (0.10 g, 27%): $^1$H NMR (300 MHz, CDCl$_3$) δ 7.95-7.89 (m, 1H), 7.23-7.00 (m, 3H), 5.80-5.64 (m, 1H), 4.79-4.54 (m, 1H), 3.49-3.20 (m, 2H), 2.42-2.26 (m, 2H), 2.13-1.92 (m, 2H), 1.89-1.56 (m, 5H), 1.06-0.62 (m, 8H); MS (ES+) m/z 473.2, 475.1 (M+1).

Example 16

Synthesis of (2S)-1-(5-cyclopropyl-4-((3,3-dimethylcyclohexyl)methoxy)-2-fluorobenzoyl)pyrrolidine-2-carboxylic Acid

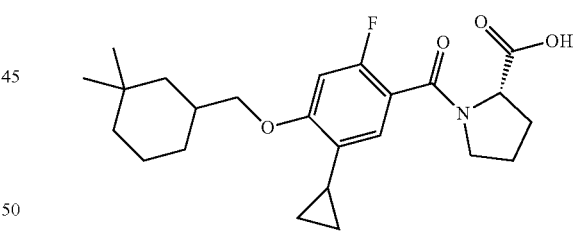

Step 1. Preparation of (2S)-tert-butyl 1-(5-cyclopropyl-4-((3,3-dimethylcyclohexyl)methoxy)-2-fluorobenzoyl)pyrrolidine-2-carboxylate

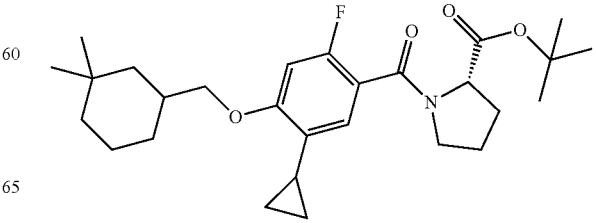

Following the procedure as described in Example 1 step 1, and making variation as required to replace 4-(adamantan-1-ylmethoxy)-5-cyclopropyl-2-fluorobenzoic acid with 5-cyclopropyl-4-((3,3-dimethylcyclohexyl)methoxy)-2-fluorobenzoic acid, the title compound was obtained as a colorless oil (0.33 g, 97%): MS (ES+) m/z 474.3 (M+1).

Step 2. Preparation of (2S)-1-(5-cyclopropyl-4-((3,3-dimethylcyclohexyl)methoxy)-2-fluorobenzoyl)pyrrolidine-2-carboxylic Acid

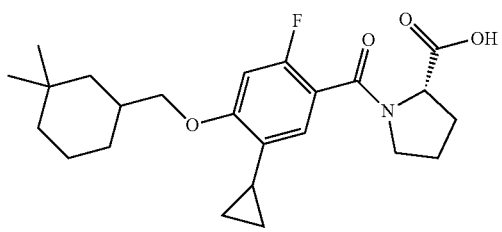 [SMILES: CC1(C)CCCC(COc2cc(F)c(C(=O)N3CCC[C@H]3C(=O)O)cc2C2CC2)C1]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (2S)-tert-butyl 1-(5-cyclopropyl-4-((3,3-dimethylcyclohexyl)methoxy)-2-fluorobenzoyl)pyrrolidine-2-carboxylate, the title compound was obtained as a colorless solid (0.23 g, 79%): $^1$H NMR (300 MHz, CDCl$_3$) δ 6.97-6.92 (m, 1H), 6.57-6.49 (m, 1H), 4.78-4.70 (m, 1H), 3.81-3.68 (m, 2H), 3.58-3.38 (m, 2H), 2.57-2.44 (m, 1H), 2.24-1.83 (m, 6H), 1.70-1.35 (m, 4H), 1.20-1.05 (m, 1H), 1.05-0.84 (m, 10H), 0.68-0.56 (m, 2H); MS (ES+) m/z 418.1 (M+1).

Example 17

Synthesis of (S)-1-(4-(adamantan-1-ylmethoxy)-2-fluoro-5-isopropylbenzoyl)pyrrolidine-2-carboxylic Acid

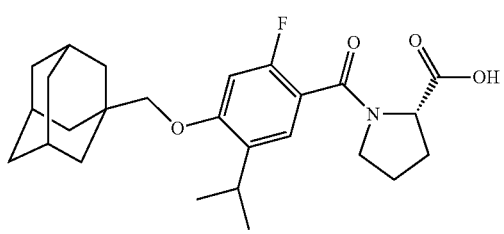 [SMILES: CC(C)c1cc(C(=O)N2CCC[C@H]2C(=O)O)c(F)cc1OCC12CC3CC(CC(C3)C1)C2]

Step 1. Preparation of (S)-tert-butyl 1-(4-(adamantan-1-ylmethoxy)-2-fluoro-5-isopropylbenzoyl)pyrrolidine-2-carboxylate

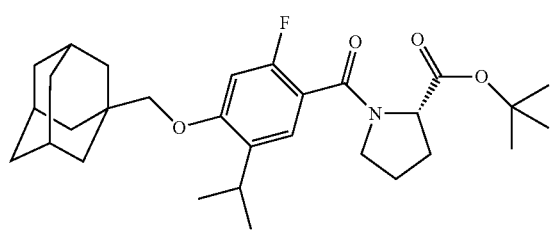 [SMILES: CC(C)c1cc(C(=O)N2CCC[C@H]2C(=O)OC(C)(C)C)c(F)cc1OCC12CC3CC(CC(C3)C1)C2]

Following the procedure as described in Example 1 step 1, and making variation as required to replace 4-(adamantan-1-ylmethoxy)-5-cyclopropyl-2-fluorobenzoic acid with 4-(adamantan-1-ylmethoxy)-2-fluoro-5-isopropylbenzoic acid, the title compound was obtained as a colorless oil (0.31 g, 86%): MS (ES+) m/z 500.3 (M+1).

Step 2. Preparation of (S)-1-(4-(adamantan-1-ylmethoxy)-2-fluoro-5-isopropylbenzoyl)pyrrolidine-2-carboxylic Acid

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-(adamantan-1-ylmethoxy)-2-fluoro-5-isopropylbenzoyl)pyrrolidine-2-carboxylate, the title compound was obtained as a colorless solid (0.22 g, 79%): $^1$H NMR (300 MHz, CDCl$_3$) δ 7.29-7.22 (m, 1H), 6.59-6.50 (m, 1H), 4.81-4.71 (m, 1H), 3.63-3.38 (m, 4H), 3.34-3.18 (m, 1H), 2.62-2.48 (m, 1H), 2.25-1.58 (m, 18H), 1.27-1.13 (m, 6H); MS (ES+) m/z 444.1 (M+1).

Example 18

Synthesis of (S)-1-(5-cyclopropyl-2-fluoro-4-(((1R,2s,3S,5R,7R)-5-fluoroadamantan-2-yl)oxy)benzoyl)pyrrolidine-2-carboxylic Acid

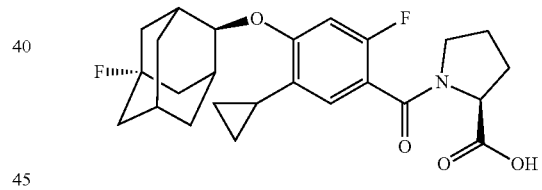

Step 1. Preparation of (S)-tert-butyl 1-(5-cyclopropyl-2-fluoro-4-(((1R,2s,3S,5R,7R)-5-fluoroadamantan-2-yl)oxy)benzoyl)pyrrolidine-2-carboxylate

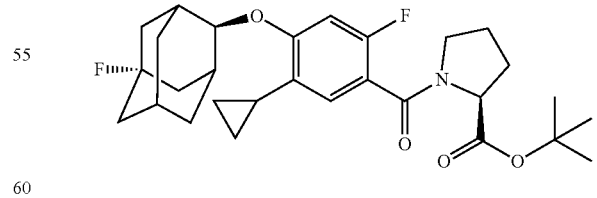

Following the procedure as described in Example 1 step 1, and making variation as required to replace 4-(adamantan-1-ylmethoxy)-5-cyclopropyl-2-fluorobenzoic acid with 5-cyclopropyl-2-fluoro-4-(((1R,2s,3S,5s,7s)-5-fluoroadamantan-2-yl)oxy)benzoic acid, the title compound was obtained as a colorless oil (0.33 g, 91%): MS (ES+) m/z 502.2 (M+1).

Step 2. Preparation of (S)-1-(5-cyclopropyl-2-fluoro-4-(((1R,2s,3S,5R,7R)-5-fluoroadamantan-2-yl)oxy)benzoyl)pyrrolidine-2-carboxylic Acid

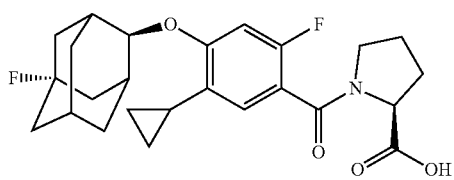 [SMILES: O=C(O)[C@@H]1CCCN1C(=O)c1cc(C2CC2)c(O[C@H]2C3CC4CC2C[C@](F)(C4)C3)cc1F]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with S)-tert-butyl 1-(5-cyclopropyl-2-fluoro-4-(((1R,2s,3S,5R,7R)-5-fluoroadamantan-2-yl)oxy)benzoyl)pyrrolidine-2-carboxylate, the title compound was obtained as a colorless solid (0.13 g, 44%): $^1$H NMR (300 MHz, CDCl$_3$) δ 7.02-6.96 (m, 1H), 6.56-6.48 (m, 1H), 4.80-4.70 (m, 1H), 4.47-4.43 (m, 1H), 3.60-3.38 (m, 2H), 2.58-2.39 (m, 3H), 2.36-1.83 (m, 13H), 1.54-1.42 (m, 2H), 0.97-0.85 (m, 2H), 0.70-0.59 (m, 2H); MS (ES+) m/z 446.0 (M+1).

Example 19

Synthesis of (S)-1-(4-(((1R,3S,5S)-3-(3-chloro-5-(trifluoromethoxy)phenoxy)-8-azabicyclo[3.2.1]octan-8-yl)methyl)-5-cyclopropyl-2-fluorobenzoyl)pyrrolidine-2-carboxylic Acid Trifluoroacetic Acid Salt

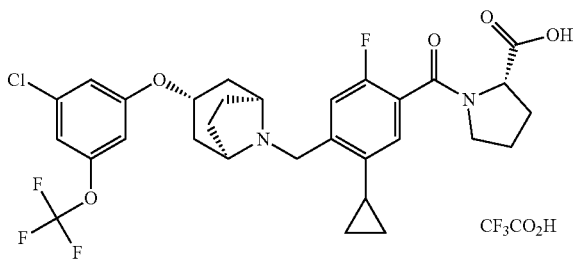 [SMILES: O=C(O)[C@@H]1CCCN1C(=O)c1cc(C2CC2)c(CN2[C@@H]3CC[C@H]2C[C@@H](Oc2cc(Cl)cc(OC(F)(F)F)c2)C3)cc1F ; "CF3CO2H"]

Step 1. Preparation of (S)-tert-butyl 1-(4-(((1R,3S,5S)-3-(3-chloro-5-(trifluoromethoxy)phenoxy)-8-azabicyclo[3.2.1]octan-8-yl)methyl)-5-cyclopropyl-2-fluorobenzoyl)pyrrolidine-2-carboxylate

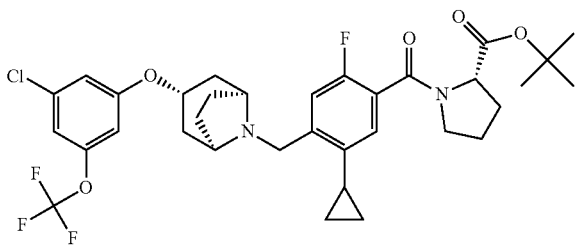 [SMILES: CC(C)(C)OC(=O)[C@@H]1CCCN1C(=O)c1cc(C2CC2)c(CN2[C@@H]3CC[C@H]2C[C@@H](Oc2cc(Cl)cc(OC(F)(F)F)c2)C3)cc1F]

A mixture of 4-(((1R,3r,5S)-3-(3-chloro-5-(trifluoromethoxy)phenoxy)-8-azabicyclo[3.2.1]-octan-8-yl)methyl)-5-cyclopropyl-2-fluorobenzoic acid hydrochloride (0.21 g, 0.39 mmol), N-(3-dimethylaminopropyl)-N'-ethylcarbodiimide hydrochloride (0.11 g, 0.57 mmol), 4-dimethylaminopyridine (0.19 g, 1.52 mmol), and (S)-tert-butyl pyrrolidine-2-carboxylate hydrochloride (0.12 g, 0.57 mmol) in dichloromethane (10 mL) was stirred at ambient temperature for 16 hours. The reaction mixture was diluted with ethyl acetate (50 mL), washed with 1.0 M hydrochloric acid (20 mL), brine (20 mL), dried over anhydrous sodium sulfate, filtered, and concentrated in vacuo. The residue was purified by flash chromatography (2:1 of hexanes:ethyl acetate) to provide the title compound as an oil (0.21 g, 81%): $^1$H NMR (300 MHz, CDCl$_3$) δ 7.29 (d, J=11.0 Hz, 1H), 7.05 (d, J=6.8 Hz, 1H), 6.76 (d, J=12.7 Hz, 2H), 6.55 (s, 1H), 4.53-4.46 (m, 2H), 3.82-3.70 (m, 1H), 3.67-3.60 (m, 2H), 3.56-3.45 (m, 1H), 3.43-3.32 (m, 1H), 3.19-3.11 (m, 2H), 2.34-2.21 (m, 1H), 2.20-2.09 (m, 2H), 2.05-2.00 (m, 3H), 2.00-1.78 (m, 6H), 1.47 (s, 9H), 0.90-0.80 (m, 2H), 0.62-0.52 (m, 2H) (Note: 2 rotamers observed. Data given for dominant rotamer.); MS (ES+) m/z 667.2, 669.2 (M+1).

Step 2. Preparation of (S)-1-(4-(((1R,3S,5S)-3-(3-chloro-5-(trifluoromethoxy)phenoxy)-8-azabicyclo[3.2.1]octan-8-yl)methyl)-5-cyclopropyl-2-fluorobenzoyl)pyrrolidine-2-carboxylic Acid Trifluoroacetic Acid Salt

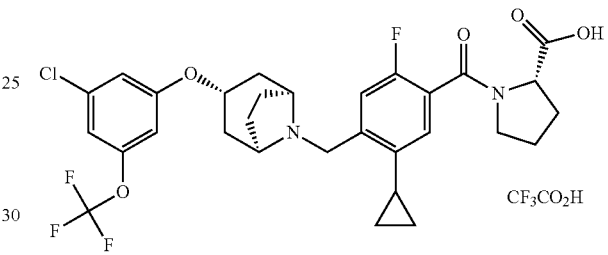

A solution of (S)-tert-butyl 1-(4-(((1R,3S,5S)-3-(3-chloro-5-(trifluoromethoxy)phenoxy)-8-azabicyclo[3.2.1] octan-8-yl)methyl)-5-cyclopropyl-2-fluorobenzoyl)pyrrolidine-2-carboxylate (0.21 g, 0.31 mmol) in dichloromethane (30 mL) was treated with trifluoroacetic acid (10 mL). The resulting mixture was stirred at ambient temperature for 16 h and then concentrated in vacuo to provide the title compound as a colorless solid (0.22 g, quant. yield): $^1$H NMR (300 MHz, DMSO-d$_6$) δ 12.62 (br s, 1H), 9.65 (br s, 1H), 7.55 (d, J=10.3 Hz, 1H), 7.22-7.18 (m, 1H), 7.11-7.03 (m, 2H), 7.01 (d, J=6.8 Hz, 1H), 4.83-4.73 (m, 1H), 4.45-4.30 (m, 2H), 4.12-3.90 (m, 3H), 3.35-3.18 (m, 2H), 2.36-2.18 (m, 5H), 2.15-2.03 (m, 2H), 1.96-1.74 (m, 3H), 1.29-1.15 (m, 2H), 1.03-0.92 (m, 2H), 0.87-0.78 (m, 1H), 0.74-0.65 (m, 2H) (Note: 2 rotamers observed. Data given for dominant rotamer.); MS (ES+) m/z 611.2, 613.3 (M+1).

Example 20

Synthesis of (S)-1-(4-((4-(3-chloro-5-(trifluoromethoxy)phenoxy)piperidin-1-yl)methyl)-5-cyclopropyl-2-fluorobenzoyl)pyrrolidine-2-carboxylic Acid Trifluoroacetic Acid Salt

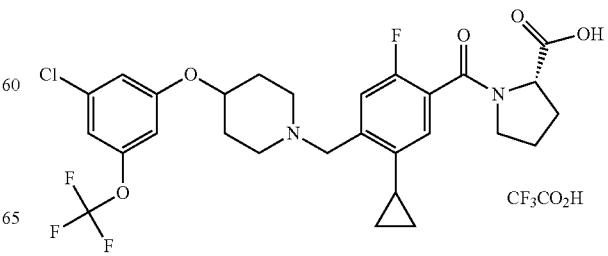

Step 1. Preparation of (S)-tert-butyl 1-(4-((4-(3-chloro-5-(trifluoromethoxy)phenoxy)-piperidin-1-yl)methyl)-5-cyclopropyl-2-fluorobenzoyl)pyrrolidine-2-carboxylate

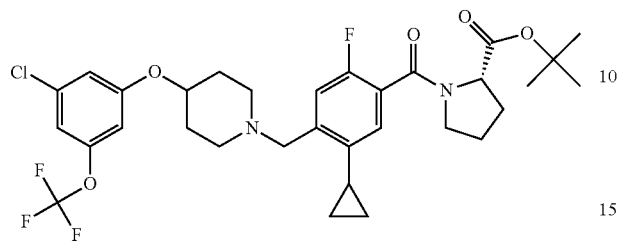

Following the procedure as described in Example 19 step 1, and making variation as required to replace 4-(((1R,3r,5S)-3-(3-chloro-5-(trifluoromethoxy)phenoxy)-8-azabicyclo[3.2.1]octan-8-yl)methyl)-5-cyclopropyl-2-fluorobenzoic acid hydrochloride with 4-((4-(3-chloro-5-(trifluoromethoxy)phenoxy)piperidin-1-yl)methyl)-5-cyclopropyl-2-fluorobenzoic acid hydrochloride, the title compound was obtained as an oil (0.39 g, 97%): $^1$H NMR (300 MHz, CDCl$_3$) δ 7.14 (d, J=10.7 Hz, 1H), 7.06 (d, J=6.7 Hz, 1H), 6.83-6.76 (m, 2H), 6.65-6.61 (m, 1H), 4.49 (dd, J=8.4, 4.8 Hz, 1H), 4.36-4.25 (m, 1H), 3.80-3.70 (m, 1H), 3.65-3.59 (m, 2H), 3.41-3.32 (m, 1H), 2.75-2.65 (m, 2H), 2.40-2.20 (m, 3H), 2.04-1.90 (m, 5H), 1.86-1.74 (m, 3H), 1.47 (s, 9H), 0.92-0.82 (m, 2H), 0.63-0.54 (m, 2H) (Note: 2 rotamers observed. Data given for dominant rotamer.); MS (ES+) m/z 641.2, 643.2 (M+1).

Step 2. (S)-1-(4-((4-(3-chloro-5-(trifluoromethoxy)phenoxy)piperidin-1-yl)methyl)-5-cyclopropyl-2-fluorobenzoyl)pyrrolidine-2-carboxylic Acid Trifluoroacetic Acid Salt

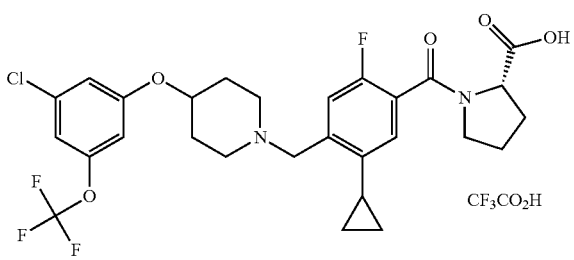 [SMILES: O=C(O)[C@@H]1CCCN1C(=O)c1cc(C2CC2)c(CN2CCC(Oc3cc(Cl)cc(OC(F)(F)F)c3)CC2)cc1F ; "CF3CO2H"]

Following the procedure as described in Example 19, step 2, and making variation as required to replace (S)-tert-butyl 1-(4-(((1R,3S,5S)-3-(3-chloro-5-(trifluoromethoxy)phenoxy)-8-azabicyclo[3.2.1]octan-8-yl)methyl)-5-cyclopropyl-2-fluorobenzoyl)pyrrolidine-2-carboxylate with (S)-tert-butyl 1-(4-((4-(3-chloro-5-(trifluoromethoxy)phenoxy)piperidin-1-yl)methyl)-5-cyclopropyl-2-fluorobenzoyl)pyrrolidine-2-carboxylate, the title compound was obtained as a colorless solid (0.28 g, 66%): $^1$H NMR (300 MHz, DMSO-d$_6$) δ 12.53 (br s, 1H), 9.83 (br s, 1H), 7.49 (d, J=10.3 Hz, 1H), 7.25-7.16 (m, 1H), 7.13-6.84 (m, 3H), 4.91-4.80 (m, 1H), 4.53 (s, 2H), 4.34 (dd, J=8.3, 4.1 Hz, 1H), 3.59-3.43 (m, 2H), 3.39-3.13 (m, 3H), 2.31-1.98 (m, 4H), 1.96-1.71 (m, 4H), 1.34-1.15 (m, 1H), 1.05-0.92 (m, 2H), 0.87-0.77 (m, 1H), 0.73-0.059 (m, 2H) (Note: 2 rotamers observed. Data given for dominant rotamer.); MS (ES+) m/z 585.2, 587.2 (M+1).

Example 21

Synthesis of (S)-1-(4-((1-(5-chloro-4-(trifluoromethyl)pyridin-2-yl)-3-methylazetidin-3-yl)methoxy)-5-cyclopropyl-2-fluorobenzoyl)pyrrolidine-2-carboxylic Acid Trifluoroacetic Acid Salt

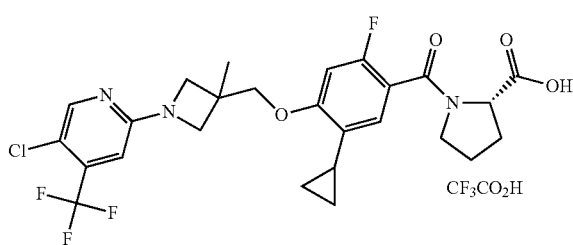 [SMILES: CC1(COc2cc(F)c(C(=O)N3CCC[C@H]3C(=O)O)cc2C2CC2)CN(c2cc(C(F)(F)F)c(Cl)cn2)C1 ; "CF3CO2H"]

Step 1. Preparation of (S)-tert-butyl 1-(4-((1-(5-chloro-4-(trifluoromethyl)pyridin-2-yl)-3-methylazetidin-3-yl)methoxy)-5-cyclopropyl-2-fluorobenzoyl)pyrrolidine-2-carboxylate

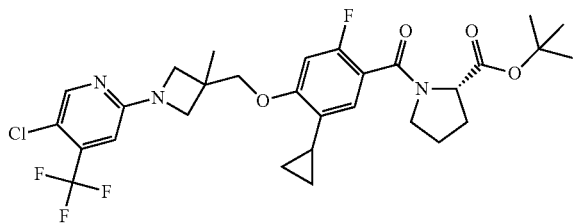 [SMILES: CC1(COc2cc(F)c(C(=O)N3CCC[C@H]3C(=O)OC(C)(C)C)cc2C2CC2)CN(c2cc(C(F)(F)F)c(Cl)cn2)C1]

Following the procedure as described in Example 19 step 1, and making variation as required to replace 4-(((1R,3r,5S)-3-(3-chloro-5-(trifluoromethoxy)phenoxy)-8-azabicyclo[3.2.1]octan-8-yl)methyl)-5-cyclopropyl-2-fluorobenzoic acid hydrochloride with 4-((1-(5-chloro-4-(trifluoromethyl)pyridin-2-yl)-3-methylazetidin-3-yl)methoxy)-5-cyclopropyl-2-fluorobenzoic acid, the title compound was obtained as an oil (0.46 g, 94%): $^1$H NMR (300 MHz, CDCl$_3$) δ 8.16 (s, 1H), 6.93 (d, J=7.7 Hz, 1H), 6.52 (d, J=11.4 Hz, 1H), 6.46 (s, 1H), 4.46 (dd, J=8.4, 5.0 Hz, 1H), 4.20-4.05 (m, 2H), 4.00-3.91 (m, 2H), 3.88-3.69 (m, 2H), 3.54-3.43 (m, 1H), 3.40-3.30 (m, 1H), 2.32-2.18 (m, 1H), 2.01-1.65 (m, 4H), 1.46 (s, 9H), 1.25 (s, 3H), 0.70-0.59 (m, 2H), 0.56-0.45 (m, 2H) (Note: 2 rotamers observed. Data given for dominant rotamer.); MS (ES+) m/z 612.1, 614.1 (M+1).

Step 2. Preparation of (S)-1-(4-((1-(5-chloro-4-(trifluoromethyl)pyridin-2-yl)-3-methyl azetidin-3-yl)methoxy)-5-cyclopropyl-2-fluorobenzoyl)pyrrolidine-2-carboxylic Acid Trifluoroacetic Acid Salt

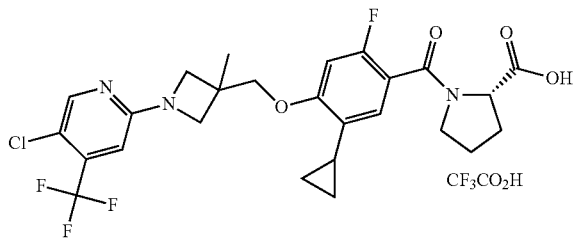 [SMILES: CC1(COc2cc(F)c(C(=O)N3CCC[C@H]3C(=O)O)cc2C2CC2)CN(c2cc(C(F)(F)F)c(Cl)cn2)C1 ; "CF3CO2H"]

Following the procedure as described in Example 19 step 2, and making variation as required to replace (S)-tert-butyl 1-(4-(((1R,3S,5S)-3-(3-chloro-5-(trifluoromethoxy)phenoxy)-8-azabicyclo[3.2.1]octan-8-yl)methyl)-5-cyclopropyl-2-fluorobenzoyl)pyrrolidine-2-carboxylate with (S)-tert-butyl 1-(4-((1-(5-chloro-4-(trifluoromethyl)pyridin-2-yl)-3-methylazetidin-3-yl)methoxy)-5-cyclopropyl-2-fluorobenzoyl)pyrrolidine-2-carboxylate and purification by HPLC (Gemini NX, 5 μm, 30×150 mm; acetonitrile (plus 0.1% trifluoroacetic acid) in water (plus 0.1% trifluoroacetic acid); 20% acetonitrile for 2.5 minutes, 20->80% over 25 minutes), the title compound was obtained as a colorless solid (0.16 g, 32%): $^1$H NMR (300 MHz, DMSO-$d_6$) δ 11.31 (br s, 2H), 8.27 (s, 1H), 6.91 (d, J=11.8 Hz, 1H), 6.77-6.72 (m, 2H), 4.29 (dd, J=8.3, 4.1 Hz, 1H), 4.08-3.98 (m, 4H), 3.78 (d, J=8.9 Hz, 2H), 3.35-3.19 (m, 2H), 2.27-2.12 (m, 1H), 1.93-1.72 (m, 3H), 1.70-1.60 (m, 1H), 1.39 (s, 3H), 0.59-0.42 (m, 4H) (Note: 2 rotamers observed. Data given for dominant rotamer.); MS (ES+) m/z 556.2, 558.2 (M+1).

Example 22

(S)-1-(4-((5-chloro-[1,1'-biphenyl]-2-yl)oxy)-2,5-difluorobenzoyl)pyrrolidine-2-carboxylic Acid

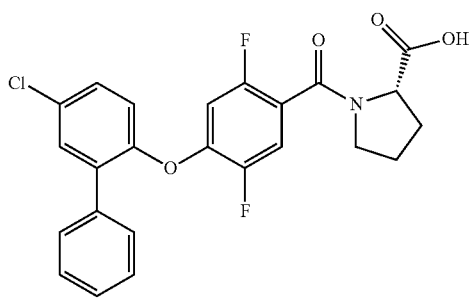 [SMILES: O=C(O)[C@@H]1CCCN1C(=O)c1cc(F)c(Oc2ccc(Cl)cc2-c2ccccc2)cc1F]

Step 1. Preparation of methyl 4-((5-chloro-[1,1'-biphenyl]-2-yl)oxy)-2,5-difluorobenzoate

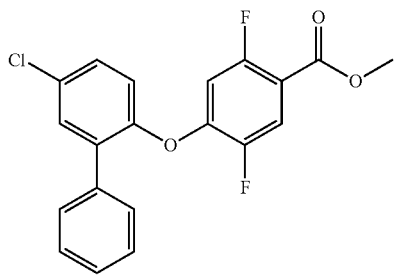 [SMILES: COC(=O)c1cc(F)c(Oc2ccc(Cl)cc2-c2ccccc2)cc1F]

To a solution of 5-chloro-[1,1'-biphenyl]-2-ol (5.0 g, 24.4 mmol) in anhydrous dimethyl sulfoxide (50 mL) was added potassium carbonate (5.1 g, 36.6 mmol) and methyl 2,4,5-trifluorobenzoate (4.4 g, 24.4 mmol) and the reaction mixture was stirred at ambient temperature for 16 hours. The reaction mixture was partitioned between ethyl acetate (400 mL) and water (100 mL), and the organic phase washed with water (50 mL×2), brine (50 mL); dried over anhydrous sodium sulfate and concentrated in vacuo to yield the title compound as a colorless foam (8.9 g, quant. yield): $^1$H NMR (300 MHz, CDCl$_3$) δ 7.61 (dd, J=10.9, 6.6 Hz, 1H), 7.48-7.42 (m, 3H), 7.37-7.26 (m, 4H), 7.05 (d, J=8.6 Hz, 1H), 6.39 (dd, J=11.1, 6.6 Hz, 1H), 3.85 (s, 3H).

Step 2. Preparation of 4-((5-chloro-[1,1'-biphenyl]-2-yl)oxy)-2,5-difluorobenzoic Acid

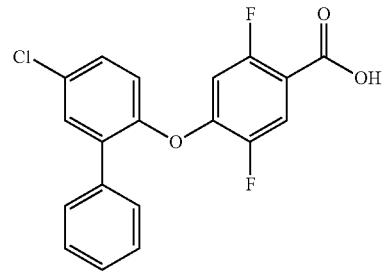 [SMILES: O=C(O)c1cc(F)c(Oc2ccc(Cl)cc2-c2ccccc2)cc1F]

To a solution of methyl 4-((5-chloro-[1,1'-biphenyl]-2-yl)oxy)-2,5-difluorobenzoate (0.5 g, 1.33 mmol) in tetrahydrofuran (5 mL) was added a solution of lithium hydroxide monohydrate (0.28 g, 6.65 mmol) in water (5 mL) and the reaction mixture was stirred at ambient temperature for 16 hours. The reaction mixture was adjusted to pH~1-2 with 1 N hydrochloric acid and diluted with dichloromethane (150 mL). The organic phase was washed with brine (15 mL), dried over anhydrous sodium sulfate and concentrated in vacuo to give the title compound as a colorless solid (0.48 g, quant. yield): MS (ES−) m/z 359.1, 361.1 (M−1).

Step 3. Preparation of (S)-tert-butyl 1-(4-((5-chloro-[1,1'-biphenyl]-2-yl)oxy)-2,5-difluorobenzoyl)pyrrolidine-2-carboxylate

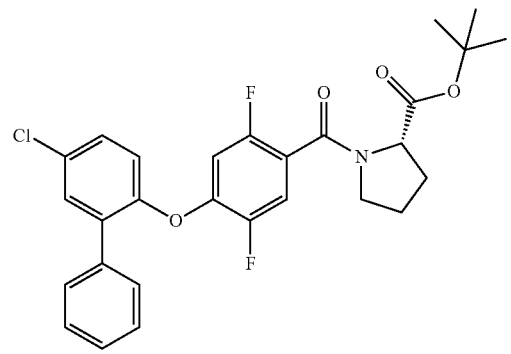 [SMILES: CC(C)(C)OC(=O)[C@@H]1CCCN1C(=O)c1cc(F)c(Oc2ccc(Cl)cc2-c2ccccc2)cc1F]

To a solution of 4-((5-chloro-[1,1'-biphenyl]-2-yl)oxy)-2,5-difluorobenzoic acid (0.48 g, 1.33 mmol) in dichloromethane (10 mL) was added N-(3-dimethylamino-propyl)-N'-ethylcarbodiimide hydrochloride (0.77 g, 4.00 mmol), 4-(dimethylamino)-pyridine (0.49 mg, 4.00 mmol), and (S)-tert-butyl pyrrolidine-2-carboxylate hydrochloride (0.42 g, 2.00 mmol), and the reaction mixture was stirred at ambient temperature for 16 hours. After dilution with dichloromethane (100 mL), the organic phase was washed with 1.0 N hydrochloride solution (2×10 mL), brine (10 mL); dried over anhydrous sodium sulfate and concentrated in vacuo to give the title compound as a colorless foam (0.68 g, 99%): MS (ES+) m/z 514.1, 516.1 (M+1).

Step 4. Preparation of (S)-1-(4-((5-chloro-[1,1'-biphenyl]-2-yl)oxy)-2,5-difluorobenzoyl) pyrrolidine-2-carboxylic Acid

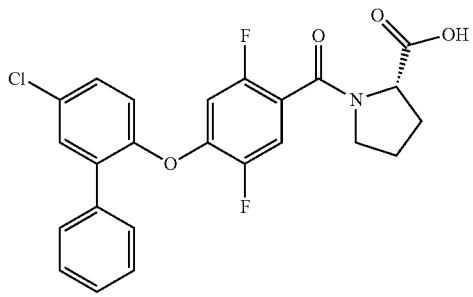 [SMILES: O=C(O)[C@@H]1CCCN1C(=O)c1cc(F)c(Oc2ccc(Cl)cc2-c2ccccc2)cc1F]

To a solution of (S)-tert-butyl 1-(4-((5-chloro-[1,1'-biphenyl]-2-yl)oxy)-2,5-difluorobenzoyl)pyrrolidine-2-carboxylate (0.68 g, 1.32 mmol) in dichloromethane (10 mL) was added trifluoroacetic acid (2 mL). The mixture was stirred at ambient temperature for 16 hours. After concentration in vacuo, the residue was purified by silica gel chromatography (0 to 100% ethyl acetate in hexanes) to provide the title compound as colorless solid (0.30 g, 49%): $^1$H NMR (300 MHz, CDCl$_3$) δ 7.50-7.41 (m, 3H), 7.39-7.25 (m, 5H), 7.17 (dd, J=10.0, 6.1 Hz, 1H), 7.01 (d, J=8.7 Hz, 1H), 6.45 (dd, J=10.0, 6.4 Hz, 1H), 4.64 (dd, J=7.2, 5.5 Hz, 1H), 3.42-3.34 (m, 2H), 2.31-2.20 (m, 2H), 2.07-1.82 (m, 2H); MS (ES−) m/z 456.2, 458.2 (M−1).

Example 23

Synthesis of (S)-1-((4-(adamantan-1-ylmethoxy))-3-chlorobenzoyl)pyrrolidine-2-carboxylic Acid

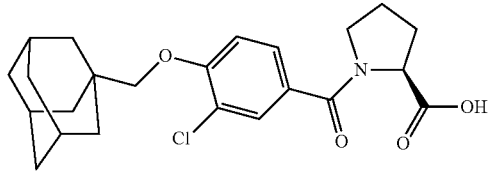 [SMILES: O=C(O)[C@@H]1CCCN1C(=O)c1ccc(OCC23CC4CC(CC(C4)C2)C3)c(Cl)c1]

Step 1. Preparation of 4-(adamantan-1-ylmethoxy)-3-chlorobenzoic Acid

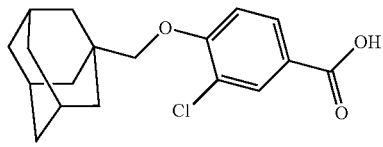 [SMILES: O=C(O)c1ccc(OCC23CC4CC(CC(C4)C2)C3)c(Cl)c1]

To a mixture of 1-adamantemethanol (19 g, 115 mmol) in anhydrous dimethyl sulfoxide (700 mL) was added potassium tert-butoxide (32 g, 290 mmol) and the reaction mixture was stirred for 10 min at ambient temperature. 3-chloro-4-fluorobenzoic acid (20 g, 115 mmol) was added to the reaction mixture, and the resulting thick suspension was allowed to stand at ambient temperature for 16 hours. The reaction mixture was poured into a mixture of 1 N hydrochloric acid (300 mL) and water (300 mL) and the precipitated solid was collected by filtration and washed with water (500 mL), and then dissolved in a mixture of ethyl acetate and tetrahydrofuran (1:1 v/v, 1000 mL). The organic phase was dried over anhydrous magnesium sulfate and concentrated in vacuo to give the title compound as a colorless solid (36.7 g, 99%): $^1$H NMR (300 MHz, DMSO-d$_6$) δ 12.90 (br s, 1H), 7.85 (d, J=2.0 Hz, 1H), 7.82 (dd, J=8.5, 2.1 Hz, 1H), 7.16 (d, J=8.6 Hz, 1H), 3.64 (s, 2H), 1.98-1.90 (m, 3H), 1.73-1.54 (m, 12H).

Step 2. Preparation of (S)-tert-butyl 1-((4-(adamantan-1-ylmethoxy))-3-chlorobenzoyl)pyrrolidine-2-carboxylate

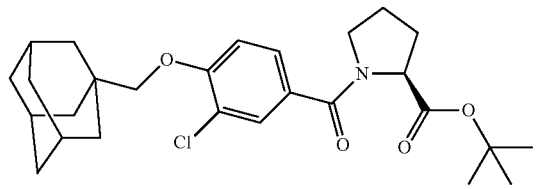 [SMILES: CC(C)(C)OC(=O)[C@@H]1CCCN1C(=O)c1ccc(OCC23CC4CC(CC(C4)C2)C3)c(Cl)c1]

Following the procedure as described in Example 22 Step 3 and making variation as required to replace 4-((5-chloro-[1,1'-biphenyl]-2-yl)oxy)-2,5-difluorobenzoic acid with 4-(adamantan-1-ylmethoxy)-3-chlorobenzoic acid, the title compound was obtained as a colorless solid (0.95 g, quant. yield): MS (ES−) m/z 476.3, 478.3 (M+1).

Step 3. Preparation of (S)-1-((4-(adamantan-1-ylmethoxy))-3-chlorobenzoyl)pyrrolidine-2-carboxylic Acid

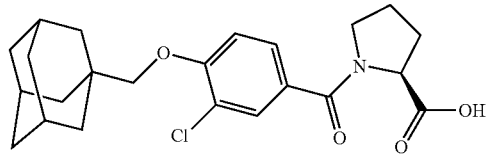 [SMILES: O=C(O)[C@@H]1CCCN1C(=O)c1ccc(OCC23CC4CC(CC(C4)C2)C3)c(Cl)c1]

Following the procedure as described in Example 22 Step 4 and making variation as required to replace (S)-tert-butyl 1-(4-((5-chloro-[1,1'-biphenyl]-2-yl)oxy)-2,5-difluorobenzoyl)pyrrolidine-2-carboxylate with (S)-tert-butyl 1-(4-(adamantan-1-ylmethoxy))-3-chlorobenzoyl)pyrrolidine-2-carboxylate, the title compound was obtained as a colorless solid (0.41 g, 48%): $^1$H NMR (300 MHz, CDCl$_3$) δ 7.60 (d, J=1.7 Hz, 1H), 7.46 (dd, J=8.5, 1.8 Hz, 1H), 6.89 (d, J=8.4 Hz, 1H), 4.76-4.67 (m, 1H), 3.66-3.53 (m, 4H), 2.45-2.26 (m, 1H), 2.27-2.13 (m, 1H), 2.10-1.97 (m, 5H), 1.96-1.84 (m, 1H), 1.80-1.63 (m, 12H); MS (ES−) m/z 416.2, 418.1 (M−1).

Example 24

Synthesis of (S)-1-(5-chloro-4-((5-chloro-6-(2,2,2-trifluoroethoxy)pyridin-3-yl)oxy)-2-fluorobenzoyl)pyrrolidine-2-carboxylic Acid Trifluoroacetic Acid Salt

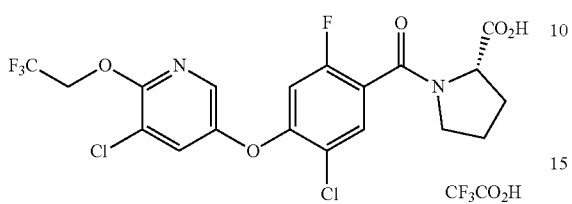

Step 1. Preparation of (S)-tert-butyl 1-(5-chloro-4-((5-chloro-6-(2,2,2-trifluoroethoxy)pyridin-3-yl)oxy)-2-fluorobenzoyl)pyrrolidine-2-carboxylate

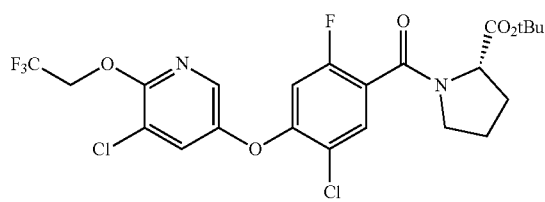 [SMILES: CC(C)(C)OC(=O)[C@@H]1CCCN1C(=O)c1cc(Cl)c(Oc2cnc(OCC(F)(F)F)c(Cl)c2)cc1F]

To a solution of 5-chloro-4-((5-chloro-6-(2,2,2-trifluoroethoxy)pyridin-3-yl)oxy)-2-fluorobenzoic acid (0.20 g, 0.50 mmol) in dichloromethane (3 mL) was added 1-ethyl-3-(3-dimethylaminopropyl)carbodiimide (0.17 g, 0.90 mmol), 4-dimethylaminopyridine (0.140 g, 1.15 mmol) and (S)-tert-butyl pyrrolidine-2-carboxylate hydrochloride (0.09 g, 0.50 mmol). The reaction mixture was stirred at ambient temperature for 16 hours and concentrated in vacuo to remove the solvent. The residue was purified by column chromatography eluting with a gradient of 30 to 70% ethyl acetate in hexanes to afford the title compound as an oil (0.20 g, 74%): MS (ES+) m/z 553.1 (M+1).

Step 2. Preparation of (S)-1-(5-chloro-4-((5-chloro-6-(2,2,2-trifluoroethoxy)pyridin-3-yl)oxy)-2-fluorobenzoyl)pyrrolidine-2-carboxylic Acid Trifluoroacetic Acid Salt

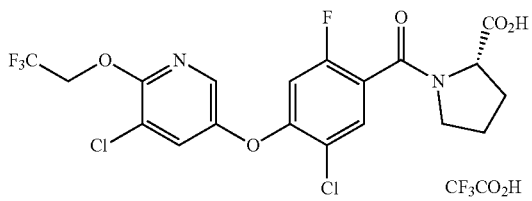 [SMILES: O=C(O)[C@@H]1CCCN1C(=O)c1cc(Cl)c(Oc2cnc(OCC(F)(F)F)c(Cl)c2)cc1F ; "CF3CO2H"]

To a solution of (S)-tert-butyl 1-(5-chloro-4-((5-chloro-6-(2,2,2-trifluoroethoxy)pyridin-3-yl)oxy)-2-fluorobenzoyl)pyrrolidine-2-carboxylate (0.20 g, 0.37 mmol) in dichloromethane (3 mL) was added trifluoroacetic acid (3 mL). After stirring at ambient temperature for 4 hours, the reaction mixture was concentrated and purified by preparative HPLC (gradient of acetonitrile in water) to afford the title compound as a colorless solid (0.07 g, 31%): $^1$H NMR (300 MHz, DMSO-$d_6$) δ 8.14-7.99 (m, 2H), 7.61-7.52 (m, 1H), 7.23-6.88 (m, 1H), 7.17-7.08 (m, 1H), 5.11-4.96 (m, 2H), 4.65-3.94 (m, 1H), 4.38-4.17 (m, 1H), 3.58-3.29 (m, 2H), 2.32-2.16 (m, 1H), 1.99-1.74 (m, 3H); MS (ES+) m/z 497.0, 499.0 (M+1).

Example 25

Synthesis of (S)-1-(4-(2-(3-aminobenzo[d]isoxazol-5-yl)-4-chlorophenoxy)-2,5-difluorobenzoyl)pyrrolidine-2-carboxylic Acid Trifluoroacetic Acid

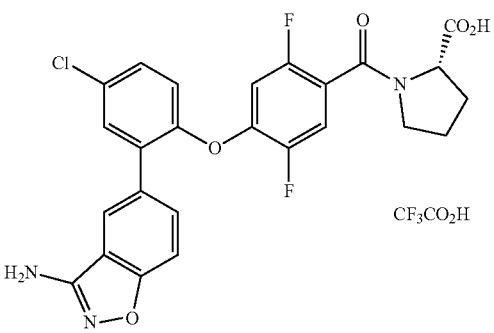 [SMILES: Nc1noc2ccc(-c3cc(Cl)ccc3Oc3cc(F)c(C(=O)N4CCC[C@H]4C(=O)O)cc3F)cc12 ; "CF3CO2H"]

To a solution of 4-(2-(3-aminobenzo[d]isoxazol-5-yl)-4-chlorophenoxy)-2,5-difluorobenzoic acid (0.21 g, 0.50 mmol) in dichloromethane (3 mL) was added 1-ethyl-3-(3-dimethylaminopropyl)-carbodiimide (0.17 g, 0.90 mmol), 4-dimethylaminopyridine (0.150 g, 1.25 mmol) and (S)-tert-butyl pyrrolidine-2-carboxylate hydrochloride (0.085 g, 0.50 mmol). The reaction mixture was stirred at ambient temperature for 16 hours and trifluoroacetic acid (3 mL) was added. After stirring at ambient temperature for 4 hours, the reaction mixture was concentrated and the residue was purified by preparative HPLC (gradient of acetonitrile in water) to afford the title compound as a white solid (0.08 g, 25%): $^1$H NMR (300 MHz, DMSO-$d_6$) δ 8.02-7.91 (m, 1H), 7.68-7.61 (m, 1H), 7.56 (d, J=2.62 Hz, 1H), 7.50-7.39 (m, 2H), 7.38-7.26 (m, 1H), 7.24-7.16 (m, 1H), 7.15-6.87 (m, 2H), 6.84-6.09 (m, 3H), 4.34-4.14 (m, 1H), 3.56-3.10 (m, 2H), 2.29-2.13 (m, 1H), 2.01-1.71 (m, 3H); MS (ES+) m/z 514.1, 516.1 (M+1).

Example 26

Synthesis of (2S)-1-(5-cyclopropyl-4-((1-((3,5-dichlorophenyl)(phenyl)methyl)piperidin-4-yl)methoxy)-2-fluorobenzoyl)pyrrolidine-2-carboxylic Acid Trifluoroacetic Acid Salt

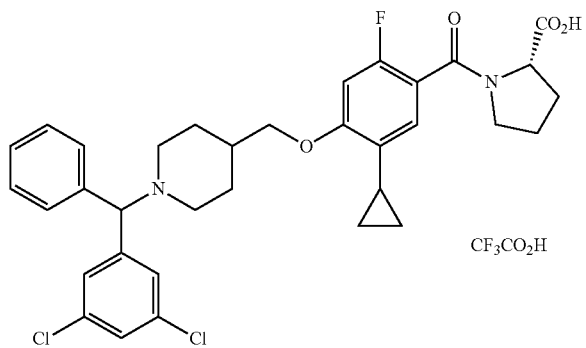 [SMILES: O=C(O)[C@@H]1CCCN1C(=O)c1cc(C2CC2)c(OCC2CCN(C(c3ccccc3)c3cc(Cl)cc(Cl)c3)CC2)cc1F ; "CF3CO2H"]

Following the procedure as described in Example 25, and making variation as required to replace 4-(2-(3-aminobenzo[d]isoxazol-5-yl)-4-chlorophenoxy)-2,5-difluorobenzoic acid with 5-cyclopropyl-4-((1-((3,5-dichlorophenyl)(phenyl)methyl)piperidin-4-yl)methoxy)-2-fluorobenzoic acid, the title compound was obtained as a colorless solid (0.03 g, 21%): $^1$H NMR (300 MHz, CDCl$_3$) δ 7.68-7.55 (m, 4H), 7.51-7.31 (m, 4H), 6.92 (d, J=7.7 Hz, 1H), 6.50 (d, J=11.6 Hz, 1H), 4.91-4.77 (br, s, 1H), 4.71 (dd, J=7.9, 4.2 Hz, 1H), 3.91-3.82 (m, 2H), 3.68-3.34 (m, 4H), 2.80-2.59 (m, 3H), 2.54-2.42 (m, 1H), 2.25-1.82 (m, 9H), 0.92-0.79 (m, 2H), 0.62-0.53 (m, 2H); MS (ES+) m/z 627.0, 625.1 (M+1).

Example 27

Synthesis of (S)-1-(4-(adamantan-1-ylmethoxy)-5-cyclobutyl-2-fluorobenzoyl)pyrrolidine-2-carboxylic Acid

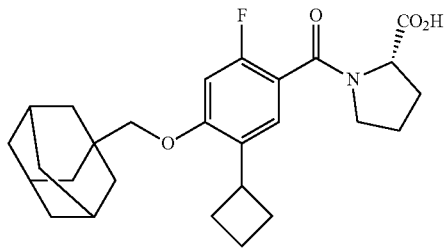 [SMILES: O=C(O)[C@@H]1CCCN1C(=O)c1cc(C2CCC2)c(OCC23CC4CC(CC(C4)C2)C3)cc1F]

Following the procedure as described in Example 25, and making variation as required to replace 4-(2-(3-aminobenzo[d]isoxazol-5-yl)-4-chlorophenoxy)-2,5-difluorobenzoic acid with 4-(adamantan-1-ylmethoxy)-5-cyclobutyl-2-fluorobenzoic acid, the title compound was obtained as a colorless solid (0.03 g, 31%): $^1$H NMR (300 MHz, DMSO-d$_6$) δ 7.08-6.94 (m, 1H), 6.85-6.72 (m, 1H), 4.37-4.09 (m, 1H), 3.97-3.81 (br, s, 2H), 3.64-3.25 (m, 5H), 2.32-2.14 (m, 3H), 2.13-1.90 (m, 6H), 1.90-1.55 (m, 16H); MS (ES+) m/z 456.1 (M+1).

Example 28

Synthesis of (2S)-1-(5-cyclopropyl-4-((1-((3,5-dichlorophenyl)(phenyl)methyl)-3-methylazetidin-3-yl)methoxy)-2-fluorobenzoyl)pyrrolidine-2-carboxylic Acid Trifluoroacetic Acid Salt

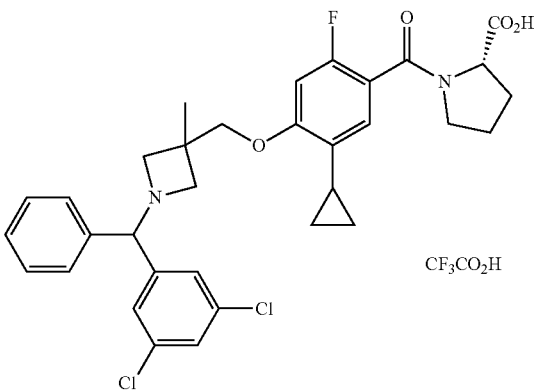 [SMILES: CC1(COc2cc(F)c(C(=O)N3CCC[C@H]3C(=O)O)cc2C2CC2)CN(C(c2ccccc2)c2cc(Cl)cc(Cl)c2)C1 ; "CF3CO2H"]

Following the procedure as described in Example 25, and making variation as required to replace 4-(2-(3-aminobenzo[d]isoxazol-5-yl)-4-chlorophenoxy)-2,5-difluorobenzoic acid with 5-cyclopropyl-4-((1-((3,5-dichlorophenyl)(phenyl)methyl)-3-methylazetidin-3-yl)methoxy)-2-fluorobenzoic acid, the title compound was obtained as a colorless solid (0.06 g, 44%): $^1$H NMR (300 MHz, DMSO-d$_6$) δ 7.64 (t, J=1.7 Hz, 1H), 7.54 (m, 2H), 7.49-7.39 (m, 5H), 6.90-6.67 (m, 2H), 5.81-5.72 (br s, 1H), 4.35-4.26 (m, 1H), 4.15-4.01 (m, 4H), 3.98-3.88 (m, 2H), 3.54-3.43 (m, 1H), 3.33-3.21 (m, 1H), 2.31-2.13 (m, 1H), 2.05-1.70 (m, 5H), 1.43 (s, 3H), 0.84-0.73 (m, 2H), 0.57-0.44 (m, 2H); MS (ES+) m/z 613.0, 611.1 (M+1).

Example 29

Synthesis of (S)-1-(4-((1-((3-(2-chlorophenyl)-1,2,4-oxadiazol-5-yl)methyl)piperidin-4-yl)methoxy)-5-cyclopropyl-2-fluorobenzoyl)pyrrolidine-2-carboxylic Acid Trifluoroacetic Acid Salt

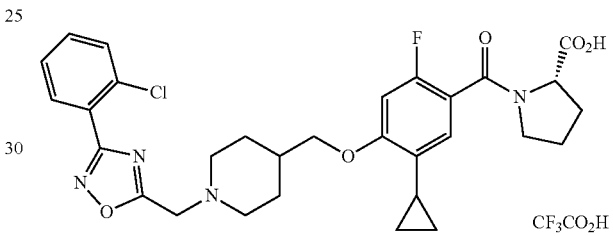

Following the procedure as described in Example 25, and making variation as required to replace 4-(2-(3-aminobenzo[d]isoxazol-5-yl)-4-chlorophenoxy)-2,5-difluorobenzoic acid with 4-((1-((3-(2-chlorophenyl)-1,2,4-oxadiazol-5-yl)methyl)piperidin-4-yl)methoxy)-5-cyclopropyl-2-fluorobenzoic acid, the title compound was obtained as a colorless solid (0.05 g, 37%): $^1$H NMR (300 MHz, CDCl$_3$) δ 7.91 (d, J=7.5 Hz, 1H), 7.55 (d, J=7.8 Hz, 1H), 7.52-7.35 (m, 2H), 6.91 (d, J=7.6 Hz, 1H), 6.47 (d, J=11.3 Hz, 1H), 5.38-4.97 (br, s, 2H), 4.74-4.60 (m, 3H), 3.93-3.68 (m, 4H), 3.50-3.39 (m, 2H), 3.21-3.06 (m, 3H), 2.44-1.78 (m, 10H), 0.97-0.78 (m, 2H), 0.60-0.48 (m, 2H); MS (ES+) m/z 585.1, 583.1 (M+1).

Example 30

Synthesis of (5)-1-(5-chloro-4-((3-chloro-4-(trifluoromethoxy)phenoxy)methyl)-2-fluorobenzoyl)pyrrolidine-2-carboxylic Acid

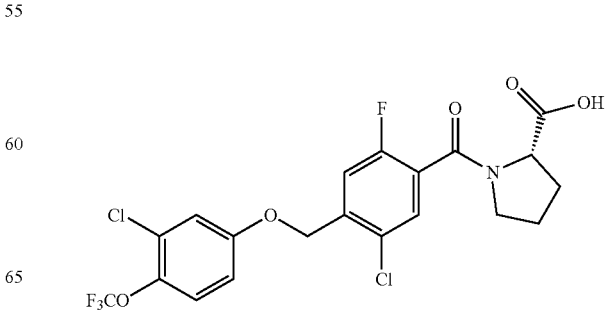

Step 1. Preparation of (S)-tert-butyl 1-(5-chloro-4-((3-chloro-4-(trifluoromethoxy)-phenoxy)methyl)-2-fluorobenzoyl)pyrrolidine-2-carboxylate

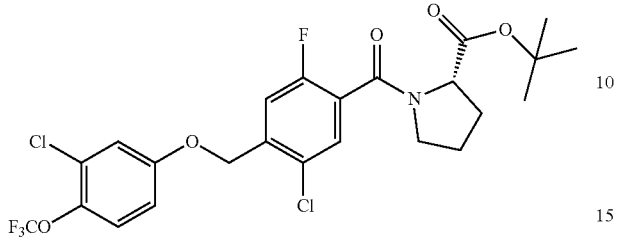

Following the procedure as described in Example 1 step 1 and making variations as required to replace 4-(adamantan-1-ylmethoxy)-5-cyclopropyl-2-fluorobenzoic acid with 5-chloro-4-((3-chloro-4-(trifluoromethoxy)phenoxy)methyl)-2-fluorobenzoic acid, the title compound was obtained as a colorless syrup (0.42 g, 92%): $^1$H NMR (300 MHz, CDCl$_3$) δ 7.48 (d, J=5.8 Hz, 0.7H), 7.38 (d, J=5.9 Hz, 0.3H), 7.32-7.22 (m, 2H), 7.07-7.05 (m, 1H), 6.88-6.82 (m, 1H), 5.09-5.07 (m, 2H), 4.50 (dd, J=8.5, 4.4 Hz, 0.7H), 4.15-4.10 (m, 0.3H), 3.83-3.68 (m, 0.6H), 3.55-3.47 (m, 0.7H), 3.42-3.35 (m, 0.7H), 2.33-2.23 (m, 1H), 2.06-1.85 (m, 3H), 1.47 (s, 6H), 1.28 (s, 3H); MS (ES+) m/z 553.9, 552.2 (M+1).

Step 2. Preparation of (S)-1-(5-chloro-4-((3-chloro-4-(trifluoromethoxy)phenoxy)methyl)-2-fluorobenzoyl)pyrrolidine-2-carboxylic Acid

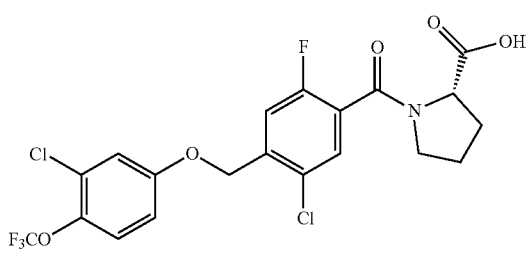 [SMILES: O=C(O)[C@@H]1CCCN1C(=O)c1cc(Cl)c(COc2ccc(OC(F)(F)F)c(Cl)c2)cc1F]

Following the procedure as described in Example 1 step 2 and making variations as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-chloro-4-((3-chloro-4-(trifluoromethoxy)phenoxy)methyl)-2-fluorobenzoyl)pyrrolidine-2-carboxylate, the title compound was obtained as a colorless solid (0.38 g, quant. yield): $^1$H NMR (300 MHz, CDCl$_3$) δ 7.56 (br s, 1H), 7.51 (d, J=5.8 Hz, 1H), 7.36 (d, J=9.8 Hz, 1H), 7.24 (s, 1H), 7.08 (d, J=3.0 Hz, 1H), 6.87 (dd, J=9.0, 3.0 Hz, 1H), 5.10 (s, 2H), 4.71 (dd, J=7.6, 5.3 Hz, 1H), 3.56-3.43 (m, 2H), 2.36-2.24 (m, 2H), 2.11-1.91 (m, 2H); MS (ES−) m/z 495.9, 493.9 (M−1).

Example 31

Synthesis of (S)-1-(5-chloro-4-((((1S,3S,5S,7S)-2-cyanoadamantan-2-yl)methoxy)-2-fluorobenzoyl)pyrrolidine-2-carboxylic Acid

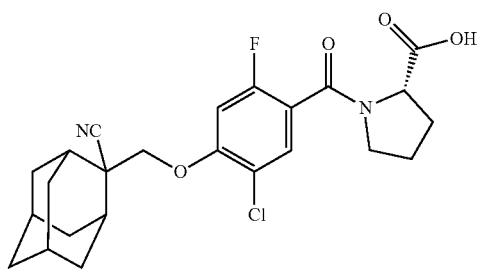 [SMILES: N#CC1(COc2cc(F)c(C(=O)N3CCC[C@H]3C(=O)O)cc2Cl)C2CC3CC(C2)CC1C3]

Step 1. Preparation of (S)-tert-butyl 1-(5-chloro-4-((((1S,3S,5S,7S)-2-cyanoadamantan-2-yl)methoxy)-2-fluorobenzoyl)pyrrolidine-2-carboxylate

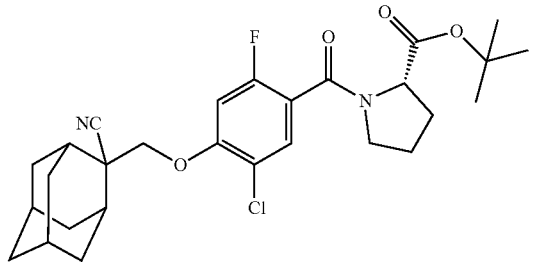 [SMILES: CC(C)(C)OC(=O)[C@@H]1CCCN1C(=O)c1cc(Cl)c(OCC2(C#N)C3CC4CC(C3)CC2C4)cc1F]

Following the procedure as described in Example 1 step 1 and making variations as required to replace 4-(adamantan-1-ylmethoxy)-5-cyclopropyl-2-fluorobenzoic acid with 5-chloro-4-(((1r,3r,5r,7r)-2-cyanoadamantan-2-yl)methoxy)-2-fluorobenzoic acid, the title compound was obtained as a colorless foam (0.37 g, 83%): $^1$H NMR (300 MHz, CDCl$_3$) δ 7.47 (d, J=7.0 Hz, 0.7H), 7.36 (d, J=7.0 Hz, 0.3H), 6.68 (d, J=10.5 Hz, 0.7H), 6.67 (d, J=10.5 Hz, 0.3H), 4.49 (dd, J=4.8, 8.4 Hz, 0.7H), 4.28 (s, 2H), 4.16-4.12 (m, 0.3H), 3.79-3.70 (m, 0.6H), 3.56-3.47 (m, 0.7H), 3.43-3.35 (m, 0.7H), 2.36-2.22 (m, 5H), 2.02-1.73 (m, 13H), 1.47 (s, 6H), 1.31 (s, 3H); MS (ES+) m/z 517.0, 519.0 (M+1).

Step 2. Preparation of (S)-1-(5-chloro-4-((((1S,3S,5S,7S)-2-cyanoadamantan-2-yl)methoxy)-2-fluorobenzoyl)pyrrolidine-2-carboxylic Acid

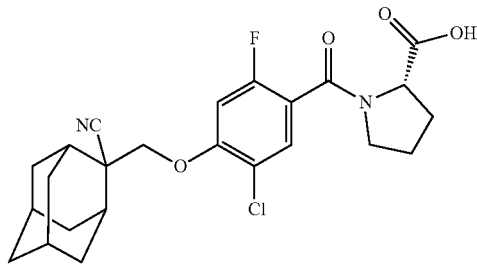 [SMILES: N#CC1(COc2cc(F)c(C(=O)N3CCC[C@H]3C(=O)O)cc2Cl)C2CC3CC(C2)CC1C3]

Following the procedure as described in Example 1 step 2 and making variations as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-chloro-4-(((1S,3S,   S5S,7S)-2-cyanoadamantan-2-yl)methoxy)-2-fluorobenzoyl)pyrrolidine-2-carboxylate, the title compound was obtained as a 1:1 complex with trifluoroacetic acid as a colorless solid (0.38 g, 97%): $^1$H NMR (300 MHz, CDCl$_3$) δ 7.93 (br s, 2H), 7.48 (d, J=7.0 Hz, 1H), 6.72 (d, J=10.7 Hz, 1H), 4.72-4.68 (m, 1H), 4.30 (s, 2H), 3.59-3.46 (m, 2H), 2.35-2.27 (m, 6H), 2.11-1.74 (m, 12H); MS (ES+) m/z 462.9, 460.9 (M+1).

Example 32

Synthesis of (S)-1-(4-(((1S,3S,5S,7S)-2-cyanoadamantan-2-yl)methoxy)-5-cyclopropyl-2-fluorobenzoyl)pyrrolidine-2-carboxylic Acid

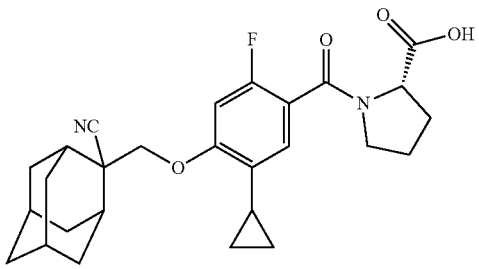 [SMILES: N#CC1(COc2cc(F)c(C(=O)N3CCC[C@H]3C(=O)O)cc2C2CC2)C2CC3CC(C2)CC1C3]

Step 1. Preparation of (S)-tert-butyl 1-(4-(((1S,3S,5S,7S)-2-cyanoadamantan-2-yl)methoxy)-5-cyclopropyl-2-fluorobenzoyl)pyrrolidine-2-carboxylate

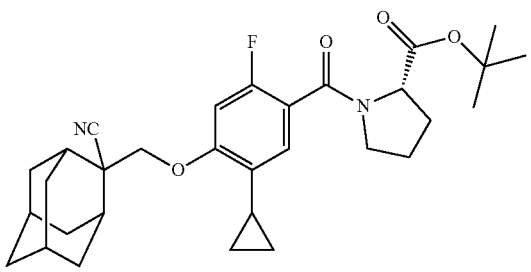 [SMILES: CC(C)(C)OC(=O)[C@@H]1CCCN1C(=O)c1cc(C2CC2)c(OCC2(C#N)C3CC4CC(C3)CC2C4)cc1F]

Following the procedure as described in Example 1 step 1 and making variations as required to replace 4-(adamantan-1-ylmethoxy)-5-cyclopropyl-2-fluorobenzoic acid with 4-(((1r,3r,5r,7r)-2-cyanoadamantan-2-yl)methoxy)-5-cyclopropyl-2-fluorobenzoic acid, the title compound was obtained as a colorless foam (0.36 g, 90%): $^1$H NMR (300 MHz, CDCl$_3$) δ 6.97 (d, J=7.7 Hz, 0.7H), 6.90 (d, J=7.8 Hz, 0.3H), 6.53 (d, J=11.2 Hz, 0.7H), 6.50 (d, J=11.1 Hz, 0.3H), 4.48 (dd, J=5.0, 8.4 Hz, 0.7H), 4.24 (s, 2H), 4.20-4.16 (m, 0.3H), 3.77-3.71 (m, 0.6H), 3.55-3.47 (m, 0.7H), 3.41-3.33 (m, 0.7H), 2.36-2.24 (m, 5H), 2.08-1.73 (m, 14H), 1.47 (s, 6H), 1.27 (s, 3H), 0.92-0.84 (m, 2H), 0.63-0.55 (m, 2H); MS (ES+) m/z 523.2 (M+1).

Step 2. Preparation of (S)-1-(4-(((1S,3S,5S,7S)-2-cyanoadamantan-2-yl)methoxy)-5-cyclopropyl-2-fluorobenzoyl)pyrrolidine-2-carboxylic Acid

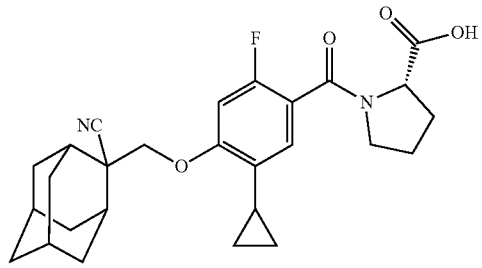 [SMILES: N#CC1(COc2cc(F)c(C(=O)N3CCC[C@H]3C(=O)O)cc2C2CC2)C2CC3CC(C2)CC1C3]

Following the procedure as described in Example 1 step 2 and making variations as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-(((1S,3S,5S,7S)-2-cyanoadamantan-2-yl)methoxy)-5-cyclopropyl-2-fluorobenzoyl)pyrrolidine-2-carboxylate, the title compound was obtained as a 1:1 complex with trifluoroacetic acid as a colorless solid (0.31 g, 81%): $^1$H NMR (300 MHz, CDCl$_3$) δ 8.48 (br s, 2H), 6.98 (d, J=7.7 Hz, 1H), 6.56 (d, J=11.3 Hz, 1H), 4.72-4.68 (m, 1H), 4.26 (s, 2H), 3.53-3.45 (m, 2H), 2.39-2.24 (m, 6H), 2.09-1.74 (m, 13H), 0.95-0.84 (m, 2H), 0.64-0.59 (m, 2H); MS (ES+) m/z 467.0 (M+1).

Example 33

Synthesis of (S)-1-(4-(2-(1-(1-(tert-butoxycarbonyl)azetidin-3-yl)-1H-pyrazol-5-yl)-4-chlorophenoxy)-2,5-difluorobenzoyl)pyrrolidine-2-carboxylic Acid

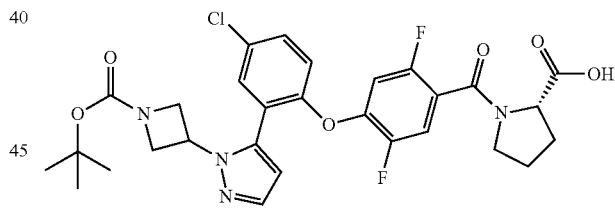

Step 1. (S)-methyl 1-(4-(2-(1-(1-(tert-butoxycarbonyl)azetidin-3-yl)-1H-pyrazol-5-yl)-4-chlorophenoxy)-2,5-difluorobenzoyl)pyrrolidine-2-carboxylate

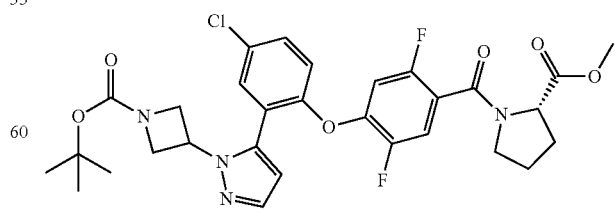

Following the procedure as described in Example 1 step 1, and making variation as required to replace 4-(adamantan-1-ylmethoxy)-5-cyclopropyl-2-fluorobenzoic acid with 4-(2-(1-(1-(tert-butoxycarbonyl)azetidin-3-yl)-1H-pyrazol-5-yl)-4-chlorophenoxy)-2,5-difluorobenzoic acid and to replace (S)-tert-butyl pyrrolidine-2-carboxylate hydrochloride with (S)-methyl pyrrolidine-2-carboxylate hydrochloride, the title compound was obtained as an colorless foam (0.29 g, 94%): $^1$H NMR (300 MHz, CDCl$_3$) δ 7.61-7.58 (m, 1H), 7.41-7.35 (m, 1H), 7.33-7.30 (m, 1H), 7.25-7.18 (m, 1H), 6.91-6.86 (m, 1H), 6.56-6.50 (m, 1H), 6.25-6.23 (m, 1H), 4.94-4.85 (m, 1H), 4.62-4.56 (m, 1H), 4.41-4.33 (m, 2H), 4.27-4.19 (m, 2H), 3.73 (s, 3H), 3.52-3.33 (m, 1H), 2.35-2.18 (m, 1H), 2.10-1.81 (m, 4H), 1.40 (s, 9H).

Step 2. Preparation of (S)-1-(4-(2-(1-(1-(tert-butoxycarbonyl)azetidin-3-yl)-1H-pyrazol-5-yl)-4-chlorophenoxy)-2,5-difluorobenzoyl)pyrrolidine-2-carboxylic Acid

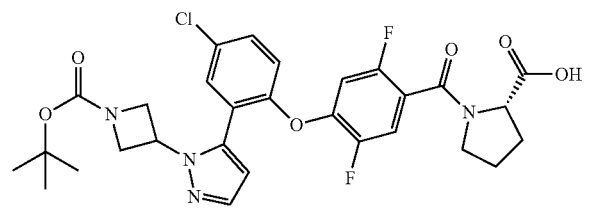 [SMILES: CC(C)(C)OC(=O)N1CC(n2nccc2-c2cc(Cl)ccc2Oc2cc(F)c(C(=O)N3CCC[C@H]3C(=O)O)cc2F)C1]

To a solution of (S)-methyl 1-(4-(2-(1-(1-(tert-butoxycarbonyl)azetidin-3-yl)-1H-pyrazol-5-yl)-4-chlorophenoxy)-2,5-difluorobenzoyl)pyrrolidine-2-carboxylate (0.29 g, 0.47 mmol) in tetrahydrofuran (20 mL) and water (4 mL) was added lithium hydroxide (0.02 g, 0.83 mmol). The reaction mixture was stirred at ambient temperature for 20 hours, and then concentrated in vacuo to remove most of tetrahydrofuran. The residue was acidified to pH~1 with 5% hydrochloric acid solution. The solid was collected by filtration and washed with water and dried to give the title compound as an colorless solid (0.22 g, 77%): $^1$H NMR (300 MHz, CDCl$_3$) δ 7.68-7.60 (m, 1H), 7.43-7.32 (m, 2H), 7.29-7.21 (m, 1H), 6.96-6.79 (m, 2H), 6.31-6.22 (m, 1H), 4.94-4.80 (m, 1H), 4.70-4.62 (m, 1H), 4.44-4.18 (m, 4H), 3.88-3.36 (m, 2H), 2.44-1.87 (m, 4H), 1.40 (s, 9H); (ES–) m/z 601.2, 603.2 (M–1).

Example 34

Synthesis of (S)-1-(4-(2-(1-(azetidin-3-yl)-1H-pyrazol-5-yl)-4-chlorophenoxy)-2,5-difluorobenzoyl)pyrrolidine-2-carboxylic Acid Trifluoroacetic Acid Salt

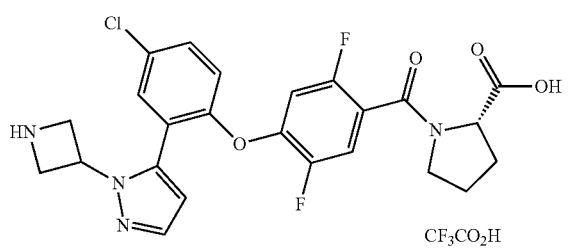 [SMILES: O=C(O)[C@@H]1CCCN1C(=O)c1cc(F)c(Oc2ccc(Cl)cc2-c2ccnn2C2CNC2)cc1F ; "CF3CO2H"]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-1-(4-(2-(1-(1-(tert-butoxycarbonyl)azetidin-3-yl)-1H-pyrazol-5-yl)-4-chlorophenoxy)-2,5-difluorobenzoyl)pyrrolidine-2-carboxylic acid, the title compound was obtained as a colorless solid (0.07 g, 54%): $^1$H NMR (300 MHz, DMSO-d$_6$) δ 10.01-8.94 br s, 2H), 7.81-7.72 (m, 1H), 7.66-7.55 (m, 2H), 7.49-7.32 (m, 1H), 7.29-7.12 (m, 2H), 6.55-6.40 (m, 1H), 5.35-4.97 (m, 1H), 4.47-3.98 (m, 5H), 3.58-3.50 (m, 2H), 2.35-2.16 (m, 1H), 2.02-1.73 (m, 3H); MS (ES–) m/z 501.0, 503.0 (M–1).

Example 35

Synthesis of 2-(4-(adamantan-1-ylmethoxy)-5-cyclopropyl-2-fluorobenzamido) acetic Acid

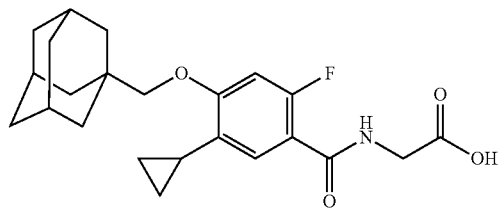 [SMILES: O=C(O)CNC(=O)c1cc(C2CC2)c(OCC23CC4CC(CC(C4)C2)C3)cc1F]

Step 1. Preparation of tert-butyl 2-(4-(adamantan-1-ylmethoxy)-5-cyclopropyl-2-fluorobenzamido)acetate

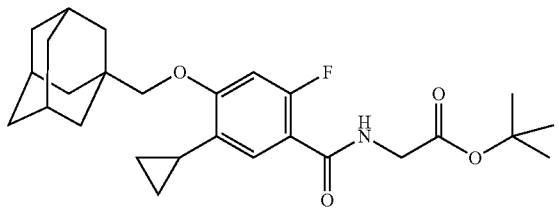 [SMILES: CC(C)(C)OC(=O)CNC(=O)c1cc(C2CC2)c(OCC23CC4CC(CC(C4)C2)C3)cc1F]

Following the procedure as described in Example 1 step 1, and making variation as required to replace (S)-tert-butyl pyrrolidine-2-carboxylate hydrochloride with tert-butyl 2-aminoacetate, the title compound was obtained as colorless solid (0.71 g, 76%): $^1$H NMR (300 MHz, DMSO-d$_6$) δ 7.60 (d, J=9.1 Hz, 1H), 7.21-7.13 (m, 1H), 6.52 (d, J=14.2 Hz, 1H), 4.14 (d, J=4.2 Hz, 2H), 3.53 (s, 2H), 2.10-2.03 (m, 4H), 1.80-1.69 (m, 12H), 1.50 (s, 9H), 0.94-0.87 (m, 2H), 0.70-0.65 (m, 2H); MS (ES+) m/z 458.2 (M+1).

Step 2. Preparation of 2-(4-(adamantan-1-ylmethoxy)-5-cyclopropyl-2-fluorobenzamido) Acetic Acid

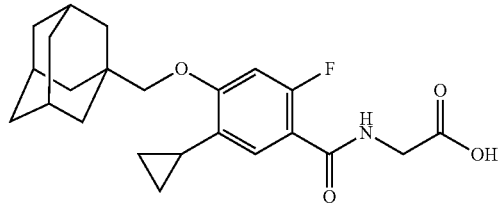 [SMILES: O=C(O)CNC(=O)c1cc(C2CC2)c(OCC23CC4CC(CC(C4)C2)C3)cc1F]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with tert-butyl 2-(4-(adamantan-1-ylmethoxy)-5-cyclopropyl-2-fluorobenzamido)acetate, the title compound was obtained as colorless solid: (0.19 g, 31%): $^1$H NMR (300 MHz, DMSO-$d_6$) δ 12.65 (s, 1H), 8.20-8.14 (m, 1H), 7.23 (d, J=8.7 Hz, 1H), 6.89 (d, J=13.4 Hz, 1H), 3.88 (d, J=5.7 Hz, 2H), 3.63 (s, 3H), 2.09-1.99 (m, 4H), 1.75-1.67 (m, 12H), 0.94-0.87 (m, 2H), 0.63-0.58 (m, 2H); MS (ES+) m/z 402.1 (M+1); MS (ES−) m/z 400.2 (M−1).

Example 36

Synthesis of 1-(5-chloro-4-(3-chloro-4-(trifluoromethoxy)phenoxy)-2-fluorobenzamido)-cyclopropanecarboxylic Acid

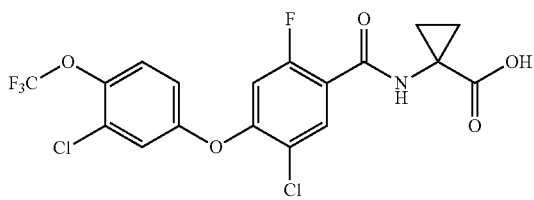

Step 1. Preparation of tert-butyl 1-(5-chloro-4-(3-chloro-4-(trifluoromethoxy)phenoxy)-2-fluorobenzamido)cyclopropanecarboxylate

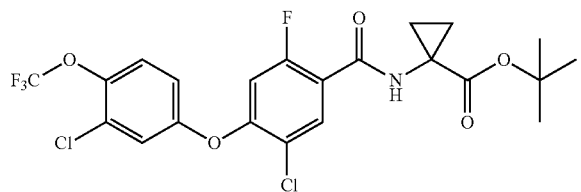 [SMILES: CC(C)(C)OC(=O)C1(NC(=O)c2cc(Cl)c(Oc3ccc(OC(F)(F)F)c(Cl)c3)cc2F)CC1]

Following the procedure as described in Example 1 step 1, and making variation as required to replace 4-(adamantan-1-ylmethoxy)-5-cyclopropyl-2-fluorobenzoic acid with 5-chloro-4-(3-chloro-4-(trifluoromethoxy)phenoxy)-2-fluorobenzoic acid, and (S)-tert-butyl pyrrolidine-2-carboxylate hydrochloride with tert-butyl 1-aminocyclopropanecarboxylate, the title compound was obtained as colorless solid (0.60 g, 90%): $^1$H NMR (300 MHz, DMSO-$d_6$) δ 8.17 (d, J=7.8 Hz, 1H), 7.33-7.29 (m, 1H), 7.15-7.10 (m, 2H), 6.92 (dd, J=2.9 Hz, 9.0 Hz, 1H), 6.68 (d, J=11.9 Hz, 1H), 3.66 (s, 3H), 1.65-1.61 (m, 2H), 1.25-1.21 (m, 2H); MS (ES+) m/z 481.9, 483.9 (M+1); MS (ES−) m/z 480.0, 482.0 (M−1).

Step 2. Preparation of 1-(5-chloro-4-(3-chloro-4-(trifluoromethoxy)phenoxy)-2-fluorobenzamido)cyclopropanecarboxylic Acid

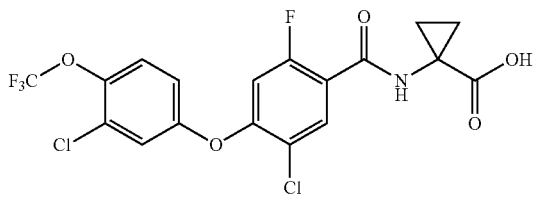

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with tert-butyl 1-(5-chloro-4-(3-chloro-4-(trifluoromethoxy)phenoxy)-2-fluorobenzamido)cyclopropanecarboxylate, the title compound was obtained as colorless solid (0.31 g, 99%): $^1$H NMR (300 MHz, DMSO-$d_6$) δ 12.49 (s, 1H), 8.92 (s, 1H), 7.81 (d, J=7.2 Hz, 1H), 7.63-7.60 (m, 1H), 7.49 (d, J=3.0 Hz, 1H), 7.33 (d, J=10.6 Hz, 1H), 7.15 (dd, J=3.0 Hz, 9.1 Hz, 1H), 1.43-1.38 (m, 2H), 1.14-1.10 (m, 2H); MS (ES+) m/z 467.8, 469.8 (M+1); MS (ES−) m/z 465.9, 467.9 (M−1).

Example 37

Synthesis of (S)-1-(5-chloro-4-(3-chloro-4-(trifluoromethoxy)phenoxy)-2-fluorobenzoyl)-pyrrolidine-2-carboxylic Acid

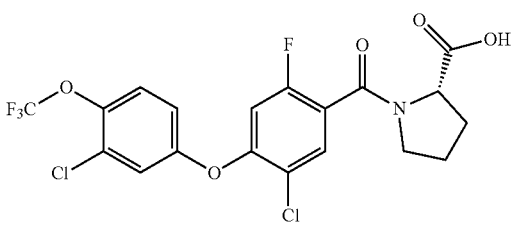 [SMILES: O=C(O)[C@@H]1CCCN1C(=O)c1cc(Cl)c(Oc2ccc(OC(F)(F)F)c(Cl)c2)cc1F]

Step 1. Preparation of (S)-tert-butyl 1-(5-chloro-4-(3-chloro-4-(trifluoromethoxy)phenoxy)-2-fluorobenzoyl)pyrrolidine-2-carboxylate

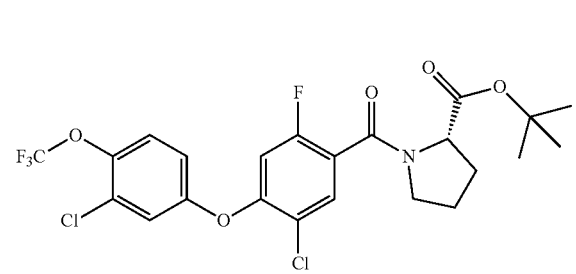 [SMILES: CC(C)(C)OC(=O)[C@@H]1CCCN1C(=O)c1cc(Cl)c(Oc2ccc(OC(F)(F)F)c(Cl)c2)cc1F]

Following the procedure as described in Example 1 step 1, and making variation as required to replace 4-(adamantan-1-ylmethoxy)-5-cyclopropyl-2-fluorobenzoic acid with 5-chloro-4-(3-chloro-4-(trifluoromethoxy)phenoxy)-2-fluorobenzoic acid, the title compound was obtained as colorless oil (0.17 g, 67%): MS (ES+) m/z 538.0, 540.0 (M+1); MS (ES−) m/z 480.0, 482.0 (M−1).

Step 2. Preparation of (S)-1-(5-chloro-4-(3-chloro-4-(trifluoromethoxy)phenoxy)-2-fluorobenzoyl)pyrrolidine-2-carboxylic Acid

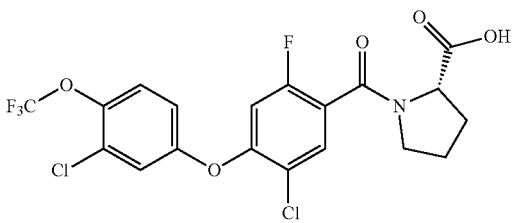 [SMILES: O=C(O)[C@@H]1CCCN1C(=O)c1cc(Cl)c(Oc2ccc(OC(F)(F)F)c(Cl)c2)cc1F]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-chloro-4-(3-chloro-4-(trifluoromethoxy)phenoxy)-2-fluorobenzoyl)pyrrolidine-2-carboxylate, the title compound was obtained as colorless solid (0.14 g, 91%): $^1$H NMR (300 MHz, CDCl$_3$) δ 7.61 (d, J=6.7 Hz, 1H), 7.34-7.31 (m, 1H), 7.12 (d, J=2.9 Hz, 1H), 6.93 (dd, J=2.9 Hz, 9.0 Hz, 1H), 6.73 (d, J=9.8 Hz, 1H), 4.70 (t, J=6.3 Hz, 1H), 3.54-3.48 (m, 2H), 2.33-2.26 (m, 2H), 2.12-1.91 (m, 2H) (OH proton not observed); MS (ES+) m/z 481.9, 483.9 (M+1); MS (ES−) m/z 480.0, 482.0 (M−1).

Example 38

Synthesis of (S)-1-(4-(((R)-1-(2-chloro-4-fluorobenzyl)piperidin-3-yl)oxy)-5-cyclopropyl-2-fluorobenzoyl)pyrrolidine-2-carboxylic Acid Trifluoroacetic Acid Salt

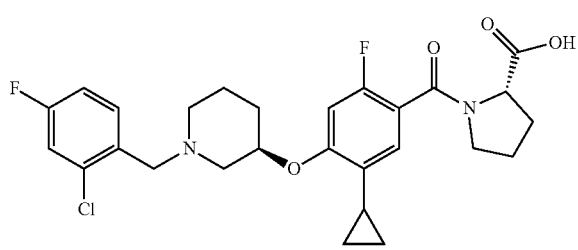 [SMILES: O=C(O)[C@@H]1CCCN1C(=O)c1cc(C2CC2)c(O[C@@H]2CCCN(Cc3ccc(F)cc3Cl)C2)cc1F]

Step 1. Preparation of (S)-tert-butyl 1-(4-(((R)-1-(2-chloro-4-fluorobenzyl)piperidin-3-yl)oxy)-5-cyclopropyl-2-fluorobenzoyl)pyrrolidine-2-carboxylate

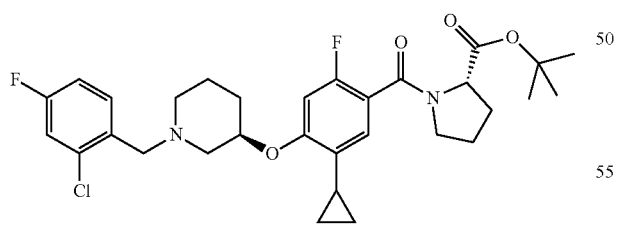

Following the procedure as described in Example 1 step 1, and making variation as required to replace 4-(adamantan-1-ylmethoxy)-5-cyclopropyl-2-fluorobenzoic acid with (R)-4-((1-(2-chloro-4-fluorobenzyl)piperidin-3-yl)oxy)-5-cyclopropyl-2-fluorobenzoic acid, the title compound was obtained as colorless oil (0.18 g, 67%): MS (ES+) m/z 575.2, 577.2 (M+1).

Step 2. Preparation of (S)-1-(4-(((R)-1-(2-chloro-4-fluorobenzyl)piperidin-3-yl)oxy)-5-cyclopropyl-2-fluorobenzoyl)pyrrolidine-2-carboxylic Acid Trifluoroacetic Acid Salt

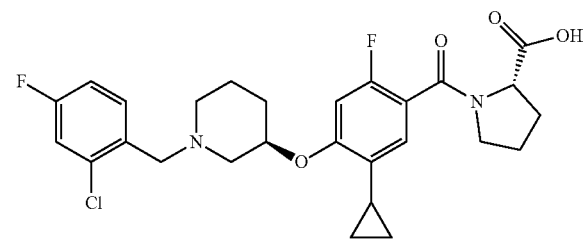 [SMILES: O=C(O)[C@@H]1CCCN1C(=O)c1cc(C2CC2)c(O[C@@H]2CCCN(Cc3ccc(F)cc3Cl)C2)cc1F]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-(((R)-1-(2-chloro-4-fluorobenzyl)piperidin-3-yl)oxy)-5-cyclopropyl-2-fluorobenzoyl)pyrrolidine-2-carboxylate, the title compound was obtained as colorless solid (0.12 g, 72%): $^1$H NMR (300 MHz, DMSO-d$_6$+drop D$_2$O at 60° C.) δ 7.76 (dd, J=6.2 Hz, 8.7 Hz, 1H), 7.53 (dd, J=2.6 Hz, 8.8 Hz, 1H), 7.32 (dt, J=2.7 Hz, 8.5 Hz, 1H), 6.98-6.72 (m, 2H), 4.74-4.73 (m, 1H), 4.45 (s, 2H), 4.41-4.37 (m, 0.7H), 4.11-4.07 (m, 0.3H), 3.53-3.48 (m, 2H), 3.34-3.23 (m, 4H), 2.32-1.80 (m, 9H), 0.90-0.88 (m, 2H), 0.61-0.60 (m, 2H); MS (ES+) m/z 519.1, 521.1 (M+1).

Example 39

Synthesis of (2S)-1-(5-cyclopropyl-4-((1-(1-(3,5-dichlorophenyl)ethyl)piperidin-4-yl)methoxy)-2-fluorobenzoyl)pyrrolidine-2-carboxylic Acid Trifluoroacetic Acid Salt

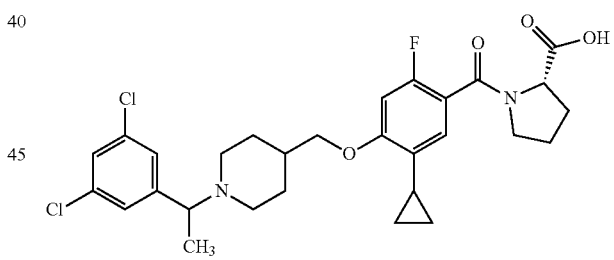

Step 1. Preparation of (2S)-tert-butyl 1-(5-cyclopropyl-4-((1-(1-(3,5-dichlorophenyl)ethyl)piperidin-4-yl)methoxy)-2-fluorobenzoyl)pyrrolidine-2-carboxylate

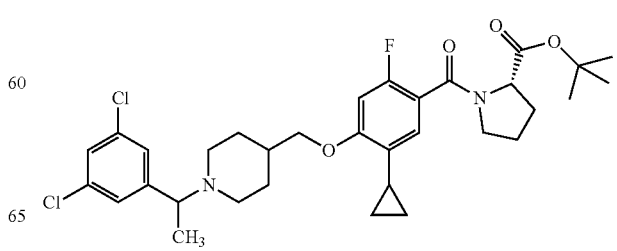

Following the procedure as described in Example 1 step 1, and making variation as required to replace 4-(adamantan-1-ylmethoxy)-5-cyclopropyl-2-fluorobenzoic acid with 5-cyclopropyl-4-((1-(1-(3,5-dichlorophenyl)ethyl)piperidin-4-yl)methoxy)-2-fluorobenzoic acid, the title compound was obtained as colorless oil (0.60 g, 52%): MS (ES+) m/z 619.2, 621.2 (M+1).

Step 2. Preparation of (2S)-1-(5-cyclopropyl-4-((1-(1-(3,5-dichlorophenyl)ethyl)piperidin-4-yl)methoxy)-2-fluorobenzoyl)pyrrolidine-2-carboxylic Acid Trifluoroacetic Acid Salt

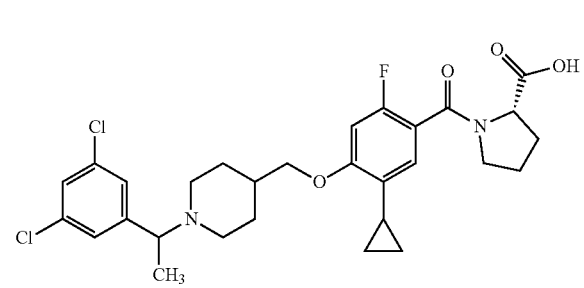 [SMILES: CC(c1cc(Cl)cc(Cl)c1)N1CCC(COc2cc(F)c(C(=O)N3CCC[C@H]3C(=O)O)cc2C2CC2)CC1]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (2S)-tert-butyl 1-(5-cyclopropyl-4-((1-(1-(3,5-dichlorophenyl)ethyl)piperidin-4-yl)methoxy)-2-fluorobenzoyl)pyrrolidine-2-carboxylate, the title compound was obtained as colorless solid (0.27 g, 57%): $^1$H NMR (300 MHz, CDCl$_3$) δ 11.21-10.82 (m, 1H), 7.44-7.37 (m, 3H), 6.90-6.79 (m, 1H), 6.47-6.38 (m, 1H), 4.65-4.61 (m, 1H), 4.45-4.27 (m, 1H), 3.82-3.72 (m, 3H), 3.57-3.38 (m, 3H), 2.72-2.65 (m, 2H), 2.33-2.17 (m, 2H), 2.05-1.75 (m, 11H), 0.85-0.76 (m, 2H), 0.51-0.48 (m, 2H); MS (ES+) m/z 563.1, 565.0 (M+1).

Example 40

Synthesis of (S)-1-(4-(adamantan-1-ylmethoxy)-2-fluoro-5-methylbenzoyl)pyrrolidine-2-carboxylic Acid

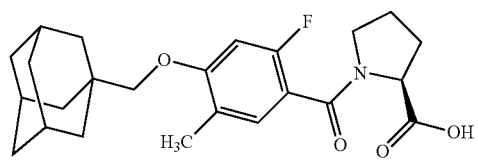 [SMILES: Cc1cc(C(=O)N2CCC[C@H]2C(=O)O)c(F)cc1OCC12CC3CC(CC(C3)C1)C2]

Step 1. Preparation of (S)-tert-butyl 1-(4-(adamantan-1-ylmethoxy)-2-fluoro-5-methylbenzoyl)pyrrolidine-2-carboxylate

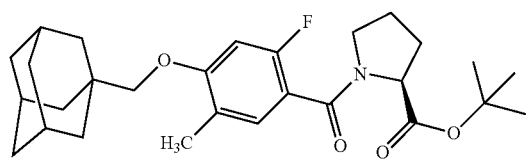 [SMILES: Cc1cc(C(=O)N2CCC[C@H]2C(=O)OC(C)(C)C)c(F)cc1OCC12CC3CC(CC(C3)C1)C2]

Following the procedure as described in Example 1 step 1, and making variation as required to replace 4-(adamantan-1-ylmethoxy)-5-cyclopropyl-2-fluorobenzoic acid with 4-(adamantan-1-ylmethoxy)-2-fluoro-5-methylbenzoic acid, the title compound was obtained as colorless oil (0.42 g, 95%): MS (ES+) m/z 472.2 (M+1).

Step 2. Preparation of (S)-1-(4-(adamantan-1-ylmethoxy)-2-fluoro-5-methylbenzoyl)pyrrolidine-2-carboxylic Acid

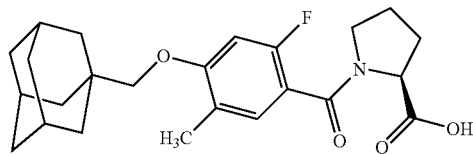 [SMILES: Cc1cc(C(=O)N2CCC[C@H]2C(=O)O)c(F)cc1OCC12CC3CC(CC(C3)C1)C2]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-(adamantan-1-ylmethoxy)-2-fluoro-5-methylbenzoyl)pyrrolidine-2-carboxylate, the title compound was obtained as colorless solid (0.32 g, 87%): $^1$H NMR (300 MHz, CDCl$_3$) δ 8.01 (br s, 1H), 7.21 (d, J=8.0 Hz, 0.7H), 7.12 (d, J=8.5 Hz, 0.3H), 6.60 (d, J=11.3 Hz, 0.3H), 6.52 (d, J=12.0 Hz, 0.7H), 4.79-4.71 (m, 1H), 3.589-3.38 (m, 4H), 2.60-2.40 (m, 1H), 2.20-2.13 (m, 4H), 2.03-1.88 (m, 5H), 1.80-1.57 (m, 12H); MS (ES+) m/z 416.0 (M+1); MS (ES-) m/z 414.1 (M-1).

Example 41

Synthesis of (S)-1-(4-(adamantan-1-ylmethoxy)-5-chloro-2-fluorobenzoyl)pyrrolidine-2-carboxylic Acid

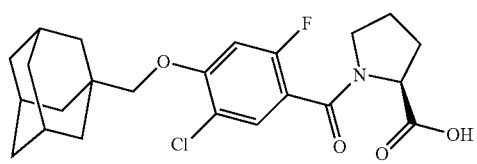 [SMILES: O=C(O)[C@@H]1CCCN1C(=O)c1cc(Cl)c(OCC23CC4CC(CC(C4)C2)C3)cc1F]

Step 1. Preparation of (S)-tert-butyl 1-(4-(adamantan-1-ylmethoxy)-5-chloro-2-fluorobenzoyl)pyrrolidine-2-carboxylate

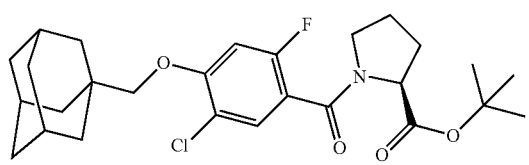 [SMILES: CC(C)(C)OC(=O)[C@@H]1CCCN1C(=O)c1cc(Cl)c(OCC23CC4CC(CC(C4)C2)C3)cc1F]

Following the procedure as described in Example 1 step 1, and making variation as required to replace 4-(adamantan-1-ylmethoxy)-5-cyclopropyl-2-fluorobenzoic acid with 4-(adamantan-1-ylmethoxy)-5-chloro-2-fluorobenzoic acid, the title compound was obtained as colorless solid (0.24 g, 65%): ¹H NMR (300 MHz, CDCl₃) δ 7.41 (d, J=7.1 Hz, 0.7H), 7.30 (d, J=7.1 Hz, 0.3H), 6.62-6.56 (m, 1H), 4.48-4.44 (m, 0.7H), 4.16-4.13 (m, 0.3H), 3.76-3.69 (m, 0.7H), 3.54-3.46 (m, 0.6H), 3.50 (s, 2H), 3.42-3.34 (m, 0.7H), 2.31-2.20 (m, 1H), 2.07-1.86 (m, 6H), 1.78-1.66 (m, 12H), 1.45 (s, 6.5H), 1.29 (s, 2.5H); MS (ES+) m/z 492.1, 494.1 (M+1).

Step 2. Preparation of (S)-1-(4-(adamantan-1-yl-methoxy)-5-chloro-2-fluorobenzoyl)pyrrolidine-2-carboxylic Acid

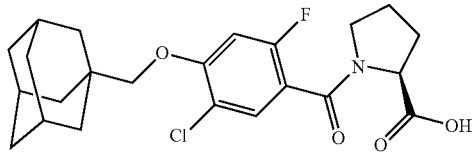 [SMILES: O=C(O)[C@@H]1CCCN1C(=O)c1cc(Cl)c(OCC23CC4CC(CC(C4)C2)C3)cc1F]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-(adamantan-1-ylmethoxy)-5-chloro-2-fluorobenzoyl)pyrrolidine-2-carboxylate, the title compound was obtained as colorless solid (0.18 g, 88%): ¹H NMR (300 MHz, CDCl₃) δ 7.46 (d, J=7.1 Hz, 0.9H), 7.35 (d, J=7.1 Hz, 0.1H), 6.65-6.57 (m, 1H), 5.29 (br s, 1H), 4.71-4.67 (m, 0.9H), 4.35-4.31 (m, 0.1H), 3.79-3.72 (m, 0.2H), 3.52 (s, 2H), 3.50-3.46 (m, 1.8H), 2.42-2.15 (m, 2H), 2.07-1.86 (m, 5H), 1.78-1.66 (m, 12H); MS (ES+) m/z 436.0, 438.0 (M+1); MS (ES−) m/z 434.1, 436.1 (M−1).

Example 42

Synthesis of cis-(S)-1-(5-cyclopropyl-2-fluoro-4-((1-methyl-4-(trifluoromethyl)-cyclohexyl)methoxy)benzoyl)pyrrolidine-2-carboxylic Acid

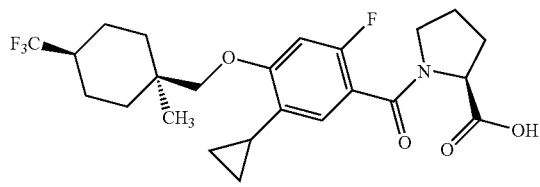 [SMILES: C[C@]1(COc2cc(F)c(C(=O)N3CCC[C@H]3C(=O)O)cc2C2CC2)CC[C@@H](C(F)(F)F)CC1]

Step 1. Preparation of cis-(S)-tert-butyl 1-(5-cyclopropyl-2-fluoro-4-((1-methyl-4-(trifluoromethyl)cyclohexyl)methoxy)benzoyl)pyrrolidine-2-carboxylate

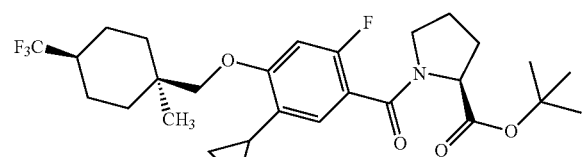

Following the procedure as described in Example 1 step 1, and making variation as required to replace 4-(adamantan-1-ylmethoxy)-5-cyclopropyl-2-fluorobenzoic acid with cis-5-cyclopropyl-2-fluoro-4-((1-methyl-4-(trifluoromethyl)cyclohexyl)methoxy)benzoic acid, the title compound was obtained as colorless solid (0.43 g, 87%): MS (ES+) m/z 528.1 (M+1), 472.1 (M−55).

Step 2. Preparation of cis-(S)-1-(5-cyclopropyl-2-fluoro-4-((1-methyl-4-(trifluoromethyl)cyclohexyl)methoxy)benzoyl)pyrrolidine-2-carboxylic Acid

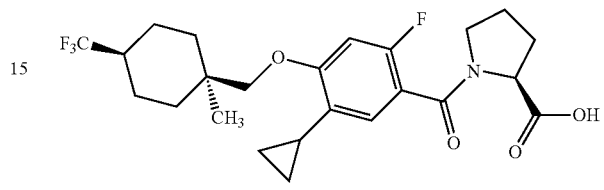

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with cis-(S)-tert-butyl 1-(5-cyclopropyl-2-fluoro-4-((1-methyl-4-(trifluoromethyl)cyclohexyl)methoxy)benzoyl)pyrrolidine-2-carboxylate, the title compound was obtained as colorless solid (0.40 g, 95%): ¹H NMR (300 MHz, CDCl₃) δ 7.93 (br s, 1H), 7.00 (d, J=7.8 Hz, 1H), 6.57 (d, J=11.8 Hz, 1H), 4.75-4.71 (m, 1H), 3.80 (s, 2H), 3.57-3.42 (m, 2H), 2.49-2.39 (m, 1H), 2.26-2.14 (m, 1H), 2.10-1.80 (m, 8H), 1.55-1.41 (m, 2H), 1.34-1.25 (m, 2H), 1.11 (s, 3H), 0.93-0.87 (m, 2H), 0.64-0.59 (m, 2H); MS (ES+) m/z 472.1 (M+1); MS (ES−) m/z 470.0 (M−1).

Example 43

Synthesis of (2S,3S)-2-(4-(adamantan-1-yl-methoxy)-5-cyclopropyl-2-fluorobenzamido)-3-methylpentanoic Acid

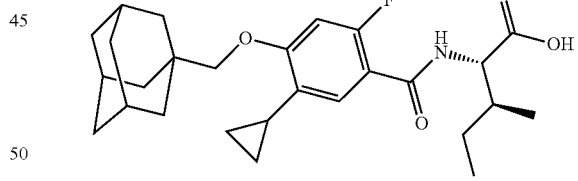

Step 1. Preparation of (2S,3S)-tert-butyl 2-(4-(adamantan-1-ylmethoxy)-5-cyclopropyl-2-fluorobenzamido)-3-methylpentanoate

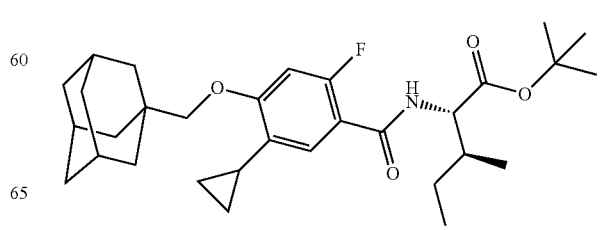

Following the procedure as described in Example 1 step 1, and making variation as required to replace (S)-tert-butyl pyrrolidine-2-carboxylate hydrochloride with (2S,3S)-tert-butyl 2-amino-3-methylpentanoate hydrochloride, the title compound was obtained as colorless oil (0.27 g, 76%): $^1$H NMR (300 MHz, CDCl$_3$) δ 7.58 (d, J=9.1 Hz, 1H), 7.25-7.18 (m, 1H), 6.50 (d, J=14.2 Hz, 1H), 4.72-4.67 (m, 1H), 3.51 (s, 2H), 2.08-1.92 (m, 5H), 1.77-1.67 (m, 12H), 1.60-1.50 (m, 1H), 1.29-1.19 (m, 1H), 0.98-0.85 (m, 9H), 0.68-0.63 (m, 2H).

Step 2. Preparation of (2S,3S)-2-(4-(adamantan-1-ylmethoxy)-5-cyclopropyl-2-fluorobenzamido)-3-methylpentanoic Acid

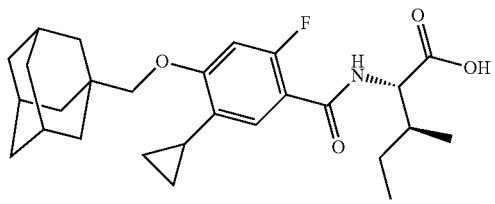 [SMILES: CC[C@H](C)[C@H](NC(=O)c1cc(C2CC2)c(OCC23CC4CC(CC(C4)C2)C3)cc1F)C(=O)O]

Following the procedure as described in Example 1 step 2, and making variation as required to replace (S)-tert-butyl 1-(4-(adamantan-1-ylmethoxy)-5-cyclopropyl-2-fluorobenzoyl)pyrrolidine-2-carboxylate with (2S,3S)-tert-butyl 2-(4-(adamantan-1-ylmethoxy)-5-cyclopropyl-2-fluorobenzamido)-3-methylpentanoate, the title compound was obtained as colorless solid (0.25 g, 95%): $^1$H NMR (300 MHz, CDCl$_3$) δ 7.58 (d, J=9.2 Hz, 1H), 7.27 (br s, 1H), 7.20-7.12 (m, 1H), 6.52 (d, J=14.3 Hz, 1H), 4.82-4.77 (m, 1H), 3.53 (s, 2H), 2.12-2.04 (m, 5H), 1.80-1.49 (m, 13H), 1.35-1.20 (m, 1H), 1.03-0.87 (m, 8H), 0.69-0.64 (m, 2H); MS (ES+) m/z 458.1 (M+1); MS (ES−) m/z 456.2 (M−1).

Example 44

Synthesis of (S)-1-(5-chloro-4-(((6,6-difluorobicyclo[3.1.0]hexan-3-yl)methoxy)-2-fluorobenzoyl)pyrrolidine-2-carboxylic Acid

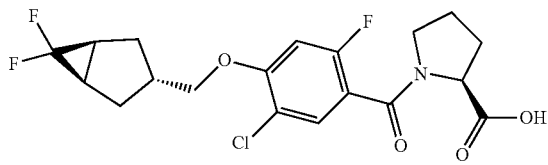 [SMILES: O=C(O)[C@@H]1CCCN1C(=O)c1cc(Cl)c(OC[C@@H]2C[C@@H]3[C@H](C2)C3(F)F)cc1F]

Step 1. Preparation of (S)-1-(5-chloro-4-(((6,6-difluorobicyclo[3.1.0]hexan-3-yl)methoxy)-2-fluorobenzoyl)pyrrolidine-2-carboxylic Acid

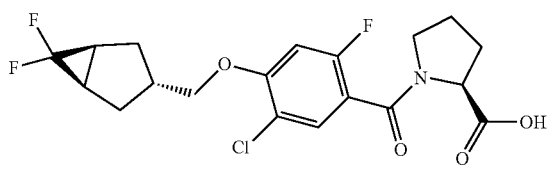 [SMILES: O=C(O)[C@@H]1CCCN1C(=O)c1cc(Cl)c(OC[C@@H]2C[C@@H]3[C@H](C2)C3(F)F)cc1F]

Following the procedure as described in Example 46, and making variations as required to replace 6-adamantan-1-ylmethoxy)-5-chloronicotinic acid with 5-chloro-4-6,6-difluorobicyclo-[3.1.0]hexan-3-yl)methoxy)-2-fluorobenzoic acid, the title compound was obtained as an colorless solid (0.25 g, 63% in two steps): $^1$H NMR (300 MHz, CDCl$_3$) δ (d, J=7.0 Hz, 1H), 6.64 (d, J=11.1 Hz, 1H), 4.72-4.68 (m, 1H), 3.91 (d, J=5.9 Hz, 2H), 3.50 (t, J=6.8 Hz, 1H), 2.63-2.44 (m, 1H), 2.42-2.15 (m, 4H), 2.12-1.85 (m, 7H). MS (ES+) m/z 418.0 (M+1).

Example 45

Synthesis of 2-(4-(adamantan-1-ylmethoxy)-5-cyclopropyl-2-fluoro-N-methylbenzamido)acetic Acid

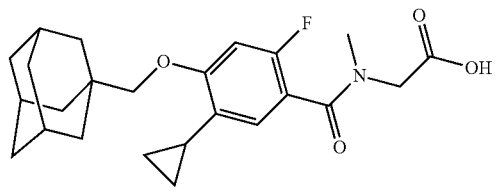 [SMILES: CN(CC(=O)O)C(=O)c1cc(C2CC2)c(OCC23CC4CC(CC(C4)C2)C3)cc1F]

Step 1. Preparation of 4-(adamantan-1-ylmethoxy)-5-cyclopropyl-2-fluorobenzoyl Chloride

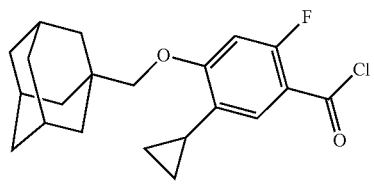 [SMILES: O=C(Cl)c1cc(C2CC2)c(OCC23CC4CC(CC(C4)C2)C3)cc1F]

To a stirred suspension of 4-(adamantan-1-ylmethoxy)-5-cyclopropyl-2-fluorobenzoic acid (2.06 g, 5.98 mmol) in dichloromethane (30 mL) was added oxalyl chloride (1.04 mL, 11.90 mmol), followed by a drop of N,N-dimethyl formamide, and the reaction mixture was stirred at ambient temperature for 140 minutes. The solution was concentrated, and azeotropic removal of oxalyl chloride using dichloromethane (20 mL) provided the title compound as a pale solid (2.19 g, quant. yield): $^1$H NMR (300 MHz, CDCl$_3$) δ 7.63 (d, J=8.3 Hz, 1H), 6.57 (d, J=12.8 Hz, 1H), 3.57 (s, 2H), 2.05-1.98 (m, 4H), 1.81-1.69 (m, 12H), 1.00-0.93 (m, 2H), 0.69-0.63 (m, 2H).

Step 2. Preparation of ethyl 2-(4-(adamantan-1-ylmethoxy)-5-cyclopropyl-2-fluoro-N-methylbenzamido)acetate

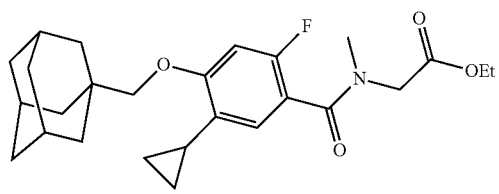 [SMILES: CCOC(=O)CN(C)C(=O)c1cc(C2CC2)c(OCC23CC4CC(CC(C4)C2)C3)cc1F]

To a solution of 4-(adamantan-1-ylmethoxy)-5-cyclopropyl-2-fluorobenzoyl chloride (0.30 g, 0.83 mmol) in dichloromethane (4 mL) was added to a mixture of sarcosine ethyl ester hydrochloride (0.19 g, 1.24 mmol) and triethylamine (0.4 mL, 2.90 mmol) in dichloromethane (4.3 mL). After stirring at ambient temperature for 16 hours, the reaction mixture was concentrated in vacuo. The residue was partitioned between ethyl acetate (40 mL) and 1.0N hydrochloric acid solution (15 mL). The organic layer was washed with saturated aqueous sodium bicarbonate solution (15 mL×2) and brine (15 mL×2); dried over anhydrous magnesium sulfate and concentrated in vacuo. Purification of the residue by column chromatography (0% to 20% ethyl acetate in hexanes) provided the title compound as a colorless foam (0.34 g, 92%): $^1$H NMR (300 MHz, CDCl$_3$) δ 6.95 (d, J=7.8 Hz, 0.7H), 6.87 (d, J=7.9 Hz, 0.3H), 6.53-6.48 (m, 1H), 4.27-4.16 (m, 3.3H), 3.95 (s, 0.7H), 3.51 (m, 2H), 3.12 (s, 1H), 3.00 (m, 2H), 2.07-2.03 (m, 4H), 1.80-1.69 (m, 12H), 1.33-1.23 (m, 3H), 0.93-0.85 (m, 2H), 0.66-0.55 (m, 2H).

Step 3. Preparation of 2-(4-(adamantan-1-ylmethoxy)-5-cyclopropyl-2-fluoro-N-methylbenzamido)acetic Acid

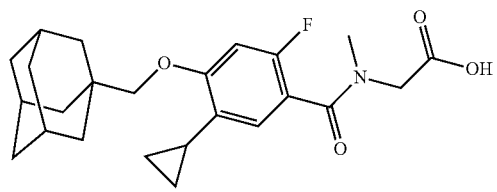 [SMILES: CN(CC(=O)O)C(=O)c1cc(C2CC2)c(OCC23CC4CC(CC(C4)C2)C3)cc1F]

To a solution of ethyl 2-(4-(adamantan-1-ylmethoxy)-5-cyclopropyl-2-fluoro-N-methylbenzamido)acetate (0.33 g, 0.74 mmol) in tetrahydrofuran (6 mL) was added a solution of lithium hydroxide monohydrate (0.05 g, 1.10 mmol) in water (1.5 mL). After stirring at ambient temperature for 3 days, the reaction mixture was diluted with diethyl ether (20 mL) and washed with 1N hydrochloric acid solution (15 mL). The aqueous layer was extracted with diethyl ether (15 mL); the combined organic layers were dried over anhydrous magnesium sulfate and concentrated in vacuo. Purification of the residue by recrystallization (acetonitrile) provided the title compound as colorless solid (0.29 g, 93%): $^1$H NMR (300 MHz, DMSO-d$_6$) δ 12.81 (br s, 1H), 6.89-6.83 (m, 1H), 6.79 (d, J=7.9 Hz, 0.6H), 6.68 (d, J=7.9 Hz, 0.4H), 4.12 (s, 1.2H), 3.88 (s, 0.8H), 3.60-3.58 (m, 2H), 2.96 (s, 1.2H), 2.87-2.86 (m, 1.8H), 2.06-1.99 (m, 4H), 1.75-1.66 (m, 12H), 0.93-0.85 (m, 2H), 0.63-0.51 (m, 2H); MS (ES+) m/z 416.1 (M+1).

Example 46

Synthesis of (2S,4S)-1-[4-(1-adamantylmethoxy)-5-cyclopropyl-2-fluoro-benzoyl]-4-hydroxy-pyrrolidine-2-carboxylic Acid

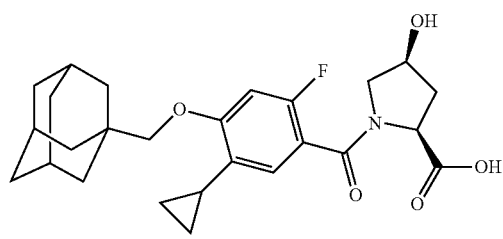 [SMILES: O=C(O)[C@@H]1C[C@H](O)CN1C(=O)c1cc(C2CC2)c(OCC23CC4CC(CC(C4)C2)C3)cc1F]

Step 1. Preparation of 4-(1-adamantylmethoxy)-5-cyclopropyl-2-fluoro-benzoyl Chloride

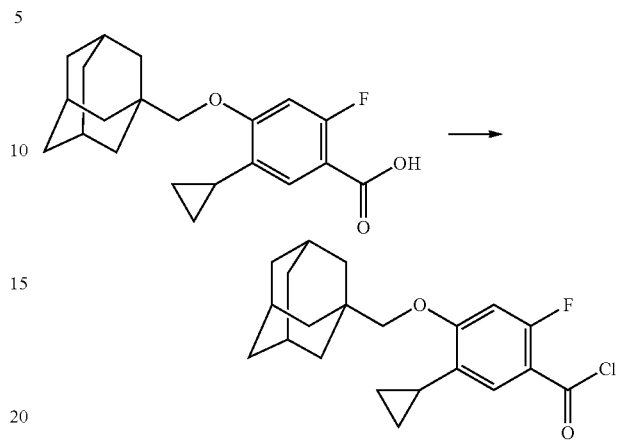

Thionyl chloride (1105 mg, 9.29 mmol) was added to a suspension of 4-(1-adamantylmethoxy)-5-cyclopropyl-2-fluoro-benzoic acid (800 mg, 2.32 mmol) in dichloromethane (5 ml). 0.5 ml of DMF was added and the mixture went onto solution. The mixture was stirred for 15 min and then concentrated to afford 815 mg (97%) of 4-(1-adamantylmethoxy)-5-cyclopropyl-2-fluoro-benzoyl chloride as a pale yellow solid. The compound was carried on to next step without purification.

Step 2. Preparation of (2S,4S)-1-[4-(1-adamantylmethoxy)-5-cyclopropyl-2-fluoro-benzoyl]-4-hydroxy-pyrrolidine-2-carboxylic Acid

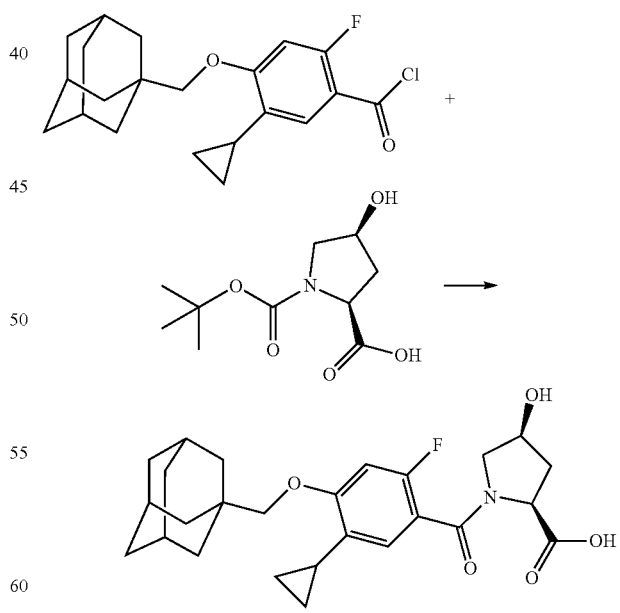

Trifluoroacetic acid (0.49 mL, 6.49 mmol) was added to a solution of (2s,4s)-1-tert-butoxycarbonyl-4-fluoro-pyrrolidine-2-carboxylic acid (150 mg, 0.65 mmol) in dichloromethane (3 ml) and the mixture was stirred at room temperature for 30 minutes. The mixture was then concentrated. The residue was taken up in dichloromethane (2 mL) and N,N-diisopropylethylamine (0.57 mL, 3.24 mmol) was added. Then, a solution of 4-(1-adamantylmethoxy)-5-cyclopropyl-2-fluoro-benzoyl chloride (247 mg, 0.68 mmol), dissolved in dichloromethane (5 ml) was added slowly. The mixture was stirred at room temperature for 20 min and then concentrated. The residue was purified by reverse phase HPLC (method) to afford 171 mg (57%) of (2S,4S)-1-[4-(1-adamantylmethoxy)-5-cyclopropyl-2-fluoro-benzoyl]-4-hydroxy-pyrrolidine-2-carboxylic acid as a white solid. LCMS (Method Waters, ESI): RT=7.1 min, m+H=458.4. $^1$H NMR (400 MHz, DMSO-d6) δ 6.88-6.77 (m, 2H), 6.77-6.71 (m, 2H), 4.26 (dd, J=9.0, 4.4 Hz, 1H), 4.12 (dq, J=14.1, 4.7 Hz, 2H), 3.83 (d, J=9.1 Hz, 1H), 3.65-3.53 (m, 5H), 3.15 (dd, J=10.5, 3.9 Hz, 1H), 2.28 (td, J=8.7, 4.5 Hz, 1H), 2.22-2.13 (m, 1H), 2.08-1.94 (m, 4H), 0.94-0.79 (m, 4H), 0.68-0.53 (m, 1H).

The compounds of Examples 47-50 were prepared using procedures similar to those described above.

Example 47

Synthesis of (2R,4R)-1-[4-(1-adamantylmethoxy)-5-cyclopropyl-2-fluoro-benzoyl]-4-hydroxy-pyrrolidine-2-carboxylic Acid

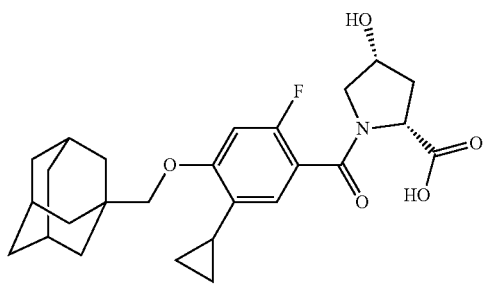 [SMILES: O=C(O)[C@H]1C[C@@H](O)CN1C(=O)c1cc(C2CC2)c(OCC23CC4CC(CC(C4)C2)C3)cc1F]

LCMS (Method Waters, ESI): RT=7.1 min, 333+H=458.4.

Example 48

Synthesis of (2S)-1-[4-(1-adamantylmethoxy)-5-cyclopropyl-2-fluoro-benzoyl]-4,4-difluoro-pyrrolidine-2-carboxylic Acid

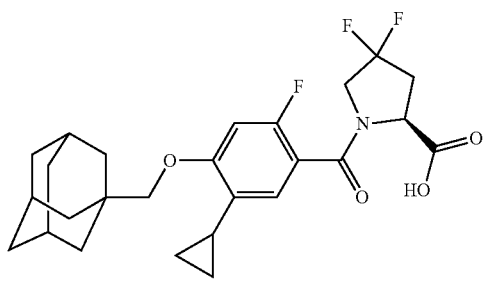 [SMILES: O=C(O)[C@@H]1CC(F)(F)CN1C(=O)c1cc(C2CC2)c(OCC23CC4CC(CC(C4)C2)C3)cc1F]

(LCMS (Method Waters, ESI): RT=7.9 min, m+H=478.2.

Example 49

Synthesis of (2S,4R)-1-[4-(1-adamantylmethoxy)-5-cyclopropyl-2-fluoro-benzoyl]-4-fluoro-pyrrolidine-2-carboxylic Acid

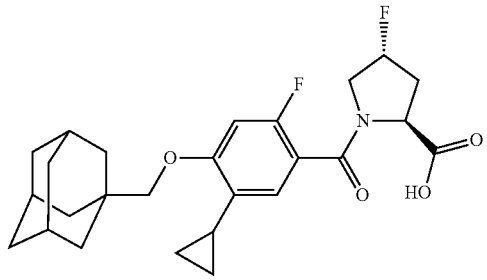 [SMILES: O=C(O)[C@@H]1C[C@@H](F)CN1C(=O)c1cc(C2CC2)c(OCC23CC4CC(CC(C4)C2)C3)cc1F]

LCMS (Method Waters, ESI): RT=7.7 min, m+H=460.2

Example 50

Synthesis of (4S)-3-[4-(1-adamantylmethoxy)-5-cyclopropyl-2-fluoro-benzoyl]thiazolidine-4-carboxylic Acid

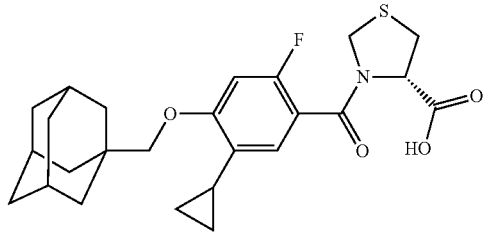 [SMILES: O=C(O)[C@H]1CSCN1C(=O)c1cc(C2CC2)c(OCC23CC4CC(CC(C4)C2)C3)cc1F]

LCMS (Method Waters, ESI): RT=7.9 min, m+H=460.2

Example 51

Synthesis of (S)-1-(4-((adamantan-1-yl)methoxy)-5-cyclopropyl-2-fluorobenzoyl)-2-methylpyrrolidine-2-carboxylic Acid Step 1. Preparation of methyl (S)-1-(4-((adamantan-1-yl)methoxy)-5-cyclopropyl-2-fluorobenzoyl)-2-methylpyrrolidine-2-carboxylate

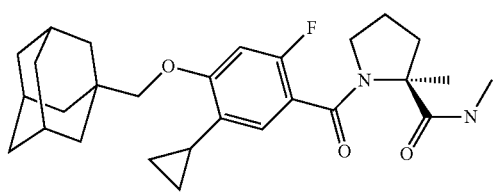 [SMILES: CNC(=O)[C@]1(C)CCCN1C(=O)c1cc(C2CC2)c(OCC23CC4CC(CC(C4)C2)C3)cc1F]

Following the procedure as described in Example 1, Step 1 and making variation as required to replace (S)-tert-butyl pyrrolidine-2-carboxylate hydrochloride with 2-methyl-L-proline methyl ester hydrochloride, the title compound was obtained as a colorless foam (0.45 g, 87%): $^1$H NMR (300 MHz, CDCl$_3$) δ 6.88 (d, J=7.8 Hz, 1H), 6.46 (d, J=12.0 Hz, 1H), 3.72 (s, 3H), 3.51-3.40 (m, 4H), 2.20-2.14 (m, 1H), 2.05-1.81 (m, 5H), 1.77-1.62 (m, 17H), 0.87-0.80 (m, 2H), 0.63-0.55 (m, 2H).

Step 2. Preparation of (S)-1-(4-((adamantan-1-yl)methoxy)-5-cyclopropyl-2-fluorobenzoyl)-2-methyl-pyrrolidine-2-carboxylic Acid

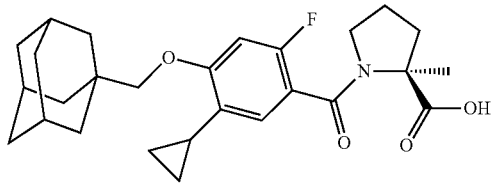 [SMILES: C[C@@]1(C(=O)O)CCCN1C(=O)c1cc(C2CC2)c(OCC23CC4CC(CC(C4)C2)C3)cc1F]

Following the procedure as described in Example 6, Step 2 and making variation as required to replace ethyl 1-(4-(adamantan-1-ylmethoxy)-5-cyclopropyl-2-fluoroben-zamido)cyclopropanecarboxylate with (S)-1-(4-((adamantan-1-yl)methoxy)-5-cyclopropyl-2-fluorobenzoyl)-2-methylpyrrolidine-2-carboxylate, the title compound was obtained as a colorless solid (0.31 g, 78%): $^1$H NMR (300 MHz, CDCl$_3$) δ 6.95 (d, J=7.8 Hz, 1H), 6.49 (d, J=12.3 Hz, 1H), 3.66-3.45 (m, 3H), 3.42-3.31 (m, 1H), 2.06-1.97 (m, 4H), 2.86-2.75 (m, 1H), 2.12-1.96 (m, 2H), 1.87-1.61 (m, 17H), 0.96-0.80 (m, 2H), 0.65-0.58 (m, 2H); MS (ES+) m/z: 456.1 (M+1).

Example 52

Synthesis of (S)-2-(4-(adamantan-1-ylmethoxy)-5-cyclopropyl-2-fluorobenzamido)-3,3-dimethylbutanoic Acid Step 1. Preparation of tert-butyl (S)-2-(4-(adamantan-1-yl)methoxy)-5-cyclopropyl-2-fluorobenzamido)-3,3-dimethylbutanoate

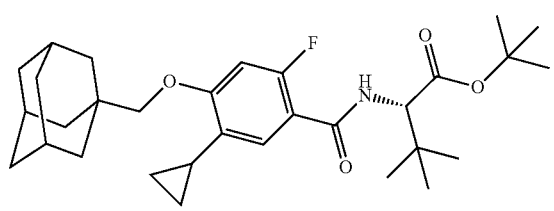 [SMILES: CC(C)(C)OC(=O)[C@@H](NC(=O)c1cc(C2CC2)c(OCC23CC4CC(CC(C4)C2)C3)cc1F)C(C)(C)C]

Following the procedure as described in Example 1, Step 1 and making variation as required to replace (S)-tert-butyl pyrrolidine-2-carboxylate hydrochloride with tert-butyl (S)-2-amino-3,3-dimethylbutanoate hydrochloride, the title compound was obtained as a colorless foam (0.20 g, 78%): $^1$H NMR (300 MHz, CDCl$_3$) δ 7.55 (d, J=9.0 Hz, 1H), 7.22-7.10 (m, 1H), 6.49 (d, J=14.4 Hz, 1H), 4.55-4.50 (m, 1H), 3.48 (s, 2H), 2.05-1.92 (m, 4H), 1.75-1.62 (m, 12H), 1.43 (s, 9H), 0.99 (s, 9H), 0.90-0.82 (m, 2H), 0.66-0.60 (m, 2H).

Step 2. Preparation of (S)-2-(4-(adamantan-1-yl-methoxy)-5-cyclopropyl-2-fluorobenzamido)-3,3-dimethylbutanoic Acid

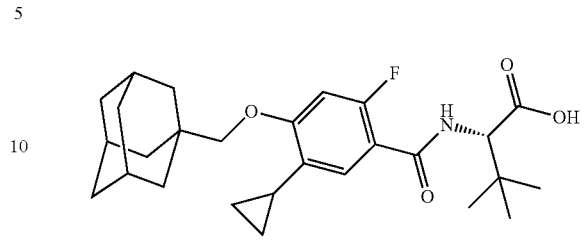

Following the procedure as described in Example 1, Step 2 and making variation as required to replace ethyl 1-(4-(adamantan-1-ylmethoxy)-5-cyclopropyl-2-fluoroben-zamido)cyclopropanecarboxylate with tert-butyl (S)-2-(4-(adamantan-1-yl)methoxy)-5-cyclopropyl-2-fluorobenzamido)-3,3-dimethylbutanoate, the title compound was obtained as a colorless solid (0.31 g, 78%): $^1$H NMR (300 MHz, DMSO-d$_6$) δ 12.76 (br s, 1H), 7.70-7.64 (m, 1H), 7.13 (d, J=8.7 Hz, 1H), 6.85 (d, J=13.5 Hz, 1H), 4.27 (d, J=9.0 Hz, 1H), 3.59 (s, 2H), 2.05-1.89 (m, 4H), 1.75-1.58 (m, 12H), 0.96 (s, 9H), 0.90-0.83 (m, 2H), 0.59-0.53 (m, 2H); MS (ES+) m/z 458.1 (M+1).

Example 53

Synthesis of (2S)-2-cyclopropyl-2-(5-cyclopropyl-4-((1-(1-(3,5-dichlorophenyl)-2,2,2-trifluoroethyl)piperidin-4-yl)methoxy)-2-fluorobenzamido)acetic Acid Step 1. Preparation of methyl (2S)-2-cyclopropyl-2-(5-cyclopropyl-4-((1-(1-(3,5-dichlorophenyl)-2,2,2-trifluoroethyl)piperidin-4-yl)methoxy)-2-fluorobenzamido)acetate

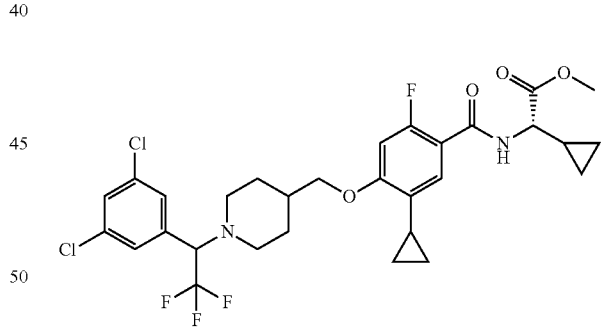

Following the procedure as described in Example 1, Step 1 and making variation as required to replace 4-((adamantan-1-yl)methoxy)-5-cyclopropyl-2-fluorobenzoic acid with 5-cyclopropyl-4-((1-(1-(3,5-dichlorophenyl)-2,2,2-trifluoroethyl)piperidin-4-yl)methoxy)-2-fluorobenzoic acid, and (S)-tert-butyl pyrrolidine-2-carboxylate hydrochloride with methyl (S)-2-amino-2-cyclopropylacetate hydrochloride, the title compound was obtained as a colorless foam (0.30 g, 48%): $^1$H NMR (300 MHz, CDCl$_3$) δ 7.60-7.48 (m, 1H), 7.38-7.23 (m, 3H), 7.17-7.09 (m, 1H), 6.49 (d, J=14.1 Hz, 1H), 4.21 (s, 1H), 4.19-4.02 (m, 1H), 3.84-3.73 (m, 4H), 3.08-2.92 (m, 2H), 2.50-2.30 (m, 2H), 2.07-1.95 (m, 2H), 2.03-1.78 (m, 4H), 1.53-1.40 (m, 2H), 0.91-0.82 (m, 2H), 0.67-0.42 (m, 6H).

Step 2. Preparation of (2S)-2-cyclopropyl-2-(5-cyclopropyl-4-((1-(1-(3,5-dichlorophenyl)-2,2,2-trifluoroethyl)piperidin-4-yl)methoxy)-2-fluorobenzamido)acetic Acid

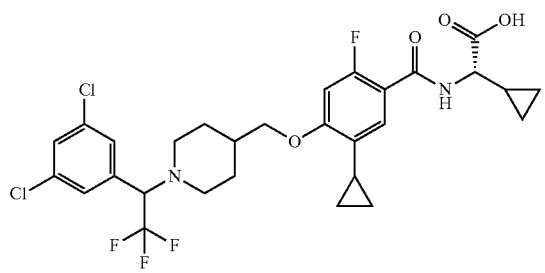 [SMILES: COC(=O)[C@@H](NC(=O)c1cc(C2CC2)c(OCC2CCN(C(c3cc(Cl)cc(Cl)c3)C(F)(F)F)CC2)cc1F)C1CC1]

Following the procedure as described in Example 6, Step 2 and making variation as required to replace ethyl 1-(4-(adamantan-1-ylmethoxy)-5-cyclopropyl-2-fluorobenzamido)-cyclopropanecarboxylate with methyl (2S)-2-cyclopropyl-2-(5-cyclopropyl-4-((1-(1-(3,5-dichlorophenyl)-2,2,2-trifluoroethyl)piperidin-4-yl)methoxy)-2-fluorobenzamido)acetate, the title compound was obtained as a colorless solid (0.11 g, 37%): $^1$H NMR (300 MHz, DMSO-$d_6$) δ 12.56 (br s, 1H), 8.15-8.10 (m, 1H), 7.69-7.67 (m, 1H), 7.42 (s, 1H), 7.09 (d, J=8.4 Hz, 1H), 6.84 (d, J=13.2 Hz, 1H), 4.79-4.68 (m, 1H), 3.88-3.06 (m, 3H), 2.97 (br s, 2H), 2.32-2.20 (m, 1H), 2.07-1.95 (m, 2H), 1.58-1.52 (m, 3H), 1.38-1.05 (m, 4H), 0.32-0.89 (m, 2H), 0.59-0.26 (m, 6H); MS (ES+) m/z 617.1, 619.1 (M+1).

Example 54

Synthesis of ((S)-2-(1H-tetrazol-5-yl)pyrrolidin-1-yl)(4-(adamantan-1-ylmethoxy)-5-cyclopropyl-2-fluorophenyl)methanone

Step 1. Preparation of (S)-1-(4-((adamantan-1-yl)methoxy)-5-cyclopropyl-2-fluorobenzoyl)pyrrolidine-2-carbonitrile

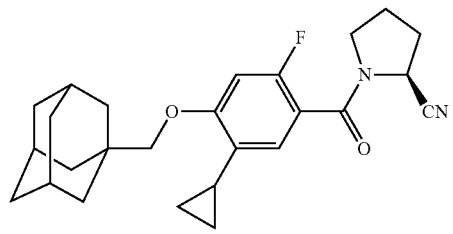 [SMILES: N#C[C@@H]1CCCN1C(=O)c1cc(C2CC2)c(OCC23CC4CC(CC(C4)C2)C3)cc1F]

Following the procedure as described in Example 1, Step 1 and making variation as required to replace (S)-tert-butyl pyrrolidine-2-carboxylate hydrochloride with (S)-pyrrolidine-2-carbonitrile hydrochloride, the title compound was obtained as a colorless foam (1.04 g, 60%): $^1$H NMR (300 MHz, CDCl$_3$) δ 6.97 (d, J=8.1 Hz, 1H), 6.49 (d, J=12.0 Hz, 1H), 4.86-4.81 (m, 1H), 3.55-3.37 (m, 4H), 2.35-1.96 (m, 7H), 1.79-1.64 (m, 13H), 0.93-0.85 (m, 2H), 0.65-0.58 (m, 2H); MS (ES+) m/z 423.1 (M+1).

Step 2. Preparation of ((S)-2-(1H-tetrazol-5-yl)pyrrolidin-1-yl)(4-(adamantan-1-ylmethoxy)-5-cyclopropyl-2-fluorophenyl)methanone

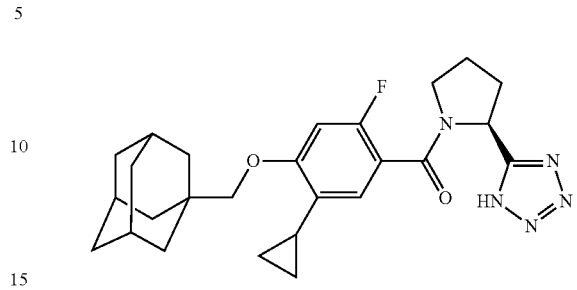

To a solution of (S)-1-(4-((adamantan-1-yl)methoxy)-5-cyclopropyl-2-fluorobenzoyl)-pyrrolidine-2-carbonitrile (0.42 g, 1.00 mmol) in N,N-dimethylformamide (20 mL) was added sodium azide (1.30 g, 20.00 mmol) and ammonium chloride (1.08 g, 20.00 mmol). The resulting mixture was heated at 100° C. for 18 hours. The reaction was cooled to ambient temperature, followed by addition of water (10.0 mL) and extraction with ethyl acetate (50 mL×3), the combined organic phase was washed with water and brine; dried over anhydrous sodium sulfate and concentrated in vacuo. The residue was purified by column chromatography eluting with ethyl acetate to afford the title compound as a colorless solid (0.35 g, 75%): $^1$H NMR (300 MHz, CDCl$_3$) δ 6.90 (d, J=7.8 Hz, 0.8H), 6.83 (d, J=12.0 Hz, 0.8H), 6.67 (d, J=12.0 Hz, 0.2H), 6.39 (d, J=7.8 Hz, 0.2H), 5.39-5.34 (m, 0.8H), 5.06-5.01 (m, 0.2H), 3.75-3.41 (m, 4H), 2.41-2.28 (m, 1H), 2.06-1.80 (m, 7H), 1.71-1.58 (m, 12H), 0.89-0.84 (m, 2H), 0.61-0.55 (m, 2H); MS (ES+) m/z 466.1 (M+1).

Example 55

Synthesis of (5-cyclopropyl-4-((1,1-difluoro-6-methylspiro[2.5]octan-6-yl)methoxy)-2-fluorobenzoyl)-L-proline

Step 1. Preparation of tert-butyl (5-cyclopropyl-4-((1,1-difluoro-6-methylspiro[2.5]octan-6-yl)methoxy)-2-fluorobenzoyl)-L-prolinate

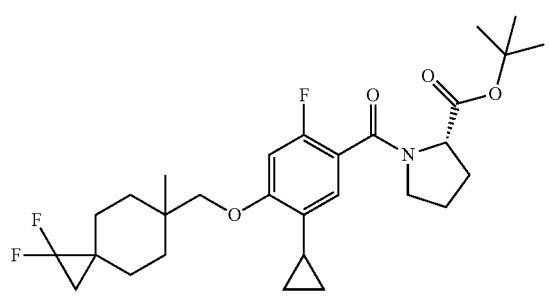 [SMILES: CC1(COc2cc(F)c(C(=O)N3CCC[C@H]3C(=O)OC(C)(C)C)cc2C2CC2)CCC2(CC1)CC2(F)F]

Following the procedure as described in Example 1, Step 1 and making variation as required to replace 4-adamantan-1-yl)methoxy)-5-cyclopropyl-2-fluorobenzoic acid with 5-cyclopropyl-4-((1,1-difluoro-6-methylspiro[2.5]octan-6-yl)methoxy)-2-fluorobenzoic acid, the title compound was obtained as a colorless foam (0.19 g, 94%): MS (ES+) m/z 522.3 (M+1).

Step 2. Preparation of (5-cyclopropyl-4-((1,1-difluoro-6-methylspiro[2.5]octan-6-yl)methoxy)-2-fluorobenzoyl)-L-proline

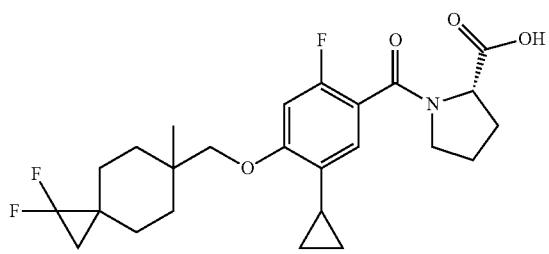 [SMILES: CC1(COc2cc(F)c(C(=O)N3CCC[C@H]3C(=O)O)cc2C2CC2)CCC2(CC1)CC2(F)F]

Following the procedure as described in Example 1, Step 2 and making variation as required to replace tert-butyl (4-adamantan-1-yl)methoxy)-5-cyclopropyl-2-fluorobenzoyl)-L-prolinate with of tert-butyl (5-cyclopropyl-4-((1,1-difluoro-6-methylspiro[2.5]octan-6-yl)methoxy)-2-fluorobenzoyl)-L-prolinate and following the residue was purified by reverse-phase HPLC, the title compound was obtained as a colorless solid (0.073 g, 44%): $^1$H NMR (300 MHz, CDCl$_3$) δ 7.00 (d, J=7.8 Hz, 1H), 6.56 (d, J=11.9 Hz, 1H), 6.54 (d, J=11.9 Hz, rotomer), 4.73 (dd, J=4.2, 8.1 Hz, 1H), 3.80-3.67 (m, 2H), 3.56-3.40 (m, 2H), 2.54-2.40 (m, 1H), 2.26-2.10 (m, 1H), 2.08-1.86 (m, 3H), 1.82-1.38 (m, 8H), 1.13 (s, 3H), 1.15 (s, rotomer), 1.07-0.97 (m, 2H), 0.99-0.83 (m, 2H), 0.65-0.57 (m, 2H); MS (ES+) m/z 466.1, 467.1, (ES−) m/z 464.2, 465.2.

Example 56

Synthesis (5-cyclopropyl-2-fluoro-4-((4-fluorobicyclo[2.2.2]octan-1-yl)methoxy)benzoyl)-L-proline Step 1. Preparation of methyl 4-fluorobicyclo[2.2.2]octane-1-carboxylate

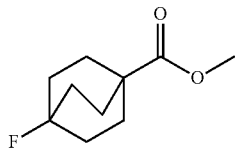

To a cooled (0° C.) solution of methyl 4-hydroxybicyclo[2.2.2]octane-1-carboxylate (2.0 g, 10.86 mmol) and anhydrous methanol (0.08 mL, 1.63 mmol) in anhydrous chloroform (12 mL), 2-chloro-N,N-diethyl-1,1,2-trifluoroethanamine (2.59 mL, 16.28 mmol) was added dropwise to minimize internal temperature. The resulting solution was heated at 60° C. for 24 h. The solution was cooled to ambient temperature and diluted with dichloromethane (50 mL) and water (50 mL). The aqueous layer was separated and extracted with dichloromethane (3×50 mL). The combined organic layers were washed with brine (30 mL), dried over anhydrous sodium sulfate, filtered and concentrated. The residue was purified using flash chromatography eluting with gradient 0% to 10% of ethyl acetate in hexanes to afford the title compound as colorless liquid (1.67 g, 83%): $^1$H NMR (300 MHz, CDCl$_3$) δ 3.64 (s, 3H), 2.05-1.96 (m, 6H), 1.86-1.79 (m, 6H).

Step 2. Preparation of (4-fluorobicyclo[2.2.2]octan-1-yl)methanol

To a cooled (0° C.) suspension of lithium aluminum hydride (1.34 g, 35.9 mmol) in anhydrous diethyl ether (50 mL) was added a solution of methyl 4-fluorobicyclo[2.2.2]octane-1-carboxylate (1.67 g, 8.97 mmol) in anhydrous diethyl ether (30 mL). The reaction was slowly warmed to ambient temperature and stirred overnight. The reaction was cooled at 0° C. and carefully quenched with water (1.4 mL) then diluted with diethyl ether (50 mL). The precipitate was removed by filtration and the filtrate was concentrated in vacuo to afford the title compound as a colorless liquid (1.33 g, 93%) which was used without further purification: $^1$H NMR (300 MHz, CDCl$_3$) δ 3.28 (s, 2H), 1.88-1.78 (m, 6H), 1.68-1.56 (m, 6H), 1.56-1.37 (br s, 1H).

Step 3. Preparation tert-butyl 5-chloro-2-fluoro-4-((4-fluorobicyclo[2.2.2]octan-1-yl)-methoxy)benzoate

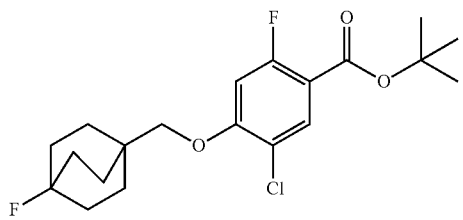 [SMILES: CC(C)(C)OC(=O)c1cc(Cl)c(OCC23CCC(F)(CC2)CC3)cc1F]

A suspension of (4-fluorobicyclo[2.2.2]octan-1-yl)methanol (0.180 g, 1.14 mmol), tert-butyl 5-chloro-2,4-difluorobenzoate (0.296 g, 1.19 mmol) and cesium carbonate (0.743 g, 2.28 mmol) in anhydrous dimethyl sulfoxide (4 mL) was heated at 80° C. and stirred overnight. The solution was quenched with 1N aqueous hydrochloric acid (10 mL) and diluted with saturated aqueous ammonium chloride (50 mL) and ethyl acetate (150 mL). The aqueous layer was separated and extracted with ethyl acetate (3×100 mL). The combined organic layers were then washed with brine (100 mL), dried over anhydrous sodium sulfate, filtered and concentrated in vacuo. The residue was purified using flash chromatography eluting with gradient 0% to 5% of ethyl acetate in hexanes to afford the title compound as a colorless gum (0.27 g, 61%): $^1$H NMR (300 MHz, CDCl$_3$) δ 7.87 (d, J=7.6 Hz, 1H), 6.57 (d, J=12.1 Hz, 1H), 3.62 (s, 2H), 1.94-1.78 (m, 12H), 1.57 (s, 9H).

Step 4. Preparation of tert-butyl 5-cyclopropyl-2-fluoro-4-((4-fluorobicyclo[2.2.2]octan-1-yl)methoxy)benzoate

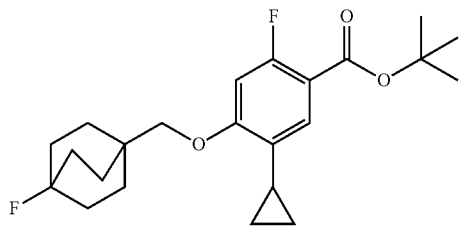 [SMILES: CC(C)(C)OC(=O)c1cc(C2CC2)c(OCC23CCC(F)(CC2)CC3)cc1F]

A suspension of tert-butyl 5-chloro-2-fluoro-4-((4-fluorobicyclo[2.2.2]octan-1-yl)methoxy)benzoate (0.26 g, 0.48 mmol), cyclopropylboronic acid (0.089 g, 1.03 mmol), tricyclohexylphosphine tetrafluoroborate (0.026 g, 0.069 mmol), potassium phosphate (0.65 g, 3.08 mmol) in toluene (5.0 mL) and water (0.5 mL) was sparged with argon for 10 minutes before palladium acetate (0.008 g, 0.034 mmol) was added. The mixture was heated at 110° C. and stirred overnight. After cooling to ambient temperature, the reaction mixture was filtered through a Celite plug and rinsed with water (10 mL), tetrahydrofuran (20 mL) and ethyl acetate (50 mL). The filtrate was concentrated and the residue was diluted with water (25 mL) and ethyl acetate (50 mL). The aqueous layer was separated and extracted with ethyl acetate (3×50 mL). The combined organics were dried over anhydrous sodium sulfate, filtered and concentrated in vacuo. The residue was purified by flash chromatography eluting with gradient 0% to 10% of ethyl acetate in hexanes to afford the title compound as a colorless gum (0.255 g, 95%): MS (ES+) m/z 337.1, 338.1 (M+1).

Step 5. Preparation of 5-cyclopropyl-2-fluoro-4-((4-fluorobicyclo[2.2.2]octan-1-yl)methoxy)benzoic Acid

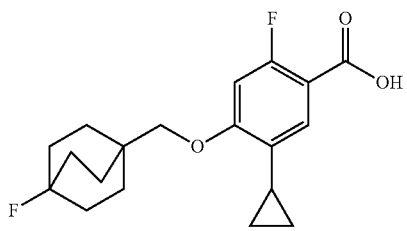 [SMILES: O=C(O)c1cc(C2CC2)c(OCC23CCC(F)(CC2)CC3)cc1F]

To a solution of tert-butyl 5-cyclopropyl-2-fluoro-4-((4-fluorobicyclo[2.2.2]octan-1-yl)methoxy)benzoate (0.20 g, 0.51 mmol) in 1,4-dioxane (8 mL) was added 12M aqueous hydrochloric acid (2.10 mL, 25.5 mmol). The mixture was stirred at ambient temperature overnight. The reaction was diluted with dichloromethane (100 mL) and water (50 mL). The aqueous layer was separated and extracted with dichloromethane (3×50 mL). The combined organics were dried over anhydrous sodium sulfate, filtered and concentrated in vacuo to afford the title compound as a gum (0.17 g, quantitative yield) which was used without further purification: $^1$H NMR (300 MHz, DMSO-$d_6$) δ 12.82 (s, 1H), 7.31 (d, J=8.5 Hz, 1H), 6.85 (d, J=13.1 Hz, 1H), 3.71 (s, 2H), 2.08-1.95 (m, 1H), 1.85-1.73 (m, 12H), 0.94-0.86 (m, 2H), 0.62-0.55 (m, 2H); MS (ES+) m/z 337.1, 338.1 (M+1).

Step 6. Preparation tert-butyl (5-cyclopropyl-2-fluoro-4-((4-fluorobicyclo[2.2.2]octan-1-yl)methoxy)benzoyl)-L-prolinate

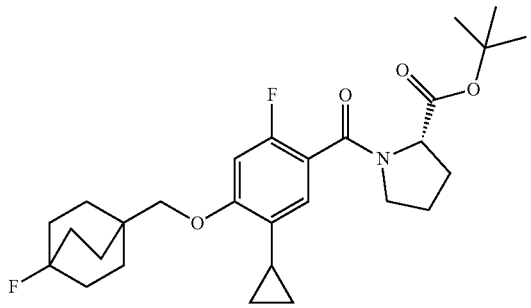 [SMILES: CC(C)(C)OC(=O)[C@@H]1CCCN1C(=O)c1cc(C2CC2)c(OCC23CCC(F)(CC2)CC3)cc1F]

A solution 5-cyclopropyl-2-fluoro-4-((4-fluorobicyclo[2.2.2]octan-1-yl)methoxy)benzoic acid (0.167 g, 0.496 mmol), O-(benzotriazol-1-yl)-N,N,N',N'-tetramethyluronium tetrafluoroborate (0.318 g, 0.992 mmol), hydroxybenzotriazole (0.087 g, 0.645 mmol) and N,N-diisopropylethylamine (0.345 mL, 1.98 mmol) in acetonitrile (12 mL) was stirred for 20 min then tert-butyl L-prolinate hydrochloride (0.123 g, 0.595 mmol) was added in one portion. The reaction was stirred at ambient temperature 16 h. The reaction was concentrated, diluted with ethyl acetate (100 mL) and washed with 5% aqueous hydrochloric acid (20 mL). The aqueous layer was separated and extracted with ethyl acetate (2×50 mL). The combined organics were washed with brine (20 mL), dried over anhydrous sodium sulfate and concentrated in vacuo. The residue was purified by flash chromatography eluting with gradient 0% to 10% of ethyl acetate in hexanes to the title compound as a colorless gum (0.22 g, 92%): MS (ES+) m/z 490.3, 491.3 (M+1).

Step 7. Preparation of (5-cyclopropyl-2-fluoro-4-((4-fluorobicyclo[2.2.2]octan-1-yl)methoxy)benzoyl)-L-proline

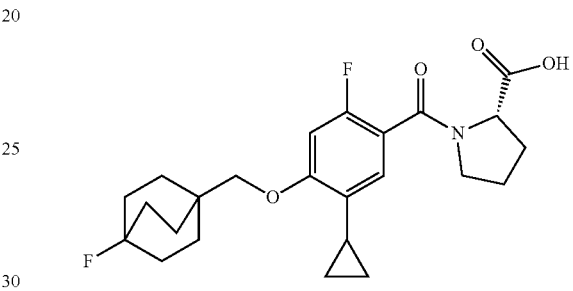

To a solution tert-butyl (5-cyclopropyl-2-fluoro-4-((4-fluorobicyclo[2.2.2]octan-1-yl)methoxy)benzoyl)-L-prolinate (0.22 g, 0.46 mmol) in 1,4-dioxane (7 mL) was added 12 M aqueous hydrochloric acid (1.9 mL, 22.8 mmol). The reaction was stirred at ambient temperature overnight. The reaction was diluted with dichloromethane (100 mL) and water (50 mL). The aqueous layer was separated and extracted with dichloromethane (3×50 mL). The combined organics were dried over anhydrous sodium sulfate, filtered and concentrated in vacuo. The residue was purified by reverse-phase HPLC to afford the title compound as colorless solid (0.17 g, 87%): $^1$H NMR (300 MHz, CDCl$_3$) δ 6.97 (d, J=7.8 Hz, 1H), 6.49 (d, J=11.8 Hz, 1H), 4.72 (dd, J=4.2, 8.1 Hz, 1H), 3.71 (s, 2H), 3.58 (s, 1H), 3.55-3.39 (m, 2H), 2.52-2.39 (m, 1H), 2.26-2.10 (m, 1H), 2.05-1.96 (m, 2H), 1.93-1.71 (m, 12H), 0.95-0.88 (m, 2H), 0.65-0.60 (m, 2H); MS (ES+) m/z 434.1, 435.1 (M+1).

Example 57

Synthesis of (4-((adamantan-1-ylmethoxy)-5-cyclopropyl-2-fluorobenzoyl)-L-threonine Step 1. Preparation of tert-butyl (4-((adamantan-1-yl)methoxy)-5-cyclopropyl-2-fluorobenzoyl)-L-threoninate

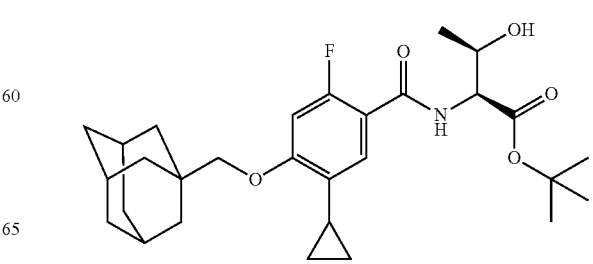

Following the procedure as described in Example 1, Step 1 and making non-critical variations to replace (S)-tert-butyl pyrrolidine-2-carboxylate hydrochloride with tert-butyl L-threoninate hydrochloride. The reaction was stirred at ambient temperature for 16 hours. The reaction was concentrated, diluted with ethyl acetate (20 mL) and washed with 5% hydrochloric acid solution (2×10 mL). The aqueous layer was separated and extracted with ethyl acetate (2×20 mL). The combined organics were washed with brine (10 mL), dried over anhydrous sodium sulfate and concentrated to yield tert-butyl (4-((adamantan-1-yl)methoxy)-5-cyclopropyl-2-fluorobenzoyl)-L-threoninate (0.23 g). The residue was used in the next step without any further purification: MS (ES+) m/z 502.3, 503.3 (M+1).

Step 2. Preparation of (4-((adamantan-1-yl-methoxy)-5-cyclopropyl-2-fluorobenzoyl)-L-threonine

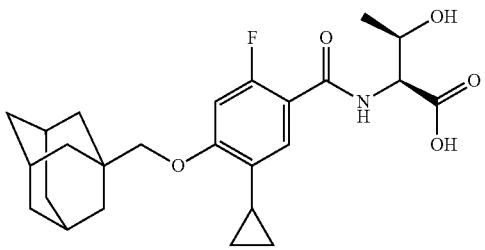 [SMILES: C[C@@H](O)[C@H](NC(=O)c1cc(C2CC2)c(OCC23CC4CC(CC(C4)C2)C3)cc1F)C(=O)O]

Following the procedure as described in Example 1, Step 2 and making variation as required to replace tert-butyl (4-adamantan-1-yl)methoxy)-5-cyclopropyl-2-fluorobenzoyl)-L-prolinate with tert-butyl (4-((adamantan-1-yl)methoxy)-5-cyclopropyl-2-fluorobenzoyl)-L-threoninate and following the residue was purified by reverse-phase HPLC, the title compound was as a colorless solid (0.068 g, 34%): $^1$H NMR (300 MHz, CDCl$_3$) δ 7.57 (d, J=8.9 Hz, 1H), 7.55-7.49 (m, 1H), 6.55 (d, J=14.3 Hz, 1H), 4.76-4.50 (m, 2H), 3.54 (s, 2H), 2.12-1.96 (m, 4H), 1.85-1.58 (m, 12H), 1.36-1.16 (m, 4H), 0.97-0.80 (m, 2H), 0.72-0.58 (m, 2H); MS (ES+) m/z 446.2, 447.2 (M+1).

Example 58

Synthesis of (5-cyclopropyl-2-fluoro-4-((6-methyl-spiro[2.5]octan-6-yl)-methoxy)benzoyl)-L-proline Step 1. Preparation methyl (5-cyclopropyl-2-fluoro-4-((6-methylspiro[2.5]-octan-6-yl)methoxy)benzoyl)-L-prolinate

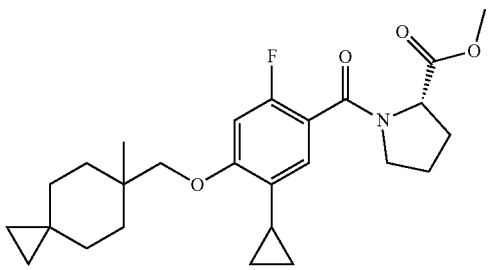 [SMILES: COC(=O)[C@@H]1CCCN1C(=O)c1cc(C2CC2)c(OCC2(C)CCC3(CC2)CC3)cc1F]

Following the procedure as described in Example 1, Step 1 and making non-critical variations to replace 4-adamantan-1-yl)methoxy)-5-cyclopropyl-2-fluorobenzoic acid with 5-cyclopropyl-2-fluoro-4-((6-methylspiro[2.5]octan-6-yl)methoxy)benzoic acid and (S)-tert-butyl pyrrolidine-2-carboxylate hydrochloride with methyl L-prolinate hydrochloride, the title compound was obtained as a colorless gum (0.120 g, 58%): MS (ES+) m/z 444.2, 445.2 (M 1+1).

Step 2. Preparation of (5-cyclopropyl-2-fluoro-4-((6-methylspiro[2.5]octan-6-yl)methoxy)benzoyl)-L-proline

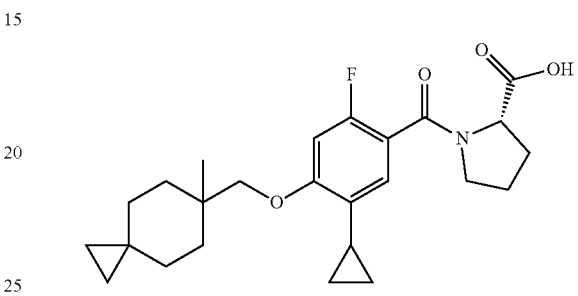

Following the procedure as described in Example 6, Step 2 and making variation as required to replace ethyl 1-(4-adamantan-1-ylmethoxy)-5-cyclopropyl-2-fluorobenzamido)cyclopropanecarboxylate with methyl (5-cyclopropyl-2-fluoro-4-((6-methylspiro[2.5]octan-6-yl)methoxy)benzoyl)-L-prolinate and following the residue was purified by reverse-phase HPLC, the title compound was obtained as a colorless solid (0.066 g, 57%): $^1$H NMR (300 MHz, CDCl$_3$) δ 6.98 (d, J=7.1 Hz, 1H), 6.56 (d, J=11.8 Hz, 1H), 4.86-4.60 (m, 1H), 3.71 (s, 2H), 3.57-3.45 (m, 2H), 2.41-2.16 (m, 2H), 2.10-1.83 (m, 3H), 1.71-1.41 (m, 6H), 1.12 (s, 3H), 1.12-1.08 (m, 2H), 0.95-0.84 (m, 2H), 0.62-0.56 (m, 2H), 0.32-0.18 (m, 4H); MS (ES+) m/z 430.1, 431.1 (M+1).

Example 59

Synthesis of (2S,4R)-1-(4-((adamantan-1-yl)methoxy)-5-cyclopropyl-2-fluorobenzoyl)-4-methoxypyrrolidine-2-carboxylic Acid Step 1. Preparation of (2S,4R)-1-(tert-butoxycarbonyl)-4-hydroxypyrrolidine-2-carboxylic Acid

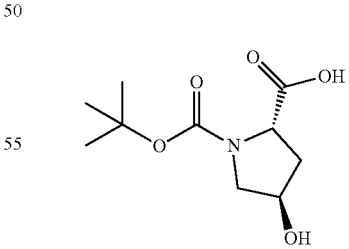

To a solution of (2S,4R)-4-hydroxypyrrolidine-2-carboxylic acid (2.54 g, 19.37 mmol) in 1N aqueous sodium hydroxide (20 mL, 20.0 mmol) and 1,4-dioxane (20 mL) was added di-tert-butyl dicarbonate (4.89 mL, 21.31 mmol) was added dropwise at 0° C. The resulting solution was slowly warmed to ambient temperature for 16 h. The reaction mixture was concentrated, acidified with 5% aqueous hydrochloric acid and diluted with ethyl acetate (50 mL). The aqueous layer was separated and extracted with ethyl acetate (3×50 mL). The combined organic layers were washed with brine (30 mL), dried over anhydrous sodium sulfate, filtered and concentrated in vacuo to afford the title compound (4.38 g) which was used without further purification: MS (ES−) m/z 230.3.

Step 2. Preparation of 1-(tert-butyl) 2-methyl (2S, 4R)-4-methoxypyrrolidine-1,2-dicarboxylate

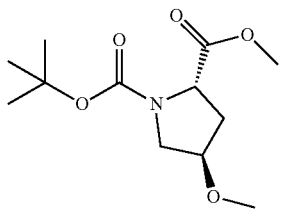 [SMILES: COC(=O)[C@@H]1C[C@@H](OC)CN1C(=O)OC(C)(C)C]

To a solution of (2S, 4R)-1-(tert-butoxycarbonyl)-4-hydroxypyrrolidine-2-carboxylic acid (1.84 g, 7.96 mmol) in anhydrous acetonitrile (140 mL) was added silver (I) oxide (9.22 g, 39.8 mmol) followed by iodomethane (4.96 mL, 79.6 mmol) cooled at 0° C. The resulting suspension was slowly warmed to ambient temperature and stirred vigorously for 2 days. The solid material was removed by suction filtration and the filtrate was concentrated in vacuo. The residue was purified by flash chromatography eluting with gradient 0% to 40% of ethyl acetate in hexane to afford the title compound as a colorless liquid (1.71 g, 83%): MS (ES+) m/z 160.1 (M+1).

Step 3. Preparation of methyl (2S, 4R)-4-methoxypyrrolidine-2-carboxylate Trifluoroacetic Acid Salt

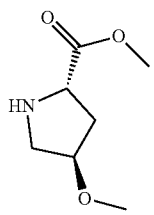

To a solution of 1-(tert-butyl) 2-methyl (2S, 4R)-4-methoxypyrrolidine-1,2-dicarboxylate (1.71 g, 6.59 mmol) in dichloromethane (55 mL) was added trifluoroacetic acid (55 mL, 724 mmol). The reaction mixture was stirred at ambient temperature for 16 h. The reaction was concentrated, diluted with toluene and concentrated in vacuo to afford the title compound as a pale yellow gum (1.62 g, 90%) which was used in the next step without any further purification: $^1$H NMR (300 MHz, CDCl$_3$) δ 4.56 (dd, J=7.4, 10.7 Hz, 1H), 4.23-4.15 (m, 1H), 3.83 (s, 3H), 3.69-3.54 (m, 2H), 3.32 (s, 3H), 2.58 (dd, J=7.1, 13.7 Hz, 1H), 2.23-2.06 (m, 1H); MS (ES+) m/z 160.1.

Step 4. Preparation methyl (2S, 4R)-1-(4-((adamantan-1-yl)methoxy)-5-cyclopropyl-2-fluorobenzoyl)-4-methoxypyrrolidine-2-carboxylate

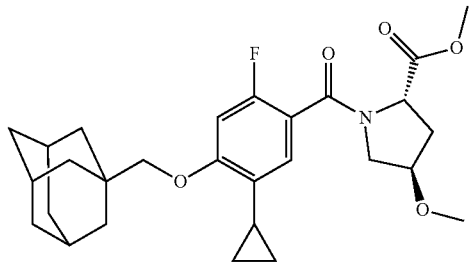 [SMILES: COC(=O)[C@@H]1C[C@@H](OC)CN1C(=O)c1cc(C2CC2)c(OCC23CC4CC(CC(C4)C2)C3)cc1F]

To a solution of methyl (2S,4R)-4-methoxypyrrolidine-2-carboxylate trifluoroacetic acid salt (0.083 g, 0.30 mmol) and triethylamine (0.134 mL, 0.966 mmol) in dichloromethane (1.5 mL) was added 4-((adamantan-1-yl)methoxy)-5-cyclopropyl-2-fluorobenzoyl chloride (0.10 g, 0.28 mmol) at 0° C. The reaction was slowly warmed to ambient temperature and stirred for 16 hours. The reaction mixture was concentrated then diluted with ethyl acetate (20 mL) and washed with 5% hydrochloric acid solution (10 mL). The aqueous layer was separated and extracted with ethyl acetate (2×20 mL). The combined organic layers were washed with brine (10 mL), dried over anhydrous sodium sulfate and concentrated in vacuo to afford the title compound (0.15 g, quantitative yield) which was used without any further purification: MS (ES+) m/z 486.2, 487.2 (M+1).

Step 5. Preparation of (2S, 4R)-1-(4-((adamantan-1-yl)methoxy)-5-cyclopropyl-2-fluorobenzoyl)-4-methoxypyrrolidine-2-carboxylic Acid

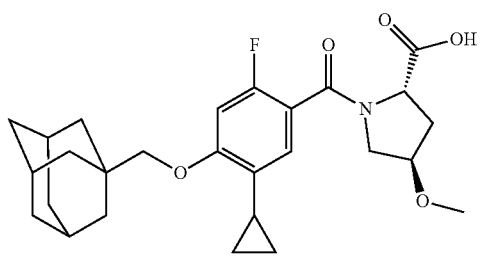 [SMILES: CO[C@@H]1C[C@@H](C(=O)O)N(C(=O)c2cc(C3CC3)c(OCC34CC5CC(CC(C5)C3)C4)cc2F)C1]

Following the procedure as described in Example 11, Step 2 and making variation as required to replace methyl (4-adamantan-1-yl)methoxy)-5-cyclopropyl-2-fluorobenzoyl)-L-alaninate with methyl (2S, 4R)-1-(4-((adamantan-1-yl)methoxy)-5-cyclopropyl-2-fluorobenzoyl)-4-methoxypyrrolidine-2-carboxylate and following the residue was purified by reverse-phase HPLC, the title compound was obtained as a colorless solid (0.093 g, 66%): $^1$H NMR (300 MHz, CDCl$_3$) δ 7.01 (d, J=7.9 Hz, 1H), 6.53 (d, J=12.1 Hz, 1H), 4.84 (t, J=8.1 Hz, 1H), 4.00-3.95 (m, 1H), 4.13-4.10 (m, 1H, rotomer), 3.65-3.55 (m, 2H), 3.51 (s, 2H), 3.24 (s, 3H), 2.61-2.51 (m, 1H), 2.40-2.31 (m, 1H), 2.09-2.00 (m, 4H), 1.80-1.62 (m, 12H), 0.95-0.88 (m, 2H), 0.66-0.61 (m, 2H); $^{19}$F MNR (300 MHz, CDCl$_3$) δ −112.84; MS (ES+) m/z 472.3, 473.3 (M+1).

Example 60

Synthesis of (1R, 3S, 5R)-2-(4-((adamantan-1-yl)methoxy)-5-cyclopropyl-2-fluorobenzoyl)-2-azabicyclo[3.1.0]hexane-3-carboxylic Acid

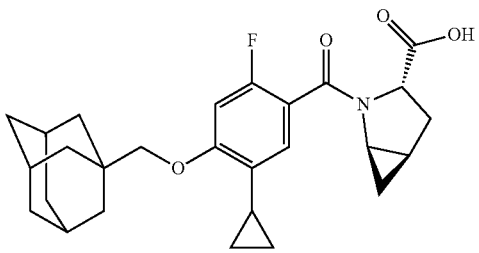 [SMILES: O=C(O)[C@@H]1C[C@H]2C[C@H]2N1C(=O)c1cc(C2CC2)c(OCC23CC4CC(CC(C4)C2)C3)cc1F]

Following the procedure as described in Example 59, Step 4 and making variation as required to replace methyl (2S, 4R)-4-methoxypyrrolidine-2-carboxylate trifluoroacetic acid salt with (1R,3S,5R)-2-azabicyclo[3.1.0]hexane-3-carboxylic acid hydrochloride, the title compound was obtained as a colorless solid (0.168 g, 89%): $^1$H NMR (300 MHz, CDCl$_3$) δ 7.01 (d, J=7.8 Hz, 1H), 6.56 (d, J=11.8 Hz, 1H), 4.63 (dd, J=4.4, 9.1 Hz, 1H), 3.52 (s, 2H), 3.21 (dt, J=2.4, 6.3 Hz, 1H), 2.85-2.70 (m, 1H), 2.27 (dd, J=9.5, 13.6 Hz, 1H), 2.10-2.03 (m, 4H), 1.89-1.62 (m, 13H), 0.98-0.82 (m, 3H), 0.73-0.58 (m, 3H); $^{19}$F NMR (300 MHz, CDCl$_3$) δ −113.25; MS (ES+) m/z 454.2, 455.2 (M+1).

Example 61

Synthesis of racemate-(1R, 3S, 5R)-2-(4-((adamantan-1-yl)methoxy)-5-cyclopropyl-2-fluorobenzoyl)-2-azabicyclo[3.1.0]hexane-3-carboxylic Acid

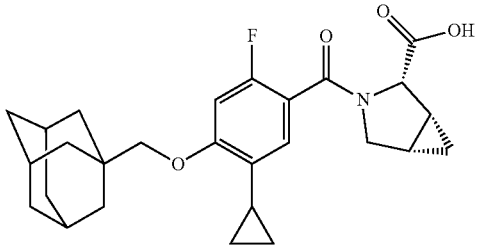 [SMILES: O=C(O)[C@@H]1[C@@H]2C[C@@H]2CN1C(=O)c1cc(C2CC2)c(OCC23CC4CC(CC(C4)C2)C3)cc1F]

Following the procedure as described in Example 59, Step 4 and making variation as required to replace methyl (2S, 4R)-4-methoxypyrrolidine-2-carboxylate trifluoroacetic acid salt with racemate-(1R, 2S,5S)-3-azabicyclo[3.1.0]hexane-2-carboxylic acid and following the residue was purified by flash chromatography eluting with gradient 0% to 60% of ethyl acetate in hexanes with 0.1% formic acid as an additive, the title compound was obtained as a colorless solid (0.060 g, 57%): $^1$H NMR (300 MHz, CDCl$_3$) δ 6.90 (d, J=7.8 Hz, 1H), 6.50 (d, J=11.8 Hz, 1H), 4.68 (d, J=5.3 Hz, 1H), 3.64-3.53 (m, 2H), 3.49 (s, 2H), 2.10-1.94 (m, 5H), 1.85-1.68 (m, 13H), 0.95-0.73 (m, 4H), 0.67-0.54 (m, 2H); MS (ES+) m/z 454.2, 455.2 (M+1).

Example 62

Synthesis of (2S, 3R)-1-(4-((adamantan-1-yl)methoxy)-5-cyclopropyl-2-fluorobenzoyl)-3-hydroxypyrrolidine-2-carboxylic Acid Step 1. Preparation of (2S, 3R)-1-(tert-butoxycarbonyl)-3-hydroxypyrrolidine-2-carboxylic Acid

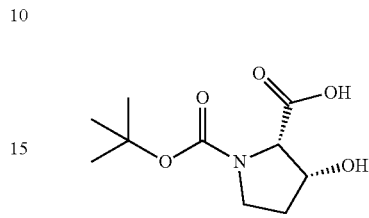

To a solution of 1-(tert-butyl) 2-methyl (2S,3S)-3-hydroxypyrrolidine-1,2-dicarboxylate (1.81 g, 7.38 mmol) in anhydrous tetrahydrofuran (60 mL) was added triphenylphosphine (2.03 g, 7.75 mmol) and para-nitrobenzoic acid (1.30 g, 7.75 mmol) at 0° C. A solution of di-isopropyl azadicarboxylate (1.55 mL, 7.89 mmol) in anhydrous tetrahydrofuran (6 mL) was added dropwise. The resulting solution was stirred at 0° C. for 3 hours before being quenched with 1N aqueous sodium hydroxide (24 mL, 24.0 mmol). The reaction mixture was warmed to ambient temperature and stirred for 1 hour. The solution was partially concentrated in vacuo to remove the tetrahydrofuran then diluted with water (30 mL) and extracted with ethyl acetate (3×30 mL). The aqueous layer acidified with 10% aqueous potassium bisulfate to pH=2 and the resulting precipitate was removed by vacuum filtration. The filtrate was treated with saturated sodium chloride and extracted with 2:1 chloroform/ethanol (4×50 mL). The combined organic layers was dried over anhydrous magnesium sulfate, filtered, and concentrated in vacuo. The residue was purified by column chromatography, eluting with a 0-30% gradient of ethyl acetate in hexanes to afford the title compound as colorless syrup (1.14 g, 67%) which was used without further purification: MS (ES+) m/z 230.3, 231.3 (M+1).

Step 2. Preparation of 2-benzyl 1-(tert-butyl) (2S, 3R)-3-hydroxypyrrolidine-1,2-dicarboxylate

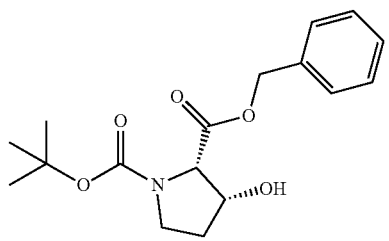 [SMILES: CC(C)(C)OC(=O)N1CC[C@@H](O)[C@H]1C(=O)OCc1ccccc1]

To a solution of (2S, 3R)-1-(tert-butoxycarbonyl)-3-hydroxypyrrolidine-2-carboxylic acid (1.14 g, 4.93 mmol) in methanol (23 mL) was added a solution of cesium carbonate (0.80 g, 2.46 mmol) in water (14 mL) at 0° C. The resulting suspension was slowly warmed to ambient temperature over 0.5 h and then concentrated in vacuo. The aqueous residue was diluted with N, N-dimethylformamide (41 mL) and the resulting slurry was cooled at 0° C. then added benzyl bromide (0.6 mL, 4.93 mmol). The reaction mixture was warmed to ambient temperature and stirred for 16 hours. The reaction mixture was filtered and the filtrate was concentrated in vacuo. The residue was diluted with ethyl acetate (250 mL) and washed with saturated aqueous sodium bicarbonate (100 mL) and water (2×75 mL). The organic layer was dried over anhydrous sodium sulfate, filtered and concentrated in vacuo. The residue was purified by column chromatography, eluting with a 0-30% gradient of ethyl acetate in hexanes to afford the title compound (0.49 g, 31%): $^1$H NMR (300 MHz, CDCl$_3$) δ 7.40-7.26 (m, 5H), 5.32-5.06 (m, 2H), 4.63-4.53 (m, 1H), 4.35 (d, J=6.8 Hz, 1H), 4.44 (d, J=6.8 Hz, 1H, rotomer), 3.71-3.53 (m, 1H), 3.50-3.33 (m, 1H), 2.15-1.90 (m, 3H), 1.31 (s, 9H), 1.43 (s, 9H, rotomer); MS (ES+) m/z 222.2 (M+1).

Step 3. Preparation of benzyl (2S, 3R)-1-(4-((adamantan-1-yl)methoxy)-5-cyclopropyl-2-fluorobenzoyl)-3-hydroxypyrrolidine-2-carboxylate

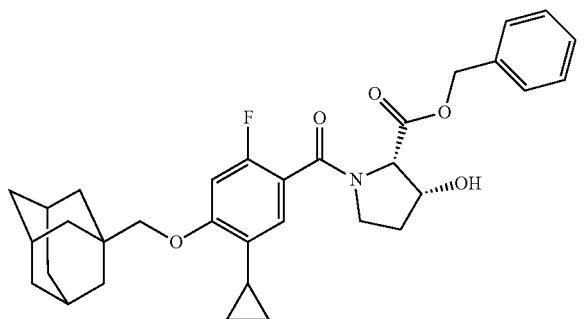 [SMILES: O=C(OCc1ccccc1)[C@@H]1[C@H](O)CCN1C(=O)c1cc(C2CC2)c(OCC23CC4CC(CC(C4)C2)C3)cc1F]

Following the procedure as described in Example 59, Step 3 and Step 4 and making variation as required to replace 1-(tert-butyl) 2-methyl (2S, 4R)-4-methoxypyrrolidine-1,2-dicarboxylate 2-benzyl 1-(tert-butyl) (2S, 3R)-3-hydroxypyrrolidine-1,2-dicarboxylate, the title compound was obtained as colorless syrup (0.16 g, 96%) which was used without any further purification: MS (ES+) m/z 548.3, 549.3 (M+1).

Step 4. Preparation of (2S, 3R)-1-(4-((adamantan-1-yl)methoxy)-5-cyclopropyl-2-fluorobenzoyl)-3-hydroxypyrrolidine-2-carboxylic Acid

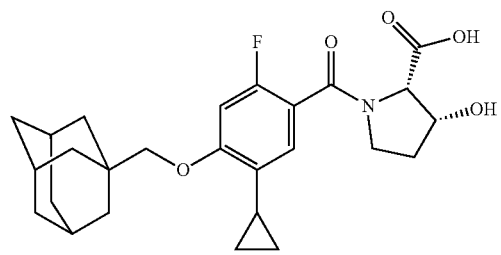 [SMILES: O=C(O)[C@@H]1[C@H](O)CCN1C(=O)c1cc(C2CC2)c(OCC23CC4CC(CC(C4)C2)C3)cc1F]

A suspension of benzyl (2S, 3R)-1-(4-((adamantan-1-yl)methoxy)-5-cyclopropyl-2-fluorobenzoyl)-3-hydroxypyrrolidine-2-carboxylate (0.16 g, 0.28 mmol) and 10% Palladium on charcoal (0.038 g, 0.036 mmol) in methanol (4 mL) was evacuated then flushed with hydrogen gas. This process was repeated three times and then purged the reaction vessel with hydrogen atmosphere. The reaction mixture was stirred at ambient temperature for 16 hours. The reaction mixture was filtered through a Celite plug and the filter bed was rinsed with methanol (2×20 mL) and ethyl acetate (2×20 mL). The filtrate was concentrated in vacuo and the residue was purified by reverse-phase HPLC to afford the title compound as a colorless solid (0.068 g, 53%): $^1$H NMR (300 MHz, CDCl$_3$) δ 7.00 (d, J=7.8 Hz, 1H), 6.55 (d, J=12.1 Hz, 1H), 4.79-4.71 (m, 2H), 3.93-3.76 (m, 1H), 3.60-3.45 (m, 1H), 3.52 (s, 2H), 2.14-1.85 (m, 5H), 1.85-1.61 (m, 12H), 0.99-0.80 (m, 3H), 0.68-0.58 (m, 2H); MS (ES+) m/z 458.2, 459.1 (M+1).

Example 63

Synthesis of (2R, 3R)-1-(4-((adamantan-1-yl)methoxy)-5-cyclopropyl-2-fluorobenzoyl)-3-fluoropyrrolidine-2-carboxylic Acid Step 1. Preparation of (2S,3S)-1-(tert-butoxycarbonyl)-3-hydroxypyrrolidine-2-carboxylic Acid

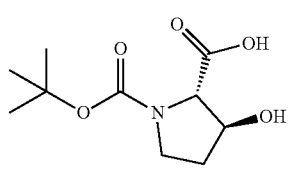 [SMILES: CC(C)(C)OC(=O)N1CC[C@H](O)[C@H]1C(=O)O]

To a solution of 1-(tert-butyl) 2-methyl (2S,3S)-3-hydroxypyrrolidine-1,2-dicarboxylate (0.30 g, 1.22 mmol) in tetrahydrofuran (12 mL) was added 0.2N aqueous lithium hydroxide (6.12 mL, 1.22 mmol). The reaction was stirred at ambient temperature for 3 hours. The reaction mixture was diluted with diethyl ether (30 mL) and extracted with 0.2N aqueous lithium hydroxide (3×5 mL). The combined aqueous layers were acidified with 5% aqueous hydrochloric acid until pH=2. The acidic aqueous layer was extracted with ethyl acetate (3×30 mL). The organic layer was dried over anhydrous sodium sulfate, filtered and concentrated in vacuo to afford the title compound as a gum (0.25 g, 88%) which was used in the next step without any further purification: MS (ES+) m/z 230.3 (M+1).

Step 2. Preparation of 2-benzyl 1-(tert-butyl) (2S, v3S)-3-hydroxypyrrolidine-1,2-dicarboxylate

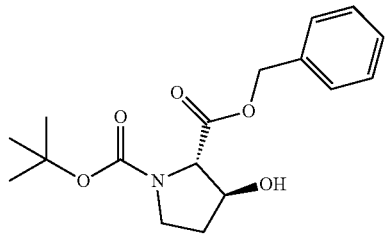 [SMILES: CC(C)(C)OC(=O)N1CC[C@H](O)[C@H]1C(=O)OCc1ccccc1]

Following the procedure as described in Example 62, Step 2 and making non-critical variations to replace (2S, 3R)-1-(tert-butoxycarbonyl)-3-hydroxypyrrolidine-2-carboxylic acid with (2S, 3S)-1-(tert-butoxycarbonyl)-3-hydroxypyrrolidine-2-carboxylic acid, the title compound was obtained as a colorless gum (0.15 g, 44%): ¹H NMR (300 MHz, CDCl₃) δ 7.46-7.28 (m, 5H), 5.29-5.04 (m, 2H), 4.46-4.42 (m, 1H), 4.21 (s, 1H) [4.34, rotomer], 3.71-3.51 (m, 2H), 2.20-1.97 (m, 2H), 1.97-1.82 (m, 1H), 1.32 (s, 9H) [1.46, rotomer]; MS (ES+) m/z 222.1, 322.1.

Step 3. Preparation of 2-benzyl 1-(tert-butyl) (2R, 3R)-3-fluoropyrrolidine-1,2-dicarboxylate

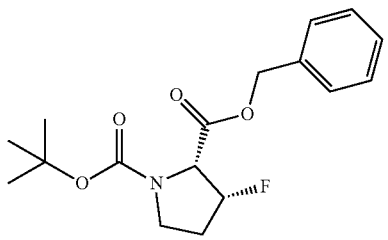 [SMILES: CC(C)(C)OC(=O)N1CC[C@@H](F)[C@H]1C(=O)OCc1ccccc1]

To a solution of 2-benzyl 1-(tert-butyl) (2S,3S)-3-hydroxypyrrolidine-1,2-dicarboxylate (0.15 g, 0.47 mmol) in dichloromethane (1.5 mL) at −78° C. was added diethylaminosulfur trifluoride (0.1 mL, 0.93 mmol). The reaction mixture was stirred at −78° C. for 2 h, then slowly warmed to ambient temperature and continued stirring for 2 days. The reaction mixture was cooled at 0° C., carefully quenched with methanol (2 mL) followed by water (30 mL) and the solvent was concentrated in vacuo. The aqueous residue was extracted with ethyl acetate (3×50 mL). The combined organics were washed with saturated aqueous sodium bicarbonate (50 mL), dried over anhydrous sodium sulfate, filtered and concentrated in vacuo. The residue was purified by column chromatography, eluting with a 0-50% gradient of ethyl acetate in hexanes to afford the title compound as a gum (0.06 g, 36%) which was directly used in the next step without any further analytical characterization.

Step 4. Preparation of benzyl (2R, 3R)-1-(4-((adamantan-1-yl)methoxy)-5-cyclopropyl-2-fluorobenzoyl)-3-fluoropyrrolidine-2-carboxylate

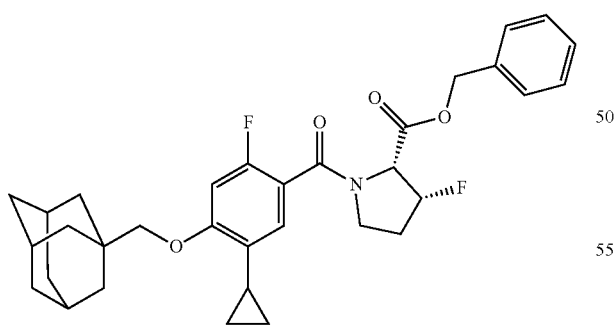

Following the procedure as described in Example 59, Step 3 and Step 4 and making variation as required to replace 1-(tert-butyl) 2-methyl (2S, 4R)-4-methoxypyrrolidine-1,2-dicarboxylate with 2-benzyl 1-(tert-butyl) (2R, 3R)-3-fluoropyrrolidine-1,2-dicarboxylate, the title compound was obtained as colorless syrup (0.041 g, 51%) which was used without any further purification: MS (ES+) m/z 550.3, 551.3 (M+1).

Step 5. Preparation of (2R, 3R)-1-(4-((adamantan-1-yl)methoxy)-5-cyclopropyl-2-fluorobenzoyl)-3-fluoropyrrolidine-2-carboxylic Acid

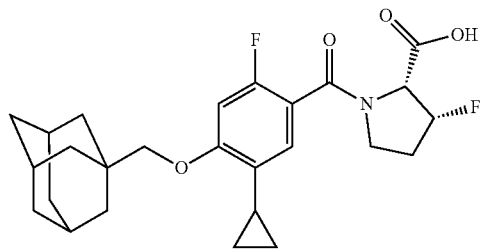 [SMILES: O=C(O)[C@@H]1[C@H](F)CCN1C(=O)c1cc(C2CC2)c(OCC23CC4CC(CC(C4)C2)C3)cc1F]

Following the procedure as described in Example 62, Step 4 and making variation as required to replace benzyl (2S, 3R)-1-(4-((adamantan-1-yl)methoxy)-5-cyclopropyl-2-fluorobenzoyl)-3-hydroxypyrrolidine-2-carboxylate with benzyl (2R, 3R)-1-(4-((adamantan-1-yl)methoxy)-5-cyclopropyl-2-fluorobenzoyl)-3-fluoropyrrolidine-2-carboxylate and following reverse-phase HPLC purification of the residue, the title compound was obtained as a colorless solid (0.013 g, 38%): ¹H NMR (300 MHz, CDCl₃) δ 7.04 (d, J=7.6 Hz, 1H), 6.53 (d, J=12.0 Hz, 1H), 5.64-5.40 (m, 1H), 5.03-4.85 (m, 1H), 3.95-3.77 (m, 1H), 3.62-3.43 (m, 1H), 3.51 (s, 2H), 2.38-2.17 (m, 1H), 2.13-1.89 (m, 4H), 1.84-1.57 (m, 12H), 0.98-0.78 (m, 3H), 0.71-0.54 (m, 2H); MS (ES+) m/z 460.1, 461.1 (M+1).

Example 64

Synthesis of (2R,3S)-1-(4-((adamantan-1-yl)methoxy)-5-cyclopropyl-2-fluorobenzoyl)-3-fluoropyrrolidine-2-carboxylic Acid Step 1-3. Preparation of 2-benzyl 1-(tert-butyl) (2R, 3S)-3-fluoropyrrolidine-1,2-dicarboxylate

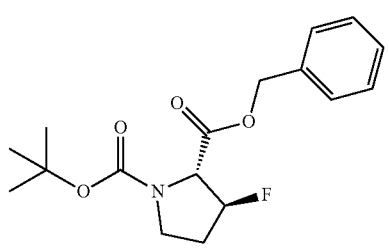 [SMILES: CC(C)(C)OC(=O)N1CC[C@H](F)[C@H]1C(=O)OCc1ccccc1]

Following the procedure as described in Example 3, Step 3 and making variation as required to replace 2-benzyl 1-(tert-butyl) (2S, 3S)-3-hydroxypyrrolidine-1,2-dicarboxylate with 2-benzyl 1-(tert-butyl) (2S, 3R)-3-hydroxypyrrolidine-1,2-dicarboxylate, the title compound was obtained as pale yellow oil (0.13 g, 86%) which was used directly in the next step without any further analytical characterization.

Step 2. Preparation of benzyl (2R, 3S)-1-(4-((adamantan-1-yl)methoxy)-5-cyclopropyl-2-fluorobenzoyl)-3-fluoropyrrolidine-2-carboxylate

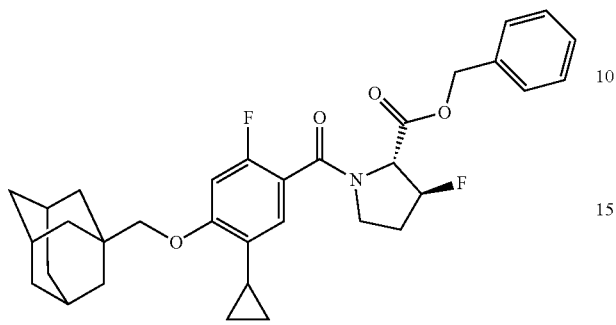

Following the procedure as described in Example 59, Step 3 and Step 4 and making variation as required to replace 1-(tert-butyl) 2-methyl (2S, 4R)-4-methoxypyrrolidine-1,2-dicarboxylate with 2-benzyl 1-(tert-butyl) (2R,3S)-3-fluoropyrrolidine-1,2-dicarboxylate, the title compound was obtained as colorless gum (0.12 g, 74%) which was used in the next step without any further analytical characterization: MS (ES+) m/z 550.3, 551.3 (M+1).

Step 3. Preparation of (2R, 3S)-1-(4-((adamantan-1-yl)methoxy)-5-cyclopropyl-2-fluorobenzoyl)-3-fluoropyrrolidine-2-carboxylic Acid

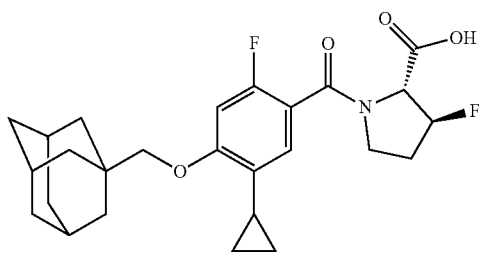 [SMILES: O=C(O)[C@@H]1[C@@H](F)CCN1C(=O)c1cc(C2CC2)c(OCC23CC4CC(CC(C4)C2)C3)cc1F]

Following the procedure as described in Example 62, Step 4 and making variation as required to replace benzyl (2S, 3R)-1-(4-((adamantan-1-yl)methoxy)-5-cyclopropyl-2-fluorobenzoyl)-3-hydroxypyrrolidine-2-carboxylate with benzyl (2R,3S)-1-(4-((adamantan-1-yl)methoxy)-5-cyclopropyl-2-fluorobenzoyl)-3-fluoropyrrolidine-2-carboxylate and following reverse-phase HPLC of the residue, the title compound was obtained as a colorless solid (0.049 g, 50%): $^1$H NMR (300 MHz, CDCl$_3$) δ 6.97 (d, J=7.8 Hz, 1H), 6.55 (d, J=12.0 Hz, 1H), 5.70-5.48 (m, 1H), 5.01-4.91 (m, 1H), 3.88-3.71 (m, 1H), 3.64-3.45 (m, 1H), 3.52 (s, 2H), 2.33-2.19 (m, 1H), 2.19-1.94 (m, 4H), 1.85-1.60 (m, 12H), 0.99-0.79 (m, 3H), 0.69-0.57 (m, 2H); MS (ES+) m/z 460.2, 461.2 (M+1).

Example 65

Synthesis of 1-(4-(adamantan-1-ylmethoxy)-5-cyclopropyl-2-fluorobenzoyl)pyrrolidine-3-carboxylic Acid

Step 1. Preparation of methyl 1-(4-(adamantan-1-ylmethoxy)-5-cyclopropyl-2-fluorobenzoyl)pyrrolidine-3-carboxylate

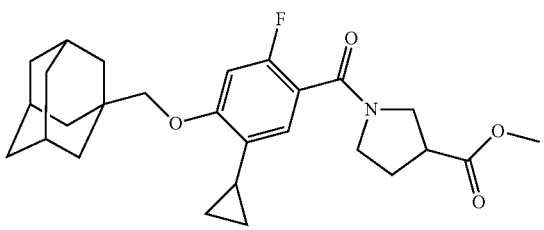 [SMILES: COC(=O)C1CCN(C(=O)c2cc(C3CC3)c(OCC34CC5CC(CC(C5)C3)C4)cc2F)C1]

Following the procedure as described in Example 1, Step 1 and making variation as required to replace (S)-tert-butyl pyrrolidine-2-carboxylate hydrochloride with methyl pyrrolidine-3-carboxylate hydrochloride, the title compound was obtained as a colorless oil (0.26 g, 78%): MS (ES+) m/z 456.3 (M+1).

Step 2. Preparation of 1-(4-(adamantan-1-ylmethoxy)-5-cyclopropyl-2-fluorobenzoyl)-pyrrolidine-3-carboxylic Acid

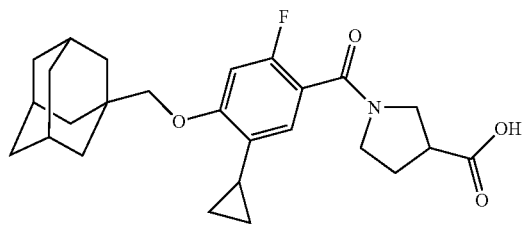 [SMILES: O=C(O)C1CCN(C(=O)c2cc(C3CC3)c(OCC34CC5CC(CC(C5)C3)C4)cc2F)C1]

Following the procedure as described in Example 6, Step 2 and making variation as required to replace ethyl 1-(4-(adamantan-1-ylmethoxy)-5-cyclopropyl-2-fluorobenzamido)-cyclopropane-1-carboxylate with methyl 1-(4-(adamantan-1-ylmethoxy)-5-cyclopropyl-2-fluorobenzoyl)pyrrolidine-3-carboxylate, the title compound was obtained as a colorless solid (0.15 g, 62%): $^1$H NMR (300 MHz, CDCl$_3$) δ 6.98-6.92 (m, 1H), 6.54-6.46 (m, 1H), 3.97-3.57 (m, 4H), 3.55-3.39 (m, 3H), 3.25-3.03 (m, 1H), 2.34-2.11 (m, 2H), 2.11-1.95 (m, 4H), 1.83-1.63 (m, 11H), 0.94-0.83 (m, 2H), 0.67-0.56 (m, 2H); MS (ES−) m/z 440.3 (M−1).

Example 66

Synthesis of (S)-2-(4-(adamantan-1-ylmethoxy)-5-cyclopropyl-2-fluorobenzamido)-3-methylbutanoic Acid

Step 1. Preparation of tert-butyl (4-(adamantan-1-ylmethoxy)-5-cyclopropyl-2-fluorobenzoyl)-L-valinate

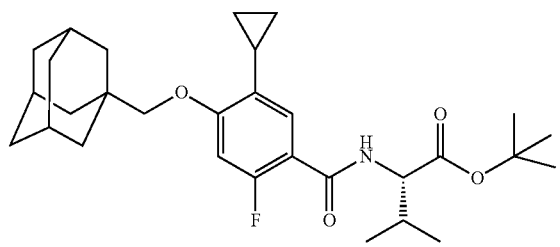 [SMILES: CC(C)[C@H](NC(=O)c1cc(C2CC2)c(OCC23CC4CC(CC(C4)C2)C3)cc1F)C(=O)OC(C)(C)C]

Following the procedure as described in Example 1, Step 1 and making variation as required to replace (S)-tert-butyl pyrrolidine-2-carboxylate hydrochloride with tert-butyl L-valinate hydrochloride, the title compound was obtained as a colorless oil (0.30 g, 82%): ¹H NMR (300 MHz, CDCl₃) δ 7.59 (m, 1H), 7.16 (m, 1H), 6.53 (m, 1H), 4.68 (m, 1H), 3.53 (s, 2H), 2.25 (m, 1H), 2.04 (m, 4H), 1.74 (m, 12H), 1.48 (s, 9H), 0.94 (m, 8H), 0.67 (m, 2H).

Step 2. Preparation of (S)-2-(4-(adamantan-1-ylmethoxy)-5-cyclopropyl-2-fluorobenzamido)-3-methylbutanoic Acid

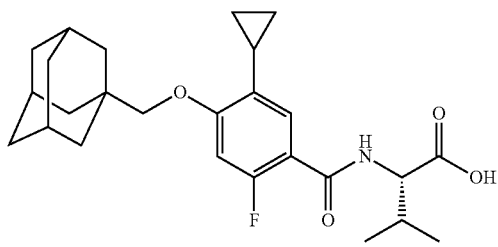

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(adamantan-1-ylmethoxy)-5-cyclopropyl-2-fluorobenzoyl)-L-valinate, the title compound was obtained as a colorless solid (0.033 g, 37%): ¹H NMR (300 MHz, CDCl₃) δ 7.64-7.56 (m, 1H), 7.17-7.06 (m, 1H), 6.58-6.49 (m, 1H), 4.79-4.65 (m, 1H), 3.53 (s, 2H), 2.45-2.27 (m, 1H), 2.14-1.97 (m, 4H), 1.87-1.61 (m, 12H), 1.13-0.98 (m, 6H), 0.95-0.83 (m, 2H), 0.75-0.57 (m, 2H); MS (ES+) m/z 444.1 (M+1).

Example 67

Synthesis of N-(4-(adamantan-1-ylmethoxy)-5-cyclopropyl-2-fluorobenzoyl)-N-methyl-L-valine

Step 1. Preparation of tert-butyl N-(4-(adamantan-1-ylmethoxy)-5-cyclopropyl-2-fluorobenzoyl)-N-methyl-L-valinate

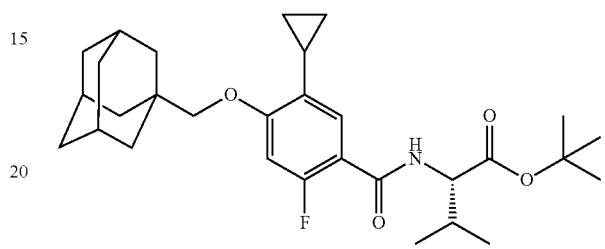

Following the procedure as described in Example 7, Step 1 and making variation as required to replace ethyl 1-(4-(adamantan-1-ylmethoxy)-5-cyclopropyl-2-fluorobenzamido)cyclopropane-1-carboxylate with tert-butyl (4-(adamantan-1-ylmethoxy)-5-cyclopropyl-2-fluorobenzoyl)-L-valinate, the title compound was obtained as a colorless oil (0.31 g, 89%):

MS (ES+) m/z 514.4 (M+1).

Step 2. Preparation of N-(4-(adamantan-1-ylmethoxy)-5-cyclopropyl-2-fluorobenzoyl)-N-methyl-L-valine

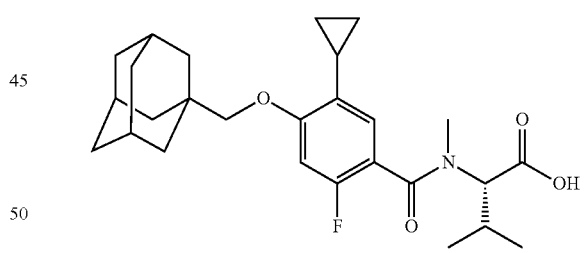

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl N-(4-(adamantan-1-ylmethoxy)-5-cyclopropyl-2-fluorobenzoyl)-N-methyl-L-valinate, the title compound was obtained as a colorless solid (0.04 g, 13%): ¹H NMR (300 MHz, CDCl₃) δ 7.05-6.79 (m, 1H), 6.58-6.47 (m, 1H), 4.24-4.05 (m, 1H), 3.58-3.45 (m, 2H), 3.13-2.95 (m, 3H), 2.66-2.46 (m, 1H), 2.12-1.95 (m, 4H), 1.87-1.64 (m, 12H), 1.16-0.98 (m, 5H), 0.96-0.84 (m, 3H), 0.70-0.54 (m, 2H); MS (ES+) m/z 458.2 (M+1).

Example 68

Synthesis of (S)-1-(5-cyclopropyl-4-((4,4-dimethyl-cyclohexyl)methoxy)-2-fluorobenzoyl)pyrrolidine-2-carboxylic Acid Step 1. Preparation of tert-butyl (5-cyclopropyl-4-((4,4-dimethylcyclohexyl)-methoxy)-2-fluorobenzoyl)-L-prolinate

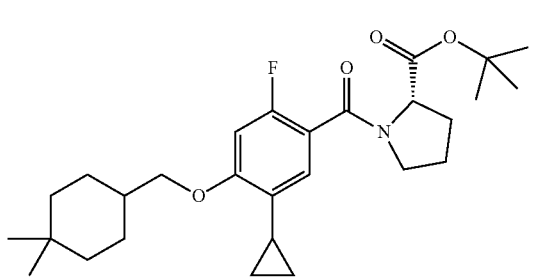 [SMILES: CC1(C)CCC(COc2cc(F)c(C(=O)N3CCC[C@H]3C(=O)OC(C)(C)C)cc2C2CC2)CC1]

Following the procedure as described in Example 1, Step 1 and making variation as required to replace 4-(adamantan-1-ylmethoxy)-5-cyclopropyl-2-fluorobenzoic acid with 5-cyclopropyl-4-((4,4-dimethylcyclohexyl)methoxy)-2-fluorobenzoic acid, the title compound was obtained as a colorless solid (0.16 g, 78%): MS (ES+) m/z 474.2 (M+1).

Step 2. Preparation of of (S)-1-(5-cyclopropyl-4-((4,4-dimethylcyclohexyl)methoxy)-2-fluorobenzoyl)pyrrolidine-2-carboxylic Acid

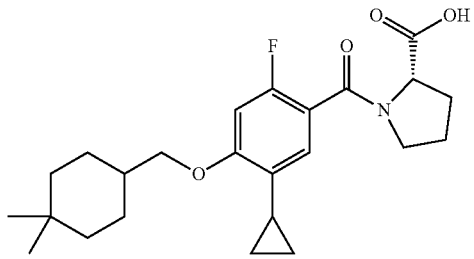 [SMILES: CC1(C)CCC(COc2cc(F)c(C(=O)N3CCC[C@H]3C(=O)O)cc2C2CC2)CC1]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (5-cyclopropyl-4-((4,4-dimethylcyclohexyl)methoxy)-2-fluorobenzoyl)-L-prolinate, the title compound was obtained as a colorless solid (0.12 g, 85%): $^1$H NMR (300 MHz, CDCl$_3$) δ 6.97-6.90 (m, 1H), 6.57-6.48 (m, 1H), 4.77-4.70 (m, 1H), 3.83-3.77 (m, 2H), 3.55-3.38 (m, 2H), 2.57-2.45 (m, 1H), 2.19-1.84 (m, 4H), 1.81-1.63 (m, 3H), 1.47-1.17 (m, 6H), 0.96-0.83 (m, 8H), 0.65-0.57 (m, 2H); MS (ES+) m/z 418.1 (M+1).

Example 69

Synthesis of (4-(bicyclo[4.1.0]heptan-1-ylmethoxy)-5-cyclopropyl-2-fluorobenzoyl)-L-proline Step 1. Preparation of methyl (4-(bicyclo[4.1.0]heptan-1-ylmethoxy)-5-cyclopropyl-2-fluorobenzoyl)-L-prolinate

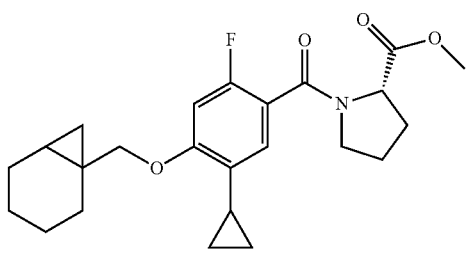 [SMILES: COC(=O)[C@@H]1CCCN1C(=O)c1cc(C2CC2)c(OCC23CCCCC2C3)cc1F]

Following the procedure as described in Example, step 1 and making variation as required to replace 4-(adamantan-1-ylmethoxy)-5-cyclopropyl-2-fluorobenzoic acid with 4-(bicyclo[4.1.0]heptan-1-ylmethoxy)-5-cyclopropyl-2-fluorobenzoic acid, and (S)-tert-butyl pyrrolidine-2-carboxylate hydrochloride with methyl L-prolinate hydrochloride, the title compound was obtained as a colorless oil (0.23 g, 80%): MS (ES+) m/z 416.2 (M+1).

Step 2. Preparation of (4-(bicyclo[4.1.0]heptan-1-ylmethoxy)-5-cyclopropyl-2-fluorobenzoyl)-L-proline

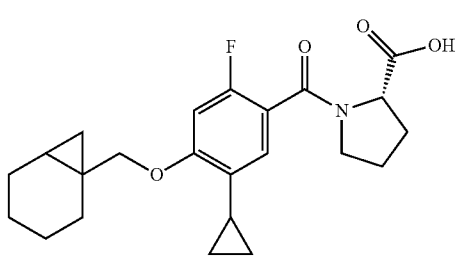 [SMILES: O=C(O)[C@@H]1CCCN1C(=O)c1cc(C2CC2)c(OCC23CCCCC2C3)cc1F]

Following the procedure as described in Example 6, step 2 and making variation as required to replace ethyl 1-(4-(adamantan-1-ylmethoxy)-5-cyclopropyl-2-fluorobenzamido)cyclopropane-1-carboxylate with methyl (4-(bicyclo[4.1.0]heptan-1-ylmethoxy)-5-cyclopropyl-2-fluorobenzoyl)-L-prolinate, the title compound was obtained as a colorless solid (0.19 g, 87%): $^1$H NMR (300 MHz, CDCl$_3$) δ 6.98-6.93 (m, 1H), 6.50-6.43 (m, 1H), 4.77-4.70 (m, 1H), 3.83-3.74 (m, 1H), 3.65-3.58 (m, 1H), 3.57-3.37 (m, 2H), 2.56-2.43 (m, 1H), 2.23-1.76 (m, 7H), 1.72-1.59 (m, 1H), 1.43-1.18 (m, 5H), 1.05-0.86 (m, 3H), 0.70-0.61 (m, 3H), 0.42-0.34 (m, 1H); MS (ES+) m/z 402.2 (M+1).

Example 70

Synthesis of (S)-1-(4-(adamantan-2-yloxy)-5-cyclopropyl-2-fluorobenzoyl)pyrrolidine-2-carboxylic Acid Step 1. Preparation of tert-butyl (4-(adamantan-2-yloxy)-5-cyclopropyl-2-fluorobenzoyl)-L-prolinate

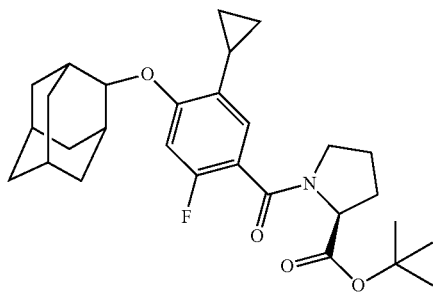 [SMILES: CC(C)(C)OC(=O)[C@@H]1CCCN1C(=O)c1cc(C2CC2)c(OC2C3CC4CC(C3)CC2C4)cc1F]

Following the procedure as described in Example 1, step 1 and making variation as required to replace 4-(adamantan-1-ylmethoxy)-5-cyclopropyl-2-fluorobenzoic acid with 4-(adamantan-2-yloxy)-5-cyclopropyl-2-fluorobenzoic acid, the title compound was obtained as a colorless oil (0.31 g, 84%): MS (ES+) m/z 484.3 (M+1).

Step 2. Preparation of (S)-1-(4-(adamantan-2-yloxy)-5-cyclopropyl-2-fluorobenzoyl)pyrrolidine-2-carboxylic Acid

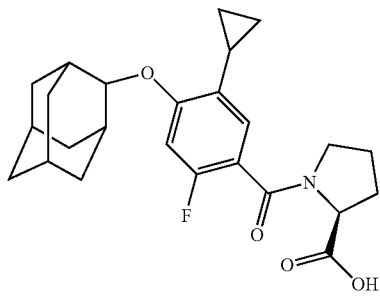 [SMILES: O=C(O)[C@@H]1CCCN1C(=O)c1cc(C2CC2)c(OC2C3CC4CC(C3)CC2C4)cc1F]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(adamantan-2-yloxy)-5-cyclopropyl-2-fluorobenzoyl)-L-prolinate, the title compound was obtained as a colorless solid (0.21 g, 77%): $^1$H NMR (300 MHz, CDCl$_3$) δ 7.00-6.94 (m, 1H), 6.57-6.49 (m, 1H), 4.79-4.69 (m, 1H), 4.48-4.38 (m, 1H), 3.61-3.37 (m, 2H), 2.58-2.44 (m, 1H), 2.24-1.71 (m, 17H), 1.65-1.50 (m, 2H), 1.00-0.83 (m, 2H), 0.68-0.56 (m, 2H); MS (ES+) m/z 428.2 (M+1).

Synthesis of (4-(adamantan-1-ylmethoxy)-2,5-difluorobenzoyl)-L-proline

Step 1. Preparation of tert-butyl (4-(adamantan-1-ylmethoxy)-2,5-difluorobenzoyl)-L-prolinate

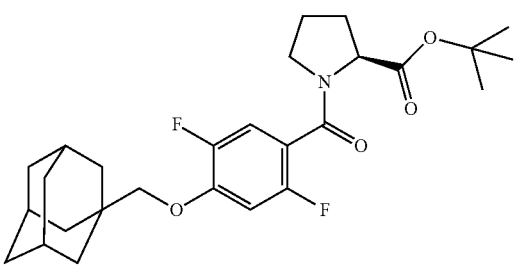 [SMILES: CC(C)(C)OC(=O)[C@@H]1CCCN1C(=O)c1cc(F)c(OCC23CC4CC(CC(C4)C2)C3)cc1F]

Following the procedure as described in Example 1, Step 1 and making variation as required to replace 4-(adamantan-1-ylmethoxy)-5-cyclopropyl-2-fluorobenzoic acid with 4-(adamantan-1-ylmethoxy)-2,5-difluorobenzoic acid, the title compound was obtained as a colorless oil (0.10 g, 95%); MS (ES+) m/z 476.3 (M+1).

Step 2. Preparation of (4-(adamantan-1-ylmethoxy)-2,5-difluorobenzoyl)-L-proline

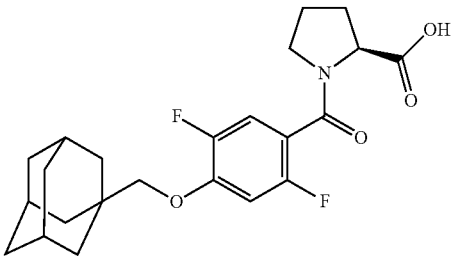 [SMILES: O=C(O)[C@@H]1CCCN1C(=O)c1cc(F)c(OCC23CC4CC(CC(C4)C2)C3)cc1F]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(adamantan-1-ylmethoxy)-2,5-difluorobenzoyl)-L-prolinate, the title compound was obtained as a colorless solid (0.08 g, 89%): $^1$H NMR (300 MHz, CDCl$_3$) δ 7.23-7.15 (m, 1H), 6.74-6.65 (m, 1H), 4.78-4.67 (m, 1H), 3.58-3.45 (m, 4H), 2.49-2.35 (m, 1H), 2.30-2.14 (m, 1H), 2.10-1.98 (m, 4H), 1.98-1.86 (m, 1H), 1.84-1.60 (m, 13H); MS (ES+) m/z 420.2 (M+1).

Example 72

Synthesis of 4-(4-(adamantan-1-ylmethoxy)-5-cyclopropyl-2-fluorobenzoyl)morpholine-3-carboxylic Acid Step 1. Preparation of methyl 4-(4-(adamantan-1-ylmethoxy)-5-cyclopropyl-2-fluorobenzoyl)morpholine-3-carboxylate

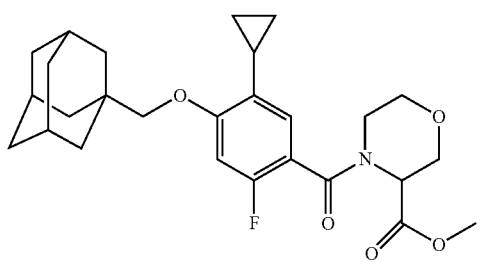 [SMILES: COC(=O)C1COCCN1C(=O)c1cc(C2CC2)c(OCC23CC4CC(CC(C4)C2)C3)cc1F]

Following the procedure as described in Example 1, Step 1 and making variation as required to replace (S)-tert-butyl pyrrolidine-2-carboxylate hydrochloride with methyl morpholine-3-carboxylate hydrochloride, the title compound was obtained as a colorless oil (0.29 g, 84%); MS (ES+) m/z 472.2 (M+1).

Step 2. Preparation of 4-(4-(adamantan-1-ylmethoxy)-5-cyclopropyl-2-fluorobenzoyl)morpholine-3-carboxylic Acid

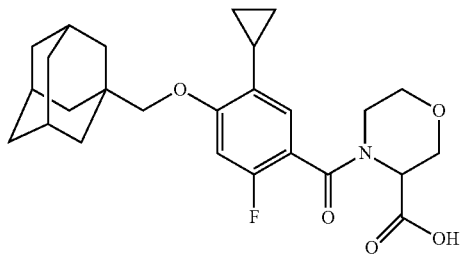 [SMILES: O=C(O)C1COCCN1C(=O)c1cc(C2CC2)c(OCC23CC4CC(CC(C4)C2)C3)cc1F]

Following the procedure as described in Example 6, Step 2 and making variation as required to replace ethyl 1-(4-(adamantan-1-ylmethoxy)-5-cyclopropyl-2-fluorobenzamido)cyclopropane-1-carboxylate with methyl 4-(4-(adamantan-1-ylmethoxy)-5-cyclopropyl-2-fluorobenzoyl)morpholine-3-carboxylate, the title compound was obtained as a colorless solid (0.08 g, 28%): $^1$H NMR (300 MHz, CDCl$_3$) δ 7.00-6.88 (m, 1H), 6.55-6.47 (m, 1H), 5.30-5.16 (m, 1H), 4.60-4.32 (m, 2H), 4.25-3.96 (m, 1H), 3.89-3.48 (m, 5H), 3.45-3.33 (m, 1H), 2.11-1.97 (m, 4H), 1.85-1.62 (m, 11H), 0.96-0.83 (m, 2H), 0.71-0.55 (m, 2H); MS (ES+) m/z 458.1 (M+1).

Example 73a and Example 73b

Synthesis of (5-cyclopropyl-4-(((S)-1-((R)-1-(3,5-dichlorophenyl)ethyl)piperidin-3-yl)methoxy)-2-fluorobenzoyl)-L-proline and (5-cyclopropyl-4-(((S)-1-((S)-1-(3,5-dichlorophenyl)ethyl)piperidin-3-yl)methoxy)-2-fluorobenzoyl)-L-proline Step 1. Preparation of tert-butyl (5-cyclopropyl-4-(((3S)-1-(1-(3,5-dichlorophenyl)ethyl)-piperidin-3-yl)methoxy)-2-fluorobenzoyl)-L-prolinate

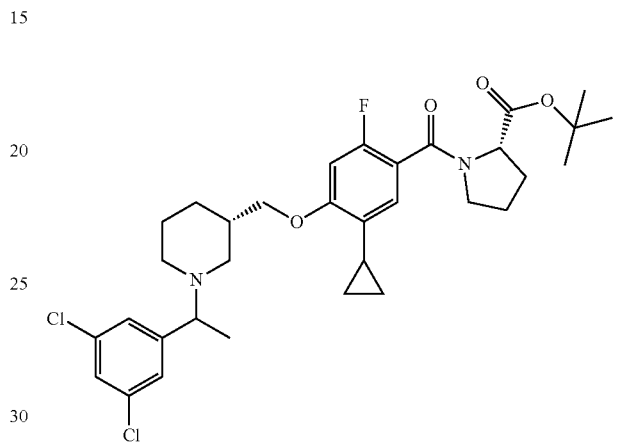

Following the procedure as described in Example 1, Step 1 and making variation as required to replace 4-(adamantan-1-ylmethoxy)-5-cyclopropyl-2-fluorobenzoic acid with 5-cyclopropyl-4-(((3S)-1-(1-(3,5-dichlorophenyl)ethyl)piperidin-3-yl)methoxy)-2-fluorobenzoic acid, the title compound was obtained as a colorless solid (0.32 g, 68%): MS (ES+) m/z 563.2, 565.2 (M−56).

Step 2. Preparation of (5-cyclopropyl-4-(((S)-1-((R)-1-(3,5-dichlorophenyl)ethyl)-piperidin-3-yl)methoxy)-2-fluorobenzoyl)-L-proline and (5-cyclopropyl-4-(((S)-1-((S)-1-(3,5-dichlorophenyl)ethyl)piperidin-3-yl)methoxy)-2-fluorobenzoyl)-L-proline

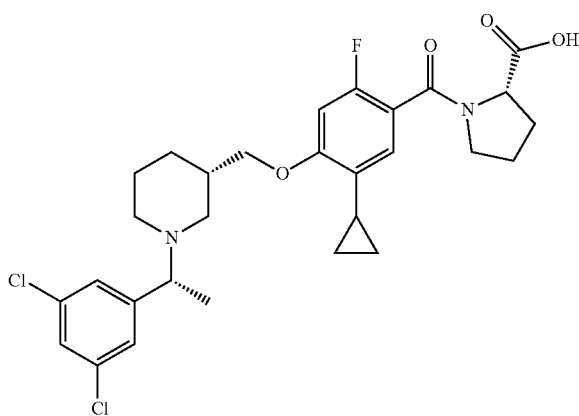

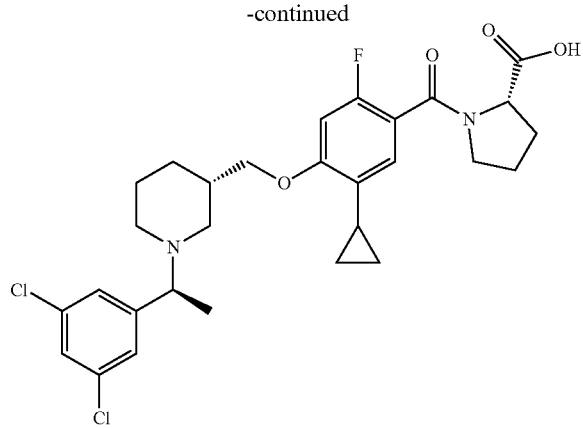

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (5-cyclopropyl-4-(((3S)-1-(1-(3,5-dichlorophenyl)ethyl)piperidin-3-yl)methoxy)-2-fluorobenzoyl)-L-prolinate, following the residue was purified by preparative HPLC (gradient of acetonitrile in water) to afford the first eluent (stereochemistry at the methyl substituted benzylic position was arbitrary assigned), the title compound as a colorless solid (0.10 g, 34%): $^1$H NMR (300 MHz, CDCl$_3$) δ 7.33-7.16 (m, 3H), 6.97-6.86 (m, 1H), 6.48-6.36 (m, 1H), 4.74-4.22 (m, 1H), 3.94-3.61 (m, 4H), 3.58-3.29 (m, 3H), 3.24-3.00 (m, 2H), 2.40-1.88 (m, 6H), 1.86-1.65 (m, 4H), 1.52-1.33 (m, 3H), 0.81-0.59 (m, 2H), 0.56-0.40 (m, 2H); MS (ES+) m/z 563.4, 565.2 (M+1); and the second eluent of the title compound as a colorless solid (0.05 g, 18%): $^1$H NMR (300 MHz, CDCl$_3$) δ 7.33-7.16 (m, 3H), 6.96-6.87 (m, 1H), 6.50-6.41 (m, 1H), 4.71-4.24 (m, 1H), 3.93-3.55 (m, 3H), 3.50-3.26 (m, 1H), 3.20-3.06 (m, 1H), 2.96-2.57 (m, 5H), 2.45-1.93 (m, 5H), 1.91-1.63 (m, 4H), 1.52-1.29 (m, 3H), 0.84-0.68 (m, 2H), 0.60-0.43 (m, 2H); MS (ES+) m/z 563.3, 565.1 (M+1).

Example 74

Synthesis of (S)-2-(4-(adamantan-1-ylmethoxy)-5-cyclopropyl-2-fluorobenzamido)-2-cyclopropylacetic Acid Step 1. Preparation of methyl (S)-2-(4-(adamantan-1-ylmethoxy)-5-cyclopropyl-2-fluorobenzamido)-2-cyclopropylacetate

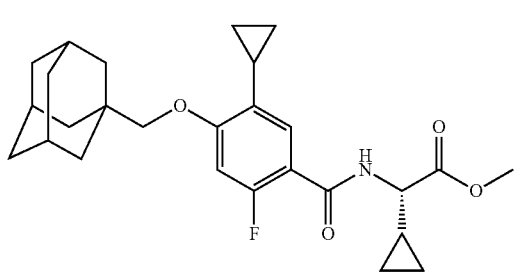 [SMILES: COC(=O)[C@@H](NC(=O)c1cc(C2CC2)c(OCC23CC4CC(CC(C4)C2)C3)cc1F)C1CC1]

Following the procedure as described in Example 1, Step 1 and making variation as required to replace (S)-tert-butyl pyrrolidine-2-carboxylate hydrochloride with methyl (S)-2-amino-2-cyclopropylacetate, the title compound was obtained as a colorless oil (0.20 g, 76%): MS (ES+) m/z 456.3 (M+1).

Step 2. Preparation of (S)-2-(4-(adamantan-1-ylmethoxy)-5-cyclopropyl-2-fluorobenzamido)-2-cyclopropylacetic Acid

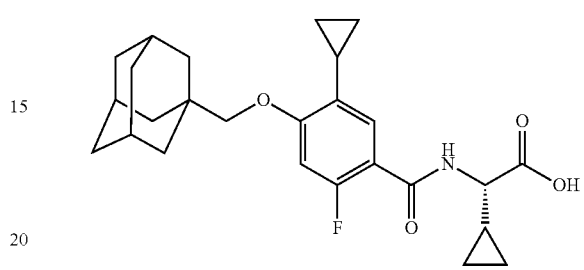

Following the procedure as described in Example 6, Step 2 and making variation as required to replace ethyl 1-(4-(adamantan-1-ylmethoxy)-5-cyclopropyl-2-fluorobenzamido)cyclopropane-1-carboxylate with methyl (S)-2-(4-(adamantan-1-ylmethoxy)-5-cyclopropyl-2-fluorobenzamido)-2-cyclopropylacetate, the title compound was obtained as a colorless solid (0.123 g, 63%): $^1$H NMR (300 MHz, CDCl$_3$) δ 7.62-7.54 (m, 1H), 7.24-7.12 (m, 1H), 6.59-6.48 (m, 1H), 4.13-4.03 (m, 1H), 3.53 (s, 2H), 2.11-1.98 (m, 4H), 1.85-1.63 (m, 12H), 1.35-1.22 (m, 1H), 0.96-0.85 (m, 2H), 0.76-0.56 (m, 5H), 0.53-0.43 (m, 1H); MS (ES+) m/z 442.3 (M+1).

Example 75

Synthesis of (2S,3S)-1-(4-(adamantan-1-ylmethoxy)-5-cyclopropyl-2-fluorobenzoyl)-3-hydroxypyrrolidine-2-carboxylic Acid Step 1. Preparation of methyl (2S,3S)-1-(4-(adamantan-1-ylmethoxy)-5-cyclopropyl-2-fluorobenzoyl)-3-hydroxypyrrolidine-2-carboxylate

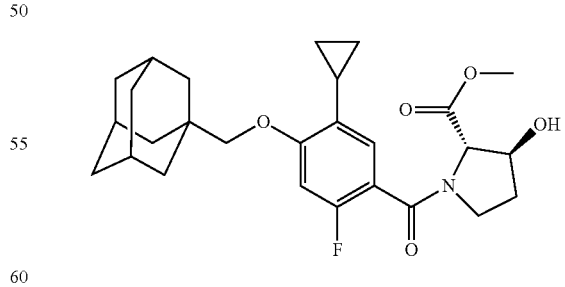

Following the procedure as described in Example 1, Step 1 and making variation as required to replace (S)-tert-butyl pyrrolidine-2-carboxylate hydrochloride with methyl (2S,3S)-3-hydroxypyrrolidine-2-carboxylate hydrochloride, the title compound was obtained as a colorless oil (0.46 g, 70%); MS (ES+) m/z 472.2 (M+1).

215

Step 2. Preparation of (2S,3S)-1-(4-(adamantan-1-ylmethoxy)-5-cyclopropyl-2-fluorobenzoyl)-3-hydroxypyrrolidine-2-carboxylic Acid

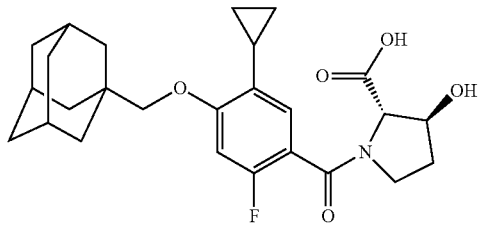 [SMILES: O=C(O)[C@@H]1[C@@H](O)CCN1C(=O)c1cc(C2CC2)c(OCC23CC4CC(CC(C4)C2)C3)cc1F]

Following the procedure as described in Example 6, Step 2 and making variation as required to replace ethyl 1-(4-(adamantan-1-ylmethoxy)-5-cyclopropyl-2-fluorobenzamido)cyclopropane-1-carboxylate with methyl (2S,3S)-1-(4-(adamantan-1-ylmethoxy)-5-cyclopropyl-2-fluorobenzoyl)-3-hydroxypyrrolidine-2-carboxylate, the title compound was obtained as a colorless solid (0.119 g, 77%): $^1$H NMR (300 MHz, CDCl$_3$) δ 6.98 (m, 1H), 6.54 (m, 1H), 4.69 (m, 2H), 3.73 (m, 1H), 3.52 (m, 2H), 3.22 (m, 5H), 2.18 (m, 1H), 2.00 (m, 4H), 1.72 (m, 10H), 0.90 (m, 2H), 0.62 (m, 2H); MS (ES+) m/z 458.2 (M+1).

Example 76

Synthesis of (2S,3S)-1-(4-(adamantan-1-ylmethoxy)-5-cyclopropyl-2-fluorobenzoyl)-3-methoxypyrrolidine-2-carboxylic Acid Step 1. Preparation of methyl (2S,3S)-1-(4-(adamantan-1-ylmethoxy)-5-cyclopropyl-2-fluorobenzoyl)-3-methoxypyrrolidine-2-carboxylate

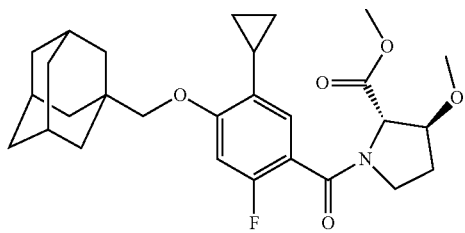 [SMILES: COC(=O)[C@@H]1[C@@H](OC)CCN1C(=O)c1cc(C2CC2)c(OCC23CC4CC(CC(C4)C2)C3)cc1F]

To a stirred solution of methyl (2S,3S)-1-(4-(adamantan-1-ylmethoxy)-5-cyclopropyl-2-fluorobenzoyl)-3-hydroxypyrrolidine-2-carboxylate (0.20 g, 0.42 mmol) in N,N-dimethylformamide (5 mL) was added iodomethane (0.13 mL, 2.10 mmol), followed by silver oxide (0.29 g, 1.26 mmol). The reaction mixture was stirred at ambient temperature for 16 h, diluted with ethyl acetate (50 mL), and filtered through a pad of Celite. The filtrate was washed with brine (20 mL), saturated aqueous sodium bicarbonate solution (20 mL), dried over anhydrous magnesium sulfate, filtered and concentrated in vacuo. The residue was purified by column chromatography eluting with a gradient of ethyl acetate in hexanes (0 to 50%) to give the title compound as a colorless oil (0.125 g, 61%): MS (ES+) m/z 486.3 (M+1).

216

Step 2. Preparation of (2S,3S)-1-(4-(adamantan-1-ylmethoxy)-5-cyclopropyl-2-fluorobenzoyl)-3-methoxypyrrolidine-2-carboxylic Acid

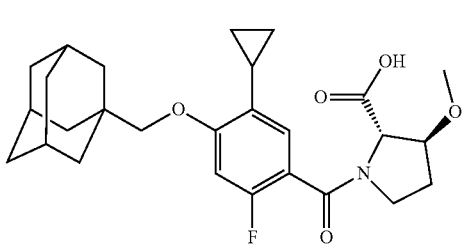 [SMILES: CO[C@H]1CCN(C(=O)c2cc(C3CC3)c(OCC34CC5CC(CC(C5)C3)C4)cc2F)[C@@H]1C(=O)O]

Following the procedure as described in Example 6, Step 2 and making variation as required to replace ethyl 1-(4-(adamantan-1-ylmethoxy)-5-cyclopropyl-2-fluorobenzamido)cyclopropane-1-carboxylate with methyl (2S,3S)-1-(4-(adamantan-1-ylmethoxy)-5-cyclopropyl-2-fluorobenzoyl)-3-methoxypyrrolidine-2-carboxylate, the title compound was obtained as a colorless solid (0.049 g, 42%): $^1$H NMR (300 MHz, CDCl$_3$) δ 7.04-6.86 (m, 1H), 6.57-6.37 (m, 1H), 4.80-4.60 (m, 1H), 4.37-4.12 (m, 1H), 3.62-3.15 (m, 6H), 3.16-2.44 (m, 4H), 2.31-1.52 (m, 15H), 0.97-0.74 (m, 2H), 0.70-0.48 (m, 2H); MS (ES+) m/z 472.2 (M+1).

Example 77

Synthesis of 3-(4-(adamantan-1-ylmethoxy)-5-cyclopropyl-2-fluorobenzamido)oxetane-3-carboxylic Acid Step 1. Preparation of methyl 3-(4-(adamantan-1-ylmethoxy)-5-cyclopropyl-2-fluorobenzamido)oxetane-3-carboxylate

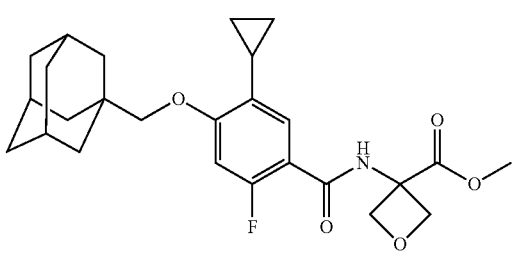 [SMILES: COC(=O)C1(NC(=O)c2cc(C3CC3)c(OCC34CC5CC(CC(C5)C3)C4)cc2F)COC1]

Following the procedure as described in Example 1, Step 1 and making variation as required to replace (S)-tert-butyl pyrrolidine-2-carboxylate hydrochloride with methyl 3-aminooxetane-3-carboxylate, the title compound was obtained as a colorless solid (0.34 g, 94%): MS (ES+) m/z 458.2 (M+1).

217

Step 2. Preparation of 3-(4-(adamantan-1-yl-methoxy)-5-cyclopropyl-2-fluorobenzamido)oxetane-3-carboxylic Acid

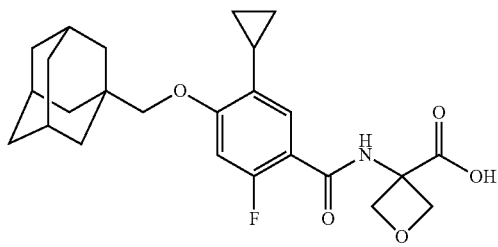 [SMILES: O=C(NC1(C(=O)O)COC1)c1cc(C2CC2)c(OCC23CC4CC(CC(C4)C2)C3)cc1F]

Following the procedure as described in Example 6, Step 2 and making variation as required to replace ethyl 1-(4-(adamantan-1-ylmethoxy)-5-cyclopropyl-2-fluorobenzamido)cyclopropane-1-carboxylate with methyl 3-(4-(adamantan-1-ylmethoxy)-5-cyclopropyl-2-fluorobenzamido)-oxetane-3-carboxylate, the title compound was obtained as a colorless solid (0.030 g, 9%): $^1$H NMR (300 MHz, CDCl$_3$) δ 7.63-7.46 (m, 3H), 6.60-6.51 (m, 1H), 5.21-5.10 (m, 2H), 4.84-4.75 (m, 2H), 3.59-3.49 (m, 2H), 2.11-1.95 (m, 4H), 1.86-1.61 (m, 12H), 0.98-0.83 (m, 2H), 0.72-0.59 (m, 2H); MS (ES+) m/z 444.2 (M+1).

Example 78

Synthesis of 3-(4-(adamantan-1-ylmethoxy)-5-cyclopropyl-2-fluorobenzoyl)thiazolidine-2-carboxylic Acid Step 1. Preparation of methyl 3-(4-(adamantan-1-ylmethoxy)-5-cyclopropyl-2-fluorobenzoyl)thiazolidine-2-carboxylate

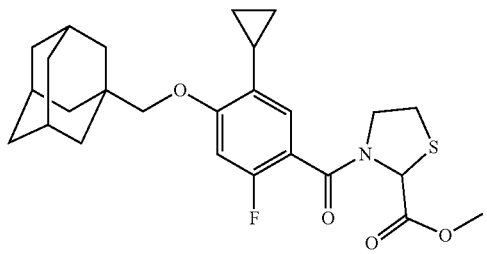 [SMILES: COC(=O)C1SCCN1C(=O)c1cc(C2CC2)c(OCC23CC4CC(CC(C4)C2)C3)cc1F]

Following the procedure as described in Example, Step 1 and making variation as required to replace (S)-tert-butyl pyrrolidine-2-carboxylate hydrochloride with methyl thiazolidine-2-carboxylate hydrochloride, the title compound was obtained as a colorless solid (0.20 g, 49%): MS (ES+) m/z 474.3 (M+1).

218

Step 2. Preparation of 3-(4-(adamantan-1-yl-methoxy)-5-cyclopropyl-2-fluorobenzoyl)thiazolidine-2-carboxylic Acid

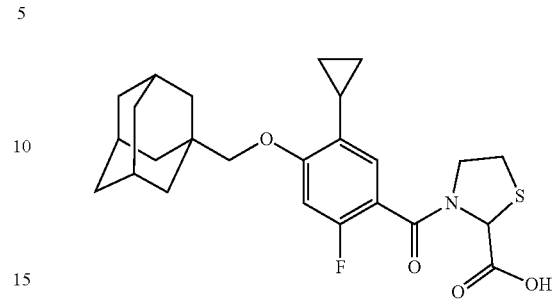

Following the procedure as described in Example 6, Step 2 and making variation as required to replace ethyl 1-(4-(adamantan-1-ylmethoxy)-5-cyclopropyl-2-fluorobenzamido)cyclopropane-1-carboxylate with methyl 3-(4-(adamantan-1-ylmethoxy)-5-cyclopropyl-2-fluorobenzoyl)-thiazolidine-2-carboxylate, the title compound was obtained as a colorless solid (0.14 g, 69%): $^1$H NMR (300 MHz, CDCl$_3$) δ 13.06 (s, 1H), 6.99-6.65 (m, 2H), 5.49-4.96 (m, 1H), 4.26-3.64 (m, 2H), 3.61 (s, 2H), 3.20-3.02 (m, 2H), 2.10-1.94 (m, 4H), 1.79-1.59 (m, 12H), 0.96-0.83 (m, 2H), 0.68-0.54 (m, 2H); MS (ES+) m/z 460.2 (M+1).

Example 79a and Example 79b

Synthesis of (2S)-1-[5-cyclopropyl-4-[[1-[(1S)-1-(3,5-dichlorophenyl)ethyl]-4-piperidyl]methoxy]-2-fluoro-benzoyl]pyrrolidine-2-carboxylic Acid and (2S)-1-[5-cyclopropyl-4-[[1-[(1R)-1-(3,5-dichlorophenyl)ethyl]-4-piperidyl]methoxy]-2-fluoro-benzoyl]pyrrolidine-2-carboxylic Acid

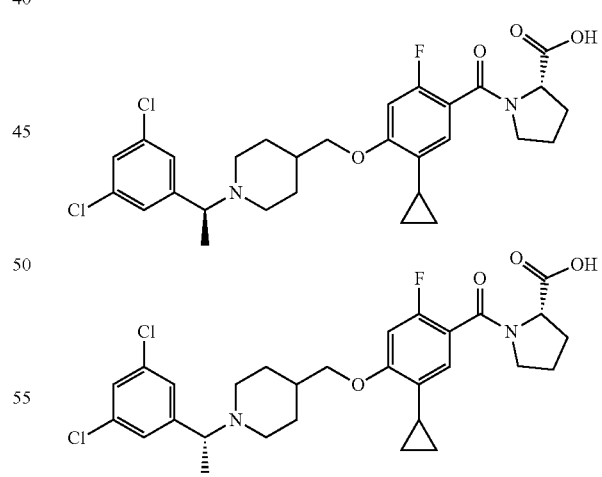

The compound was synthesized as described in Example 39. The enantiomer was separated by chiral SFC from mixture of diastereomers using Chiral HPLC conditions as described in Example 113. The first eluting fraction of the title compound was arbitrarily assigned: $^1$H NMR (400 MHz, DMSO-d$_6$) δ 7.47 (t, J=1.9 Hz, 1H), 7.36 (d, J=1.9 Hz, 2H), 6.93-6.65 (m, 2H), 4.34 (dd, J=8.6, 4.5 Hz, 1H), 3.87 (dd, J=12.4, 5.8 Hz, 2H), 3.61-3.49 (m, 2H), 2.86 (dd, J=59.2, 11.0 Hz, 2H), 2.24 (ddd, J=8.5, 6.7, 4.9 Hz, 1H), 2.07-1.66 (m, 9H), 1.42-1.22 (m, 5H), 0.91-0.82 (m, 2H), 0.58 (qd, J=5.8, 2.6 Hz, 2H); MS (ES+) m/z 563.2 (M) and the second eluent of the title compound was arbitrarily assigned: $^1$H NMR (400 MHz, DMSO-$d_6$) δ 7.47 (t, J=1.9 Hz, 1H), 7.36 (d, J=1.9 Hz, 2H), 6.95-6.63 (m, 2H), 4.39-4.27 (m, 1H), 3.87 (dd, J=12.2, 5.9 Hz, 2H), 3.54 (dd, J=15.7, 7.4 Hz, 2H), 2.93 (d, J=11.0 Hz, 1H), 2.79 (d, J=11.0 Hz, 1H), 2.30-2.16 (m, 1H), 2.06-1.65 (m, 9H), 1.30 (t, J=7.3 Hz, 5H), 1.04 (d, J=6.1 Hz, 2H), 0.94-0.78 (m, 2H), 0.65-0.51 (m, 2H); MS (ES+) m/z 563.2 (M).

Example 80

Synthesis of (S)-1-(4-(((1R, 3S, 5R, 7R)-5-chloro-adamantan-2-yl)oxy)-5-cyclopropyl-2-fluorobenzoyl)pyrrolidine-2-carboxylic Acid (Arbitrarily Assigned)

Step 1. Preparation of (S)-tert-butyl (4-(((1R, 3S, 5R, 7R)-5-chloroadamantan-2-yl)oxy)-5-cyclopropyl-2-fluorobenzoyl)-prolinate

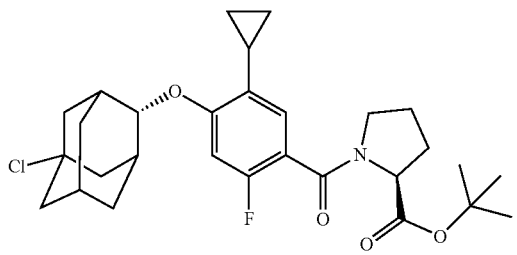

Following the procedure as described in Example 1, Step 1 and making variation as required to replace 4-(adamantan-1-ylmethoxy)-5-cyclopropyl-2-fluorobenzoic acid with 4-(((1R,3S,5S,7S)-5-chloroadamantan-2-yl)oxy)-5-cyclopropyl-2-fluorobenzoic acid, the title compound was obtained as a colorless solid (in quantitative yield): MS (ES+) m/z 518.1, 520.1 (M+1).

Step 2. Preparation of (S)-1-(4-(((1R,3S,5R,7R)-5-chloroadamantan-2-yl)oxy)-5-cyclopropyl-2-fluorobenzoyl)pyrrolidine-2-carboxylic Acid (Arbitrarily Assigned)

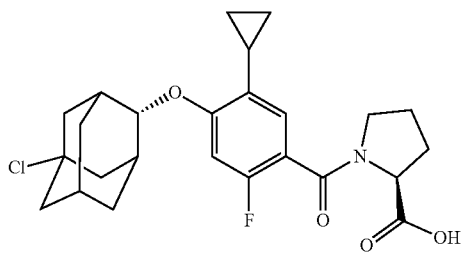

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl (4-(((1R,3S,5R,7R)-5-chloroadamantan-2-yl)oxy)-5-cyclopropyl-2-fluorobenzoyl)prolinate, the title compound was obtained as a colorless solid (0.07 g, 19%): $^1$H NMR (300 MHz, CDCl$_3$) δ 6.99-6.97 (m, 0.85H), 6.88-6.85 (m, 0.15H), 6.63 (br, 1H), 6.53-6.47 (m, 1H), 4.70 (m, 1H), 4.47 (s, 1H), 3.79 (t, J=6.7 Hz, 0.2H), 3.51 (t, J=6.4 Hz, 1.8H), 2.36-1.86 (m, 16H), 1.54 (d, J=12.3 Hz, 2H), 0.92-0.85 (m, 2H), 0.65-0.62 (m, 2H); MS (ES+) m/z 462.0, 464.0 (M+1).

Example 81

Synthesis of (S)-1-(5-chloro-4-(((1R,3S,5R,7R)-5-chloroadamantan-2-yl)oxy)-2-fluorobenzoyl)pyrrolidine-2-carboxylic Acid (Arbitrarily Assigned)

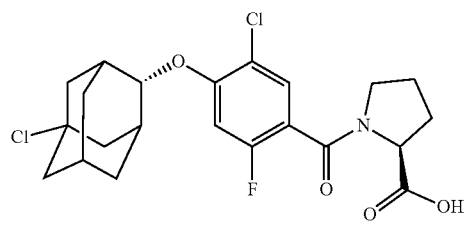

Following the procedure as described in Example, Step 2 and making variation as required to replace (S)-tert-butyl 1-(4-(adamantan-1-ylmethoxy)-5-cyclopropyl-2-fluorobenzoyl)-pyrrolidine-2-carboxylate with (S)-tert-butyl (5-chloro-4-(((1R,3S,5R,7R)-5-chloroadamantan-2-yl)oxy)-2-fluorobenzoyl)-prolinate, the title compound was obtained as a colorless solid (0.01 g, 19%): $^1$H NMR (300 MHz, CDCl$_3$) δ 7.50-7.48 (m, 0.85H), 7.40-7.38 (m, 0.15H), 6.67.6.60 (m, 1H), 4.70 (br, 1H), 4.50 (br, 1H), 4.49 (s, 1H), 3.81-3.74 (m, 0.3H), 3.52 (t, J=6.3 Hz, 1.7H), 2.34-1.88 (m, 15H), 1.52 (d, J=12.0 Hz, 2H); MS (ES+) m/z 456.0, 458.0 (M+1).

Example 82

Synthesis of (S)-1-(4-(((1R,3S,5R,7R)-5-chloroadamantan-2-yl)oxy)-5-cyclopropyl-2-fluorobenzoyl)pyrrolidine-2-carboxylic Acid (Arbitrarily Assigned)

Step 1. Preparation of tert-butyl (4-(((1R,2S,3S,5R,7R)-5-chloroadamantan-2-yl)oxy)-5-cyclopropyl-2-fluorobenzoyl)-L-prolinate

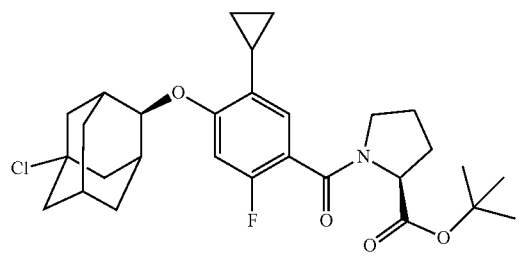

Following the procedure as described in Example 1, Step 1 and making variation as required to replace 4-(adamantan-1-ylmethoxy)-5-cyclopropyl-2-fluorobenzoic acid with 4-(((1R,2S,3S,5S,7S)-5-chloroadamantan-2-yl)oxy)-5-cyclopropyl-2-fluorobenzoic acid, the title compound was obtained as a colorless solid (0.23 g, 64%): MS (ES+) m/z 518.1, 520.1 (M+1).

Step 2. Preparation of (S)-1-(4-(((1R,2S,3S,5R,7R)-5-chloroadamantan-2-yl)oxy)-5-cyclopropyl-2-fluorobenzoyl)pyrrolidine-2-carboxylic Acid (Arbitrarily Assigned)

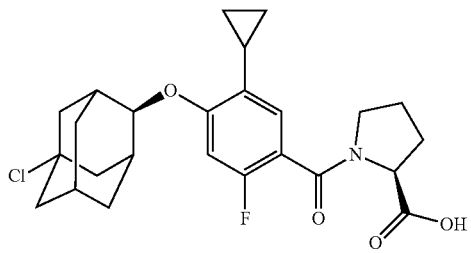

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(((1R,2S,3S,5R,7R)-5-chloroadamantan-2-yl)oxy)-5-cyclopropyl-2-fluorobenzoyl)-L-prolinate, the title compound was obtained as a colorless solid (0.09 g, 45%): $^1$H NMR (300 MHz, CDCl$_3$) δ 7.00 (d, J=7.9 Hz, 0.85H), 6.87 (d, J=7.9 Hz, 0.15H), 6.78 (br, 1H), 6.53-6.46 (m, 1H), 4.73-4.68 (m, 1H), 4.33-4.32 (m, 1H), 3.80-3.75 (m, 0.2H), 3.52-3.47 (m, 1.8H), 2.57-2.53 (m, 2H), 2.43-1.85 (m, 14H), 1.75-1.71 (m, 2H), 0.97-0.91 (m, 2H), 0.66-0.61 (m, 2H); MS (ES+) m/z 462.1, 464.1 (M+1).

Example 83

Synthesis of (S)-1-(4-(adamantan-1-ylmethoxy)-5-cyclopropyl-2-fluorobenzoyl)piperidine-2-carboxylic Acid Step 1. Preparation of methyl (S)-1-(4-(((3S,5S,7S)-adamantan-1-yl)methoxy)-5-cyclopropyl-2-fluorobenzoyl)piperidine-2-carboxylate

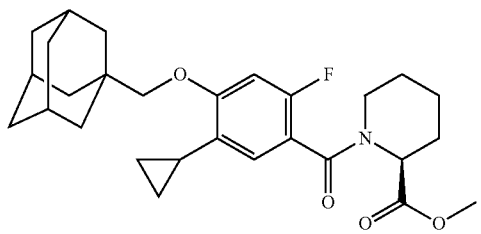 [SMILES: COC(=O)[C@@H]1CCCCN1C(=O)c1cc(C2CC2)c(OCC23CC4CC(CC(C4)C2)C3)cc1F]

Following the procedure as described in Example 1, Step 1 and making variation as required to replace (S)-tert-butyl pyrrolidine-2-carboxylate hydrochloride with methyl (S)-piperidine-2-carboxylate, the title compound was obtained as a colorless oil (0.22 g, 67%): MS (ES+) m/z 470.2 (M+1).

Step 2. Preparation of (S)-1-(4-(adamantan-1-ylmethoxy)-5-cyclopropyl-2-fluorobenzoyl)piperidine-2-carboxylic Acid

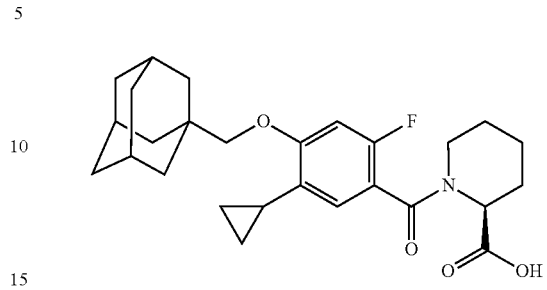

Following the procedure as described in Example 6, Step 2 and making variation as required to replace ethyl 1-(4-adamantan-1-ylmethoxy)-5-cyclopropyl-2-fluorobenzamido)cyclopropanecarboxylate with methyl (S)-1-(4-(((3S,5S,7S)-adamantan-1-yl)methoxy)-5-cyclopropyl-2-fluorobenzoyl)piperidine-2-carboxylate and following the residue by column chromatography eluting with 10% ethyl acetate in hexanes, the title compound was obtained as a colorless solid (0.15 g, 68%): $^1$H NMR (300 MHz, CDCl$_3$) δ 7.59 (br, 1H), 6.95-6.87 (m, 1H), 6.53-6.48 (m, 1H), 5.48 (br, 0.75H), 4.66-4.62 (m, 0.25H), 4.39 (br, 0.25H), 3.57-3.48 (m, 2.75H), 3.25-2.88 (m, 1H), 2.37-2.17 (m, 1H), 2.06-2.02 (m, 4H), 1.79-1.47 (m, 17H), 0.92-0.86 (m, 2H), 0.66-0.58 (m, 2H); MS (ES+) m/z 456.1 (M+1).

Example 84

Synthesis of (S)-2-(4-(adamantan-1-ylmethoxy)-5-cyclopropyl-2-fluorobenzamido)succinic Acid Step 1. Preparation of di-tert-butyl (4-(((3S,5S,7S)-adamantan-1-yl)methoxy)-5-cyclopropyl-2-fluorobenzoyl)-L-aspartate

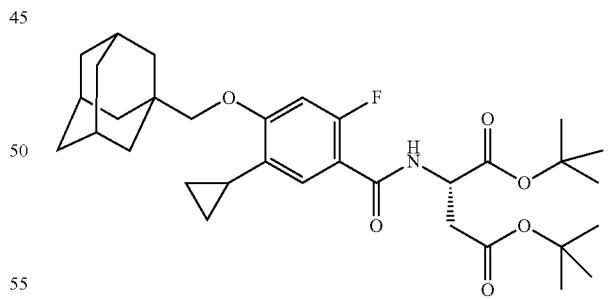

Following the procedure as described in Example, Step 1 and making variation as required to replace (S)-tert-butyl pyrrolidine-2-carboxylate hydrochloride with di-tert-butyl L-aspartate, the title compound was obtained as a colorless solid (0.24 g, 95%): $^1$H NMR (300 MHz, CDCl$_3$) δ 7.63-7.53 (m, 2H), 6.49 (d, J=14.0 Hz, 1H), 4.89-4.83 (m, 1H), 3.49 (s, 2H), 2.94 (dd, J=4.2 Hz, 16.9 Hz, 1H), 2.81 (dd, J=4.6 Hz, 16.9 Hz, 1H), 2.08-1.98 (m, 4H), 1.75-1.65 (m, 12H), 1.44 (s, 9H), 1.40 (s, 9H), 0.89-0.83 (m, 2H), 0.66-0.61 (m, 2H);

223
Step 2. Preparation of (S)-2-(4-(adamantan-1-yl-methoxy)-5-cyclopropyl-2-fluorobenzamido)succinic Acid

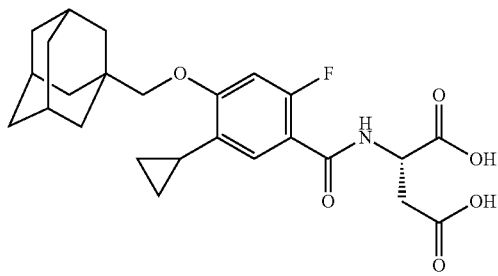 [SMILES: O=C(O)C[C@H](NC(=O)c1cc(C2CC2)c(OCC23CC4CC(CC(C4)C2)C3)cc1F)C(=O)O]

Following the procedure as described in Example, Step 2 and making variation as required to replace (S)-tert-butyl 1-(4-(adamantan-1-ylmethoxy)-5-cyclopropyl-2-fluorobenzoyl)pyrrolidine-2-carboxylate with di-tert-butyl (4-(((3S,5S,7S)-adamantan-1-yl)methoxy)-5-cyclopropyl-2-fluorobenzoyl)-L-aspartate, the title compound was obtained as a colorless solid (0.18 g, 92%): $^1$H NMR (300 MHz, CDCl$_3$) δ 8.62 (br, 2H), 7.80-7.73 (m, 1H), 7.54 (d, J=9.0 Hz, 1H), 6.49 (d, J=14.2 Hz, 1H), 5.12-5.10 (m, 1H), 3.50 (s, 2H), 3.22-3.00 (m, 2H), 2.02 (br, 4H), 1.79-1.67 (m, 12H), 0.92-0.86 (m, 2H), 0.67-0.62 (m, 2H); MS (ES+) m/z 460.1 (M+1).

224
Step 2. Preparation of (S)-1-(4-(adamantan-1-yl-methoxy)-3-(trifluoromethyl)benzoyl)pyrrolidine-2-carboxylic Acid

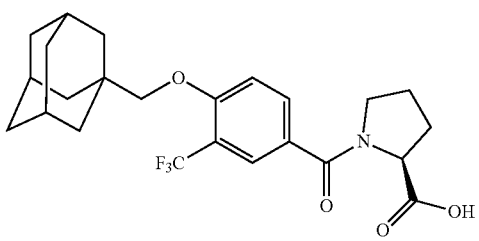

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(((3S,5S,7S)-adamantan-1-yl)methoxy)-3-(trifluoromethyl)benzoyl)-L-prolinate, the title compound was obtained as a colorless solid (0.09 g, 53%): $^1$H NMR (300 MHz, CDCl$_3$) δ 9.93 (br, 1H), 7.83 (s, 1H), 7.76 (d, J=8.6 Hz, 1H), 6.99 (d, J=8.7 Hz, 1H), 4.76-4.71 (m, 1H), 3.66-3.60 (m, 4H), 2.38-2.20 (m, 2H), 2.11-1.89 (m, 5H), 1.79-1.66 (m, 12H); MS (ES+) m/z 452.1 (M+1).

Example 85

Synthesis of (S)-1-(4-(adamantan-1-ylmethoxy)-3-(trifluoromethyl)benzoyl)-pyrrolidine-2-carboxylic Acid Step 1. Preparation of tert-butyl (4-(((3S,5S,7S)-adamantan-1-yl)methoxy)-3-(trifluoromethyl)benzoyl)-L-prolinate

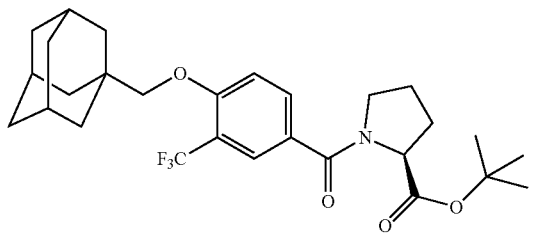 [SMILES: CC(C)(C)OC(=O)[C@@H]1CCCN1C(=O)c1ccc(OCC23CC4CC(CC(C4)C2)C3)c(C(F)(F)F)c1]

Following the procedure as described in Example 1, Step 1 and making variation as required to replace 4-(adamantan-1-ylmethoxy)-5-cyclopropyl-2-fluorobenzoic acid with 4-adamantan-1-yl)methoxy)-3-(trifluoromethyl)benzoic acid, the title compound was obtained as a colorless solid (0.18 g, 81%): MS (ES+) m/z 508.1 (M+1).

Example 86

Synthesis of (S)-1-(4-(adamantan-1-ylmethoxy)-5-cyclopropyl-2-fluorobenzoyl)azetidine-2-carboxylic Acid Step 1. Preparation of methyl (S)-1-(4-(((3S,5S,7S)-adamantan-1-yl)methoxy)-5-cyclopropyl-2-fluorobenzoyl)azetidine-2-carboxylate

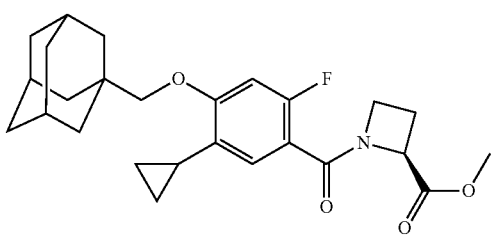 [SMILES: COC(=O)[C@@H]1CCN1C(=O)c1cc(C2CC2)c(OCC23CC4CC(CC(C4)C2)C3)cc1F]

Following the procedure as described in Example 1, Step 1 and making variation as required to (S)-tert-butyl pyrrolidine-2-carboxylate hydrochloride with methyl (S)-azetidine-2-carboxylate hydrochloride, the title compound was obtained as a colorless solid (0.16 g, 84%): MS (ES+) m/z 442.1 (M+1).

225

Step 2. Preparation of (S)-1-(4-(adamantan-1-yl-methoxy)-5-cyclopropyl-2-fluorobenzoyl)azetidine-2-carboxylic Acid

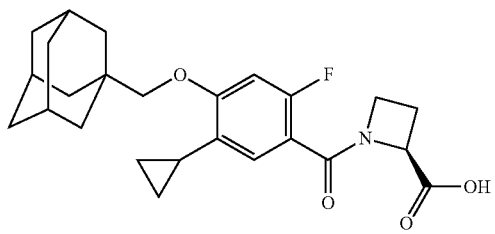 [SMILES: O=C(O)[C@@H]1CCN1C(=O)c1cc(C2CC2)c(OCC23CC4CC(CC(C4)C2)C3)cc1F]

Following the procedure as described in Example 6, Step 2 and making variation as required to replace ethyl 1-(4-adamantan-1-ylmethoxy)-5-cyclopropyl-2-fluorobenzamido)cyclopropanecarboxylate with methyl (S)-1-(4-(((3S,5S,7S)-adamantan-1-yl)methoxy)-5-cyclopropyl-2-fluorobenzoyl)azetidine-2-carboxylate, the title compound was obtained as colorless solid (0.12 g, 78%): $^1$H NMR (300 MHz, CDCl$_3$) δ 8.92 (br, 1H), 7.08 (d, J=7.9 Hz, 1H), 6.53 (d, J=12.5 Hz, 1H), 5.20-5.15 (m, 1H), 4.23-4.08 (m, 2H), 3.52 (s, 2H), 2.80-2.68 (m, 1H), 2.60-2.48 (m, 1H), 2.03-1.99 (m, 4H), 1.80-1.68 (m, 12H), 0.96-0.89 (m, 2H), 0.65-0.60 (m, 2H); MS (ES+) m/z 428.1 (M+1).

Example 87

Synthesis of (S)-2-(4-(adamantan-1-ylmethoxy)-5-cyclopropyl-2-fluorobenzamido)butanoic Acid Step 1. Preparation of tert-butyl (S)-2-(4-(((3S,5S,7S)-adamantan-1-yl)methoxy)-5-cyclopropyl-2-fluorobenzamido)butanoate

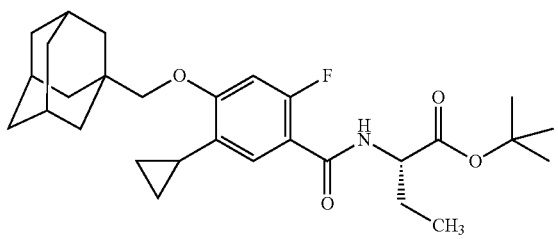 [SMILES: CC[C@H](NC(=O)c1cc(C2CC2)c(OCC23CC4CC(CC(C4)C2)C3)cc1F)C(=O)OC(C)(C)C]

Following the procedure as described in Example 1, Step 1 and making variation as required to replace (S)-tert-butyl pyrrolidine-2-carboxylate hydrochloride with tert-butyl (S)-2-aminobutanoate hydrochloride, the title compound was obtained as a colorless oil (0.21 g, 95%): MS (ES+) m/z 486.2 (M+1).

226

Step 2. Preparation of (S)-2-(4-(adamantan-1-yl-methoxy)-5-cyclopropyl-2-fluorobenzamido)butanoic Acid

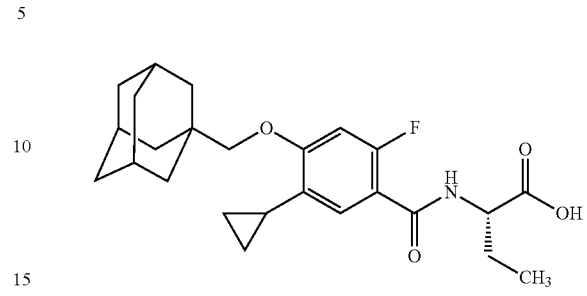

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (S)-2-(4-(((3S,5S,7S)-adamantan-1-yl)methoxy)-5-cyclopropyl-2-fluorobenzamido)butanoate, the title compound was obtained as a colorless solid (0.17 g, 96%): $^1$H NMR (300 MHz, CDCl$_3$) δ 8.28 (br, 1H), 7.57 (d, J=9.1 Hz, 1H), 7.22-7.15 (m, 1H), 6.53 (d, J=14.3 Hz, 1H), 4.78-4.72 (m, 1H), 3.53 (s, 2H), 2.12-2.04 (m, 5H), 1.96-1.84 (m, 1H), 1.80-1.69 (m, 12H), 1.02 (t, J=7.4 Hz, 3H), 0.94-0.87 (m, 2H), 0.69-0.64 (m, 2H); MS (ES+) m/z 430.1 (M+1).

Example 88

Synthesis of (S)-2-(4-(adamantan-1-ylmethoxy)-5-cyclopropyl-2-fluorobenzamido)-4-methylpentanoic Acid Step 1. Preparation of tert-butyl (4-(((3S,5S,7S)-adamantan-1-yl)methoxy)-5-cyclopropyl-2-fluorobenzoyl)-L-leucinate

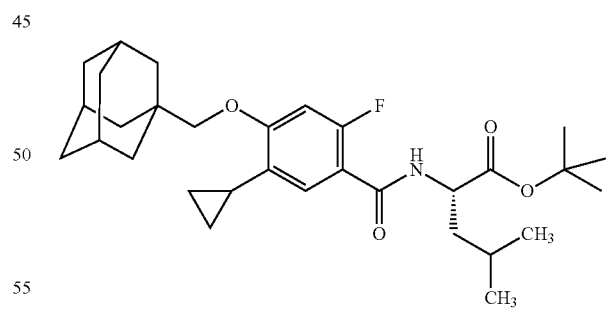

Following the procedure as described in Example 1, Step 1 and making variation as required to replace (S)-tert-butyl pyrrolidine-2-carboxylate hydrochloride with tert-butyl (S)-2-aminobutanoate hydrochloride, the title compound was obtained as a colorless oil (0.19 g, 95%): $^1$H NMR (300 MHz, CDCl$_3$) δ 7.57 (d, J=9.1 Hz, 1H), 7.08-7.00 (m, 1H), 6.48 (d, J=14.3 Hz, 1H), 4.73-4.66 (m, 1H), 3.49 (s, 2H), 2.04-1.99 (m, 4H), 1.76-1.65 (m, 15H), 1.44 (s, 9H), 0.95-0.83 (m, 8H), 0.66-0.61 (m, 2H).

Step 2. Preparation of (S)-2-(4-(adamantan-1-yl-methoxy)-5-cyclopropyl-2-fluorobenzamido)-4-methylpentanoic Acid

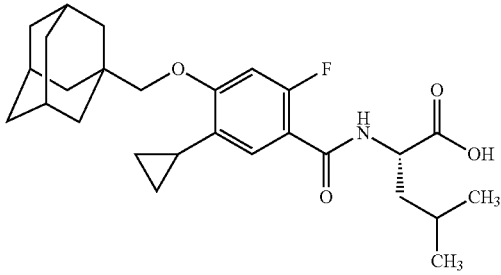 [SMILES: CC(C)C[C@H](NC(=O)c1cc(C2CC2)c(OCC23CC4CC(CC(C4)C2)C3)cc1F)C(=O)O]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(((3S,5S,7S)-adamantan-1-yl)methoxy)-5-cyclopropyl-2-fluorobenzoyl)-L-leucinate, the title compound was obtained as a colorless solid (0.16 g, 95%): $^1$H NMR (300 MHz, CDCl$_3$) δ 7.59 (d, J=9.1 Hz, 1H), 7.04-6.96 (m, 1H), 6.82 (br, 1H), 6.53 (d, J=14.3 Hz, 1H), 4.79-4.73 (m, 1H), 3.53 (s, 2H), 2.07-2.00 (m, 4H), 1.85-1.69 (m, 15H), 1.00-0.87 (m, 8H), 0.69-0.64 (m, 2H); MS (ES+) m/z 458.1 (M+1).

Example 89

Synthesis of (S)-1-(4-(adamantan-1-ylmethoxy)-5-ethyl-2-fluorobenzoyl)pyrrolidine-2-carboxylic Acid

Step 1. Preparation of tert-butyl (4-(((3S, 5S, 7S)-adamantan-1-yl)methoxy)-5-ethyl-2-fluorobenzoyl)-L-prolinate

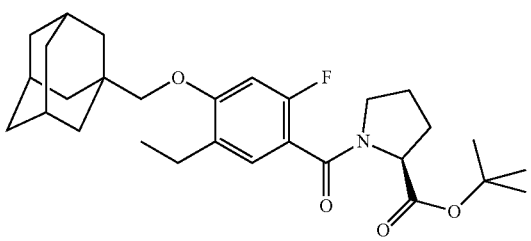 [SMILES: CCc1cc(C(=O)N2CCC[C@H]2C(=O)OC(C)(C)C)c(F)cc1OCC12CC3CC(CC(C3)C1)C2]

Following the procedure as described in Example 1, Step 1 and making variation as required to replace 4-(adamantan-1-ylmethoxy)-5-cyclopropyl-2-fluorobenzoic acid with 4-(((3r,5r,7r)-adamantan-1-yl)methoxy)-5-ethyl-2-fluorobenzoic acid, the title compound was obtained as a colorless oil (0.23 g, in quantitative yield): $^1$H NMR (300 MHz, CDCl$_3$) δ 7.15-7.03 (m, 1H), 6.47-6.40 (m, 1H), 4.45-4.17 (m, 1H), 3.74-3.31 (m, 4H), 2.58-2.48 (m, 2H), 2.25-2.14 (m, 1H), 2.00-1.89 (m, 5H), 1.72-1.60 (m, 13H), 1.42 (s, 9H), 1.21-1.16 (m, 3H).

Step 2. Preparation of (S)-1-(4-(adamantan-1-yl-methoxy)-5-ethyl-2-fluorobenzoyl)pyrrolidine-2-carboxylic Acid

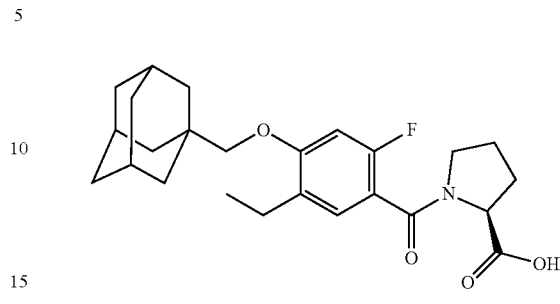

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(((3S,5S,7S)-adamantan-1-yl)methoxy)-5-ethyl-2-fluorobenzoyl)-L-prolinate, the title compound was obtained as a colorless solid (0.13 g, 67%): $^1$H NMR (300 MHz, CDCl$_3$) δ 9.05 (br s. 1H), 7.22 (d, J=8.0 Hz, 1H), 6.53 (d, J=12.1 Hz, 1H), 4.74-4.69 (m, 1H), 3.54-3.47 (m, 2H), 3.47 (s, 2H), 2.61 (q, J=7.5 Hz, 2H), 2.41-2.16 (m, 2H), 2.04-1.97 (m, 4H), 1.96-1.85 (m, 1H), 1.79-1.66 (m, 12H), 1.19 (t, J=7.5 Hz, 3H); MS (ES+) m/z 430.1 (M+1).

Example 90

Synthesis of (S)-1-(5-cyclopropyl-4-(((1S, 2S, 5S)-6,6-dimethylbicyclo[3.1.1]heptan-2-yl)methoxy)-2-fluorobenzoyl)pyrrolidine-2-carboxylic Acid

Step 1. Preparation of tert-butyl (5-cyclopropyl-4-(((1S, 2S,5S)-6,6-dimethylbicyclo-[3.1.1]heptan-2-yl)methoxy)-2-fluorobenzoyl)-L-prolinate

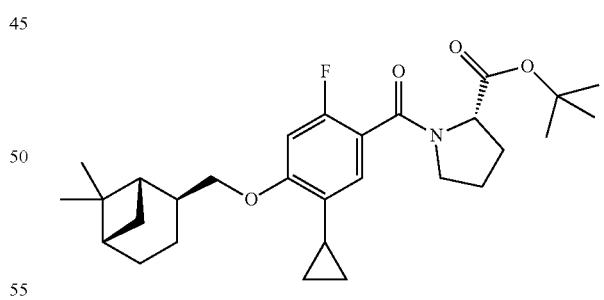

Following the procedure as described in Example 1, Step 1 and making variation as required to replace 4-(adamantan-1-ylmethoxy)-5-cyclopropyl-2-fluorobenzoic acid with 5-cyclopropyl-4-(((1S,2S,5S)-6,6-dimethylbicyclo[3.1.1]heptan-2-yl)methoxy)-2-fluorobenzoic acid, the title compound was obtained as a colorless oil (0.13 g, 51%): $^1$H NMR (300 MHz, CDCl$_3$) δ 6.89-6.79 (m, 1H), 6.50-6.43 (m, 1H), 4.46-4.16 (m, 1H), 3.75-3.31 (m, 4H), 2.53-2.43 (m, 1H), 2.28-2.17 (m, 1H), 2.10-1.65 (m, 10H), 1.44-1.19 (m, 14H), 0.84-0.77 (m, 5H), 0.59-0.51 (m, 2H).

Step 2. Preparation of (S)-1-(5-cyclopropyl-4-(((1S, 2S, 5S)-6,6-dimethylbicyclo-[3.1.1]heptan-2-yl)methoxy)-2-fluorobenzoyl)pyrrolidine-2-carboxylic Acid

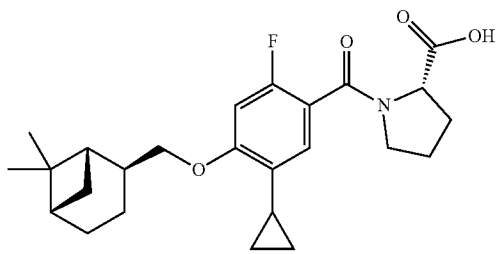 [SMILES: CC1(C)[C@H]2CC[C@H](COc3cc(F)c(C(=O)N4CCC[C@H]4C(=O)O)cc3C3CC3)[C@@H]1C2]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (5-cyclopropyl-4-(((1S, 2S, 5S)-6,6-dimethylbicyclo[3.1.1]heptan-2-yl)methoxy)-2-fluorobenzoyl)-L-prolinate, the title compound was obtained as a colorless solid (0.08 g, 81%): $^1$H NMR (300 MHz, CDCl$_3$) δ 7.40 (br s. 1H), 6.94 (d, J=6.5 Hz, 1H), 6.54 (d, J=12.0 Hz, 1H), 4.74-4.70 (m, 1H), 3.82-3.73 (m, 2H), 3.56-3.41 (m, 2H), 2.58-2.40 (m, 2H), 2.25-1.71 (m, 10H), 1.52-1.41 (m, 2H), 1.24 (s, 3H), 0.91-0.89 (m, 5H), 0.63-0.62 (m, 2H); MS (ES+) m/z 430.1 (M+1).

Synthesis of (2S, 4R)-1-(5-cyclopropyl-4-((1-(1-(3,5-dichlorophenyl)ethyl)piperidin-4-yl)methoxy)-2-fluorobenzoyl)-4-fluoropyrrolidine-2-carboxylic Acid

Step 1. Preparation of methyl (2S, 4R)-1-(5-cyclopropyl-4-((1-(1-(3,5-dichlorophenyl)-ethyl)piperidin-4-yl)methoxy)-2-fluorobenzoyl)-4-fluoropyrrolidine-2-carboxylate

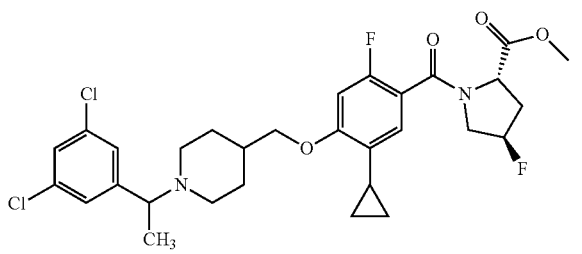 [SMILES: COC(=O)[C@@H]1C[C@@H](F)CN1C(=O)c1cc(C2CC2)c(OCC2CCN(C(c3cc(Cl)cc(Cl)c3)C(F)(F)F)CC2)cc1F]

Following the procedure as described in Example 1, Step 1 and making variation as required to replace 4-(adamantan-1-ylmethoxy)-5-cyclopropyl-2-fluorobenzoic acid with 5-cyclopropyl-4-((1-(1-(3,5-dichlorophenyl)ethyl)piperidin-4-yl)methoxy)-2-fluorobenzoic acid, and replace (S)-tert-butyl pyrrolidine-2-carboxylate hydrochloride with methyl (2S, 4R)-4-fluoropyrrolidine-2-carboxylate, the title compound was obtained as brown oil (0.25 g, in quantitative yield): MS (ES+) m/z 595.2, 597.2 (M+1).

Step 2. Preparation of (2S, 4R)-1-(5-cyclopropyl-4-((1-(1-(3,5-dichlorophenyl)ethyl)-piperidin-4-yl)methoxy)-2-fluorobenzoyl)-4-fluoropyrrolidine-2-carboxylic Acid

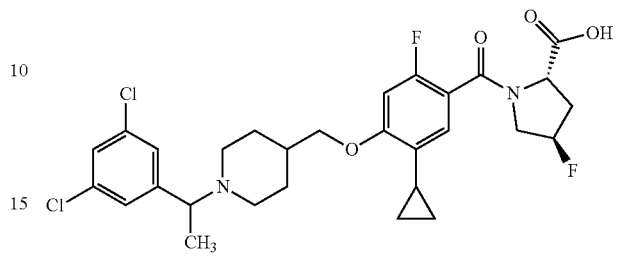

Following the procedure as described in Example 6, Step 2 and making variation as required to replace ethyl 1-(4-adamantan-1-ylmethoxy)-5-cyclopropyl-2-fluorobenzamido)cyclopropanecarboxylate with methyl (2S,4R)-1-(5-cyclopropyl-4-((1-(1-(3,5-dichlorophenyl)ethyl)piperidin-4-yl)methoxy)-2-fluorobenzoyl)-4-fluoropyrrolidine-2-carboxylate, the title compound was obtained as a colorless solid (0.05 g, 23%): $^1$H NMR (300 MHz, CDCl$_3$) δ 7.26 (br s, 1H), 7.38-7.33 (m, 3H), 6.90-6.87 (m, 1H), 6.35-6.29 (m, 1H), 5.28 (brs, 0.5H), 0.51 (brs, 0.5H), 4.76-4.70 (m, 1H), 4.32-4.11 (m, 1H), 3.89-3.30 (m, 6H), 2.76-2.62 (m, 1H), 2.42-2.24 (m, 3H), 1.91-1.64 (m, 9H), 0.80-0.78 (m, 2H), 0.56-0.47 (m, 2H); MS (ES+) m/z 581.1, 583.0 (M+1).

Example 92

Synthesis of (2S, 4R)-1-(5-cyclopropyl-4-((1-(1-(3,5-dichlorophenyl)-2,2,2-trifluoroethyl)piperidin-4-yl)methoxy)-2-fluorobenzoyl)-4-fluoropyrrolidine-2-carboxylic Acid

Step 1. Preparation of methyl (2S,4R)-1-(5-cyclopropyl-4-((1-(1-(3,5-dichlorophenyl)-2,2,2-trifluoroethyl)piperidin-4-yl)methoxy)-2-fluorobenzoyl)-4-fluoropyrrolidine-2-carboxylate Following the procedure as described in Example 1, Step 1 and making variation as required to replace 4-(adamantan-1-ylmethoxy)-5-cyclopropyl-2-fluorobenzoic acid with 5-cyclopropyl-4-((1-(1-(3,5-dichlorophenyl)-2,2,2-trifluoroethyl)piperidin-4-yl)methoxy)-2-fluorobenzoic acid, and (S)-tert-butyl pyrrolidine-2-carboxylate hydrochloride with methyl (2S, 4R)-4-fluoropyrrolidine-2-carboxylate, the title compound was obtained as a brown oil (0.74 g, 40%): MS (ES+) m/z 649.1, 651.1 (M+1).

231

Step 2. Preparation of (2S, 4R)-1-(5-cyclopropyl-4-((1-(1-(3,5-dichlorophenyl)-2,2,2-trifluoroethyl)piperidin-4-yl)methoxy)-2-fluorobenzoyl)-4-fluoropyrrolidine-2-carboxylic Acid

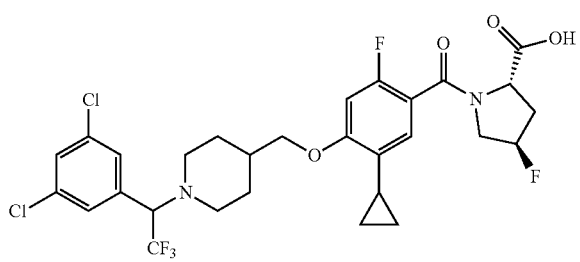 [SMILES: O=C(O)[C@@H]1C[C@@H](F)CN1C(=O)c1cc(C2CC2)c(OCC2CCN(C(c3cc(Cl)cc(Cl)c3)C(F)(F)F)CC2)cc1F]

Following the procedure as described in Example 6, Step 2 and making variation as required to replace ethyl 1-(4-adamantan-1-ylmethoxy)-5-cyclopropyl-2-fluorobenzamido)cyclopropanecarboxylate with methyl (2S, 4R)-1-(5-cyclopropyl-4-((1-(1-(3,5-dichlorophenyl)-2,2,2-trifluoroethyl)piperidin-4-yl)methoxy)-2-fluorobenzoyl)-4-fluoropyrrolidine-2-carboxylate, the title compound was obtained as a colorless solid (0.48 g, 82%): $^1$H NMR (300 MHz, CDCl$_3$) δ 7.38-7.37 (m, 1H), 7.32 (br, 2H), 7.01 (d, J=7.8 Hz, 1H), 6.52 (d, J=11.9 Hz, 1H), 6.23 (br, 1H), 5.29 (br, 0.5H), 5.12 (br, 0.5H), 4.93 (t, J=8.7 Hz, 1H), 4.08 (q, J=8.5 Hz, 1H), 3.86-3.70 (m, 4H), 3.02-2.96 (m, 2H), 2.67-2.31 (m, 4H), 2.05-1.95 (m, 1H), 1.87-1.83 (m, 3H), 1.53-1.41 (m, 2H), 0.93-0.88 (m, 2H), 0.64-0.60 (m, 2H); MS (ES+) m/z 635.1, 637.1 (M+1).

Example 93

Synthesis of (2S, 4R)-1-(5-cyclopropyl-4-((1-((6-cyclopropyl-4-(trifluoromethyl)-pyridin-2-yl)methyl)piperidin-4-yl)methoxy)-2-fluorobenzoyl)-4-fluoropyrrolidine-2-carboxylic Acid Step 1. Preparation of methyl (2S, 4R)-1-(5-cyclopropyl-4-((1-((6-cyclopropyl-4-(trifluoromethyl)pyridin-2-yl)methyl)piperidin-4-yl)methoxy)-2-fluorobenzoyl)-4-fluoropyrrolidine-2-carboxylate

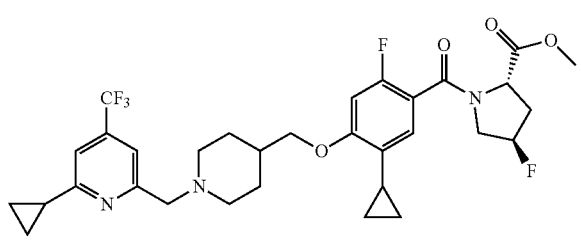 [SMILES: COC(=O)[C@@H]1C[C@@H](F)CN1C(=O)c1cc(C2CC2)c(OCC2CCN(Cc3cc(C(F)(F)F)cc(C4CC4)n3)CC2)cc1F]

Following the procedure as described in Example 1, Step 1 and making variation as required to replace 4-(adamantan-1-ylmethoxy)-5-cyclopropyl-2-fluorobenzoic acid with 5-cyclopropyl-4-((1-((6-cyclopropyl-4-(trifluoromethyl)pyridin-2-yl)methyl)piperidin-4-yl)methoxy)-2-fluorobenzoic acid, and (S)-tert-butyl pyrrolidine-2-carboxylate hydrochloride with methyl (2S,4R)-4-fluoropyrrolidine-2-carboxylate, the title compound was obtained which was used directly without further purification: MS (ES+) m/z 622.3 (M+1).

Step 2. Preparation of (2S, 4R)-1-(5-cyclopropyl-4-((1-((6-cyclopropyl-4-(trifluoromethyl)-pyridin-2-yl)methyl)piperidin-4-yl)methoxy)-2-fluorobenzoyl)-4-fluoropyrrolidine-2-carboxylic Acid

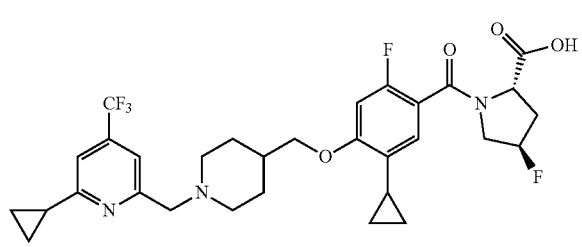 [SMILES: O=C(O)[C@@H]1C[C@@H](F)CN1C(=O)c1cc(C2CC2)c(OCC2CCN(Cc3cc(C(F)(F)F)cc(C4CC4)n3)CC2)cc1F]

Following the procedure as described in Example 6, Step 2 and making variation as required to replace ethyl 1-(4-adamantan-1-ylmethoxy)-5-cyclopropyl-2-fluorobenzamido)-cyclopropanecarboxylate with methyl (2S, 4R)-1-(5-cyclopropyl-4-((1-((6-cyclopropyl-4-(trifluoromethyl)pyridin-2-yl)methyl)piperidin-4-yl)methoxy)-2-fluorobenzoyl)-4-fluoropyrrolidine-2-carboxylate, the title compound was obtained as a colorless solid (0.03 g, 23% over steps): $^1$H NMR (300 MHz, CDCl$_3$) δ 7.47-7.46 (m, 1H), 7.38 (s, 1H), 6.95 (d, J=7.8 Hz, 1H), 6.46 (d, J=11.6 Hz, 1H), 5.28 (brs, 0.5H), 0.51 (brs, 0.5H), 4.77-4.71 (m, 1H), 4.35 (s, 2H), 3.87-3.56 (m, 6H), 2.98-2.92 (m, 2H), 2.74-2.55 (m, 2H), 2.36-1.86 (m, 8H), 1.10-1.04 (m, 4H), 0.86-0.83 (m, 2H), 0.56-0.53 (m, 2H); MS (ES+) m/z 608.2 (M+1).

Example 94

Synthesis of (2S, 4R)-1-(5-cyclopropyl-4-(2-(1-(3,5-dichlorobenzyl)piperidin-4-yl)ethoxy)-2-fluorobenzoyl)-4-fluoropyrrolidine-2-carboxylic Acid Step 1. Preparation of methyl (2S, 4R)-1-(5-cyclopropyl-4-(2-(1-(3,5-dichlorobenzyl)-piperidin-4-yl)ethoxy)-2-fluorobenzoyl)-4-fluoropyrrolidine-2-carboxylate

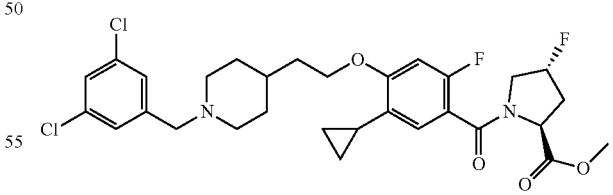

Following the procedure as described in Example 1, Step 1 and making variation as required to replace 4-(adamantan-1-ylmethoxy)-5-cyclopropyl-2-fluorobenzoic acid with 5-cyclopropyl-4-(2-(1-(3,5-dichlorobenzyl)piperidin-4-yl)ethoxy)-2-fluorobenzoic acid and (S)-tert-butyl pyrrolidine-2-carboxylate hydrochloride with methyl (2S,4R)-4-fluoropyrrolidine-2-carboxylate, the title compound was obtained as a brown oil (0.20 g, 92%): MS (ES+) m/z 595.3, 597.1 (M+1).

Step 2. Preparation of (2S, 4R)-1-(5-cyclopropyl-4-(2-(1-(3,5-dichlorobenzyl)piperidin-4-yl)ethoxy)-2-fluorobenzoyl)-4-fluoropyrrolidine-2-carboxylic Acid

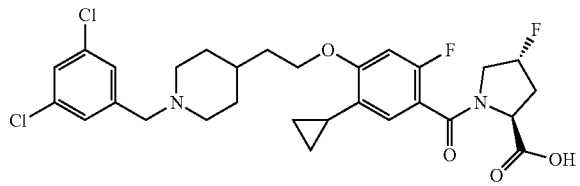 [SMILES: O=C(O)[C@@H]1C[C@@H](F)CN1C(=O)c1cc(C2CC2)c(OCCC2CCN(Cc3cc(Cl)cc(Cl)c3)CC2)cc1F]

Following the procedure as described in Example 6, Step 2 and making variation as required to replace ethyl 1-(4-adamantan-1-ylmethoxy)-5-cyclopropyl-2-fluorobenzamido)cyclopropanecarboxylate with methyl (2S,4R)-1-(5-cyclopropyl-4-(2-(1-(3,5-dichlorobenzyl)piperidin-4-yl)ethoxy)-2-fluorobenzoyl)-4-fluoropyrrolidine-2-carboxylate, the title compound was obtained as a colorless solid (0.07 g, 27%): $^1$H NMR (300 MHz, CDCl$_3$) δ 7.36-7.29 (m, 3H), 7.05 (br, 1H), 6.96-6.87 (m, 1H), 6.47-6.42 (m, 1H), 5.40-5.11 (m, 1H), 4.80-4.51 (m, 1H), 4.26-3.57 (m, 6H), 3.37-3.22 (m, 2H), 2.77-2.63 (m, 1H), 2.40-2.22 (m, 3H), 1.97-1.90 (m, 1H), 1.78-1.64 (m, 7H), 0.85-0.82 (m, 2H), 0.63-0.55 (m, 2H); MS (ES+) m/z 581.1, 583.1 (M+1).

Example 95

Synthesis of (S)-1-(4-(((S)-1-(2-chloro-4-fluorobenzyl)piperidin-3-yl)oxy)-5-cyclopropyl-2-fluorobenzoyl)pyrrolidine-2-carboxylic Acid

Step 1. Preparation of tert-butyl (4-(((S)-1-(2-chloro-4-fluorobenzyl)piperidin-3-yl)oxy)-5-cyclopropyl-2-fluorobenzoyl)-L-prolinate

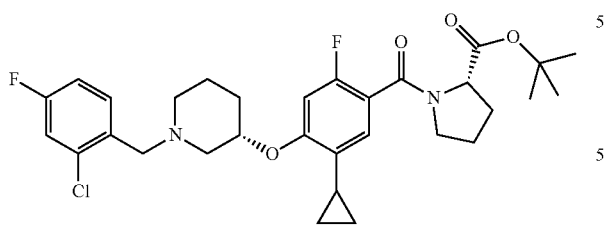

Following the procedure as described in Example 1, Step 1 and making variation as required to replace 4-(adamantan-1-ylmethoxy)-5-cyclopropyl-2-fluorobenzoic acid with (S)-4-((1-(2-chloro-4-fluorobenzyl)piperidin-3-yl)oxy)-5-cyclopropyl-2-fluorobenzoic acid, the title compound was obtained as colorless oil (0.40 g, 83%): MS (ES+) m/z 575.3, 577.2 (M+1).

Step 2. Preparation of (S)-1-(4-(((S)-1-(2-chloro-4-fluorobenzyl)piperidin-3-yl)oxy)-5-cyclopropyl-2-fluorobenzoyl)pyrrolidine-2-carboxylic Acid

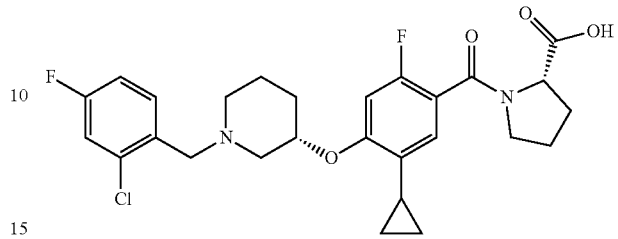

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-(((S)-1-(2-chloro-4-fluorobenzyl)-piperidin-3-yl)oxy)-5-cyclopropyl-2-fluorobenzoyl)-L-prolinate, the title compound was obtained as a colorless solid (0.31 g, 86%): $^1$H NMR (300 MHz, DMSO-d$_6$) δ 7.55 (br, 1H), 7.42-7.40 (m, 1H), 7.16-7.15 (m, 1H), 6.93-6.87 (m, 1H), 6.80-6.64 (m, 1H), 4.56 (br, 1H), 4.34-4.07 (m, 1H), 3.69-3.25 (m, 7H), 2.94-2.57 (m, 3H), 2.26-2.19 (m, 1H), 2.07-2.03 (m, 1H), 1.89-1.79 (m, 5H), 1.60 (br, 2H), 0.88-0.85 (m, 2H), 0.60-0.53 (m, 2H); MS (ES+) m/z 519.1, 521.1 (M+1).

Example 96

Synthesis of 1-(4-(adamantan-1-ylmethoxy)-5-cyclopropyl-2-fluorobenzoyl)-4,5-dihydro-1H-pyrazole-5-carboxylic Acid

Step 1. Preparation of ethyl 1-(4-adamantan-1-yl)methoxy)-5-cyclopropyl-2-fluorobenzoyl)-4,5-dihydro-1H-pyrazole-5-carboxylate

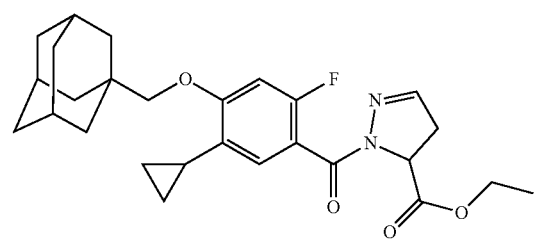 [SMILES: CCOC(=O)C1CC=NN1C(=O)c1cc(C2CC2)c(OCC23CC4CC(CC(C4)C2)C3)cc1F]

To a mixture of ethyl 4,5-dihydro-1H-pyrazole-5-carboxylate (0.77 g, 3.0 mmol) and N,N-dimethylpyridin-4-amine (1.22 g, 10.0 mmol) in dichloromethane (20 mL) was added a 4-(adamantan-1-yl)methoxy)-5-cyclopropyl-2-fluorobenzoyl chloride (0.73 g, 2.0 mmol) in dichloromethane (10 mL). The mixture was stirred at ambient temperature for 24 hours, adjusted pH to 4 with hydrochloride 1N solution and then extracted with dichloromethane (2×40 mL), and washed with 25% ammonium chloride solution and brine; dried over anhydrous sodium sulfate and concentrated in vacuo. The residue was purified by column chromatography eluting with gradient 10% to 40% of ethyl acetate in hexanes, the title compound was obtained as colorless solid (0.60 g, 64%): MS (ES+) m/z 469.2 (M+1).

Step 2. Preparation of 1-(4-(adamantan-1-yl-methoxy)-5-cyclopropyl-2-fluorobenzoyl)-4,5-dihydro-1H-pyrazole-5-carboxylic Acid

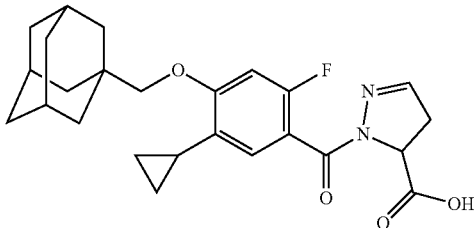 [SMILES: O=C(O)C1CC=NN1C(=O)c1cc(C2CC2)c(OCC23CC4CC(CC(C4)C2)C3)cc1F]

To a mixture of ethyl 1-(4-adamantan-1-yl)methoxy)-5-cyclopropyl-2-fluorobenzoyl)-4,5-dihydro-1H-pyrazole-5-carboxylate (0.60 g, 1.28 mmol) in methanol (6 mL) was added a solution of lithium hydroxide (0.09 g, 3.84 mmol) in water (2 mL). The reaction mixture was stirred at ambient temperature for 5 hours and concentrated in vacuo. The residue was diluted with ethyl acetate (50 mL), washed with hydrochloride 1N solution and 25% ammonium chloride solution; dried over anhydrous sodium sulfate and concentrated in vacuo. The residue was purified by column chromatography eluting with gradient 2%-10% dichloromethane in methanol, the title compound was obtained as a colorless solid (0.23 g, 41%): $^1$H NMR (300 MHz, CDCl$_3$) δ 10.98 (s, 1H), 7.09 (d, J=7.6 Hz 1H), 6.98 (br, 1H), 5.08-5.02 (m, 1H), 3.50 (s, 2H), 3.39-3.20 (m, 2H), 2.04-1.98 (m, 4H), 1.79-1.67 (m, 12H), 0.91-0.85 (m, 2H), 0.65-0.60 (m, 2H); $^{13}$C-APT NMR (75 MHz, CDCl$_3$) δ 171.4, 166.2, 161.6 (d, J=10.0 Hz), 158.6 (d, J=251 Hz), 148.0, 127.9 (d, J=2.9 Hz), 126.9 (d, J=4.3 Hz), 112.6 (d, J=14.7 Hz), 98.7 (d, J=25.9 Hz), 78.4, 56.9, 39.4, 37.8, 36.9, 33.7, 28.0, 9.5, 6.7; MS (ES+) m/z 441.2 (M+1).

Example 97

Synthesis of 5-chloro-4-((5-chloro-6-isobutoxypyridin-3-yl)oxy)-2-fluorobenzoyl)-L-proline Trifluoroacetic Acid Salt

Step 1. Preparation of tert-butyl (5-chloro-4-((5-chloro-6-isobutoxypyridin-3-yl)oxy)-2-fluorobenzoyl)-L-prolinate

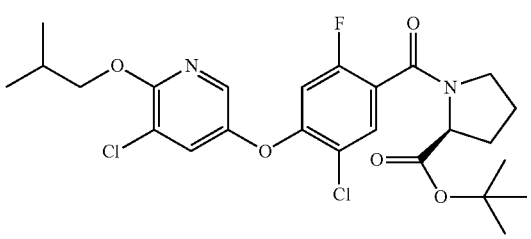 [SMILES: CC(C)COc1ncc(Oc2cc(F)c(C(=O)N3CCC[C@H]3C(=O)OC(C)(C)C)cc2Cl)cc1Cl]

Following the procedure as described in Example 1, Step 1 and making variation as required to replace 4-(adamantan-1-ylmethoxy)-5-cyclopropyl-2-fluorobenzoic acid with 5-chloro-4-((5-chloro-6-isobutoxypyridin-3-yl)oxy)-2-fluorobenzoic acid, the title compound was obtained as a colorless syrup (1.36 g, 96% yield): MS (ES+) m/z 528.9, 527.0 (M+1).

Step 2. Preparation of 5-chloro-4-((5-chloro-6-isobutoxypyridin-3-yl)oxy)-2-fluorobenzoyl)-L-proline Trifluoroacetic Acid Salt

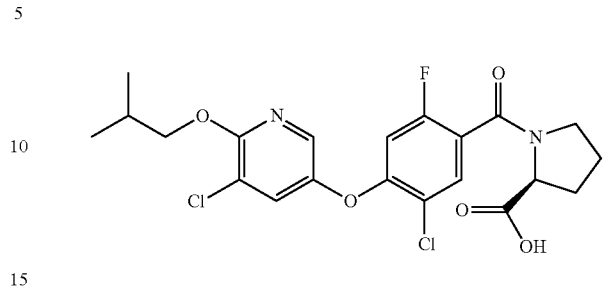

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (5-chloro-4-((5-chloro-6-isobutoxypyridin-3-yl)oxy)-2-fluorobenzoyl)-L-prolinate, the title compound (0.87 g, 75% yield) was obtained as a colorless solid: $^1$H NMR (300 MHz, DMSO-d$_6$) δ 12.05 (br, s, 0.5H), 8.07 (d, J=2.7 Hz, 0.7H), 8.01 (d, J=2.7 Hz, 0.3H), 7.98 (d, J=2.7 Hz, 0.7H) 7.93 (d, J=2.7 Hz, 0.3H), 7.60 (d, J=6.8 Hz, 0.7H), 7.57 (d, J=6.8 Hz, 0.3H), 7.42 (br, s, 0.5H), 7.09 (d, J=10.5 Hz, 0.7H), 7.07 (d, J=10.4 Hz, 0.3H), 4.36-4.31 (m, 0.8H), 4.22-4.18 (m, 0.4H), 4.11-4.64 (m, 2H), 3.55-3.50 (m, 0.6H), 3.40-3.30 (m, 2H), 2.30-2.18 (m, 1H), 2.10-1.77 (m, 4H), 0.99 (d, J=6.7 Hz, 6H); MS (ES+) m/z 473.0, 471.0 (M+1).

Example 98

Synthesis of (5-cyclopropyl-4-((5-cyclopropyl-6-isobutoxypyridin-3-yl)oxy)-2-fluorobenzoyl)-L-proline Trifluoroacetic Acid Salt and (4-((5-chloro-6-isobutoxypyridin-3-yl)oxy)-5-cyclopropyl-2-fluorobenzoyl)-L-proline Trifluoroacetic Acid Salt

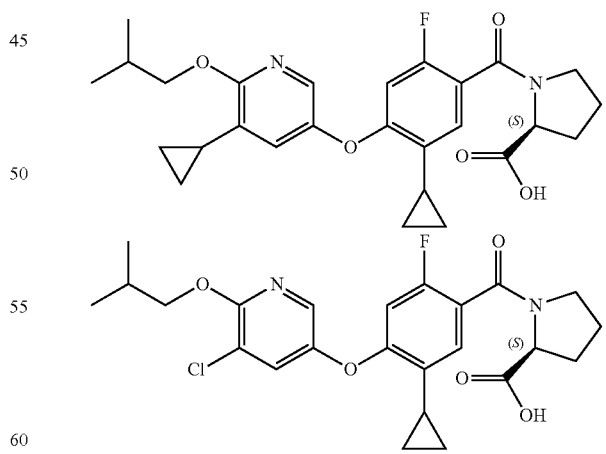

To a mixture of 5-chloro-4-((5-chloro-6-isobutoxypyridin-3-yl)oxy)-2-fluorobenzoyl)-L-proline (0.53 g, 1.12 mmol), cyclopropylboronic acid (0.57 g, 6.75 mmol), potassium phosphate (1.19 g, 5.6 mmol) and tricyclohexylphosphine tetrafluoroborate (0.082 g, 0.224 mmol) in toluene (10 mL) and water (1 mL) under a nitrogen atmosphere was added palladium acetate (0.056 g, 0.168 mmol). The reaction mixture was heated at 100° C. for 16 h and cooled to ambient temperature. To the reaction mixture was added Water (20 mL) and extracted with ethyl acetate (3×20 mL). The combined organic extracts was washed with brine, dried over anhydrous sodium sulfate and filtered. The solvent was concentrated in vacuo and the residue was purified by column chromatography eluting with 5% methanol in dichloromethane to afford the first title compound as a colorless solid (0.064 g, 12% yield): $^1$H NMR (300 MHz, CDCl$_3$) δ 7.71 (d, J=2.3 Hz, 0.8H), 7.61 (d, J=2.6 Hz, 0.2H), 7.58-7.26 (br, s, 2H), 7.00 (d, J=7.4 Hz, 1H), 6.86 (d, J=2.3 Hz, 1H), 6.45 (d, J=10.3 Hz, 0.2H), 6.35 (d, J=10.9 Hz, 0.8H), 4.72-4.59 (m, 1H), 4.08 (d, J=6.6 Hz, 2H), 3.45 (t, J=6.6, 6.6 Hz, 2H), 2.34-1.82 (m, 8H), 1.04 (d, J=6.7 Hz, 6H), 1.00-0.98 (m, 4H), 0.72-0.61 (m, 4H); MS (ES+) m/z 484.0, 483.0 (M+1) and second the title compound was obtained as a colorless solid (0.29 g, 53%): $^1$H NMR (300 MHz, CDCl$_3$) δ 8.80-8.44 (br, s, 2H), 7.76 (d, J=2.5 Hz, 0.8H), 7.70 (d, J=1.8 Hz, 0.2H), 7.55 (d, J=6.7 Hz, 0.8H), 7.51 (d, J=6.7 Hz, 0.2H), 7.17 (d, J=2.1 Hz, 0.2H), 6.92 (d, J=2.6 Hz, 0.8H), 6.68 (d, J=9.7 Hz, 0.2H), 6.47 (d, J=10.4 Hz, 0.8H), 4.68 (t, J=6.2 Hz, 1H), 4.18 (d, J=6.3 Hz, 0.4H), 4.10 (d, J=6.5 Hz, 1.6H), 3.86-3.74 (m, 0.4H), 3.56-3.43 (m, 1.6H), 2.32-2.25 (m, 2H), 2.20-1.88 (m, 4H), 1.05 (d, J=6.7 Hz, 6H), 1.15-0.95 (m, 2H), 0.75-0.70 (m, 0.4H), 0.68-0.63 (m, 1.6H); MS (ES+) m/z 479.0, 477.0 (M+1).

Example 99

Synthesis of 1-(4-((1-(4-chloro-2-(trifluoromethyl)benzyl)-3-fluoroazetidin-3-yl)methoxy)-5-cyclopropyl-2-fluorobenzoyl)pyrrolidine-2-carboxylic Acid Trifluoroacetic Acid Salt Step 1. Preparation tert-butyl (4-((1-(4-chloro-2-(trifluoromethyl)benzyl)-3-fluoroazetidin-3-yl)methoxy)-5-cyclopropyl-2-fluorobenzoyl)-L-prolinate

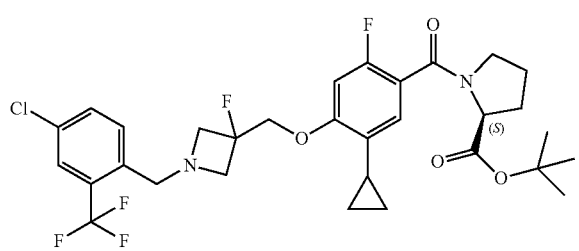

Following the procedure as described in Example 1, Step 1 and making variation as required to replace 4-(adamantan-1-ylmethoxy)-5-cyclopropyl-2-fluorobenzoic acid with 4-((1-(4-chloro-2-(trifluoromethyl)benzyl)-3-fluoroazetidin-3-yl)methoxy)-5-cyclopropyl-2-fluorobenzoic acid, the title compound was obtained as a colorless solid (0.14 g, 30%): MS (ES+) m/z 631.2, 629.2 (M+1).

Step 2. Preparation of 1-(4-((1-(4-chloro-2-(trifluoromethyl)benzyl)-3-fluoroazetidin-3-yl)methoxy)-5-cyclopropyl-2-fluorobenzoyl)pyrrolidine-2-carboxylic Acid Trifluoroacetic Acid Salt

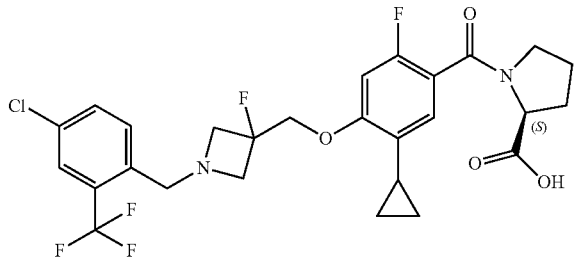

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with tert-butyl (4-((1-(4-chloro-2-(trifluoromethyl)benzyl)-3-fluoroazetidin-3-yl)methoxy)-5-cyclopropyl-2-fluorobenzoyl)-L-prolinate, the title compound was obtained as a colorless solid (0.10 g, 79%): $^1$H NMR (300 MHz, CDCl$_3$) δ 8.96-8.05 (br, s, 2.5H), 7.92 (s, 1H), 7.67-7.60 (m, 2H), 6.87 (d, J=7.64 Hz, 1H), 6.44 (d, J=11.23, 1H), 4.88-4.77 (m, 4H), 4.58 (dd, J=5.90 Hz, 7.72 Hz, 1H), 4.42-4.32 (m, 4H), 3.76-3.72 (m, 0.2H), 3.52-3.43 (m, 1.8H), 2.35-2.26 (m, 2H), 2.00-1.83 (m, 4H), 1.26 (t, J=7.14 Hz, 1H), 0.88-0.80 (m, 2H), 0.56-0.50 (m, 2H); MS (ES+) m/z 575.0, 573.0 (M+1).

Example 100

Synthesis of (S)-1-(4-((1-(3-Chloro-4-fluorobenzyl)piperidin-4-yl)methoxy)-5-cyclopropyl-2-fluorobenzoyl)pyrrolidine-2-carboxylic Acid Step 1. Preparation of (S)-5-cyclopropyl-4-((1-(1-(3,5-dichlorophenyl)ethyl)piperidin-4-yl)methoxy)-2-fluorobenzoyl Chloride

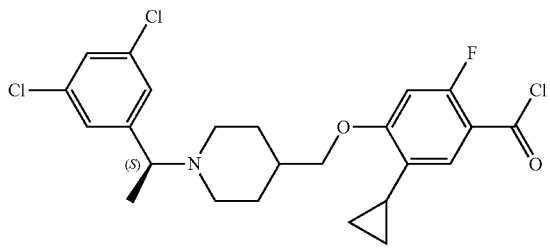

Following the procedure as described in Example 046, Step 1 and making non-critical variations as required to replace 4-(1-adamantylmethoxy)-5-cyclopropyl-2-fluorobenzoic acid with (S)-5-cyclopropyl-4-((1-(1-(3,5-dichlorophenyl)ethyl)piperidin-4-yl)methoxy)-2-fluorobenzoic acid, the title compound was obtained as a pale yellow solid that was used in the next step without purification.

239

Step 2. Preparation of (S)-1-(4-((1-(3-chloro-4-fluorobenzyl)piperidin-4-yl)methoxy)-5-cyclopropyl-2-fluorobenzoyl)pyrrolidine-2-carboxylic Acid

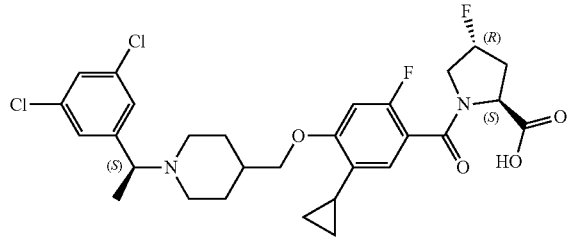

Following the procedure as described in Example 046, Step 2 and making non-critical variations as required to replace 4-(1-adamantylmethoxy)-5-cyclopropyl-2-fluorobenzoyl chloride with (S)-5-cyclopropyl-4-((1-(1-(3,5-dichlorophenyl)ethyl)piperidin-4-yl)methoxy)-2-fluorobenzoyl chloride and (2S,4S)-4-hydroxypyrrolidine-2-carboxylic acid trifluoroacetic acid salt with (2S,4R)-4-fluoropyrrolidine-2-carboxylic acid hydrochloric acid salt, the title compound was obtained as a colorless solid (0.023 g, 6.2% yield): $^1$H NMR (300 MHz, CDCl$_3$) δ 7.37-7.32 (m, 3H), 6.89 (d, J=7.8 Hz, 1H), 6.32 (d, J=11.8 Hz, 1H), 5.28 (s, 0.5H), 5.11 (s, 0.5H), 4.74 (t, J=8.2 Hz, 1H), 4.10 (dd, J=13.6, 6.6 Hz, 1H), 3.90-3.52 (m, 6.5H), 3.32-3.21 (m, 1.5H), 2.76-2.62 (m, 1H), 2.45-2.18 (m, 3H), 1.98-1.78 (m, 4H), 1.73-1.60 (m, 4H), 0.84-0.74 (m, 2H), 0.58-0.45 (m, 2H); MS (ES+) m/z 582.0, 581.0 (M+1).

Example 101

Synthesis of (2S,4R)-1-(4-((1-(3-chloro-2-fluoro-5-(trifluoromethyl)benzyl)-piperidin-4-yl)methoxy)-5-cyclopropyl-2-fluorobenzoyl)-4-fluoropyrrolidine-2-carboxylic Acid Step 1

Preparation of 4-((1-(3-chloro-2-fluoro-5-(trifluoromethyl)-benzyl)piperidin-4-yl)methoxy)-5-cyclopropyl-2-fluorobenzoyl Chloride

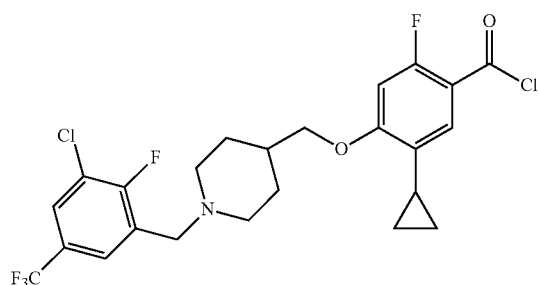

Following the procedure as described in Example 046, Step 1 and making non-critical variations as required to replace 4-(1-adamantylmethoxy)-5-cyclopropyl-2-fluorobenzoic acid with 4-((1-(3-chloro-2-fluoro-5-(trifluoromethyl)benzyl)piperidin-4-yl)methoxy)-5-cyclopropyl-2-fluorobenzoic acid, the title compound was obtained as a pale yellow solid that was used in the next step without purification.

240

Step 2. Preparation of (2S,4R)-1-(4-((1-(3-chloro-2-fluoro-5-(trifluoromethyl)benzyl)-piperidin-4-yl)methoxy)-5-cyclopropyl-2-fluorobenzoyl)-4-fluoropyrrolidine-2-carboxylic Acid

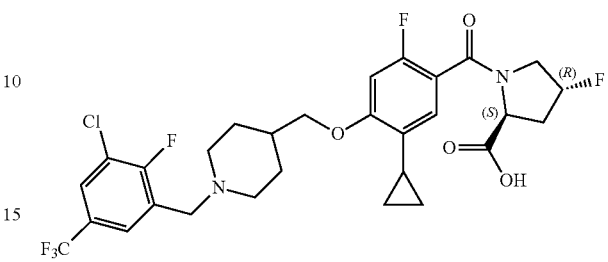

Following the procedure as described in Example 046, Step 2 and making non-critical variations as required to replace 4-(1-adamantylmethoxy)-5-cyclopropyl-2-fluorobenzoyl chloride with 4-((1-(3-chloro-2-fluoro-5-(trifluoromethyl)benzyl)piperidin-4-yl)methoxy)-5-cyclopropyl-2-fluorobenzoyl chloride and (2S,4S)-4-hydroxypyrrolidine-2-carboxylic acid trifluoroacetic acid salt with (2S,4R)-4-fluoropyrrolidine-2-carboxylic acid hydrochloric acid salt, the title compound was obtained as a colorless solid (0.010 g, 3.3% yield): $^1$H NMR (300 MHz, CDCl$_3$) δ 8.06 (s, 1H)), 7.70 (d, J=4.5 Hz, 1H), 6.89 (d, J=7.8 Hz, 1H), 6.34 (d, J=11.7 Hz, 1H), 5.26 (s, 0.5H), 5.08 (s, 0.5H), 4.74 (t, J=8.6 Hz, 1H), 4.31-3.52 (m, 9H), 2.75-1.63 (m, 9H), 0.86-0.79 (m, 2H), 0.56-0.47 (m, 2H); Note: Acidic proton not observed; MS (ES+) m/z 621.2, 619.2 (M+1).

Example 102

Synthesis of (2S,4R)-1-(4-((1-(3-chloro-2-fluoro-5-(trifluoromethyl)benzyl)-4-fluoropiperidin-4-yl)methoxy)-5-cyclopropyl-2-fluorobenzoyl)-4-fluoropyrrolidine-2-carboxylic Acid Step 1. Preparation of 4-((1-(3-chloro-2-fluoro-5-(trifluoromethyl)benzyl)-4-fluoropiperidin-4-yl)methoxy)-5-cyclopropyl-2-fluorobenzoyl Chloride

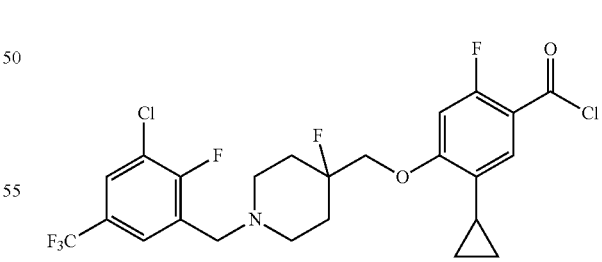

Following the procedure as described in Example 046, Step 1 and making non-critical variations as required to replace 4-(1-adamantylmethoxy)-5-cyclopropyl-2-fluorobenzoic acid with 4-((1-(3-chloro-2-fluoro-5-(trifluoromethyl)benzyl)-4-fluoropiperidin-4-yl)methoxy)-5-cyclopropyl-2-fluorobenzoic acid, the title compound was obtained as a pale yellow solid that was used in the next step without purification.

Step 2. Preparation of (2S,4R)-1-(4-((1-(3-chloro-2-fluoro-5-(trifluoromethyl)benzyl)-4-fluoropiperidin-4-yl)methoxy)-5-cyclopropyl-2-fluorobenzoyl)-4-fluoropyrrolidine-2-carboxylic Acid

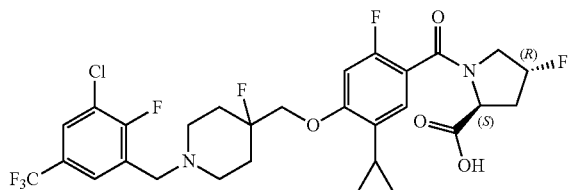

Following the procedure as described in Example 046, Step 2 and making non-critical variations as required to replace 4-(1-adamantylmethoxy)-5-cyclopropyl-2-fluorobenzoyl chloride with with 4-((1-(3-chloro-2-fluoro-5-(trifluoromethyl)benzyl)-4-fluoropiperidin-4-yl)methoxy)-5-cyclopropyl-2-fluorobenzoyl chloride and (2S,4S)-4-hydroxypyrrolidine-2-carboxylic acid trifluoroacetic acid salt with (2S,4R)-4-fluoropyrrolidine-2-carboxylic acid hydrochloric acid salt, the title compound was obtained as a colorless solid (0.010 g, 2.7%): $^1$H NMR (300 MHz, CDCl$_3$) δ 8.16 (s, 1H)), 7.77 (d, J=5.2 Hz, 1H), 6.85 (d, J=7.7 Hz, 1H), 6.30 (d, J=11.3 Hz, 1H), 5.27 (s, 0.5H), 5.10 (s, 0.5H), 4.69 (t, J=8.7 Hz, 1H), 4.37-3.37 (m, 8H), 3.04-2.12 (m, 9H), 0.89-0.83 (m, 2H), 0.57-0.44 (m, 2H); Note: Acidic proton not observed; MS (ES+) m/z 639.2, 637.2 (M+1).

Step 2. Preparation (2S,4R)-1-(5-cyclopropyl-2-fluoro-4-((1-(2-fluoro-5-(trifluoromethyl)benzyl)-piperidin-4-yl)methoxy)benzoyl)-4-fluoropyrrolidine-2-carboxylic Acid

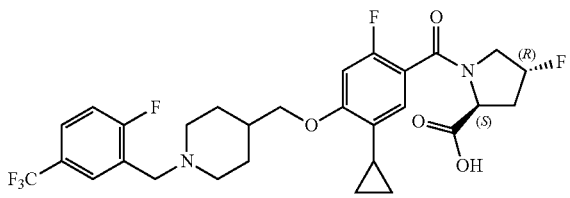

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(5-cyclopropyl-2-fluoro-4-((1-(2-fluoro-5-(trifluoromethyl)benzyl)piperidin-4-yl)methoxy)benzoyl)-4-fluoropyrrolidine-2-carboxylate, the title compound was obtained as a colorless solid (0.07 g, 23% yield): $^1$H NMR (300 MHz, CDCl$_3$) δ 8.14 (d, J=5.2 Hz, 1H), 7.67-7.62 (m, 1H), 7.22 (t, J=8.9 Hz, 1H), 6.88 (d, J=7.8 Hz, 1H), 6.34 (d, J=11.8 Hz, 1H), 5.25 (s, 0.5H), 5.08 (s, 0.5H), 4.72 (t, J=8.5 Hz, 1H), 4.40-4.03 (m, 2H), 3.80-3.49 (m, 7H), 2.74-2.48 (m, 3H), 2.03-1.67 (m, 6H), 0.85-0.76 (m, 2H), 0.57-0.46 (m, 2H); Note: Acidic proton not observed; MS (ES+) m/z 585.3 (M+1).

Example 103

Synthesis of (2S,4R)-1-(5-cyclopropyl-2-fluoro-4-((1-(2-fluoro-5-(trifluoromethyl)benzyl)-piperidin-4-yl)methoxy)benzoyl)-4-fluoropyrrolidine-2-carboxylic Acid Step 1. Preparation methyl (2S,4R)-1-(5-cyclopropyl-2-fluoro-4-((1-(2-fluoro-5-(trifluoromethyl)benzyl)piperidin-4-yl)methoxy)benzoyl)-4-fluoropyrrolidine-2-carboxylate

Example 104

Synthesis of (2S,4R)-1-(4-((1-(4-chloro-3-fluorobenzyl)piperidin-4-yl)methoxy)-5-cyclopropyl-2-fluorobenzoyl)-4-fluoropyrrolidine-2-carboxylic Acid Step 1. Preparation methyl (2S,4R)-1-(4-((1-(4-chloro-3-fluorobenzyl)piperidin-4-yl)methoxy)-5-cyclopropyl-2-fluorobenzoyl)-4-fluoropyrrolidine-2-carboxylate

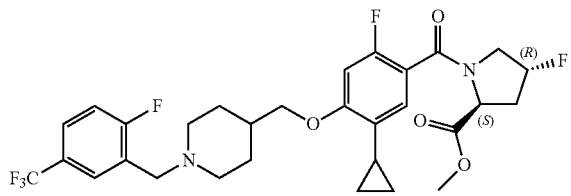

Following the procedure as described in Example 1, Step 1 and making non-critical variations as required to replace 4-(adamantan-1-ylmethoxy)-5-cyclopropyl-2-fluorobenzoic acid with 5-cyclopropyl-2-fluoro-4-((1-(2-fluoro-5-(trifluoromethyl)benzyl)piperidin-4-yl)methoxy)benzoic acid and (S)-tert-butyl pyrrolidine-2-carboxylate hydrochloride with methyl (2S,4R)-4-fluoropyrrolidine-2-carboxylate hydrochloric acid salt, the title compound was obtained as a colorless solid (0.30 g, 90% yield): MS (ES+) m/z 599.2 (M+1).

Following the procedure as described in Example 1, Step 1 and making non-critical variations as required to replace 4-(adamantan-1-ylmethoxy)-5-cyclopropyl-2-fluorobenzoic acid with 4-((1-(4-chloro-3-fluorobenzyl)piperidin-4-yl)methoxy)-5-cyclopropyl-2-fluorobenzoic acid and (S)-tert-butyl pyrrolidine-2-carboxylate hydrochloride with methyl (2S,4R)-4-fluoropyrrolidine-2-carboxylate hydrochloric acid salt, the title compound was obtained as a colorless solid (0.28 g, 91% yield): MS (ES+) m/z 567.1, 565.1 (M+1).

243

Step 2. Preparation (2S,4R)-1-(4-((1-(4-chloro-3-fluorobenzyl)piperidin-4-yl)methoxy)-5-cyclopropyl-2-fluorobenzoyl)-4-fluoropyrrolidine-2-carboxylic Acid

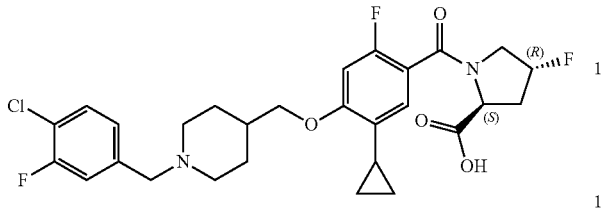

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(4-((1-(4-chloro-3-fluorobenzyl)piperidin-4-yl)methoxy)-5-cyclopropyl-2-fluorobenzoyl)-4-fluoropyrrolidine-2-carboxylate, the title compound was obtained as a colorless solid (0.04 g, 13%): $^{1}$H NMR (300 MHz, CDCl$_3$) δ 7.59 (d, J=6.6 Hz, 1H), 7.40-7.34 (m, 1H), 7.14 (t, J=8.6 Hz, 1H), 6.89 (d, J=7.8 Hz, 1H), 6.32 (d, J=11.7 Hz, 1H), 5.28 (s, 0.5H), 5.10 (s, 0.5H), 4.72 (t, J=8.6 Hz, 1H), 4.51-4.34 (m, 1H), 3.89-3.67 (m, 3H), 3.62-3.10 (m, 2H), 2.78-2.17 (m, 4H), 2.02-1.59 (m, 6H), 0.83-0.76 (m, 2H), 0.57-0.45 (m, 2H); Note: Acidic proton not observed; MS (ES+) m/z 553.2, 551.2 (M+1).

Example 105

Synthesis of (2S,4R)-1-(4-((1-(3-chloro-5-(trifluoromethoxy)benzyl)piperidin-4-yl)methoxy)-5-cyclopropyl-2-fluorobenzoyl)-4-fluoropyrrolidine-2-carboxylic Acid Step 1. Preparation methyl (2S,4R)-1-(4-((1-(3-chloro-5-(trifluoromethoxy)benzyl)piperidin-4-yl)methoxy)-5-cyclopropyl-2-fluorobenzoyl)-4-fluoropyrrolidine-2-carboxylate

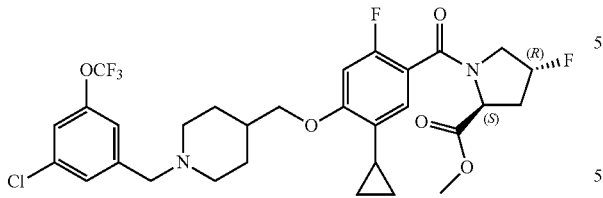

Following the procedure as described in Example 1, Step 1 and making non-critical variations as required to replace 4-(adamantan-1-ylmethoxy)-5-cyclopropyl-2-fluorobenzoic acid with 4-((1-(3-chloro-5-(trifluoromethoxy)benzyl)piperidin-4-yl)methoxy)-5-cyclopropyl-2-fluorobenzoic acid and (S)-tert-butyl pyrrolidine-2-carboxylate hydrochloride with methyl (2S,4R)-4-fluoropyrrolidine-2-carboxylate hydrochloric acid salt, the title compound was obtained as a colorless solid (0.37 g, 95%): MS (ES+) m/z 633.2, 631.2 (M+1).

244

Step 2. Preparation (2S,4R)-1-(4-((1-(3-chloro-5-(trifluoromethoxy)benzyl)piperidin-4-yl)methoxy)-5-cyclopropyl-2-fluorobenzoyl)-4-fluoropyrrolidine-2-carboxylic Acid

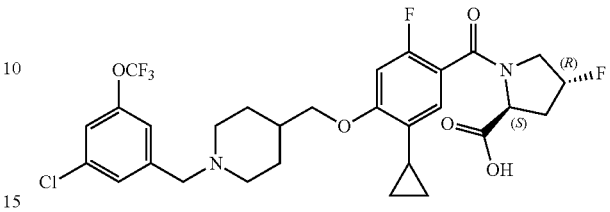

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(4-((1-(3-chloro-5-(trifluoromethoxy)benzyl)piperidin-4-yl)methoxy)-5-cyclopropyl-2-fluorobenzoyl)-4-fluoropyrrolidine-2-carboxylate, the title compound was obtained as a colorless solid (0.10 g, 27%): $^{1}$H NMR (300 MHz, CDCl$_3$) δ 8.20 (br, s, 0.5H), 7.41 (s, 1H), 7.26 (m, 1H), 7.20 (m, 1H), 6.83 (d, J=7.8 Hz, 1H), 6.30-6.24 (m, 1H), 5.23 (s, 0.5H), 5.05 (s, 0.5H), 4.66 (t, J=8.6 Hz, 1H), 4.28-4.23 (m, 1H), 3.87-3.46 (m, 6H), 3.34-3.23 (m, 1H), 2.71-2.46 (m, 3H), 2.34-2.07 (m, 1H), 1.99-1.54 (m, 6H), 0.79-0.68 (m, 2H), 0.52-0.36 (m, 2H); MS (ES+) m/z 619.3, 617.3 (M+1).

Example 106

Synthesis of (2S,4R)-1-(4-((1-(2-chloro-5-(trifluoromethyl)benzyl)-4-fluoropiperidin-4-yl)methoxy)-5-cyclopropyl-2-fluorobenzoyl)-4-fluoropyrrolidine-2-carboxylic Acid Step 1. Preparation methyl (2S,4R)-1-(4-((1-(2-chloro-5-(trifluoromethyl)benzyl)-4-fluoropiperidin-4-yl)methoxy)-5-cyclopropyl-2-fluorobenzoyl)-4-fluoropyrrolidine-2-carboxylate

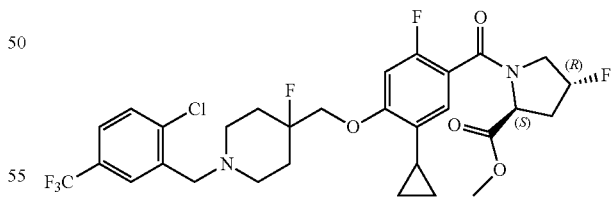

Following the procedure as described in Example 1, Step 1 and making non-critical variations as required to replace 4-(adamantan-1-ylmethoxy)-5-cyclopropyl-2-fluorobenzoic acid with 4-((1-(2-chloro-5-(trifluoromethyl)benzyl)-4-fluoropiperidin-4-yl)methoxy)-5-cyclopropyl-2-fluorobenzoic acid and (S)-tert-butyl pyrrolidine-2-carboxylate hydrochloride with methyl (2S,4R)-4-fluoropyrrolidine-2-carboxylate hydrochloric acid salt, the title compound was obtained as a colorless solid (0.53 g, 50%): MS (ES+) m/z 635.0, 633.0 (M+1).

Step 2. Preparation (2S,4R)-1-(4-((1-(2-chloro-5-(trifluoromethyl)benzyl)-4-fluoropiperidin-4-yl)methoxy)-5-cyclopropyl-2-fluorobenzoyl)-4-fluoropyrrolidine-2-carboxylic Acid

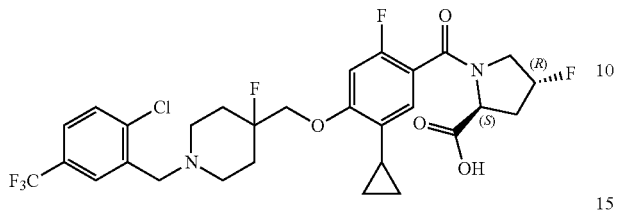

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(4-((1-(2-chloro-5-(trifluoromethyl)benzyl)-4-fluoropiperidin-4-yl)methoxy)-5-cyclopropyl-2-fluorobenzoyl)-4-fluoropyrrolidine-2-carboxylate, the title compound was obtained as a colorless solid (0.21 g, 42%): $^1$H NMR (300 MHz, CDCl$_3$) δ 8.24 (s, 1H), 7.60-7.54 (m, 2H), 6.82 (d, J=7.7 Hz, 1H), 6.24 (d, J=11.5 Hz, 1H), 5.26 (s, 0.5H), 5.08 (s, 0.5H), 4.65 (t, J=8.7 Hz, 1H), 4.46-4.36 (m, 1H), 4.31-4.22 (m, 1H), 4.09 (dd, J=25.5, 10.5 Hz, 1H), 3.90-3.44 (m, 4H), 3.32-3.21 (m, 1H), 3.07-2.90 (m, 2H), 2.75-2.39 (m, 2H), 2.34-2.04 (m, 4H), 1.94-1.81 (m, 1H), 0.87-0.76 (m, 2H), 0.54-0.39 (m, 2H); Note: Acidic proton not observed; MS (ES+) m/z 621.2, 619.2 (M+1).

Example 107

Synthesis of (2S,4R)-1-(5-cyclopropyl-2-fluoro-4-((1-(5-fluoro-2-(isopropylamino)benzyl)-piperidin-4-yl)methoxy)benzoyl)-4-fluoropyrrolidine-2-carboxylic Acid Step 1. Preparation methyl (2S,4R)-1-(5-cyclopropyl-2-fluoro-4-((1-(5-fluoro-2-(isopropylamino)benzyl)piperidin-4-yl)methoxy)benzoyl)-4-fluoropyrrolidine-2-carboxylate

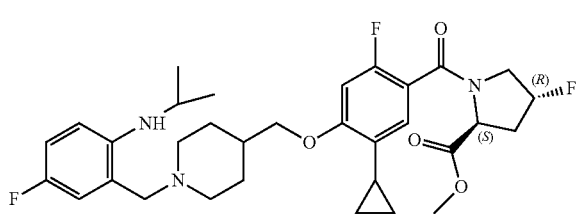

Following the procedure as described in Example 1, Step 1 and making non-critical variations as required to replace 4-(adamantan-1-ylmethoxy)-5-cyclopropyl-2-fluorobenzoic acid with 5-cyclopropyl-2-fluoro-4-((1-(5-fluoro-2-(isopropylamino)benzyl)piperidin-4-yl)methoxy)benzoic acid and (S)-tert-butyl pyrrolidine-2-carboxylate hydrochloride with methyl (2S,4R)-4-fluoropyrrolidine-2-carboxylate hydrochloric acid salt, the title compound was obtained as a colorless solid (0.19 g, 36%): MS (ES+) m/z 588.3 (M+1).

Step 2. Preparation (2S,4R)-1-(5-cyclopropyl-2-fluoro-4-((1-(5-fluoro-2-(isopropylamino)benzyl)piperidin-4-yl)methoxy)benzoyl)-4-fluoropyrrolidine-2-carboxylic Acid

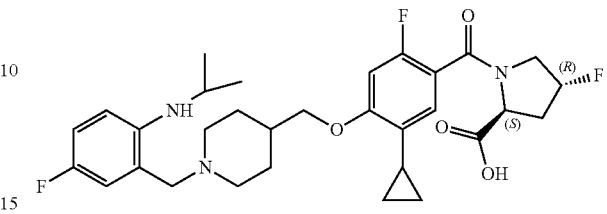

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(5-cyclopropyl-2-fluoro-4-((1-(5-fluoro-2-(isopropylamino)benzyl)piperidin-4-yl)methoxy)benzoyl)-4-fluoropyrrolidine-2-carboxylate, the title compound was obtained as a colorless solid (0.03 g, 18%): $^1$H NMR (300 MHz, CDCl$_3$) δ 6.97-6.88 (m, 2H), 6.84-6.76 (m, 1H), 6.65-6.55 (m, 1H), 6.34 (d, J=11.8 Hz, 1H), 5.84 (br, s, 1H), 5.26 (s, 0.5H), 5.08 (s, 0.5H), 4.82-4.70 (m, 1H), 4.14-4.00 (m, 1H), 3.88-3.49 (m, 6H), 3.46-3.18 (m, 2H), 2.76-2.55 (m, 1H), 2.49-2.16 (m, 3H), 2.00-1.51 (m, 6H), 1.29-1.09 (m, 7H), 0.87-0.69 (m, 2H), 0.59-0.42 (m, 2H); MS (ES+) m/z 574.3 (M+1).

Example 108

Synthesis of (2S,4R)-1-(5-cyclopropyl-4-((1-(2,4-dichloro-5-fluorobenzyl)piperidin-4-yl)methoxy)-2-fluorobenzoyl)-4-fluoropyrrolidine-2-carboxylic Acid Step 1. Preparation methyl (2S,4R)-1-(5-cyclopropyl-4-((1-(2,4-dichloro-5-fluorobenzyl)piperidin-4-yl)methoxy)-2-fluorobenzoyl)-4-fluoropyrrolidine-2-carboxylate

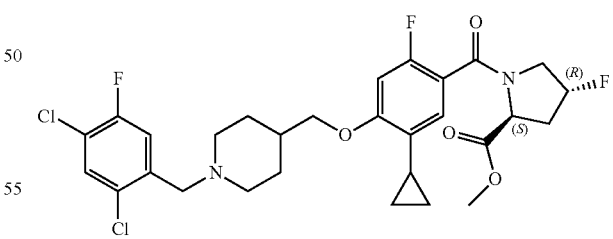

Following the procedure as described in Example 1, Step 1 and making non-critical variations as required to replace 4-(adamantan-1-ylmethoxy)-5-cyclopropyl-2-fluorobenzoic acid with 5-cyclopropyl-4-((1-(2,4-dichloro-5-fluorobenzyl)piperidin-4-yl)methoxy)-2-fluorobenzoic acid and (S)-tert-butyl pyrrolidine-2-carboxylate hydrochloride with methyl (2S,4R)-4-fluoro-pyrrolidine-2-carboxylate hydrochloric acid salt, the title compound was obtained as a colorless solid (0.03 g, 18%): MS (ES+) m/z 601.1, 599.1 (M+1).

247

Step 2. Preparation (2S,4R)-1-(5-cyclopropyl-4-((1-(2,4-dichloro-5-fluorobenzyl)piperidin-4-yl)methoxy)-2-fluorobenzoyl)-4-fluoropyrrolidine-2-carboxylic Acid

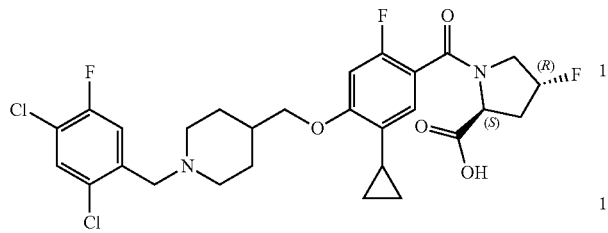

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(5-cyclopropyl-4-((1-(2,4-dichloro-5-fluorobenzyl)piperidin-4-yl)methoxy)-2-fluorobenzoyl)-4-fluoropyrrolidine-2-carboxylate, the title compound was obtained as colorless solid (0.040 g, 19%): ¹H NMR (300 MHz, CDCl₃) δ 7.63-7.45 (m, 1H), 7.41 (d, J=6.6 Hz, 1H), 6.70-6.89 (m, 1H), 6.42 (d, J=11.4 Hz, 1H), 5.18 (s, 0.5H), 5.01 (s, 0.5H), 4.69 (s, 2H), 3.94-3.63 (m, 5H), 3.60-3.43 (m, 1H), 3.22-2.95 (m, 2H), 2.64-2.15 (m, 3H), 2.03-1.77 (m, 4H), 1.68-1.44 (m, 2H), 1.42-1.33 (s, 1H), 0.89-0.73 (m, 2H), 0.66-0.49 (m, 2H); MS (ES+) m/z 587.2, 585.2 (M+1).

Example 109

Synthesis of (2S,4R)-1-(4-((1-((5-chloro-6-isopropoxypyridin-3-yl)methyl)-4-fluoropiperidin-4-yl)methoxy)-5-cyclopropyl-2-fluorobenzoyl)-4-fluoropyrrolidine-2-carboxylic Acid Step 1. Preparation methyl (2S,4R)-1-(4-((1-((5-chloro-6-isopropoxypyridin-3-yl)methyl)-4-fluoropiperidin-4-yl)methoxy)-5-cyclopropyl-2-fluorobenzoyl)-4-fluoropyrrolidine-2-carboxylate

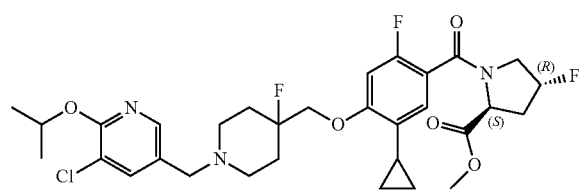

Following the procedure as described in Example 1, Step 1 and making non-critical variations as required to replace 4-(adamantan-1-ylmethoxy)-5-cyclopropyl-2-fluorobenzoic acid with 4-((1-((5-chloro-6-isopropoxypyridin-3-yl)methyl)-4-fluoropiperidin-4-yl)methoxy)-5-cyclopropyl-2-fluorobenzoic acid and (S)-tert-butyl pyrrolidine-2-carboxylate hydrochloride with methyl (2S,4R)-4-fluoropyrrolidine-2-carboxylate hydrochloric acid salt, the title compound was obtained as a colorless solid (0.38 g, 98%): MS (ES+) m/z 626.2, 624.2 (M+1).

248

Step 2. Preparation (2S,4R)-1-(4-((1-((5-chloro-6-isopropoxypyridin-3-yl)methyl)-4-fluoropiperidin-4-yl)methoxy)-5-cyclopropyl-2-fluorobenzoyl)-4-fluoropyrrolidine-2-carboxylic Acid

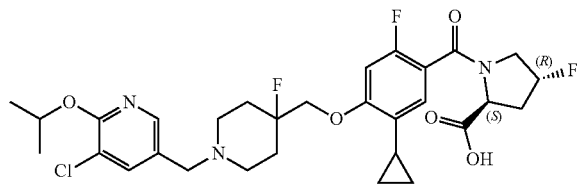

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(4-((1-((5-chloro-6-isopropoxypyridin-3-yl)methyl)-4-fluoropiperidin-4-yl)methoxy)-5-cyclopropyl-2-fluorobenzoyl)-4-fluoropyrrolidine-2-carboxylate, the title compound was obtained as a colorless solid (0.15 g, 41%): ¹H NMR (300 MHz, DMSO-d₆) δ 7.89 (s, 1H), 7.86 (s, 1H), 6.82 (d, J=7.3 Hz, 1H), 6.21 (d, J=11.3 Hz, 1H), 5.43-5.19 (m, 3H), 4.63 (t, J=7.2 Hz, 1H), 4.26-3.93 (m, 2H), 3.88-3.58 (m, 4H), 3.49 (m, 2H), 3.25-3.04 (m, 1H), 2.89-2.58 (m, 3H), 2.23-1.9 (m, 4H), 1.92-1.76 (m, 1H), 1.39 (d, J=6.2 Hz, 6H), 0.93-0.70 (m, 2H), 0.60-0.33 (m, 2H); MS (ES+) m/z 612.2, 610.2 (M+1).

Example 110

Synthesis of 2-(4-((1-(2-chloro-5-(trifluoromethyl)benzyl)-4-fluoropiperidin-4-yl)methoxy)-5-cyclopropyl-2-fluorobenzamido)-2-cyclobutyl Acetic Acid

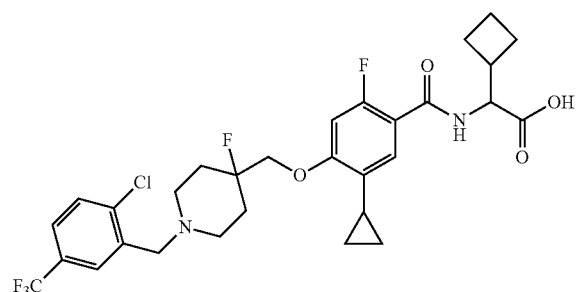

To a stirred solution of 4-((1-(2-chloro-5-(trifluoromethyl)benzyl)-4-fluoropiperidin-4-yl)methoxy)-5-cyclopropyl-2-fluorobenzoic acid (0.25 g, 0.50 mmol) in tetrahydrofuran (10 mL) was added 2-amino-2-cyclobutylacetic acid (0.128 g, 1.0 mmol) 1,1'-carbonyldiimidazole (CDI) (0.097 g, 0.60 mmol) and 1,8-diazabicyclo[5.4.0]undec-7-ene (DBU) (0.379 g, 2.50 mmol). The reaction mixture was stirred at ambient temperature for 16 h then diluted with dichloromethane (50 mL), washed with saturated ammonium chloride solution, brine, dried over anhydrous sodium sulfate and concentrated in vacuo. The residue was purified by reverse phase preparative HPLC (gradient of acetonitrile in water) to afford the title compound as a colorless solid (0.054 g, 18%): ¹H NMR (300 MHz, CDCl₃) δ 9.36-8.59

(br, s, 1H), 8.02 (s, 1H), 7.60-7.43 (m, 3H), 7.12 (dd, J=12.1, 7.5 Hz, 1H), 6.38 (d, J=13.5 Hz, 1H), 4.56 (t, J=7.0 Hz, 1H), 4.24-4.07 (m, 2H), 4.06-3.84 (m, 2H), 3.19 (t, J=12.8 Hz, 2H), 2.93-2.67 (m, 3H), 2.29-2.14 (m, 2H), 2.14-1.70 (m, 9H), 0.94-0.79 (m, 2H), 0.70-0.54 (m, 2H); MS (ES+) m/z 617.2, 615.2 (M+1).

Example 111

Synthesis of (2S,3R,4R)-1-(4-((1-(2-chloro-5-(trifluoromethyl)benzyl)-4-fluoropiperidin-4-yl)methoxy)-5-cyclopropyl-2-fluorobenzoyl)-4-fluoro-3-methylpyrrolidine-2-carboxylic Acid Step 1. Preparation of 1-(tert-butyl) 2-methyl (2S)-3-methyl-4-oxopyrrolidine-1,2-dicarboxylate

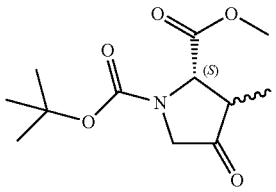

To a solution of 1-(tert-butyl) 2-methyl (S,Z)-3-((dimethylamino)methylene)-4-oxopyrrolidine-1,2-dicarboxylate (12.0 g, 40.3 mmol) in anhydrous acetone (250 mL) under nitrogen, was added palladium on carbon (2.40 g). This reaction mixture was purged with hydrogen and stirring was continued under one atmosphere hydrogen gas for two days. This mixture was filtered through a pad of Celite and washed with acetone. The filtrate was concentrated in vacuo. The residue was purified by column chromatography (50% ethyl acetate in hexane) to afford the title compound as a light yellow syrup (7.00 g, 67%): $^1$H NMR (300 MHz, CDCl$_3$) δ 4.74 (dd, J=23.2, 9.8 Hz, 0.5H), 4.24-4.07 (m, 0.5H), 3.93-3.78 (m, 2H), 3.67 (d, J=3.7 Hz, 3H), 2.91-2.75 (m, 0.5H), 2.64-2.49 (m, 0.5H), 1.38 (d, J=6.6 Hz, 9H), 1.24 (d, J=7.4 Hz, 1.5H), 0.99 (d, J=7.2 Hz, 1.5H).

Step 2, Preparation of methyl (2S)-3-methyl-4-oxopyrrolidine-2-carboxylate Trifluoroacetate

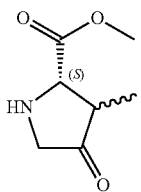

To a stirred solution of 1-(tert-butyl) 2-methyl (2S)-3-methyl-4-oxopyrrolidine-1,2-dicarboxylate (2.50 g, 9.72 mmol) in dichloromethane (15 mL) was added trifluoroacetic acid (1.50 mL, 19.5 mmol). This reaction mixture was stirred at ambient temperature for 6 h. The crude product was concentrated in vacuo to afford the title compound (2.80 g, quantitative yield) as dark brown syrup that was used in next step without any purification.

Step 3. Preparation of methyl (2S)-1-(4-((1-(2-chloro-5-(trifluoromethyl)benzyl)-4-fluoropiperidin-4-yl)methoxy)-5-cyclopropyl-2-fluorobenzoyl)-3-methyl-4-oxopyrrolidine-2-carboxylate

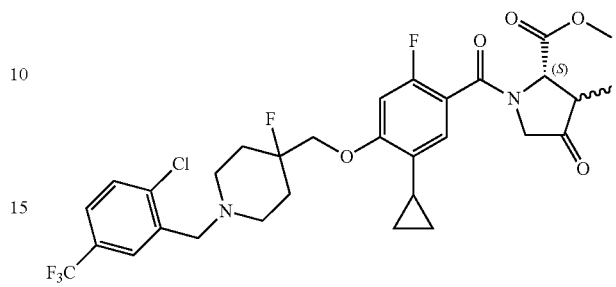

Following the procedure as described in Example 1, Step 1 and making non-critical variations as required to replace 4-(adamantan-1-ylmethoxy)-5-cyclopropyl-2-fluorobenzoic acid with 4-((1-(2-chloro-5-(trifluoromethyl)benzyl)-4-fluoropiperidin-4-yl)methoxy)-5-cyclopropyl-2-fluorobenzoic acid and (S)-tert-butyl pyrrolidine-2-carboxylate hydrochloride with methyl (2S)-3-methyl-4-oxopyrrolidine-2-carboxylate trifluoroacetic acid salt, the title compound was obtained as a colorless solid (1.60 g, 91%): MS (ES+) m/z 644.2, 642.2 (M+1).

Step 4. Preparation of methyl (2S)-1-(4-((1-(2-chloro-5-(trifluoromethyl)benzyl)-4-fluoropiperidin-4-yl)methoxy)-5-cyclopropyl-2-fluorobenzoyl)-4-hydroxy-3-methylpyrrolidine-2-carboxylate

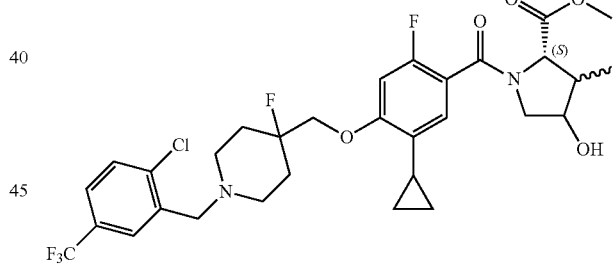

To a stirred solution of methyl (2S)-1-(4-((1-(2-chloro-5-(trifluoromethyl)benzyl)-4-fluoropiperidin-4-yl)methoxy)-5-cyclopropyl-2-fluorobenzoyl)-3-methyl-4-oxopyrrolidine-2-carboxylate (0.50 g, 0.78 mmol) in tetrahydrofuran (10 mL), (S)-(−)-2-methyl-CBS-oxazaborolidine solution (0.8 mL, 0.78 mmol) in a single portion. This mixture was cooled to −78° C. then borane dimethylsulfide (74 μL, 0.78 mmol) was added over 5 minutes. The reaction mixture was stirred at −78° C. for 20 minutes then placed in a water bath at ambient temperature and continued stirring at ambient temperature for 7 minutes. The reaction was quenched by dropwise addition of methanol (5 mL) and continued stirring for 2.5 hours. The solvent concentrated in vacuo. The residue was dissolved in ethyl acetate (50 mL) and washed with 0.2 M hydrochloride acid solution (50 mL×2). The organic layer was dried over anhydrous sodium sulfate and concentrated in vacuo. The residue was purified by column chromatography eluting with 3% methanol in dichlorometh-

251 ane to afford the title compound as a colorless solid (0.23 g, 45%): MS (ES+) m/z 647.3, 645.3 (M+1).

Step 5. Preparation of methyl (2S)-1-(4-((1-(2-chloro-5-(trifluoromethyl)benzyl)-4-fluoropiperidin-4-yl)methoxy)-5-cyclopropyl-2-fluorobenzoyl)-4-fluoro-3-methylpyrrolidine-2-carboxylate

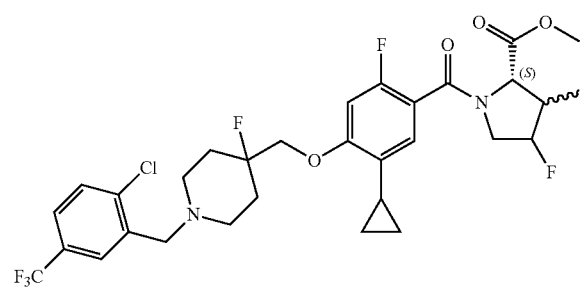

To a stirred solution of methyl (2S)-1-(4-((1-(2-chloro-5-(trifluoromethyl)benzyl)-4-fluoropiperidin-4-yl)methoxy)-5-cyclopropyl-2-fluorobenzoyl)-4-hydroxy-3-methylpyrrolidine-2-carboxylate (0.45 g, 0.70 mmol) in dichloromethane (7 mL), a solution of diethylaminosulfur trifluoride (369 µL, 2.80 mmol) and hydrogen fluoride pyridine (72 µL, 2.80 mmol) in dichloromethane (2.80 mL) dropwise at 0° C. This reaction mixture was warmed to ambient temperature and continued stirring for 3 hours. The reaction was quenched by the addition of saturated sodium bicarbonate solution (50 mL) and extracted with ethyl acetate (2×50 mL). The combined organic extracts was washed with brine, dried over anhydrous sodium sulfate and filtered. The solvent was concentrated in vacuo and the residue was purified by column chromatography eluting with 50% ethyl acetate in hexane to afford the title compound (0.16 g, 34%) as a colorless solid: MS (ES+) m/z 649.1, 647.1 (M+1).

Step 6. Preparation of Synthesis of (2S,3R,4R)-1-(4-((1-(2-chloro-5-(trifluoromethyl)benzyl)-4-fluoropiperidin-4-yl)methoxy)-5-cyclopropyl-2-fluorobenzoyl)-4-fluoro-3-methylpyrrolidine-2-carboxylic Acid

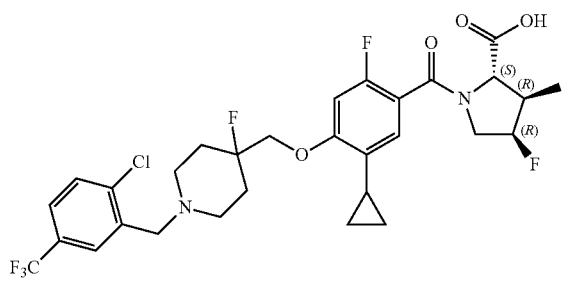

Following the procedure as described in Example 33 (step 2), and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S)-1-(4-((1-(2-chloro-5-(trifluoromethyl)benzyl)-4-fluoropiperidin-4-yl)methoxy)-5-cyclopropyl-2-fluorobenzoyl)-4-fluoro-3-methylpyrrolidine-2-carboxylate, the title compound was

252 obtained as colorless solid (0.047 g, 34%): $^1$H NMR (300 MHz, DMSO-$d_6$) δ 8.13 (s, 1H), 7.55 (s, 2H), 6.89-6.72 (m, 2H), 6.32-6.15 (m, 2H), 4.89 (d, J=53.3 Hz, 1H), 4.37-4.97 (m, 4H), 3.88-3.39 (m, 4H), 3.15-2.76 (m, 2H), 2.72-2.28 (m, 2H), 2.25-1.77 (m, 4H), 1.44-1.23 (m, 3H), 0.91-0.70 (m, 2H), 0.56-0.30 (m, 2H); MS (ES+) m/z 635.1, 633.1 (M+1).

Example 112

Synthesis of (S)-1-(5-cyclopropyl-4-(1-(3,5-dichlorobenzyl)piperidin-4-yloxy)-2-fluorobenzoyl)pyrrolidine-2-carboxylic Acid

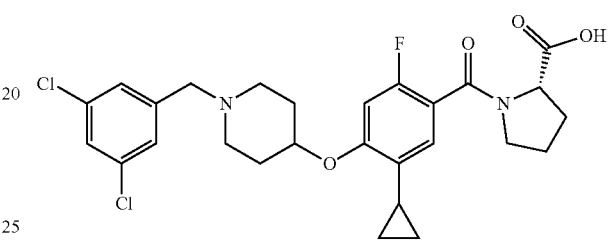

The title compound was synthesized as described in Example 39: LCMS (ESI) Method A: RT=5.20 min, m/z 535.2 [M+1]; $^1$H NMR (400 MHz, DMSO-$d_6$) δ 7.50 (s, 1H), 7.38 (s, 2H), 7.00-6.90 (m, 1H), 6.81-6.66 (m, 1H), 4.61-4.50 (m, 1H), 4.34-4.10 (m, 1H), 3.56-3.51 (m, 3H), 2.65-2.57 (m, 2H), 2.39-2.30 (m, 2H), 2.28-2.18 (m, 1H), 2.05-1.65 (m, 9H), 0.88-0.84 (m, 2H), 0.59-0.51 (m, 2H).

Example 113

Synthesis of (S)-2-cyclopropyl-2-(5-cyclopropyl-4-((1-((R)-(3,5-dichlorophenyl)(phenyl)methyl)-3-methylazetidin-3-yl)methoxy)-2-fluorobenzamido) acetic Acid

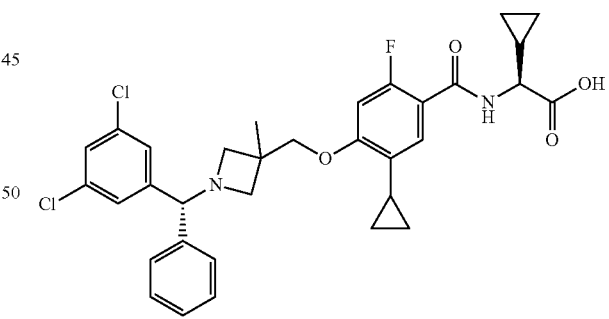

The title compound was synthesized as described in Example 28. The enantiomer was separated by chiral SFC from mixture of diastereomers. The second eluting fraction was arbitrarily assigned as ((S)-2-cyclopropyl-2-(5-cyclopropyl-4-((1-((S)-(3,5-dichlorophenyl)(phenyl)methyl)-3-methylazetidin-3-yl)methoxy)-2-fluorobenzamido)acetic acid: Chiral HPLC (Cellulose-1, 4.6×250 mm, 5 µm; mobile Phase: A: supercritical CO$_2$, B: methanol (0.5% DEA), A:B=65:35; flow: 3.0 mL/min; column temperature: 42.6° C.; RT=5.34 min); LCMS (ESI) Method C: RT=6.89 min, m/z 611.2 [M+1]; $^1$H NMR (400 MHz, DMSO-$d_6$) δ 7.99 (br s, 1H), 7.48-7.43 (m, 5H), 7.32-7.19 (m, 4H), 7.01-6.99 (m, 1H), 4.56 (s, 1H), 4.10-4.08 (m, 2H), 3.89-3.88 (m, 1H), 3.51-3.48 (m, 2H), 3.16-3.14 (m, 2H), 2.10-2.05 (m, 1H), 1.34 (s, 3H), 1.23-1.20 (m, 1H), 0.91-0.85 (m, 2H), 0.61-0.68 (m, 2H), 0.42-0.32 (m, 4H).

Example 114

Synthesis of (S)-2-cyclopropyl-2-(5-cyclopropyl-4-((1-((S)-(3,5-dichlorophenyl)(phenyl)methyl)-3-methylazetidin-3-yl)methoxy)-2-fluorobenzamido) acetic Acid

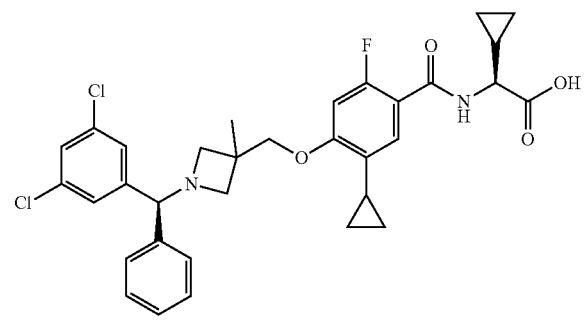 [SMILES: CC1(COc2cc(F)c(C(=O)N[C@H](C(=O)O)C3CC3)cc2C2CC2)CN([C@@H](c2ccccc2)c2cc(Cl)cc(Cl)c2)C1]

The title compound was synthesized as described in Example 28. The enantiomer was separated by chiral SFC from mixture of diastereomers using Chiral HPLC conditions as described in Example 113. The first eluting fraction was arbitrarily assigned as ((S)-2-cyclopropyl-2-(5-cyclopropyl-4-((1-((S)-(3,5-dichlorophenyl)(phenyl)methyl)-3-methylazetidin-3-yl)methoxy)-2-fluorobenzamido)acetic acid: LCMS (ESI) Method C: RT=6.89 min, m/z 611.0 [M+1]; $^1$H NMR (400 MHz, DMSO-$d_6$) δ 7.92 (br s, 1H), 7.48-7.43 (m, 5H), 7.32-7.19 (m, 4H), 7.01-6.98 (m, 1H), 4.55 (s, 1H), 4.12-4.07 (m, 2H), 3.93-3.92 (m, 1H), 3.51-3.50 (m, 2H), 3.16-3.14 (m, 2H), 2.10-2.06 (m, 1H), 1.34 (s, 3H), 1.23-1.18 (m, 1H), 0.91-0.89 (m, 2H), 0.61-0.60 (m, 2H), 0.44-0.36 (m, 4H).

Example 115

Synthesis of (2S,3S)-1-(5-cyclopropyl-4-((1-((R)-(3,5-dichlorophenyl)(phenyl)methyl)-3-methylazetidin-3-yl)methoxy)-2-fluorobenzoyl)-3-methylpyrrolidine-2-carboxylic Acid

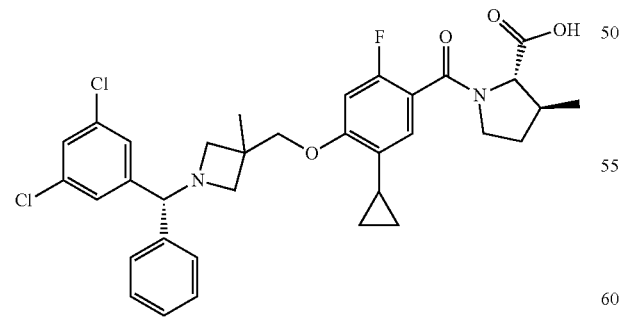

The title compound was synthesized as described in Example 28. The enantiomer was separated by chiral SFC from mixture of diastereomers using Chiral HPLC conditions as described in Example 113. The second eluting fraction was arbitrarily assigned as (2S,3S)-1-(5-cyclopropyl-4-((1-((R)-(3,5-dichlorophenyl)(phenyl)methyl)-3-methylazetidin-3-yl)methoxy)-2-fluorobenzoyl)-3-methylpyrrolidine-2-carboxylic acid: LCMS (ESI) Method C: RT=6.67 min, m/z 625.0 [M+1]; $^1$H NMR (400 MHz, DMSO-$d_6$) δ 7.48-7.48 (m, 2H), 7.45-7.40 (m, 3H), 7.32-7.28 (m, 2H), 7.23-7.19 (m, 1H), 6.99-6.72 (m, 2H), 4.56 (s, 1H), 4.08-4.04 (m, 2H), 3.63-3.49 (m, 2H), 3.15-3.13 (m, 2H), 2.86-2.84 (m, 2H), 2.33-2.25 (m, 1H), 2.07-1.97 (m, 2H), 1.55-1.46 (m, 2H), 1.34-1.33 (m, 3H), 1.15-1.14 (m, 2H), 1.05-1.03 (m, 1H), 0.89-0.84 (m, 2H), 0.60-0.57 (m, 2H).

Example 116

Synthesis of (2S,3S)-1-(5-cyclopropyl-4-((1-((S)-(3,5-dichlorophenyl)(phenyl)methyl)-3-methylazetidin-3-yl)methoxy)-2-fluorobenzoyl)-3-methylpyrrolidine-2-carboxylic Acid

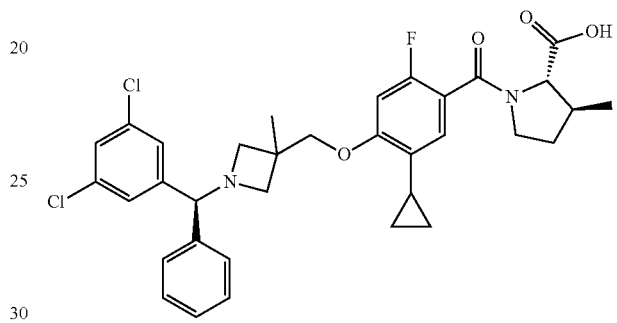

The title compound was synthesized as described in Example 28. The enantiomer was separated by chiral SFC from mixture of diastereomers using Chiral HPLC conditions as described in Example 113. The first eluting fraction was arbitrarily assigned as (2S,3S)-1-(5-cyclopropyl-4-((1-((S)-(3,5-dichlorophenyl)(phenyl)methyl)-3-methylazetidin-3-yl)methoxy)-2-fluorobenzoyl)-3-methylpyrrolidine-2-carboxylic acid: LCMS (ESI) Method C: RT=6.67 min, m/z 625.0 [M+1]; $^1$H NMR (400 MHz, DMSO-$d_6$) δ 7.45-7.48 (m, 2H), 7.45-7.43 (m, 3H), 7.32-7.28 (m, 2H), 7.23-7.19 (m, 1H), 6.98-6.74 (m, 2H), 4.56 (s, 1H), 4.07-4.03 (m, 2H), 3.63-3.43 (m, 2H), 3.16-3.13 (m, 2H), 2.86-2.84 (m, 2H), 2.33-2.25 (m, 1H), 2.28-2.25 (m, 2H), 1.49-1.45 (m, 2H), 1.34-1.33 (m, 3H), 1.15-1.13 (m, 2H), 1.03-1.02 (m, 1H), 0.89-0.83 (m, 2H), 0.59-0.55 (m, 2H).

Example 117

Synthesis of (2S,4R)-1-(5-cyclopropyl-4-((1-((S)-(3,5-dichlorophenyl)(phenyl)methyl)-3-methylazetidin-3-yl)methoxy)-2-fluorobenzoyl)-4-fluoropyrrolidine-2-carboxylic Acid

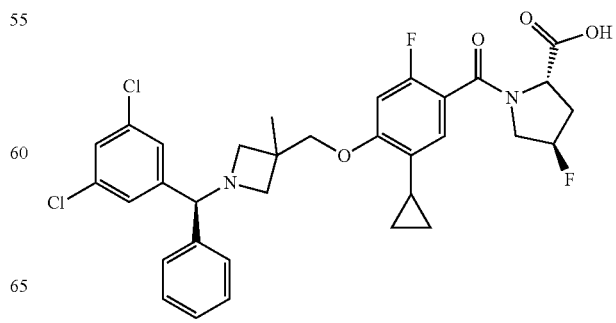

The title compound was synthesized as described in Example 28. The enantiomer was separated by chiral SFC from mixture of diastereomers using Chiral HPLC conditions as described in Example 113. The first eluting fraction was arbitrarily assigned as (2S,4R)-1-(5-cyclopropyl-4-((1-((S)-(3,5-dichlorophenyl)(phenyl)methyl)-3-methylazetidin-3-yl)methoxy)-2-fluorobenzoyl)-4-fluoropyrrolidine-2-carboxylic acid: LCMS (ESI) Method A: RT=6.45 min, m/z 629.2 [M+1]; $^1$H NMR (400 MHz, DMSO-$d_6$) δ 7.49-7.48 (m, 2H), 7.45-7.43 (m, 3H), 7.32-7.28 (m, 2H), 7.23-7.21 (m, 1H), 7.00-6.84 (m, 2H), 5.37-5.18 (m, 1H), 4.56 (s, 1H), 4.46-4.42 (m, 1H), 4.08-3.88 (m, 3H), 3.64-3.40 (m, 2H), 3.16-3.13 (m, 2H), 2.86-2.84 (m, 2H), 2.23-2.08 (m, 2H), 1.34-1.35 (m, 3H), 0.90-0.83 (m, 2H), 0.61-0.58 (m, 2H).

Example 118

Synthesis of (S)-2-cyclopropyl-2-(5-cyclopropyl-4-((1-((R)-(3,5-dichlorophenyl)-(phenyl)methyl)piperidin-4-yl)methoxy)-2-fluorobenzamido)acetic Acid

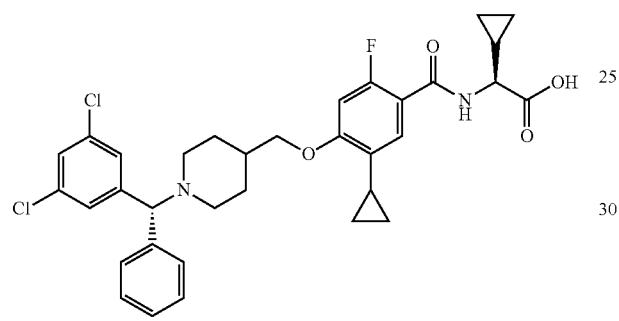

The title compound was synthesized as described in Example 26. The enantiomer was arbitrarily assigned as (S)-2-cyclopropyl-2-(5-cyclopropyl-4-((1-((R)-(3,5-dichlorophenyl)-(phenyl)methyl)piperidin-4-yl)methoxy)-2-fluorobenzamido)acetic acid: LCMS (ESI) Method A: RT=6.87 min, m/z 625.2 [M+1]; $^1$H NMR (400 MHz, DMSO-$d_6$) δ 7.49-7.06 (m, 9H), 6.93-6.86 (m, 1H), 4.44 (s, 1H), 3.99-3.94 (m, 2H), 3.81-3.73 (m, 1H), 2.84-2.76 (m, 2H), 2.03-1.95 (m, 1H), 1.87-1.76 (m, 4H), 1.48-1.38 (m, 2H), 1.24-1.19 (m, 2H), 0.90-0.82 (m, 2H), 0.61-0.58 (m, 2H), 0.52-0.30 (m, 4H).

Example 119

Synthesis of (S)-2-cyclopropyl-2-(5-cyclopropyl-4-((1-((S)-(3,5-dichlorophenyl)-(phenyl)methyl)piperidin-4-yl)methoxy)-2-fluorobenzamido)acetic Acid

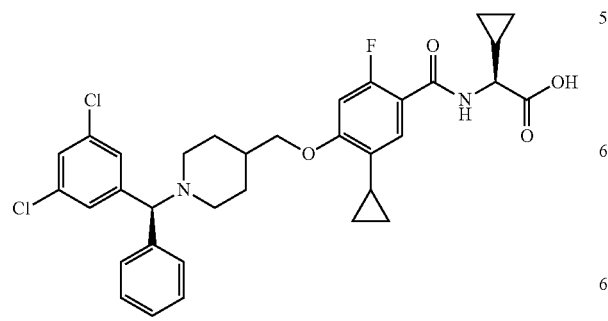

The title compound was synthesized as described in Example 26. The enantiomer was arbitrarily assigned as (S)-2-cyclopropyl-2-(5-cyclopropyl-4-((1-((S)-(3,5-dichlorophenyl)(phenyl)methyl)piperidin-4-yl)methoxy)-2-fluorobenzamido)acetic acid: LCMS (ESI) Method A: RT=6.98 min, m/z 625.2 [M+1]; $^1$H NMR (400 MHz, DMSO-$d_6$) δ 7.47-7.20 (m, 9H), 6.93-6.89 (m, 1H), 4.44 (s, 1H), 3.95-3.93 (m, 2H), 3.85-3.81 (m, 1H), 2.82-2.71 (m, 2H), 2.03-1.95 (m, 1H), 1.89-1.71 (m, 4H), 1.48-1.33 (m, 2H), 1.25-1.13 (m, 2H), 0.91-0.80 (m, 2H), 0.61-0.55 (m, 2H), 0.51-0.31 (m, 4H).

Example 120

Synthesis of (R)-2-(4-((3-chloro-5-(trifluoromethoxy)phenoxy)methyl)-5-cyclopropyl-2-fluorobenzamido)-2-cyclopropylacetic Acid

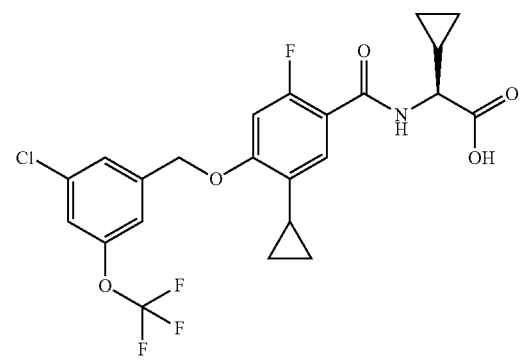

The title compound was synthesized as described in Example 9: LCMS (ESI) Method A: RT=7.78 min, m/z 502.1 [M+1]; $^1$H NMR (400 MHz, DMSO-$d_6$) δ 8.51 (br s, 1H), 7.42-7.16 (m, 5H), 5.374 (s, 2H), 3.83-3.79 (m, 1H), 2.05-2.01 (m, 1H), 1.23-1.17 (m, 1H), 0.98-0.93 (m, 2H), 0.70-0.66 (m, 2H), 0.54-0.36 (m, 4H).

Example 121a and Example 121b

Synthesis of (2S,3S)-1-(5-cyclopropyl-4-((1-((R)-1-(3,5-dichlorophenyl)-2,2,2-trifluoroethyl)piperidin-4-yl)methoxy)-2-fluorobenzoyl)-3-methylpyrrolidine-2-carboxylic Acid and (2S,3S)-1-(5-cyclopropyl-4-((1-((S)-1-(3,5-dichlorophenyl)-2,2,2-trifluoroethyl)piperidin-4-yl)methoxy)-2-fluorobenzoyl)-3-methylpyrrolidine-2-carboxylic Acid

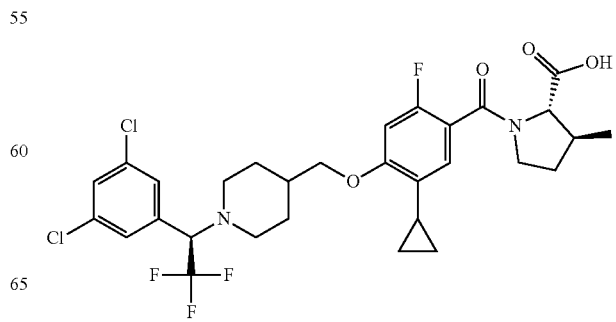

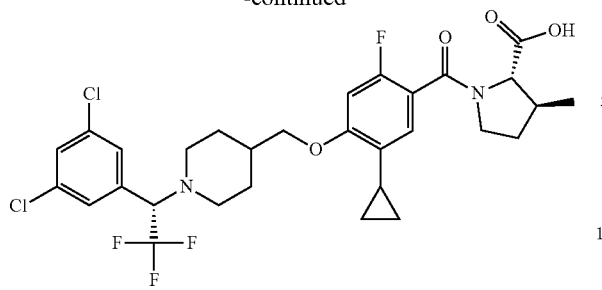

The title compound was synthesized as described in Example 39. The enantiomer was separated by chiral SFC from mixture of diastereomers using Chiral HPLC conditions as described in Example 113. The first eluting fraction was arbitrarily assigned as (2S,3S)-1-(5-cyclopropyl-4-((1-((R)-1-(3,5-dichlorophenyl)-2,2,2-trifluoroethyl)piperidin-4-yl)methoxy)-2-fluorobenzoyl)-3-methylpyrrolidine-2-carboxylic acid: LCMS (ESI) Method A: RT=6.45 min, m/z 631.1 [M+1]; $^1$H NMR (400 MHz, DMSO-$d_6$) δ 7.71 (s, 1H), 7.45 (s, 2H), 6.87-6.68 (m, 2H), 4.77-4.75 (m, 1H), 3.88-3.82 (m, 3H), 3.57-3.41 (m, 2H), 3.00 (s, 2H), 2.32-2.26 (m, 2H), 2.05-1.94 (m, 3H), 1.79-1.36 (m, 6H), 1.13 (d, J=6.8 Hz, 3H), 0.87-0.81 (m, 2H), 0.57-0.56 (m, 2H); and the second eluting fraction was arbitrarily assigned as (2S, 3S)-1-(5-cyclopropyl-4-((1-((S)-1-(3,5-dichlorophenyl)-2,2,2-trifluoroethyl)piperidin-4-yl)methoxy)-2-fluorobenzoyl)-3-methylpyrrolidine-2-carboxylic acid: LCMS (ESI) Method A: RT=6.47 min, m/z 631.1 [M+1]; $^1$H NMR (400 MHz, DMSO-$d_6$) δ 7.71 (s, 1H), 7.45 (s, 2H), 6.86-6.74 (m, 2H), 4.78-4.75 (m, 1H), 3.88-3.83 (m, 3H), 3.57-3.42 (m, 2H), 3.00 (m, 2H), 2.33-2.27 (m, 2H), 2.07-1.94 (m, 3H), 1.79-1.36 (m, 6H), 1.13 (d, J=6.8 Hz, 3H), 0.87-0.81 (m, 2H), 0.57-0.56 (m, 2H).

Example 122

Synthesis of (5-cyclopropyl-4-((3-(3,5-dichlorophenoxy)azetidin-1-yl)methyl)-2-fluorobenzoyl)-L-proline Step 1. Preparation of tert-butyl (5-cyclopropyl-4-((3-(3,5-dichlorophenoxy)azetidin-1-yl)methyl)-2-fluorobenzoyl)-L-prolinate

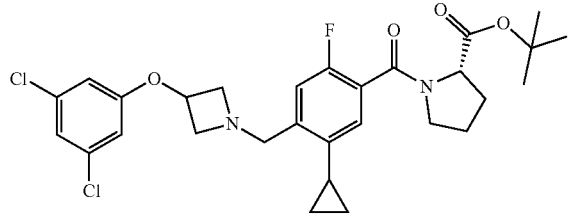 [SMILES: CC(C)(C)OC(=O)[C@@H]1CCCN1C(=O)c1cc(C2CC2)c(CN2CC(Oc3cc(Cl)cc(Cl)c3)C2)cc1F]

Following the procedure as described in Example 1, Step 1 and making variation as required to replace 4-adamantan-1-yl)methoxy)-5-cyclopropyl-2-fluorobenzoic acid with 5-cyclopropyl-4-((3-(3,5-dichlorophenoxy)azetidin-1-yl)methyl)-2-fluorobenzoic acid, the title compound was obtained as a colorless foam (0.24 g, 45%): MS (ES+) m/z 563.0, 564.9 (M+1).

Step 2. Preparation of (5-cyclopropyl-4-((3-(3,5-dichlorophenoxy)azetidin-1-yl)methyl)-2-fluorobenzoyl)-L-proline

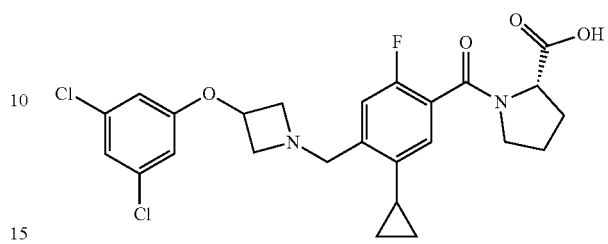

Following the procedure as described in Example 1, Step 2 and making variation as required to replace (S)-tert-butyl 1-(4-(adamantan-1-ylmethoxy)-5-cyclopropyl-2-fluorobenzoyl)-pyrrolidine-2-carboxylate with tert-butyl (5-cyclopropyl-4-((3-(3,5-dichlorophenoxy)azetidin-1-yl)methyl)-2-fluorobenzoyl)-L-prolinate, the title compound was obtained as a colorless solid: $^1$H NMR (300 MHz, DMSO-$d_6$) δ 12.67 (br s, 1H), 11.06 (br s, 1H), 7.38-7.26 (m, 1H), 7.26-7.21 (m, 1H), 7.03-6.88 (m, 3H), 5.16 (br s, 1H), 4.76-4.54 (m, 4H), 4.38-4.15 (m, 3H), 3.56-3.46 (m, 1H), 3.32-3.17 (m, 1H), 2.29-2.13 (m, 1H), 2.09-1.98 (m, 1H), 1.94-1.73 (m, 3H), 1.01-0.87 (m, 2H), 0.70-0.53 (m, 2H); MS (ES+) m/z 509.1, 507.1 (M+1)

Example 123a and Example 123b

Synthesis of(S)-1-(5-cyclopropyl-4-((1-((R)-1-(3,5-dichlorophenyl)-2,2,2-trifluoroethyl)piperidin-4-yl)methoxy)-2-fluorobenzoyl)pyrrolidine-2-carboxylic Acid and (S)-1-(5-cyclopropyl-4-((1-((S)-1-(3,5-dichlorophenyl)-2,2,2-trifluoroethyl)piperidin-4-yl)-methoxy)-2-fluorobenzoyl)pyrrolidine-2-carboxylic Acid

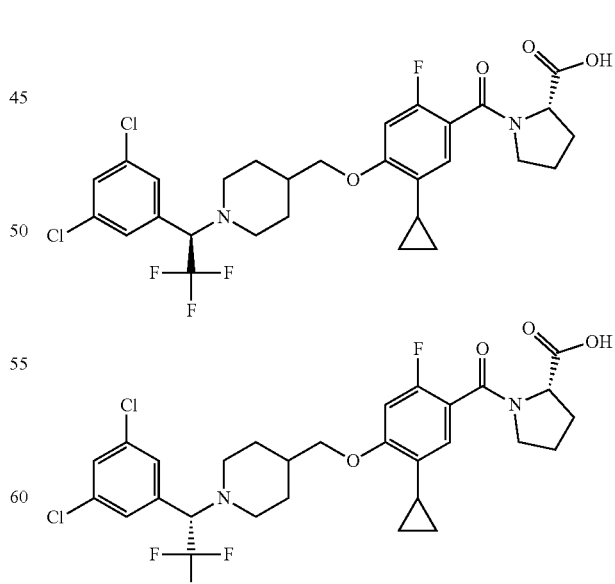

The title compound was synthesized as described in Example 39. The enantiomer was separated by chiral SFC from mixture of diastereomers using Chiral HPLC conditions as described in Example 113. The first eluting fraction was arbitrarily assigned as (S)-1-(5-cyclopropyl-4-((1-((R)-1-(3,5-dichlorophenyl)-2,2,2-trifluoroethyl)piperidin-4-yl)methoxy)-2-fluorobenzoyl)pyrrolidine-2-carboxylic acid: LCMS (ESI) Method A: RT=6.40 min, m/z 617.0 [M+1]; $^1$H NMR (400 MHz, DMSO-$d_6$) δ 7.71 (s, 1H), 7.42 (s, 2H), 6.88-6.76 (m, 2H), 4.77-4.75 (m, 1H), 4.32 (m, 1H), 3.88-3.83 (m, 2H), 3.51-3.48 (m, 1H), 3.01-2.97 (m, 2H), 2.33-2.30 (m, 2H), 2.08-1.97 (m, 3H), 1.89-1.76 (m, 6H), 1.37-1.34 (m, 2H), 0.82-0.79 (m, 2H), 0.60-0.51 (m, 2H) and the second eluting fraction was arbitrarily assigned as (S)-1-(5-cyclopropyl-4-((1-((S)-1-(3,5-dichlorophenyl)-2,2,2-trifluoroethyl)piperidin-4-yl)methoxy)-2-fluorobenzoyl)pyrrolidine-2-carboxylic acid: LCMS (ESI) Method A: RT=6.40 min, m/z 617.0 [M+1]; $^1$H NMR (400 MHz, DMSO-$d_6$) δ 7.71 (s, 1H), 7.45 (s, 2H), 6.88-6.72 (m, 2H), 4.83-4.71 (m, 1H), 4.34-3.83 (m, 3H), 3.51-3.47 (m, 1H), 3.01-2.99 (m, 2H), 2.33-1.68 (m, 11H), 1.37-1.35 (m, 2H), 0.87-0.81 (m, 2H), 0.59-0.54 (m, 2H).

Example 124

Synthesis of (S)-5-(4-((1-(2-chloro-4-(trifluoromethyl)benzyl)-4-fluoropiperidin-4-yl)methoxy)-5-cyclopropyl-2-fluorobenzoyl)-5-azaspiro[2.4]heptane-6-carboxylic Acid Step 1. Preparation of 4-((1-(2-chloro-4-(trifluoromethyl)benzyl)-4-fluoropiperidin-4-yl)methoxy)-5-cyclopropyl-2-fluorobenzoyl Chloride

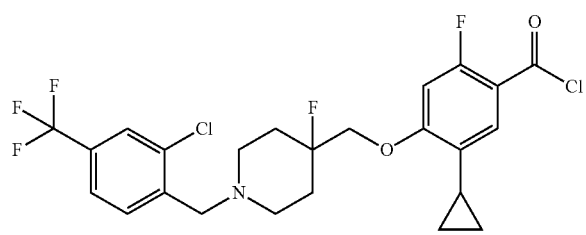 [SMILES: O=C(Cl)c1cc(C2CC2)c(OCC2(F)CCN(Cc3ccc(C(F)(F)F)cc3Cl)CC2)cc1F]

To a solution of 4-((1-(2-chloro-4-(trifluoromethyl)benzyl)-4-fluoropiperidin-4-yl)methoxy)-5-cyclopropyl-2-fluorobenzoic acid (1.84 mmol) in anhydrous acetonitrile (12.30 mL) was added oxalyl chloride (2.40 mL, 27.6 mmol) and N,N-dimethylformamide (0.020 mL). The reaction mixture was stirred at ambient temperature for 1.5 h, and then evaporated to dryness in vacuo. The resulting residue was used without further purification or characterization.

Step 2. Preparation of (S)-5-(4-((1-(2-chloro-4-(trifluoromethyl)benzyl)-4-fluoropiperidin-4-yl)methoxy)-5-cyclopropyl-2-fluorobenzoyl)-5-azaspiro[2.4]heptane-6-carboxylic Acid

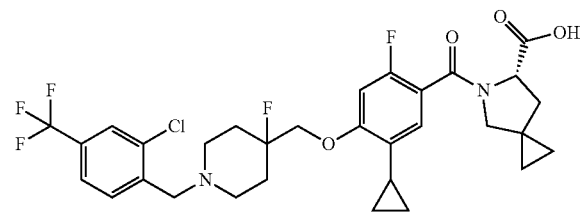 [SMILES: O=C(O)[C@@H]1CC2(CC2)CN1C(=O)c1cc(C2CC2)c(OCC2(F)CCN(Cc3ccc(C(F)(F)F)cc3Cl)CC2)cc1F]

To a solution of 4-((1-(2-chloro-4-(trifluoromethyl)benzyl)-4-fluoropiperidin-4-yl)methoxy)-5-cyclopropyl-2-fluorobenzoyl chloride (1.84 mmol) in acetonitrile (5.0 mL) was added N,N-diisopropylethylamine (0.64 mL, 3.68 mmol) followed by (S)-6-carboxy-5-azaspiro[2.4]heptan-5-ium trifluoroacetate (0.21 g, 0.83 mmol) dissolved in acetonitrile (1.0 mL). The reaction mixture was stirred at ambient temperature overnight, and then diluted with aqueous hydrochloric acid (1 mol/L, 10 mL). After extraction with ethyl acetate (3×75 mL), the pooled organic extracts were dried over anhydrous magnesium sulfate, filtered, and evaporated in vacuo. The residue was purified by preparatory HPLC (acetonitrile and water with 0.1% formic acid) to obtain (S)-5-(4-((1-(2-chloro-4-(trifluoromethyl)benzyl)-4-fluoropiperidin-4-yl)methoxy)-5-cyclopropyl-2-fluorobenzoyl)-5-azaspiro[2.4]heptane-6-carboxylic acid as a colorless solid (0.11 g, 21% yield): $^1$H NMR (300 MHz, CDCl$_3$) δ 7.84 (d, J=8.1 Hz, 1H), 7.66 (s, 1H), 7.52 (d, J=7.2 Hz, 1H), 6.79 (d, J=7.5 Hz, 1H), 6.25 (d, J=11.4 Hz, 1H), 4.64 (t, J=7.5 Hz, 1H), 4.16-3.99 (m, 3H), 3.84-3.75 (m, 1H), 3.54 (d, J=10.2 Hz, 1H), 3.34-3.22 (m, 1H), 3.07-2.90 (m, 2H), 2.82-2.65 (m, 2H), 2.24-1.84 (m, 7H), 0.80 (d, J=8.4 Hz, 2H), 0.61-0.42 (m, 6H); Note: COOH proton not observed; MS (ES+) m/z 627.1 (M+1).

Example 125

Synthesis of (2S,4R)-1-(5-cyclopropyl-4-((1-((S)-(3,5-dichlorophenyl)(phenyl)methyl)-piperidin-4-yl)methoxy)-2-fluorobenzoyl)-4-fluoropyrrolidine-2-carboxylic Acid

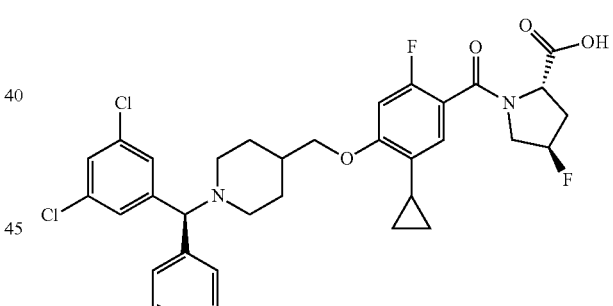

The title compound was synthesized as described in Example 26. The enantiomer was separated by chiral SFC from mixture of diastereomers. The first eluting fraction was arbitrarily assigned as (2S,4R)-1-(5-cyclopropyl-4-((1-((S)-(3,5-dichlorophenyl)(phenyl)methyl)piperidin-4-yl)methoxy)-2-fluorobenzoyl)-4-fluoropyrrolidine-2-carboxylic acid: Chiral HPLC (column: OJ-H, 4.6×250 mm, 5 μm; mobile Phase: A: supercritical CO$_2$, B: methanol (0.5% NH$_4$OH), A:B=70:30; flow: 2.1 mL/min; column temperature: 41.4° C.; RT=5.24 min); LCMS (ESI) Method A: RT=6.77 min, m/z 643.2 [M+1]; $^1$H NMR (400 MHz, DMSO-$d_6$) δ 7.46-7.22 (m, 8H), 6.93-6.81 (m, 2H), 5.41-5.18 (m, 1H), 4.47-4.03 (m, 2H), 3.94-3.87 (m, 2H), 3.78-3.54 (m, 1H), 3.46-3.41 (m, 2H), 2.82-2.77 (m, 2H), 2.23-2.17 (m, 1H), 2.01-1.93 (m, 3H), 1.81-1.72 (m, 3H), 1.48-1.37 (m, 2H), 0.89-0.79 (m, 2H), 0.70-0.61 (m, 2H).

Example 126a and Example 126b

Synthesis of (2S,4R)-1-(4-((4-cyano-1-((R)-1-(3,5-dichlorophenyl)ethyl)piperidin-4-yl)methoxy)-5-cyclopropyl-2-fluorobenzoyl)-4-fluoropyrrolidine-2-carboxylic Acid and (2S,4R)-1-(4-((4-cyano-1-((S)-1-(3,5-dichlorophenyl)ethyl)piperidin-4-yl)methoxy)-5-cyclopropyl-2-fluorobenzoyl)-4-fluoropyrrolidine-2-carboxylic Acid

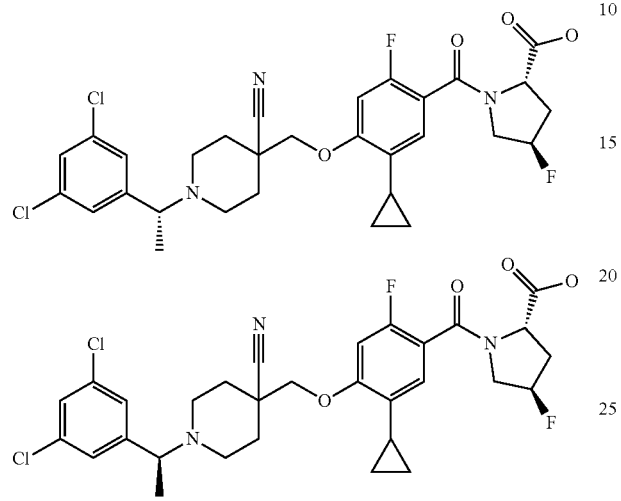

The title compound was synthesized as described in Example 39. The enantiomer was separated by chiral SFC from mixture of diastereomers using Chiral HPLC conditions as described in Example 113. The first eluting fraction was arbitrarily assigned as (2S,4R)-1-(4-((4-cyano-1-((R)-1-(3,5-dichlorophenyl)ethyl)piperidin-4-yl)methoxy)-5-cyclopropyl-2-fluorobenzoyl)-4-fluoropyrrolidine-2-carboxylic acid: LCMS (ESI) Method A: RT=6.00 min, m/z 606.2 [M+1]; $^1$H NMR (400 MHz, DMSO-$d_6$) δ 7.49 (s, 1H), 7.40 (s, 2H), 6.96-6.80 (m, 2H), 4.17 (m, 4H), 3.64 (m, 4H), 3.04 (m, 2H), 2.16 (m, 7H), 1.27 (m, 5H), 0.75 (m, 3H) and the second eluting fraction was arbitrarily assigned as (2S,4R)-1-(4-((4-cyano-1-((S)-1-(3,5-dichlorophenyl)ethyl)piperidin-4-yl)methoxy)-5-cyclopropyl-2-fluorobenzoyl)-4-fluoropyrrolidine-2-carboxylic acid: LCMS (ESI) Method A: RT=6.05 min, m/z 606.2 [M+1]; $^1$H NMR (400 MHz, DMSO-$d_6$) δ 7.49 (s, 1H), 7.40 (s, 2H), 6.97-6.81 (m, 2H), 4.17 (m, 4H), 3.64 (m, 4H), 3.04 (m, 2H), 2.16 (m, 7H), 1.27 (m, 5H), 0.75 (m, 3H).

Example 127

Synthesis of (2S, 4R)-1-(4-((1-(2-chloro-4-(trifluoromethyl)benzyl)-4-fluoropiperidin-4-yl)methoxy)-5-cyclopropyl-2-fluorobenzoyl)-4-fluoropyrrolidine-2-carboxylic Acid

Step 1. Preparation of tert-butyl 4-((1-(2-chloro-4-(trifluoromethyl)benzyl)-4-fluoropiperidin-4-yl)methoxy)-5-cyclopropyl-2-fluorobenzoate

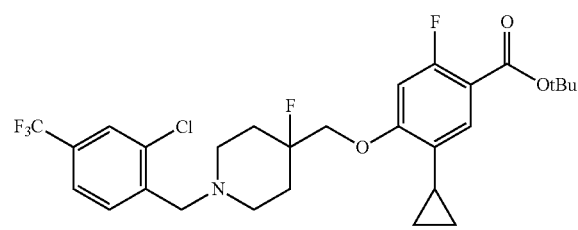 [SMILES: CC(C)(C)OC(=O)c1cc(C2CC2)c(OCC2(F)CCN(Cc3ccc(C(F)(F)F)cc3Cl)CC2)cc1F]

Following the procedure as described in Example 128, Step 1 and making variation as required to replace 3-chloro-4-fluorobenzyl 4-methylbenzenesulfonate with 2-chloro-4-(trifluoromethyl)-benzyl methanesulfonate, the title compound was obtained as yellow oil (2.74 g, 54% yield): $^1$H NMR (300 MHz, CDCl$_3$) δ 7.67-7.60 (m, 2H), 7.55-7.45 (m, 1H), 7.40 (d, J=8.3 Hz, 1H), 6.50 (d, J=12.4 Hz, 1H), 3.99 (d, J=18.0 Hz, 2H), 3.68 (s, 2H), 2.85-2.71 (m, 2H), 2.52 (t, J=10.6 Hz, 2H), 2.10-1.90 (m, 4H), 1.91-1.75 (m, 1H), 1.55 (s, 9H), 0.95-0.85 (m, 2H), 0.67-0.59 (m, 2H); MS (ES+) m/z 559.8, 562.2 (M+1).

Step 3. Preparation of 4-((1-(2-chloro-4-(trifluoromethyl)benzyl)-4-fluoropiperidin-4-yl)methoxy)-5-cyclopropyl-2-fluorobenzoic Acid

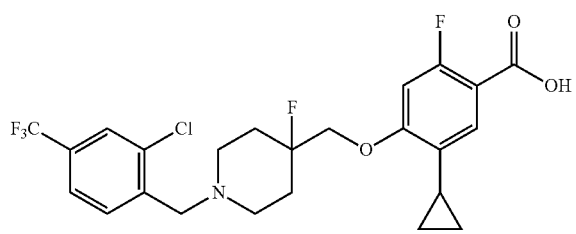 [SMILES: O=C(O)c1cc(C2CC2)c(OCC2(F)CCN(Cc3ccc(C(F)(F)F)cc3Cl)CC2)cc1F]

Following the procedure as described in Example 1, Step 2 and making variation as required to replace ethyl 1-(4-(adamantan-1-ylmethoxy)-5-cyclopropyl-2-fluorobenzamido)cyclopropanecarboxylate with tert-butyl 4-((1-(2-chloro-4-(trifluoromethyl)benzyl)-4-fluoropiperidin-4-yl)methoxy)-5-cyclopropyl-2-fluorobenzoate, the title compound obtained was used without further purification.

Step 4. Preparation of methyl (2S,4R)-1-(4-((1-(2-chloro-4-(trifluoromethyl)benzyl)-4-fluoropiperidin-4-yl)methoxy)-5-cyclopropyl-2-fluorobenzoyl)-4-fluoropyrrolidine-2-carboxylate

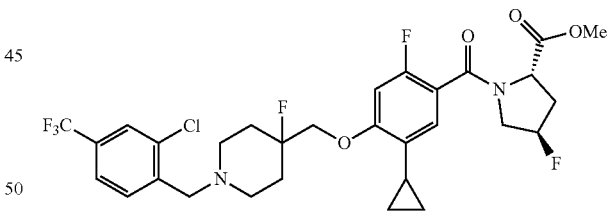

Following the procedure as described in Example 1, Step 1 and making non-critical variations to replace 4-adamantan-1-yl)methoxy)-5-cyclopropyl-2-fluorobenzoic acid with 4-((1-(3-chloro-4-fluorobenzyl)-4-fluoropiperidin-4-yl)methoxy)-5-cyclopropyl-2-fluorobenzoic acid and 4-((1-(2-chloro-4-(trifluoromethyl)benzyl)-4-fluoropiperidin-4-yl)methoxy)-5-cyclopropyl-2-fluorobenzoic acid, the title compound was obtained as yellow oil (0.29 g, 38% yield): $^1$H NMR (300 MHz, CDCl$_3$) δ 7.70-7.60 (m, 2H), 7.55-7.40 (m, 2H), 7.01 (d, J=7.8 Hz, 1H), 6.52 (d, J=11.7 Hz, 1H), 5.20 (d, J=51.9 Hz, 1H), 4.80 (t, J=8.6 Hz, 1H), 3.98 (d, J=18.0 Hz, 2H), 3.75 (s, 3H), 3.72-3.59 (m, 4H), 2.82-2.46 (m, 6H), 2.30-2.12 (m, 1H), 2.00-1.69 (m, 3H), 0.90-0.85 (m, 2H), 0.64-0.57 (m, 2H); MS (ES+) m/z 633.3, 635.2 (M+1).

Step 5. Preparation of (2S,4R)-1-(4-((1-(2-chloro-4-(trifluoromethyl)benzyl)-4-fluoropiperidin-4-yl)methoxy)-5-cyclopropyl-2-fluorobenzoyl)-4-fluoropyrrolidine-2-carboxylic Acid

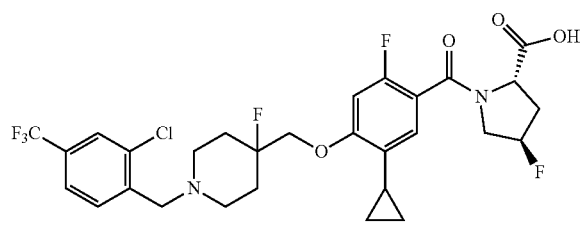 [SMILES: O=C(O)[C@@H]1C[C@@H](F)CN1C(=O)c1cc(C2CC2)c(OCC2(F)CCN(Cc3ccc(C(F)(F)F)cc3Cl)CC2)cc1F]

Following the procedure as described in Example 230, Step 2 and making non-critical variations as required to replace methyl (2S,3R,4S)-1-(4-(adamantan-1-ylmethoxy)-5-cyclopropyl-2-fluorobenzoyl)-4-hydroxy-3-methylpyrrolidine-2-carboxylate with methyl (2S,4R)-1-(4-((1-(2-chloro-4-(trifluoromethyl)benzyl)-4-fluoropiperidin-4-yl)methoxy)-5-cyclopropyl-2-fluorobenzoyl)-4-fluoropyrrolidine-2-carboxylate, the title compound was obtained as a colorless solid (0.11 g, 39% yield): $^1$H NMR (300 MHz, CDCl$_3$) δ 7.90 (d, J=7.8 Hz, 1H), 7.73 (s, 1H), 7.62 (d, J=7.8 Hz, 1H), 6.91 (d, J=7.8 Hz, 1H), 6.40 (d, J=11.4 Hz, 1H), 5.19 (d, J=52.2 Hz, 1H), 4.86-4.70 (m, 1H), 4.55 (s, 2H), 4.00 (sextet, J=9.9 Hz, 2H), 3.77-3.65 (m, 5H), 3.20 (t, J=10.2 Hz, 2H), 2.75-2.55 (m, 1H), 2.52-2.16 (m, 4H), 1.95-1.80 (m, 1H), 0.84 (d, J=8.4 Hz, 2H), 0.51 (s, 2H); Note: acidic proton not observed; MS (ES+) m/z 619.1 (M+1).

Example 128

Synthesis of (2S,4R)-1-(4-((1-(3-chloro-4-fluorobenzyl)-4-fluoropiperidin-4-yl)methoxy)-5-cyclopropyl-2-fluorobenzoyl)-4-fluoropyrrolidine-2-carboxylic Acid Step 1. Preparation of tert-butyl 4-((1-(3-chloro-4-fluorobenzyl)-4-fluoropiperidin-4-yl)methoxy)-5-cyclopropyl-2-fluorobenzoate

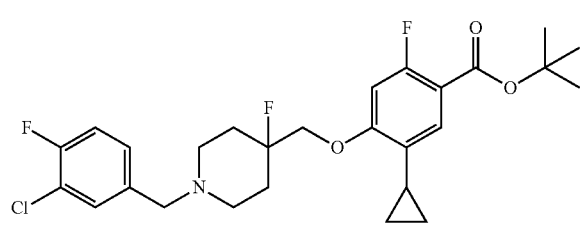 [SMILES: CC(C)(C)OC(=O)c1cc(C2CC2)c(OCC2(F)CCN(Cc3ccc(F)c(Cl)c3)CC2)cc1F]

To a solution of 3-chloro-4-fluorobenzyl 4-methylbenzenesulfonate (0.46 g, 1.46 mmol) in N,N-dimethylformamide (4.5 mL) was added potassium carbonate (0.47 g, 3.37 mmol) and 4-((4-carboxy-2-cyclopropyl-5-fluorophenoxy)methyl)-4-fluoropiperidin-1-ium chloride (0.43 g, 1.12 mmol). The reaction mixture was stirred at 70° C. for 2 h then diluted with brine (100 mL) and extracted with ethyl acetate (3×80 mL). The combined organic extracts were dried over anhydrous magnesium sulfate and filtered. The filtrate was concentrated in vacuo and the residue was purified by column chromatography to afford the title compound as a colorless solid (0.35 g, 47% yield): $^1$H NMR (300 MHz, CDCl$_3$) δ 7.42-7.34 (m, 2H), 7.21-7.12 (m, 1H), 7.06 (t, J=8.6 Hz, 1H), 6.49 (d, J=12.4 Hz, 1H), 3.97 (d, J=18.1 Hz, 2H), 3.47 (s, 2H), 2.80-2.65 (m, 2H), 2.37 (t, J=10.7 Hz, 2H), 2.05-1.90 (m, 4H), 1.85-1.72 (m, 1H), 1.55 (s, 9H), 0.94-0.82 (m, 2H), 0.68-0.57 (m, 2H); MS (ES+) m/z 554.3, 556.3 (M+45).

Step 2. Preparation of 4-((1-(3-chloro-4-fluorobenzyl)-4-fluoropiperidin-4-yl)methoxy)-5-cyclopropyl-2-fluorobenzoic Acid

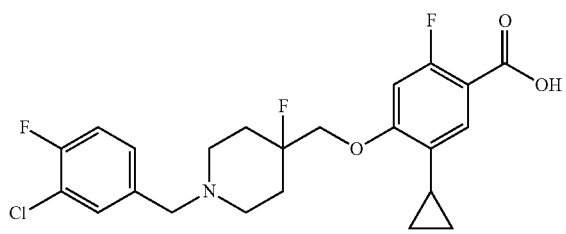 [SMILES: O=C(O)c1cc(C2CC2)c(OCC2(F)CCN(Cc3ccc(F)c(Cl)c3)CC2)cc1F]

Following the procedure as described in Example 1, Step 2 and making variation as required to replace ethyl 1-(4-(adamantan-1-ylmethoxy)-5-cyclopropyl-2-fluorobenzamido)cyclopropanecarboxylate with tert-butyl 4-((1-(3-chloro-4-fluorobenzyl)-4-fluoropiperidin-4-yl)methoxy)-5-cyclopropyl-2-fluorobenzoate, the title compound obtained was used without further purification.

Step 3. Preparation of methyl (2S,4R)-1-(4-((1-(3-chloro-4-fluorobenzyl)-4-fluoropiperidin-4-yl)methoxy)-5-cyclopropyl-2-fluorobenzoyl)-4-fluoropyrrolidine-2-carboxylate

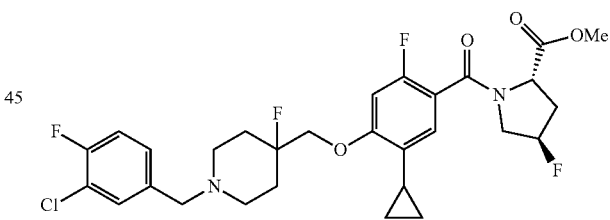

Following the procedure as described in Example 1, Step 1 and making non-critical variations to replace 4-adamantan-1-yl)methoxy)-5-cyclopropyl-2-fluorobenzoic acid with 4-((1-(3-chloro-4-fluorobenzyl)-4-fluoropiperidin-4-yl)methoxy)-5-cyclopropyl-2-fluorobenzoic acid and (S)-tert-butyl pyrrolidine-2-carboxylate hydrochloride with (2S,4R)-4-fluoro-2-(methoxycarbonyl)pyrrolidin-1-ium chloride, the title compound was obtained as yellow oil (0.29 g, 73% yield): $^1$H NMR (300 MHz, CDCl$_3$) δ 7.42 (dd, J=7.2, 1.9 Hz, 1H), 7.24-7.17 (m, 1H), 7.13-7.01 (m, 2H), 6.55 (d, J=11.7 Hz, 1H), 5.24 (d, J=52.2 Hz, 1H), 4.93-4.77 (m, 1H), 4.00 (d, J=18.1 Hz, 2H), 3.80 (m, 3H), 3.79-3.62 (m, 2H), 3.51 (s, 2H), 3.47-3.38 (m, 1H), 2.80-2.65 (m, 3H), 2.41 (t, J=10.8 Hz, 2H), 2.31-2.15 (m, 1H), 2.08-1.85 (m, 4H), 0.97-0.85 (m, 2H), 0.69-0.60 (m, 2H); MS (ES+) m/z 583.2, 585.3 (M+1).

Step 4. Preparation of (2S, 4R)-1-(4-((1-(3-chloro-4-fluorobenzyl)-4-fluoropiperidin-4-yl)methoxy)-5-cyclopropyl-2-fluorobenzoyl)-4-fluoropyrrolidine-2-carboxylic Acid

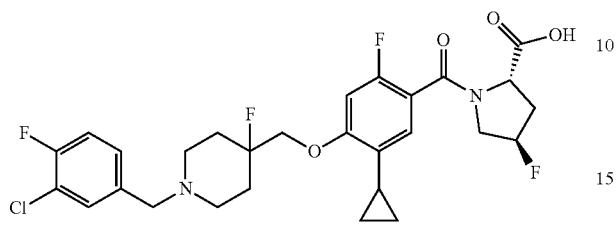

Following the procedure as described in Example 230, Step 2 and making non-critical variations as required to replace methyl (2S,3R,4S)-1-(4-(adamantan-1-ylmethoxy)-5-cyclopropyl-2-fluorobenzoyl)-4-hydroxy-3-methylpyrrolidine-2-carboxylate with methyl (2S,4R)-1-(4-((1-(3-chloro-4-fluorobenzyl)-4-fluoropiperidin-4-yl)methoxy)-5-cyclopropyl-2-fluorobenzoyl)-4-fluoropyrrolidine-2-carboxylate, the title compound was obtained as a colorless solid (0.044 g, 15% yield): $^1$H NMR (300 MHz, CDCl$_3$) δ 7.52 (d, J=4.8 Hz, 1H), 7.42-7.32 (m, 1H), 7.18 (t, J=8.7 Hz, 1H), 6.87 (d, J=7.8 Hz, 1H), 6.34 (d, J=11.4 Hz, 1H), 5.18 (d, J=51.9 Hz, 1H), 4.72 (t, J=8.7, 1H), 4.22 (q, J=13.2 Hz, 2H), 4.10-3.87 (m, 2H), 3.81-3.43 (m, 4H), 3.13-2.85 (m, 2H), 2.76-2.55 (m, 1H), 2.50-2.10 (m, 5H), 1.92-1.78 (m, 1H), 0.82 (d, J=8.2 Hz, 2H), 0.49 (br s, 2H); Note: acidic proton not observed; MS (ES+) m/z 569.2, 571.2 (M+1).

Example 129

Synthesis of (2S,4R)-1-(5-cyclopropyl-4-((1-(1-(3,5-dichlorophenyl)ethyl)-4-fluoropiperidin-4-yl)methoxy)-2-fluorobenzoyl)-4-fluoropyrrolidine-2-carboxylic Acid

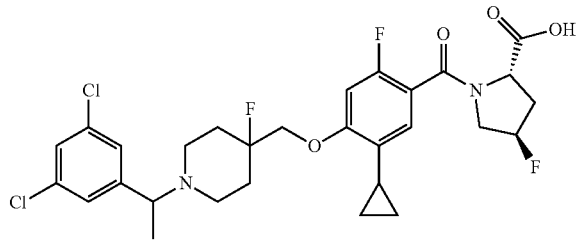 [SMILES: CC(c1cc(Cl)cc(Cl)c1)N1CCC(F)(COc2cc(F)c(C(=O)N3C[C@H](F)C[C@H]3C(=O)O)cc2C2CC2)CC1]

The compound was synthesized as described in Example 39: LCMS (ESI) Method A: RT=5.96 min, m/z 599.0 [M+1]; $^1$H NMR (400 MHz, DMSO-d$_6$) δ 7.48 (s, 1H), 7.38 (s, 2H), 6.98-9.73 (m, 2H), 5.42-5.20 (m, 1H), 4.50-3.42 (m, 6H), 2.78-2.58 (m, 3H), 2.27-1.73 (m, 8H), 1.30 (d, J=6.4 Hz, 3H), 0.89-0.87 (m, 2H), 0.64-0.59 (m, 2H).

Example 130

Synthesis of (2S,4R)-1-(5-cyclopropyl-4-((1-((S)-1-(3,5-dichlorophenyl)-2-methoxyethyl)piperidin-4-yl)methoxy)-2-fluorobenzoyl)-4-fluoropyrrolidine-2-carboxylic Acid The compound was synthesized as described in Example 39: LCMS (ESI) Method C: RT=5.57 min, m/z 611.0 [M+1]; $^1$H NMR (400 MHz, DMSO-d$_6$) δ 7.49 (s, 1H), 7.38-7.37 (m, 2H), 6.91-6.71 (m, 2H), 5.42-5.20 (m, 1H), 4.50-4.16 (m, 1H), 3.92-3.81 (m, 2H), 3.78-3.62 (m, 4H), 3.51-3.42 (m, 2H), 3.21 (s, 3H), 2.98-2.94 (m, 1H), 2.80-2.76 (m, 1H), 2.26-1.90 (m, 4H), 1.80-1.64 (m, 3H), 1.40-1.23 (m, 2H), 0.89-0.81 (m, 2H), 0.61-0.52 (m, 2H).

Example 131

Synthesis of (2S,4R)-1-(5-cyclopropyl-4-((1-((R)-1-(3,5-dichlorophenyl)-2-methoxyethyl)piperidin-4-yl)methoxy)-2-fluorobenzoyl)-4-fluoropyrrolidine-2-carboxylic Acid The compound was synthesized as described in Example 39: LCMS (ESI) Method C: RT=5.54 min, m/z 611.0 [M+1]; $^1$H NMR (400 MHz, DMSO-d$_6$) δ 7.49 (s, 1H), 7.38-7.37 (m, 2H), 6.91-6.71 (m, 2H), 5.40-5.20 (m, 1H), 4.49-4.13 (m, 1H), 3.90-3.81 (m, 2H), 3.78-3.60 (m, 4H), 3.50-3.43 (m, 2H), 3.21 (s, 3H), 2.98-2.94 (m, 1H), 2.80-2.76 (m, 1H), 2.24-1.90 (m, 4H), 1.80-1.67 (m, 3H), 1.40-1.20 (m, 2H), 0.90-0.81 (m, 2H), 0.61-0.52 (m, 2H).

Example 132

Synthesis of (2S,4R)-1-(5-cyclopropyl-4-((1-((R)-1-(3,5-dichlorophenyl)ethyl)-4-methylpiperidin-4-yl)methoxy)-2-fluorobenzoyl)-4-fluoropyrrolidine-2-carboxylic Acid and (2S,4R)-1-(5-cyclopropyl-4-((1-((R)-1-(3,5-dichlorophenyl)ethyl)-4-methylpiperidin-4-yl)-methoxy)-2-fluorobenzoyl)-4-fluoropyrrolidine-2-carboxylic Acid

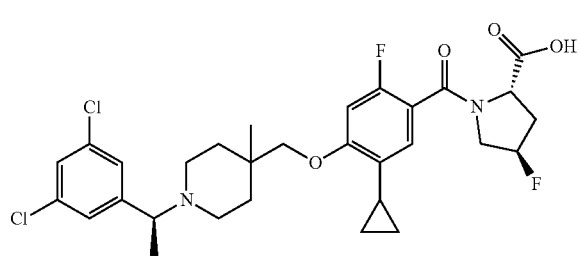

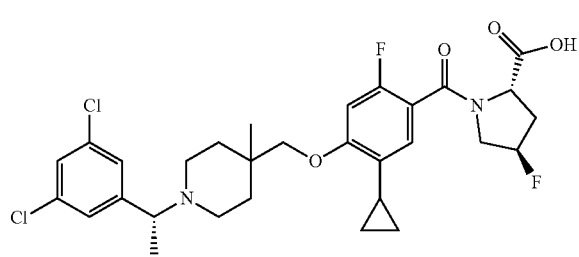

The compound was synthesized as described in Example 39. The enantiomer was separated by chiral SFC from mixture of diastereomers using Chiral HPLC conditions as described in Example 113. The first eluting fraction was arbitrarily assigned as (2S,4R)-1-(5-cyclopropyl-4-((1-((S)-1-(3,5-dichlorophenyl)ethyl)-4-methylpiperidin-4-yl)methoxy)-2-fluorobenzoyl)-4-fluoropyrrolidine-2-carboxylic acid: LCMS (ESI) Method C: RT=6.29 min, m/z 595.2 [M+1]; $^1$H NMR (400 MHz, DMSO-d$_6$) δ 7.46 (s, 1H), 7.37 (s, 2H), 6.94-6.85 (m, 2H), 5.35-5.22 (m, 1H), 4.51-4.46 (m, 1H), 3.80-3.74 (m, 3H), 3.59-3.46 (m, 2H), 2.60-2.57 (m, 2H), 2.50-2.25 (m, 4H), 2.01-1.99 (m, 1H), 1.67-1.64 (m, 2H), 1.43-1.38 (m, 2H), 1.29-1.27 (m, 3H), 1.08 (s, 3H), 0.90-0.86 (m, 2H), 0.62-0.56 (m, 2H) and the second eluting fraction was arbitrarily assigned as (2S,4R)-1-(5-cyclopropyl-4-((1-((R)-1-(3,5-dichlorophenyl)ethyl)-4-methylpiperidin-4-yl)methoxy)-2-fluorobenzoyl)-4-fluoropyrrolidine-2-carboxylic acid: LCMS (ESI) Method C: RT=6.29 min, m/z 595.1 [M+1]; $^1$H NMR (400 MHz, DMSO-d$_6$) δ 7.47 (s, 1H), 7.37 (s, 2H), 6.94-6.85 (m, 2H), 5.35-5.22 (m, 1H), 4.51-4.46 (m, 1H), 3.80-3.74 (m, 3H), 3.59-3.46 (m, 2H), 2.60-2.57 (m, 2H), 2.46-2.25 (m, 4H), 2.01-1.99 (m, 1H), 1.67-1.63 (m, 2H), 1.43-1.38 (m, 2H), 1.29-1.26 (m, 3H), 1.02 (s, 3H), 0.90-0.86 (m, 2H), 0.62-0.56 (m, 2H).

Example 133

Synthesis of (S)-3-(4-(adamantan-1-ylmethoxy)-5-cyclopropyl-2-fluorobenzoyl)-2-oxooxazolidine-4-carboxylic Acid Step 1. Preparation of (S)-3-(4-(adamantan-1-ylmethoxy)-5-cyclopropyl-2-fluorobenzoyl)-2-oxooxazolidine-4-carboxylic Acid

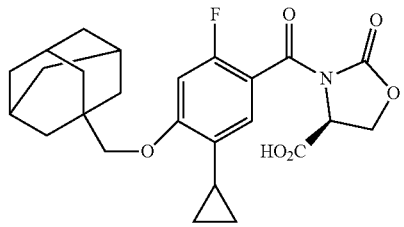 [SMILES: O=C(O)[C@@H]1COC(=O)N1C(=O)c1cc(C2CC2)c(OCC23CC4CC(CC(C4)C2)C3)cc1F]

To a stirred solution of 4-(adamantan-1-ylmethoxy)-5-cyclopropyl-2-fluorobenzoic acid (0.25 g, 0.7 mmol) in anhydrous dichloromethane (10 mL) was added anhydrous dimethylformamide (0.1 mL, 1.3 mmol) and oxalyl chloride (0.18 mL, 2.1 mmol). The reaction mixture was stirred at ambient temperature for 1 h and concentrated in vacuo to afford crude 4-(adamantan-1-ylmethoxy)-5-cyclopropyl-2-fluorobenzoyl chloride, which was used directly in the subsequent step. To a stirred solution of 4-(adamantan-1-ylmethoxy)-5-cyclopropyl-2-fluorobenzoyl chloride in anhydrous tetrahydrofuran (10 mL) was added (S)-2-oxooxazolidine-4-carboxylic acid (0.11 g, 0.9 mmol) and 1,8-diazabicyclo[5.4.0]undec-7-ene (0.5 mL, 3.6 mmol). The reaction mixture was stirred at ambient temperature for 16 h and ethyl acetate (50 mL) was added. The mixture was washed with hydrochloric acid (1 M, 2×40 mL) and brine (40 mL); dried over anhydrous sodium sulfate, filtered and concentrated in vacuo. The residue was purified by column chromatography (0% to 30% ethyl acetate+0.2% formic acid in hexanes) to afford (S)-3-(4-(adamantan-1-ylmethoxy)-5-cyclopropyl-2-fluorobenzoyl)-2-oxooxazolidine-4-carboxylic acid as a colorless solid (0.055 g, 17%): $^1$H NMR (300 MHz, DMSO-d$_6$) δ 12.79 (s, 1H), 7.32 (d, J=8.5 Hz, 1H), 6.87 (d, J=13.2 Hz, 1H), 3.63 (s, 2H), 3.33 (s, 2H), 2.06-1.99 (m, 4H), 1.75-1.66 (m, 13H), 0.94-0.88 (m, 2H), 0.62-0.56 (m, 2H); $^{19}$F NMR (282 MHz, DMSO-d$_6$) δ −109.3 (s, 1F); MS (ES−) m/z 412.3 (M−45).

Example 134

Synthesis of (5)-1-(4-cyclopropyl-5-((3,5-dichlorophenoxy)methyl)thiophene-2-carbonyl)pyrrolidine-2-carboxylic Acid Step 1. Preparation of methyl 4-bromo-5-methylthiophene-2-carboxylate

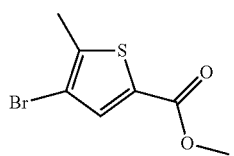

To a solution of methyl 5-methylthiophene-2-carboxylate (9.8 g, 62.8 mmol) in acetic acid (100 mL) was added ferric chloride (2.0 g, 12.4 mmol) and bromine (3.1 mL, 75 mmol) in acetic acid (50 mL) at 0° C. and it was stirred at room temperature for 5 hours. The reaction mixture was quenched with sodium dithionite (5.00 g, 28.7 mmol) and concentrated. The residue was dissolved in ethyl acetate (100 mL), washed with brine (50×2 mL), dried over anhydrous magnesium sulfate, concentrated and purified by chromatography (eluting with petroleum ether) to give methyl 4-bromo-5-methylthiophene-2-carboxylate (10.7 g, 72%) as a yellow solid: LCMS (ESI) m/z 235.0, 237.0 [M+1]; $^1$H NMR (400 MHz, DMSO-$d_6$) δ 7.69 (s, 1H), 3.82 (s, 3H), 2.43 (s, 3H).

Step 2. Preparation of methyl 4-bromo-5-(bromomethyl)thiophene-2-carboxylate

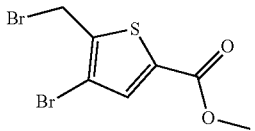

To a solution of methyl 4-bromo-5-methylthiophene-2-carboxylate (10.7 g, 45.9 mmol) in carbon tetrachloride (200 mL) was added N-bromosuccinimide (9.7 g, 55.1 mmol) and 2,2'-Azobis(2-methylpropionitrile) (0.38 g, 2.30 mmol). The reaction mixture was refluxed for 16 h, concentrated, and purified by chromatography eluting with petroleum ether to give methyl 4-bromo-5-(bromomethyl)thiophene-2-carboxylate (6.1 g, 43%) as a white solid: $^1$H NMR (400 MHz, DMSO-$d_6$) δ 7.79 (s, 1H), 4.92 (s, 2H), 3.84 (s, 3H).

Step 3. Preparation of methyl 4-bromo-5-((3,5-dichlorophenoxy)methyl)thiophene-2-carboxylate

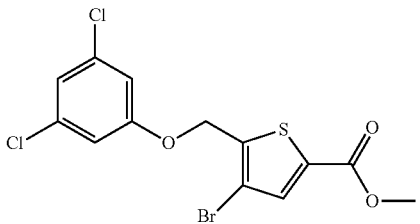 [SMILES: COC(=O)c1cc(Br)c(COc2cc(Cl)cc(Cl)c2)s1]

A mixture of methyl 4-bromo-5-(bromomethyl)thiophene-2-carboxylate (6.1 g, 19.6 mmol) and 3,5-dichlorophenol (3.2 g, 19.6 mmol) and potassium carbonate (8.3 g, 60.0 mmol) in DMF (200 mL) was stirred at room temperature for 16 h. The reaction mixture was filtered, diluted with ethyl acetate (100×3 mL), washed with brine (150 mL), dried over anhydrous sodium sulfate and concentrated to give methyl 4-bromo-5-((3,5-dichlorophenoxy)methyl)thiophene-2-carboxylate (7 g, 90%) as a yellow solid: LCMS (ESI) m/z 395.1, 397.1 [M+1].

Step 4. Preparation of methyl 4-cyclopropyl-5-((3,5-dichlorophenoxy)methyl)thiophene-2-carboxylate

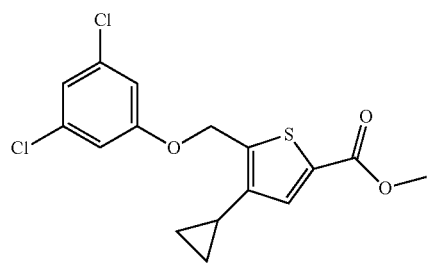 [SMILES: COC(=O)c1cc(C2CC2)c(COc2cc(Cl)cc(Cl)c2)s1]

A mixture of methyl 4-bromo-5-((3,5-dichlorophenoxy)methyl)thiophene-2-carboxylate (100 mg, 0.25 mmol), cyclopropylboronic acid (64 mg, 0.75 mmol), potassium phosphate (265 mg, 1.25 mmol) and (1,1'-Bis(diphenylphosphino)ferrocene)dichloropalladium(II) (29 mg, 0.04 mmol) in acetonitrile (20 mL) and water (1 mL), was stirred at 80° C. under nitrogen for 16 h. The reaction mixture was cooled down to room temperature, filtered, diluted with ethyl acetate (20 mL), and concentrated. The residue was purified by chromatography (eluting with 2-20% ethyl acetate in petroleum ether) to afford the target compound (60 mg, 66%) as a pale yellow oil: LCMS (ESI) m/z 357.0 [M+1].

Step 5. Preparation of 4-cyclopropyl-5-((3,5-dichlorophenoxy)methyl)thiophene-2-carboxylic Acid

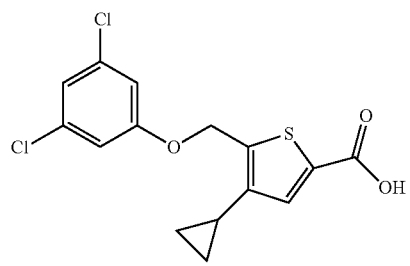 [SMILES: O=C(O)c1cc(C2CC2)c(COc2cc(Cl)cc(Cl)c2)s1]

A mixture of methyl 4-cyclopropyl-5-((3,5-dichlorophenoxy)methyl)thiophene-2-carboxylate (60 mg, 0.17 mmol) and lithium hydroxide (20 mg, 0.84 mmol) in THF (10 mL) and water (4 mL) was stirred at 50° C. for 16 h. The reaction mixture was quenched with aqueous HCl (1N, 20 ml), extracted with ethyl acetate (20 mL×3), dried over anhydrous sodium sulfate and concentrated to give target compound (50 mg, 87%) as a yellow solid: LCMS (ESI) m/z 341.0 [M−1].

Step 6. Preparation of (S)-methyl 1-(4-cyclopropyl-5-((3,5-dichlorophenoxy)methyl)thiophene-2-carbonyl)pyrrolidine-2-carboxylate

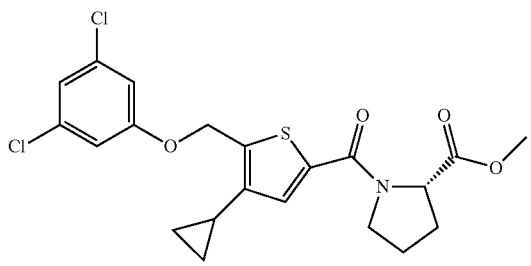 [SMILES: COC(=O)[C@@H]1CCCN1C(=O)c1cc(C2CC2)c(COc2cc(Cl)cc(Cl)c2)s1]

A solution of 4-cyclopropyl-5-((3,5-dichlorophenoxy)methyl)thiophene-2-carboxylic acid (50 mg, 0.14 mmol), (S)-methyl pyrrolidine-2-carboxylate hydrochloride salt (36 mg, 0.22 mmol), 1-ethyl-(3-dimethylaminopropyl)carbodiimide hydrochloride (54 mg, 0.28 mmol), 4-dimethylaminopyridine (51 mg, 0.42 mmol) in dichloromethane (10 mL) was stirred at room temperature for 16 h. The reaction mixture was quenched with HCl (1N, 20 mL), extracted with dichloromethane (10 mL×3), dried over anhydrous sodium sulfate and concentrated to give target compound (35 mg, 53%) as yellow oil: LCMS (ESI) m/z 454.0 [M+1].

Step 7. Preparation of (S)-1-(4-cyclopropyl-5-((3,5-dichlorophenoxy)methyl)thiophene-2-carbonyl)pyrrolidine-2-carboxylic Acid

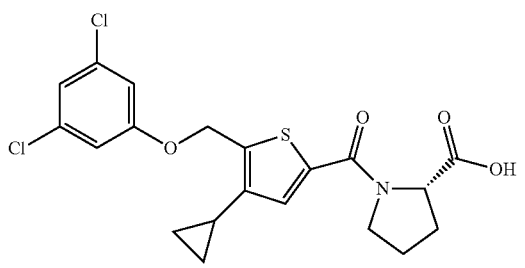 [SMILES: O=C(O)[C@@H]1CCCN1C(=O)c1cc(C2CC2)c(COc2cc(Cl)cc(Cl)c2)s1]

A mixture of (S)-methyl 1-(4-cyclopropyl-5-((3,5-dichlorophenoxy)methyl)-thiophene-2-carbonyl)pyrrolidine-2-carboxylate (35 mg, 0.08 mmol), and lithium hydroxide (10 mg, 0.4 mmol) in THF (10 mL) and water (4 mL) was stirred at 50° C. for 16 h. The reaction was quenched with aqueous HCl (1N, 20 mL), extracted with ethyl acetate (20 mL×3) and concentrated. The residue was purified by prep-HPLC (0-35% acetonitrile in 5% HCOOH) to afford the title compound as a colorless solid (15 mg, 44%): LCMS (ESI) m/z 440.0 [M+1]; $^1$H NMR (400 MHz, DMSO-d$_6$) δ 7.18 (m, 3H), 7.05 (m, 1H), 5.51-3.45 (m, 2H), 4.36-4.35 (m, 1H), 3.80-3.76 (m, 1H), 3.50-3.45 (m, 1H), 2.11-1.75 (m, 5H), 0.95-0.88 (m, 2H), 0.74-0.64 (m, 2H).

Example 135

Synthesis of (S)-1-(4-(((S)-1-(5-chloro-4-(trifluoromethyl)pyridin-2-yl)-3-methylpyrrolidin-3-yl)methoxy)-5-cyclopropyl-2-fluorobenzoyl)pyrrolidine-2-carboxylic Acid

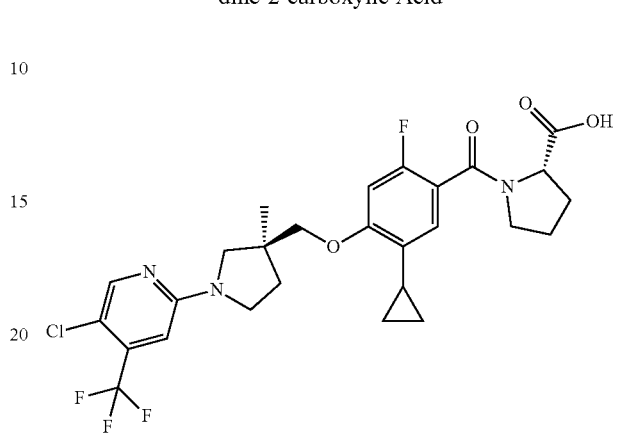

The compound was synthesized as described in Example 39: LCMS (ESI) Method A: RT=5.51 min, m/z 570.2 [M+1]; $^1$H NMR (400 MHz, CD$_3$OD) δ 6.91 (d, J=8.0 Hz, 1H), 6.79-6.64 (m, 3H), 4.42-4.39 (m, 1H), 3.90-3.87 (m, 2H), 3.64-3.53 (m, 4H), 3.41-3.24 (m, 2H), 2.28-2.14 (m, 2H), 2.00-1.78 (m, 5H), 1.27 (s, 3H), 0.84-0.69 (m, 2H), 0.52-0.49 (m, 2H).

Example 136

Synthesis of (S)-1-(4-(((R)-1-(5-chloro-4-(trifluoromethyl)pyridin-2-yl)-3-methylpyrrolidin-3-yl)methoxy)-5-cyclopropyl-2-fluorobenzoyl)pyrrolidine-2-carboxylic Acid

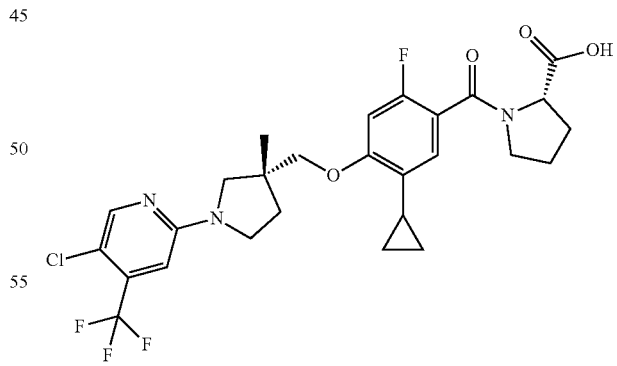

The compound was synthesized as described in Example 39: LCMS (ESI) Method A: RT=5.49 min, m/z 570.2 [M+1]; $^1$H NMR (400 MHz, CD$_3$OD) δ 6.91 (d, J=8.0 Hz, 1H), 6.77-6.64 (m, 3H), 4.44-4.41 (m, 1H), 3.90-3.87 (m, 2H), 3.64-3.50 (m, 4H), 3.41-3.24 (m, 2H), 2.29-2.13 (m, 2H), 2.00-1.78 (m, 5H), 1.27 (s, 3H), 0.83-0.69 (m, 2H), 0.54-0.47 (m, 2H).

Example 137a and Example 137b

Synthesis of (4-(((R)-1-(3-chloro-5-fluorobenzyl)-3-methylpyrrolidin-3-yl)methoxy)-5-cyclopropyl-2-fluorobenzoyl)-L-proline and (S)-1-(4-(((S)-1-(3-chloro-5-fluorobenzyl)-3-methylpyrrolidin-3-yl)methoxy)-5-cyclopropyl-2-fluorobenzoyl)pyrrolidine-2-carboxylic Acid

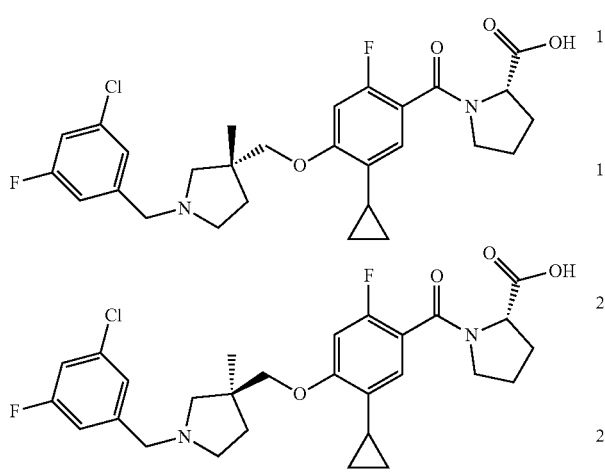

The compound was synthesized as described in Example 39: The enantiomer was separated by chiral SFC from mixture of diastereomers using Chiral HPLC conditions as described in Example 113: The first eluting fraction of the title compound was arbitrarily assigned: LCMS (ESI) Method C: RT=4.86 min, m/z 533.0 [M+H]$^+$. $^1$H NMR (400 MHz, DMSO-d$_6$) δ 7.30-7.14 (m, 3H), 6.94-6.72 (m, 2H), 4.36-4.10 (m, 1H), 3.91-3.78 (m, 2H), 3.65-3.61 (m, 2H), 3.58-3.52 (m, 1H), 2.69-2.52 (m, 4H), 2.27-2.22 (m, 2H), 1.99-1.79 (m, 5H), 1.60-1.54 (m, 1H), 1.21 (s, 3H), 0.85-0.81 (m, 2H), 0.60-0.54 (m, 2H) and the second eluting fraction of the title compound was arbitrarily assigned: LCMS (ESI) Method C: RT=4.90 min, m/z 533.0 [M+1]; $^1$H NMR (400 MHz, DMSO-d$_6$) δ 7.30-7.14 (m, 3H), 6.94-6.72 (m, 2H), 4.36-4.10 (m, 1H), 3.91-3.78 (m, 2H), 3.65-3.60 (m, 2H), 3.57-3.52 (m, 1H), 2.69-2.52 (m, 4H), 2.28-2.22 (m, 2H), 2.00-1.79 (m, 5H), 1.60-1.55 (m, 1H), 1.19 (s, 3H), 0.87-0.81 (m, 2H), 0.60-0.53 (m, 2H).

Example 138a and Example 138b

Synthesis of (4S,5R)-3-[5-cyclopropyl-4-[[1-[(1S)-1-(3,5-dichlorophenyl)-2,2,2-trifluoro-ethyl]-4-piperidyl]methoxy]-2-fluoro-benzoyl]-5-methyl-oxazolidine-4-carboxylic Acid and (4S,5R)-3-[5-cyclopropyl-4-[[1-[(1R)-1-(3,5-dichlorophenyl)-2,2,2-trifluoro-ethyl]-4-piperidyl]methoxy]-2-fluoro-benzoyl]-5-methyl-oxazolidine-4-carboxylic Acid

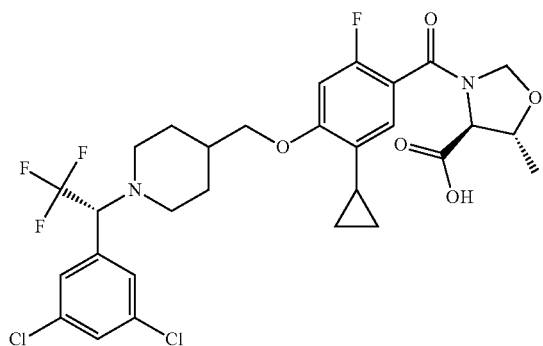

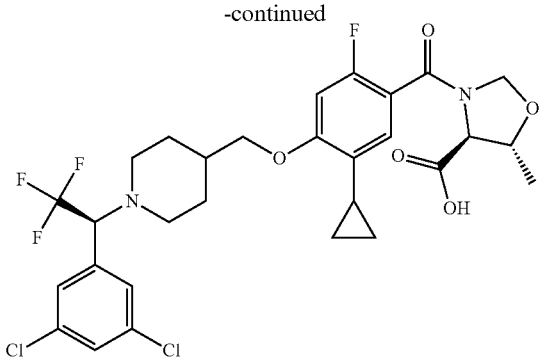

The title compounds were synthesized as described in Example 225. The enantiomer was separated by chiral SFC from mixture of diastereomers using Chiral HPLC conditions as described in Example 113. The first eluting fraction of the title compound was arbitrarily assigned: $^1$H NMR (400 MHz, DMSO-d$_6$) δ 12.41 (s, 1H), 7.03-6.70 (m, 2H), 3.83 (dt, J=11.6, 8.3 Hz, 2H), 3.57 (d, J=10.1 Hz, 2H), 2.22 (s, 2H), 2.03 (d, J=32.3 Hz, 4H), 1.83 (s, 2H), 1.79-1.60 (m, 10H), 0.89 (dd, J=8.7, 2.2 Hz, 2H), 0.57 (d, J=35.8 Hz, 2H); MS (ES+) m/z 454.2 (M+1) and the second eluent of the title compound was arbitrarily assigned: $^1$H NMR (400 MHz, DMSO-d$_6$) δ 7.71 (t, J=1.9 Hz, 1H), 7.45 (d, J=1.9 Hz, 2H), 6.86 (dt, J=22.1, 10.6 Hz, 2H), 4.88-4.71 (m, 3H), 4.25-3.99 (m, 2H), 3.94-3.81 (m, 2H), 3.01 (t, J=9.7 Hz, 2H), 2.36-2.25 (m, 1H), 2.12-1.94 (m, 2H), 1.75 (t, J=17.7 Hz, 3H), 1.47-1.22 (m, 6H), 0.87 (d, J=8.5 Hz, 2H), 0.66-0.50 (m, 2H); MS (ES+) m/z 633.2 (M).

Example 139a and Example 139b

Synthesis of (S)-1-(4-(((S)-1-benzhydrylpyrrolidin-3-yl)methoxy)-5-cyclopropyl-2-fluorobenzoyl)pyrrolidine-2-carboxylic Acid and (4-(((R)-1-benzhydrylpyrrolidin-3-yl)methoxy)-5-cyclopropyl-2-fluorobenzoyl)-L-proline

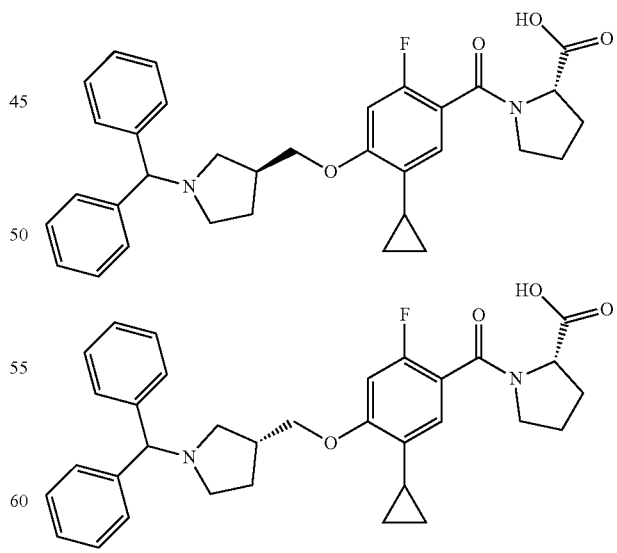

The compound was synthesized as described in Example 28: The enantiomer was separated by chiral SFC from mixture of diastereomers using Chiral HPLC conditions as described in Example 113. The first eluting fraction was arbitrarily assigned as (S)-1-(4-(((S)-1-benzhydrylpyrrolidin-3-yl) methoxy)-5-cyclopropyl-2-fluorobenzoyl) pyrrolidine-2-carboxylic acid: LCMS (ESI) Method C: RT=5.04 min, m/z 543.2 [M+1]; $^1$H NMR (400 MHz, DMSO-d$_6$) δ 7.46-7.45 (m, 4H), 7.29-7.24 (m, 4H), 7.18-7.14 (m, 2H), 6.93-6.71 (m, 2H), 4.35-4.32 (m, 1H), 4.25 (s, 1H), 4.01-3.94 (m, 2H), 3.53-3.49 (m, 2H), 2.61-2.50 (m, 2H), 2.46-2.36 (m, 3H), 2.25-2.14 (m, 1H), 1.98-1.79 (m, 5H), 1.63-1.57 (m, 1H), 0.81-0.72 (m, 2H), 0.55-0.48 (m, 2H) and the second eluting fraction was arbitrarily assigned as the title compound: LCMS (ESI) Method C: RT=5.03 min, m/z 543.1 [M+1]; $^1$H NMR (400 MHz, DMSO-d$_6$) δ 12.5 (brs, 1H), 7.47-7.18 (m, 10H), 6.94-6.68 (m, 2H), 4.36-4.33 (m, 4H), 3.55-3.35 (m, 2H), 2.73-2.53 (m, 2H), 2.50-2.36 (m, 3H), 2.27-2.23 (m, 1H), 1.95-1.79 (m, 5H), 1.61 (brs, 1H), 0.80-0.72 (m, 2H), 0.56-0.48 (m, 2H).

Example 140a and Example 140b

Synthesis of (2S,4R)-1-[5-cyclopropyl-4-[[1-[(1R)-1-(3,5-dichlorophenyl)-2,2,2-trifluoro-ethyl]-4-piperidyl]methoxy]-2-fluoro-benzoyl]-4-fluoro-pyrrolidine-2-carboxylic Acid and (2S,4R)-1-(5-cyclopropyl-4-((1-((S)-1-(3,5-dichlorophenyl)-2,2,2-trifluoroethyl)piperidin-4-yl)methoxy)-2-fluorobenzoyl)-4-fluoropyrrolidine-2-carboxylic Acid

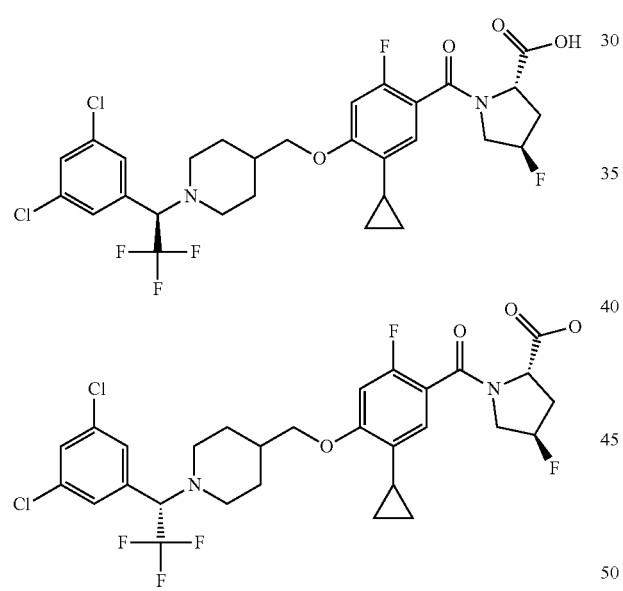

The title compounds were synthesized as described in Example 92. The enantiomer was separated by chiral SFC from mixture of diastereomers using Chiral HPLC conditions as described in Example 113. The first eluting fraction of the title compound was arbitrarily assigned: $^1$H NMR (400 MHz, DMSO-d$_6$) δ 7.71 (q, J=1.9 Hz, 1H), 7.45 (d, J=1.8 Hz, 2H), 6.89 (d, J=12.2 Hz, 1H), 6.86-6.71 (m, 1H), 5.43-5.14 (m, 1H), 4.77 (q, J=9.7 Hz, 1H), 4.47 (dd, J=9.3, 8.2 Hz, 1H), 4.00-3.80 (m, 2H), 3.09-2.92 (m, 2H), 2.38-1.89 (m, 4H), 1.86-1.62 (m, 3H), 1.46-1.28 (m, 2H), 0.93-0.78 (m, 2H), 0.66-0.50 (m, 2H); MS (ES+) m/z 635.2 (M) and the second eluting fraction was arbitrarily assigned as the tile compound: $^1$H NMR (400 MHz, DMSO-d$_6$) δ 7.71 (t, J=1.9 Hz, 1H), 7.45 (d, J=1.9 Hz, 2H), 6.89 (d, J=12.1 Hz, 1H), 6.83 (d, J=7.7 Hz, 1H), 5.31 (dd, J=53.0, 27.1 Hz, 1H), 4.76 (q, J=9.3 Hz, 1H), 4.48 (t, J=8.8 Hz, 1H), 3.95-3.81 (m, 2H), 3.81-3.43 (m, 2H), 3.11-2.92 (m, 3H), 2.39-1.92 (m, 4H), 1.86-1.65 (m, 3H), 1.48-1.28 (m, 2H), 0.92-0.77 (m, 2H), 0.66-0.51 (m, 2H); MS (ES+) m/z 635.2 (M).

Example 141

Synthesis of (S)-1-(4-(1-benzhydrylazetidin-3-yloxy)-5-cyclopropyl-2-fluorobenzoyl)pyrrolidine-2-carboxylic Acid

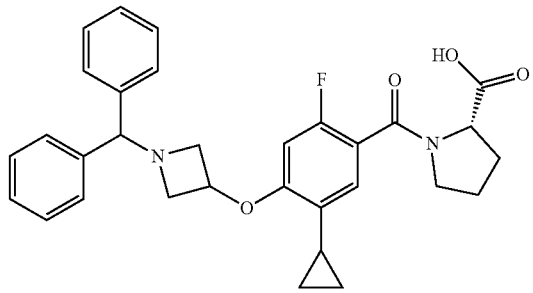 [SMILES: O=C(O)[C@@H]1CCCN1C(=O)c1cc(C2CC2)c(OC2CN(C(c3ccccc3)c3ccccc3)C2)cc1F]

The compound was synthesized as described in Example 28: LCMS (ESI) Method A: RT=5.06 min, m/z 515.2 [M+1]; $^1$H NMR (400 MHz, DMSO-d$_6$) δ 12.5 (br s, 1H), 7.46-7.44 (m, 4H), 7.31-7.27 (m, 4H), 7.21-7.17 (m, 2H), 6.79-6.59 (m, 2H), 4.94-4.89 (m, 1H), 4.54 (s, 1H), 4.34-4.07 (m, 1H), 3.71-3.49 (m, 3H), 3.27-3.23 (m, 1H), 3.01-2.99 (m, 2H), 2.26-2.21 (m, 1H), 2.09-2.03 (m, 1H), 1.91-1.78 (m, 3H), 0.94-0.88 (m, 2H), 0.64-0.56 (m, 2H).

Example 142a and Example 142b

Synthesis of (4R,5S)-3-[4-(1-adamantylmethoxy)-5-cyclopropyl-2-fluoro-benzoyl]-5-methyl-thiazolidine-4-carboxylic Acid and (4S,5S)-3-[4-(1-adamantylmethoxy)-5-cyclopropyl-2-fluoro-benzoyl]-5-methyl-thiazolidine-4-carboxylic Acid Step 1. Preparation of methyl (2 S,3R)-2-(benzenecarbonothioylamino)-3-hydroxy-butanoate

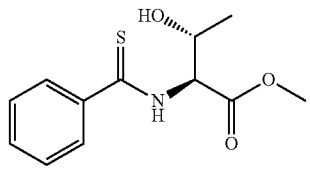 [SMILES: COC(=O)[C@@H](NC(=S)c1ccccc1)[C@@H](C)O]

Triethylamine (4.1 mL, 29 mmol) was added to a mixture of methyl (2S,3R)-2-amino-3-hydroxy-butanoate (1.4 g, 11 mmol) in pyridine (10 mL). The mixture was stirred for 5 min then 2-(benzothioylthio)acetic acid (2.4 g, 11 mmol) was added. The reaction was stirred at room temperature for 4 hours then diluted with dichloromethane (30 mL), washed with 1N hydrochloric acid (2×30 mL) and saturated aqueous solution of sodium bicarbonate (2×30 mL). The organic phase was dried with magnesium sulfate, filtered and concentrated to afford the title compound (2.38 g (89%) as a yellow solid: $^1$H NMR (400 MHz, CDCl$_3$) δ 8.20 (d, J=8.6 Hz, 1H), 7.89-7.78 (m, 2H), 7.56-7.46 (m, 1H), 7.47-7.38 (m, 2H), 5.50 (dd, J=8.6, 2.3 Hz, 1H), 4.57 (qd, J=6.5, 2.3 Hz, 1H), 3.83 (s, 3H), 1.35 (d, J=6.5 Hz, 3H); MS (ES+) m/z 253.9 (M).

Step 2. Preparation of methyl (4R,5S)-5-methyl-2-phenyl-4,5-dihydrothiazole-4-carboxylate

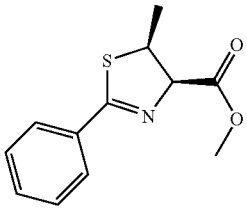 [SMILES: COC(=O)[C@H]1N=C(c2ccccc2)S[C@H]1C]

Xtalfluor-E(R) (913.2 mg, 3.95 mmol) was added to a solution of methyl (2S,3R)-2-(benzenecarbonothioylamino)-3-hydroxy-butanoate (500 mg, 1.97 mmol) in dichloromethane (20 mL) and the mixture was stirred at room temperature for 2 h. The mixture was concentrated and purified by flash chromatography (0 to 100% EtOAc/Heptane gradient) to afford the title compound (240 mg, 52%) as a yellow solid: $^1$H NMR (400 MHz, CDCl$_3$) δ 7.95-7.81 (m, 2H), 7.54-7.45 (m, 1H), 7.45-7.37 (m, 2H), 5.14 (d, J=7.6 Hz, 1H), 4.23 (dq, J=7.7, 7.0 Hz, 1H), 3.85 (s, 3H), 1.29 (d, J=7.0 Hz, 3H); MS (ES+) m/z 236.0 (M+1).

Step 3. Preparation of (3 S)-2-amino-3-sulfanyl-butanoic Acid Hydrochloride

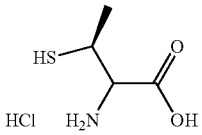

Methyl (4R,5S)-5-methyl-2-phenyl-4,5-dihydrothiazole-4-carboxylate (240 mg, 1.02 mmol) was stirred at 100° C. in 1N hydrochloric acid (5 mL) for 16 h. The reaction was then cooled down and extracted with ethyl ether (2×20 mL). The aqueous phase was concentrated to give 175 mg (99%) of (3S)-2-amino-3-sulfanyl-butanoic acid hydrochloride as a white solid. The compound was used for next step without purification.

Step 4. Preparation of (5S)-5-methylthiazolidine-4-carboxylic Acid

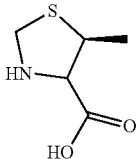

1,3,5-trioxane (275 mg, 3.06 mmol) was added to a mixture of methyl (3S)-2-amino-3-sulfanyl-butanoic acid hydrochloride (175 mg, 1.02 mmol) and triethylamine (0.28 mL, 2.04 mmol in toluene (3 mL). The mixture was stirred at 65° C. until it turned to a mostly clear solution (4 h). The mixture was concentrated to dryness and the residue was taken up in dichloromethane (15 mL). The organic phase was washed with a saturated aqueous solution of sodium bicarbonate (25 mL), dried with magnesium sulfate and concentrated to give a mixture of compounds, containing (5S)-5-methylthiazolidine-4-carboxylic acid, as a colorless oil. The mixture was carried on to next step without purification.

Step 5. Preparation of (4R,5S)-3-[4-(1-adamantylmethoxy)-5-cyclopropyl-2-fluoro-benzoyl]-5-methyl-thiazolidine-4-carboxylic Acid and (4S,5S)-3-[4-(1-adamantylmethoxy)-5-cyclopropyl-2-fluoro-benzoyl]-5-methyl-thiazolidine-4-carboxylic Acid

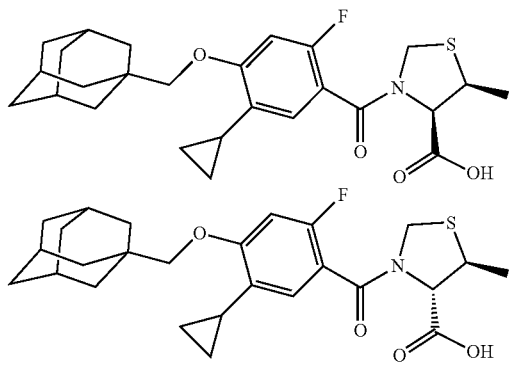

Following the procedure as described in Example 046, Step 1 and making non-critical variations as required to replace (2S,4S)-4-hydroxypyrrolidine-2-carboxylic acid with (5S)-5-methylthiazolidine-4-carboxylic acid and the residue, a mixture of diastereomers was separated by chiral SFC, the first compound obtained (4R,5S)-3-[4-(1-adamantylmethoxy)-5-cyclopropyl-2-fluoro-benzoyl]-5-methyl-thiazolidine-4-carboxylic acid as a colorless solid: $^1$H NMR (400 MHz, DMSO-d$_6$) δ 6.93-6.72 (m, 2H), 4.79 (dd, J=31.8, 8.2 Hz, 1H), 4.60 (dd, J=9.4, 3.5 Hz, 1H), 3.83 (dt, J=55.7, 6.9 Hz, 1H), 3.59 (d, J=13.0 Hz, 2H), 2.06-1.95 (m, 4H), 1.69 (d, J=20.4 Hz, 11H), 1.32 (d, J=6.9 Hz, 1H), 1.23 (d, J=6.8 Hz, 1H), 0.94-0.81 (m, 2H), 0.68-0.56 (m, 2H); MS (ES+) m/z 474.2 (M+1) and the second compound obtained (4S,5S)-3-[4-(1-adamantylmethoxy)-5-cyclopropyl-2-fluoro-benzoyl]-5-methyl-thiazolidine-4-carboxylic acid as a colorless solid: $^1$H NMR (400 MHz, DMSO-d$_6$) δ 6.95-6.77 (m, 2H), 4.94 (d, J=9.3 Hz, 1H), 4.59-4.39 (m, 1H), 4.35 (d, J=9.4 Hz, 1H), 3.84-3.70 (m, 1H), 3.60 (d, J=12.4 Hz, 2H), 2.07-1.93 (m, 4H), 1.78-1.59 (m, 11H), 1.41 (d, J=6.7 Hz, 1H), 1.26 (d, J=6.8 Hz, 2H), 0.95-0.82 (m, 2H), 0.66-0.49 (m, 2H); MS (ES+) m/z 474.2 (M+1).

Example 143

Synthesis of (4R)-3-[4-(1-adamantylmethoxy)-5-cyclopropyl-2-fluoro-benzoyl]-1,1-dioxo-1,3-thiazolidine-4-carboxylic Acid

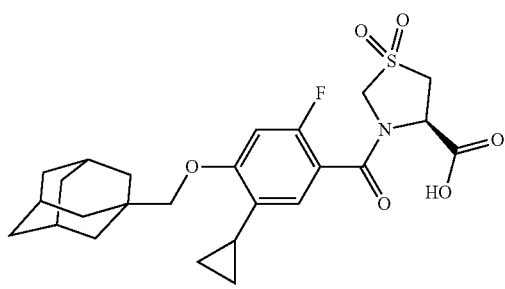 [SMILES: O=C(O)[C@@H]1CS(=O)(=O)CN1C(=O)c1cc(C2CC2)c(OCC23CC4CC(CC(C4)C2)C3)cc1F]

3-chloroperoxybenzoic acid (42.9 mg 0.17 mmol) was added to a solution of (4R)-3-[4-(1-adamantylmethoxy)-5-cyclopropyl-2-fluoro-benzoyl]thiazolidine-4-carboxylic acid (80 mg, 0.17 mmol) in dichloromethane (5 mL). The mixture was stirred at ambient temperature for 48 hours. The mixture was then diluted with dichloromethane (10 mL) and washed with a saturated aqueous solution of sodium thiosulfate. The organic phase was dried with magnesium sulfate, filtered, concentrated in vacuo. The residue was purified by reverse-phase HPLC to afford the title compound (11.3 mg, 13%) as a colorless solid: $^1$H NMR (400 MHz, DMSO-$d_6$) δ 6.90 (t, J=9.9 Hz, 2H), 5.29 (s, 1H), 4.69 (d, J=12.1 Hz, 2H), 4.49 (d, J=12.1 Hz, 2H), 3.86 (q, J=15.3, 13.6 Hz, 2H), 3.62 (dp, J=7.2, 2.7 Hz, 4H), 2.58-2.50 (m, 1H), 2.10-1.96 (m, 6H), 1.78-1.62 (m, 6H), 0.95-0.86 (m, 2H), 0.62 (s, 2H); MS (ES+) m/z 491.2 (M+1).

Example 144

Synthesis of (2S,4S)-1-[4-(1-adamantylmethoxy)-5-cyclopropyl-2-fluoro-benzoyl]-4-cyano-pyrrolidine-2-carboxylic Acid Step 1. Preparation of methyl (2S,4S)-1-(4-(((3S, 5S,7S)-adamantan-1-yl)methoxy)-5-cyclopropyl-2-fluorobenzoyl)-4-cyanopyrrolidine-2-carboxylate

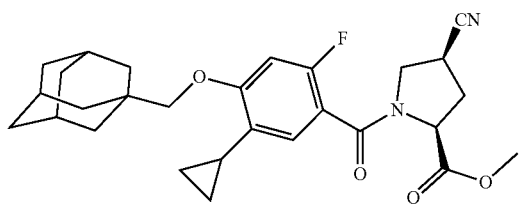 [SMILES: COC(=O)[C@@H]1C[C@H](C#N)CN1C(=O)c1cc(C2CC2)c(OCC23CC4CC(CC(C4)C2)C3)cc1F]

Following the procedure as described in Example 046, Step 2 and making non-critical variations as required to replace (2S,4S)-4-hydroxypyrrolidine-2-carboxylic acid trifluoroacetic acid salt with methyl (2S,4S)-4-cyanopyrrolidine-2-carboxylate trifluoroacetic acid, the title compound was obtained as a colorless solid: $^1$H NMR (300 MHz, CDCl$_3$) δ 7.37-7.32 (m, 3H), 6.89 (d, J=7.8 Hz, 1H), 6.32 (d, J=11.8 Hz, 1H), 5.28 (s, 0.5H), 5.11 (s, 0.5H), 4.74 (t, J=8.2 Hz, 1H), 4.10 (dd, J=13.6, 6.6 Hz, 1H), 3.90-3.52 (m, 6.5H), 3.32-3.21 (m, 1.5H), 2.76-2.62 (m, 1H), 2.45-2.18 (m, 3H), 1.98-1.78 (m, 4H), 1.73-1.60 (m, 4H), 0.84-0.74 (m, 2H), 0.58-0.45 (m, 2H); MS (ES+) m/z 582.0, 581.0 (M+1).

Step 2. Preparation of (2S,4S)-1-[4-(1-adamantyl-methoxy)-5-cyclopropyl-2-fluoro-benzoyl]-4-cyano-pyrrolidine-2-carboxylic Acid

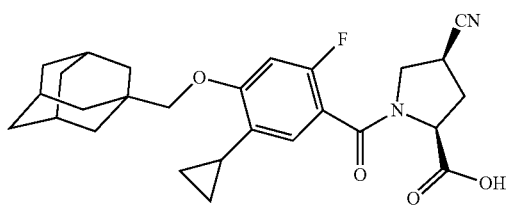 [SMILES: N#C[C@H]1C[C@@H](C(=O)O)N(C(=O)c2cc(C3CC3)c(OCC34CC5CC(CC(C5)C3)C4)cc2F)C1]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4S)-1-(4-(((3S,5S,7S)-adamantan-1-yl)methoxy)-5-cyclopropyl-2-fluorobenzoyl)-4-cyanopyrrolidine-2-carboxylate, the title compound was obtained as a colorless solid: $^1$H NMR (400 MHz, DMSO-$d_6$) δ 6.94-6.76 (m, 3H), 4.46 (q, J=8.3 Hz, 1H), 3.72 (dd, J=10.4, 7.4 Hz, 1H), 3.67-3.46 (m, 5H), 3.43 (p, J=8.0 Hz, 1H), 2.75 (dt, J=12.5, 7.9 Hz, 1H), 2.24-1.97 (m, 4H), 1.78-1.63 (m, 6H), 0.89 (ddd, J=11.0, 8.2, 4.0 Hz, 2H), 0.67-0.53 (m, 3H); MS (ES+) m/z 467.2 (M+1).

Example 145

Synthesis of (2S)-1-[4-(1-adamantylmethoxy)-5-cyclopropyl-2-fluoro-benzoyl]-4,4-difluoro-pyrrolidine-2-carboxylic Acid Step 1. Preparation of 4-(1-adamantylmethoxy)-5-cyclopropyl-2-fluoro-benzoyl Chloride

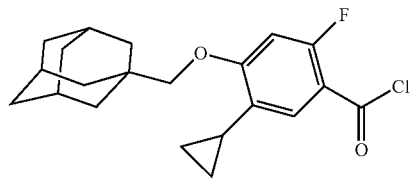 [SMILES: O=C(Cl)c1cc(C2CC2)c(OCC23CC4CC(CC(C4)C2)C3)cc1F]

Thionyl chloride (0.73 mL, 10.0 mmol) was added to a suspension of 4-(1-adamantylmethoxy)-5-cyclopropyl-2-fluoro-benzoic acid (860 mg, 2.50 mmol) in dichloromethane (5 mL). 0.5 mL of DMF was added and the mixture was stirred at room temperature for 30 minutes. The solution was then concentrated to afford the title compound (900 mg, 99.3%) as a colorless solid that was used for next step without purification.

Step 2. Preparation of (2S)-1-[4-(1-adamantyl-methoxy)-5-cyclopropyl-2-fluoro-benzoyl]-4,4-difluoro-pyrrolidine-2-carboxylic Acid

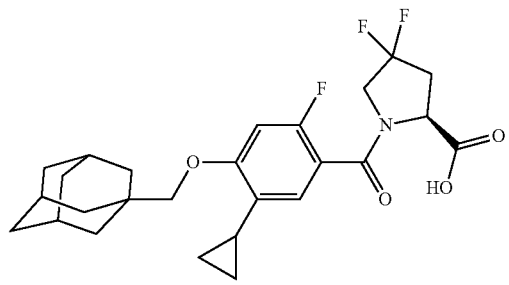 [SMILES: O=C(O)[C@@H]1CC(F)(F)CN1C(=O)c1cc(C2CC2)c(OCC23CC4CC(CC(C4)C2)C3)cc1F]

A solution of (2S)-1-(9H-fluoren-9-ylmethoxycarbonyl)-4,4-difluoro-pyrrolidine-2-carboxylic acid (155 mg, 0.41 mmol) was stirred with N,N-diisopropylethylamine (0.36 mL, 2.08 mmol) in DMF (1 mL) at 40° C. for 12 h. Then, 4-(1-adamantylmethoxy)-5-cyclopropyl-2-fluoro-benzoyl chloride (50 mg, 0.14 mmol) was added and the mixture was stirred at 40° C. for 10 min. The solvent was concentrated and purified by reverse-phase HPLC to afford the title compound (4.4 mg, 7%) as a colorless solid: $^1$H NMR (400

MHz, DMSO-d$_6$) δ 6.95-6.76 (m, 2H), 4.73-4.62 (m, 1H), 3.90-3.70 (m, 2H), 3.60 (d, J=12.0 Hz, 2H), 2.98-2.82 (m, 1H), 2.10-1.94 (m, 4H), 1.79-1.58 (m, 11H), 0.89 (t, J=9.4 Hz, 2H), 0.67-0.53 (m, 2H); MS (ES+) m/z 478.2 (M+1).

Example 146

Synthesis of (1S,2S,4R)-3-[4-(1-adamantyl-methoxy)-5-cyclopropyl-2-fluoro-benzoyl]-3-azabi-cyclo[2.2.1]heptane-2-carboxylic Acid

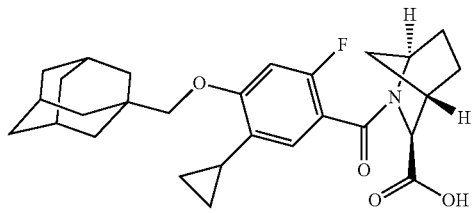 [SMILES: O=C(O)[C@@H]1[C@H]2CC[C@H](C2)N1C(=O)c1cc(C2CC2)c(OCC23CC4CC(CC(C4)C2)C3)cc1F]

4-(1-adamantylmethoxy)-5-cyclopropyl-2-fluoro-benzoyl chloride (50 mg, 0.14 mmol) dissolved in dichloromethane (3 mL) was added to a solution of (1S,2S,4R)-3-azabicyclo[2.2.1]heptane-2-carboxylic acid hydrochloride (36.7 mg, 0.21 mmol) and triethylamine (0.06 mL, 0.41 mmol) in dichloromethane (3 mL). The mixture was stirred at ambient temperature for 2 h and solvent was concentration. The residue was purified by reverse-phase HPLC to afford the title compound (25.9 mg, 50.2%) as a colorless solid: $^1$H NMR (400 MHz, DMSO-d$_6$) δ 6.87 (d, J=12.0 Hz, 1H), 6.83-6.64 (m, 1H), 3.88 (d, J=3.3 Hz, 2H), 3.65-3.53 (m, 2H), 2.59-2.51 (m, 1H), 2.10-1.89 (m, 3H), 1.77-1.43 (m, 12H), 1.32-1.25 (m, 1H), 0.95-0.81 (m, 2H), 0.65-0.51 (m, 2H); MS (ES+) m/z 468.2 (M+1).

Example 147

Synthesis of 1-[4-(1-adamantylmethoxy)-5-cyclo-propyl-2-fluoro-benzoyl]-5,5-dimethylpyrrolidine-2-carboxylic Acid

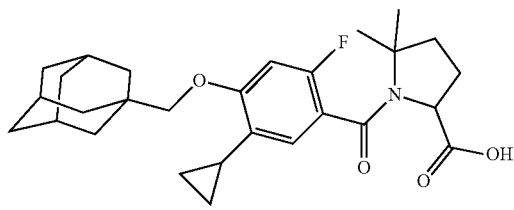 [SMILES: CC1(C)CCC(C(=O)O)N1C(=O)c1cc(C2CC2)c(OCC23CC4CC(CC(C4)C2)C3)cc1F]

Following the procedure as described in Example 145, Step 2 and making non-critical variations as required to replace (1S,2S,4R)-3-azabicyclo[2.2.1]heptane-2-carboxylic acid hydrochloride with 5,5-dimethylpyrrolidine-2-carboxylic acid, the title compound was obtained as a solid: $^1$H NMR (400 MHz, DMSO-d$_6$) δ 12.70 (s, 1H), 6.76 (d, J=11.8 Hz, 1H), 6.62 (d, J=7.8 Hz, 1H), 4.01 (d, J=8.2 Hz, 1H), 3.56 (s, 2H), 3.35 (s, 3H), 2.54 (s, 6H), 2.22-2.13 (m, 1H), 1.99 (dq, J=7.1, 4.3, 3.6 Hz, 4H), 1.86-1.63 (m, 8H), 1.56 (s, 3H), 1.43 (s, 3H), 0.93-0.82 (m, 2H), 0.55 (tt, J=5.3, 2.8 Hz, 2H): MS (ES+) m/z 470.2 (M+1).

Example 148

Synthesis of (2S,4S)-1-[4-(1-adamantylmethoxy)-5-cyclopropyl-2-fluoro-benzoyl]-4-methyl-pyrrolidine-2-carboxylic Acid

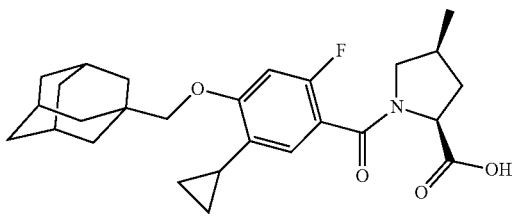 [SMILES: C[C@H]1C[C@@H](C(=O)O)N(C(=O)c2cc(C3CC3)c(OCC34CC5CC(CC(C5)C3)C4)cc2F)C1]

Following the procedure as described in Example 145, Step 2 and making non-critical variations as required to replace (1S,2S,4R)-3-azabicyclo[2.2.1]heptane-2-carboxylic acid hydrochloride with (2S,4S)-4-methylpyrrolidine-2-carboxylic acid, the title compound was obtained as a solid: $^1$H NMR (400 MHz, DMSO-d$_6$) δ 12.55 (s, 1H), 6.90-6.71 (m, 2H), 4.32 (dd, J=9.6, 7.9 Hz, 1H), 3.63-3.53 (m, 2H), 2.49-2.33 (m, 1H), 2.26-1.95 (m, 4H), 1.77-1.63 (m, 6H), 1.54-1.37 (m, 1H), 1.02 (d, J=6.6 Hz, 1H), 0.98-0.82 (m, 2H), 0.66-0.53 (m, 2H); MS (ES+) m/z 456.2 (M+1).

Example 149

Synthesis of (2S,3S)-1-[4-(1-adamantylmethoxy)-5-cyclopropyl-2-fluoro-benzoyl]-3-methyl-pyrrolidine-2-carboxylic Acid

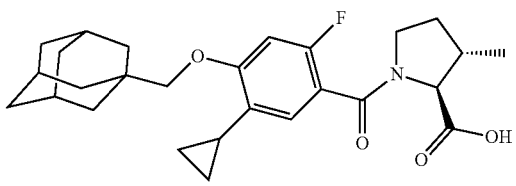 [SMILES: C[C@H]1CCN(C(=O)c2cc(C3CC3)c(OCC34CC5CC(CC(C5)C3)C4)cc2F)[C@@H]1C(=O)O]

Following the procedure as described in Example 145, Step 2 and making non-critical variations as required to replace (1S,2S,4R)-3-azabicyclo[2.2.1]heptane-2-carboxylic acid hydrochloride with (2S,3S)-3-methylpyrrolidine-2-carboxylic acid, the title compound was obtained as a solid: $^1$H NMR (400 MHz, DMSO-d$_6$) δ 12.64 (s, 1H), 6.90-6.75 (m, 2H), 3.86 (d, J=7.2 Hz, 1H), 3.71-3.54 (m, 3H), 3.49-3.31 (m, 2H), 2.37-2.18 (m, 1H), 2.01 (ddddd, J=18.4, 15.8, 12.2, 6.2, 3.9 Hz, 4H), 1.78-1.63 (m, 6H), 1.52 (dddd, J=20.8, 16.7, 11.9, 7.4 Hz, 1H), 1.15 (d, J=6.7 Hz, 3H), 1.05 (d, J=6.8 Hz, 1H), 0.98-0.81 (m, 2H), 0.58 (ddq, J=14.4, 5.4, 3.0, 2.2 Hz, 2H); MS (ES+) m/z 456.1 (M+1).

Example 150

Synthesis of (2S,4R)-1-[4-(1-adamantylmethoxy)-5-cyclopropyl-2-fluoro-benzoyl]-4-methyl-pyrrolidine-2-carboxylic Acid

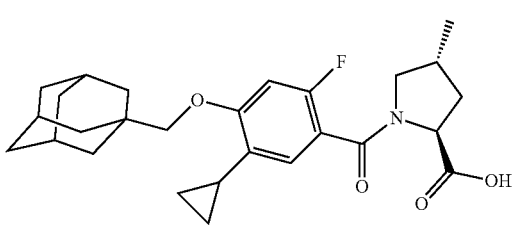 [SMILES: C[C@@H]1C[C@@H](C(=O)O)N(C(=O)c2cc(C3CC3)c(OCC34CC5CC(CC(C5)C3)C4)cc2F)C1]

Following the procedure as described in Example 145, Step 2 and making non-critical variations as required to replace (1S,2S,4R)-3-azabicyclo[2.2.1]heptane-2-carboxylic acid hydrochloride with (2S,4R)-4-methylpyrrolidine-2-carboxylic acid, the title compound was obtained as a solid: $^1$H NMR (400 MHz, DMSO-$d_6$) δ 6.86 (d, J=12.0 Hz, 1H), 6.83-6.78 (m, 1H), 4.38 (dd, J=8.8, 3.5 Hz, 1H), 3.60 (s, 2H), 3.57 (s, 1H), 3.44 (dd, J=10.0, 7.0 Hz, 1H), 2.89 (dd, J=10.1, 7.8 Hz, 1H), 2.09-1.94 (m, 6H), 1.93-1.80 (m, 1H), 1.76-1.59 (m, 12H), 1.02 (d, J=6.6 Hz, 1H), 0.92 (d, J=6.7 Hz, 3H), 0.90-0.83 (m, 2H), 0.58 (ddt, J=15.2, 5.3, 2.8 Hz, 2H); MS (ES+) m/z 456.2 (M+1).

Example 151

Synthesis of (2R)-1-[4-(1-adamantylmethoxy)-5-cyclopropyl-2-fluoro-benzoyl]-3,3-dimethylpyrrolidine-2-carboxylic Acid

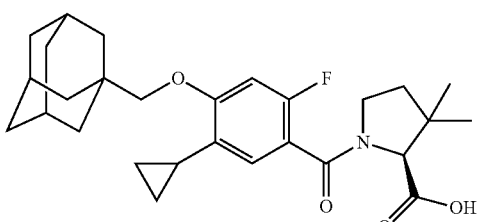

Following the procedure as described in Example 145, Step 2 and making non-critical variations as required to replace (1S,2S,4R)-3-azabicyclo[2.2.1]heptane-2-carboxylic acid hydrochloride with (S)-3,3-dimethylpyrrolidine-2-carboxylic acid, the title compound was obtained as a solid: $^1$H NMR (400 MHz, DMSO-$d_6$) δ 6.86 (d, J=12.1 Hz, 1H), 6.84-6.81 (m, 1H), 3.59 (d, J=12.2 Hz, 3H), 2.01 (d, J=16.5 Hz, 4H), 1.84-1.58 (m, 11H), 1.16 (s, 2H), 1.04 (d, J=9.1 Hz, 3H), 0.96 (s, 1H), 0.89 (ddt, J=9.6, 7.6, 4.9 Hz, 2H), 0.67-0.51 (m, 2H); MS (ES+) m/z 470.2 (M+1).

Example 152

Synthesis of (2S,5R)-1-[4-(1-adamantylmethoxy)-5-cyclopropyl-2-fluoro-benzoyl]-5-methyl-pyrrolidine-2-carboxylic Acid

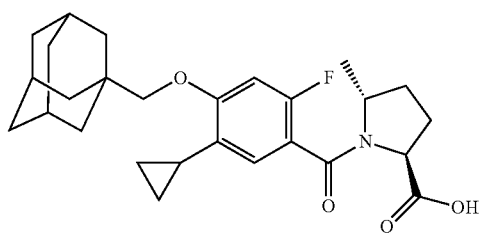 [SMILES: C[C@@H]1CC[C@@H](C(=O)O)N1C(=O)c1cc(C2CC2)c(OCC23CC4CC(CC(C4)C2)C3)cc1F]

Following the procedure as described in Example 145, Step 2 and making non-critical variations as required to replace (1S,2S,4R)-3-azabicyclo[2.2.1]heptane-2-carboxylic acid hydrochloride with (2S,5R)-5-methylpyrrolidine-2-carboxylic acid, the title compound was obtained as a solid: MS (ES+) m/z 456.2 (M+1).

Example 153

Synthesis of (2S,5S)-1-[4-(1-adamantylmethoxy)-5-cyclopropyl-2-fluoro-benzoyl]-5-methyl-pyrrolidine-2-carboxylic Acid

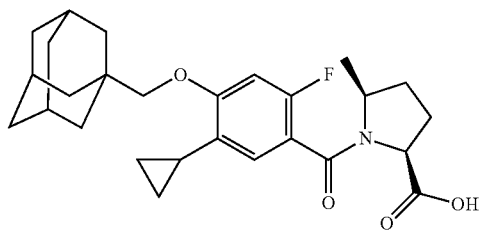 [SMILES: C[C@H]1CC[C@@H](C(=O)O)N1C(=O)c1cc(C2CC2)c(OCC23CC4CC(CC(C4)C2)C3)cc1F]

Following the procedure as described in Example 145, Step 2 and making non-critical variations as required to replace (1S,2S,4R)-3-azabicyclo[2.2.1]heptane-2-carboxylic acid hydrochloride with (2S,5S)-5-methylpyrrolidine-2-carboxylic acid, the title compound was obtained as a solid: MS (ES+) m/z 456.2 (M+1).

Example 154

Synthesis of (4R)-3-[4-(1-adamantylmethoxy)-5-cyclopropyl-2-fluoro-benzoyl]oxazolidine-4-carboxylic Acid

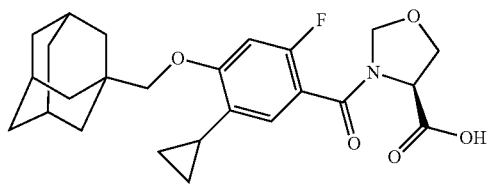 [SMILES: O=C(O)[C@@H]1COCN1C(=O)c1cc(C2CC2)c(OCC23CC4CC(CC(C4)C2)C3)cc1F]

Following the procedure as described in Example 145, Step 2 and making non-critical variations as required to replace (1S,2S,4R)-3-azabicyclo[2.2.1]heptane-2-carboxylic acid hydrochloride with (S)-oxazolidine-4-carboxylic acid, the title compound was obtained as a solid: ¹H NMR (400 MHz, DMSO-d₆) δ 13.06 (s, 1H), 6.89 (d, J=13.6 Hz, 2H), 4.80 (s, 1H), 4.33 (d, J=14.2 Hz, 1H), 3.61 (s, 2H), 2.10-1.95 (m, 4H), 1.77-1.62 (m, 10H), 0.90 (dd, J=8.5, 2.0 Hz, 2H), 0.61 (s, 2H); MS (ES+) m/z 444.2 (M+1).

Example 155

Synthesis of (4R)-3-[4-(1-adamantylmethoxy)-5-cyclopropyl-2-fluoro-benzoyl]-5,5-dimethylthiazolidine-4-carboxylic Acid

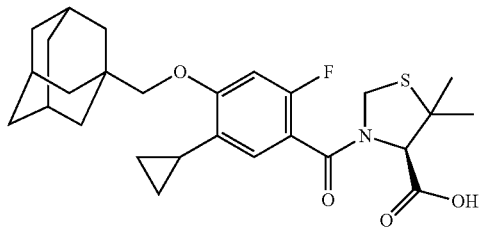 [SMILES: CC1(C)SCN(C(=O)c2cc(C3CC3)c(OCC34CC5CC(CC(C5)C3)C4)cc2F)[C@@H]1C(=O)O]

Following the procedure as described in Example 145, Step 2 and making non-critical variations as required to replace (1S,2S,4R)-3-azabicyclo[2.2.1]heptane-2-carboxylic acid hydrochloride with (R)-5,5-dimethylthiazolidine-4-carboxylic acid, the title compound was obtained as a solid: ¹H NMR (400 MHz, DMSO-d₆) δ 6.94-6.81 (m, 2H), 4.91 (d, J=9.6 Hz, 1H), 4.66 (d, J=9.7 Hz, 1H), 4.48 (d, J=9.5 Hz, 1H), 4.41 (s, 1H), 3.60 (d, J=11.7 Hz, 2H), 2.09-1.96 (m, 4H), 1.77-1.63 (m, 8H), 1.58 (s, 1H), 1.43 (d, J=3.3 Hz, 6H), 1.34 (s, 1H), 0.90 (td, J=8.3, 7.5, 5.4 Hz, 2H), 0.64 (td, J=5.8, 3.8 Hz, 1H), 0.58 (s, 1H); MS (ES+) m/z 488.2 (M+11).

Example 156

Synthesis of (1R,3S,5R)-4-[5-cyclopropyl-4-[[1-[(1S)-1-(3,5-dichlorophenyl)ethyl]-4-piperidyl]methoxy]-2-fluoro-benzoyl]-4-azabicyclo[3.1.0]hexane-3-carboxylic Acid Step 1. Preparation of 5-cyclopropyl-4-[[1-[(1S)-1-(3,5-dichlorophenyl)ethyl]-4-piperidyl]methoxy]-2-fluoro-benzoyl Chloride

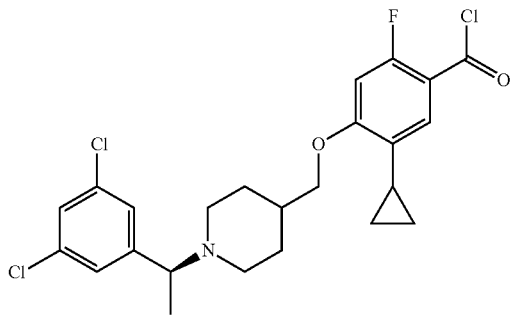 [SMILES: C[C@@H](c1cc(Cl)cc(Cl)c1)N1CCC(COc2cc(F)c(C(=O)Cl)cc2C2CC2)CC1]

Following the procedure as described in Example 145, Step 1 and making non-critical variations as required to replace 4-(1-adamantylmethoxy)-5-cyclopropyl-2-fluoro-benzoic acid with 4-(1-adamantylmethoxy)-5-cyclopropyl-2-fluoro-benzoic acid, the title compound was obtained as solid that was used directly without any further analytical characterization.

Step 2. Preparation of (1R,3S,5R)-4-[5-cyclopropyl-4-[[1-[(1S)-1-(3,5-dichlorophenyl)ethyl]-4-piperidyl]methoxy]-2-fluoro-benzoyl]-4-azabicyclo[3.1.0]hexane-3-carboxylic Acid

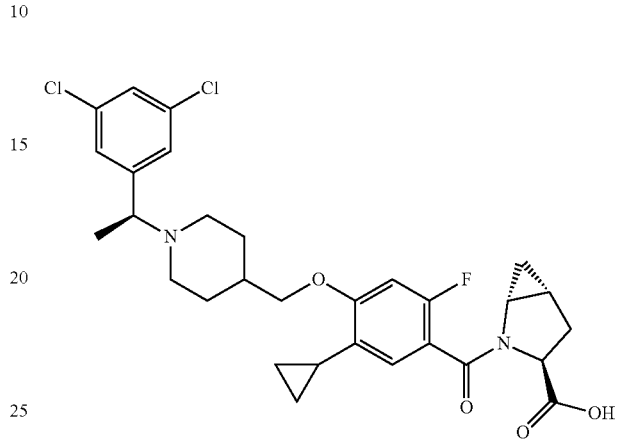

Following the procedure as described in Example 145, Step 2 and making non-critical variations as required to replace 4-(1-adamantylmethoxy)-5-cyclopropyl-2-fluoro-benzoyl chloride with 5-cyclopropyl-4-[[1-[(1S)-1-(3,5-dichlorophenyl)ethyl]-4-piperidyl]methoxy]-2-fluoro-benzoyl chloride and (1S,2S,4R)-3-azabicyclo[2.2.1]heptane-2-carboxylic acid hydrochloride with (1R,3S,5R)-2-azabicyclo[3.1.0]hexane-3-carboxylic acid, the title compound was obtained as a solid: ¹H NMR (400 MHz, DMSO-d₆) δ 7.47 (t, J=1.9 Hz, 1H), 7.36 (d, J=2.0 Hz, 2H), 6.92-6.85 (m, 2H), 4.22 (dd, J=9.2, 5.5 Hz, 1H), 3.94-3.86 (m, 2H), 3.56 (q, J=6.7 Hz, 1H), 3.15-3.06 (m, 1H), 2.93 (d, J=10.9 Hz, 1H), 2.79 (d, J=11.1 Hz, 1H), 2.37-2.26 (m, 1H), 2.16 (dt, J=12.8, 6.1 Hz, 1H), 2.08-1.85 (m, 4H), 1.83-1.65 (m, 4H), 1.41-1.31 (m, 2H), 1.30 (d, 3H), 0.89 (dd, J=8.3, 2.2 Hz, 2H), 0.73-0.53 (m, 4H); MS (ES+) m/z 575.2 (M+1).

Example 157

Synthesis of (2S,3S)-1-[5-cyclopropyl-4-[[1-[(1S)-1-(3,5-dichlorophenyl)ethyl]-4-piperidyl]methoxy]-2-fluoro-benzoyl]-3-methyl-pyrrolidine-2-carboxylic Acid

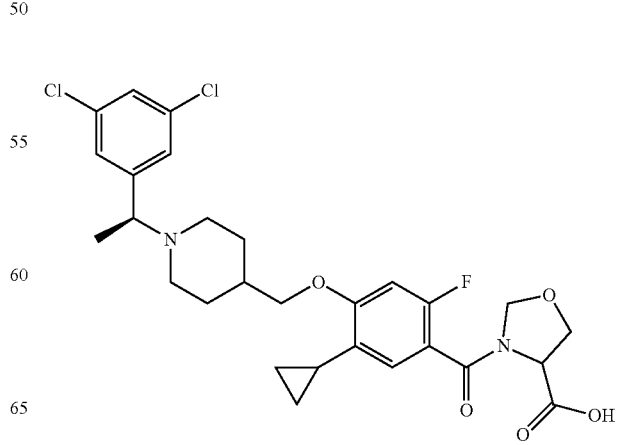

Following the procedure as described in Example 145, Step 2 and making non-critical variations as required to replace 4-(1-adamantylmethoxy)-5-cyclopropyl-2-fluoro-benzoyl chloride with 5-cyclopropyl-4-[[1-[(1S)-1-(3,5-dichlorophenyl)ethyl]-4-piperidyl]methoxy]-2-fluoro-benzoyl chloride and (1S,2S,4R)-3-azabicyclo[2.2.1]heptane-2-carboxylic acid hydrochloride with oxazolidine-4-carboxylic acid, the title compound was obtained as a solid: $^1$H NMR (4 00 MHz, DMSO-$d_6$) δ 12.57 (s, 1H), 7.46 (t, J=1.9 Hz, 1H), 7.36 (d, J=1.9 Hz, 2H), 6.91-6.76 (m, 2H), 3.87 (dd, J=14.9, 6.3 Hz, 3H), 3.67-3.50 (m, 2H), 2.93 (d, J=10.8 Hz, 1H), 2.78 (d, J=11.1 Hz, 1H), 2.27 (dq, J=15.4, 7.1, 6.6 Hz, 1H), 2.11-1.86 (m, 4H), 1.83-1.70 (m, 4H), 1.49 (dq, J=11.8, 8.4 Hz, 2H), 1.42-1.25 (m, 5H), 1.14 (d, J=6.7 Hz, 2H), 1.04 (d, J=6.8 Hz, 1H), 0.92-0.80 (m, 2H), 0.63-0.50 (m, 2H); MS (ES+) m/z 577.2 (M+1).

Example 158

Synthesis of (2S,4R)-1-[5-cyclopropyl-4-[[1-[(1S)-1-(3,5-dichlorophenyl)ethyl]-4-piperidyl]methoxy]-2-fluoro-benzoyl]-4-fluoro-pyrrolidine-2-carboxylic Acid

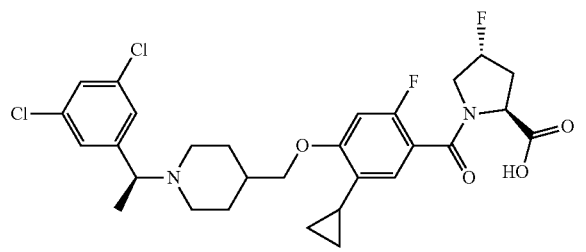 [SMILES: C[C@@H](c1cc(Cl)cc(Cl)c1)N1CCC(COc2cc(F)c(C(=O)N3C[C@H](F)C[C@H]3C(=O)O)cc2C2CC2)CC1]

Following the procedure as described in Example 145, Step 2 and making non-critical variations as required to replace 4-(1-adamantylmethoxy)-5-cyclopropyl-2-fluoro-benzoyl chloride with 5-cyclopropyl-4-[[1-[(1S)-1-(3,5-dichlorophenyl)ethyl]-4-piperidyl]methoxy]-2-fluoro-benzoyl chloride and (1S,2S,4R)-3-azabicyclo[2.2.1]heptane-2-carboxylic acid hydrochloride with (2S,4R)-4-fluoropyrrolidine-2-carboxylic acid, the title compound was obtained as a colorless solid: $^1$H NMR (400 MHz, DMSO-$d_6$) δ 7.47 (t, J=1.8 Hz, 1H), 7.36 (d, J=1.9 Hz, 2H), 6.96-6.71 (m, 2H), 5.29 (dd, J=53.3, 18.4 Hz, 1H), 4.47 (t, J=9.2, 8.1 Hz, 1H), 3.97-3.61 (m, 4H), 2.93 (d, J=10.9 Hz, 1H), 2.79 (d, J=10.9 Hz, 1H), 2.06-1.85 (m, 3H), 1.85-1.66 (m, 3H), 1.43-1.21 (m, 5H), 1.02 (t, J=7.2 Hz, 1H), 0.92-0.80 (m, 2H), 0.64-0.51 (m, 2H); MS (ES+) m/z 581.2 (M+1).

Example 159

Synthesis of (4R)-3-[5-cyclopropyl-4-[[1-[(1S)-1-(3,5-dichlorophenyl)ethyl]-4-piperidyl]methoxy]-2-fluoro-benzoyl]thiazolidine-4-carboxylic Acid

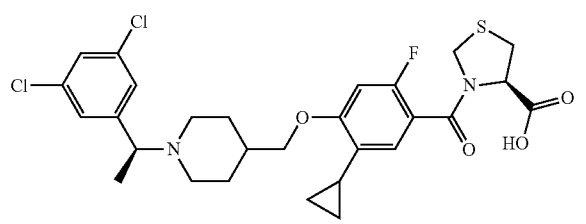 [SMILES: C[C@@H](c1cc(Cl)cc(Cl)c1)N1CCC(COc2cc(F)c(C(=O)N3CSC[C@H]3C(=O)O)cc2C2CC2)CC1]

Following the procedure as described in Example 145, Step 2 and making non-critical variations as required to replace 4-(1-adamantylmethoxy)-5-cyclopropyl-2-fluoro-benzoyl chloride with 5-cyclopropyl-4-[[1-[(1S)-1-(3,5-dichlorophenyl)ethyl]-4-piperidyl]methoxy]-2-fluoro-benzoyl chloride and (1S,2S,4R)-3-azabicyclo[2.2.1]heptane-2-carboxylic acid hydrochloride with (R)-thiazolidine-4-carboxylic acid, the title compound was obtained as a solid: $^1$H NMR (400 MHz, DMSO-$d_6$) δ 7.47 (t, J=2.0 Hz, 1H), 7.36 (d, J=2.0 Hz, 2H), 6.91 (d, J=12.3 Hz, 1H), 6.84 (s, 2H), 4.42 (s, 2H), 3.89 (s, 3H), 3.56 (q, J=6.8 Hz, 2H), 3.37 (s, 6H), 3.27 (s, 2H), 3.19 (s, 2H), 2.94 (d, J=11.0 Hz, 2H), 2.79 (d, J=11.1 Hz, 2H), 2.55 (dd, J=4.2, 2.3 Hz, 3H), 2.45 (dt, J=3.7, 1.9 Hz, 1H), 2.03-1.87 (m, 4H), 1.83-1.70 (m, 4H), 1.29 (d, J=6.7 Hz, 6H), 0.86 (d, J=8.4 Hz, 2H), 0.60 (s, 2H); MS (ES+) m/z 581.2 (M+1).

Example 160

Synthesis of (2S)-1-[4-(1-adamantylmethoxy)-5-cyclopropyl-2-fluoro-benzoyl]-4,4-difluoro-pyrrolidine-2-carboxylic Acid

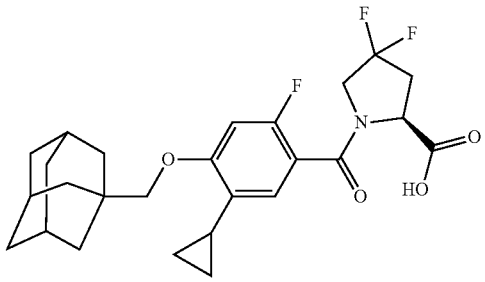 [SMILES: O=C(O)[C@@H]1CC(F)(F)CN1C(=O)c1cc(C2CC2)c(OCC23CC4CC(CC(C4)C2)C3)cc1F]

A solution of (2S)-1-(9H-fluoren-9-ylmethoxycarbonyl)-4,4-difluoro-pyrrolidine-2-carboxylic acid (155 mg, 0.41 mmol) was stirred with N,N-diisopropylethylamine (0.36 mL, 2.08 mmol) in N,N-dimethylformamide (1 mL) at 40° C. for 12 h. To this reaction mixture 4-(1-adamantyl-methoxy)-5-cyclopropyl-2-fluoro-benzoyl chloride (50 mg, 0.14 mmol) was added and the mixture was stirred at 40° C. for 10 min. The solvent was concentrated in vacuo. The residue was purified by reverse-phase HPLC to afford the title compound (4.4 mg, 7%) as a colorless solid: $^1$H NMR (400 MHz, DMSO-$d_6$) δ 6.95-6.76 (m, 2H), 4.73-4.62 (m, 1H), 3.90-3.70 (m, 2H), 3.60 (d, J=12.0 Hz, 2H), 2.98-2.82 (m, 1H), 2.10-1.94 (m, 4H), 1.79-1.58 (m, 11H), 0.89 (t, J=9.4 Hz, 2H), 0.67-0.53 (m, 2H); MS (ES+) m/z 478.2 (M+1).

Example 161

Synthesis of (2S,4S)-1-[4-(1-adamantylmethoxy)-5-cyclopropyl-2-fluoro-benzoyl]-4-hydroxy-pyrrolidine-2-carboxylic Acid

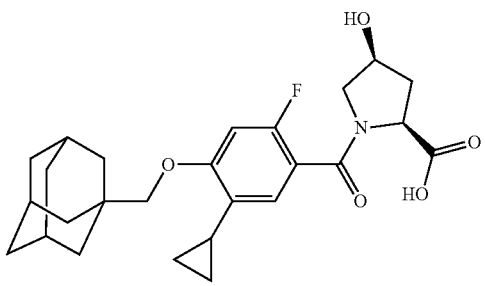 [SMILES: O=C(O)[C@@H]1C[C@H](O)CN1C(=O)c1cc(C2CC2)c(OCC23CC4CC(CC(C4)C2)C3)cc1F]

Following the procedure as described in Example 160 and making non-critical variations as required to replace (2S)-1-(9H-fluoren-9-ylmethoxycarbonyl)-4,4-difluoro-pyrrolidine-2-carboxylic with (2S,4S)-1-(((9H-fluoren-9-yl)methoxy)carbonyl)-4-hydroxypyrrolidine-2-carboxylic acid, the title compound was obtained as a colorless solid: $^1$H NMR (400 MHz, DMSO-$d_6$) δ 6.88-6.77 (m, 2H), 6.77-6.71 (m, 2H), 4.26 (dd, J=9.0, 4.4 Hz, 1H), 4.12 (dq, J=14.1, 4.7 Hz, 2H), 3.83 (d, J=9.1 Hz, 1H), 3.65-3.53 (m, 5H), 3.15 (dd, J=10.5, 3.9 Hz, 1H), 2.28 (td, J=8.7, 4.5 Hz, 1H), 2.22-2.13 (m, 1H), 2.08-1.94 (m, 4H), 0.94-0.79 (m, 4H), 0.68-0.53 (m, 1H); MS (ES+) m/z 458.2 (M+1).

Example 162

Synthesis of (4S,5R)-3-[4-(1-adamantylmethoxy)-5-cyclopropyl-2-fluoro-benzoyl]-5-methyl-oxazolidine-4-carboxylic Acid Step 1. Preparation of methyl (4S,5R)-5-methyloxazolidine-4-carboxylate

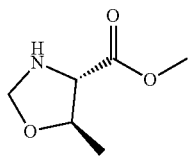

1,3,5-trioxane (797 mg, 8.84 mmol) was added to a mixture of methyl (2S,3R)-2-amino-3-hydroxy-butanoate hydrochloride (500 mg, 2.95 mmol) and triethylamine (0.82 mL, 5.89 mmol in toluene (5 mL). The mixture was stirred at 65° C. until it turned to a mostly clear solution (4 h). The mixture was concentrated to dryness and the residue was taken up in dichloromethane (15 mL). The organic phase was washed with a saturated aqueous solution of sodium bicarbonate (25 mL), dried with magnesium sulfate and concentrated in vacuo to afford the title compound as colorless oil. This residue was used in the next step without purification and analytical characterization.

Step 2. Preparation of methyl (4S, 5R)-3-[4-(1-adamantylmethoxy)-5-cyclopropyl-2-fluorobenzoyl]-5-methyl-oxazolidine-4-carboxylate

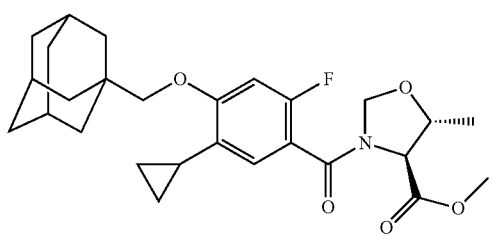 [SMILES: COC(=O)[C@@H]1[C@@H](C)OCN1C(=O)c1cc(C2CC2)c(OCC23CC4CC(CC(C4)C2)C3)cc1F]

A solution of 4-(1-adamantylmethoxy)-5-cyclopropyl-2-fluoro-benzoyl chloride (50 mg, 0.69 mmol) dissolved in acetonitrile (2 mL) was added dropwise to a solution of methyl (4S,5R)-5-methyloxazolidine-4-carboxylate (50 mg, 0.34 mmol) in a 1:1 mixture of acetonitrile (2 mL) and sodium carbonate (15 mass %) in water (2 mL). The mixture was stirred at ambient temperature for 2 hours and the solvent was concentrated in vacuo. The residue was redissolved in dichloromethane (25 mL), washed with a saturated aqueous solution of sodium bicarbonate (25 mL), dried with magnesium sulfate and concentrated in vacuo to afford the title compound (115 mg, 71%) as a colorless solid which was used in the next step without purification: MS (ES+) m/z 472.2 (M+1).

Step 3. Preparation of (4S,5R)-3-[4-(1-adamantylmethoxy)-5-cyclopropyl-2-fluoro-benzoyl]-5-methyl-oxazolidine-4-carboxylic Acid

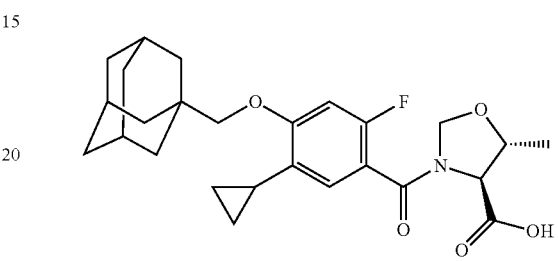

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-[4-(1-adamantylmethoxy)-5-cyclopropyl-2-fluoro-benzoyl]-5-methyl-oxazolidine-4-carboxylate and following the residue was purified by reverse-phase HPLC, the title compound was obtained as a colorless solid (110 mg, 99%): $^1$H NMR (400 MHz, DMSO-$d_6$) δ 6.97-6.69 (m, 2H), 4.81 (s, 1H), 4.26-3.96 (m, 1H), 3.59 (d, J=17.2 Hz, 2H), 1.99 (s, 3H), 1.69 (d, J=20.0 Hz, 10H), 1.39 (d, J=6.0 Hz, 1H), 1.27 (d, J=6.1 Hz, 1H), 0.90 (d, J=9.8 Hz, 2H), 0.71-0.51 (m, 2H); MS (ES+) m/z 458.2 (M+1).

Example 163

Synthesis of (4R,5S)-3-[4-(1-adamantylmethoxy)-5-cyclopropyl-2-fluoro-benzoyl]-5-methyl-oxazolidine-4-carboxylic Acid

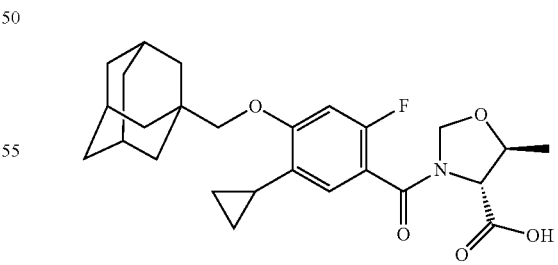

Following the procedure as described in Example 162, Step 2 and Step 3 and making non-critical variations as required to replace methyl (4S,5R)-5-methyloxazolidine-4-carboxylate with methyl (4R,5S)-5-methyloxazolidine-4-carboxylate, the title compound was obtain as a colorless solid: MS (ES+) m/z 458.2 (M+1).

Example 164

Synthesis of (4S,5R)-3-[5-cyclopropyl-4-[[1-[(1S)-1-(3,5-dichlorophenyl)ethyl]-4-piperidyl]methoxy]-2-fluoro-benzoyl]-5-methyl-oxazolidine-4-carboxylic Acid

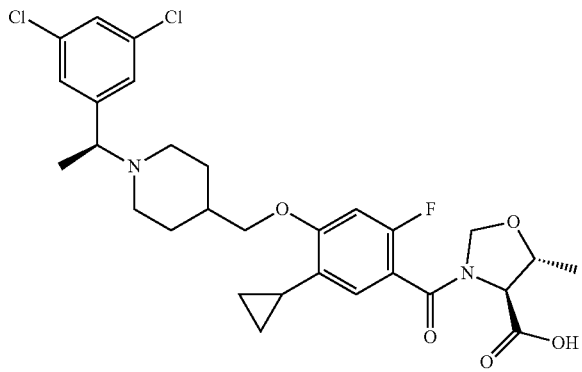 [SMILES: C[C@H]1OCN(C(=O)c2cc(C3CC3)c(OCC3CCN([C@@H](C)c4cc(Cl)cc(Cl)c4)CC3)cc2F)[C@@H]1C(=O)O]

Following the procedure as described in Example 62, Step 2 and Step 3 and making non-critical variations as required to replace 4-(1-adamantylmethoxy)-5-cyclopropyl-2-fluoro-benzoyl chloride with 5-cyclopropyl-4-[[1-[(1S)-1-(3,5-dichlorophenyl)ethyl]-4-piperidyl]methoxy]-2-fluoro-benzoyl chloride, the title compound was obtain as a colorless solid: $^1$H NMR (400 MHz, DMSO-$d_6$) δ 7.47 (t, J=1.9 Hz, 1H), 7.36 (d, J=2.0 Hz, 2H), 6.97-6.77 (m, 2H), 4.83 (s, 2H), 4.10 (dd, J=32.1, 8.0 Hz, 2H), 3.89 (d, J=12.5 Hz, 2H), 3.58 (d, J=7.0 Hz, 1H), 3.00-2.72 (m, 3H), 2.10-1.88 (m, 3H), 1.85-1.67 (m, 3H), 1.35 (dd, J=45.3, 6.3 Hz, 10H), 0.87 (d, J=8.3 Hz, 2H), 0.59 (d, J=10.5 Hz, 2H); MS (ES+) m/z 479.2 (M+1).

Example 165

Synthesis of (4S,5R)-3-[5-cyclopropyl-4-[(3,5-dichlorophenoxy)methyl]-2-fluorobenzoyl]-5-methyl-oxazolidine-4-carboxylic Acid

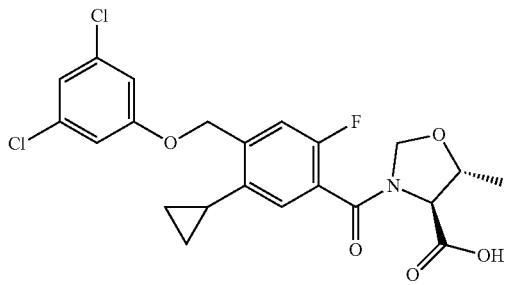 [SMILES: C[C@H]1OCN(C(=O)c2cc(C3CC3)c(COc3cc(Cl)cc(Cl)c3)cc2F)[C@@H]1C(=O)O]

Following the procedure as described in Example 162, Step 2 and Step 3 and making non-critical variations as required to replace 4-(1-adamantylmethoxy)-5-cyclopropyl-2-fluoro-benzoyl chloride with 5-cyclopropyl-4-((3,5-dichlorophenoxy)methyl)-2-fluorobenzoyl chloride, the title compound was obtain as a colorless solid: $^1$H NMR (400 MHz, DMSO-$d_6$) δ 7.39 (dd, J=30.9, 10.5 Hz, 1H), 7.25 (dd, J=3.9, 1.8 Hz, 2H), 7.23-7.18 (m, 1H), 7.05 (dd, J=10.6, 6.7 Hz, 1H), 5.32 (d, J=17.6 Hz, 2H), 4.90-4.79 (m, 1H), 4.21 (dt, J=23.3, 6.2 Hz, 1H), 4.08 (d, J=7.5 Hz, 1H), 2.10-1.92 (m, 1H), 1.42 (d, J=6.0 Hz, 3H), 1.31 (d, J=6.1 Hz, 1H), 0.93 (ddd, J=10.4, 8.3, 1.9 Hz, 2H), 0.75-0.58 (m, 2H); MS (ES+) m/z 468.1 (M+1).

Example 166

Synthesis of (4S,5R)-3-[4-(1-adamantylmethoxy)-5-cyclopropyl-2-fluoro-benzoyl]-2,5-dimethyloxazolidine-4-carboxylic Acid

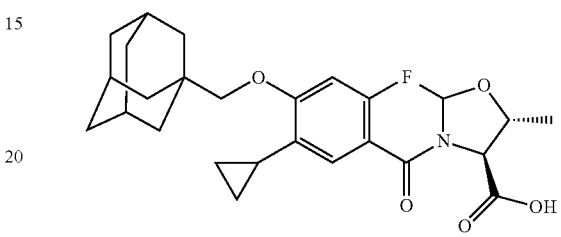

Following the procedure as described in Example 162, Step 2 and Step 3 and making non-critical variations as required to replace methyl (4S,5R)-5-methyloxazolidine-4-carboxylate with (4S,5R)-2,5-dimethyloxazolidine-4-carboxylic acid, the title compound was obtain as a colorless solid: the title compound was obtain as a colorless solid: $^1$H NMR (400 MHz, DMSO-d6) δ 6.83 (dd, J=17.0, 10.2 Hz, 2H), 5.55 (d, J=6.9 Hz, 1H), 4.52-4.34 (m, 1H), 3.59 (s, 2H), 2.02 (d, J=18.8 Hz, 4H), 1.80-1.60 (m, 11H), 1.50-1.04 (m, 6H), 0.89 (t, J=7.4 Hz, 2H), 0.59 (d, J=14.6 Hz, 2H): MS (ES+) m/z 472.2 (M+1).

Example 167

Synthesis of 1-[4-(1-adamantylmethoxy)-5-cyclopropyl-2-fluoro-benzoyl]-2,3-dihydropyrrole-5-carboxylic Acid Step 1. Preparation of methyl 1-[4-(1-adamantylmethoxy)-5-cyclopropyl-2-fluoro-benzoyl]-2,3-dihydropyrrole-5-carboxylate

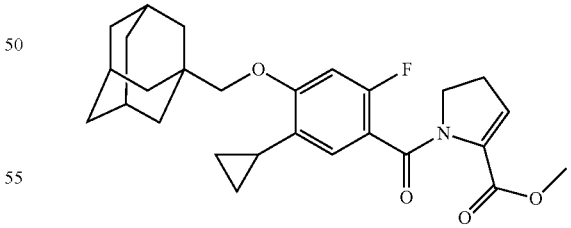

To a solution of methyl (2S)-pyrrolidine-2-carboxylate hydrochloride (300 mg, 1.81 mmol) in dichloromethane (10 mL) at 0° C. (stirring vigorously), triethylamine (0.55 mL, 3.98 mmol) was added, followed by N-chlorosuccinimide (266 mg, 1.99 mmol) in small portions. The solution was stirred at ambient temperature for 15 min. Pyridine (0.34 mL, 4.17 mmol) was then added slowly and the reaction was allowed to stir for 30 min. The mixture was cooled to −40° C. and 4-(1-adamantylmethoxy)-5-cyclopropyl-2-fluorobenzoyl chloride (1.45 g, 3.98 mmol) was added slowly. The mixture was allowed to warm up to ambient temperature and stirred for 48 hours. The mixture was diluted with dichloromethane (20 mL) and was washed with 1N hydrochloric acid and aqueous sodium bicarbonate. The organic phase was dried with magnesium sulfate, concentrated and purified by flash chromatography eluting with gradient 0 to 80% of ethyl acetate in heptane gradient to afford the title compound (215 mg, 26%) as a colorless solid: MS (ES+) m/z 454.2 (M+1).

Step 3. Preparation of 1-[4-(1-adamantylmethoxy)-5-cyclopropyl-2-fluoro-benzoyl]-2,3-dihydropyrrole-5-carboxylic Acid

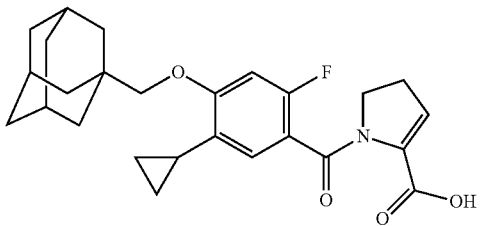 [SMILES: O=C(O)C1=CCCN1C(=O)c1cc(C2CC2)c(OCC23CC4CC(CC(C4)C2)C3)cc1F]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl 1-[4-(1-adamantylmethoxy)-5-cyclopropyl-2-fluoro-benzoyl]-2,3-dihydropyrrole-5-carboxylate and following the residue was purified by reverse-phase HPLC, the title compound was obtained as a colorless solid (25.2 mg, 69%): $^1$H NMR (400 MHz, DMSO-$d_6$) δ 12.85 (s, 1H), 6.93-6.75 (m, 2H), 6.13-5.97 (m, 1H), 5.87 (ddq, J=30.0, 6.4, 2.2 Hz, 1H), 5.14-4.77 (m, 1H), 4.35-3.95 (m, 2H), 3.66-3.55 (m, 2H), 2.10-1.96 (m, 4H), 1.78-1.63 (m, 12H), 0.89 (tdd, J=7.7, 3.9, 2.0 Hz, 2H), 0.60 (ddt, J=13.1, 5.3, 2.5 Hz, 2H); MS (ES+) m/z 440.2 (M+1).

Example 168a and Example 168b

Synthesis of (2S,3S)-1-[4-(1-adamantylmethoxy)-5-cyclopropyl-2-fluoro-benzoyl]-3-ethyl-pyrrolidine-2-carboxylic Acid and (2R,3R)-1-[4-(1-adamantylmethoxy)-5-cyclopropyl-2-fluoro-benzoyl]-3-ethyl-pyrrolidine-2-carboxylic Acid Step 1. Preparation of 1-benzyl 2-methyl 4,5-dihydro-1H-pyrrole-1,2-dicarboxylate

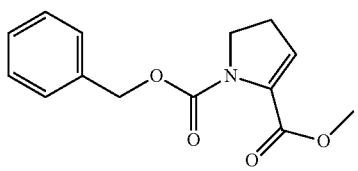 [SMILES: COC(=O)C1=CCCN1C(=O)OCc1ccccc1]

To a solution of methyl (2S)-pyrrolidine-2-carboxylate hydrochloride 2.0 g, 12 mmol) in dichloromethane (60 mL) at 0° C. (stirring vigorously), triethylamine (3.7 mL, 27 mmol) was added, followed by N-chlorosuccinimide (1.8 g, 13 mmol) in small portions. The solution was stirred at room temperature for 4 h. Pyridine (2.2 mL, 28 mmol) was then added slowly and the reaction was allowed to stir for 30 min. The mixture was cooled to −40° C. and benzyl chloroformate (3.9 mL, 27 mmol) was added slowly. The mixture was allowed to warm to ambient temperature and stirred for 48 h. The mixture was diluted with dichloromethane (20 mL) and was washed with 1N hydrochloric acid and aqueous sodium bicarbonate. The organic phase was dried with magnesium sulfate and concentrated in vacuo. The residue was purified by flash chromatography eluting with gradient 0 to 80% of ethyl acetate in heptane to afford the title compound (2.71 g, 86%) as pale yellow oil: MS (ES+) m/z 262.2 (M+1).

Step 2. Preparation of 1-benzyl 2-methyl (2S)-3-vinylpyrrolidine-1,2-dicarboxylate

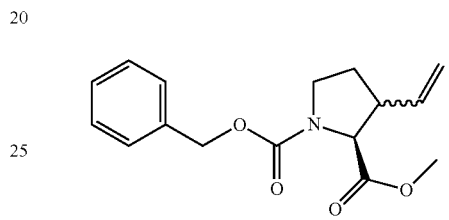

Copper (I) bromide-dimethyl sulfide (39.3 mg, 0.19 mmol) was added to a solution of vinylmagnesium chloride (0.9 mL, 1.43 mmol, 1.6 M in tetrahydrofuran) in tetrahydrofuran (5 mL) at −40° C. The mixture was stirred at −40° C. for 3 h. A solution of 1-benzyl-5-methyl 2,3-dihydropyrrole-1,5-dicarboxylate (250 mg, 0.96 mmol) in tetrahydrofuran 1.0 N (5 mL) was added dropwise to the mixture at −40° C. The reaction was warm to ambient temperature over 5 hours. The reaction was quenched with addition of saturated ammonium chloride and extracted with dichloromethane (2×20 mL). The organic phase was dried with magnesium sulfate, filtered, concentrated on silica gel and purified by flash chromatography eluting with gradient 0 to 100% of ethyl acetate in heptane to afford the title compound as pale yellow oil: MS (ES+) m/z 290.1 (M+1).

Step 3. Preparation of methyl (2S)-3-ethylpyrrolidine-2-carboxylate

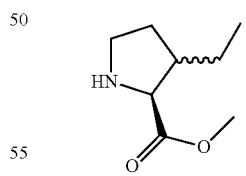

A mixture of 1-benzyl 2-methyl (2S)-3-vinylpyrrolidine-1,2-dicarboxylate (175 mg, 0.60 mmol) and palladium, 10% on carbon (64.36 mg, 0.06 mmol) in methanol (5 mL) was stirred overnight under an atmosphere of hydrogen. The mixture was then filtered over celite and washed with methanol. The filtrate was concentrated to afford the title compound (45 mg, 47%) as a colorless solid: $^1$H NMR (400 MHz, DMSO-$d_6$) δ 3.69-3.54 (m, 3H), 2.91-2.76 (m, 2H), 2.00-1.79 (m, 1H), 1.53 (tt, J=13.3, 7.4 Hz, 1H), 1.39-1.21 (m, 2H), 0.88 (td, J=7.4, 3.5 Hz, 3H).

Step 4. Preparation methyl (2S)-1-(4-(((3S,5S,7S)-adamantan-1-yl)methoxy)-5-cyclopropyl-2-fluorobenzoyl)-3-ethylpyrrolidine-2-carboxylate

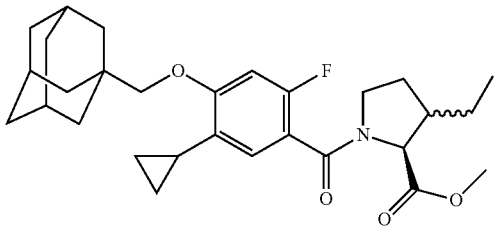 [SMILES: CCC1CCN(C(=O)c2cc(C3CC3)c(OCC34CC5CC(CC(C5)C3)C4)cc2F)[C@@H]1C(=O)OC]

A solution of methyl (2S)-3-ethylpyrrolidine-2-carboxylate (45 mg, 0.29 mmol) in N,N-dimethylformamide (1 mL) was added to a solution of 4-(1-adamantylmethoxy)-5-cyclopropyl-2-fluoro-benzoic acid (99 mg, 0.29 mmol), HATU (131 mg, 0.34 mmol) and N,N-diisopropylethylamine (0.07 mL, 0.43 mmol) in N,N-dimethylformamide (1 mL). The reaction mixture was stirred at ambient temperature for 2 hours. A saturated aqueous solution of sodium bicarbonate was then added and the aqueous phase was extracted with dichloromethane (2×15 mL). The organic phase was dried with magnesium sulfate, filtered and concentrated to afford the title compound (135 mg, 97%) as colorless oil that was carried to next step without purification.

Step 5. Preparation of (2S,3S)-1-[4-(1-adamantylmethoxy)-5-cyclopropyl-2-fluoro-benzoyl]-3-ethyl-pyrrolidine-2-carboxylic Acid and (2R,3R)-1-[4-(1-adamantylmethoxy)-5-cyclopropyl-2-fluoro-benzoyl]-3-ethyl-pyrrolidine-2-carboxylic Acid

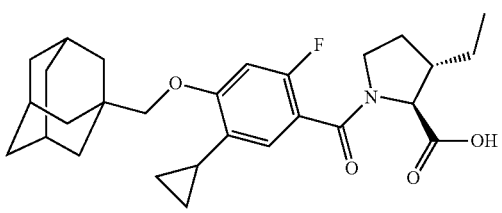

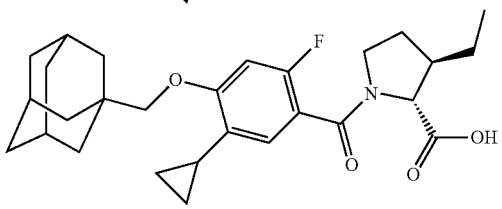

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S)-1-(4-(((3S,5S,7S)-adamantan-1-yl)methoxy)-5-cyclopropyl-2-fluorobenzoyl)-3-ethylpyrrolidine-2-carboxylate and following the residue was purified by SFC chiral separation to obtain first title compound (15.9 mg, 12%) as colorless solid: $^1$H NMR (400 MHz, DMSO-$d_6$) δ 6.94-6.75 (m, 2H), 3.95 (d, J=6.6 Hz, 1H), 3.59 (d, J=9.4 Hz, 2H), 2.21-1.89 (m, 4H), 1.80-1.58 (m, 8H), 1.56-1.30 (m, 2H), 1.05-0.76 (m, 4H), 0.67-0.45 (m, 2H); MS (ES+) m/z 470.2 (M+1) and the second compound as a colorless solid: $^1$H NMR (400 MHz, DMSO-$d_6$) δ 12.55 (s, 1H), 6.90-6.76 (m, 2H), 3.71-3.55 (m, 2H), 2.18-1.92 (m, 6H), 1.77-1.29 (m, 10H), 1.23 (d, J=5.1 Hz, 1H), 0.99-0.81 (m, 5H), 0.57 (dtd, J=19.9, 5.7, 3.8 Hz, 2H); MS (ES+) m/z 470.2 (M+1).

Example 169

Synthesis of (2S,4R)-4-chloro-1-(5-cyclopropyl-4-((1-((S)-1-(3,5-dichlorophenyl)ethyl)piperidin-4-yl)methoxy)-2-fluorobenzoyl)pyrrolidine-2-carboxylic Acid

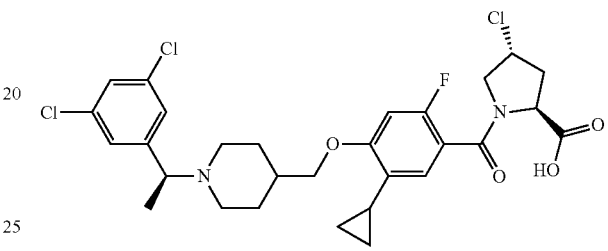

Following the procedure as described in Example 145, Step 2 and making non-critical variations as required to replace (1S,2S,4R)-3-azabicyclo[2.2.1]heptane-2-carboxylic acid hydrochloride with (2S,4R)-4-chloropyrrolidine-2-carboxylic acid, the title compound was obtained as a colorless solid (0.026 g, 10% yield): $^1$H NMR (400 MHz, DMSO-$d_6$) δ 7.46 (q, J=2.0 Hz, 1H), 7.36 (d, J=2.0 Hz, 3H), 6.90 (d, J=12.1 Hz, 1H), 6.86-6.72 (m, 2H), 6.68 (s, 1H), 4.70 (s, 2H), 4.52 (t, J=8.4 Hz, 1H), 3.93-3.73 (m, 5H), 3.61-3.50 (m, 2H), 3.39 (d, J=12.6 Hz, 1H), 2.93 (d, J=11.1 Hz, 2H), 2.78 (d, J=10.9 Hz, 2H), 2.50-2.32 (m, 3H), 2.07-1.86 (m, 5H), 1.76 (dd, J=20.4, 13.0 Hz, 5H), 1.39-1.21 (m, 9H), 0.89-0.84 (m, 3H), 0.61-0.56 (m, 3H); MS (ES−) m/z 613 (M−1).

Example 170

Synthesis (2S)-2-[[4-(1-adamantylmethoxy)-5-cyclopropyl-2-fluorobenzoyl]amino]-2-cyclobutyl-acetic Acid

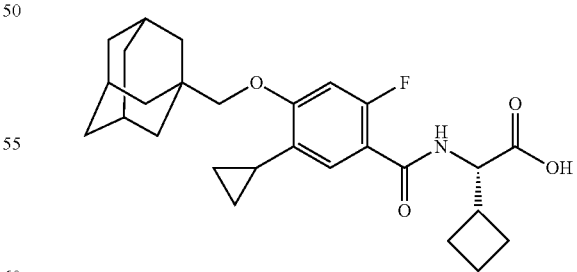

Following the procedure as described in Example 145, Step 2 and making non-critical variations as required to replace (1S,2S,4R)-3-azabicyclo[2.2.1]heptane-2-carboxylic acid hydrochloride with (S)-2-amino-2-cyclobutylacetic acid, the title compound was obtained as a colorless solid: $^1$H NMR (400 MHz, DMSO-$d_6$) δ 7.95 (dd, J=7.8, 5.1 Hz, 1H), 7.16 (d, J=8.5 Hz, 1H), 6.87 (d, J=13.2 Hz, 1H), 4.31 (t, J=8.0 Hz, 1H), 3.63 (s, 2H), 2.71 (q, J=8.2 Hz, 1H), 2.58-2.51 (m, 1H), 2.45 (p, J=1.8 Hz, 1H), 2.09-1.97 (m, 4H), 1.96-1.62 (m, 17H), 0.95-0.86 (m, 2H), 0.65-0.56 (m, 2H); MS (ES+) m/z 456.4 (M+1).

Example 171

Synthesis of 3-[4-(1-adamantylmethoxy)-5-cyclopropyl-2-fluoro-benzoyl]-3-azabicyclo[3.1.0]hexane-4-carboxylic Acid Step 1. Preparation of (1S,2S,5R)-3-azabicyclo[3.1.0]hexane-2-carboxylic Acid Trifluoroacetic Acid Salt

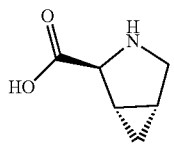

A solution of lithium diisopropylamide (0.13 mL, 0.26 mmol, 2.0 M solution in tetrahydrofuran) was added dropwise to a solution of cis-3-tert-butoxycarbonyl-3-azabicyclo[3.1.0]hexane-4-carboxylic acid (30 mg, 0.12 mmol) in tetrahydrofuran (0.6 mL) at −40° C. After 5 minutes the reaction was warmed to room temperature and stirred for 1.5 h. The reaction was quenched with 10% aqueous HCl (1 mL), extracted with ethyl acetate, dried over anhydrous sodium sulfate and concentrated in vacuo. The crude mixture of diastereomers (~1:1 by LCMS) was redissolved in dichloromethane (3 mL) and trifluoroacetic acid (0.09 mL, 1.18 mmol) was added dropwise at room temperature. After 2.5 hours the reaction was concentrated in vacuo to afford the title compound that was used in the next step without further purification.

Step 2. Preparation of 3-[4-(1-adamantylmethoxy)-5-cyclopropyl-2-fluoro-benzoyl]-3-azabicyclo[3.1.0]hexane-4-carboxylic Acid

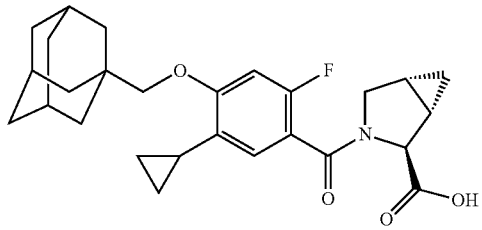 [SMILES: O=C(O)[C@@H]1[C@H]2C[C@H]2CN1C(=O)c1cc(C2CC2)c(OCC23CC4CC(CC(C4)C2)C3)cc1F]

Following the procedure as described in Example 145, Step 2 and making non-critical variations as required to replace (1S,2S,4R)-3-azabicyclo[2.2.1]heptane-2-carboxylic acid hydrochloride with (2S,4R)-4-chloropyrrolidine-2-carboxylic acid, the title compound was obtained as a colorless solid (3.2 mg, 6% yield): MS (ES+) m/z 454.3 (M+1).

Example 172

Synthesis of (2R,3R,6R)-1-(5-cyclopropyl-4-((1-((R)-1-(3,5-dichlorophenyl)ethyl)piperidin-4-yl)methoxy)-2-fluorobenzoyl)octahydrocyclopenta[b]pyrrole-2-carboxylic Acid

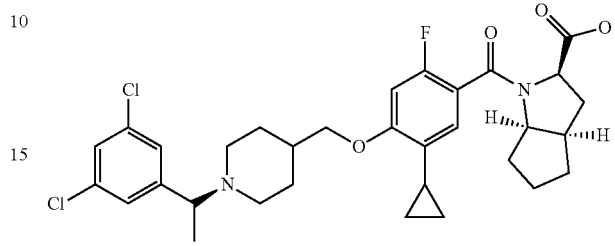

Following the procedure as described in Example 145, Step 2 and making non-critical variations as required to replace (1S,2S,4R)-3-azabicyclo[2.2.1]heptane-2-carboxylic acid hydrochloride with (2S,4R)-4-chloropyrrolidine-2-carboxylic acid, the title compound was obtained as a colorless solid (0.0064 g, 20%): MS (ES+) m/z 605.1, 603.1 (M+1).

Example 173

Synthesis of (2S,4R)-1-(4-((1-(3-chloro-5-(trifluoromethyl)benzyl)piperidin-4-yl)methoxy)-5-cyclopropyl-2-fluorobenzoyl)-4-fluoropyrrolidine-2-carboxylic Acid Step 1. Preparation of methyl 4-((1-(3-chloro-5-(trifluoromethyl)benzyl)piperidin-4-yl)methoxy)-5-cyclopropyl-2-fluorobenzoate

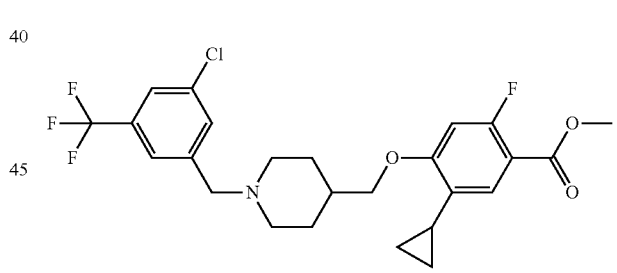

To a solution of methyl 5-cyclopropyl-2-fluoro-4-(4-piperidylmethoxy)benzoate (0.090 g, 0.29 mmol) in 4-methyl-2-pentanone (9 mL), [3-chloro-5-(trifluoromethyl)phenyl]methyl methanesulfonate (0.10 g, 0.35 mmol) was added. To this reaction mixture, water (1 mL) was added followed by potassium carbonate (0.061 g, 0.44 mmol). The reaction mixture was heated at 60° C. and stirred for 24 h. The crude solution was cooled to room temperature, diluted with water and was extracted with ethyl acetate (3×10 mL). The organic layer was separated, dried with anhydrous magnesium sulfate and concentrated in vacuo. The residue was purified by column chromatography eluting with ethyl acetate in hexanes to afford pale yellow oil (0.046 g, 32% yield): $^1$H NMR (400 MHz, CDCl$_3$) δ 7.57-7.41 (m, 4H), 6.54 (d, J=12.7 Hz, 1H), 3.92-3.83 (m, 5H), 3.53 (s, 2H), 2.90 (dt, J=11.2, 2.9 Hz, 2H), 2.13-1.97 (m, 3H), 1.98-1.80 (m, 3H), 1.56-1.41 (m, 2H), 1.26 (s, 1H), 0.95-0.82 (m, 2H), 0.71-0.60 (m, 2H).

Step 4. Preparation of 4-((1-(3-chloro-5-(trifluoromethyl)benzyl)piperidin-4-yl)methoxy)-5-cyclopropyl-2-fluorobenzoic Acid

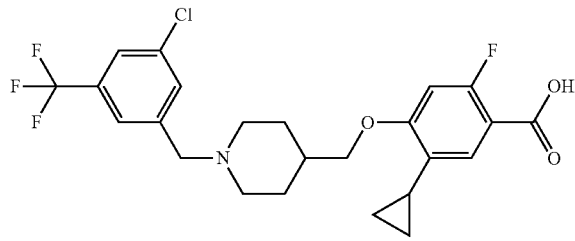 [SMILES: O=C(O)c1cc(C2CC2)c(OCC2CCN(Cc3cc(Cl)cc(C(F)(F)F)c3)CC2)cc1F]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl 4-[[1-[[3-chloro-5-(trifluoromethyl)phenyl]methyl]-4-piperidyl]methoxy]-5-cyclopropyl-2-fluoro-benzoate, the title compound (0.48 g, 95% yield) was obtained as a colorless solid: MS (ES−) m/z 484 (M−1).

Step 5. Preparation of 4-((1-(3-chloro-5-(trifluoromethyl)benzyl)piperidin-4-yl)methoxy)-5-cyclopropyl-2-fluorobenzoyl Chloride

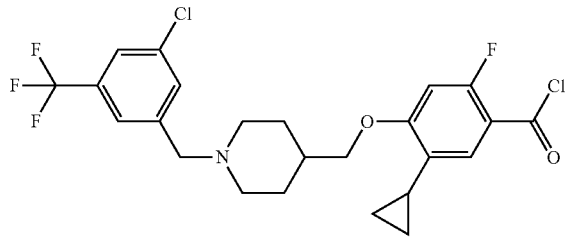 [SMILES: O=C(Cl)c1cc(C2CC2)c(OCC2CCN(Cc3cc(Cl)cc(C(F)(F)F)c3)CC2)cc1F]

Following the procedure as described in Example 046, Step 1 and making non-critical variations as required to replace 4-(1-adamantylmethoxy)-5-cyclopropyl-2-fluorobenzoic acid with 4-((1-(3-chloro-5-(trifluoromethyl)benzyl)piperidin-4-yl)methoxy)-5-cyclopropyl-2-fluorobenzoic acid, the title compound was obtained as a pale yellow solid that was used in the next step without purification.

Step 6. Preparation of (2S,4R)-1-(4-((1-(3-chloro-5-(trifluoromethyl)benzyl)piperidin-4-yl)methoxy)-5-cyclopropyl-2-fluorobenzoyl)-4-fluoropyrrolidine-2-carboxylic Acid

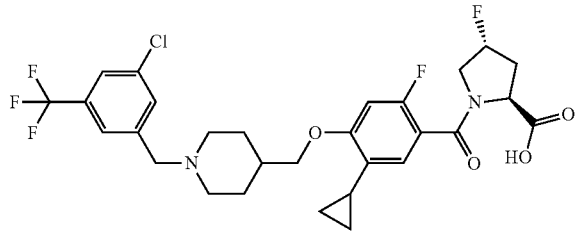 [SMILES: O=C(O)[C@@H]1C[C@@H](F)CN1C(=O)c1cc(C2CC2)c(OCC2CCN(Cc3cc(Cl)cc(C(F)(F)F)c3)CC2)cc1F]

Following the procedure as described in Example 046, Step 2 and making non-critical variations as required to replace 4-(1-adamantylmethoxy)-5-cyclopropyl-2-fluorobenzoyl chloride with 4-((1-(3-chloro-5-(trifluoromethyl)benzyl)piperidin-4-yl)methoxy)-5-cyclopropyl-2-fluorobenzoyl chloride and (2S,4S)-4-hydroxypyrrolidine-2-carboxylic acid trifluoroacetic acid salt with (2S,4R)-4-fluoropyrrolidine-2-carboxylic acid hydrochloric acid salt, the title compound (0.009 g, 29% yield) was obtained as a colorless solid: $^1$H NMR (400 MHz, DMSO-$d_6$) δ 12.77 (s, 1H), 7.24 (s, 2H), 7.11 (s, 2H), 6.84 (d, J=8.0 Hz, 4H), 4.49 (dd, J=9.4, 8.1 Hz, 1H), 3.94 (s, 2H), 3.71-3.55 (m, 2H), 3.53-3.32 (m, 24H), 3.27 (s, 1H), 2.84 (s, 1H), 2.67 (t, J=1.9 Hz, 1H), 2.54 (d, J=2.4 Hz, 4H), 2.03 (ddd, J=14.1, 8.6, 5.4 Hz, 2H), 1.82 (s, 4H), 1.41 (s, 2H), 1.29-1.21 (m, 1H), 0.87 (ddt, J=9.2, 6.3, 4.5 Hz, 2H), 0.60 (tt, J=8.7, 4.3 Hz, 2H); MS (ES+) m/z 601.2 (M+1).

Example 174

Synthesis of (2S,4R)-1-(5-cyclopropyl-4-((1-(2,4-dichlorobenzyl)piperidin-4-yl)methoxy)-2-fluorobenzoyl)-4-fluoropyrrolidine-2-carboxylic Acid

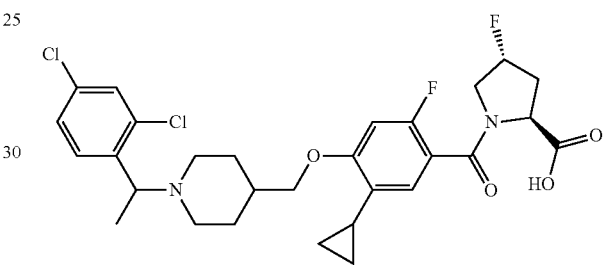

Following the procedure as described in Example 173, Step 2-6, and making non-critical variations as required to replace (3-chloro-5-(trifluoromethyl)phenyl)methanol in Step 2 with (2,4-dichlorophenyl)methanol, the title compound was obtained as a colorless solid (0.042 g, 43% yield): $^1$H NMR (400 MHz, DMSO-$d_6$) δ 12.75 (s, 1H), 7.61-7.54 (m, 2H), 7.43 (dd, J=8.4, 2.2 Hz, 1H), 6.96-6.78 (m, 2H), 6.51 (s, 1H), 4.49 (dd, J=9.5, 8.1 Hz, 1H), 3.89 (dt, J=14.2, 5.0 Hz, 3H), 3.13 (d, J=10.3 Hz, 1H), 2.72 (d, J=13.2 Hz, 1H), 2.66-2.51 (m, 1H), 2.28-1.93 (m, 3H), 1.83 (t, J=15.1 Hz, 2H), 1.71 (d, J=12.8 Hz, 1H), 1.42-1.34 (m, 1H), 1.29-1.20 (m, 4H), 0.87 (ddd, J=8.6, 4.5, 1.9 Hz, 2H), 0.58 (ddq, J=10.4, 5.3, 2.8, 1.9 Hz, 2H); MS (ES+) m/z 581 (M+1).

Example 175

Synthesis of (2S,4R)-1-(5-cyclopropyl-4-((1-(3,4-dichlorobenzyl)piperidin-4-yl)methoxy)-2-fluorobenzoyl)-4-fluoropyrrolidine-2-carboxylic Acid

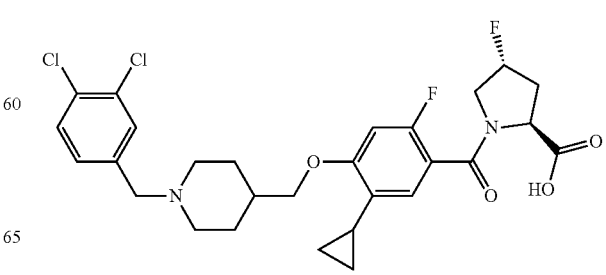

Following the procedure as described in Example 173, Step 2-6, and making non-critical variations as required to replace (3-chloro-5-(trifluoromethyl)phenyl)methanol in Step 2 with (3,4-dichlorophenyl)methanol, the title compound (0.016 g, 50% yield) was obtained as a colorless solid: MS (ES−) m/z 579 (M−1).

Example 176

Synthesis of 3-[4-(1-adamantylmethoxy)-5-cyclopropyl-2-fluoro-benzoyl]-3-azabicyclo[2.1.1]hexane-4-carboxylic Acid

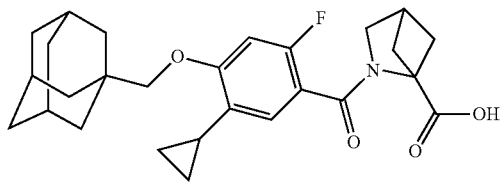 [SMILES: O=C(c1cc(C2CC2)c(OCC23CC4CC(CC(C4)C2)C3)cc1F)N1CC2CC1(C(=O)O)C2]

Following the procedure as described in Example 046, Step 2 and making non-critical variations as required to replace 4-(1-adamantylmethoxy)-5-cyclopropyl-2-fluorobenzoyl chloride with 4-((1-(3-chloro-5-(trifluoromethyl)benzyl)piperidin-4-yl)methoxy)-5-cyclopropyl-2-fluorobenzoyl chloride and (2S,4S)-4-hydroxypyrrolidine-2-carboxylic acid trifluoroacetic acid salt with 2-azabicyclo[2.1.1]hexane-1-carboxylic acid, the title compound was obtained as a colorless solid (0.009 g, 29% yield): $^1$H NMR (400 MHz, DMSO-$d_6$) δ 6.95 (d, J=8.0 Hz, 1H), 6.87 (d, J=10.2 Hz, 1H), 2.71-2.65 (m, 2H), 2.09-1.95 (m, 6H), 1.79-1.55 (m, 10H), 0.93 (t, J=7.1 Hz, 1H), 0.89 (d, J=8.6 Hz, 2H), 0.66-0.59 (m, 2H); MS (ES+) m/z 454.2 (M+1).

Example 177

Synthesis of (2S,4R,5S)-1-[4-(1-adamantyl-methoxy)-5-cyclopropyl-2-fluorobenzoyl]-4-fluoro-5-methyl-pyrrolidine-2-carboxylic Acid

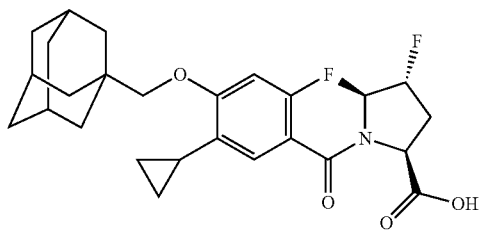 [SMILES: C[C@H]1[C@H](F)C[C@@H](C(=O)O)N1C(=O)c1cc(C2CC2)c(OCC23CC4CC(CC(C4)C2)C3)cc1F]

Following the procedure as described in Example 046, Step 2 and making non-critical variations as required to replace 4-(1-adamantylmethoxy)-5-cyclopropyl-2-fluorobenzoyl chloride with 4-((1-(3-chloro-5-(trifluoromethyl)benzyl)piperidin-4-yl)methoxy)-5-cyclopropyl-2-fluorobenzoyl chloride and (2S,4S)-4-hydroxypyrrolidine-2-carboxylic acid trifluoroacetic acid salt with 2(2S,4R,5S)-4-fluoro-5-methylpyrrolidine-2-carboxylic acid trifluoroacetic acid, the title compound was obtained as a colorless solid: $^1$H NMR (400 MHz, DMSO-$d_6$) δ 6.95-6.65 (m, 3H), 5.04 (d, J=3.6 Hz, 1H), 4.91 (d, J=3.6 Hz, 1H), 4.44 (t, J=8.9 Hz, 1H), 4.37-4.22 (m, 1H), 4.05 (s, 1H), 3.77 (dd, J=19.2, 7.3 Hz, 1H), 3.58 (d, J=18.7 Hz, 2H), 2.35-2.12 (m, 1H), 2.09-1.93 (m, 4H), 1.80-1.60 (m, 10H), 1.20 (d, J=6.9 Hz, 1H), 0.99-0.81 (m, 2H), 0.57 (dq, J=7.7, 4.6 Hz, 2H); MS (ES+) m/z 474.2 (M+1).

Example 178

Synthesis of (2R)-3-[4-(1-adamantylmethoxy)-5-cyclopropyl-2-fluoro-benzoyl]-3-azabicyclo[2.1.1]hexane-2-carboxylic Acid

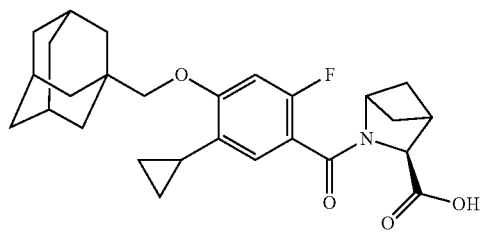 [SMILES: O=C(O)[C@@H]1C2CC(C2)N1C(=O)c1cc(C2CC2)c(OCC23CC4CC(CC(C4)C2)C3)cc1F]

Following the procedure as described in Example 046, Step 2 and making non-critical variations as required to replace 4-(1-adamantylmethoxy)-5-cyclopropyl-2-fluorobenzoyl chloride with 4-((1-(3-chloro-5-(trifluoromethyl)benzyl)piperidin-4-yl)methoxy)-5-cyclopropyl-2-fluorobenzoyl chloride and (2S,4S)-4-hydroxypyrrolidine-2-carboxylic acid trifluoroacetic acid salt with (S)-2-azabicyclo[2.1.1]hexane-3-carboxylic acid trifluoroacetic acid, the title compound was obtained as a colorless solid: $^1$H NMR (400 MHz, DMSO-$d_6$) δ 6.91-6.80 (m, 2H), 4.30 (s, 1H), 4.01-3.91 (m, 1H), 3.65-3.52 (m, 2H), 2.08-1.95 (m, 4H), 1.93-1.84 (m, 1H), 1.77-1.60 (m, 11H), 1.45 (dt, J=10.4, 5.4 Hz, 1H), 0.95-0.80 (m, 2H), 0.65-0.52 (m, 2H); MS (ES+) m/z 454.2 (M+1).

Example 179

Synthesis of (S)-1-(4-((5-chloro-6-isopropoxypyridin-3-yl)oxy)-2-fluoro-5-(2-methoxypyridin-3-yl)benzoyl)pyrrolidine-2-carboxylic Acid Step 1. Preparation of (S)-tert-butyl (4-((5-chloro-6-isopropoxypyridin-3-yl)oxy)-2-fluoro-5-(2-methoxypyridin-3-yl)benzyl)pyrrolidine-2-carboxylate

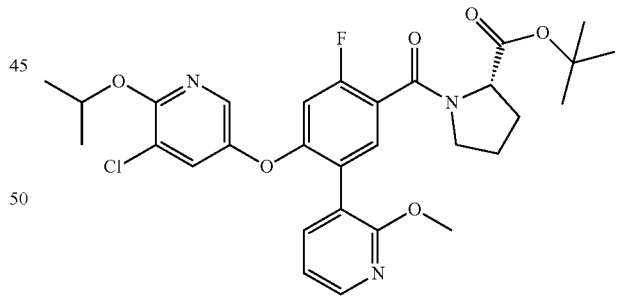

Following the procedure as described in Example 1, Step 1 and making variation as required to replace 4-((adamantan-1-yl)methoxy)-5-cyclopropyl-2-fluorobenzoic acid with 4-((5-chloro-6-isopropoxypyridin-3-yl)oxy)-2-fluoro-5-(2-methoxypyridin-3-yl)benzoic acid and (S)-tert-butyl pyrrolidine-2-carboxylate hydrochloride with (S)-tert-butyl pyrrolidine-2-carboxylate hydrochloride, the title compound was obtained as a colorless syrup (0.091 g, 20% yield): $^1$H NMR (300 MHz, CDCl$_3$) δ 8.16-8.12 (m, 1H), 7.78-7.75 (m, 1H), 7.54-7.48 (m, 1H), 7.44-7.31 (m, 2H), 6.94-6.89 (m, 1H), 6.58-6.53 (m, 1H), 5.32-5.19 (m, 1H), 4.50 (dd, J=4.6, 8.3 Hz, 0.7H), 4.28 (dd, J=2.8, 8.4 Hz, 0.3H), 3.91-3.47 (m, 5H), 2.32-2.20 (m, 1.3H), 2.05-1.85 (m, 2.7H), 1.46 (s, 6H), 1.36 (d, J=6.2 Hz, 6H), 1.26 (s, 3H) (2:1 mix of rotamers); MS (ES+) m/z: 586.1, 588.1 (M+1).

Step 2. Preparation of (S)-1-(4-((5-chloro-6-isopropoxypyridin-3-yl)oxy)-2-fluoro-5-(2-methoxypyridin-3-yl)benzoyl)pyrrolidine-2-carboxylic Acid

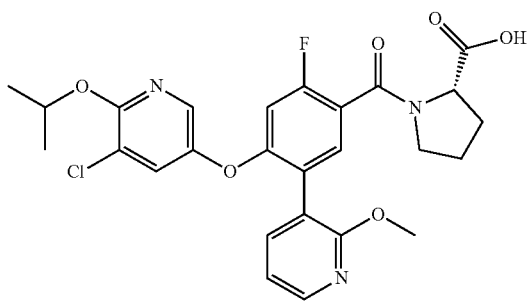 [SMILES: COc1ncccc1-c1cc(C(=O)N2CCC[C@H]2C(=O)O)c(F)cc1Oc1cnc(OC(C)C)c(Cl)c1]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl (4-((5-chloro-6-isopropoxypyridin-3-yl)oxy)-2-fluoro-5-(2-methoxypyridin-3-yl)benzoyl)pyrrolidine-2-carboxylate, the title compound was obtained as a colorless solid (0.09 g, 75% yield): $^1$H NMR (300 MHz, CDCl$_3$) δ 8.22 (dd, J=1.7, 5.2 Hz, 1H), 7.80 (d, J=2.6 Hz, 1H), 7.62 (dd, J=1.8, 7.3 Hz, 1H), 7.44 (d, J=7.6 Hz, 1H), 7.37 (d, J=2.6 Hz, 1H), 7.01 (dd, J=5.2, 7.2 Hz, 1H), 6.58 (d, J=10.8 Hz, 1H), 6.11 (br s, 3H), 5.31-5.23 (m, 1H), 4.74 (dd, J=4.4, 8.2 Hz, 1H), 3.91 (s, 3H), 3.59-3.55 (m, 2H), 2.44-2.18 (m, 2H), 2.10-1.90 (m, 2H), 1.38 (d, J=6.2 Hz, 6H); MS (ES+) m/z 529.9, 531.9 (M+1).

Example 180

Synthesis of (S)-1-(5-chloro-4-(((5-chloro-6-(2,2,3,3-tetrafluoropropoxy)pyridin-3-yl)oxy)methyl)-2-fluorobenzoyl)pyrrolidine-2-carboxylic Acid Step 1. Preparation of (S)-tert-butyl 1-(5-chloro-4-(((5-chloro-6-(2,2,3,3-tetrafluoro-propoxy)pyridin-3-yl)oxy)methyl)-2-fluorobenzoyl)pyrrolidine-2-carboxylate

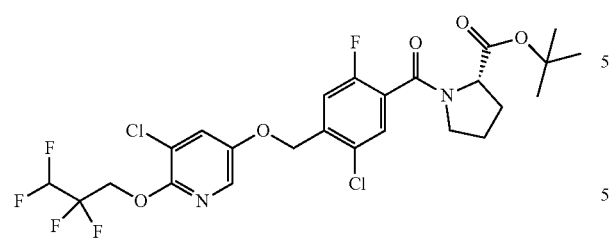

To a solution of 5-chloro-4-(((5-chloro-6-(2,2,3,3-tetrafluoropropoxy)pyridin-3-yl)oxy)methyl)-2-fluorobenzoic acid (0.15 g, 0.34 mmol) in anhydrous acetonitrile (8 mL) were added O-(benzotriazol-1-yl)-N,N,N',N'-tetramethyluronium tetrafluoroborate (0.34 g, 1.1 mmol), hydroxybenzotriazole (0.090 g, 0.67 mmol), N,N-diisoprypylethylamine (0.29 mL, 1.7 mmol), and (S)-tert-butyl pyrrolidine-2-carboxylate hydrochloride (0.14 g, 0.68 mmol). The solution was stirred at ambient temperature for 17 h, then diluted with ethyl acetate (100 mL) and washed with 1 M hydrochloric acid (2×100 mL) and brine (2×100 mL). The organic layer was dried over anhydrous magnesium sulfate, filtered, and concentrated in vacuo. The residue was purified by column chromatography eluting with a 0-30% gradient of ethyl acetate in hexanes to afford the title compound as a colorless syrup (0.14 g, 67% yield): $^1$H NMR (300 MHz, CDCl$_3$) δ 7.76-7.74 (m, 1H), 7.49 (d, J=5.8 Hz, 0.7H), 7.42-7.24 (m, 2.3H), 6.05 (tt, J=4.9, 53.1 Hz, 1H), 5.10-5.08 (m, 2H), 4.73-4.65 (m, 2H), 4.50 (dd, J=4.2, 8.3 Hz, 0.7H), 4.14-4.11 (m, 0.3H), 3.83-3.68 (m, 0.6H), 3.54-3.46 (m, 0.7H), 3.42-3.34 (m, 0.7H), 2.32-2.23 (m, 1H), 2.06-1.85 (m, 3H), 1.47 (s, 6H), 1.29 (s, 3H) (2:1 mix of rotamers); MS (ES+) m/z: 599.0, 601.0 (M+1).

Step 2. Preparation of (S)-1-(5-chloro-4-(((5-chloro-6-(2,2,3,3-tetrafluoropropoxy)pyridin-3-yl)oxy)methyl)-2-fluorobenzoyl)pyrrolidine-2-carboxylic Acid

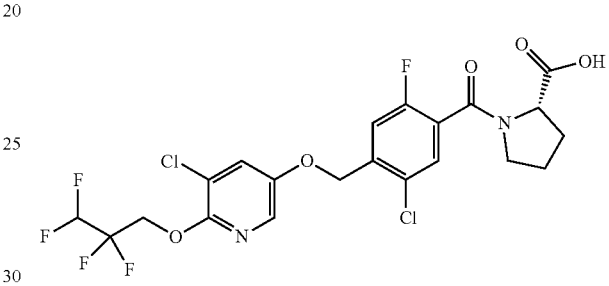

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(5-chloro-4-(((5-chloro-6-(2,2,3,3-tetrafluoropropoxy)pyridin-3-yl)oxy)methyl)-2-fluorobenzoyl)pyrrolidine-2-carboxylate, the title compound was obtained as a colorless solid (0.12 g, 80%): $^1$H NMR (300 MHz, CDCl$_3$) δ 7.77 (d, J=2.7 Hz, 1H), 7.52 (d, J=5.8 Hz, 1H), 7.43 (d, J=2.7 Hz, 1H), 7.35 (d, J=9.7 Hz, 1H), 6.06 (tt, J=4.9, 4.9, 53.1, 53.1 Hz, 1H), 5.68 (br s, 2H), 5.11 (s, 2H), 4.74-4.66 (m, 3H), 3.51-3.44 (m, 2H), 2.34-2.26 (m, 2H), 2.13-1.88 (m, 2H); MS (ES+) m/z 543.0, 544.9 (M+1).

Example 181

Synthesis of (S)-1-(4-((1-(5-chloro-2-(trifluoromethyl)benzyl)piperidin-4-yl)methoxy)-5-cyclopropyl-2-fluorobenzoyl)pyrrolidine-2-carboxylic Acid Step 1. Preparation of (S)-tert-butyl 1-(4-((1-(5-chloro-2-(trifluoromethyl)benzyl)piperidin-4-yl)methoxy)-5-cyclopropyl-2-fluorobenzoyl)pyrrolidine-2-carboxylate

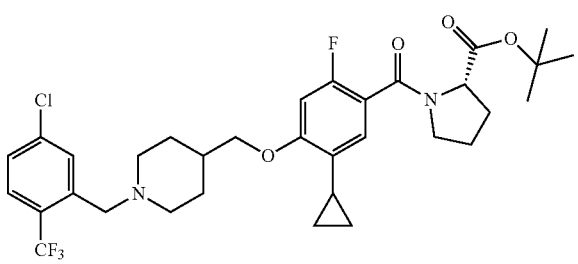 [SMILES: CC(C)(C)OC(=O)[C@@H]1CCCN1C(=O)c1cc(C2CC2)c(OCC2CCN(Cc3cc(Cl)ccc3C(F)(F)F)CC2)cc1F]

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 4-((1-(5-chloro-2-(trifluoromethyl)benzyl)piperidin-4-yl)methoxy)-5-cyclopropyl-2-fluorobenzoic acid, the title compound was obtained as a colorless syrup (0.15 g, 23% yield): $^1$H NMR (300 MHz, CDCl$_3$) δ 7.78 (s, 1H), 7.45-7.38 (m, 2H), 6.91 (d, J=7.8 Hz, 0.7H), 6.84 (d, J=7.9 Hz, 0.3H), 6.52-6.45 (m, 1H), 4.46 (dd, J=5.1, 8.3 Hz, 0.7H), 4.21-4.18 (m, 0.3H), 3.84-3.70 (m, 3H), 3.64 (s, 2H), 3.55-3.47 (m, 0.7H), 3.41-3.32 (m, 0.7H), 3.12-3.04 (m, 0.6H), 2.94-2.90 (m, 2H), 2.30-2.13 (m, 3H), 1.99-1.81 (m, 8H), 1.46 (s, 6H), 1.25 (s, 3H), 0.88-0.79 (m, 2H), 0.61-0.53 (m, 2H) (2:1 mix of rotamers); MS (ES+) m/z 639.1, 641.1 (M+1).

Step 2. Preparation of (S)-1-(4-((1-(5-chloro-2-(trifluoromethyl)benzyl)piperidin-4-yl)methoxy)-5-cyclopropyl-2-fluorobenzoyl)pyrrolidine-2-carboxylic Acid

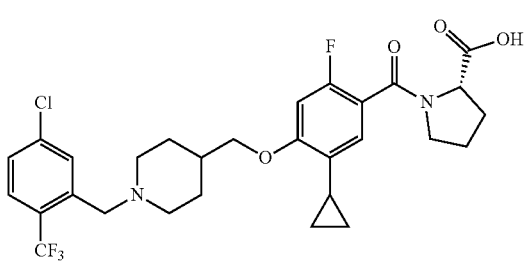 [SMILES: O=C(O)[C@@H]1CCCN1C(=O)c1cc(C2CC2)c(OCC2CCN(Cc3cc(Cl)ccc3C(F)(F)F)CC2)cc1F]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-((1-(5-chloro-2-(trifluoromethyl)benzyl)piperidin-4-yl)methoxy)-5-cyclopropyl-2-fluorobenzoyl)pyrrolidine-2-carboxylate, the title compound was obtained following purification by reverse-phase HPLC as colorless solid (0.098 g, 59% yield): $^1$H NMR (300 MHz, CDCl$_3$) δ 12.11 (br s, 1H), 8.01 (s, 1H), 7.66-7.58 (m, 2H), 6.89 (d, J=7.4 Hz, 1H), 6.46 (d, J=11.5 Hz, 1H), 4.84-4.65 (m, 4H), 4.50 (s, 2H), 3.86-3.73 (m, 4H), 3.46-3.42 (m, 2H), 2.94-2.85 (m, 2H), 2.41-2.33 (m, 1H), 2.25-1.83 (m, 7H), 0.88-0.82 (m, 2H), 0.55-0.50 (m, 2H); MS (ES+) m/z 583.1, 585.1 (M+1).

Example 182

Synthesis of (S)-1-(4-((3-chloro-5-(trifluoromethoxy)phenoxy)methyl)-5-cyclopropyl-2-fluorobenzoyl)pyrrolidine-2-carboxylic Acid Step 1. Preparation of (S)-tert-butyl (4-((3-chloro-5-(trifluoromethoxy)phenoxy)methyl)-5-cyclopropyl-2-fluorobenzoyl)pyrrolidine-2-carboxylate

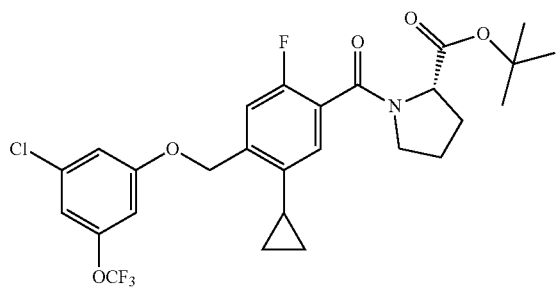 [SMILES: CC(C)(C)OC(=O)[C@@H]1CCCN1C(=O)c1cc(C2CC2)c(COc2cc(Cl)cc(OC(F)(F)F)c2)cc1F]

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 4-((3-chloro-5-(trifluoromethoxy)-phenoxy)methyl)-5-cyclopropyl-2-fluorobenzoic acid, the title compound was obtained as a colorless syrup (0.16 g, 57% yield): $^1$H NMR (300 MHz, CDCl$_3$) δ 7.18-7.09 (m, 2H), 6.91-6.86 (m, 2H), 6.73 (br s, 1H), 5.19 (s, 2H), 4.50 (dd, J=4.7 Hz, 8.5 Hz, 0.7H), 4.17 (dd, J=2.6, 8.5 Hz, 0.3H), 3.81-3.71 (m, 0.6H), 3.54-3.46 (m, 0.7H), 3.40-3.33 (m, 0.7H), 2.34-2.22 (m, 1H), 2.01-1.77 (m, 4H), 1.48 (s, 6H), 1.24 (s, 3H), 0.97-0.88 (m, 2H), 0.70-0.64 (m, 2H) (2:1 mix of rotamers); MS (ES+) m/z 558.1, 560.0 (M+1).

Step 2. Preparation of (S)-1-(4-((3-chloro-5-(trifluoromethoxy)phenoxy)methyl)-5-cyclopropyl-2-fluorobenzoyl)pyrrolidine-2-carboxylic Acid

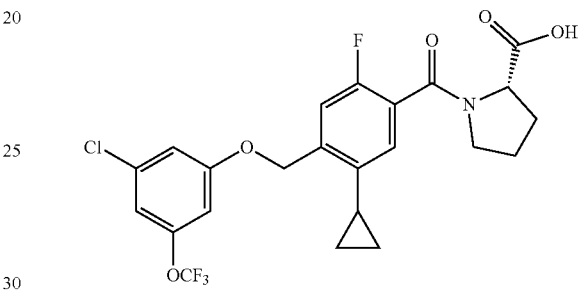

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl (4-((3-chloro-5-(trifluoromethoxy)-phenoxy)methyl)-5-cyclopropyl-2-fluorobenzoyl)pyrrolidine-2-carboxylate, the title compound was obtained as a colorless solid (0.077 g, 94% yield): $^1$H NMR (300 MHz, CDCl$_3$) δ 7.24 (s, 1H), 7.20-7.17 (m, 1H), 6.92-6.88 (m, 2H), 6.73 (br s, 1H), 6.24 (br s, 1H), 5.21 (s, 2H), 4.73 (dd, J=4.1, 8.3 Hz, 1H), 3.48-3.44 (m, 2H), 2.44-2.35 (m, 1H), 2.29-2.17 (m, 1H), 2.07-1.78 (m, 3H), 1.01-0.94 (m, 2H), 0.72-0.67 (m, 2H); MS (ES+) m/z 501.9, 503.8 (M+1).

Example 183

Synthesis of (S)-2-(4-((3-chloro-5-(trifluoromethoxy)phenoxy)methyl)-5-cyclopropyl-2-fluorobenzamido)-3-methylbutanoic Acid Step 1. Preparation of (S)-tert-butyl 2-(4-((3-chloro-5-(trifluoromethoxy)phenoxy)methyl)-5-cyclopropyl-2-fluorobenzamido)-3-methylbutanoate

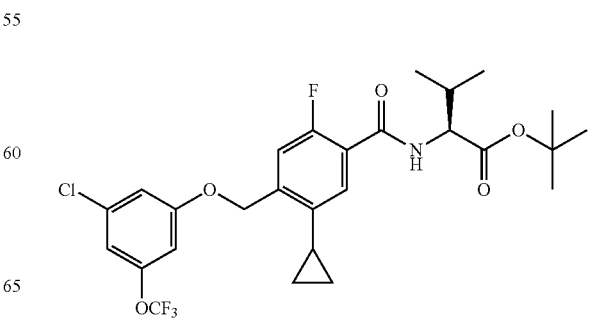

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 4-((3-chloro-5-(trifluoromethoxy)-phenoxy)methyl)-5-cyclopropyl-2-fluorobenzoic acid and (S)-tert-butyl pyrrolidine-2-carboxylate hydrochloride with tert-butyl L-valinate hydrochloride, the title compound was obtained as a colorless syrup (0.18 g, 74% yield): $^1$H NMR (300 MHz, CDCl$_3$) δ 7.68 (d, J=7.7 Hz, 1H), 7.24-7.18 (m, 2H), 6.91-6.87 (m, 2H), 6.74 (s, 1H), 5.22 (s, 2H), 4.69-4.64 (m, 1H), 2.31-2.21 (m, 1H), 1.86-1.76 (m, 1H), 1.47 (s, 9H), 1.00-0.95 (m, 8H), 0.75-0.70 (m, 2H); MS (ES+) m/z 560.1, 562.1 (M+1).

Step 2. Preparation of (S)-2-(4-((3-chloro-5-(trifluoromethoxy)phenoxy)methyl)-5-cyclopropyl-2-fluorobenzamido)-3-methylbutanoic Acid

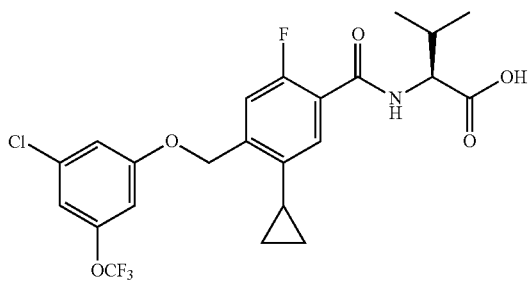 [SMILES: CC(C)[C@H](NC(=O)c1cc(C2CC2)c(COc2cc(Cl)cc(OC(F)(F)F)c2)cc1F)C(=O)O]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 2-(4-((3-chloro-5-(trifluoromethoxy)phenoxy)methyl)-5-cyclopropyl-2-fluorobenzamido)-3-methylbutanoate, the title compound was obtained as a colorless solid (0.053 g, 75% yield): $^1$H NMR (300 MHz, CDCl$_3$) δ 7.79 (d, J=7.7 Hz, 1H), 7.23 (d, J=12.5 Hz, 1H), 7.16 (dd, J=8.2, 13.7 Hz, 1H), 6.91-6.88 (m, 2H), 6.74 (s, 1H), 5.22 (s, 2H), 4.79-4.74 (m, 1H), 2.41-2.30 (m, 1H), 1.86-1.76 (m, 1H), 1.06-0.95 (m, 8H), 0.76-0.71 (m, 2H) (acidic proton not observed); MS (ES+) m/z 503.9, 505.9 (M+1).

Example 184

Synthesis of (S)-1-(5-cyclopropyl-4-(((5-cyclopropyl-6-(2,2,3,3-tetrafluoropropoxy)pyridin-3-yl)oxy)methyl)-2-fluorobenzoyl)pyrrolidine-2-carboxylic Acid

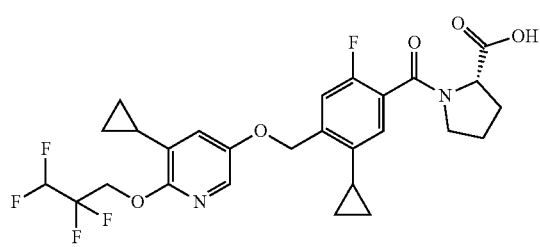 [SMILES: O=C(O)[C@@H]1CCCN1C(=O)c1cc(C2CC2)c(COc2cnc(OCC(F)(F)C(F)F)c(C3CC3)c2)cc1F]

To a degassed mixture of (S)-1-(5-chloro-4-(((5-chloro-6-(2,2,3,3-tetrafluoropropoxy)-pyridin-3-yl)oxy)methyl)-2-fluorobenzoyl)pyrrolidine-2-carboxylic acid (0.10 g, 0.18 mmol) in toluene (15 mL) and water (1.5 mL) were added cyclopropylboronic acid (0.10 g, 1.2 mmol), tribasic potassium phosphate (0.12 g, 0.56 mmol), tricyclohexylphosphine tetrafluoroborate (0.019 g, 0.062 mmol), and palladium(II) acetate trimer (0.008 g, 0.036 mmol). The mixture was heated to reflux under an argon atmosphere for 10 h then cooled to ambient temperature. A further amount of cyclopropylboronic acid (0.050 g, 0.58 mmol), tribasic potassium phosphate (0.12 g, 0.56 mmol), tricyclohexylphosphine tetrafluoroborate (0.017 g, 0.055 mmol), and palladium(II) acetate trimer (0.006 g, 0.03 mmol) were added and the mixture was heated to reflux under an argon atmosphere for 4 h. After cooling to ambient temperature, the mixture was diluted with ethyl acetate (100 mL) and washed with saturated aqueous ammonium chloride (2×100 mL). The organic layer was dried over anhydrous magnesium sulfate, filtered, and concentrated in vacuo. The residue was purified by reverse-phase HPLC to afford the title compound as a colorless solid (0.043 g, 42% yield): $^1$H NMR (300 MHz, CDCl$_3$) δ 7.60 (d, J=2.8 Hz, 1H), 7.24-7.15 (m, 2H), 6.88 (d, J=2.7 Hz, 1H), 6.01 (tt, J=4.7, 53.2 Hz, 1H), 5.18 (s, 2H), 4.73-4.65 (m, 3H), 3.46-3.42 (m, 2H), 2.43-2.37 (m, 1H), 2.26-2.14 (m, 1H), 2.04-1.77 (m, 4H), 1.00-0.94 (m, 4H), 0.70-0.62 (m, 4H) (acidic proton not observed); MS (ES+) m/z 555.1 (M+1).

Example 185

Synthesis of (S)-2-(5-chloro-4-((5-chloro-6-isobutoxypyridin-3-yl)oxy)-2-fluorobenzamido)-3-methylbutanoic Acid Step 1. Preparation of (S)-tert-butyl 2-(5-chloro-4-((5-chloro-6-isobutoxypyridin-3-yl)oxy)-2-fluorobenzamido)-3-methylbutanoate

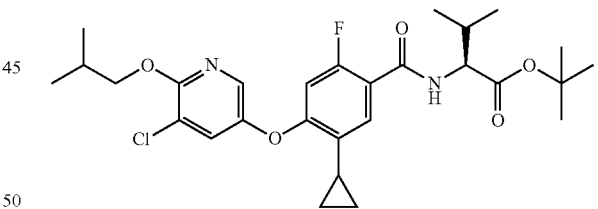

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 5-chloro-4-((5-chloro-6-isobutoxypyridin-3-yl)oxy)-2-fluorobenzoic acid and (S)-tert-butyl pyrrolidine-2-carboxylate hydrochloride with tert-butyl L-valinate hydrochloride, the title compound was obtained as a colorless syrup (0.30 g, 81% yield): $^1$H NMR (300 MHz, CDCl$_3$) δ 8.18 (d, J=7.8 Hz, 1H), 7.87 (dd, J=0.9, 2.6 Hz, 1H), 7.43 (dd, J=1.0, 2.6 Hz, 1H), 7.10 (dd, J=8.6, 12.3 Hz, 1H), 6.54 (d, J=12.3 Hz, 1H), 4.66-4.62 (m, 1H), 4.12 (dd, J=0.7, 6.7 Hz, 2H), 2.30-2.06 (m, 2H), 1.46 (s, 9H), 1.03 (dd, J=0.7, 6.7 Hz, 6H), 0.96 (t, J=7.1 Hz, 6H); MS (ES+) m/z 529.0, 531.0 (M+1).

Step 2. Preparation of (S)-2-(5-chloro-4-((5-chloro-6-isobutoxypyridin-3-yl)oxy)-2-fluorobenzamido)-3-methylbutanoic Acid

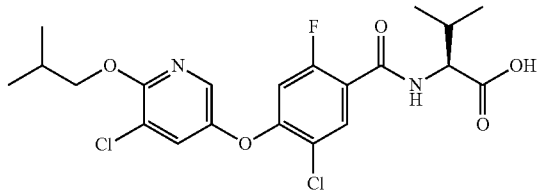 [SMILES: CC(C)COc1ncc(Oc2cc(F)c(C(=O)N[C@H](C(=O)O)C(C)C)cc2Cl)cc1Cl]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 2-(5-chloro-4-((5-chloro-6-isobutoxypyridin-3-yl)oxy)-2-fluorobenzamido)-3-methylbutanoate, the title compound was obtained as a colorless solid (0.14 g, quant. yield): $^1$H NMR (300 MHz, CDCl$_3$) δ 8.18 (d, J=7.8 Hz, 1H), 7.89-7.88 (m, 1H), 7.47 (br s, 1H), 7.45-7.44 (m, 1H), 7.05 (dd, J=8.3, 12.9 Hz, 1H), 6.54 (d, J=12.4 Hz, 1H), 4.79-4.74 (m, 1H), 4.13 (d, J=6.6 Hz, 2H), 2.39-2.29 (m, 1H), 2.20-2.07 (m, 1H), 1.05-0.99 (m, 12H); MS (ES+) m/z 473.0, 474.9 (M+1).

Example 186

Synthesis of (2S,3R)-2-(5-chloro-4-((5-chloro-6-isobutoxypyridin-3-yl)oxy)-2-fluorobenzamido)-3-methylpentanoic Acid Step 1. Preparation of (2S,3R)-tert-butyl 2-(5-chloro-4-((5-chloro-6-isobutoxypyridin-3-yl)oxy)-2-fluorobenzamido)-3-methylpentanoate

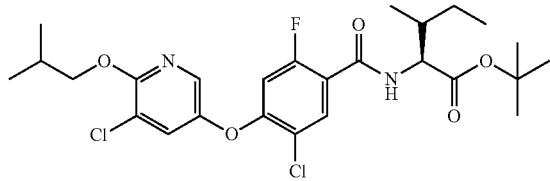 [SMILES: CCC(C)[C@H](NC(=O)c1cc(Cl)c(Oc2cnc(OCC(C)C)c(Cl)c2)cc1F)C(=O)OC(C)(C)C]

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 5-chloro-4-((5-chloro-6-isobutoxypyridin-3-yl)oxy)-2-fluorobenzoic acid and (S)-tert-butyl pyrrolidine-2-carboxylate hydrochloride with tert-butyl L-isoleucinate hydrochloride, the title compound was obtained as a colorless syrup (0.31 g, 82% yield): $^1$H NMR (300 MHz, CDCl$_3$) δ 8.18 (d, J=7.9 Hz, 1H), 7.87 (d, J=2.7 Hz, 1H), 7.42 (d, J=2.7 Hz, 1H), 7.15 (dd, J=8.2, 12.5 Hz, 1H), 6.53 (d, J=12.3 Hz, 1H), 4.68 (ddd, J=2.4, 4.3, 8.0 Hz, 1H), 4.12 (d, J=6.7 Hz, 2H), 2.20-2.06 (m, 1H), 2.00-1.91 (m, 1H), 1.55-1.48 (m, 1H), 1.46 (s, 9H), 1.30-1.15 (m, 1H), 1.03 (d, J=6.7 Hz, 6H), 0.97-0.92 (m, 6H); MS (ES+) m/z 543.1, 545.1 (M+1).

Step 2. Preparation of of (2S,3R)-2-(5-chloro-4-((5-chloro-6-isobutoxypyridin-3-yl)oxy)-2-fluorobenzamido)-3-methylpentanoic Acid

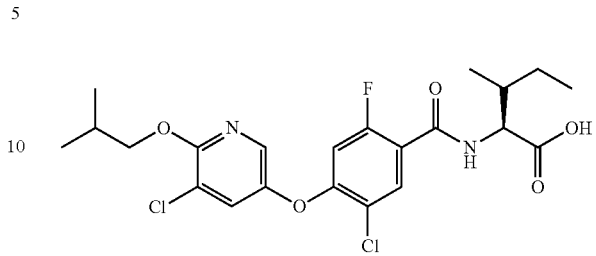

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (2S,3R)-tert-butyl 2-(5-chloro-4-((5-chloro-6-isobutoxypyridin-3-yl)oxy)-2-fluorobenzamido)-3-methylpentanoate, the title compound was obtained as a colorless solid (0.12 g, 95% yield): $^1$H NMR (300 MHz, CDCl$_3$) δ 8.18 (d, J=7.9 Hz, 1H), 8.05 (br s, 1H), 7.88 (d, J=2.7 Hz, 1H), 7.44 (d, J=2.6 Hz, 1H), 7.08 (dd, J=8.1, 13.0 Hz, 1H), 6.54 (d, J=12.4 Hz, 1H), 4.83-4.78 (m, 1H), 4.12 (d, J=6.7 Hz, 2H), 2.20-2.02 (m, 2H), 1.61-1.48 (m, 1H), 1.33-1.18 (m, 1H), 1.05-0.93 (m, 12H); MS (ES+) m/z 487.0, 489.0 (M+1).

Example 187

Synthesis of (S)-2-(4-((3-chloro-5-(trifluoromethoxy)phenoxy)methyl)-5-cyclopropyl-2-fluoro-N-methylbenzamido)-3-methylbutanoic Acid Step 1. Preparation of (S)-tert-butyl 2-(4-((3-chloro-5-(trifluoromethoxy)phenoxy)methyl)-5-cyclopropyl-2-fluoro-N-methylbenzamido)-3-methylbutanoate

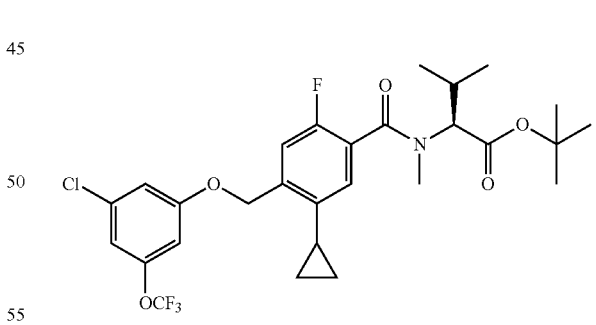

To a 0° C. solution of (S)-tert-butyl 2-(4-((3-chloro-5-(trifluoromethoxy)phenoxy)methyl)-5-cyclopropyl-2-fluorobenzamido)-3-methylbutanoate (0.094 g, 0.17 mmol) in anhydrous N,N-dimethylformamide (4 mL) was added sodium hydride as a 60% dispersion in mineral oil (0.016 g, 0.40 mmol). The mixture was stirred at 0° C. for 1 h. To this mixture was added iodomethane (0.04 mL, 0.6 mmol). The mixture was stirred for 3 h while warming to ambient temperature and was then diluted with diethyl ether (75 mL), washed with 1 M hydrochloric acid (100 mL) and brine (2×75 mL), dried over anhydrous magnesium sulfate, and filtered. The filtrate was concentrated in vacuo and the residue was purified by column chromatography, eluting with a 0-20% gradient of ethyl acetate in hexanes to afford the title compound as a colorless syrup (0.062 g, 65% yield): $^1$H NMR (300 MHz, CDCl$_3$) δ 7.20-7.14 (m, 1H), 7.08 (d, J=6.5 Hz, 0.5H), 7.02-7.01 (m, 0.5H), 6.93-6.90 (m, 1H), 6.87 (br s, 1H), 6.74-6.73 (m, 1H), 5.19 (s, 2H), 4.90 (d, J=10.5 Hz, 0.5H), 3.54 (d, J=10.5 Hz, 0.5H), 3.08 (s, 1.5H), 2.85 (s, 1.5H), 2.30-2.16 (m, 1H), 1.89-1.78 (m, 1H), 1.47 (s, 4.5H), 1.44 (s, 4.5H), 1.07 (d, J=6.5 Hz, 2H), 0.97-0.94 (m, 3H), 0.87-0.82 (m, 3H), 0.71-0.66 (m, 2H) (1:1 mix of rotamers); MS (ES+) m/z 574.1, 576.1 (M+1).

Step 2. Preparation of (S)-2-(4-((3-chloro-5-(trifluoromethoxy)phenoxy)methyl)-5-cyclopropyl-2-fluoro-N-methylbenzamido)-3-methylbutanoic Acid

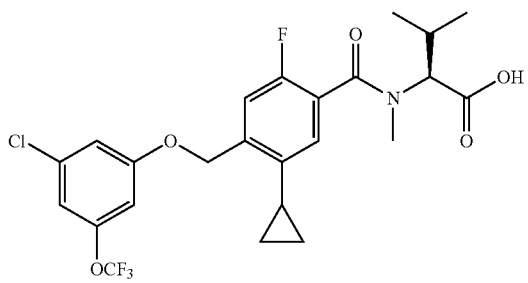 [SMILES: CC(C)[C@@H](C(=O)O)N(C)C(=O)c1cc(C2CC2)c(COc2cc(Cl)cc(OC(F)(F)F)c2)cc1F]

Following the procedure as described in Example 1, Step 2 and making variation as required to replace (S)-tert-butyl 1-(4-(adamantan-1-ylmethoxy)-5-cyclopropyl-2-fluorobenzoyl)-pyrrolidine-2-carboxylate with (S)-tert-butyl 2-(4-((3-chloro-5-(trifluoromethoxy)phenoxy)-methyl)-5-cyclopropyl-2-fluoro-N-methylbenzamido)-3-methylbutanoate, the title compound was obtained as a colorless solid (0.057 g, quant. yield): $^1$H NMR (300 MHz, CDCl$_3$) δ 7.22-7.17 (m, 2H), 6.92-6.88 (m, 2H), 6.74 (s, 1H), 5.21 (s, 2H), 5.04 (br s, 1H), 4.53-4.50 (m, 1H), 2.96-2.95 (m, 3H), 2.52-2.40 (m, 1H), 1.87-1.78 (m, 1H), 1.11 (d, J=6.5 Hz, 3H), 1.04 (d, J=6.6 Hz, 3H), 0.99-0.88 (m, 2H), 0.73-0.66 (m, 2H); MS (ES+) m/z 518.0, 520.0 (M+1).

Example 188

Synthesis of (S)-1-(4-((3-chloro-5-(trifluoromethoxy)phenoxy)methyl)-5-cyclopropyl-2-fluorobenzoyl)pyrrolidine-2-carboxamide

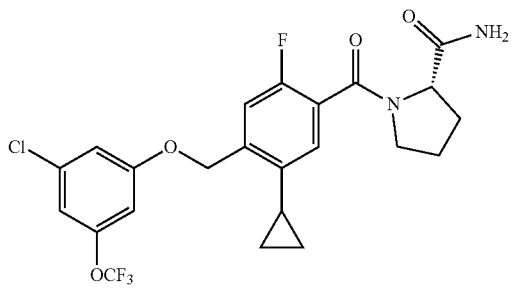 [SMILES: NC(=O)[C@@H]1CCCN1C(=O)c1cc(C2CC2)c(COc2cc(Cl)cc(OC(F)(F)F)c2)cc1F]

To a solution of (S)-1-(4-((3-chloro-5-(trifluoromethoxy)phenoxy)methyl)-5-cyclopropyl-2-fluorobenzoyl)pyrrolidine-2-carboxylic acid (0.36 g, 0.72 mmol) in anhydrous tetrahydrofuran (12 mL) was added 1,1'-carbonyldiimidazole (0.58 g, 3.6 mmol). The solution was heated to reflux under a nitrogen atmosphere for 40 minutes then cooled to ambient temperature. To this solution was added 30% aqueous ammonium hydroxide (3 mL) that was then stirred at ambient temperature for 5 h. The solution was diluted with ethyl acetate (100 mL), washed with 1 M hydrochloric acid (2×100 mL), brine (100 mL), dried over anhydrous magnesium sulfate, and filtered. The filtrate was concentrated in vacuo to afford the title compound as a colorless solid (0.35 g, 95% yield): $^1$H NMR (300 MHz, CDCl$_3$) δ 7.22-7.13 (m, 1H), 6.91-6.88 (m, 3H), 6.73 (br s, 1H), 5.61 (br s, 1H), 5.20 (s, 2H), 4.76 (dd, J=3.8, 7.6 Hz, 1H), 3.50-3.42 (m, 1H), 3.38-3.30 (m, 1H), 2.53-2.37 (m, 2H), 2.14-1.99 (m, 2H), 1.92-1.78 (m, 2H), 1.00-0.94 (m, 2H), 0.72-0.66 (m, 2H); MS (ES+) m/z 501.0, 503.0 (M+1).

Example 189

Synthesis of (S)-2-(4-((3S,5S,7S)-adamantan-1-ylmethoxy)-5-cyclopropyl-2-fluorobenzamido)-3-cyclopropylpropanoic Acid

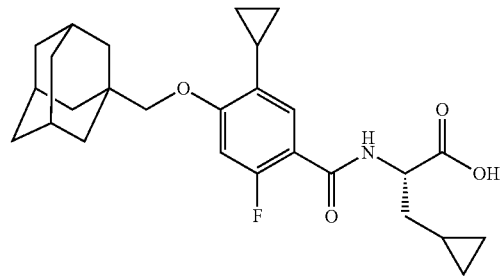 [SMILES: O=C(N[C@@H](CC1CC1)C(=O)O)c1cc(C2CC2)c(OCC23CC4CC(CC(C4)C2)C3)cc1F]

To a solution of 4-(adamantan-1-yl)methoxy)-5-cyclopropyl-2-fluorobenzoic acid (0.26 g, 0.76 mmol) in anhydrous tetrahydrofuran (12 mL) was added 1,1'-carbonyldiimidazole (0.13 g, 0.83 mmol). The solution was heated to reflux under a nitrogen atmosphere for 40 minutes, then cooled to ambient temperature. To this solution was added L-3-cyclopropylalanine (0.12 g, 0.90 mmol) and 1,8-diazabicycloundec-7-ene (0.32 mL, 2.3 mmol). The solution was stirred at ambient temperature for 15 h, then diluted with ethyl acetate (100 mL), washed with 1 M hydrochloric acid (2×100 mL) and brine (100 mL), dried over anhydrous magnesium sulfate, filtered, and concentrated in vacuo. The residue was purified by reverse-phase HPLC to afford the title compound as a colorless solid (0.16 g, 45% yield): $^1$H NMR (300 MHz, CDCl$_3$) δ 7.56 (d, J=9.1 Hz, 1H), 7.39 (dd, J=6.4, 13.9 Hz, 1H), 6.52 (d, J=14.3 Hz, 1H), 5.75 (br s, 1.25H), 4.82-4.77 (m, 1H), 3.52 (s, 2H), 2.07-2.02 (m, 4H), 1.89-1.82 (m, 1H), 1.78-1.68 (m, 13H), 0.93-0.87 (m, 2H), 0.83-0.74 (m, 1H), 0.68-0.63 (m, 2H), 0.55-0.49 (m, 2H), 0.17-0.13 (m, 2H); $^{19}$F NMR (282 MHz, CDCl$_3$) δ −75.8 (s, 0.7F), −113.1 (s, 1F); MS (ES+) m/z 456.1 (M+1).

Example 190

Synthesis of (S)-1-(4-((1-(3-chloro-5-fluorobenzyl)piperidin-4-yl)methoxy)-5-cyclopropyl-2-fluorobenzoyl)pyrrolidine-2-carboxylic Acid

Step 1. Preparation of (S)-tert-butyl 1-(4-((1-(3-chloro-5-fluorobenzyl)piperidin-4-yl)methoxy)-5-cyclopropyl-2-fluorobenzoyl)pyrrolidine-2-carboxylate

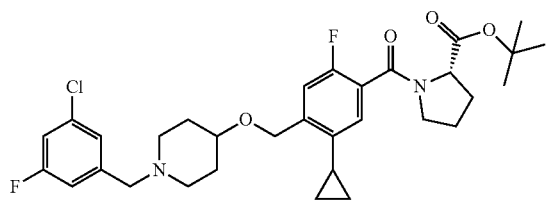 [SMILES: CC(C)(C)OC(=O)[C@@H]1CCCN1C(=O)c1cc(C2CC2)c(COC2CCN(Cc3cc(F)cc(Cl)c3)CC2)cc1F]

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 4-((1-(3-chloro-5-fluorobenzyl)piperidin-4-yl)methoxy)-5-cyclopropyl-2-fluorobenzoic acid, the title compound was obtained as a light yellow syrup (0.25 g, 64% yield): $^1$H NMR (300 MHz, CDCl$_3$) δ 7.09 (br s, 1H), 6.96-6.89 (m, 2.7H), 6.83 (d, J=7.8 Hz, 0.3H), 6.48 (d, J=11.7 Hz, 0.7H), 6.45 (d, J=11.5 Hz, 0.3H), 4.45 (dd, J=5.1, 8.4 Hz, 0.7H), 4.18 (dd, J=2.5, 8.3 Hz, 0.3H), 3.79-3.71 (m, 2.7H), 3.53-3.31 (m, 3.3H), 2.88-2.84 (m, 2H), 2.31-2.18 (m, 1H), 2.04-1.79 (m, 9H), 1.47-1.35 (m, 8H), 1.24 (s, 3H), 0.86-0.78 (m, 2H), 0.60-0.52 (m, 2H) (2:1 mix of rotamers); MS (ES+) m/z 589.2, 591.1 (M+1).

Step 2. Preparation of (S)-1-(4-((1-(3-chloro-5-fluorobenzyl)piperidin-4-yl)methoxy)-5-cyclopropyl-2-fluorobenzoyl)pyrrolidine-2-carboxylic Acid

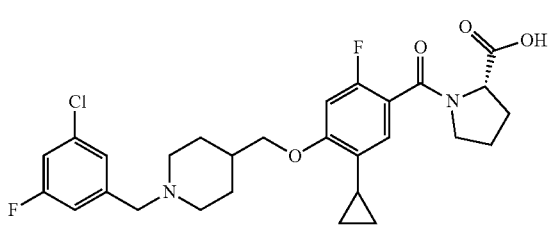 [SMILES: O=C(O)[C@@H]1CCCN1C(=O)c1cc(C2CC2)c(OCC2CCN(Cc3cc(F)cc(Cl)c3)CC2)cc1F]

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-butyl 1-(4-((1-(3-chloro-5-fluorobenzyl)piperidin-4-yl)methoxy)-5-cyclopropyl-2-fluorobenzoyl)pyrrolidine-2-carboxylate and following purification by reverse-phase HPLC, the title compound was obtained as a colorless solid (0.14 g, 50% yield): $^1$H NMR (300 MHz, CDCl$_3$) δ 12.37 (br s, 1H), 7.18-7.12 (m, 3H), 6.88 (d, J=7.7 Hz, 1H), 6.44 (d, J=11.6 Hz, 1H), 4.65-4.61 (m, 1H), 4.20 (s, 2H), 3.82-3.63 (m, 5H), 3.48-3.39 (m, 2H), 2.77-2.69 (m, 2H), 2.34-2.19 (m, 2H), 2.03-1.84 (m, 8H), 0.88-0.82 (m, 2H), 0.54-0.49 (m, 2H); $^{19}$F NMR (282 MHz, CDCl$_3$) δ −75.7 (s, 3F), −108.2 (s, 1F), −113.7 (s, 1F); MS (ES+) m/z 533.0, 535.0 (M+1).

Example 191

Synthesis of (S)-1-(5-Chloro-4-((5-chloro-6-(2,2,2-trifluoroethoxy)pyridin-3-yl)oxy)-2-fluorobenzoyl)pyrrolidine-2-carboxylic Acid Trifluoroacetate

Step 1. Preparation of (S)-tert-Butyl 1-(5-chloro-4-((5-chloro-6-(2,2,2-trifluoroethoxy)-pyridin-3-yl)oxy)-2-fluorobenzoyl)pyrrolidine-2-carboxylate

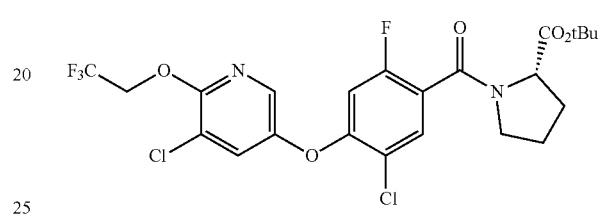

Following the procedure as described in Example 180, Step 1 and making non-critical variations to replace 5-chloro-4-(((5-chloro-6-(2,2,3,3-tetrafluoropropoxy)pyridin-3-yl)oxy)methyl)-2-fluorobenzoic acid with 5-chloro-4-((5-chloro-6-(2,2,2-trifluoroethoxy)pyridin-3-yl)oxy)-2-fluorobenzoic acid (0.20 g, 0.50 mmol), the title was obtained compound as an oil (0.20 g, 74%): MS (ES+) m/z 553.1 (M+1).

Step 2. Preparation of (S)-1-(5-chloro-4-((5-chloro-6-(2,2,2-trifluoroethoxy)pyridin-3-yl)oxy)-2-fluorobenzoyl)pyrrolidine-2-carboxylic Acid Trifluoroacetate

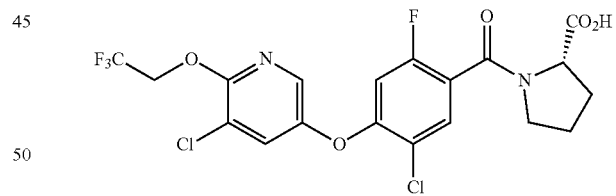

Following the procedure as described in Example 1, Step 2 and making variation as required to replace (S)-tert-butyl 1-(4-(adamantan-1-ylmethoxy)-5-cyclopropyl-2-fluorobenzoyl)pyrrolidine-2-carboxylate with (S)-tert-Butyl 1-(5-chloro-4-((5-chloro-6-(2,2,2-trifluoroethoxy)pyridin-3-yl)oxy)-2-fluorobenzoyl)pyrrolidine-2-carboxylate, the title compound was obtained following purification by reverse-phase HPLC as colorless solid (0.070 g, 31%): $^1$H NMR (300 MHz, DMSO-d$_6$) δ 8.14-7.99 (m, 2H), 7.61-7.52 (m, 1H), 7.23-6.88 (m, 1H), 7.17-7.08 (m, 1H), 5.11-4.96 (m, 2H), 4.65-3.94 (m, 1H), 4.38-4.17 (m, 1H), 3.58-3.29 (m, 2H), 2.32-2.16 (m, 1H), 1.99-1.74 (m, 3H); MS (ES+) m/z 499.0, 497.0 (M+1).

Example 192

Synthesis of (S)-1-(4-(2-(3-aminobenzo[d]isoxazol-5-yl)-4-chlorophenoxy)-2,5-difluorobenzoyl)pyrrolidine-2-carboxylic Acid Trifluoroacetate

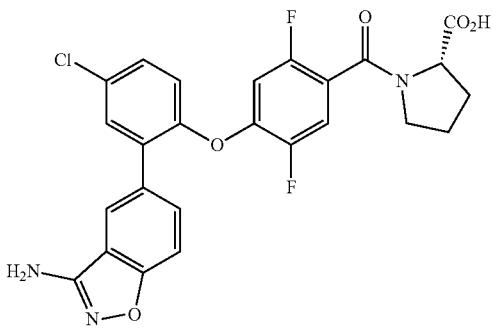 [SMILES: Nc1noc2ccc(-c3cc(Cl)ccc3Oc3cc(F)c(C(=O)N4CCC[C@H]4C(=O)O)cc3F)cc12]

Following the procedure as described in Example 180, Step 1 and 2, and making non-critical variations to replace 5-chloro-4-(((5-chloro-6-(2,2,3,3-tetrafluoropropoxy)pyridin-3-yl)oxy)methyl)-2-fluorobenzoic acid with 4-(2-(3-aminobenzo[d]isoxazol-5-yl)-4-chlorophenoxy)-2,5-difluorobenzoic acid, the title compound was obtained following purification by reverse-phase HPLC as colorless solid (0.079 g, 25%): $^1$H NMR (300 MHz, DMSO-$d_6$) δ 8.02-7.91 (m, 1H), 7.68-7.61 (m, 1H), 7.56 (d, J=2.62 Hz, 1H), 7.50-7.39 (m, 2H), 7.38-7.26 (m, 1H), 7.24-7.16 (m, 1H), 7.15-6.87 (m, 2H), 6.84-6.09 (m, 3H), 4.34-4.14 (m, 1H), 3.56-3.10 (m, 2H), 2.29-2.13 (m, 1H), 2.01-1.71 (m, 3H); MS (ES+) m/z 516.1, 514.1 (M+1).

Example 193

Synthesis of (2S)-1-(5-Cyclopropyl-4-((1-((3,5-dichlorophenyl)(phenyl)methyl)piperidin-4-yl)methoxy)-2-fluorobenzoyl)pyrrolidine-2-carboxylic Acid Trifluoroacetate

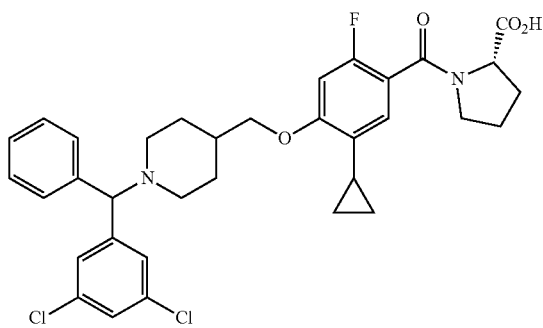 [SMILES: O=C(O)[C@@H]1CCCN1C(=O)c1cc(C2CC2)c(OCC2CCN(C(c3ccccc3)c3cc(Cl)cc(Cl)c3)CC2)cc1F]

Following the procedure as described in Example 180, Step 1 and 2, and making non-critical variations to replace 5-chloro-4-(((5-chloro-6-(2,2,3,3-tetrafluoropropoxy)pyridin-3-yl)oxy)methyl)-2-fluorobenzoic acid with 5-cyclopropyl-4-((1-((3,5-dichlorophenyl)-(phenyl)methyl)piperidin-4-yl)methoxy)-2-fluorobenzoic acid and following purification of the residue by reverse-phase HPLC, the title compound was obtained as a colorless solid (0.032 g, 21%): $^1$H NMR (300 MHz, CDCl$_3$) δ 7.68-7.55 (m, 4H), 7.51-7.31 (m, 4H), 6.92 (d, J=7.7 Hz, 1H), 6.50 (d, J=11.6 Hz, 1H), 4.91-4.77 (br, s, 1H), 4.71 (dd, J=7.9, 4.2 Hz, 1H), 3.91-3.82 (m, 2H), 3.68-3.34 (m, 4H), 2.80-2.59 (m, 2H), 2.54-2.42 (m, 1H), 2.25-1.82 (m, 9H), 0.92-0.79 (m, 2H), 0.62-0.53 (m, 2H); MS (ES+) m/z 627.0, 625.1 (M+1).

Example 194

Synthesis of (S)-1-(4-(adamantan-1-ylmethoxy)-5-cyclobutyl-2-fluorobenzoyl)pyrrolidine-2-carboxylic Acid Trifluoroacetate

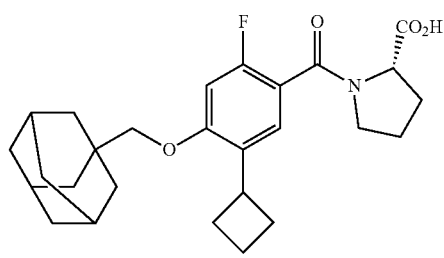 [SMILES: O=C(O)[C@@H]1CCCN1C(=O)c1cc(C2CCC2)c(OCC23CC4CC(CC(C4)C2)C3)cc1F]

Following the procedure as described in Example 180, Step 1 and 2, and making non-critical variations to replace 5-chloro-4-(((5-chloro-6-(2,2,3,3-tetrafluoropropoxy)pyridin-3-yl)oxy)methyl)-2-fluorobenzoic acid with 4-(adamantan-1-ylmethoxy)-5-cyclobutyl-2-fluorobenzoic acid and following purification of the residue by reverse-phase HPLC, the title compound was obtained as a colorless solid (0.036 g, 31%): $^1$H NMR (300 MHz, DMSO-$d_6$) δ 7.08-6.94 (m, 1H), 6.85-6.72 (m, 1H), 4.37-4.09 (m, 1H), 3.97-3.81 (br, s, 2H), 3.64-3.25 (m, 5H), 2.32-2.14 (m, 3H), 2.13-1.90 (m, 6H), 1.90-1.55 (m, 16H); MS (ES+) m/z 456.1 (M+1).

Example 195

Synthesis of (S)-1-(1-(1-(5-chloro-6-(trifluoromethyl)pyridin-2-yl)piperidin-4-yl)-6-fluoro-3-methyl-1H-indazole-5-carbonyl)pyrrolidine-2-carboxylic Acid Trifluoroacetate

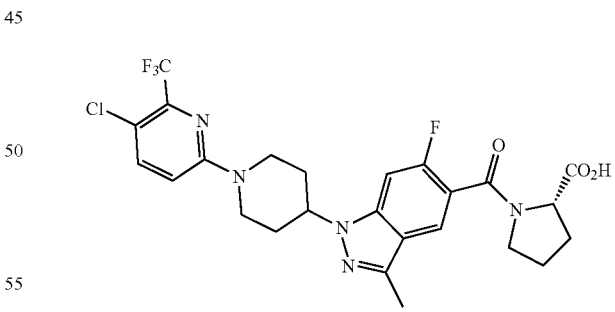

Following the procedure as described in Example 180, Step 1 and 2, and making non-critical variations to replace 5-chloro-4-(((5-chloro-6-(2,2,3,3-tetrafluoropropoxy)pyridin-3-yl)oxy)methyl)-2-fluorobenzoic acid with 1-(1-(5-chloro-6-(trifluoromethyl)pyridin-2-yl)piperidin-4-yl)-6-fluoro-3-methyl-1H-indazole-5-carboxylic acid and following purification of the residue by reverse-phase HPLC, the title compound was obtained as a colorless solid (0.057 g, 43%): $^1$H NMR (300 MHz, DMSO-$d_6$) δ 7.80 (d, J=9.1 Hz, 1H), 7.75-7.42 (m, 2H), 7.26-7.04 (m, 1H), 4.93-4.76 (m, 1H), 4.51-4.41 (m, 2H), 4.41-4.18 (m, 1H), 3.61-3.25 (m, 2H), 3.20-3.04 (m, 2H), 2.44-2.38 (m, 3H), 2.33-1.73 (m, 8H); MS (ES+) m/z 556.0, 554.0 (M+1).

Example 196

Synthesis of (2S)-1-(5-cyclopropyl-4-((1-((3,5-dichlorophenyl)(phenyl)methyl)-3-methylazetidin-3-yl)methoxy)-2-fluorobenzoyl)pyrrolidine-2-carboxylic Acid Trifluoroacetate

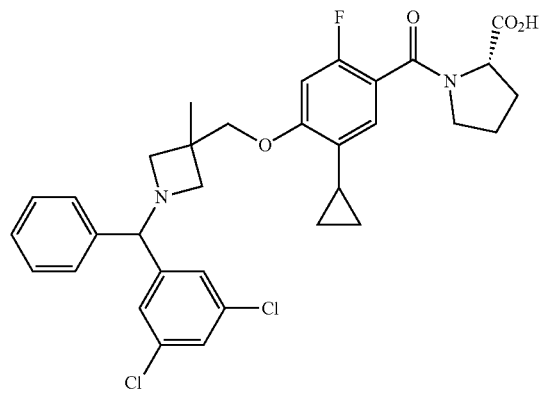 [SMILES: CC1(COc2cc(F)c(C(=O)N3CCC[C@H]3C(=O)O)cc2C2CC2)CN(C(c2ccccc2)c2cc(Cl)cc(Cl)c2)C1]

Following the procedure as described in Example 180, Step 1 and 2, and making non-critical variations to replace 5-chloro-4-(((5-chloro-6-(2,2,3,3-tetrafluoropropoxy)pyridin-3-yl)oxy)methyl)-2-fluorobenzoic acid with 5-cyclopropyl-4-((1-((3,5-dichlorophenyl)-(phenyl)methyl)-3-methylazetidin-3-yl)methoxy)-2-fluorobenzoic acid and following purification of the residue by reverse-phase HPLC, the title compound was as a colorless solid (0.064 g, 44%): $^1$H NMR (300 MHz, DMSO-$d_6$) δ 7.64 (t, J=1.7 Hz, 1H), 7.54 (m, 2H), 7.49-7.39 (m, 5H), 6.90-6.67 (m, 2H), 5.81-5.72 (br s, 1H), 4.35-4.26 (m, 1H), 4.15-4.01 (m, 4H), 3.98-3.88 (m, 2H), 3.54-3.43 (m, 1H), 3.33-3.21 (m, 1H), 2.31-2.13 (m, 1H), 2.05-1.70 (m, 4H), 1.43 (s, 3H), 0.84-0.73 (m, 2H), 0.57-0.44 (m, 2H); MS (ES+) m/z 613.0, 611.1 (M+1).

Example 197

Synthesis of (S)-1-(4-((1-((3-(2-chlorophenyl)-1,2,4-oxadiazol-5-yl)methyl)piperidin-4-yl)methoxy)-5-cyclopropyl-2-fluorobenzoyl)pyrrolidine-2-carboxylic Acid Trifluoroacetate

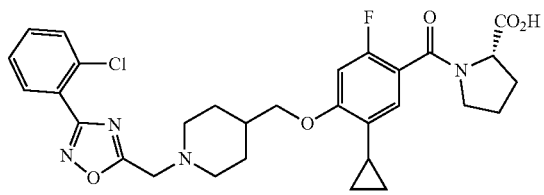 [SMILES: O=C(O)[C@@H]1CCCN1C(=O)c1cc(C2CC2)c(OCC2CCN(Cc3nc(-c4ccccc4Cl)no3)CC2)cc1F]

Following the procedure as described in Example 180, Step 1 and 2, and making non-critical variations to replace 5-chloro-4-(((5-chloro-6-(2,2,3,3-tetrafluoropropoxy)pyridin-3-yl)oxy)methyl)-2-fluorobenzoic acid with 4-((1-((3-(2-chlorophenyl)-1,2,4-oxadiazol-5-yl)methyl)piperidin-4-yl)methoxy)-5-cyclopropyl-2-fluorobenzoic acid and following purification of the residue by reverse-phase HPLC, the title compound was obtained as a colorless solid (0.052 g, 37%): $^1$H NMR (300 MHz, CDCl$_3$) δ 7.91 (d, J=7.5 Hz, 1H), 7.55 (d, J=7.8 Hz, 1H), 7.52-7.35 (m, 2H), 6.91 (d, J=7.6 Hz, 1H), 6.47 (d, J=11.3 Hz, 1H), 5.38-4.97 (br, s, 2H), 4.74-4.60 (m, 3H), 3.93-3.68 (m, 4H), 3.50-3.39 (m, 2H), 3.21-3.06 (m, 2H), 2.44-1.78 (m, 10H), 0.97-0.78 (m, 2H), 0.60-0.48 (m, 2H); MS (ES+) m/z 585.1, 583.1 (M+1).

Example 198

Synthesis of (S)-1-(4-(adamantan-1-ylmethoxy)-5-cyclopropyl-2-fluorobenzoyl)-5-oxopyrrolidine-2-carboxylic Acid

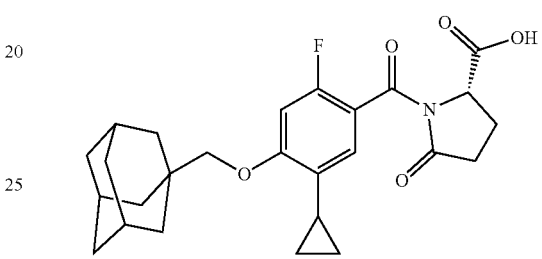

To a solution of 4-(1-adamantylmethoxy)-5-cyclopropyl-2-fluoro-benzoyl chloride (0.17 g, 0.50 mmol) in dichloromethane (2 mL), (S)-5-oxopyrrolidine-2-carboxylic acid (0.07 g, 0.50 mmol) was added followed by N,N-diisopropylethylamine (0.11 mL, 0.75 mmol). The reaction mixture was stirred at ambient temperature for 16 h. The solvent concentrated in vacuo. The residue was purified by column chromatography eluting with a gradient 0 to 10% methanol in dichloromethane and 2% acetic acid to afford the title compound as a colorless solid (0.014 g, 6%): $^1$H NMR (300 MHz, DMSO-$d_6$) δ 6.93 (d, J=8.0 Hz, 1H), 6.83 (d, J=12.6 Hz, 1H), 4.69 (dd, J=9.0, 3.5 Hz, 1H), 3.63 (s, 2H), 3.36 (s, 1H), 2.61-2.52 (m, 2H), 2.47-2.33 (m, 1H), 2.08-1.93 (m, 5H), 1.85-1.50 (m, 12H), 0.94-0.83 (m, 2H), 0.63-0.52 (m, 2H); MS (ES+) m/z 456.2 (M+1).

Example 199

Synthesis of 1-(4-(adamantan-1-ylmethoxy)-5-cyclopropyl-2-fluorobenzoyl)-4-fluoro-N-hydroxypyrrolidine-2-carboxamide Step 1. Preparation of 1-(4-(adamantan-1-ylmethoxy)-5-cyclopropyl-2-fluorobenzoyl)-4-fluoro-N-hydroxypyrrolidine-2-carboxamide

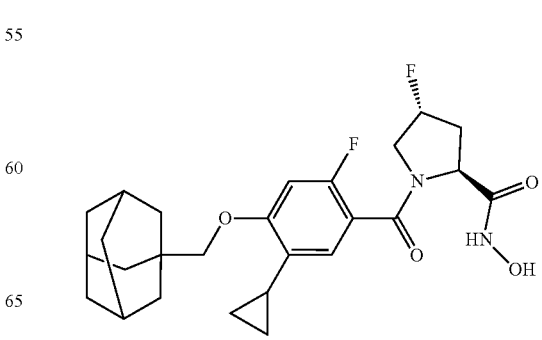

To a solution of (2S,4R)-1-(4-(adamantan-1-ylmethoxy)-5-cyclopropyl-2-fluorobenzoyl)-4-fluoropyrrolidine-2-carboxylic acid (0.10 g, 0.22 mmol), hydroxylamine hydrochloride salt (0.023 g, 0.330 mmol), O-(benzotriazol-1-yl)-N,N,N',N'-tetramethyluronium tetrafluoroborate (0.14 g, 0.44 mmol) and 1-hydroxybenzotriazole (0.044 g, 0.330 mmol) in acetonitrile (1.7 mL), was added N,N-diisopropylethylamine (0.19 mL, 1.1 mmol) and stirred under a nitrogen atmosphere at ambient temperature for 16 hours. The reaction mixture was then acidified using aqueous hydrochloric acid (1.0 N, 2 mL) and extracted using dichloromethane (4×20 mL). The organic layers were then combined and washed with saturated aqueous sodium chloride solution (10 mL), dried over magnesium sulfate, concentrated and purified using preparative HPLC. The resulting compound in aqueous solution was extracted using dichloromethane (3×20 mL) and concentrated in vacuo to give the title compound as a colorless solid (0.014 g, 14%): $^1$H NMR (300 MHz, DMSO-$d_6$) δ 10.89-10.32 (m, 1H), 9.39-8.66 (m, 1H), 6.95-6.61 (m, 2H), 5.49-5.13 (m, 1H), 4.46-3.93 (m, 1H), 3.83-3.40 (m, 4H), 2.48-1.92 (m, 6H), 1.79-1.59 (m, 12H), 0.96-0.83 (m, 2H), 0.66-0.54 (m, 2H); MS (ES+) m/z 475.2 (M+1).

Example 200

Synthesis of (S)-5-(4-(adamantan-1-ylmethoxy)-5-cyclopropyl-2-fluorobenzoyl)-5-azaspiro[2.4]heptane-6-carboxylic Acid

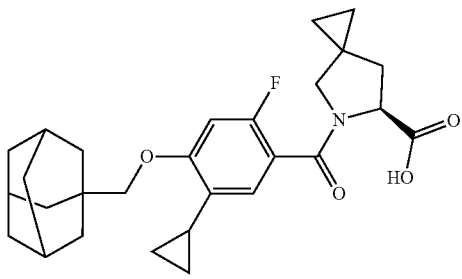 [SMILES: O=C(O)[C@@H]1CC2(CC2)CN1C(=O)c1cc(C2CC2)c(OCC23CC4CC(CC(C4)C2)C3)cc1F]

Following the procedure as described in Example 198, and making variations as required to replace (S)-5-oxopyrrolidine-2-carboxylic acid with (S)-5-azaspiro[2.4]heptane-6-carboxylic acid, the title compound was obtained as a colorless solid (0.22 g, 56%): $^1$H NMR (300 MHz, DMSO-$d_6$) δ 12.72-12.42 (s, br, 1H), 6.86-6.67 (m, 2H), 4.51-4.15 (m, 1H), 3.59-3.49 (m, 2H), 3.33-3.09 (m, 2H), 2.44-2.13 (m, 1H), 2.03-1.79 (m, 5H), 1.76-1.52 (m, 12H), 0.90-0.79 (m, 2H), 0.66-0.40 (m, 6H); MS (ES+) m/z 468.3 (M+1).

Example 201

Synthesis of (4-(adamantan-1-ylmethoxy)-5-cyclopropyl-2-fluorophenyl)((2S,4R)-4-fluoro-2-(1,1,1,3,3,3-hexafluoro-2-hydroxypropan-2-yl)pyrrolidin-1-yl)methanone

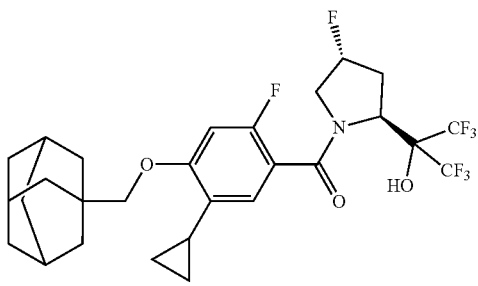 [SMILES: O=C(c1cc(C2CC2)c(OCC23CC4CC(CC(C4)C2)C3)cc1F)N1C[C@H](F)C[C@H]1C(O)(C(F)(F)F)C(F)(F)F]

To a solution of (2S,4R)-1-(4-(adamantan-1-ylmethoxy)-5-cyclopropyl-2-fluorobenzoyl)-4-fluoropyrrolidine-2-carboxylic acid (0.20 g, 0.44 mmol) and dimethylformamide (0.05 mL) in dichloromethane (1.7 mL), oxalyl chloride (0.06 mL, 0.65 mmol) was added. The reaction solution was stirred at ambient temperature for 30 minutes and the solvent was concentrated in vacuo to afford a colorless solid. This solid was re-dissolved in 1,2-dimethoxyethane (1.7 mL) and cooled to −50° C. To this solution trimethyl(trifluoromethyl)silane (0.46 mL, 3.1 mmol) was added. The reaction solution was to warm to −30° C. and tetramethylammonium fluoride (0.29 g, 3.1 mmol) was added. The reaction mixture stirred at ambient temperature for 1 hour and acidified with aqueous hydrochloric acid (1.0 N, 4 mL). The reaction mixture was extracted with dichloromethane (4×20 mL), washed with a saturated aqueous solution of sodium chloride (10 mL) and the solvent concentrated in vacuo. The residue was purified by preparative HPLC to give the title compound as a colorless solid (0.001 g, 0.4%): $^1$H NMR (300 MHz, CDCl$_3$) δ 8.60-8.52 (m, 1H), 7.01 (d, J=8.0 Hz, 1H), 6.53 (d, J=12.2 Hz, 1H), 5.25-4.91 (m, 2H), 3.86-3.62 (m, 2H), 3.58-3.47 (m, 2H), 2.71-2.53 (m, 2H), 2.14-1.97 (m, 4H), 1.89-1.64 (m, 12H), 0.99-0.86 (m, 2H), 0.70-0.53 (m, 2H); MS (ES+) m/z 582.2 (M+1).

Example 202

Synthesis of (1R,2S,5S)-3-(4-(adamantan-1-ylmethoxy)-5-cyclopropyl-2-fluorobenzoyl)-6,6-dimethyl-3-azabicyclo[3.1.0]hexane-2-carboxylic Acid Step 1. Preparation of (1R,2S,5S)-Methyl 3-(4-(adamantan-1-ylmethoxy)-5-cyclopropyl-2-fluorobenzoyl)-6,6-dimethyl-3-azabicyclo[3.1.0]hexane-2-carboxylate

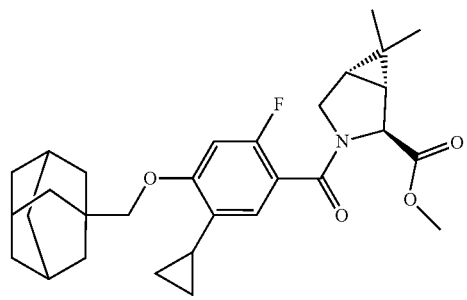 [SMILES: COC(=O)[C@@H]1[C@@H]2[C@H](CN1C(=O)c1cc(C3CC3)c(OCC34CC5CC(CC(C5)C3)C4)cc1F)C2(C)C]

Following the procedure as described in Example 198, and making variations as required to replace (S)-5-oxopyrrolidine-2-carboxylic acid with ((1R,2S,5S)-methyl 6,6-dimethyl-3-azabicyclo[3.1.0]hexane-2-carboxylate, the title compound was obtained as a colorless solid, the title compound was obtained as a clear oil (0.20 g, 83%): MS (ES+) m/z 496.3 (M+1).

Step 2. Preparation of (1R,2S,5S)-3-(4-(Adamantan-1-ylmethoxy)-5-cyclopropyl-2-fluorobenzoyl)-6,6-dimethyl-3-azabicyclo[3.1.0]hexane-2-carboxylic Acid

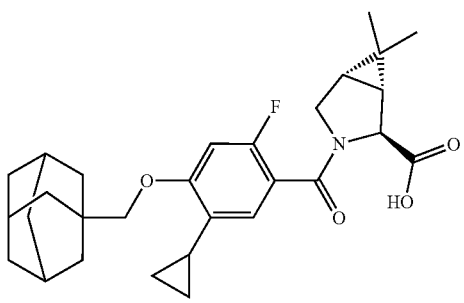 [SMILES: CC1(C)[C@@H]2[C@@H](C(=O)O)N(C(=O)c3cc(C4CC4)c(OCC45CC6CC(CC(C6)C4)C5)cc3F)C[C@@H]21]

Following the procedure as described in Example 6, Step 2 and making variation as required to replace ethyl 1-(4-adamantan-1-ylmethoxy)-5-cyclopropyl-2-fluorobenzamido)-cyclopropanecarboxylate with (1R,2S,5S)-methyl 3-(4-(adamantan-1-ylmethoxy)-5-cyclopropyl-2-fluorobenzoyl)-6,6-dimethyl-3-azabicyclo[3.1.0]hexane-2-carboxylate, the title compound was obtained following purification using column chromatography eluting with gradient 5 to 30% of ethyl acetate in hexanes) as a colorless solid (0.007 g, 19%): $^1$H NMR (300 MHz, CDCl$_3$) δ 6.89-6.76 (m, 1H), 6.49 (d, J=11.8 Hz, 1H), 4.50 (s, 1H), 3.81-3.68 (m, 1H), 3.50-3.43 (m, 2H), 3.30 (d, J=10.9 Hz, 1H), 2.86 (s, 1H), 2.06-1.95 (m, 4H), 1.83-1.63 (m, 13H), 1.41-1.30 (m, 1H), 1.09-0.93 (m, 6H), 0.90-0.84 (m, 2H), 0.65-0.55 (m, 2H); MS (ES+) m/z 482.3 (M+1).

Example 203

Synthesis of (S)-1-(4-adamantan-1-ylmethoxy)-5-cyclopropyl-2-fluorobenzoyl)-4-(trifluoromethyl)-2,5-dihydro-1H-pyrrole-2-carboxylic Acid Step 1. Preparation of (2S)-Methyl 1-(4-(adamantan-1-ylmethoxy)-5-cyclopropyl-2-fluorobenzoyl)-4-hydroxy-4-(trifluoromethyl)pyrrolidine-2-carboxylate

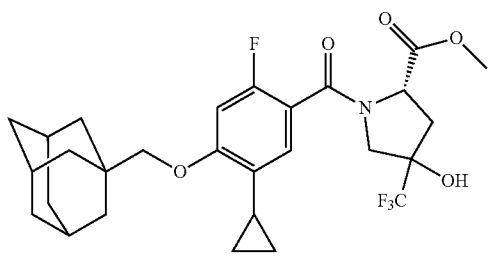 [SMILES: COC(=O)[C@@H]1CC(O)(C(F)(F)F)CN1C(=O)c1cc(C2CC2)c(OCC23CC4CC(CC(C4)C2)C3)cc1F]

To a solution of 4-(adamantan-1-ylmethoxy)-5-cyclopropyl-2-fluorobenzoic acid (0.072 g, 0.200 mmol) in dichloromethane (2 mL) was added 1-ethyl-3-(3-dimethylaminopropyl)carbodiimide (0.071 g, 0.360 mmol), 4-dimethylaminopyridine (0.061 g, 0.500 mmol) and (2S)-methyl 4-hydroxy-4-(trifluoromethyl)pyrrolidine-2-carboxylate (0.041 g, 0.240 mmol). After stirring at ambient temperature for 16 h, the reaction mixture was acidified using aqueous hydrochloric acid (1.0 N, 5 mL) and extracted using dichloromethane (4×20 mL). The organic layers were then combined and washed with saturated aqueous sodium chloride solution (10 mL), dried over magnesium sulfate, concentrated in vacuo. The residue was purified by column chromatography eluting with ethyl acetate in hexanes to afford the title compound as a clear oil (0.83 g, 75%): MS (ES+) m/z 540.2 (M+1).

Step 2. Preparation of (S)-methyl 1-(4-(adamantan-1-ylmethoxy)-5-cyclopropyl-2-fluorobenzoyl)-4-(trifluoromethyl)-2,5-dihydro-1H-pyrrole-2-carboxylate

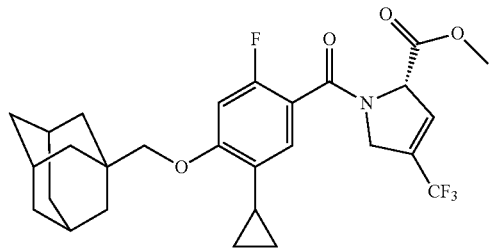 [SMILES: COC(=O)[C@@H]1C=C(C(F)(F)F)CN1C(=O)c1cc(C2CC2)c(OCC23CC4CC(CC(C4)C2)C3)cc1F]

To a solution of (2S)-methyl 1-(4-(adamantan-1-ylmethoxy)-5-cyclopropyl-2-fluorobenzoyl)-4-hydroxy-4-(trifluoromethyl)pyrrolidine-2-carboxylate in pyridine (3 mL), was added thionyl chloride (0.32 mL, 4.4 mmol) and stirred under a nitrogen atmosphere at 80° C. for 1 hour. The reaction mixture was then diluted with ether (20 mL) and washed with aqueous hydrochloric acid (1.0 N, 3×20 mL). The organic layers were then combined and washed with saturated aqueous sodium chloride solution (20 mL), concentrated in vacuo. The residue was purified by column chromatography eluting with ethyl acetate in hexanes to afford the title compound as oil (0.070 g, 25%): MS (ES+) m/z 522.3 (M+1).

Step 3. Preparation of (S)-1-(4-adamantan-1-ylmethoxy)-5-cyclopropyl-2-fluorobenzoyl)-4-(trifluoromethyl)-2,5-dihydro-1H-pyrrole-2-carboxylic Acid

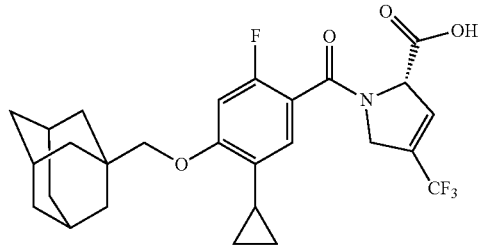 [SMILES: O=C(O)[C@@H]1C=C(C(F)(F)F)CN1C(=O)c1cc(C2CC2)c(OCC23CC4CC(CC(C4)C2)C3)cc1F]

Following the procedure as described in Example 12, Step 2 and making variations as required to replace (1R,2S,5S)-methyl 3-(4-(adamantan-1-ylmethoxy)-5-cyclopropyl-2-fluorobenzoyl)-6,6-dimethyl-3-azabicyclo[3.1.0]hexane-2-carboxylate with (S)-methyl 1-(4-(adamantan-1-ylmethoxy)-5-cyclopropyl-2-fluorobenzoyl)-4-(trifluoromethyl)-2,5-dihydro-1H-pyrrole-2-carboxylate and aqueous hydrochloric acid with saturated aqueous ammonium chloride solution. The residue was purified using preparative HPLC to afford the title compound as a colorless solid (0.003 g, 4%): $^1$H NMR (300 MHz, DMSO-d$_6$) δ 7.35-6.82 (m, 2H), 6.55 (s, 1H), 5.97 (s, 1H), 4.27-3.84 (m, 3H), 3.67-3.56 (m, 2H), 2.10-1.92 (m, 4H), 1.81-1.57 (m, 12H), 0.97-0.82 (m, 2H), 0.68-0.54 (m, 2H); MS (ES+) m/z 508.3 (M+1).

Example 204

Synthesis of (2S,4R)-1-(4-(adamantan-1-yl-methoxy)-2-cyclopropyl-6-fluorobenzoyl)-4-fluoro-pyrrolidine-2-carboxylic Acid Step 1. Preparation of tert-butyl 2-chloro-4,6-difluorobenzoate

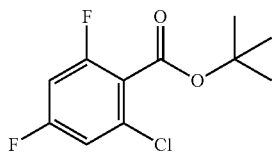 [SMILES: CC(C)(C)OC(=O)c1c(F)cc(F)cc1Cl]

To a solution of 2-chloro-4,6-difluorobenzoic acid (3.00 g, 15.7 mmol) in tetrahydrofuran (30 mL) was added di-tert-butyl dicarbonate (3.77 g, 17.3 mmol) and N,N-dimethyl-aminopyridine (0.38 g, 3.1 mmol) and the reaction mixture was stirred at reflux for 18 hours. The reaction was cooled to ambient temperature, concentrated and aqueous hydrochloric acid (0.25 M, 40 mL) was added and the mixture was extracted with diethyl ether (3×50 mL). The organic layers were washed with aqueous sodium hydroxide (2N, 15 mL) and brine (30 mL) and then dried over anhydrous magnesium sulfate, filtered and concentrated to give the title compound as an oil (3.9 g, 100%).

Step 2. Preparation of tert-butyl 4-((adamantan-1-yl)methoxy)-2-chloro-6-fluorobenzoate

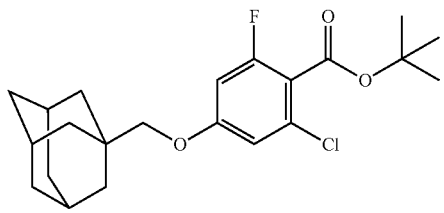 [SMILES: CC(C)(C)OC(=O)c1c(F)cc(OCC23CC4CC(CC(C4)C2)C3)cc1Cl]

A mixture of tert-butyl 2-chloro-4,6-difluorobenzoate (0.49 g, 2.0 mmol), 1-adamantyl methanol (0.33 g, 2.0 mmol) with cesium carbonate (2.1 g, 4.0 mmol) in dimethyl sulfoxide (6 mL) was stirred at 70° C. for 2 h. The reaction was cooled down to ambient temperature and quenched by addition of water (10 mL). The reaction mixture was extracted with ethyl acetate (3×15 mL), washed with brine (15 mL) and concentrated in vacuo. The residue was purified by chromatography eluting with ethyl acetate in hexanes to afford the title compound as colorless solid (0.61 g, 78%): MS (ES+) m/z 339.1 (M−56+1).

Step 3. Preparation of tert-butyl 4-((adamantan-1-yl)methoxy)-2-cyclopropyl-6-fluorobenzoate

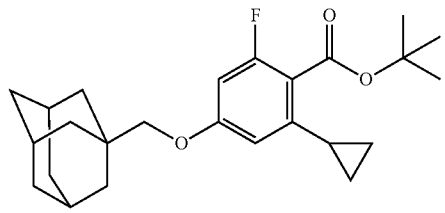 [SMILES: CC(C)(C)OC(=O)c1c(F)cc(OCC23CC4CC(CC(C4)C2)C3)cc1C1CC1]

A mixture of tert-butyl 4-((adamantan-1-yl)methoxy)-2-chloro-6-fluorobenzoate (1.15 g, 2.92 mmol), cyclopropyl boronic acid (0.37 g, 4.3 mmol), added palladium(II) acetate (0.1 g, 0.3 mmol), tricyclohexylphosphine tetrafluoroborate (0.21 g, 0.58 mmol), potassium phosphate (1.2 g, 5.8 mmol) and water (2 mL) in toluene (6 mL) was degassed and flushed with nitrogen for 10 minutes. The reaction mixture was heated at 150° C. in the microwave for 90 minutes. The mixture was filtered over diatomaceous earth. The filtrate was concentrated in vacuo and the residue was purified by chromatography eluting with ethyl acetate in hexanes to afford the title compound as a colorless oil (1.14 g, 98%): $^1$H NMR (300 MHz, CDCl$_3$) δ 6.39 (dd, J=11.6, 2.2 Hz, 1H), 6.28 (d, J=1.7 Hz, 1H), 3.41 (s, 2H), 2.03-1.94 (m, 4H), 1.79-1.52 (m, 21H), 0.96-0.86 (m, 2H), 0.71-0.62 (m, 2H).

Step 4. Preparation of 4-(adamantan-1-ylmethoxy)-2-cyclopropyl-6-fluorobenzoic Acid

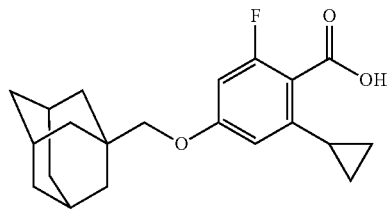 [SMILES: O=C(O)c1c(F)cc(OCC23CC4CC(CC(C4)C2)C3)cc1C1CC1]

A mixture of tert-butyl 4-((adamantan-1-yl)methoxy)-2-cyclopropyl-6-fluorobenzoate (1.1 g, 2.9 mmol) and added trifluoroacetic acid (2 mL) in dichloromethane (4 mL) was stirred at ambient temperature for 2 hours. The solvent was concentrated and purified by chromatography eluting with ethyl acetate in hexanes to afford the title compound (0.60 g, 59%): MS (ES−) m/z 343.1 (M−1).

Step 5. Preparation of (2S,4R)-methyl 1-(4-(adamantan-1-ylmethoxy)-2-cyclopropyl-6-fluorobenzoyl)-4-fluoropyrrolidine-2-carboxylate

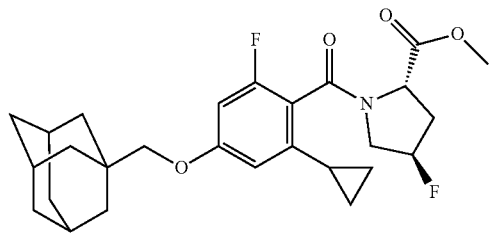 [SMILES: COC(=O)[C@@H]1C[C@@H](F)CN1C(=O)c1c(F)cc(OCC23CC4CC(CC(C4)C2)C3)cc1C1CC1]

Following the procedure as described in Example 191, Step 1 and making variations as required to replace 5-chloro-4-((5-chloro-6-(2,2,2-trifluoroethoxy)pyridin-3-yl) oxy)-2-fluorobenzoic acid with 4-(adamantan-1-ylmethoxy)-2-cyclopropyl-6-fluorobenzoic acid and (S)-tert-butyl pyrrolidine-2-carboxylate hydrochloride with (2S,4R)-methyl 4-fluoropyrrolidine-2-carboxylate, the title compound was obtained as clear oil (0.098 g, 49%): MS (ES+) m/z 474.3 (M+1).

Step 6. Preparation of (2S,4R)-1-(4-(adamantan-1-ylmethoxy)-2-cyclopropyl-6-fluorobenzoyl)-4-fluoropyrrolidine-2-carboxylic Acid

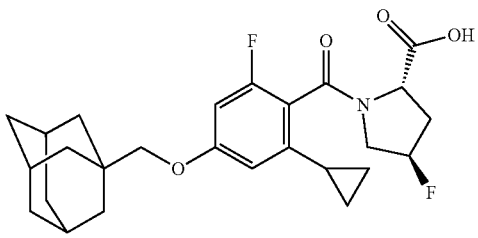 [SMILES: O=C(O)[C@@H]1C[C@@H](F)CN1C(=O)c1c(F)cc(OCC23CC4CC(CC(C4)C2)C3)cc1C1CC1]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S,4R)-methyl 1-(4-(adamantan-1-ylmethoxy)-2-cyclopropyl-6-fluorobenzoyl)-4-fluoropyrrolidine-2-carboxylate, the title compound was obtained as a colorless solid (0.004 g, 4%): $^1$H NMR (300 MHz, DMSO-$d_6$) δ 12.93-12.52 (s, br, 1H), 6.65 (td, J=11.4, 2.3 Hz, 1H), 6.27-6.16 (m, 1H), 5.37-5.14 (m, 1H), 4.45 (dd, J=16.3, 8.1 Hz, 1H), 3.67-3.55 (m, 1H), 3.54-3.46 (m, 2H), 3.46-3.33 (m, 1H), 2.71-2.55 (m, 1H), 2.29-2.01 (m, 2H), 1.99-1.89 (m, 3H), 1.74-1.52 (m, 12H), 0.96-0.64 (m, 4H); MS (ES+m/z 460.2 (M+1).

Example 205

Synthesis of (2S,4R)-1-(4-(adamantan-1-ylmethoxy)-5-cyclopropyl-2-fluorobenzoyl)-4-methoxy-3-methylpyrrolidine-2-carboxylic Acid Step 1. Preparation of 4-(adamantan-1-ylmethoxy)-5-cyclopropyl-2-fluorobenzoic Pivalic Anhydride

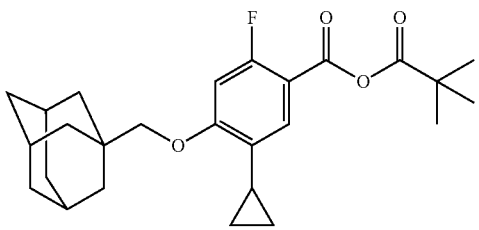 [SMILES: CC(C)(C)C(=O)OC(=O)c1cc(C2CC2)c(OCC23CC4CC(CC(C4)C2)C3)cc1F]

To a solution of 4-(adamantan-1-ylmethoxy)-5-cyclopropyl-2-fluorobenzoic acid (2.78 g, 8.07 mmol) in dichloromethane (32 mL), was added triethylamine (1.4 mL, 9.68 mmol) and pivaloyl chloride (1.0 mL, 8.5 mmol) at 0° C. and stirred at ambient temperature for 1 hour. The reaction mixture was then acidified with aqueous hydrochloric acid (1.0 N, 20 mL) and extracted with dichloromethane (4×20 mL). The organic layers were combined and washed with saturated aqueous sodium chloride solution (10 mL), dried over magnesium sulfate, filtered and concentrated in vacuo to afford the title compound as yellow solid (3.25 g, 94%) that was used directly in the next step.

Step 2. Preparation of (2S,4R)-methyl 1-(4-(adamantan-1-ylmethoxy)-5-cyclopropyl-2-fluorobenzoyl)-4-hydroxy-3-methylpyrrolidine-2-carboxylate

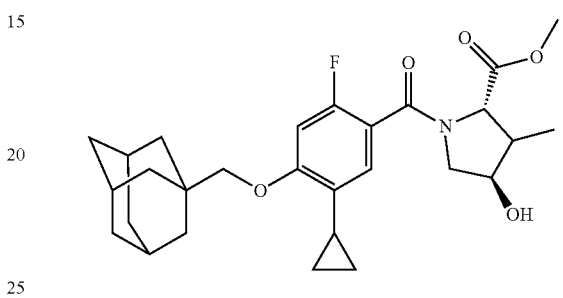

To a solution of 4-(adamantan-1-ylmethoxy)-5-cyclopropyl-2-fluorobenzoic pivalic anhydride (1.1 g, 2.6 mmol) in dichloromethane (10 mL), triethylamine (1.80 mL, 12.8 mmol) and (2S,4R)-methyl 4-hydroxy-3-methylpyrrolidine-2-carboxylate trifluoroacetic acid salt (0.70 g, 2.56 mmol) were added. The reaction solution was stirred at ambient temperature for 16 hours. The reaction mixture was acidified with aqueous hydrochloric acid (1 N, 10 mL) and extracted with dichloromethane (4×20 mL). The combined organic layers were washed with saturated aqueous sodium chloride solution and concentrated in vacuo. The residue was purified by column chromatography eluting with ethyl acetate in hexanes to afford the title compound as clear oil (0.060 g, 5%): MS (ES+) m/z 486.3 (M+1).

Step 3. Preparation of (2S,4R)-methyl 1-(4-(adamantan-1-ylmethoxy)-5-cyclopropyl-2-fluorobenzoyl)-4-methoxy-3-methylpyrrolidine-2-carboxylate

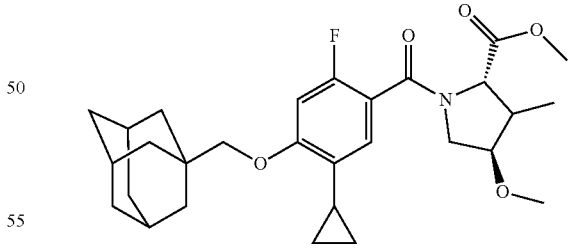

To a solution of (2S,4R)-methyl 1-(4-(adamantan-1-ylmethoxy)-5-cyclopropyl-2-fluorobenzoyl)-4-hydroxy-3-methylpyrrolidine-2-carboxylate (0.15 g, 0.31 mmol) in dimethylformamide (1.2 mL), sodium hydride (60% in mineral oil) (0.031 g, 0.77 mmol) was added. The reaction mixture was stirred at ambient temperature for 45 minutes then methyl iodide (0.08 mL, 1.2 mmol) was added and continued stirring for 16 hours. The reaction was quenched with saturated aqueous ammonium chloride (2 mL), extracted with ethyl acetate (4×20 mL) and the solvent was concentrated to afford the title compound as clear oil (0.15 g, 100%), which was used directly in the next step.

Step 4. Preparation of (2S,4R)-1-(4-(Adamantan-1-ylmethoxy)-5-cyclopropyl-2-fluorobenzoyl)-4-methoxy-3-methylpyrrolidine-2-carboxylic Acid

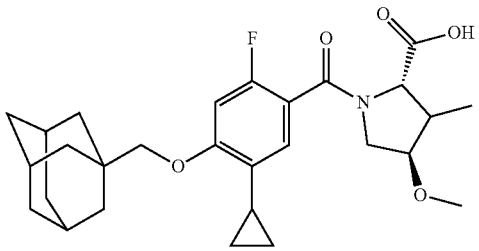 [SMILES: CO[C@H]1CN(C(=O)c2cc(C3CC3)c(OCC34CC5CC(CC(C5)C3)C4)cc2F)[C@H](C(=O)O)C1C]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S,4R)-methyl 1-(4-(adamantan-1-ylmethoxy)-5-cyclopropyl-2-fluorobenzoyl)-4-methoxy-3-methylpyrrolidine-2-carboxylate, the title compound was obtained as a colorless solid (0.004 g, 4%): $^1$H NMR (300 MHz, DMSO-$d_6$) δ 12.57 (s, 1H), 6.93-6.62 (m, 2H), 3.98 (d, J=7.5 Hz, 1H), 3.93-3.82 (m, 1H), 3.75-3.46 (m, 4H), 3.39-3.27 (m, 1H), 3.20 (d, J=2.0 Hz, 3H), 2.07-1.90 (m, 4H), 1.82-1.54 (m, 12H), 1.18-0.99 (m, 3H), 0.94-0.83 (m, 2H), 0.65-0.48 (m, 2H); MS (ES+) m/z 486.2 (M+1).

Example 206

Synthesis of 2-((S)-1-(4-(adamantan-1-ylmethoxy)-5-cyclopropyl-2-fluorobenzoyl)pyrrolidin-2-yl)acetic Acid

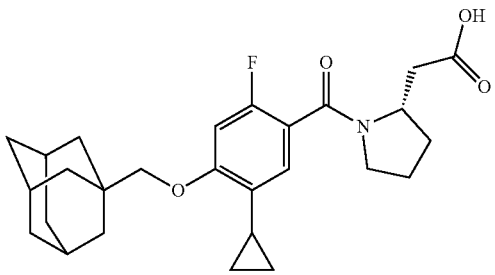 [SMILES: O=C(O)C[C@@H]1CCCN1C(=O)c1cc(C2CC2)c(OCC23CC4CC(CC(C4)C2)C3)cc1F]

Following the procedure as described in Example 198, and making variations as required to replace (S)-5-oxopyrrolidine-2-carboxylic acid with (S)-2-(pyrrolidin-2-yl)acetic acid, hydrochloride salt and rather stirring the initial oxalyl chloride reaction mixture for 16 hours. The reaction mixture was then purified using preparative HPLC to give the title compound as a colorless solid (0.070 g, 30%): $^1$H NMR (300 MHz, DMSO-$d_6$) δ 12.26 (s, 1H), 6.89-6.78 (m, 2H), 4.31-3.86 (m, 1H), 3.58 (s, 2H), 3.31-3.09 (m, 2H), 2.90 (dd, J=15.7, 3.2 Hz, 1H), 2.34 (dd, J=15.6, 9.8 Hz, 1H), 2.05-1.94 (m, 4H), 1.92-1.58 (m, 16H), 0.91-0.83 (m, 2H), 0.64-0.56 (m, 2H); MS (ES+) m/z 456.2 (M+1).

Example 207

Synthesis of (2S,3R,4S)-1-(4-(adamantan-1-ylmethoxy)-5-cyclopropyl-2-fluorobenzoyl)-4-methoxy-3-methylpyrrolidine-2-carboxylic Acid Step 1. Preparation of (2S,3R,4S)-methyl 1-(4-(adamantan-1-ylmethoxy)-5-cyclopropyl-2-fluorobenzoyl)-4-methoxy-3-methylpyrrolidine-2-carboxylate

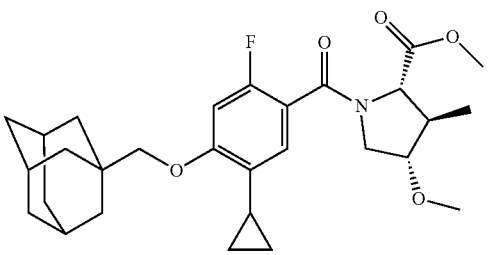 [SMILES: COC(=O)[C@@H]1[C@@H](C)[C@H](OC)CN1C(=O)c1cc(C2CC2)c(OCC23CC4CC(CC(C4)C2)C3)cc1F]

Following the procedure as described in Example 191, Step 1 and making variations as required to replace of 5-chloro-4-((5-chloro-6-(2,2,2-trifluoroethoxy)pyridin-3-yl)oxy)-2-fluorobenzoic acid with (2S,3R,4S)-methyl 1-(4-(adamantan-1-ylmethoxy)-5-cyclopropyl-2-fluorobenzoyl)-4-hydroxy-3-methylpyrrolidine-2-carboxylate and (S)-tert-butyl pyrrolidine-2-carboxylate hydrochloride with methyl (2S,3R,4S)-4-methoxy-3-methylpyrrolidine-2-carboxylate trifluoroacetate, the title compound was obtained as a clear oil (0.040 g, 40%): MS (ES+) m/z 500.3 (M+1).

Step 2. Preparation of (2S,3R,4S)-1-(4-(Adamantan-1-ylmethoxy)-5-cyclopropyl-2-fluorobenzoyl)-4-methoxy-3-methylpyrrolidine-2-carboxylic Acid

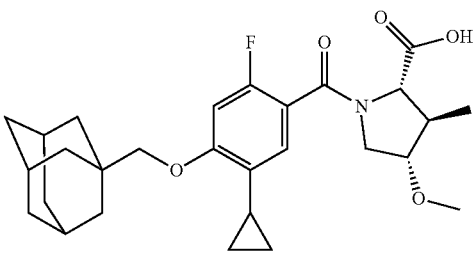 [SMILES: CO[C@@H]1CN(C(=O)c2cc(C3CC3)c(OCC34CC5CC(CC(C5)C3)C4)cc2F)[C@H](C(=O)O)[C@H]1C]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S,3R,4S)-methyl 1-(4-(adamantan-1-ylmethoxy)-5-cyclopropyl-2-fluorobenzoyl)-4-methoxy-3-methylpyrrolidine-2-carboxylate and following the residue purified by column chromatography eluting with a gradient 20 to 40% of ethyl acetate containing 0.5% of formic acid in hexanes, the title compound was obtained as a colorless solid (0.050 g, 100%): $^1$H NMR (300 MHz, DMSO-$d_6$) δ 12.63 (s, 1H), 6.92-6.71 (m, 2H), 4.01-3.85 (m, 1H), 3.74-3.46 (m, 5H), 3.24-3.12 (m, 4H), 2.09-1.92 (m, 4H), 1.79-1.56 (m, 12H), 1.18-0.98 (m, 3H), 0.94-0.82 (m, 2H), 0.65-0.47 (m, 2H); MS (ES+) m/z 486.3 (M+1).

Example 208

Synthesis of (2S,4S)-1-(5-Cyclopropyl-4-((1-((S)-1-(3,5-dichlorophenyl)ethyl)-4-fluoropiperidin-4-yl)methoxy)-2-fluorobenzoyl)-4-hydroxy-3-methylpyrrolidine-2-carboxylic Acid Step 1. Preparation of (2S,4S)-methyl 1-(5-cyclopropyl-4-((1-((S)-1-(3,5-dichlorophenyl)ethyl)-4-fluoropiperidin-4-yl)methoxy)-2-fluorobenzoyl)-4-hydroxy-3-methylpyrrolidine-2-carboxylate

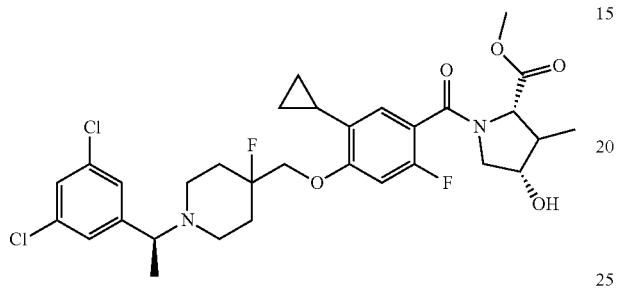

To a solution of (2S)-methyl 1-(5-cyclopropyl-4-((1-((S)-1-(3,5-dichlorophenyl)ethyl)-4-fluoropiperidin-4-yl)methoxy)-2-fluorobenzoyl)-3-methyl-4-oxopyrrolidine-2-carboxylate (0.710 g, 1.16 mmol) and (S)-1-methyl-3,3-diphenylhexahydropyrrolo[1,2-c][1,3,2]oxazaborole (1.4 mL, 1.4 mmol) in tetrahydrofuran (5 mL), borane dimethylsulfide complex (0.13 mL, 1.4 mmol) slowly was added at −78° C. The reaction mixture was stirred at −78° C. for 30 minutes then warmed to ambient temperature over 1 h and continued stirring for another 30 minutes. The reaction was quenched with methanol and stirred for 16 h. The reaction mixture was diluted with ethyl acetate (5 mL), acidified with saturated aqueous ammonium chloride (5 mL) and extracted with ethyl acetate (4×20 mL). The combined organic layers were washed with saturated aqueous sodium chloride solution (10 mL) and the solvent was concentrated in vacuo. The residue was purified column chromatography eluting with a gradient 0 to 5% of methanol in dichloromethane with 0.5% formic acid to afford the title compound as a clear oil (0.25 g, 35%): MS (ES+) m/z 625.2 (M+1).

Step 2. Preparation of (2S,4S)-1-(5-cyclopropyl-4-((1-((S)-1-(3,5-dichlorophenyl)ethyl)-4-fluoropiperidin-4-yl)methoxy)-2-fluorobenzoyl)-4-hydroxy-3-methylpyrrolidine-2-carboxylic Acid

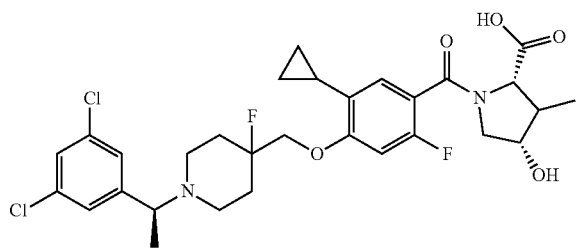 [SMILES: CC1[C@H](O)CN(C(=O)c2cc(C3CC3)c(OCC3(F)CCN([C@@H](C)c4cc(Cl)cc(Cl)c4)CC3)cc2F)[C@@H]1C(=O)O]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S,4S)-methyl 1-(5-cyclopropyl-4-((1-((S)-1-(3,5-dichlorophenyl)ethyl)-4-fluoropiperidin-4-yl)methoxy)-2-fluorobenzoyl)-4-hydroxy-3-methylpyrrolidine-2-carboxylate, the title compound was obtained as a colorless solid (0.003 g, 8%): $^1$H NMR (300 MHz, DMSO $d_6$) δ 12.56 (s, 1H), 7.77 (s, 1H), 7.66 (s, 2H), 6.97 (d, J=12.0 Hz, 1H), 6.89-6.73 (m, 1H), 4.70-4.55 (m, 1H), 4.28-4.17 (m, 2H), 3.87 (d, J=9.0 Hz, 2H), 3.29-2.95 (m, 6H), 2.38-2.10 (m, 4H), 2.05-1.86 (m, 3H), 1.76-1.58 (m, 3H), 1.16-0.99 (m, 3H), 0.92-0.81 (m, 2H), 0.65-0.53 (m, 2H); MS (ES+) m/z 611.3, 613.3 (M+1).

Example 209

Synthesis of (2S,4R)-1-(5-cyclopropyl-4-((1-((S)-1-(3,5-dichlorophenyl)ethyl)-4-fluoropiperidin-4-yl)methoxy)-2-fluorobenzoyl)-4-fluoro-3-methylpyrrolidine-2-carboxylic Acid Step 1. Preparation of (2S,4R)-methyl 1-(5-cyclopropyl-4-((1-((S)-1-(3,5-dichlorophenyl)ethyl)-4-fluoropiperidin-4-yl)methoxy)-2-fluorobenzoyl)-4-fluoro-3-methylpyrrolidine-2-carboxylate

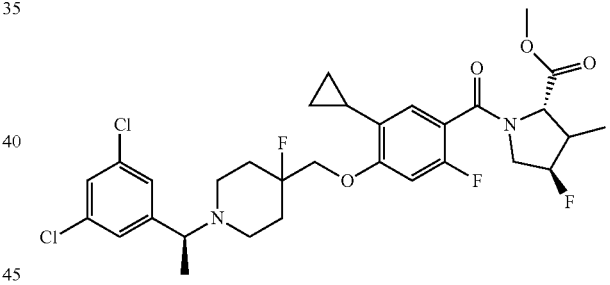

To a solution of (2S,4S)-methyl 1-(5-cyclopropyl-4-((1-((S)-1-(3,5-dichlorophenyl)ethyl)-4-fluoropiperidin-4-yl)methoxy)-2-fluorobenzoyl)-4-hydroxy-3-methylpyrrolidine-2-carboxylate (0.030 g, 0.047 mmol) in dichloromethane (0.2 mL), N,N-diethylaminosulfur trifluoride (0.03 mL, 0.19 mmol) and hydrofluoric acid in pyridine (70%, 0.005 mL, 0.190 mmol) were added. The reaction mixture was stirred at 0° C. for 10 minutes then warmed to ambient temperature and continued stirring for another 30 minutes. The reaction was quenched with sodium bicarbonate (2 mL) and extracted with dichloromethane (4×20 mL), dried over magnesium sulfate and filtered. The solvent was concentrated and the residue was purified by column chromatography eluting with a gradient from 0 to 20% of a mixture composed of 80% ethyl acetate, 10% isopropyl alcohol and 10% triethylamine in hexanes to afford the title compound as a clear oil (0.040 g, 16%): MS (ES+) m/z 627.2 (M+1).

Step 2. Preparation of (2S,4R)-1-(5-cyclopropyl-4-((1-((S)-1-(3,5-dichlorophenyl)ethyl)-4-fluoropiperidin-4-yl)methoxy)-2-fluorobenzoyl)-4-fluoro-3-methylpyrrolidine-2-carboxylic Acid

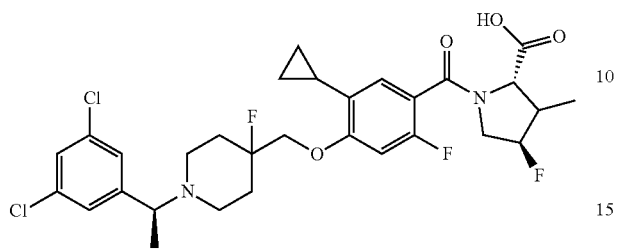

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S,4R)-methyl 1-(5-cyclopropyl-4-((1-((S)-1-(3,5-dichlorophenyl)ethyl)-4-fluoropiperidin-4-yl)methoxy)-2-fluorobenzoyl)-4-fluoro-3-methylpyrrolidine-2-carboxylate, the title compound was obtained as a colorless solid (0.0065 g, 16%): $^1$H NMR (300 MHz, DMSO d$_6$) δ 13.00-12.64 (m, 1H), 7.79-7.70 (m, 1H), 7.68-7.58 (m, 2H), 7.00-6.89 (m, 1H), 6.88-6.80 (m, 1H), 4.69-4.55 (m, 1H), 4.29-4.11 (m, 2H), 3.94-3.88 (m, 1H), 3.85-3.58 (m, 4H), 3.21-3.13 (m, 1H), 3.10-2.93 (m, 2H), 2.41-2.12 (m, 4H), 2.03-1.92 (m, 2H), 1.73-1.55 (m, 3H), 1.18-1.05 (m, 3H), 0.90-0.80 (m, 2H), 0.65-0.53 (m, 2H); MS (ES+) m/z 615.2, 613.2 (M+1).

Example 210a and Example 210b

Synthesis of (2S,3S,4S)-1-(4-(adamantan-1-ylmethoxy)-5-cyclopropyl-2-fluorobenzoyl)-4-fluoro-3-methylpyrrolidine-2-carboxylic acid and (2S,3R,4S)-1-(4-(adamantan-1-ylmethoxy)-5-cyclopropyl-2-fluorobenzoyl)-4-fluoro-3-methylpyrrolidine-2-carboxylic Acid

Step 1. Preparation of methyl (2S,4S)-1-(4-(adamantan-1-ylmethoxy)-5-cyclopropyl-2-fluorobenzoyl)-4-fluoro-3-methylpyrrolidine-2-carboxylate

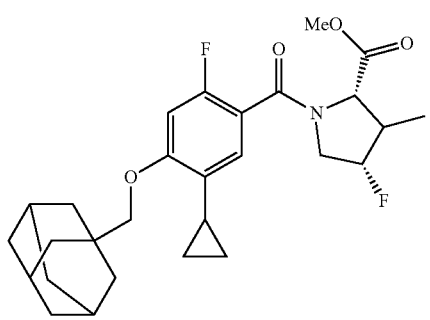 [SMILES: COC(=O)[C@@H]1C(C)[C@H](F)CN1C(=O)c1cc(C2CC2)c(OCC23CC4CC(CC(C4)C2)C3)cc1F]

To a solution of (2S,4R)-methyl 1-(4-(adamantan-1-ylmethoxy)-5-cyclopropyl-2-fluorobenzoyl)-4-hydroxy-3-methylpyrrolidine-2-carboxylate (0.140 g, 0.289 mmol) in dichloromethane (1.5 mL) was added N,N-diethylaminosulfur trifluoride (0.185 mg, 1.15 mmol) and stirred at ambient temperature for 2 hours. The reaction was then quenched by addition of a saturated aqueous solution of sodium bicarbonate (2 mL) and the mixture was extracted with dichloromethane (4×10 mL), dried over magnesium sulfate, filtered. The filtrate was concentrated in vacuo. The residue was purified by normal phase column chromatography eluting with a gradient from 0 to 20% of ethyl acetate in hexanes to give the title compound: MS (ES+) m/z 488.2 (M+1).

Step 2. Preparation of (2S,3S,4S)-1-(4-(adamantan-1-ylmethoxy)-5-cyclopropyl-2-fluorobenzoyl)-4-fluoro-3-methylpyrrolidine-2-carboxylic Acid

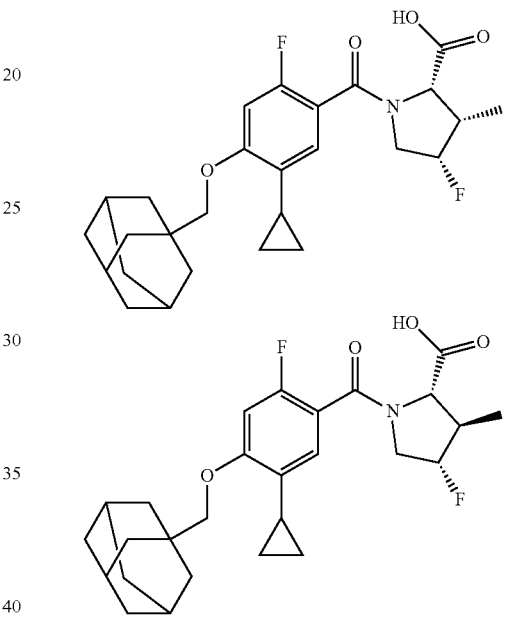

To a solution of crude (2S,4S)-1-(4-(adamantan-1-ylmethoxy)-5-cyclopropyl-2-fluorobenzoyl)-4-fluoro-3-methylpyrrolidine-2-carboxylate (0.136 g, 0.280 mmol) in methanol (0.5 mL), tetrahydrofuran (0.5 mL) and water (0.5 mL) was added lithium hydroxide (0.067 g, 2.8 mmol) and the mixture was stirred at ambient temperature for 16 h. The solvents were concentrated in vacuo. The residue was filtered to removed any solid particles and purified by preparative HPLC to afford first eluent of the title compound as a colorless solid (0.006 g, 5%): $^1$H NMR (300 MHz, DMSO-d$_6$) δ 13.02-12.14 (s, br, 1H), 6.90-6.65 (m, 2H), 5.23-4.86 (m, 1H), 4.42 and 4.10 (rotamers)—(2×d, J=9.6 Hz, 1H), 3.94-3.65 (m, 2H), 3.59-3.52 (m, 2H), 2.85-2.56 (m, 1H), 2.07-1.88 (m, 4H), 1.79-1.51 (m, 12H), 1.03 and 0.98 (rotamers)—(2×d, J=7.1 Hz, 3H), 0.92-0.79 (m, 2H), 0.62-0.48 (m, 2H) and the second eluent of the title compound as a colorless solid (0.002 g, 2%): $^1$H NMR (300 MHz, DMSO-d$_6$) 13.16-12.45 (s, br, 1H), 6.90-6.65 (m, 2H), 5.14-4.74 (m, 1H), 4.17 and 3.79 (rotamers) (d, J=3.0 Hz, 1H), 4.06-3.85 (m, 1H), 3.77-3.60 (m, 1H), 3.56 and 3.54 (rotamers) (s, 2H), 2.77-2.54 (m, 1H), 2.09-1.90 (m, 4H), 1.80-1.50 (m, 12H), 1.05 and 0.98 (rotamers) (d, J=7.0 Hz, 3H), 0.94-0.79 (m, 2H), 0.65-0.43 (m, 2H); MS (ES+) m/z 474.2 (M+1).

Example 211

Synthesis of (2S,4S)-1-(4-((adamantan-1-yl)methoxy)-5-cyclopropyl-2-fluorobenzoyl)-4-(trifluoromethyl)pyrrolidine-2-carboxylic Acid Step 1. Preparation of methyl (2S,4S)-1-(4-((adamantan-1-yl)methoxy)-5-cyclopropyl-2-fluorobenzoyl)-4-(trifluoromethyl)pyrrolidine-2-carboxylate

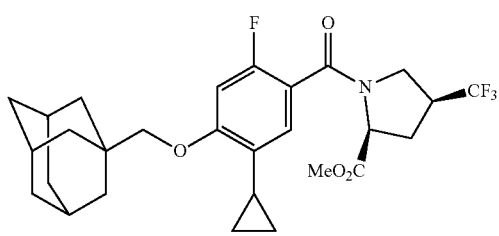 [SMILES: COC(=O)[C@@H]1C[C@H](C(F)(F)F)CN1C(=O)c1cc(C2CC2)c(OCC23CC4CC(CC(C4)C2)C3)cc1F]

Following the procedure as described in Example 191, Step 1 and making variations as required to replace 5-chloro-4-((5-chloro-6-(2,2,2-trifluoroethoxy)pyridin-3-yl)oxy)-2-fluorobenzoic acid with 4-((adamantan-1-yl)methoxy)-5-cyclopropyl-2-fluorobenzoic acid and (S)-tert-butyl pyrrolidine-2-carboxylate hydrochloride with methyl (2S,4S)-4-(trifluoromethyl)pyrrolidine-2-carboxylate hydrochloride, the title compound was obtained as a clear oil and used directly in the next step.

Step 2. Preparation of (2S,4S)-1-(4-((Adamantan-1-yl)methoxy)-5-cyclopropyl-2-fluorobenzoyl)-4-(trifluoromethyl)pyrrolidine-2-carboxylic Acid

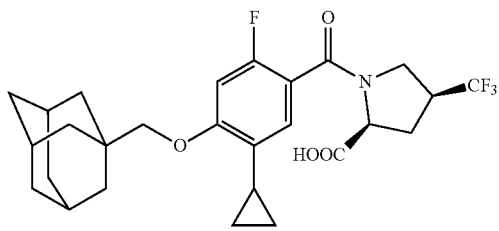 [SMILES: O=C(O)[C@@H]1C[C@H](C(F)(F)F)CN1C(=O)c1cc(C2CC2)c(OCC23CC4CC(CC(C4)C2)C3)cc1F]

Following the procedure as described in Example 210, Step 2, and making variations as required to replace (2S,4S)-1-(4-(adamantan-1-ylmethoxy)-5-cyclopropyl-2-fluorobenzoyl)-4-fluoro-3-methylpyrrolidine-2-carboxylate with methyl (2S,4S)-1-(4-((adamantan-1-yl)methoxy)-5-cyclopropyl-2-fluorobenzoyl)-4-(trifluoromethyl)pyrrolidine-2-carboxylate, the title compound was obtained as a colorless solid (0.056 g, 19%): $^1$H NMR (300 MHz, DMSO-$d_6$) δ 6.90-6.69 (m, 2H), 4.54-4.24 (m, 1H), 3.74-3.71 (m, 1H), 3.54 (s, 2H), 3.49-3.25 (m, 3H), 2.75-2.37 (m, 2H), 2.07-1.82 (m, 5H), 1.77-1.54 (m, 11H), 0.91-0.82 (m, 2H), 0.63-0.47 (m, 2H); MS (ES+) m/z 510.2 (M+1).

Example 212

Synthesis of 2-(4-((Adamantan-1-yl)methoxy)-5-cyclopropyl-2-fluorobenzoyl)-2-azabicyclo[3.1.0]hexane-1-carboxylic Acid

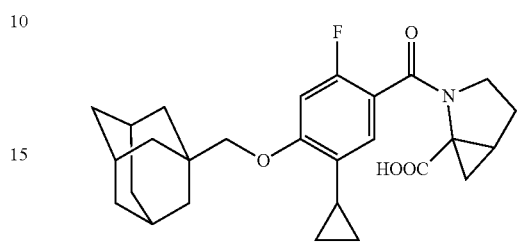

Following the procedure as described in Example 198, and making variations as required to replace (S)-5-oxopyrrolidine-2-carboxylic acid with 2-azabicyclo[3.1.0]hexane-1-carboxylic acid, hydrochloric acid salt, the title compound was obtained as a colorless solid (0.125 g, 37%): $^1$H NMR (300 MHz, CDCl$_3$) δ 7.12-6.84 (m, 1H), 6.59-6.40 (m, 1H), 4.19-3.86 (m, 2H), 3.47 (s, 2H), 3.16-2.86 (m, 1H), 2.41-1.92 (m, 8H), 1.88-1.58 (m, 13H), 0.96-0.78 (m, 2H), 0.73-0.46 (m, 2H); MS (ES+) m/z 454.3 (M+1).

Example 213

Synthesis of (2S)-1-(4-((adamantan-1-yl)methoxy)-5-cyclopropyl-2-fluorobenzoyl)-4-hydroxy-4-(trifluoromethyl)pyrrolidine-2-carboxylic Acid Step 1. Preparation of methyl (2S)-4-hydroxy-4-(trifluoromethyl)pyrrolidine-2-carboxylate Hydrochloride

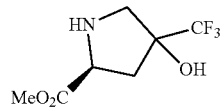

To a solution of (2S)-1-(tert-butoxycarbonyl)-4-hydroxy-4-(trifluoromethyl)-pyrrolidine-2-carboxylic acid (2.55 g, 8.15 mmol) in 1,4-dioxane (10 mL) at 0° C., a solution of hydrochloric acid in 1,4-dioxane (4N, 3 mL) was added. The reaction mixture was warm up to ambient temperature over 1 hour. The stirring was continued for another 4 h at which point a precipitate formed. The precipitate was filtered and rinsed with diethyl ether (3×10 mL) and dried in vacuo to afford the title compound (0.45 g, 28%): $^1$H NMR (300 MHz, CDCl$_3$) δ 10.50-9.98 (s, br, 2H), 4.72 (dd, J=9.6, 3.3 Hz, 1H), 3.73 (s, 3H), 3.45-3.37 (m, 2H), 2.55 (dd, J=14.0, 9.7 Hz, 1H), 2.39 (dd, J=13.7, 3.0 Hz, 1H).

Step 2. Preparation of methyl (2S)-1-(4-((adamantan-1-yl)methoxy)-5-cyclopropyl-2-fluorobenzoyl)-4-hydroxy-4-(trifluoromethyl)pyrrolidine-2-carboxylate

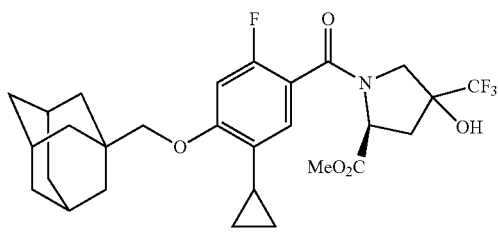 [SMILES: COC(=O)[C@@H]1CC(O)(C(F)(F)F)CN1C(=O)c1cc(C2CC2)c(OCC23CC4CC(CC(C4)C2)C3)cc1F]

To a solution of 4-(adamantan-1-ylmethoxy)-5-cyclopropyl-2-fluorobenzoic acid (0.137 g, 0.400 mmol) in dichloromethane (2 mL) and DMF (0.05 mL), was added oxalyl chloride (0.04 mL, 0.50 mmol) and stirred under a nitrogen atmosphere at ambient temperature for 30 minutes. The reaction mixture was then concentrated and dried under high vacuum to produce a colorless solid, which was then dissolved in dichloromethane (2 mL). (2S)-4-hydroxy-4-(trifluoro-methyl)pyrrolidine-2-carboxylic acid, hydrochloric acid salt (0.075 g, 0.300 mmol) was then added to the reaction mixture, followed by N,N-diisopropylethylamine (0.26 mL, 0.50 mmol) and the reaction mixture was stirred under a nitrogen atmosphere for 30 minutes at ambient temperature. The reaction was then quenched by addition of a saturated aqueous solution of sodium bicarbonate (10 mL) and the mixture was extracted with dichloromethane (4×10 mL), dried over magnesium sulfate, filtered. The filtrated was concentrated in vacuo and the residue was purified by column chromatography eluting with a gradient from 0 to 40% of ethyl acetate containing 0.5% of acetic acid in hexanes to afford the title compound which was used directly in the next step.

Step 3. Preparation of (2S)-1-(4-((Adamantan-1-yl)methoxy)-5-cyclopropyl-2-fluorobenzoyl)-4-hydroxy-4-(trifluoromethyl)pyrrolidine-2-carboxylic Acid

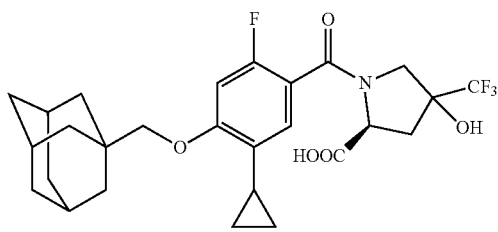 [SMILES: O=C(O)[C@@H]1CC(O)(C(F)(F)F)CN1C(=O)c1cc(C2CC2)c(OCC23CC4CC(CC(C4)C2)C3)cc1F]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S)-Methyl 1-(4-(adamantan-1-ylmethoxy)-5-cyclopropyl-2-fluorobenzoyl)-4-hydroxy-4-(trifluoromethyl)pyrrolidine-2-carboxylate and following the residue purified by preparative HPLC, the title compound was obtained as a colorless solid (0.081 g, 38%): $^1$H NMR (300 MHz, DMSO-$d_6$) δ 6.92-6.73 (m, 2H), 4.71-4.24 m, 1H), 3.88-3.61 (m, 1H), 3.61-3.45 (m, 3H), 3.12-2.49 (m, 2H), 2.23-2.08 (m, 1H), 2.07-1.89 (m, 4H), 1.78-1.53 (m, 12H), 0.92-0.80 (m, 2H), 0.63-0.45 (m, 2H); MS (ES+) m/z 526.3 (M+1).

Example 214

Synthesis of (2S)-1-(4-((Adamantan-1-yl)methoxy)-5-cyclopropyl-2-fluorobenzoyl)-4-methoxy-4-(trifluoromethyl)pyrrolidine-2-carboxylic Acid Step 1. Preparation of methyl (2S)-1-(4-((adamantan-1-yl)methoxy)-5-cyclopropyl-2-fluorobenzoyl)-4-methoxy-4-(trifluoromethyl)pyrrolidine-2-carboxylate

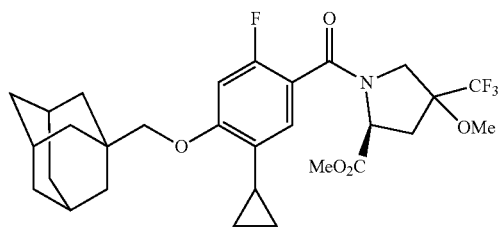 [SMILES: COC(=O)[C@@H]1CC(OC)(C(F)(F)F)CN1C(=O)c1cc(C2CC2)c(OCC23CC4CC(CC(C4)C2)C3)cc1F]

Following the procedure as described in Example 205, Step 3 and making non-critical variations as required to replace (2S,4R)-methyl 1-(4-(adamantan-1-ylmethoxy)-5-cyclopropyl-2-fluorobenzoyl)-4-hydroxy-3-methylpyrrolidine-2-carboxylate (2S)-methyl 1-(4-(adamantan-1-ylmethoxy)-5-cyclopropyl-2-fluorobenzoyl)-4-hydroxy-4-(trifluoromethyl)pyrrolidine-2-carboxylate, the residue obtained was directly used in the next step.

Step 2. Preparation of (2S)-1-(4-((Adamantan-1-yl)methoxy)-5-cyclopropyl-2-fluorobenzoyl)-4-methoxy-4-(trifluoromethyl)pyrrolidine-2-carboxylic Acid

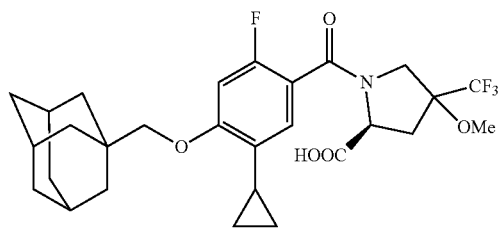 [SMILES: COC1(C(F)(F)F)C[C@@H](C(=O)O)N(C(=O)c2cc(C3CC3)c(OCC34CC5CC(CC(C5)C3)C4)cc2F)C1]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with (2S)-1-(4-((adamantan-1-yl)methoxy)-5-cyclopropyl-2-fluorobenzoyl)-4-methoxy-4-(trifluoromethyl)pyrrolidine-2-carboxylate and following the residue purified by preparative HPLC, the title compound was obtained as a colorless solid (0.028 g, 14%): $^1$H NMR (300 MHz, DMSO-$d_6$) δ 6.92-6.73 (m, 2H), 4.70-4.19 (m, 1H), 3.90-3.63 (m, 2H), 3.62-3.50 (m, 2H), 3.26 (s, 4H), 2.70-2.51 (m, 1H), 2.42-2.30 (m, 1H), 2.07-1.90 (m, 4H), 1.78-1.53 (m, 12H), 0.92-0.80 (m, 2H), 0.63-0.44 (m, 2H); MS (ES+) m/z 540.3 (M+1).

Example 215

Synthesis of 2-((S)-1-(4-((adamantan-1-yl)methoxy)-5-cyclopropyl-2-fluorobenzoyl)azetidin-2-yl)acetic Acid Step 1. Preparation of tert-butyl (S)-2-(2-diazoacetyl)azetidine-1-carboxylate

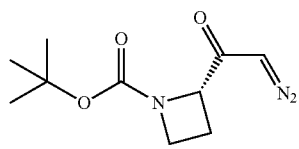

To a solution of (S)-1-(tert-butoxycarbonyl)azetidine-2-carboxylic acid (0.57 g, 2.8 mmol) and triethylamine (0.48 mL, 3.4 mmol) in tetrahydrofuran (3 mL) at 0° C., isobutyl chloroformate (0.41 mL, 3.1 mmol) was added. The reaction mixture was stirred at ambient temperature for 1 hour and then filtered through a pad of diatomaceous earth, rinsing with small amounts of acetonitrile (3×5 mL). The filtrate was concentrated in vacuo and the re-dissolved in acetonitrile (3 mL) and trimethylsilyldiazomethane (1.34 mL, 8.47 mmol) was added under nitrogen. The reaction mixture was stirred at ambient temperature for 16 hours and quenched by addition of a saturated aqueous solution of sodium bicarbonate (10 mL). The mixture was extracted with ethyl acetate (2×15 mL), washed with brine (20 mL), dried over anhydrous magnesium sulfate and filtered. The filtrate was concentrated in vacuo to afford the title compound which was used directly into the next step.

Step 2. Preparation of tert-butyl (S)-2-(2-methoxy-2-oxoethyl)azetidine-1-carboxylate

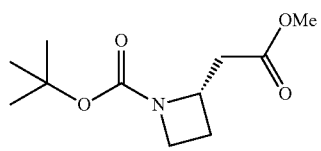 [SMILES: COC(=O)C[C@@H]1CCN1C(=O)OC(C)(C)C]

To a solution of tert-butyl (S)-2-(2-diazoacetyl)azetidine-1-carboxylate (0.64 g, 2.8 mmol) in methanol was added triethylamine (2.0 mL, 14 mmol) followed by silver (I) trifluoroacetate (0.43 mg, 1.7 mmol). The reaction mixture was stirred at 60° C. for 2 h, then cooled to ambient temperature and the solvents were concentrated in vacuo. The residue was purified by flash chromatography eluting with ethyl acetate in hexanes to afford the title compound (0.25 g, 39%): MS (ES+) m/z 230.1 (M+1).

Step 3. Preparation of methyl (S)-2-(azetidin-2-yl)acetate Hydrochloride

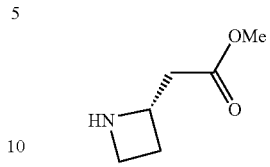

Tert-butyl (S)-2-(2-methoxy-2-oxoethyl)azetidine-1-carboxylate (0.13 g, 0.56 mmol) was dissolved in a solution of hydrochloric acid in 1,4-dioxane (4N, 1 mL) and stirred for 1 hour at ambient temperature. The solvent was concentrated in vacuo to afford the title compound: MS (ES+) m/z 130.1 (M+1).

Step 4. Preparation of methyl 2-((S)-1-(4-((adamantan-1-yl)methoxy)-5-cyclopropyl-2-fluorobenzoyl)azetidin-2-yl)acetate

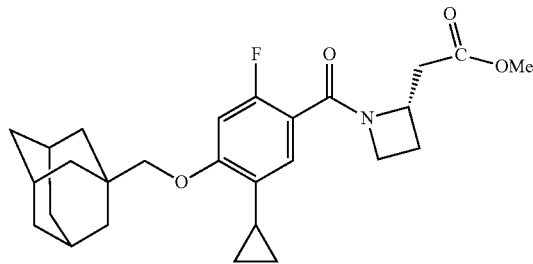 [SMILES: COC(=O)C[C@@H]1CCN1C(=O)c1cc(C2CC2)c(OCC23CC4CC(CC(C4)C2)C3)cc1F]

Following the procedure as described in Example 198, and making variations as required to replace (S)-5-oxopyrrolidine-2-carboxylic acid with methyl (S)-2-(azetidin-2-yl)acetate hydrochloride, the title compound was obtained as a colorless oil (0.025 g, 14%): MS (ES+) m/z 456.2 (M+1).

Step 4. Preparation of 2-((S)-1-(4-((Adamantan-1-yl)methoxy)-5-cyclopropyl-2-fluorobenzoyl)azetidin-2-yl)acetic Acid

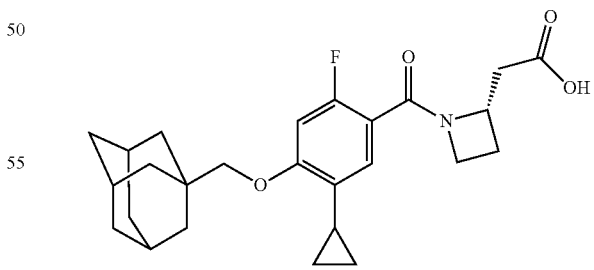

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl 2-((S)-1-(4-((adamantan-1-yl)methoxy)-5-cyclopropyl-2-fluorobenzoyl)azetidin-2-yl)acetate, the title compound was obtained as a colorless solid (0.004 g, 16%): $^1$H NMR (300 MHz, DMSO-$d_6$) δ 12.48-12.11 (s, br, 1H), 7.06-6.70 (m, 2H), 4.60-4.46 (m, 1H), 4.04-3.67 (m, 2H), 3.55 (s, 2H), 3.00-2.84 (m, 1H), 2.75-2.57 (m, 1H), 2.55-2.49 (m, 1H), 2.43-2.30 (m, 1H), 2.05-1.86 (m, 4H), 1.74-1.52 (m, 12H), 0.91-0.80 (m, 2H), 0.61-0.51 (m, 2H); MS (ES+) m/z 442.2 (M+1).

Example 216

Synthesis of (4-((1-(3-Chloro-5-(trifluoromethyl) benzyl)-4-fluoropiperidin-4-yl)methoxy)-5-cyclopropyl-2-fluorobenzoyl)-L-valine

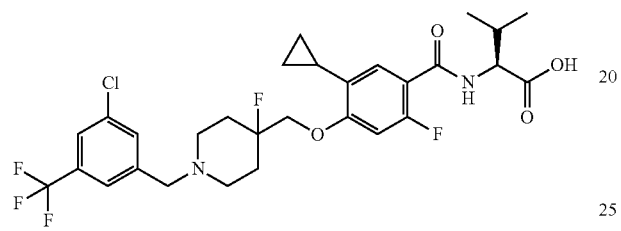

Following the procedures as described in Example 191, Step 1 and 2 and making variations as required to replace of 5-chloro-4-((5-chloro-6-(2,2,2-trifluoroethoxy)pyridin-3-yl)oxy)-2-fluorobenzoic acid with 4-((1-(3-chloro-5-(trifluoromethyl)benzyl)-4-fluoropiperidin-4-yl)methoxy)-5-cyclopropyl-2-fluorobenzoic acid and (S)-tert-butyl pyrrolidine-2-carboxylate hydrochloride with tert-butyl L-valinate, the title compound was obtained as a colorless solid (0.006, 5%): $^1$H NMR (300 MHz, DMSO-$d_6$) δ 8.03-7.93 (m, 1H), 7.78-7.68 (m, 2H), 7.21 (d, J=8.8 Hz, 1H), 6.87 (d, J=13.7 Hz, 1H), 4.08-3.99 (m, 1H), 3.92-3.86 (m, 2H), 3.61 (s, 2H), 3.35-3.29 (m, 2H), 2.87-2.77 (m, 2H), 2.72-2.55 (m, 2H), 2.14-1.93 (m, 4H), 1.80-1.70 (m, 2H), 0.90-0.77 (m, 8H), 0.58-0.51 (m, 2H); MS (ES+) m/z 605.2, 603.2 (M+1).

Example 217

Synthesis of (S)-1-(5-Chloro-4-((5-chloro-6-(2,2,2-trifluoroethoxy)pyridin-3-yl)oxy)-2-fluorobenzoyl) pyrrolidine-2-carboxylic Acid Trifluoroacetate

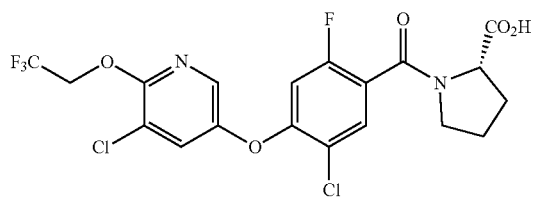 [SMILES: O=C(O)[C@@H]1CCCN1C(=O)c1cc(Cl)c(Oc2cnc(OCC(F)(F)F)c(Cl)c2)cc1F]

Following the procedures as described in Example 191, Step 1 and 2 and making variations as required to replace of 5-chloro-4-((5-chloro-6-(2,2,2-trifluoroethoxy)pyridin-3-yl)oxy)-2-fluorobenzoic acid with 5-chloro-4-((5-chloro-6-(2,2,2-trifluoroethoxy)pyridin-3-yl)oxy)-2-fluorobenzoic acid, the title compound was obtained as a colorless solid (0.071, 23%): $^1$H NMR (300 MHz, DMSO-$d_6$) δ 8.14-7.99 (m, 2H), 7.61-7.52 (m, 1H), 7.23-6.88 (m, 1H), 7.17-7.08 (m, 1H), 5.11-4.96 (m, 2H), 4.65-3.94 (m, 1H), 4.38-4.17 (m, 1H), 3.58-3.29 (m, 2H), 2.32-2.16 (m, 1H), 1.99-1.74 (m, 3H); MS (ES+) m/z 499.0, 497.0 (M+1).

Example 218

Synthesis of (2S)-1-(4-(adamantan-1-ylmethoxy)-5-cyclopropyl-2-fluorobenzoyl)-4-hydroxy-4-methyl-pyrrolidine-2-carboxylic Acid Step 1. Preparation of (S)-2-(methoxycarbonyl)-4-oxopyrrolidin-1-ium Trifluoroacetate

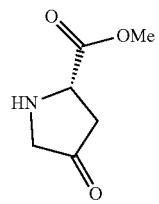

To a solution of 1-(tert-butyl) 2-methyl (S)-4-oxopyrrolidine-1,2-dicarboxylate (3.00 g, 12.3 mmol) in dichloromethane (72 mL) was added trifluoroacetic acid (2.8 mL, 37.0 mmol). The reaction mixture was stirred at ambient temperature 2 h, after which it was evaporated in vacuo. The residue was used directly for the next step.

Step 2. Preparation of methyl (S)-1-(4-(adamantan-1-ylmethoxy)-5-cyclopropyl-2-fluorobenzoyl)-4-oxopyrrolidine-2-carboxylate

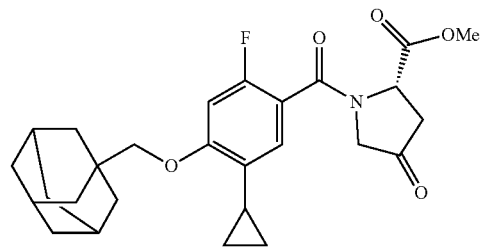 [SMILES: COC(=O)[C@@H]1CC(=O)CN1C(=O)c1cc(C2CC2)c(OCC23CC4CC(CC(C4)C2)C3)cc1F]

Following the procedure as described in Example 1, Step 1 and making variation as required to replace (S)-tert-butyl pyrrolidine-2-carboxylate hydrochloride with (S)-2-(methoxycarbonyl)-4-oxopyrrolidin-1-ium trifluoroacetate, the title compound was obtained as a colorless solid (1.95 g, 69%): $^1$H NMR (300 MHz, CDCl$_3$) δ 6.95 (d, J=7.5 Hz, 1H), 6.51 (d, J=11.9 Hz, 1H), 5.24 (d, J=10.1 Hz, 1H), 4.05-3.95 (m, 1H), 3.79 (s, 3H), 3.65 (s, 1H), 3.49 (s, 2H), 3.10-2.92 (m, 1H), 2.75-2.50 (m, 1H), 2.02 (s, 4H), 1.87-1.60 (m, 12H), 0.89 (d, J=8.3 Hz, 2H), 0.70-0.55 (m, 2H).

Step 3. Preparation of methyl (2S)-1-(4-(adamantan-1-ylmethoxy)-5-cyclopropyl-2-fluorobenzoyl)-4-hydroxy-4-methylpyrrolidine-2-carboxylate

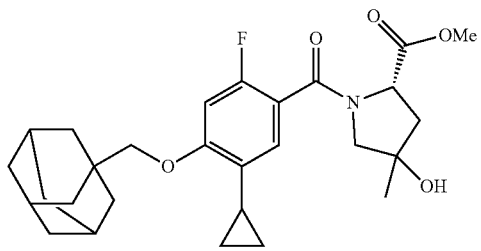 [SMILES: COC(=O)[C@@H]1CC(C)(O)CN1C(=O)c1cc(C2CC2)c(OCC23CC4CC(CC(C4)C2)C3)cc1F]

To a cooled (−78° C.) solution of methyl (S)-1-(4-(adamantan-1-ylmethoxy)-5-cyclopropyl-2-fluorobenzoyl)-4-oxopyrrolidine-2-carboxylate (0.30 g, 0.64 mmol) in tetrahydrofuran (4.5 mL), a solution of methyl magnesium bromide (0.30 mL, 3.0 mol/L in diethyl ether) was added dropwise under nitrogen atmosphere. The reaction mixture was warmed to −15° C. over 5 h, quenched with the addition of saturated ammonium chloride (50 mL) and extracted with ethyl acetate (3×50 mL). The combined organic layers were dried over anhydrous magnesium sulfate, filtered and concentrated in vacuo. The residue was purified by column chromatography to afford the title compound as a colorless oil (0.098 g, 27%): MS (ES+) m/z 486.3 (M+1).

Step 4. Preparation of (2S)-1-(4-(adamantan-1-ylmethoxy)-5-cyclopropyl-2-fluorobenzoyl)-4-hydroxy-4-methylpyrrolidine-2-carboxylic Acid

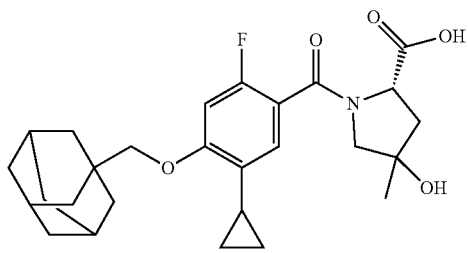 [SMILES: CC1(O)C[C@@H](C(=O)O)N(C(=O)c2cc(C3CC3)c(OCC34CC5CC(CC(C5)C3)C4)cc2F)C1]

Following the procedure as described in Example 230, Step 2 and making non-critical variations as required to replace methyl (2S,3R,4S)-1-(4-(adamantan-1-ylmethoxy)-5-cyclopropyl-2-fluorobenzoyl)-4-hydroxy-3-methylpyrrolidine-2-carboxylate with methyl (2S)-1-(4-(adamantan-1-ylmethoxy)-5-cyclopropyl-2-fluorobenzoyl)-4-hydroxy-4-methylpyrrolidine-2-carboxylate, the tile compound was obtained as a colorless solid (0.042 g, 44%): $^1$H NMR (300 MHz, CDCl$_3$) δ 7.28-7.22 (m, 1H), 6.49 (d, J=11.7 Hz, 1H), 4.76 (m, 1H), 3.48-3.45 (m, 4H), 2.55-2.16 (m, 2H), 2.02 (s, 4H), 1.73-1.67 (m, 12H), 1.34 (s, 3H), 0.87 (m, 2H), 0.61 (m, 2H); Note: COOH and OH signals were not observed; $^{19}$F NMR (282 MHz, CDCl$_3$) δ −113.9 (s, 1F); MS (ES−) m/z 470.2 (M−1).

Example 219

Synthesis of (2S,3R,4R)-1-(4-(adamantan-1-ylmethoxy)-5-cyclopropyl-2-fluorobenzoyl)-4-fluoro-3-methylpyrrolidine-2-carboxylic Acid

Step 1. Preparation of methyl (2S, 3R, 4R)-1-(4-(adamantan-1-ylmethoxy)-5-cyclopropyl-2-fluorobenzoyl)-4-fluoro-3-methylpyrrolidine-2-carboxylate

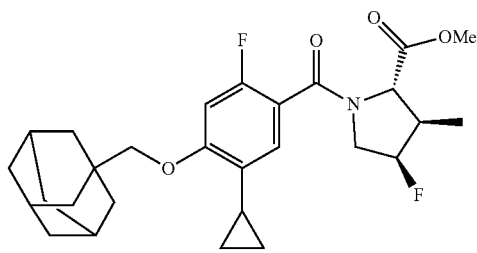 [SMILES: COC(=O)[C@@H]1[C@@H](C)[C@@H](F)CN1C(=O)c1cc(C2CC2)c(OCC23CC4CC(CC(C4)C2)C3)cc1F]

A premixed solution of hydrofluoric acid (70% in pyridine, 0.012 mL, 0.44 mmol) and diethylaminosulfur trifluoride (0.059 mL, 0.44 mmol) in 1,2-dichloroethane was added dropwise to a solution of methyl (2S, 3R, 4S)-1-(4-(adamantan-1-ylmethoxy)-5-cyclopropyl-2-fluorobenzoyl)-4-hydroxy-3-methylpyrrolidine-2-carboxylate (0.050 g, 0.10 mmol) in 1,2-dichloroethane (5.0 mL) 0° C. The reaction mixture was warmed to ambient temperature overnight and quenched with the addition of solid sodium bicarbonate (0.015 g). The heterogeneous mixture was purified by column chromatography to afford the title compound as a colorless oil (0.029 g, 58% yield): MS (ES+) m/z 488.3 (M+1).

Step 2. Preparation of (2S, 3R, 4R)-1-(4-(adamantan-1-ylmethoxy)-5-cyclopropyl-2-fluorobenzoyl)-4-fluoro-3-methylpyrrolidine-2-carboxylic Acid

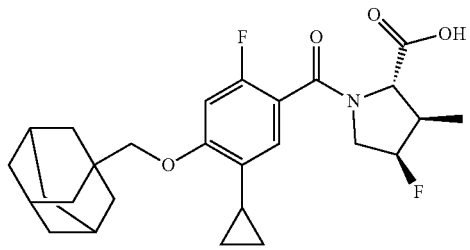 [SMILES: C[C@@H]1[C@@H](C(=O)O)N(C(=O)c2cc(C3CC3)c(OCC34CC5CC(CC(C5)C3)C4)cc2F)C[C@@H]1F]

Following the procedure as described in Example 229, Step 2 and making non-critical variations as required to replace methyl (2S,3R,4S)-1-(4-(adamantan-1-ylmethoxy)-5-cyclopropyl-2-fluorobenzoyl)-4-hydroxy-3-methylpyrrolidine-2-carboxylate with methyl (2S,3R, 4R)-1-(4-(adamantan-1-ylmethoxy)-5-cyclopropyl-2-fluorobenzoyl)-4-fluoro-3-methylpyrrolidine-2-carboxylate, the title compound was obtained as a colorless solid (0.020 g, 20% yield): $^1$H NMR 300 MHz, CDCl$_3$) δ 7.00 (d, J=6.2 Hz, 1H), 6.51 (d, J=11.8 Hz, 1H), 5.78 (br s, 1H), 4.90 (d, J=53.4 Hz, 1H), 4.36 (d, J=10.5 Hz, 1H), 3.96-3.60 (m, 2H), 3.49 (s, 2H), 2.71-2.60 (m, 1H), 2.02 (s, 4H), 1.81-1.59 (m, 12H), 1.24 (d, J=5.1 Hz, 3H), 0.91 (d, J=7.9 Hz, 2H), 0.61 (s, 2H); $^{19}$F NMR (282 MHz, CDCl$_3$) δ −112.9 (s), −195.9 (s); $^{13}$C NMR (75 MHz, CDCl$_3$) δ 173.2, 168.2, 161.6, 159.1, 156.2, 129.0, 126.4, 113.1, 98.8, 93.4 (d, J=182.3 Hz), 78.8, 64.2, 55.2, 44.7, 39.5, 37.1, 33.9, 28.1, 11.2, 9.5, 7.0; MS (ES+) m/z 474.1 (M+1).

Example 220

Synthesis of (2S,4R)-1-(4-((1-((5-(2-chlorophenyl)-1,2,4-oxadiazol-3-yl)methyl)piperidin-4-yl)methoxy)-5-cyclopropyl-2-fluorobenzoyl)-4-fluoropyrrolidine-2-carboxylic Acid Step 1. Synthesis of methyl (2S,4R)-1-(4-((1-((5-(2-chlorophenyl)-1,2,4-oxadiazol-3-yl)methyl)-piperidin-4-yl)methoxy)-5-cyclopropyl-2-fluorobenzoyl)-4-fluoropyrrolidine-2-carboxylate

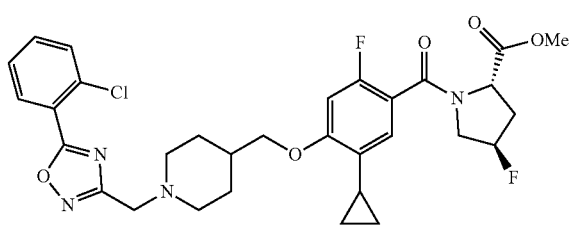 [SMILES: COC(=O)[C@@H]1C[C@@H](F)CN1C(=O)c1cc(C2CC2)c(OCC2CCN(Cc3noc(-c4ccccc4Cl)n3)CC2)cc1F]

To a solution of 4-((1-((5-(2-chlorophenyl)-1,2,4-oxadiazol-3-yl)methyl)piperidin-4-yl)methoxy)-5-cyclopropyl-2-fluorobenzoic acid (0.10 g, 0.21 mmol) in acetonitrile (2.5 mL) was added N,N-diisopropylethylamine (0.18 mL, 1.03 mmol), hydroxybenzotriazole (0.042 g, 0.31 mmol), O-(Benzotriazol-1-yl)-N,N,N',N'-tetramethyluronium tetrafluoroborate (0.13 g, 0.41 mmol) and trans-4-fluoro-L-proline methyl ester (0.08 g, 0.31 mmol). The reaction mixture was stirred at ambient temperature overnight, then diluted with saturated sodium carbonate, and extracted with ethyl acetate (3×75 mL). The combined organic extracts were dried over anhydrous magnesium sulfate, filtered and concentrated in vacuo. The residue was purified by column chromatography eluting with ethyl acetate in hexanes to afford the title compound as yellow oil (0.03 g, 25%): $^1$H NMR (300 MHz, CDCl$_3$) δ 7.92 (dd, J=7.5 Hz, 1.8 Hz, 1H), 7.55-7.48 (m, 1H), 7.44-7.33 (m, 2H), 6.60 (d, J=8.1 Hz, 1H), 6.49 (d, J=8.1 Hz, 1H), 5.19 (d, J=51.3 Hz, 1H), 4.79 (t, J=8.7 Hz, 1H), 3.97 (s, 2H), 3.85-3.62 (m, 6H), 3.15-3.00 (m, 2H), 2.75-2.55 (m, 1H), 2.32 (t, J=10.2 Hz, 2H), 2.04-1.77 (m, 5H), 1.61-1.45 (m, 2H), 1.23 (t, J=7.2 Hz, 1H), 0.92-0.77 (m, 2H), 0.65-0.52 (m, 2H); MS (ES+) m/z 615.2 (M+1).

Step 2. Synthesis of (2S,4R)-1-(4-((1-((5-(2-chlorophenyl)-1,2,4-oxadiazol-3-yl)methyl)piperidin-4-yl)methoxy)-5-cyclopropyl-2-fluorobenzoyl)-4-fluoropyrrolidine-2-carboxylic Acid

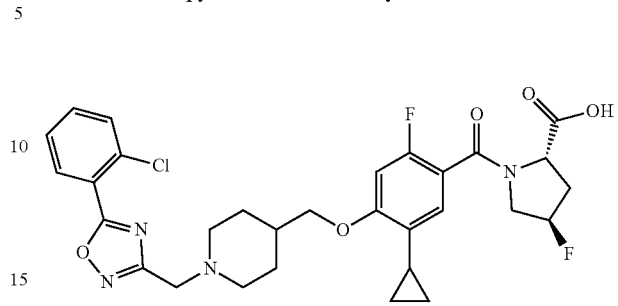

To a solution of methyl (2S,4R)-1-(4-((1-((5-(2-chlorophenyl)-1,2,4-oxadiazol-3-yl)methyl)piperidin-4-yl)methoxy)-5-cyclopropyl-2-fluorobenzoyl)-4-fluoropyrrolidine-2-carboxylate (0.032 g, 0.052 mmol) in tetrahydrofuran (1 mL), water (1 mL) and methanol (0.4 mL) was added potassium carbonate (0.036 g, 0.26 mmol). The reaction was fitted with a condenser and heated at reflux for 2 h. The reaction mixture was diluted with saturated ammonium chloride, extracted with ethyl acetate (3×50 mL), dried over anhydrous magnesium sulfate, filtered, and evaporated to dryness. The residue was purified by preparative HPLC (acetonitrile and water with 0.1% trifluoroacetic acid) to afford the title compound as a colorless solid (0.029 g, 92%): $^1$H NMR (300 MHz, CDCl$_3$) δ 7.91 (s, 1H), 7.53-7.35 (m, 3H), 7.28-7.23 (m, 1H), 6.99-6.86 (m, 1H), 6.54-6.34 (m, 1H), 5.18 (d, J=53.7 Hz, 1H), 4.81 (br s, 1H), 4.43 (s, 2H), 3.75-3.51 (m, 6H), 2.84 (br s, 2H), 2.63-2.35 (m, 2H), 1.95-1.78 (m, 6H), 0.83 (br s, 2H), 0.53 (br s, 1H); Note: acidic proton not observed; MS (ES+) m/z 601.2 (M+1).

Example 221

Synthesis of (S)-5-(4-((1-(2-chloro-5-(trifluoromethyl)benzyl)-4-fluoropiperidin-4-yl)methoxy)-5-cyclopropyl-2-fluorobenzoyl)-5-azaspiro[2.4]heptane-6-carboxylic Acid Step 1. Preparation of (S)-6-carboxy-5-azaspiro[2.4]heptan-5-ium Trifluoroacetate

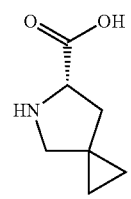

To a solution of (6S)-5-(tert-butoxycarbonyl)-5-azaspiro[2.4]heptane-6-carboxylic acid (0.40 g, 1.66 mmol) in dichloromethane (20 mL) was added trifluoroacetic acid (3.8 mL, 49.8 mmol). The solution was stirred at ambient temperature for 2 hours, and then evaporated to dryness in vacuo. The residue was used without further purification.

Step 2. Preparation of 4-((1-(2-chloro-5-(trifluoromethyl)benzyl)-4-fluoropiperidin-4-yl)methoxy)-5-cyclopropyl-2-fluorobenzoyl Chloride

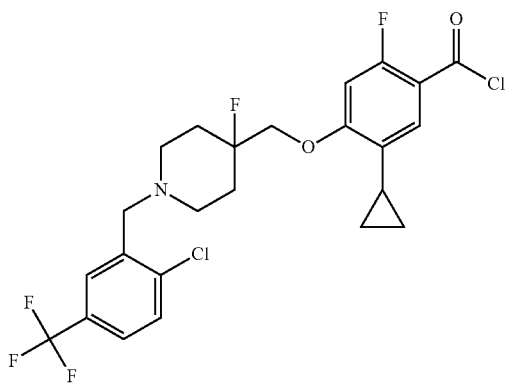 [SMILES: O=C(Cl)c1cc(C2CC2)c(OCC2(F)CCN(Cc3cc(C(F)(F)F)ccc3Cl)CC2)cc1F]

To a solution of 4-((1-(2-chloro-5-(trifluoromethyl)benzyl)-4-fluoropiperidin-4-yl)methoxy)-5-cyclopropyl-2-fluorobenzoic acid (0.38 g, 0.76 mmol) in acetonitrile (5.1 mL) was added oxalyl chloride (0.98 mL, 11.4 mmol), followed by N,N-dimethylformamide (0.02 mL). The reaction mixture was stirred under nitrogen for 2 h, and then concentrated in vacuo. The residue was used without further purification or characterization.

Step 3. Preparation of (S)-5-(4-((1-(2-chloro-5-(trifluoromethyl)benzyl)-4-fluoropiperidin-4-yl)methoxy)-5-cyclopropyl-2-fluorobenzoyl)-5-azaspiro[2.4]heptane-6-carboxylic Acid

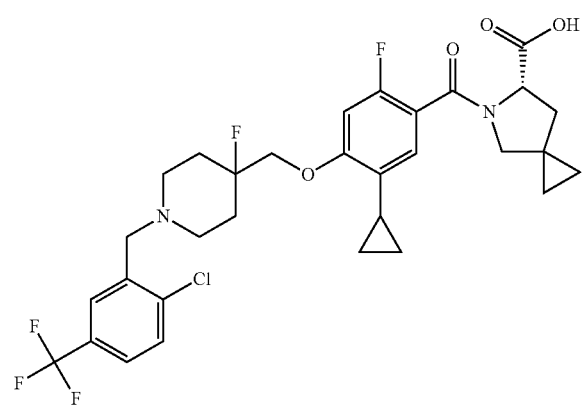 [SMILES: O=C(O)[C@@H]1CC2(CC2)CN1C(=O)c1cc(C2CC2)c(OCC2(F)CCN(Cc3cc(C(F)(F)F)ccc3Cl)CC2)cc1F]

To a solution of 4-((1-(2-chloro-5-(trifluoromethyl)benzyl)-4-fluoropiperidin-4-yl)methoxy)-5-cyclopropyl-2-fluorobenzoyl chloride (obtained from 0.38 g of 4-((1-(2-chloro-5-(trifluoromethyl)benzyl)-4-fluoropiperidin-4-yl)methoxy)-5-cyclopropyl-2-fluorobenzoic acid) in acetonitrile (2 mL) was added N,N-diisopropylethylamine (1.3 mL, 7.6 mmol), followed by (S)-6-carboxy-5-azaspiro[2.4]heptan-5-ium trifluoroacetate (1.66 mmol). The reaction mixture was stirred at ambient temperature for 16 h, after which it was diluted with aqueous hydrochloric acid (1 mol/L, 15 mL). The pooled organic fractions were extracted with ethyl acetate (3×100 mL), dried over anhydrous magnesium sulfate, filtered, and concentrated in vacuo. The residue was purified by preparative HPLC (acetonitrile and water with 0.1% trifluoroacetic acid) to afford the title compound as a colorless solid (0.069 g, 15%): $^1$H NMR (300 MHz, CDCl$_3$) δ 8.00 (s, 1H), 7.52 (s, 1H), 6.77 (d, J=7.8 Hz, 1H), 6.23 (d, J=11.4 Hz, 1H), 4.61 (t, J=7.8 Hz, 1H), 4.15-3.83 (m, 5H), 3.56 (d, J=10.2 Hz, 1H), 3.38-3.24 (m, 1H), 3.06-2.95 (m, 1H), 2.90 (d, J=10.2 Hz, 1H), 2.84-2.66 (m, 2H), 2.25-1.84 (m, 7H), 0.90-0.70 (m, 2H), 0.63-0.42 (m, 6H); MS (ES+) m/z 625.1 (M−1). Note: acidic proton not observed.

Example 222

Synthesis of (2S,4R)-1-(5-cyclopropyl-4-((1-(2,6-dichlorobenzyl)piperidin-4-yl)methoxy)-2-fluorobenzoyl)-4-fluoropyrrolidine-2-carboxylic Acid

Step 1. Preparation of methyl (2S,4R)-1-(5-cyclopropyl-4-((1-(2,6-dichlorobenzyl)piperidin-4-yl)methoxy)-2-fluorobenzoyl)-4-fluoropyrrolidine-2-carboxylate

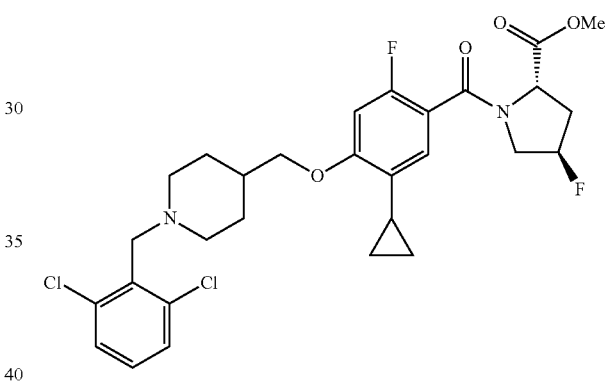

To a solution of 5-cyclopropyl-4-((1-(2,6-dichlorobenzyl)piperidin-4-yl)methoxy)-2-fluorobenzoic acid (0.52 g, 0.91 mmol) in dichloromethane (5.5 mL) was added N,N-dimethylaminopyridine (0.33 g, 2.73 mmol), (2S,4R)-4-fluoro-2-(methoxycarbonyl)pyrrolidin-1-ium chloride (0.50 g, 2.73 mmol) and N-(3-dimethylaminopropyl)-N'-ethylcarbodiimide hydrochloride (0.53 g, 2.73 mmol). The reaction mixture was stirred at ambient temperature for 16 h, and then diluted with saturated ammonium chloride (50 mL). The solution was extracted with dichloromethane (3×50 mL), dried over anhydrous magnesium sulfate, filtered, and concentrated in vacuo to afford a residue that was purified by column chromatography eluting with ethyl acetate in hexanes to afford methyl (2S,4R)-1-(5-cyclopropyl-4-((1-(2,6-dichlorobenzyl)piperidin-4-yl)methoxy)-2-fluorobenzoyl)-4-fluoropyrrolidine-2-carboxylate as a white foam (0.23 g, 42%): $^1$H NMR (300 MHz, CDCl$_3$) δ 7.32-7.25 (m, 2H), 7.15-7.07 (m, 1H), 6.96 (d, J=8.1 Hz, 1H), 6.48 (d, J=12.0 Hz, 1H), 5.20 (d, J=52.2 Hz, 1H), 4.80 (t, J=8.4 Hz, 1H), 3.80-3.70 (m, 7H), 3.05-2.90 (m, 2H), 2.75-2.55 (m, 1H), 2.35-2.16 (m, 3H), 2.05-1.68 (m, 5H), 1.45-1.20 (m, 3H), 0.90-0.84 (m, 2H), 0.65-0.55 (m, 2H); MS (ES+) m/z 581.2, 583.2 (M+1).

Step 2. Preparation of (2S,4R)-1-(5-cyclopropyl-4-((1-(2,6-dichlorobenzyl)piperidin-4-yl)methoxy)-2-fluorobenzoyl)-4-fluoropyrrolidine-2-carboxylic Acid

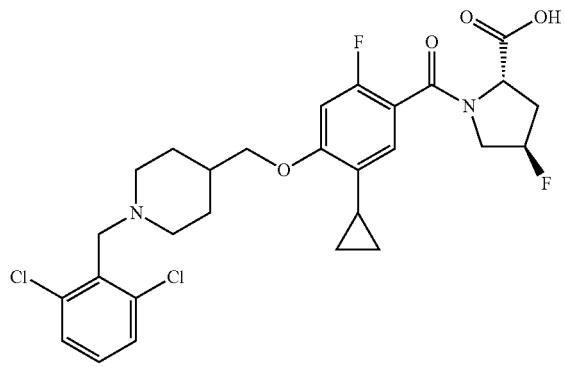 [SMILES: O=C(O)[C@@H]1C[C@@H](F)CN1C(=O)c1cc(C2CC2)c(OCC2CCN(Cc3c(Cl)cccc3Cl)CC2)cc1F]

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (2S,4R)-1-(5-cyclopropyl-4-((1-(2,6-dichlorobenzyl)piperidin-4-yl)methoxy)-2-fluorobenzoyl)-4-fluoropyrrolidine-2-carboxylate, the title compound was obtained as colorless solid (0.18 g, 82%): $^1$H NMR (300 MHz, DMSO-d$_6$) δ 9.85 (br s, 1H), 7.70-7.45 (m, 3H), 7.11-6.70 (m, 2H), 5.25 (d, J=52.8 Hz, 1H), 4.70-4.40 (m, 3H), 4.35-4.05 (m, 1H), 3.95-3.80 (m, 2H), 3.75-3.40 (m, 5H), 2.72-2.50 (m, 1H), 2.35-1.95 (m, 5H), 1.85-1.65 (m, 2H), 0.92-0.77 (m, 2H), 0.65-50 (m, 2H); MS (ES−) m/z 567.0 (M−1), 569.0 (M−1)

Example 223

Synthesis of 2-(4-(adamantan-1-ylmethoxy)-5-cyclopropyl-2-fluorobenzamido)-3,3,3-trifluoropropanoic Acid

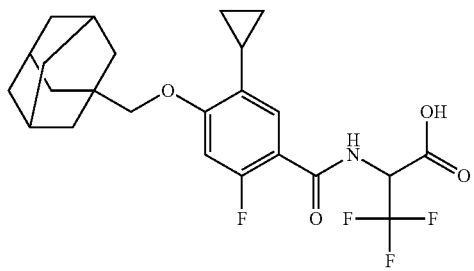 [SMILES: O=C(NC(C(=O)O)C(F)(F)F)c1cc(C2CC2)c(OCC23CC4CC(CC(C4)C2)C3)cc1F]

To a solution of 4-(adamantan-1-ylmethoxy)-5-cyclopropyl-2-fluorobenzoyl chloride (1.0 mmol) in acetonitrile (7 mL) was added N,N-diisopropylethylamine (1.7 mL, 10 mmol) and 2-amino-3,3,3-trifluoropropanoic acid (0.32 g, 2.2 mmol). The reaction mixture was stirred at ambient temperature overnight, diluted with aqueous hydrochloric acid (1 mol/L, 50 mL), and then extracted with ethyl acetate (5×75 mL). The combined organic extracts were dried over anhydrous magnesium sulfate, filtered and concentrated in vacuo to obtain a residue that was purified by column chromatography eluting with ethyl acetate in hexanes with 0.2% trifluoroacetic acid, followed by preparative HPLC (acetonitrile and water with 0.1% trifluoroacetic acid) to afford the title compound as colorless solid (0.52 g, 11%): $^1$H NMR (300 MHz, CDCl$_3$) δ 8.80-8.76 (m, 1H), 7.14 (d, J=9.0 Hz, 1H), 6.87 (d, J=14.0 Hz, 1H), 5.35-5.27 (m, 1H), 3.60 (s, 2H), 2.10-1.95 (m, 4H), 1.80-1.55 (m, 12H), 0.95-0.85 (m, 2H), 0.65-0.55 (m, 2H); Note: carboxylic acid (COOH) proton not observed; MS (ES+) m/z 470.1 (M+1).

Example 224

Synthesis of (4S,5R)-3-(5-cyclopropyl-4-((1-(2,6-dichlorobenzyl)piperidin-4-yl)methoxy)-2-fluorobenzoyl)-5-methyloxazolidine-4-carboxylic Acid

Step 1. Preparation of dimethyl 3,3'-methylene(4S,4'S,5R,5'R)-bis(5-methyloxazolidine-4-carboxylate)

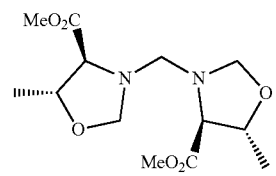

To a suspension of L-threonine methyl ester hydrochloride (2.80 g, 16.50 mmol) in dichloromethane (100 mL) was added triethylamine (2.75 mL, 17.80 mmol) and paraformaldehyde (1.03 g). The solution was stirred at ambient temperature for 16 h. The reaction mixture was then evaporated to dryness in vacuo, and triturated with diethyl ether. The precipitated solid was washed with diethyl ether (250 mL), after which the filtrate was evaporated in vacuo. The resulting clear oil was used in the next without further purification or characterization.

Step 2. Preparation of methyl (4S,5R)-3-(5-cyclopropyl-4-((1-(2,6-dichlorobenzyl)-piperidin-4-yl)methoxy)-2-fluorobenzoyl)-5-methyloxazolidine-4-carboxylate

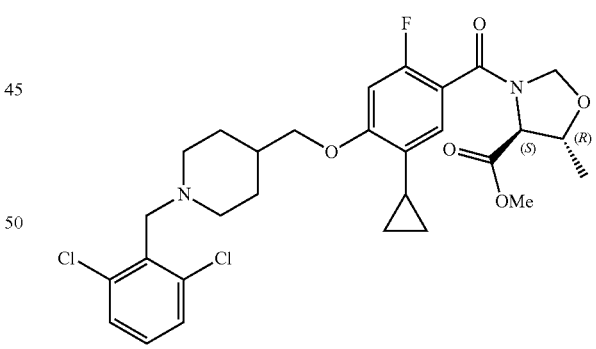

To a solution of dimethyl 3,3'-methylene(4S,4'S,5R,5'R)-bis(5-methyloxazolidine-4-carboxylate) (0.41 g, 1.32 mmol) in acetonitrile (7.0 mL) and saturated sodium carbonate (7.0 mL) was dropwise added a solution of 4-((4-(chlorocarbonyl)-2-cyclopropyl-5-fluorophenoxy)-methyl)-1-(2,6-dichlorobenzyl)piperidin-1-ium trifluoroacetate (1.55 g, 2.64 mmol) in acetonitrile (6.0 mL). The reaction mixture was stirred at ambient temperature for 16 h, after which it was diluted with water and extracted with ethyl acetate (4×75 mL). The combined organic extracts were dried over anhydrous magnesium sulfate, filtered and concentrated in vacuo. The residue was purified by column chromatography to afford the title compound as a colorless solid (0.48 g, 63%): $^1$H NMR (300 MHz, CDCl$_3$) δ 7.30 (s, 1H), 7.27 (s, 1H), 7.18-7.09 (m, 1H), 7.00 (d, J=8.1 Hz, 1H), 6.49 (d, J=12.0 Hz, 1H), 4.97-4.88 (m, 1H), 4.44-4.03 (m, 2H), 3.81-3.63 (m, 6H), 3.05-2.87 (m, 2H), 2.25 (t, J=11.4 Hz, 2H), 1.85-1.73 (m, 2H), 1.59 (s, 3H), 1.49 (d, J=6.0 Hz, 2H), 1.44-1.20 (m, 4H), 0.87-0.80 (m, 2H), 0.69-0.50 (m, 2H); MS (ES+) m/z 579.0, 581.0 (M+1).

Step 3. Preparation of (4S,5R)-3-(5-cyclopropyl-4-((1-(2,6-dichlorobenzyl)piperidin-4-yl)methoxy)-2-fluorobenzoyl)-5-methyloxazolidine-4-carboxylic Acid

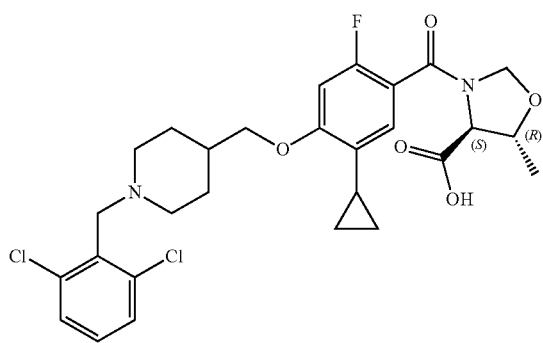

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-(5-cyclopropyl-4-((1-(2,6-dichlorobenzyl)piperidin-4-yl)methoxy)-2-fluorobenzoyl)-5-methyloxazolidine-4-carboxylate, the title compound was obtained as colorless solid (0.36 g, 77% yield): $^1$H NMR (300 MHz, CDCl$_3$) δ 10.30-9.70 (br s, 1H), 7.65-7.57 (m, 2H), 7.55-7.45 (m, 1H), 7.00-6.75 (m, 2H), 4.88-4.72 (m, 2H), 4.49 (s, 2H), 4.22-4.05 (m, 2H), 3.97-3.77 (m, 2H), 3.65-3.40 (m, 4H), 2.15-1.70 (m, 6H), 1.37 (d, J=5.7 Hz, 2H), 1.29 (d, J=4.8 Hz, 1H), 0.85 (d, J=8.1 Hz, 2H), 0.65-0.52 (m, 2H); MS (ES+) m/z 565.0, 567.0 (M+1).

Example 225

Preparation of (4S,5R)-3-(4-((1-(3-chloro-2-fluoro-5-(trifluoromethyl)benzyl)-4-fluoropiperidin-4-yl)methoxy)-5-cyclopropyl-2-fluorobenzoyl)-5-methyloxazolidine-4-carboxylic Acid Step 1. Preparation of 4-((1-(3-chloro-2-fluoro-5-(trifluoromethyl)benzyl)-4-fluoropiperidin-4-yl)methoxy)-5-cyclopropyl-2-fluorobenzoyl Chloride

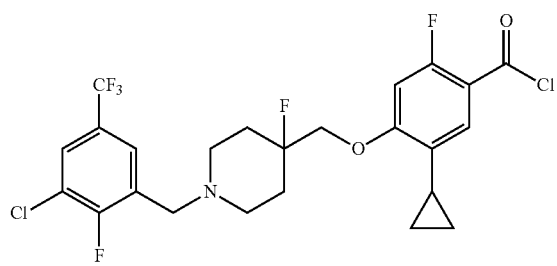 [SMILES: O=C(Cl)c1cc(C2CC2)c(OCC2(F)CCN(Cc3cc(C(F)(F)F)cc(Cl)c3F)CC2)cc1F]

To a solution of 4-((1-(3-chloro-2-fluoro-5-(trifluoromethyl)benzyl)-4-fluoropiperidin-4-yl)methoxy)-5-cyclopropyl-2-fluorobenzoic acid (0.30 g, 0.60 mmol) in dichloromethane (3.0 mL) was added thionyl chloride (3.0 mL). The reaction mixture was stirred at ambient temperature for 12 h then solvent was concentrated in vacuo and used without further purification or characterization.

Step 2. Preparation of methyl (4S,5R)-3-(4-((1-(3-chloro-2-fluoro-5-(trifluoromethyl)benzyl)-4-fluoropiperidin-4-yl)methoxy)-5-cyclopropyl-2-fluorobenzoyl)-5-methyloxazolidine-4-carboxylate

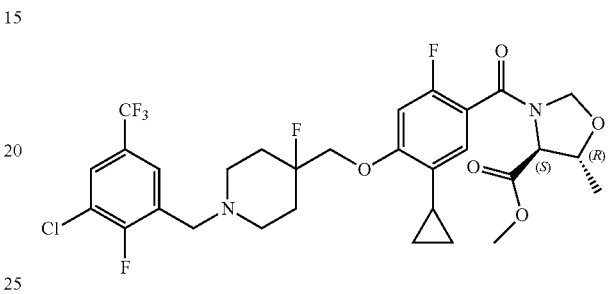

Following the procedure as described in Example 223, Step 2 and making non-critical variations as required to replace 4-((4-(chlorocarbonyl)-2-cyclopropyl-5-fluorophenoxy)methyl)-1-(2,6-dichlorobenzyl)piperidin-1-ium trifluoroacetate with 4-((1-(3-chloro-2-fluoro-5-(trifluoromethyl)benzyl)-4-fluoropiperidin-4-yl)methoxy)-5-cyclopropyl-2-fluorobenzoyl chloride, the title compound was obtained as pale yellow oil (0.22 g, 58% yield): MS (ES+) m/z 649.0, 651.0 (M+1)

Step 3. Preparation of (4S,5R)-3-(4-((1-(3-chloro-2-fluoro-5-(trifluoromethyl)benzyl)-4-fluoropiperidin-4-yl)methoxy)-5-cyclopropyl-2-fluorobenzoyl)-5-methyloxazolidine-4-carboxylic Acid

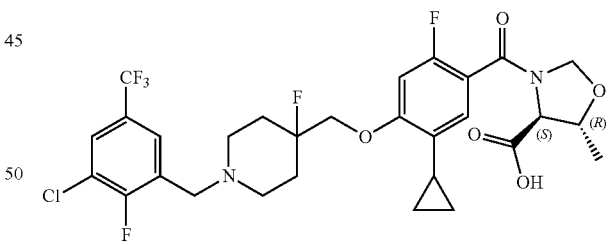

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-(4-((1-(3-chloro-2-fluoro-5-(trifluoromethyl)benzyl)-4-fluoropiperidin-4-yl)methoxy)-5-cyclopropyl-2-fluorobenzoyl)-5-methyloxazolidine-4-carboxylate, the tile compound was obtained as a colorless solid (0.20 g, 86%): $^1$H NMR (300 MHz, CDCl$_3$) δ 11.15 (s, 1H), 8.22 (s, 2H), 7.12-6.80 (m, 2H), 4.91-4.70 (m, 2H), 4.62-4.35 (m, 1H), 4.27-4.08 (m, 3H), 4.05-3.96 (m, 1H), 3.60-3.02 (m, 5H), 2.38-2.06 (m, 4H), 2.06-1.97 (m, 1H), 1.37 (d, J=6.0 Hz, 2H), 1.29 (d, J=5.4 Hz, 1H), 0.86 (d, J=8.4 Hz, 2H), 0.65-0.50 (m, 2H); MS (ES+) m/z 635.1 (M+1).

Example 226

Synthesis of (4S,5R)-3-(5-cyclopropyl-4-((1-(1-(3,5-dichlorophenyl)-2,2,2-trifluoroethyl)-piperidin-4-yl)methoxy)-2-fluorobenzoyl)-5-methyloxazolidine-4-carboxylic Acid Step 1. Preparation of methyl (4I,5R)-3-(5-cyclopropyl-4-((1-(1-(3,5-dichlorophenyl)-2,2,2-trifluoroethyl)piperidin-4-yl)methoxy)-2-fluorobenzoyl)-5-methyloxazolidine-4-carboxylate

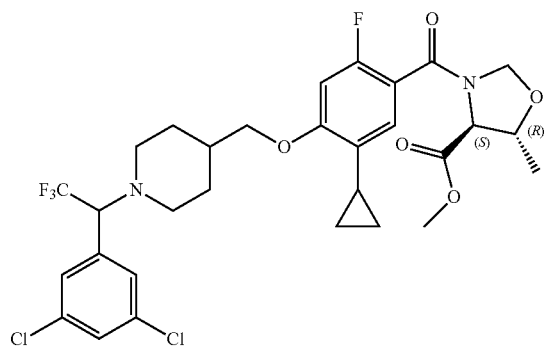

Following the procedure as described in Example 223, Step 2 and making non-critical variations as required to replace 4-((4-(chlorocarbonyl)-2-cyclopropyl-5-fluorophenoxy)methyl)-1-(2,6-dichlorobenzyl)piperidin-1-ium trifluoroacetate with 5-cyclopropyl-4-((1-(1-(3,5-dichlorophenyl)-2,2,2-trifluoroethyl)piperidin-4-yl)methoxy)-2-fluorobenzoyl chloride, the title compound was obtained that used directly in the next step without any analytical characterization.

Step 2. Preparation of (4S,5R)-3-(5-cyclopropyl-4-((1-(1-(3,5-dichlorophenyl)-2,2,2-trifluoroethyl)piperidin-4-yl)methoxy)-2-fluorobenzoyl)-5-methyloxazolidine-4-carboxylic Acid

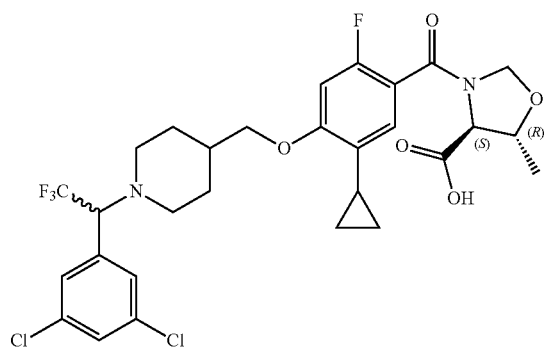

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-(5-cyclopropyl-4-((1-(1-(3,5-dichlorophenyl)-2,2,2-trifluoroethyl)piperidin-4-yl)methoxy)-2-fluorobenzoyl)-5-methyloxazolidine-4-carboxylate and following the residue was purified by reverse phase HPLC, the tile compound was obtained as a colorless solid (0.025 g, 15%): $^1$H NMR (300 MHz, DMSO-$d_6$) δ 7.67 (t, J=1.8 Hz, 1H), 7.41 (d, J=1.5 Hz, 2H), 6.90-6.75 (m, 2H), 4.85-4.63 (m, 3H), 4.25-3.96 (m, 2H), 3.91-3.77 (m, 2H), 3.95-2.89 (m, 2H), 2.26 (m, 2H), 2.09-1.87 (m, 2H), 1.87-1.57 (m, 3H), 1.38-1.25 (m, 4H), 0.88-0.75 (m, 2H), 0.49-0.62 (m, 2H); Note: COOH proton not observed; MS (ES+) m/z 633.2, 635.1 (M+1).

Example 227

Synthesis of (4S,5R)-3-(4-((1-(3-chloro-2-fluoro-5-(trifluoromethyl)benzyl)piperidin-4-yl)methoxy)-5-cyclopropyl-2-fluorobenzoyl)-5-methyloxazolidine-4-carboxylic Acid Step 1. Preparation of 4-((1-(3-chloro-2-fluoro-5-(trifluoromethyl)benzyl)piperidin-4-yl)methoxy)-5-cyclopropyl-2-fluorobenzoyl Chloride Following the procedure as described in Example 224, Step 1 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(3-chloro-2-fluoro-5-(trifluoromethyl)benzyl)piperidin-4-yl)methoxy)-5-cyclopropyl-2-fluorobenzoic acid, the title compound was used without further purification.

Step 2. Preparation of methyl (4S,5R)-3-(4-((1-(3-chloro-2-fluoro-5-(trifluoromethyl)-benzyl)piperidin-4-yl)methoxy)-5-cyclopropyl-2-fluorobenzoyl)-5-methyloxazolidine-4-carboxylate Following the procedure as described in Example 223, Step 2 and making non-critical variations as required to replace 4-((4-(chlorocarbonyl)-2-cyclopropyl-5-fluorophenoxy)methyl)-1-(2,6-dichlorobenzyl)piperidin-1-ium trifluoroacetate with 4-((1-(3-chloro-2-fluoro-5-(trifluoromethyl)benzyl)piperidin-4-yl)methoxy)-5-cyclopropyl-2-fluorobenzoyl chloride, the title compound was obtained as pale yellow oil (0.24 g, 86%): MS (ES+) m/z 631.0, 633.0 (M+1).

Step 3. Preparation of (4S,5R)-3-(4-((1-(3-chloro-2-fluoro-5-(trifluoromethyl)benzyl)piperidin-4-yl)methoxy)-5-cyclopropyl-2-fluorobenzoyl)-5-methyloxazolidine-4-carboxylic Acid

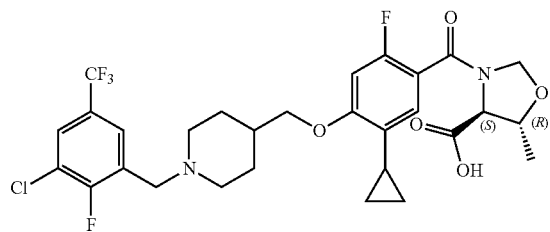

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-(4-((1-(3-chloro-2-fluoro-5-(trifluoromethyl)benzyl)piperidin-4-yl)methoxy)-5-cyclopropyl-2-fluorobenzoyl)-5-methyloxazolidine-4-carboxylate, the title compound was obtained as colorless solid (83%, 0.17 g): $^1$H NMR (300 MHz, CDCl$_3$) δ 12.6 (br s, 1H), 8.35-8.05 (m, 2H), 6.98-6.70 (m, 2H), 4.88-4.74 (m, 2H), 4.55-4.20 (br s, 1H), 4.25-4.07 (m, 1H), 4.04-4.00 (m, 1H), 3.97-3.82 (m, 2H), 3.55-3.17 (m, 4H), 3.10-2.85 (m, 1H), 2.12-1.85 (m, 4H), 1.80-1.51 (m, 2H), 1.37 (d, J=6.0 Hz, 2H), 1.29 (d, J=5.7 Hz, 1H), 0.85 (d, J=8.1 Hz, 2H), 0.65-0.50 (m, 2H); MS (ES+) m/z 617.1, 619.1 (M+1).

Example 228

Synthesis of (4S,5R)-3-(4-((1-(2-chloro-5-(trifluoromethyl)benzyl)piperidin-4-yl)methoxy)-5-cyclopropyl-2-fluorobenzoyl)-5-methyloxazolidine-4-carboxylic Acid Step 1. Preparation of methyl (4S,5R)-3-(4-(benzyloxy)-5-cyclopropyl-2-fluorobenzoyl)-5-methyloxazolidine-4-carboxylate

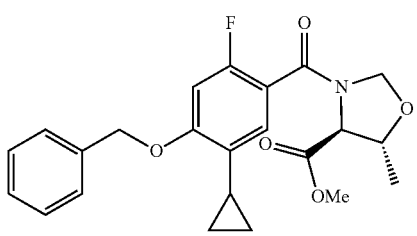 [SMILES: COC(=O)[C@@H]1[C@@H](C)OCN1C(=O)c1cc(C2CC2)c(OCc2ccccc2)cc1F]

Following the procedure as described in Example 223, Step 2 and making non-critical variations as required to replace 4-((4-(chlorocarbonyl)-2-cyclopropyl-5-fluorophenoxy)methyl)-1-(2,6-dichlorobenzyl)piperidin-1-ium trifluoroacetate with 4-(benzyloxy)-5-cyclopropyl-2-fluorobenzoyl chloride, the title compound was obtained as pale yellow oil (0.28 g, 50% yield): $^1$H NMR (300 MHz, CDCl$_3$) δ 7.44-7.34 (m, 5H), 7.04 (d, J=7.8 Hz, 1H), 6.60 (d, J=11.9 Hz, 1H), 5.10 (s, 2H), 4.93 (m, 1H), 4.34 (d, J=7.6 Hz, 1H), 4.23-4.01 (m, 1H), 3.79 (s, 2H), 2.09 (m, 1H), 1.58 (s, 1H), 1.50 (d, J=6.0 Hz, 3H), 1.39-132 (m, 1H), 0.90 (d, J=8.5 Hz, 2H), 0.68-0.58 (m, 2H); MS (ES+) m/z 414.2 (M+1)

Step 2. Preparation of methyl (4S,5R)-3-(5-cyclopropyl-2-fluoro-4-hydroxybenzoyl)-5-methyloxazolidine-4-carboxylate

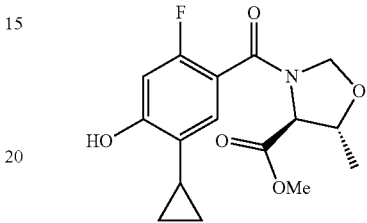

To a solution of methyl (4S,5R)-3-(4-(benzyloxy)-5-cyclopropyl-2-fluorobenzoyl)-5-methyloxazolidine-4-carboxylate (0.41 g, 0.69 mmol) in anhydrous methanol (4.5 mL) was added wetted palladium on charcoal (0.15 g). The flask was fitted with an atmosphere of hydrogen and stirred for 4 h. The reaction mixture was filtered over Celite and the filter pad was washed with ethyl acetate (50 mL). The filtrate was concentrated in vacuo to afford the title compound as colorless solid (0.26 g, quantitative yield): MS (ES+) m/z 324.2 (M+1).

Step 3. Preparation of methyl (4S,5R)-3-(4-((1-(tert-butoxycarbonyl)piperidin-4-yl)methoxy)-5-cyclopropyl-2-fluorobenzoyl)-5-methyloxazolidine-4-carboxylate

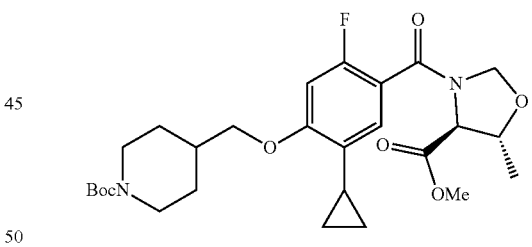

To a solution of methyl (4S,5R)-3-(5-cyclopropyl-2-fluoro-4-hydroxybenzoyl)-5-methyloxazolidine-4-carboxylate (0.26 g, 0.69 mmol) in N,N-dimethylformamide (5.0 mL) was added cesium carbonate (0.34 g, 1.04 mmol) and tert-butyl 4-((tosyloxy)methyl)piperidine-1-carboxylate (0.38 g, 1.04 mmol). The reaction mixture was heated to 75° C. for 8 h, after which it was diluted saturated ammonium chloride (50 mL) and extracted with ethyl acetate (3×50 mL). The combined organic extracts were washed with 5% lithium chloride (50 mL) and then dried over anhydrous magnesium sulfate, filtered and concentrated in vacuo. The resulting residue was purified by column chromatography to afford the title compound as colorless solid (0.26 g, 71% yield): $^1$H NMR (300 MHz, CDCl$_3$) δ 7.02 (d, J=7.8 Hz, 1H), 6.50 (d, J=11.9 Hz, 1H), 4.92 (dd, J=19.4, 4.6 Hz, 2H), 4.33 (d, J=7.7 Hz, 1H), 4.20-4.11 (m, 3H), 3.85-3.70 (m, 4H), 2.74 (t, J=11.9 Hz, 2H), 2.04-1.95 (m, 2H), 1.90-1.77

(m, 2H), 1.48 (d, J=6.0 Hz, 3H), 1.44 (s, 9H), 1.36-1.15 (m, 3H), 0.87 (m, 2H), 0.64-0.56 (m, 2H).

Step 4. Preparation of 4-((2-cyclopropyl-5-fluoro-4-((4S,5R)-4-(methoxycarbonyl)-5-methyloxazolidine-3-carbonyl)phenoxy)methyl)piperidin-1-ium Trifluoroacetate

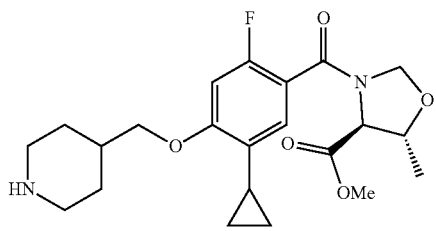 [SMILES: COC(=O)[C@@H]1[C@@H](C)OCN1C(=O)c1cc(C2CC2)c(OCC2CCNCC2)cc1F]

To a solution of methyl (4S,5R)-3-(4-((1-(tert-butoxycarbonyl)piperidin-4-yl)methoxy)-5-cyclopropyl-2-fluorobenzoyl)-5-methyloxazolidine-4-carboxylate (0.12 g, 0.23 mmol) in dichloromethane (2.3 mL) was added trifluoroacetic acid (0.18 mL). The solution was stirred overnight, and the evaporated in vacuo to afford the title compound, which was used directly for the next step without further purification.

Step 5. Preparation of methyl (4S,5R)-3-(4-((1-(2-chloro-5-(trifluoromethyl)benzyl)piperidin-4-yl)methoxy)-5-cyclopropyl-2-fluorobenzoyl)-5-methyloxazolidine-4-carboxylate

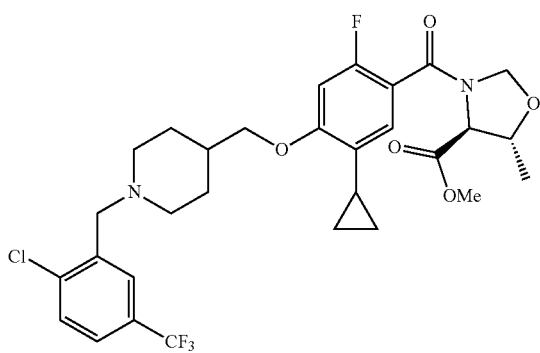 [SMILES: COC(=O)[C@@H]1[C@@H](C)OCN1C(=O)c1cc(C2CC2)c(OCC2CCN(Cc3cc(C(F)(F)F)ccc3Cl)CC2)cc1F]

To a solution of 4-((2-cyclopropyl-5-fluoro-4-((4S,5R)-4-(methoxycarbonyl)-5-methyloxazolidine-3-carbonyl)phenoxy)methyl)piperidin-1-ium trifluoroacetate (0.23 mmol) in N,N-dimethylformamide (2.3 mL) was added cesium carbonate (0.35 g, 1.06 mmol) and 2-chloro-5-(trifluoromethyl)benzyl methanesulfonate (0.11 g, 0.37 mmol). The reaction mixture was stirred at 85° C. for 3 h, diluted with saturated sodium bicarbonate (40 mL), and then extracted with ethyl acetate (3×40 mL). The combined organic extracts were washed with 5% lithium chloride (40 mL) and then dried over anhydrous magnesium sulfate, filtered and concentrated in vacuo. The resulting residue was purified by column chromatography to afford the title compound as a pale yellow oil (0.091 g, 65%): MS (ES+) m/z 613.2, 615.3 (M+1).

Step 6. Preparation of (4S,5R)-3-(4-((1-(2-chloro-5-(trifluoromethyl)benzyl)piperidin-4-yl)methoxy)-5-cyclopropyl-2-fluorobenzoyl)-5-methyloxazolidine-4-carboxylic Acid

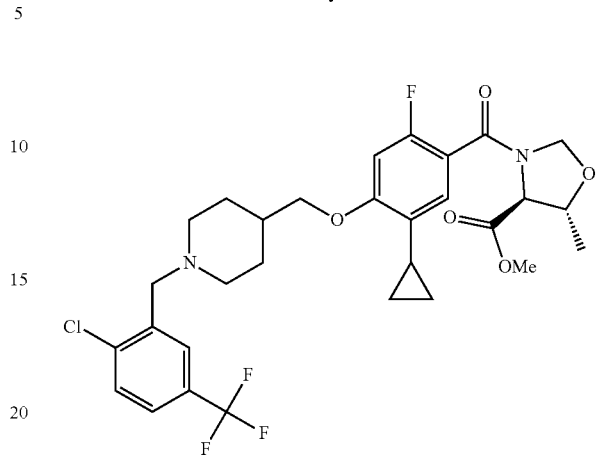

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-(4-((1-(2-chloro-5-(trifluoromethyl)benzyl)piperidin-4-yl)methoxy)-5-cyclopropyl-2-fluorobenzoyl)-5-methyloxazolidine-4-carboxylate, the title compound was obtained as a colorless solid (0.022 g, 24%): $^1$H NMR (300 MHz, CDCl$_3$) δ 7.79 (s, 1H), 7.70-7.55 (m, 2H), 6.97-6.70 (m, 2H), 4.79 (s, 2H), 4.25-4.01 (m, 1H), 4.00-3.90 (m, 2H), 3.89 (s, 2H), 2.88-2.79 (m, 2H), 2.10 (t, J=11.4 Hz, 2H), 1.85-1.70 (m, 3H), 1.40-1.28 (m, 4H), 1.28-1.23 (m, 1H), 1.37 (t, J=6.2 Hz, 2H), 0.82-0.75 (m, 2H), 0.65-0.48 (m, 2H); MS (ES+) m/z 599.2, 601.2 (M+1); Note: COOH proton not observed.

Example 229

Synthesis of (4S,5R)-3-(5-cyclopropyl-4-((1-((R)-(3,5-dichlorophenyl)(phenyl)methyl)-3-methylazetidin-3-yl)methoxy)-2-fluorobenzoyl)-5-methyloxazolidine-4-carboxylic Acid Step 1. Preparation of methyl (4O,5R)-3-(5-cyclopropyl-4-((1-((R)-(3,5-dichlorophenyl)-(phenyl)methyl)-3-methylazetidin-3-yl)methoxy)-2-fluorobenzoyl)-5-methyloxazolidine-4-carboxylate

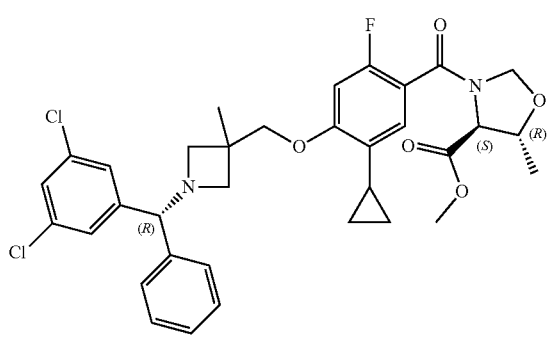

Following the procedure as described in Example 223, Step 2 and making non-critical variations as required to replace 4-((4-(chlorocarbonyl)-2-cyclopropyl-5-fluorophenoxy)methyl)-1-(2,6-dichlorobenzyl)piperidin-1-ium trifluoroacetate with (R)-5-cyclopropyl-4-(((1-((3,5-dichlorophenyl)(phenyl)methyl)-3-methylazetidin-3-yl)methoxy)-2-fluorobenzoyl chloride, the title compound was obtained that was used in the next step without any further analytical characterization.

Step 2. Preparation of (4S,5R)-3-(5-cyclopropyl-4-((1-((R)-(3,5-dichlorophenyl)(phenyl)-methyl)-3-methylazetidin-3-yl)methoxy)-2-fluorobenzoyl)-5-methyloxazolidine-4-carboxylic Acid

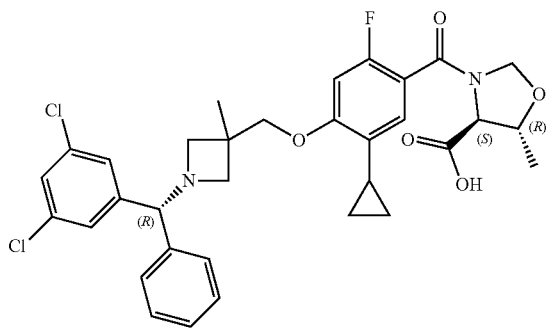

Following the procedure as described in Example 33, Step 2 and making non-critical variations as required to replace (S)-methyl 1-(4-(2-(1-(1-(tert-butoxycarbonyl)azetidin-3-yl)-1H-pyrazol-5-yl-4-chlorophenoxy)-2,5-difluorobenzoyl)pyrrolidine-2-carboxylate with methyl (4S,5R)-3-(5-cyclopropyl-4-((1-((R)-(3,5-dichlorophenyl)(phenyl)methyl)-3-methylazetidin-3-yl)methoxy)-2-fluorobenzoyl)-5-methyloxazolidine-4-carboxylate, the tile compound was obtained as a colorless solid (0.043 g, 76%): $^1$H NMR (300 MHz, CDCl$_3$) δ 12.59 (br s, 1H), 7.90-7.56 (m, 2H), 7.56-7.15 (m, 6H), 7.02-6.77 (m, 2H), 4.81 (s, 1H), 4.28-3.75 (m, 5H), 2.83 (br s, 1H), 2.2-1.85 (m, 1H), 1.62-1.05 (m, 8H), 0.90-0.70 (m, 2H), 0.60-0.45 (m, 2H); MS (ES+) m/z 627.2, 629.2 (M+1). Note: 2H proton signal is underneath water signal (δ=3.12 ppm).

Example 230

Synthesis of (2S,3R,4S)-1-(4-(adamantan-1-ylmethoxy)-5-cyclopropyl-2-fluorobenzoyl)-4-hydroxy-3-methylpyrrolidine-2-carboxylic Acid Step 1. Preparation of methyl (2S,3R,4S)-1-(4-(adamantan-1-ylmethoxy)-5-cyclopropyl-2-fluorobenzoyl)-4-hydroxy-3-methylpyrrolidine-2-carboxylate and methyl (2S,3S,4S)-1-(4-(adamantan-1-ylmethoxy)-5-cyclopropyl-2-fluorobenzoyl)-4-hydroxy-3-methylpyrrolidine-2-carboxylate

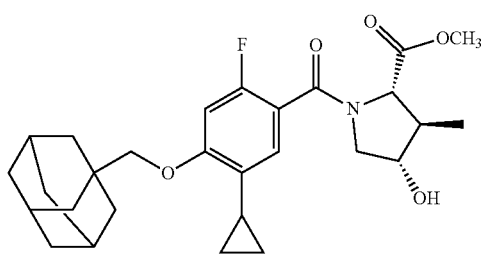

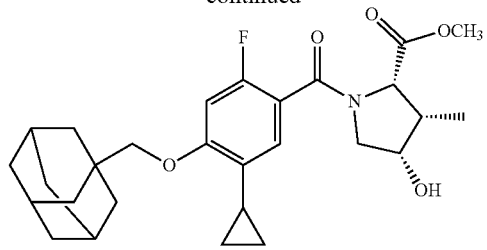

To a solution of methyl (2S)-1-(4-(adamantan-1-yl-methoxy)-5-cyclopropyl-2-fluorobenzoyl)-3-methyl-4-oxopyrrolidine-2-carboxylate (0.25 g, 0.51 mmol) in tetrahydrofuran (5.0 mL) cooled to −78° C. was added (S)-3,3-diphenyl-1-methyltetrahydro-3H-pyrrolo[1,2-c][1,3,2]oxazaborole (0.55 mL, 0.51 mmol), followed by the dropwise addition of borane dimethylsulfide complex (0.05 mL, 0.52 mmol). The reaction mixture was stirred at −78° C. for 0.5 h, warmed to ambient temperature for 0.5 h and quenched with the addition of methanol (2.0 mL). After 0.5 h, the reaction mixture was diluted with aqueous hydrochloric acid (50 mL, 0.2 mol/L) and extracted with ethyl acetate (3×50 mL). The combined organic extracts were dried over anhydrous magnesium sulfate, filtered, concentrated in vacuo. The residue was purified by column purification eluting with ethyl acetate in hexanes to afford the two title compounds: first eluent of the title compound as colorless gum (0.11 g, 46%) and the second eluent of the title compound as a colorless solid (0.13 g, 51%); MS (ES+) m/z 486.3 (M+1).

Step 2. Preparation of (2S,3R,4S)-1-(4-(adamantan-1-ylmethoxy)-5-cyclopropyl-2-fluorobenzoyl)-4-hydroxy-3-methylpyrrolidine-2-carboxylic Acid

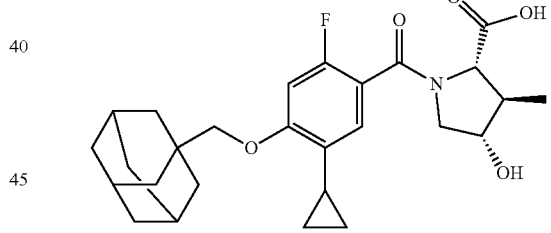

To a solution of methyl (2S,3R,4S)-1-(4-(adamantan-1-ylmethoxy)-5-cyclopropyl-2-fluorobenzoyl)-4-hydroxy-3-methylpyrrolidine-2-carboxylate (0.11 g, 0.24 mmol) in tetrahydrofuran (6.0 mL) and water (3.0 mL) was added potassium carbonate (0.43 g, 3.11 mmol). The reaction mixture was fitted with a condenser, and stirred at reflux for 16 h, after which it was diluted with aqueous hydrochloric acid (1 mol/L, 50 mL), and extracted with ethyl acetate (4×50 mL). The combined organic extracts were dried over anhydrous magnesium sulfate, filtered, and concentrated in vacuo. The residue was purified by preparatory HPLC (acetonitrile and water) to afford the title compound as a colorless solid (0.03 g, 27% yield): $^1$H NMR (300 MHz, CDCl$_3$) δ 6.96 (d, J=7.4 Hz, 1H), 6.50 (d, J=11.8 Hz, 1H), 4.15-3.92 (m, 2H), 3.80-3.65 (m, 1H), 3.48-3.35 (m, 3H), 2.61 (br s, 1H), 2.01 (s, 4H), 1.81-1.60 (m, 12H), 1.14 (d, J=5.9 Hz, 3H), 0.90-0.80 (m, 2H), 0.61 (d, J=3.0 Hz, 2H); Note: COOH and OH protons not observed; MS (ES+) m/z 472.3 (M+1).

Example 231

Synthesis of (2S,3S,4S)-1-(4-(adamantan-1-yl-methoxy)-5-cyclopropyl-2-fluorobenzoyl)-4-hydroxy-3-methylpyrrolidine-2-carboxylic Acid Step 1. Preparation of (2S,3S,4S)-1-(4-(adamantan-1-ylmethoxy)-5-cyclopropyl-2-fluorobenzoyl)-4-hydroxy-3-methylpyrrolidine-2-carboxylic Acid

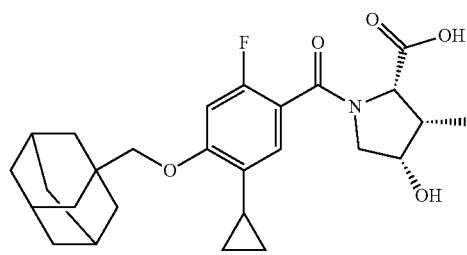 [SMILES: C[C@@H]1[C@H](O)CN(C(=O)c2cc(C3CC3)c(OCC34CC5CC(CC(C5)C3)C4)cc2F)[C@@H]1C(=O)O]

Following the procedure as described in Example 230, Step 2 and making non-critical variations as required to replace methyl (2S,3R,4S)-1-(4-(adamantan-1-ylmethoxy)-5-cyclopropyl-2-fluorobenzoyl)-4-hydroxy-3-methylpyrrolidine-2-carboxylate with methyl (2S,3S,4S)-1-(4-(adamantan-1-ylmethoxy)-5-cyclopropyl-2-fluorobenzoyl)-4-hydroxy-3-methylpyrrolidine-2-carboxylate, title compound was obtained as a colorless solid (0.061 g, 50%): $^1$H NMR (300 MHz, CDCl$_3$) δ 7.00 (d, J=7.8 Hz, 1H), 6.48 (d, J=12.0 Hz, 1H), 4.52 (d, J=8.8 Hz, 1H), 4.06 (s, 1H), 3.85-3.70 (m, 1H), 3.58-3.42 (m, 3H), 2.54 (br s, 1H), 2.11-1.95 (m, 4H), 1.75-1.62 (m, 12H), 1.15 (d, J=6.6 Hz, 3H), 0.84 (d, J=8.3 Hz, 2H), 0.65-0.55 (m, 2H); Note: COOH and OH protons not observed; MS (ES+) m/z 472.3.

Example 232

Electrophysiological Assay (EP) (In Vitro Assay)

Patch voltage clamp electrophysiology allows for the direct measurement and quantification of block of voltage-gated sodium channels (NaV's), and allows the determination of the time- and voltage-dependence of block which has been interpreted as differential binding to the resting, open, and inactivated states of the sodium channel (Hille, B., Journal of General Physiology (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel α-subunit, grown in culture media containing 10% FBS, 1% PSG, and 0.5 mg/mL G418 at 37° C. with 5% CO2. HEK cells used for the electrophysiology (EP) recordings had a passage number of less than 40 for all studies and were used within three days from the time of plating. NaV1.7 and NaV1.5 cDNAs (NM_002977 and AC137587; SCN5A, respectively) were stably expressed in HEK-293 cells. The β1 subunit was coexpressed in both the NaV1.7 and NaV1.5 cell lines.

Sodium currents were measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of: 5 mM NaCl, 10 mM CsCl, 120 mM CsF, 0.1 mM CaCl2, 2 mM MgCl2, 10 mM HEPES, 10 mM EGTA; and adjusted to pH 7.2 with CsOH. The external solution had the following composition: 140 mM NaCl, 5 mM KCl, 2 mM CaCl2, 1 mM MgCl2, 10 mM HEPES; and adjusted to pH 7.4 with NaOH. In some studies, the external sodium was reduced by equimolar replacement with choline. Osmolarity in the CsF internal and NaCl external solutions was adjusted to 300 mOsm/kg and 310 mOsm/kg with glucose, respectively. All recordings were performed at ambient temperature in a bath chamber with a volume of 150 µL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon Instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where inactivation of the channel is complete (which was −60 mV for both NaV1.7 and NaV1.5). The voltage is then stepped back to a very negative (Vhold=150 mV) voltage for 20 ms and then a test pulse is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels. Data for representative compounds of formula (I) is provided in Table 1.

Example 233

Tritiated Compound Binding to Membranes Isolated from Cells that Heterologously Express hNav1.7 and the β1 Subunit Preparation of membranes containing recombinantly expressed sodium channels: Frozen recombinant cell pellets were thawed on ice and diluted to 4 times the cell pellet weight with ice cold 50 mM Tris HCl, pH 7.4 buffer. The cell suspensions were homogenized on ice using a motorized glass dounce homogeniser. Homogenates were further diluted 8.4 times with ice cold 50 mM Tris HCl, pH 7.4 buffer and then centrifuged at 200×g at 4° C. for 15 min. The supernatants were collected and centrifuged at 10000×g at 4° C. for 50 min. The pellets were then re-suspended in 100 mM NaCl, 20 mM Tris HCl, pH 7.4 buffer containing 1% v/v protease inhibitors (Calbiochem) and re-homogenized on ice. The homogenized membranes were then processed through a syringe equipped with a 26 gauge needle. Protein concentrations were determined by Bradford Assay and the membranes were stored at −80° C.

Radioligand Binding Studies:

Saturation experiments. A representative compound of formula (I) having a methyl group was tritiated. Three tritiums were incorporated in place of methyl hydrogens to generate [$^3$H]compound. Binding of this radioligand was performed in 5 mL borosilicate glass test tubes at room temperature. Binding was initiated by adding membranes to increasing concentrations of [$^3$H]compound in 100 mM NaCl, 20 mM Tris HCl, pH 7.4 buffer containing 0.01% w/v bovine serum albumin (BSA) for 18 h. Non-specific binding was determined in the presence of 1 µM unlabeled compound. After 18 h, the reactants were filtered through GF/C glass fiber filters presoaked in 0.5% w/v polyethylene imine. Filters were washed with 15 mL ice cold 100 mM NaCl, 20 mM Tris HCl, pH7.4 buffer containing 0.25% BSA to separate bound from free ligand. [$^3$H]compound bound to filters was quantified by liquid scintillation counting.

Competitive Binding Experiments:

Binding reactions were performed in 96-well polypropylene plates at room temperature for 18 h. In 360 µL, membranes were incubated with 100 pM [$^3$H]compound and increasing concentrations of Test Compound. Non-specific binding was defined in the presence of 1 µM unlabeled compound. Reactions were transferred and filtered through 96-well glass fiber/C filter plates presoaked with 0.5% polyethylene imine. The filtered reactions were washed 5 times with 200 µL ice cold buffer containing 0.25% BSA. Bound radioactivity was determined by liquid scintillation counting.

Data Analysis: For saturation experiments, non-specific binding was subtracted from total binding to provide specific binding and these values were recalculated in terms of pmol ligand bound per mg protein. Saturation curves were constructed and dissociation constants were calculated using the single site ligand binding model: Beq=(Bmax*X)/(X+Kd), where Beq is the amount of ligand bound at equilibrium, Bmax is the maximum receptor density, Kd is the dissociation constant for the ligand, and X is the free ligand concentration. For competition studies percent inhibition was determined and IC$_{50}$ values were calculated using a 4 parameter logistic model (% inhibition=(A+((B−A)/(1+((x/C)^D)))) using XLfit, where A and B are the maximal and minimum inhibition respectively, C is the IC$_{50}$ concentration and D is the (Hill) slope.

Representative compounds, when tested in this model, demonstrated affinities as set forth in Table 1.

TABLE 1

| Example | Structure | LBA (µM) | Nav1.7 (µM) | Nav1.5 (µM) |
|---|---|---|---|---|
| 1 | 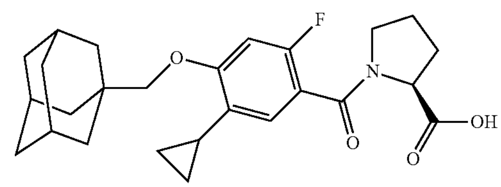 [SMILES: O=C(O)[C@@H]1CCCN1C(=O)c1cc(C2CC2)c(OCC23CC4CC(CC(C4)C2)C3)cc1F] | 0.0196 | 0.0135 | 3.505 |
| 2 | 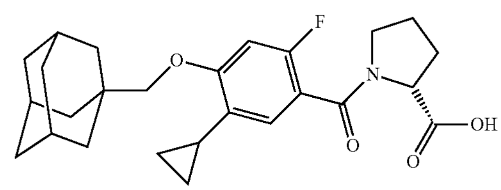 | 0.4261 | | |
| 3 | 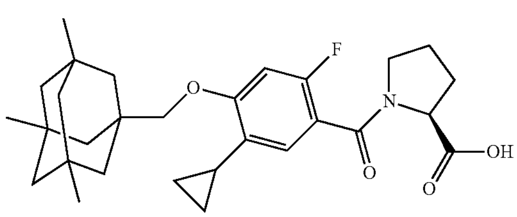 [SMILES: CC12CC3(C)CC(C)(C1)CC(COc1cc(F)c(C(=O)N4CCC[C@H]4C(=O)O)cc1C1CC1)(C2)C3] | 0.0089 | | |
| 4 | 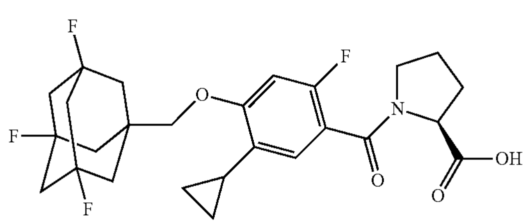 [SMILES: O=C(O)[C@@H]1CCCN1C(=O)c1cc(C2CC2)c(OCC23CC4(F)CC(F)(CC(F)(C4)C2)C3)cc1F] | 0.8172 | | |

TABLE 1-continued
| Example | Structure | LBA (μM) | Nav1.7 (μM) | Nav1.5 (μM) |
|---|---|---|---|---|
| 5 | 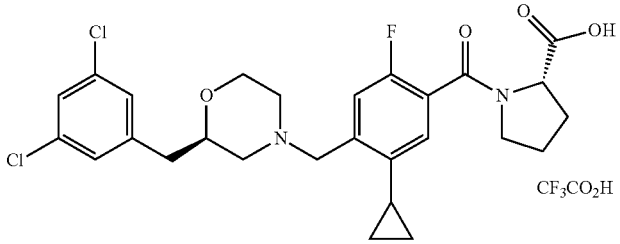 [SMILES: O=C(O)[C@@H]1CCCN1C(=O)c1cc(C2CC2)c(CN2CCO[C@H](Cc3cc(Cl)cc(Cl)c3)C2)cc1F ; "CF3CO2H"] | 0.4682 | | |
| 6 | 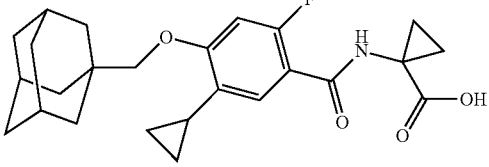 | 3.5794 | 0.5318 | 2.1157 |
| 7 | 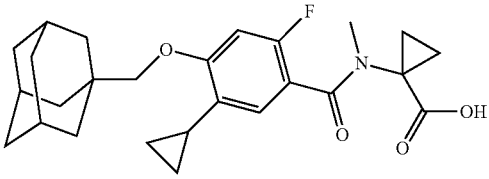 [SMILES: CN(C(=O)c1cc(C2CC2)c(OCC23CC4CC(CC(C4)C2)C3)cc1F)C1(C(=O)O)CC1] | 3.0467 | | |
| 8 | 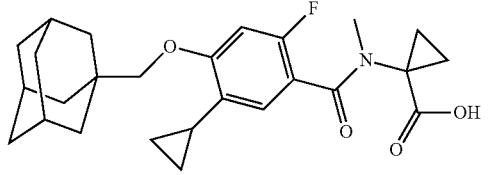 [SMILES: CN(C(=O)c1cc(C2CC2)c(OCC23CC4CC(CC(C4)C2)C3)cc1F)C1(C(=O)O)CC1] | 1.6922 | | |
| 9 | 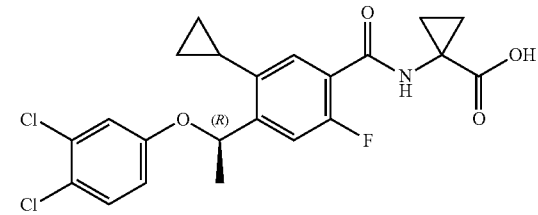 | >10 | | |
| 10 | 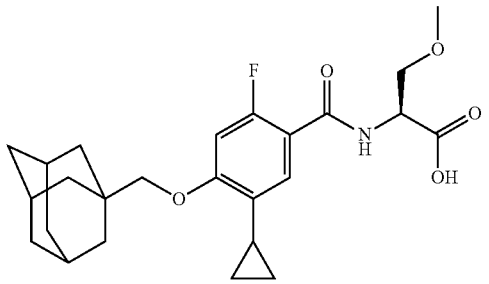 [SMILES: COC[C@H](NC(=O)c1cc(C2CC2)c(OCC23CC4CC(CC(C4)C2)C3)cc1F)C(=O)O] | 0.6809 | | |
| 11 | 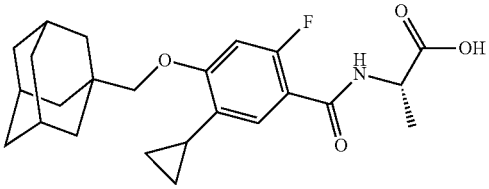 [SMILES: C[C@H](NC(=O)c1cc(C2CC2)c(OCC23CC4CC(CC(C4)C2)C3)cc1F)C(=O)O] | 0.2005 | 0.0361 | 2.1872 |

TABLE 1-continued

| Example | Structure | LBA (μM) | Nav1.7 (μM) | Nav1.5 (μM) |
|---|---|---|---|---|
| 12 | 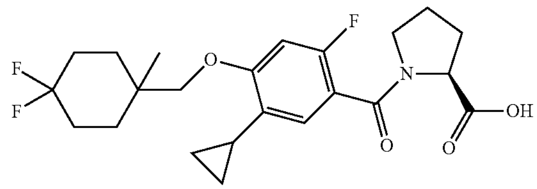 [SMILES: CC1(COc2cc(F)c(C(=O)N3CCC[C@H]3C(=O)O)cc2C2CC2)CCC(F)(F)CC1] | 0.9836 | | |
| 13 | 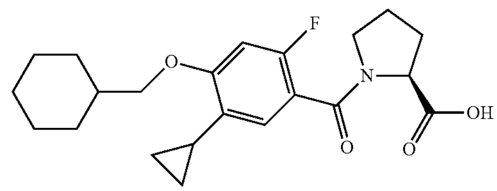 [SMILES: O=C(O)[C@@H]1CCCN1C(=O)c1cc(C2CC2)c(OCC2CCCCC2)cc1F] | 0.1726 | | |
| 14 | 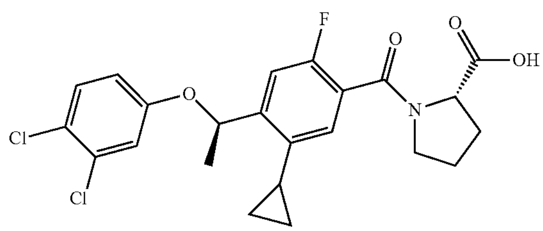 [SMILES: C[C@@H](Oc1ccc(Cl)c(Cl)c1)c1cc(F)c(C(=O)N2CCC[C@H]2C(=O)O)cc1C1CC1] | 2.3711 | | |
| 15 | 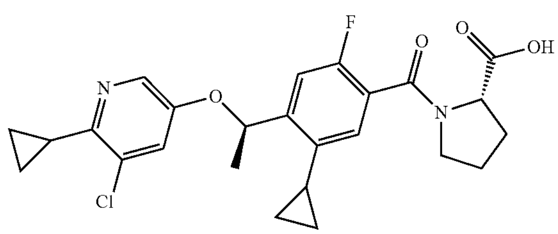 [SMILES: C[C@@H](Oc1cnc(C2CC2)c(Cl)c1)c1cc(F)c(C(=O)N2CCC[C@H]2C(=O)O)cc1C1CC1] | 6.9628 | | |
| 16 | 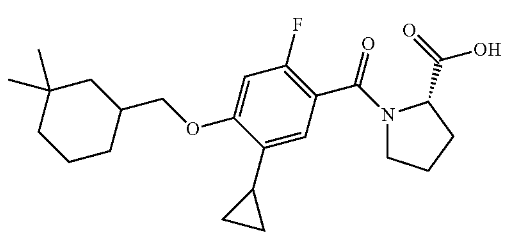 [SMILES: CC1(C)CCCC(COc2cc(F)c(C(=O)N3CCC[C@H]3C(=O)O)cc2C2CC2)C1] | 0.0398 | | |
| 17 | 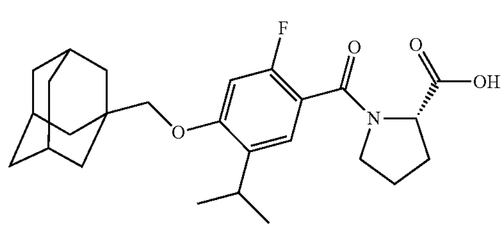 [SMILES: CC(C)c1cc(C(=O)N2CCC[C@H]2C(=O)O)c(F)cc1OCC12CC3CC(CC(C3)C1)C2] | 0.0872 | | |
| 18 | 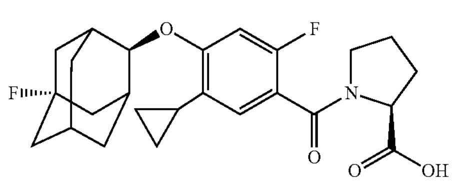 [SMILES: O=C(O)[C@@H]1CCCN1C(=O)c1cc(C2CC2)c(O[C@H]2C3CC4CC2C[C@](F)(C4)C3)cc1F] | 4.5009 | | |

TABLE 1-continued

| Example | Structure | LBA (μM) | Nav1.7 (μM) | Nav1.5 (μM) |
|---|---|---|---|---|
| 19 | 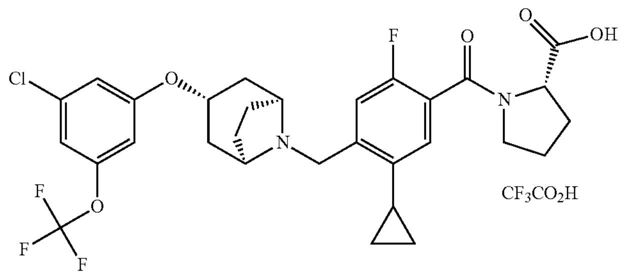 [SMILES: O=C(O)[C@@H]1CCCN1C(=O)c1cc(C2CC2)c(CN2[C@@H]3CC[C@H]2C[C@@H](Oc2cc(Cl)cc(OC(F)(F)F)c2)C3)cc1F ; "CF3CO2H"] | 0.4432 | | |
| 20 | 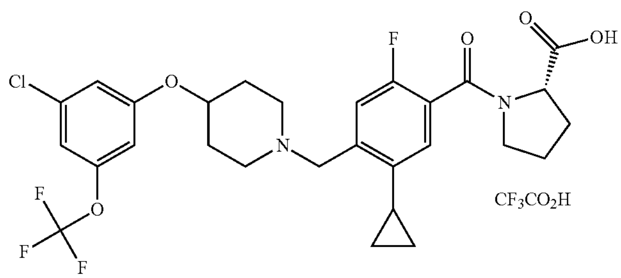 [SMILES: O=C(O)[C@@H]1CCCN1C(=O)c1cc(C2CC2)c(CN2CCC(Oc3cc(Cl)cc(OC(F)(F)F)c3)CC2)cc1F ; "CF3CO2H"] | 0.5542 | | |
| 21 | 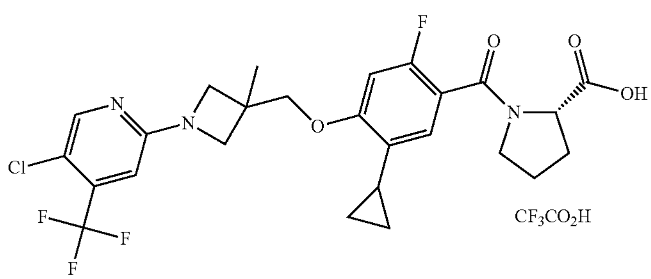 [SMILES: CC1(COc2cc(F)c(C(=O)N3CCC[C@H]3C(=O)O)cc2C2CC2)CN(c2cc(C(F)(F)F)c(Cl)cn2)C1 ; "CF3CO2H"] | 0.3594 | | |
| 22 | 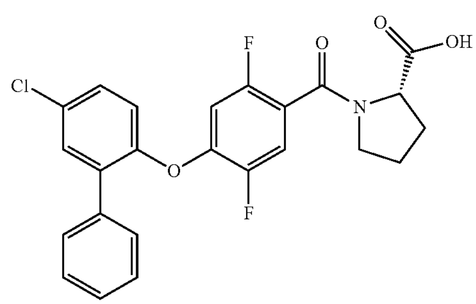 [SMILES: O=C(O)[C@@H]1CCCN1C(=O)c1cc(F)c(Oc2ccc(Cl)cc2-c2ccccc2)cc1F] | >10 | | |
| 23 | 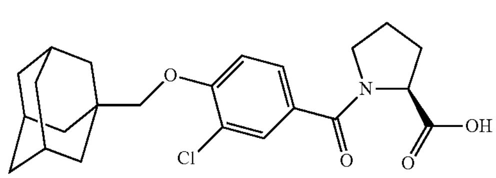 [SMILES: O=C(O)[C@@H]1CCCN1C(=O)c1ccc(OCC23CC4CC(CC(C4)C2)C3)c(Cl)c1] | 3.9606 | | |
| 24 | 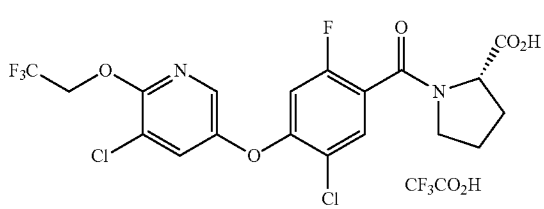 | 2.7250 | | |

TABLE 1-continued

| Example | Structure | LBA (µM) | Nav1.7 (µM) | Nav1.5 (µM) |
|---|---|---|---|---|
| 25 | 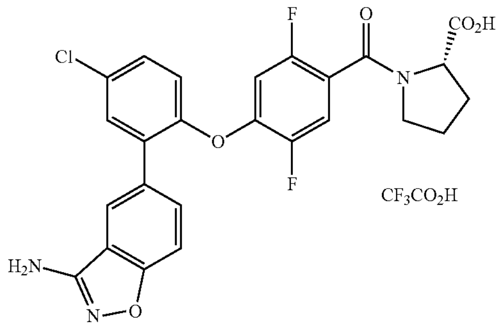 [SMILES: Nc1noc2ccc(-c3cc(Cl)ccc3Oc3cc(F)c(C(=O)N4CCC[C@H]4C(=O)O)cc3F)cc12 ; "CF3CO2H"] | >10 | | |
| 26 | 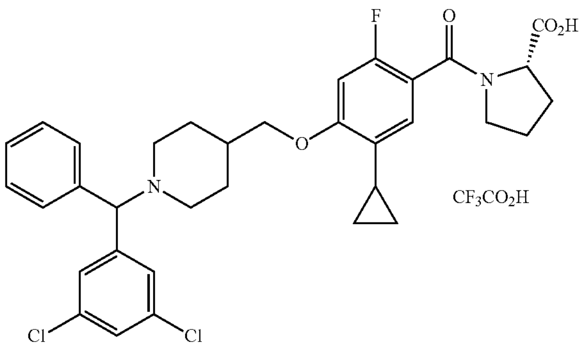 [SMILES: O=C(O)[C@@H]1CCCN1C(=O)c1cc(C2CC2)c(OCC2CCN(C(c3ccccc3)c3cc(Cl)cc(Cl)c3)CC2)cc1F ; "CF3CO2H"] | 0.0181 | | |
| 27 | 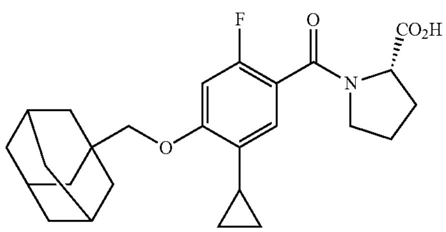 [SMILES: O=C(O)[C@@H]1CCCN1C(=O)c1cc(C2CC2)c(OCC23CC4CC(CC(C4)C2)C3)cc1F] | 0.0217 | | |
| 28 | 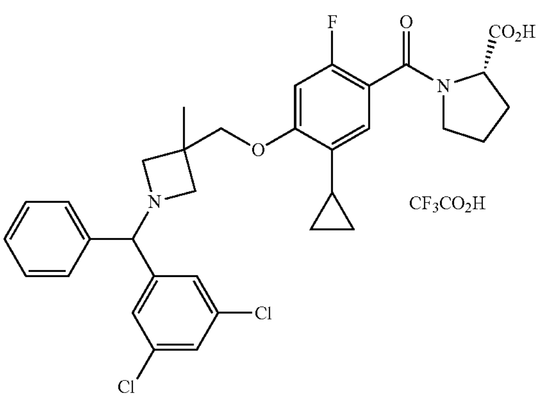 [SMILES: CC1(COc2cc(F)c(C(=O)N3CCC[C@H]3C(=O)O)cc2C2CC2)CN(C(c2ccccc2)c2cc(Cl)cc(Cl)c2)C1 ; "CF3CO2H"] | 0.0176 | | |
| 29 | 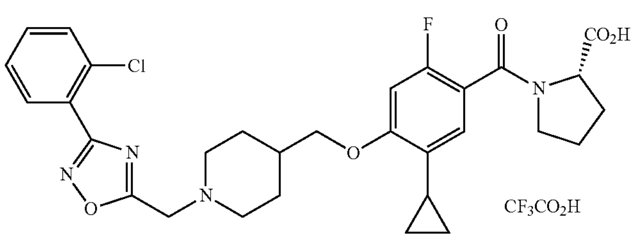 [SMILES: O=C(O)[C@@H]1CCCN1C(=O)c1cc(C2CC2)c(OCC2CCN(Cc3nc(-c4ccccc4Cl)no3)CC2)cc1F ; "CF3CO2H"] | 0.6287 | | |

TABLE 1-continued

| Example | Structure | LBA (µM) | Nav1.7 (µM) | Nav1.5 (µM) |
|---|---|---|---|---|
| 30 | 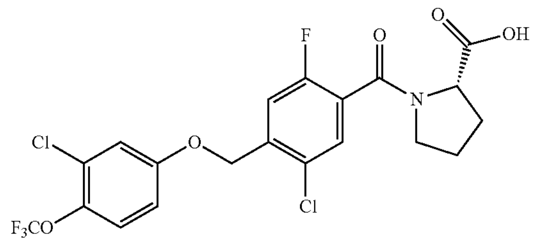 [SMILES: O=C(O)[C@@H]1CCCN1C(=O)c1cc(Cl)c(COc2ccc(OC(F)(F)F)c(Cl)c2)cc1F] | 0.3447 | | |
| 31 | 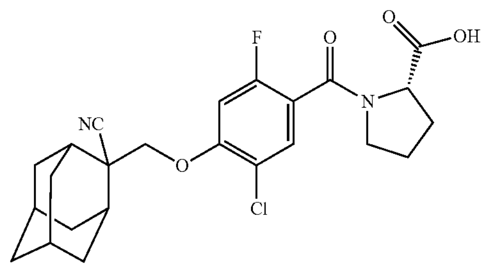 [SMILES: N#CC1(COc2cc(F)c(C(=O)N3CCC[C@H]3C(=O)O)cc2Cl)C2CC3CC(C2)CC1C3] | >10 | | |
| 32 | 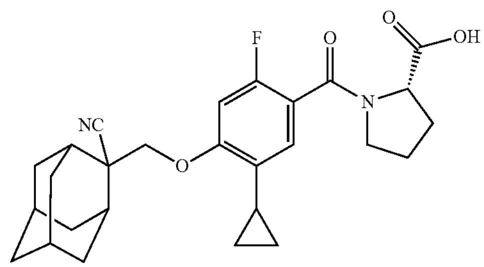 [SMILES: N#CC1(COc2cc(F)c(C(=O)N3CCC[C@H]3C(=O)O)cc2C2CC2)C2CC3CC(C2)CC1C3] | 1.5368 | | |
| 33 | 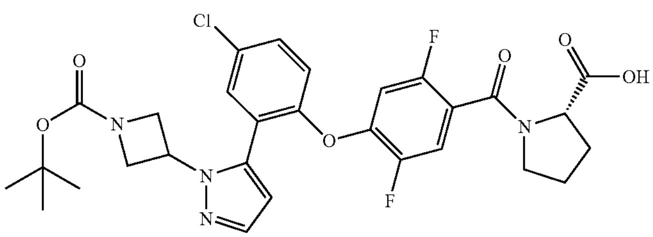 [SMILES: CC(C)(C)OC(=O)N1CC(n2nccc2-c2cc(Cl)ccc2Oc2cc(F)c(C(=O)N3CCC[C@H]3C(=O)O)cc2F)C1] | >10 | | |
| 34 | 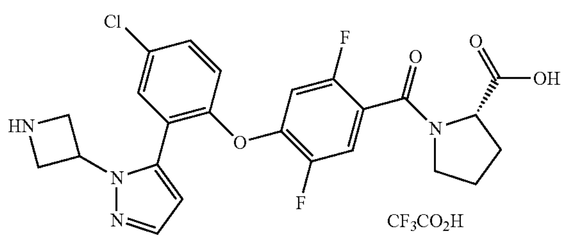 [SMILES: O=C(O)[C@@H]1CCCN1C(=O)c1cc(F)c(Oc2ccc(Cl)cc2-c2ccnn2C2CNC2)cc1F ; "CF3CO2H"] | >10 | | |
| 35 | 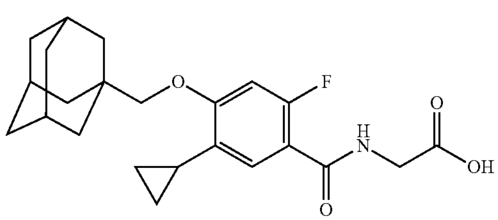 [SMILES: O=C(O)CNC(=O)c1cc(C2CC2)c(OCC23CC4CC(CC(C4)C2)C3)cc1F] | 7.8288 | | |

TABLE 1-continued

| Example | Structure | LBA (μM) | Nav1.7 (μM) | Nav1.5 (μM) |
|---|---|---|---|---|
| 36 | 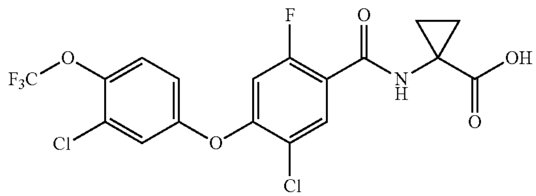 [SMILES: O=C(NC1(C(=O)O)CC1)c1cc(Cl)c(Oc2ccc(OC(F)(F)F)c(Cl)c2)cc1F] | >10 | | |
| 37 | 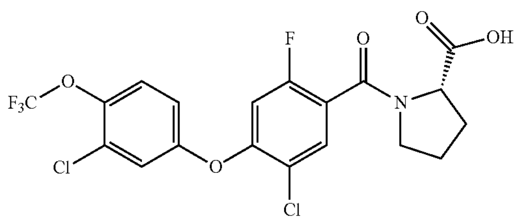 [SMILES: O=C(O)[C@@H]1CCCN1C(=O)c1cc(Cl)c(Oc2ccc(OC(F)(F)F)c(Cl)c2)cc1F] | 5.2302 | | |
| 38 | 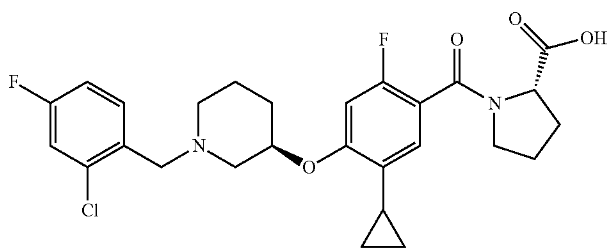 [SMILES: O=C(O)[C@@H]1CCCN1C(=O)c1cc(C2CC2)c(O[C@@H]2CCCN(Cc3ccc(F)cc3Cl)C2)cc1F] | 0.1521 | | |
| 39 | 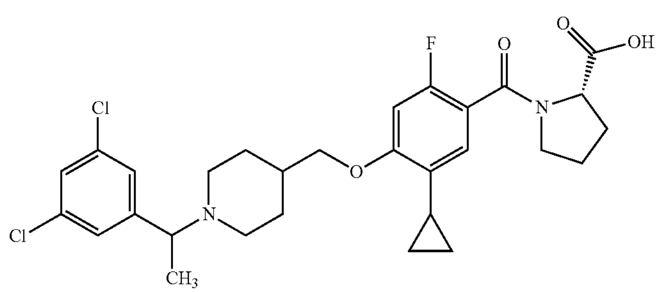 [SMILES: CC(c1cc(Cl)cc(Cl)c1)N1CCC(COc2cc(F)c(C(=O)N3CCC[C@H]3C(=O)O)cc2C2CC2)CC1] | 0.0436 | | |
| 40 | 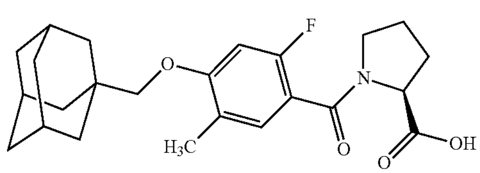 [SMILES: Cc1cc(C(=O)N2CCC[C@H]2C(=O)O)c(F)cc1OCC12CC3CC(CC(C3)C1)C2] | 0.452 | | |
| 41 | 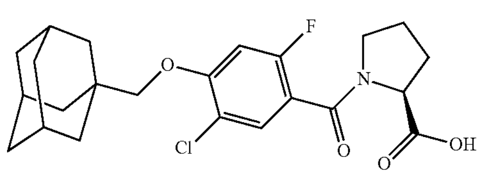 [SMILES: O=C(O)[C@@H]1CCCN1C(=O)c1cc(Cl)c(OCC23CC4CC(CC(C4)C2)C3)cc1F] | 0.6401 | | |
| 42 | 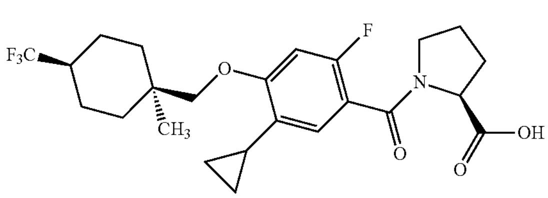 [SMILES: C[C@]1(COc2cc(F)c(C(=O)N3CCC[C@H]3C(=O)O)cc2C2CC2)CC[C@@H](C(F)(F)F)CC1] | 0.2313 | | |

TABLE 1-continued

| Example | Structure | LBA (μM) | Nav1.7 (μM) | Nav1.5 (μM) |
|---|---|---|---|---|
| 43 | 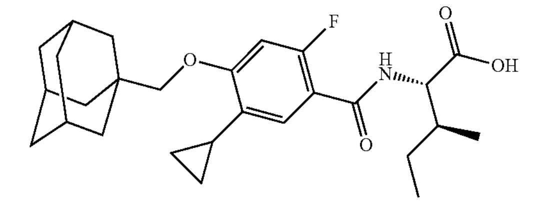 [SMILES: CC[C@H](C)[C@H](NC(=O)c1cc(C2CC2)c(OCC23CC4CC(CC(C4)C2)C3)cc1F)C(=O)O] | 0.0823 | | |
| 44 | 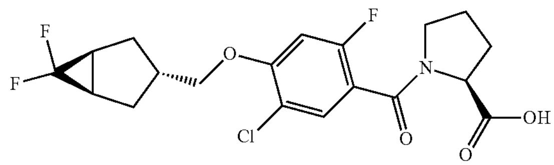 [SMILES: O=C(O)[C@@H]1CCCN1C(=O)c1cc(Cl)c(OC[C@@H]2C[C@@H]3[C@H](C2)C3(F)F)cc1F] | 10 | 30 | |
| 45 | 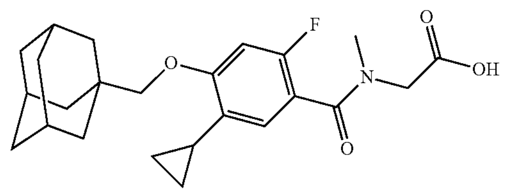 [SMILES: CN(CC(=O)O)C(=O)c1cc(C2CC2)c(OCC23CC4CC(CC(C4)C2)C3)cc1F] | 8.4 | 11.7 | |
| 46 | 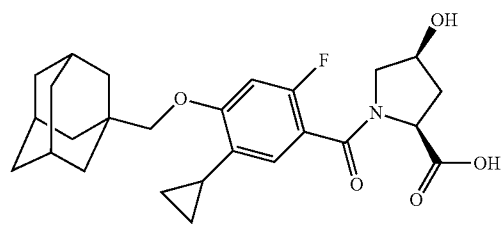 [SMILES: O=C(O)[C@@H]1C[C@H](O)CN1C(=O)c1cc(C2CC2)c(OCC23CC4CC(CC(C4)C2)C3)cc1F] | 0.15 | 0.87 | |
| 47 | 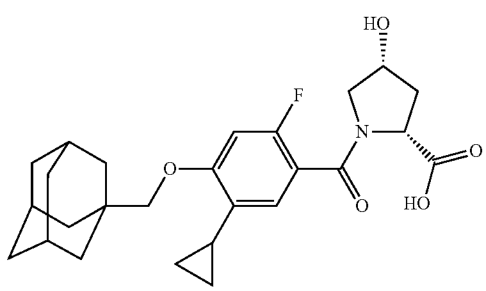 [SMILES: O=C(O)[C@H]1C[C@@H](O)CN1C(=O)c1cc(C2CC2)c(OCC23CC4CC(CC(C4)C2)C3)cc1F] | 10 | 16 | |
| 48 | 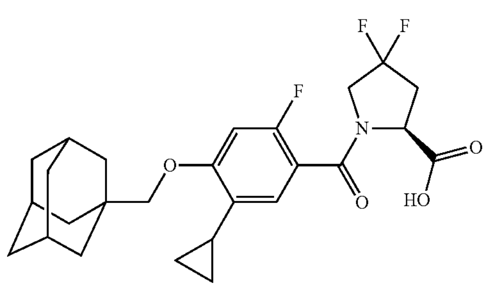 [SMILES: O=C(O)[C@@H]1CC(F)(F)CN1C(=O)c1cc(C2CC2)c(OCC23CC4CC(CC(C4)C2)C3)cc1F] | 0.04 | 0.64 | |

TABLE 1-continued

| Example | Structure | LBA (μM) | Nav1.7 (μM) | Nav1.5 (μM) |
|---|---|---|---|---|
| 49 | 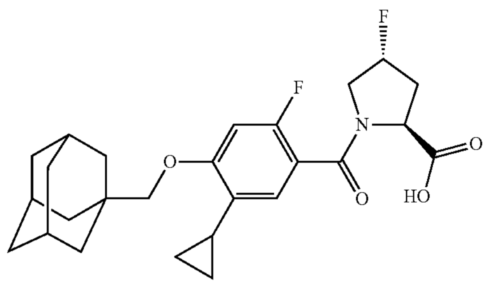 [SMILES: O=C(O)[C@@H]1C[C@@H](F)CN1C(=O)c1cc(C2CC2)c(OCC23CC4CC(CC(C4)C2)C3)cc1F] | 0.01 | 0.23 | |
| 50 | 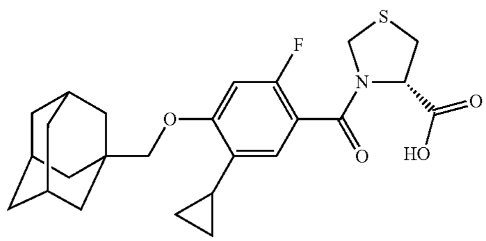 [SMILES: O=C(O)[C@H]1CSCN1C(=O)c1cc(C2CC2)c(OCC23CC4CC(CC(C4)C2)C3)cc1F] | 0.03 | 0.34 | 19.41 |
| 51 | 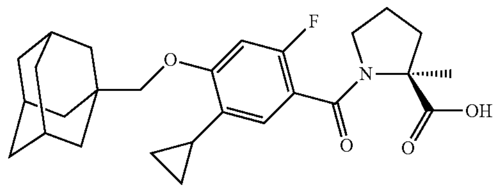 [SMILES: C[C@@]1(C(=O)O)CCCN1C(=O)c1cc(C2CC2)c(OCC23CC4CC(CC(C4)C2)C3)cc1F] | 0.1 | 0.92 | 14 |
| 52 | 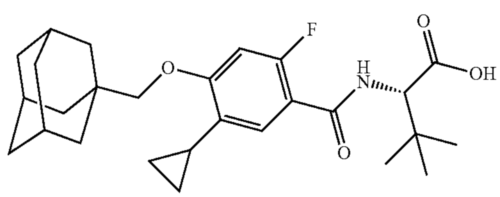 [SMILES: CC(C)(C)[C@H](NC(=O)c1cc(C2CC2)c(OCC23CC4CC(CC(C4)C2)C3)cc1F)C(=O)O] | 0.098 | 1.4 | 7.5 |
| 53 | 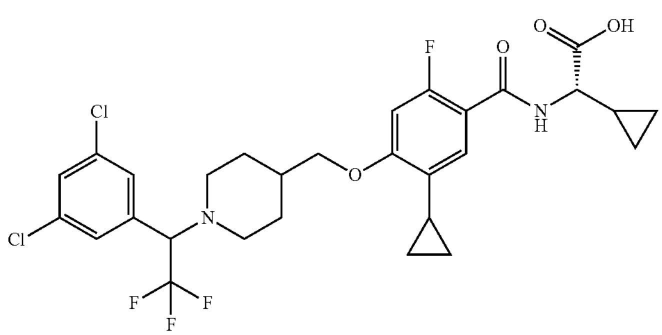 [SMILES: O=C(N[C@H](C(=O)O)C1CC1)c1cc(C2CC2)c(OCC2CCN(C(c3cc(Cl)cc(Cl)c3)C(F)(F)F)CC2)cc1F] | 0.017 | 2 | 14 |
| 54 | 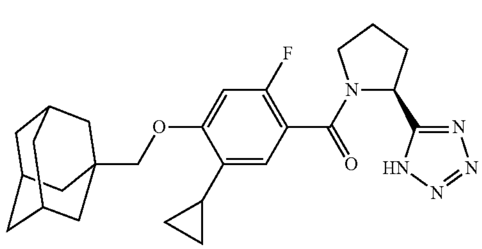 [SMILES: O=C(c1cc(C2CC2)c(OCC23CC4CC(CC(C4)C2)C3)cc1F)N1CCC[C@H]1c1nnn[nH]1] | 0.058 | 0.62 | 9.7 |

TABLE 1-continued

| Example | Structure | LBA (μM) | Nav1.7 (μM) | Nav1.5 (μM) |
| --- | --- | --- | --- | --- |
| 55 | 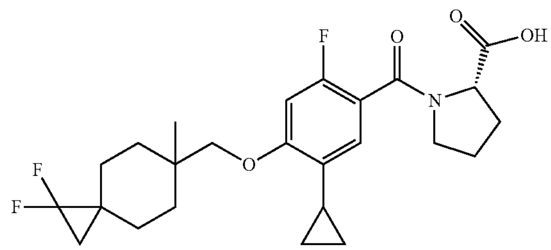 [SMILES: CC1(COc2cc(F)c(C(=O)N3CCC[C@H]3C(=O)O)cc2C2CC2)CCC2(CC1)CC2(F)F] | 0.25 | 0.79 | 29 |
| 56 | 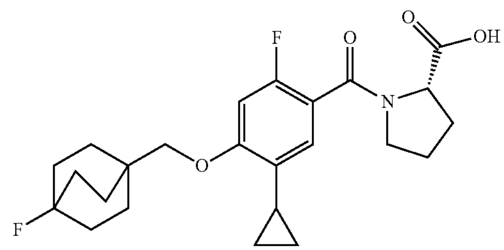 [SMILES: O=C(O)[C@@H]1CCCN1C(=O)c1cc(C2CC2)c(OCC23CCC(F)(CC2)CC3)cc1F] | 0.41 | 1.8 | 30 |
| 57 | 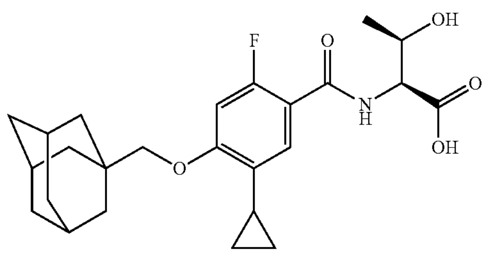 [SMILES: C[C@@H](O)[C@H](NC(=O)c1cc(C2CC2)c(OCC23CC4CC(CC(C4)C2)C3)cc1F)C(=O)O] | 0.43 | 2.1 | 23 |
| 58 | 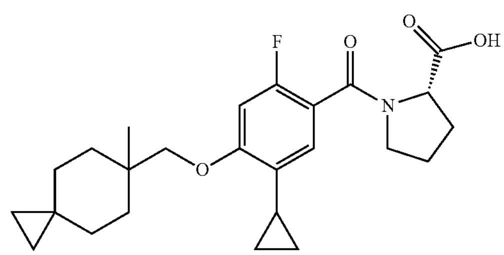 [SMILES: CC1(COc2cc(F)c(C(=O)N3CCC[C@H]3C(=O)O)cc2C2CC2)CCC2(CC1)CC2] | 0.083 | 0.63 | 21 |
| 59 | 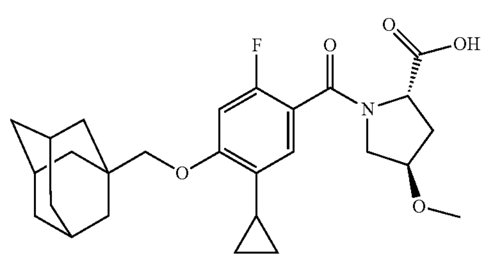 [SMILES: CO[C@@H]1C[C@@H](C(=O)O)N(C(=O)c2cc(C3CC3)c(OCC34CC5CC(CC(C5)C3)C4)cc2F)C1] | 0.034 | 0.55 | 26 |
| 60 | 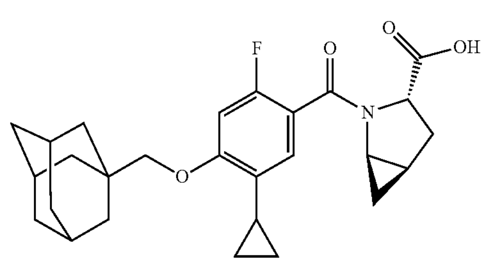 [SMILES: O=C(O)[C@@H]1C[C@H]2C[C@H]2N1C(=O)c1cc(C2CC2)c(OCC23CC4CC(CC(C4)C2)C3)cc1F] | 0.34 | 1.9 | 13 |

TABLE 1-continued

| Example | Structure | LBA (μM) | Nav1.7 (μM) | Nav1.5 (μM) |
| --- | --- | --- | --- | --- |
| 61 | 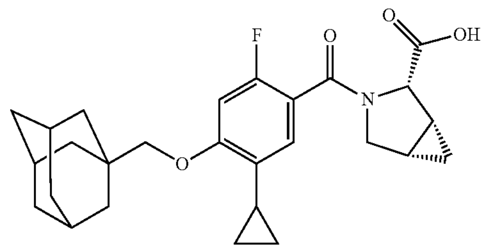 [SMILES: O=C(O)[C@@H]1[C@@H]2C[C@@H]2CN1C(=O)c1cc(C2CC2)c(OCC23CC4CC(CC(C4)C2)C3)cc1F] | 0.97 | 2.7 | 12 |
| 62 | 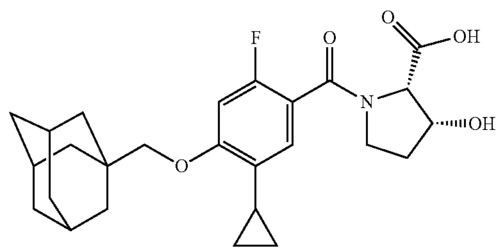 [SMILES: O=C(O)[C@@H]1[C@H](O)CCN1C(=O)c1cc(C2CC2)c(OCC23CC4CC(CC(C4)C2)C3)cc1F] | 0.16 | 1.1 | 28 |
| 63 | 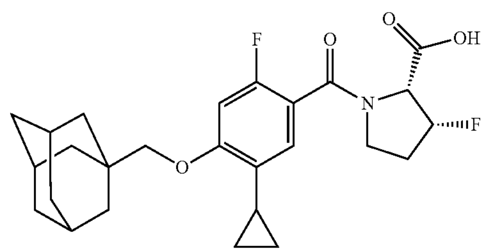 [SMILES: O=C(O)[C@@H]1[C@H](F)CCN1C(=O)c1cc(C2CC2)c(OCC23CC4CC(CC(C4)C2)C3)cc1F] | 0.17 | 0.98 | 18 |
| 64 | 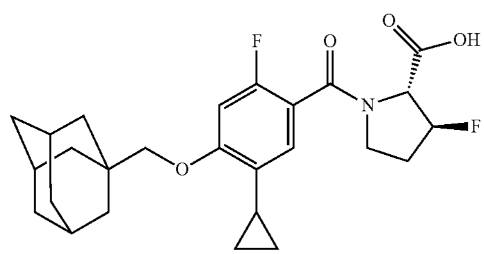 [SMILES: O=C(O)[C@@H]1[C@@H](F)CCN1C(=O)c1cc(C2CC2)c(OCC23CC4CC(CC(C4)C2)C3)cc1F] | 0.06 | 0.79 | 8.5 |
| 65 | 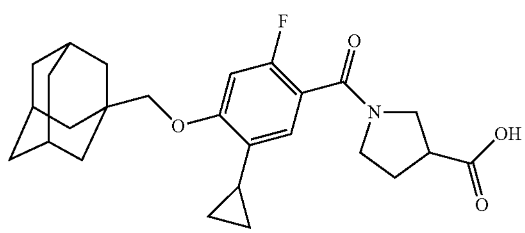 [SMILES: O=C(O)C1CCN(C(=O)c2cc(C3CC3)c(OCC34CC5CC(CC(C5)C3)C4)cc2F)C1] | 10 | 5.3 | 23 |
| 66 | 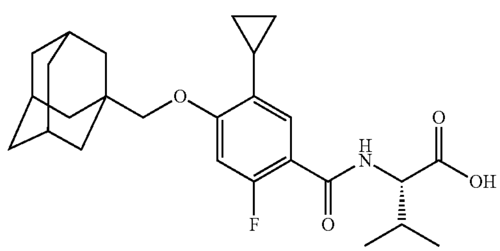 [SMILES: CC(C)[C@H](NC(=O)c1cc(C2CC2)c(OCC23CC4CC(CC(C4)C2)C3)cc1F)C(=O)O] | 0.07 | 0.8 | 8.1 |

TABLE 1-continued

| Example | Structure | LBA (μM) | Nav1.7 (μM) | Nav1.5 (μM) |
|---|---|---|---|---|
| 67 | 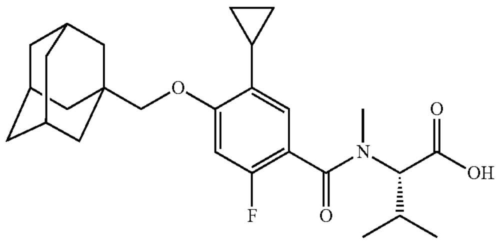 [SMILES: CC(C)[C@@H](C(=O)O)N(C)C(=O)c1cc(C2CC2)c(OCC23CC4CC(CC(C4)C2)C3)cc1F] | 1 | 3 | 7.5 |
| 68 | 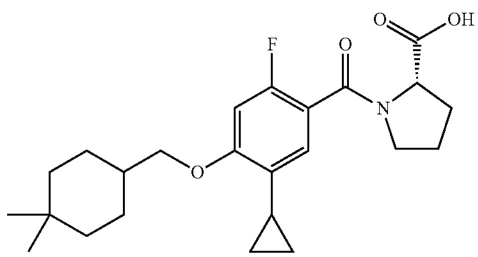 [SMILES: CC1(C)CCC(COc2cc(F)c(C(=O)N3CCC[C@H]3C(=O)O)cc2C2CC2)CC1] | 0.1 | 0.52 | 19 |
| 69 | 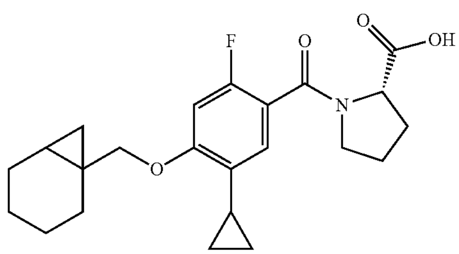 [SMILES: O=C(O)[C@@H]1CCCN1C(=O)c1cc(C2CC2)c(OCC23CCCCC2C3)cc1F] | 0.17 | 0.52 | 30 |
| 70 | 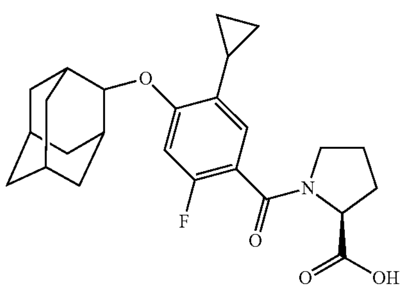 [SMILES: O=C(O)[C@@H]1CCCN1C(=O)c1cc(C2CC2)c(OC2C3CC4CC(C3)CC2C4)cc1F] | 0.31 | 1.6 | 30 |
| 71 | 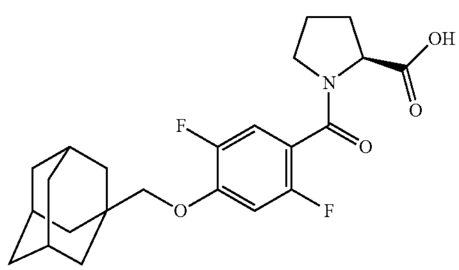 [SMILES: O=C(O)[C@@H]1CCCN1C(=O)c1cc(F)c(OCC23CC4CC(CC(C4)C2)C3)cc1F] | 6.1 | 11 | 30 |
| 72 | 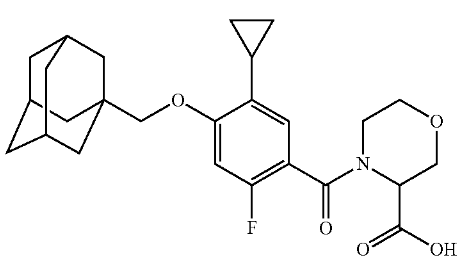 [SMILES: O=C(O)C1COCCN1C(=O)c1cc(C2CC2)c(OCC23CC4CC(CC(C4)C2)C3)cc1F] | 3.6 | 5.6 | 24 |

TABLE 1-continued

| Example | Structure | LBA (μM) | Nav1.7 (μM) | Nav1.5 (μM) |
|---------|-----------|----------|-------------|-------------|
| 73a | 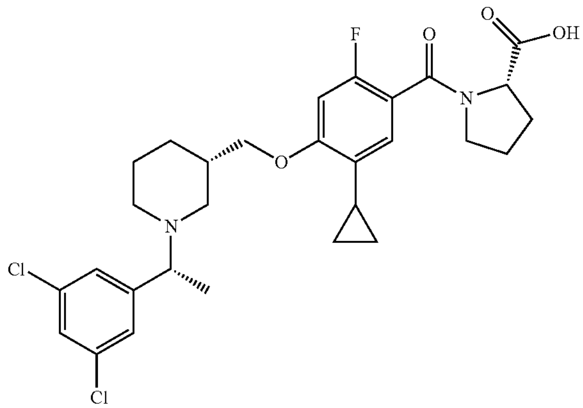 [SMILES: C[C@H](c1cc(Cl)cc(Cl)c1)N1CCC[C@H](COc2cc(F)c(C(=O)N3CCC[C@H]3C(=O)O)cc2C2CC2)C1] | 0.36 | 2.2 | 12 |
| 73b | 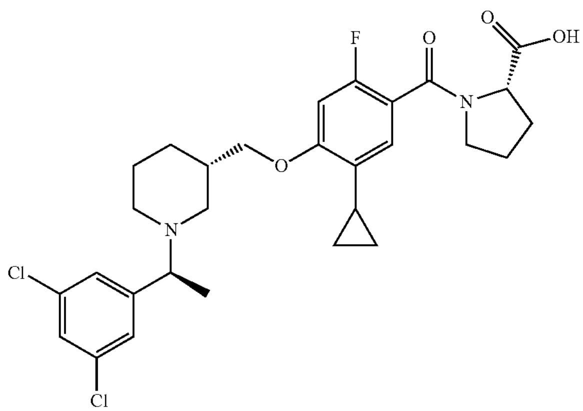 [SMILES: C[C@@H](c1cc(Cl)cc(Cl)c1)N1CCC[C@H](COc2cc(F)c(C(=O)N3CCC[C@H]3C(=O)O)cc2C2CC2)C1] | 0.093 | 1.5 | 22 |
| 74 | 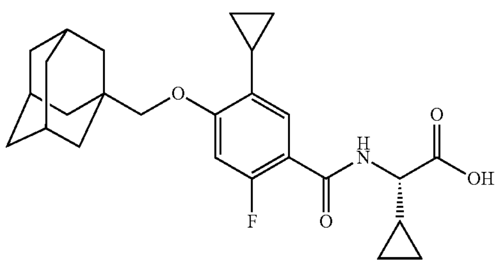 [SMILES: O=C(N[C@H](C(=O)O)C1CC1)c1cc(C2CC2)c(OCC23CC4CC(CC(C4)C2)C3)cc1F] | 0.024 | 0.7 | 7.5 |
| 75 | 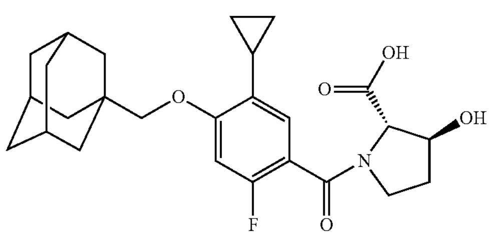 [SMILES: O=C(O)[C@@H]1[C@@H](O)CCN1C(=O)c1cc(C2CC2)c(OCC23CC4CC(CC(C4)C2)C3)cc1F] | 0.6 | 1.3 | 25 |
| 76 | 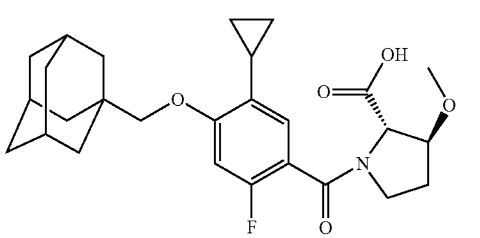 [SMILES: CO[C@H]1CCN(C(=O)c2cc(C3CC3)c(OCC34CC5CC(CC(C5)C3)C4)cc2F)[C@@H]1C(=O)O] | 0.087 | 1 | 17 |

TABLE 1-continued

| Example | Structure | LBA (µM) | Nav1.7 (µM) | Nav1.5 (µM) |
|---|---|---|---|---|
| 77 | 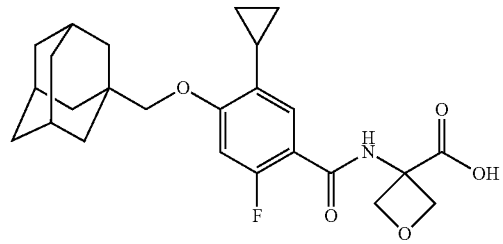 [SMILES: O=C(NC1(C(=O)O)COC1)c1cc(C2CC2)c(OCC23CC4CC(CC(C4)C2)C3)cc1F] | 7.4 | 11 | 12 |
| 78 | 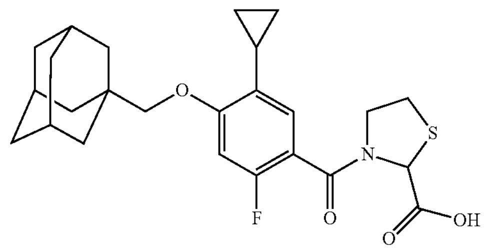 [SMILES: O=C(O)C1SCCN1C(=O)c1cc(C2CC2)c(OCC23CC4CC(CC(C4)C2)C3)cc1F] | 0.0094 | 0.087 | 13 |
| 79a | 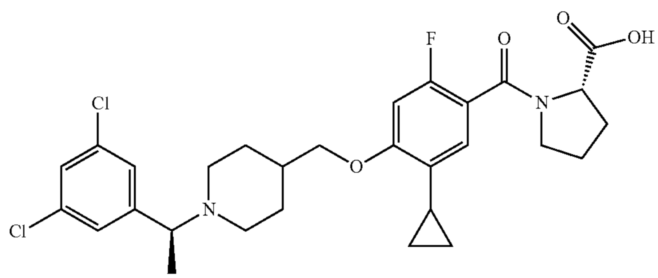 [SMILES: C[C@@H](c1cc(Cl)cc(Cl)c1)N1CCC(COc2cc(F)c(C(=O)N3CCC[C@H]3C(=O)O)cc2C2CC2)CC1] | 0.047 | 0.69 | 30 |
| 79b | 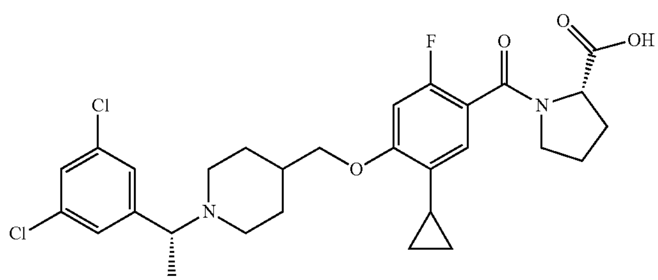 [SMILES: C[C@H](c1cc(Cl)cc(Cl)c1)N1CCC(COc2cc(F)c(C(=O)N3CCC[C@H]3C(=O)O)cc2C2CC2)CC1] | 0.073 | 0.79 | 30 |
| 80 | 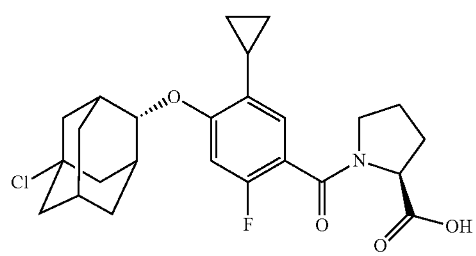 | 0.59 | 1.5 | 30 |
| 81 | 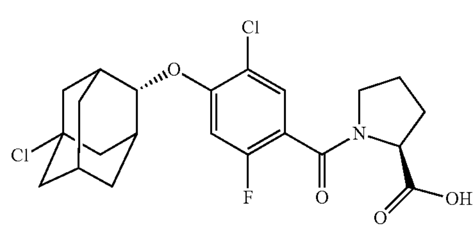 | 8.9 | 16 | 30 |

TABLE 1-continued

| Example | Structure | LBA (μM) | Nav1.7 (μM) | Nav1.5 (μM) |
|---|---|---|---|---|
| 82 | 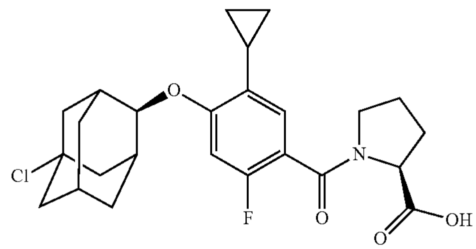 | 1.1 | 1.8 | 30 |
| 83 | 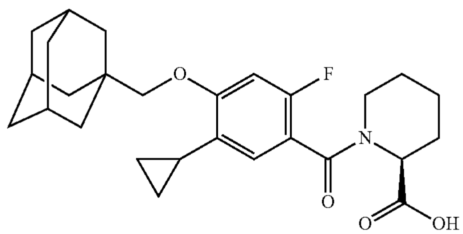 [SMILES: O=C(O)[C@@H]1CCCCN1C(=O)c1cc(C2CC2)c(OCC23CC4CC(CC(C4)C2)C3)cc1F] | 0.48 | 2 | 14 |
| 84 | 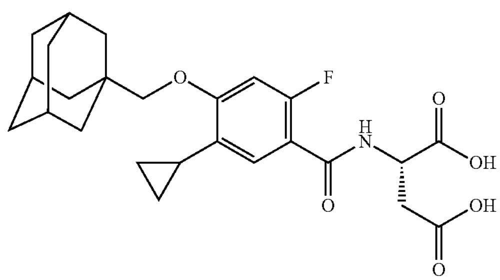 [SMILES: O=C(O)C[C@H](NC(=O)c1cc(C2CC2)c(OCC23CC4CC(CC(C4)C2)C3)cc1F)C(=O)O] | 10 | 17 | 30 |
| 85 | 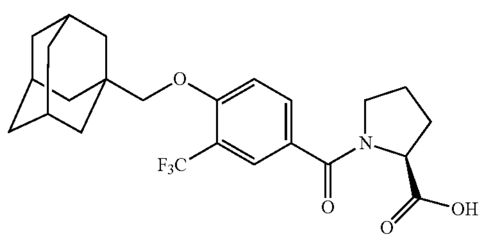 [SMILES: O=C(O)[C@@H]1CCCN1C(=O)c1ccc(OCC23CC4CC(CC(C4)C2)C3)c(C(F)(F)F)c1] | 0.59 | 1.1 | 17 |
| 86 | 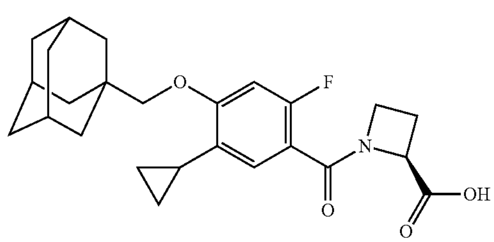 [SMILES: O=C(O)[C@@H]1CCN1C(=O)c1cc(C2CC2)c(OCC23CC4CC(CC(C4)C2)C3)cc1F] | 1.6 | 1.9 | 26 |
| 87 | 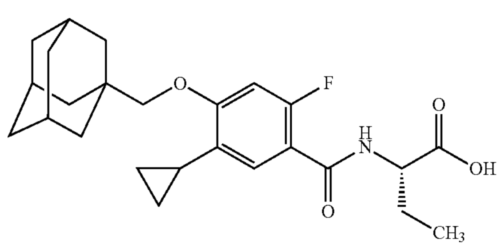 [SMILES: CC[C@H](NC(=O)c1cc(C2CC2)c(OCC23CC4CC(CC(C4)C2)C3)cc1F)C(=O)O] | 0.056 | 1.3 | 7.1 |

TABLE 1-continued

| Example | Structure | LBA (μM) | Nav1.7 (μM) | Nav1.5 (μM) |
|---|---|---|---|---|
| 88 | 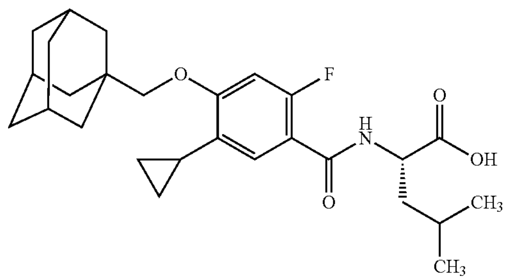 [SMILES: CC(C)C[C@H](NC(=O)c1cc(C2CC2)c(OCC23CC4CC(CC(C4)C2)C3)cc1F)C(=O)O] | 0.43 | 7 | 8.2 |
| 89 | 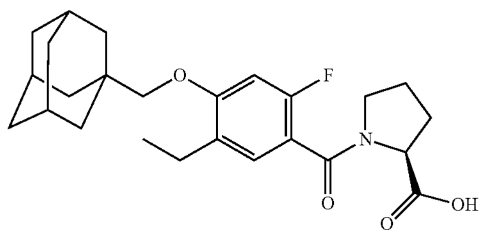 [SMILES: CCc1cc(C(=O)N2CCC[C@H]2C(=O)O)c(F)cc1OCC12CC3CC(CC(C3)C1)C2] | 0.13 | 0.79 | 17 |
| 90 | 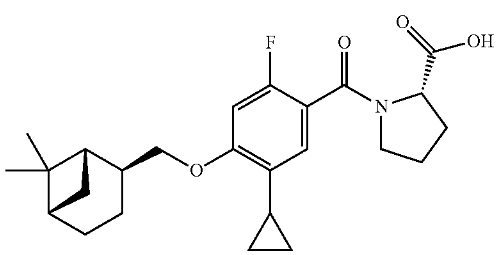 [SMILES: CC1(C)[C@H]2CC[C@H](COc3cc(F)c(C(=O)N4CCC[C@H]4C(=O)O)cc3C3CC3)[C@@H]1C2] | 0.021 | 0.16 | 13 |
| 91 | 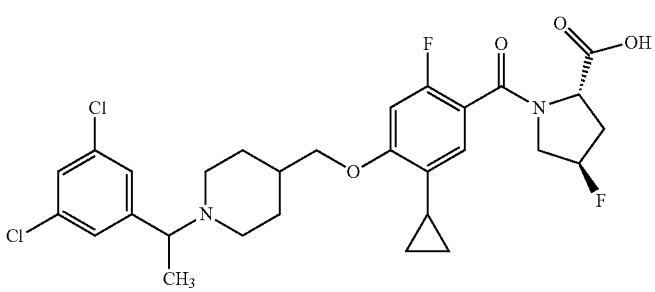 | 0.015 | 0.3 | 23 |
| 92 | 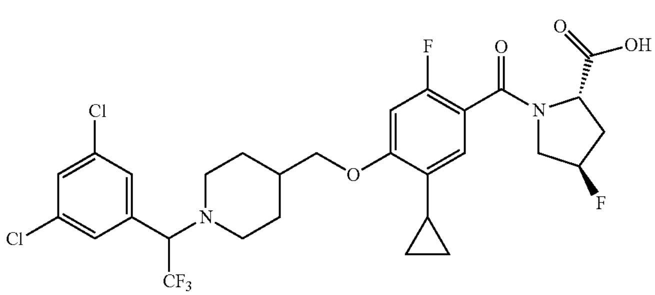 [SMILES: CC(c1cc(Cl)cc(Cl)c1)N1CCC(COc2cc(F)c(C(=O)N3C[C@H](F)C[C@H]3C(=O)O)cc2C2CC2)CC1] | 0.016 | 0.31 | 11 |

TABLE 1-continued

| Example | Structure | LBA (µM) | Nav1.7 (µM) | Nav1.5 (µM) |
|---|---|---|---|---|
| 93 | 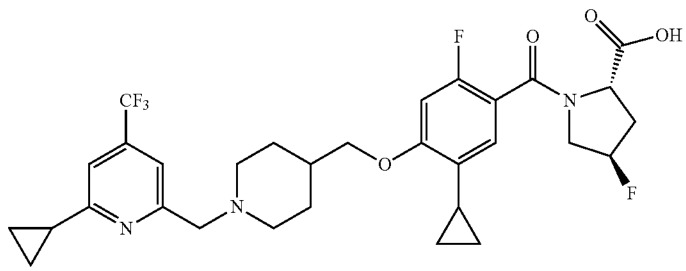 [SMILES: O=C(O)[C@@H]1C[C@@H](F)CN1C(=O)c1cc(C2CC2)c(OCC2CCN(Cc3cc(C(F)(F)F)cc(C4CC4)n3)CC2)cc1F] | 0.081 | 0.66 | 30 |
| 94 | 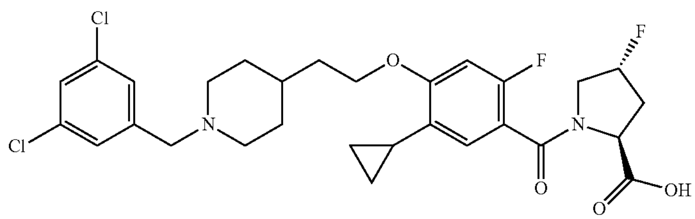 [SMILES: O=C(O)[C@@H]1C[C@@H](F)CN1C(=O)c1cc(C2CC2)c(OCCC2CCN(Cc3cc(Cl)cc(Cl)c3)CC2)cc1F] | 0.1 | 0.6 | 30 |
| 95 | 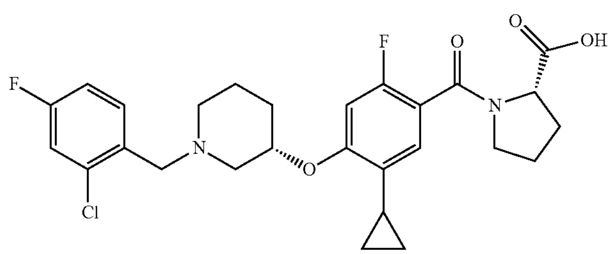 [SMILES: O=C(O)[C@@H]1CCCN1C(=O)c1cc(C2CC2)c(O[C@H]2CCCN(Cc3ccc(F)cc3Cl)C2)cc1F] | 10 | 30 | 30 |
| 96 | 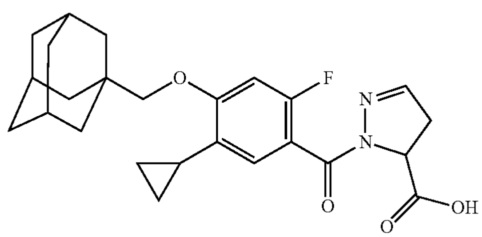 [SMILES: O=C(O)C1CC=NN1C(=O)c1cc(C2CC2)c(OCC23CC4CC(CC(C4)C2)C3)cc1F] | 0.38 | 1.5 | 30 |
| 97 | 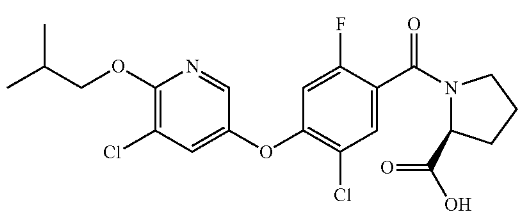 [SMILES: CC(C)COc1ncc(Oc2cc(F)c(C(=O)N3CCC[C@H]3C(=O)O)cc2Cl)cc1Cl] | 0.44 | 0.57 | 30 |
| 98 | 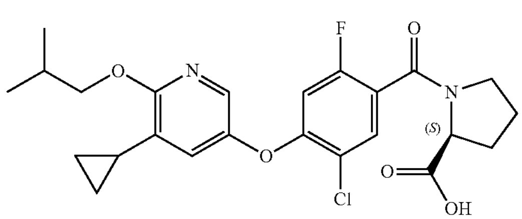 | 0.44 | 0.74 | 30 |

TABLE 1-continued

| Example | Structure | LBA (μM) | Nav1.7 (μM) | Nav1.5 (μM) |
|---|---|---|---|---|
| 99 | 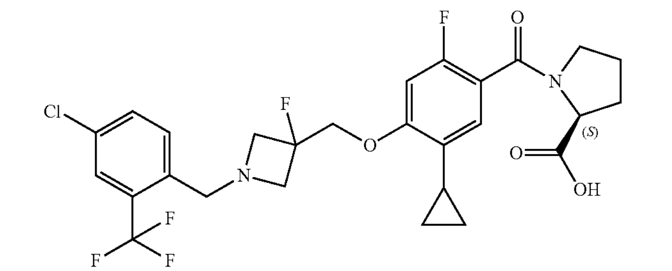 | 0.23 | 0.55 | 30 |
| 100 | 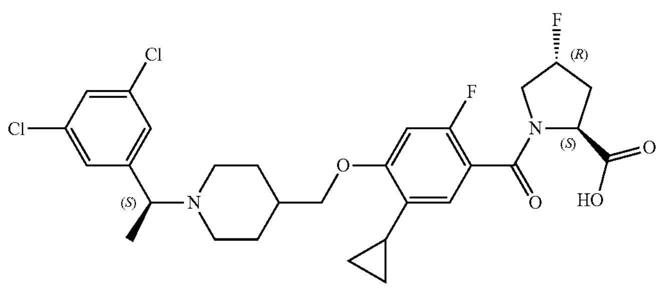 | 0.031 | 0.44 | 18 |
| 101 | 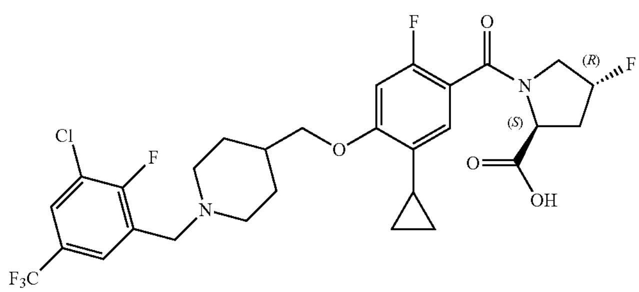 | 0.066 | 0.52 | 30 |
| 102 | 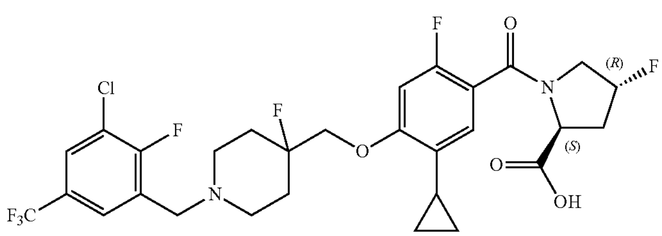 | 0.065 | 0.33 | 23 |
| 103 | 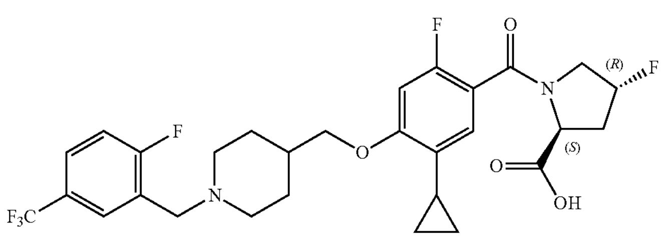 | 0.033 | 0.34 | 30 |
| 104 | 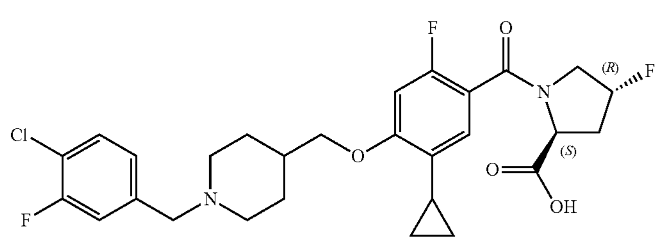 | 0.13 | 1.6 | 30 |

TABLE 1-continued

| Example | Structure | LBA (μM) | Nav1.7 (μM) | Nav1.5 (μM) |
|---|---|---|---|---|
| 105 | 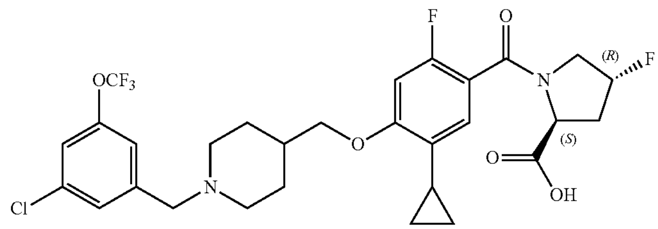 | 0.037 | 0.22 | 22 |
| 106 | 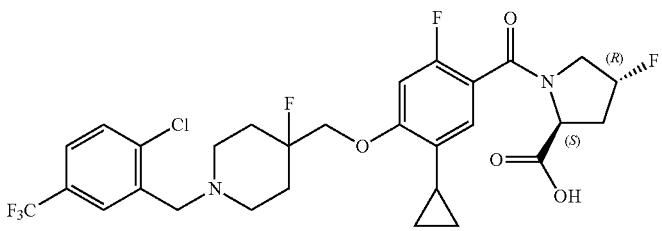 | 0.027 | 0.13 | 21 |
| 107 | 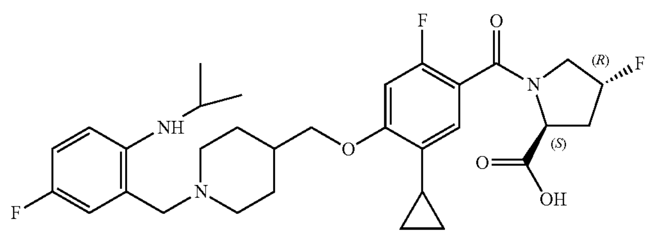 | 0.039 | 0.73 | 12 |
| 108 | 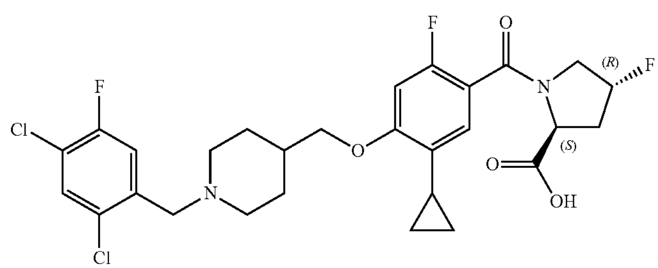 | 0.017 | 0.22 | 9.6 |
| 109 | 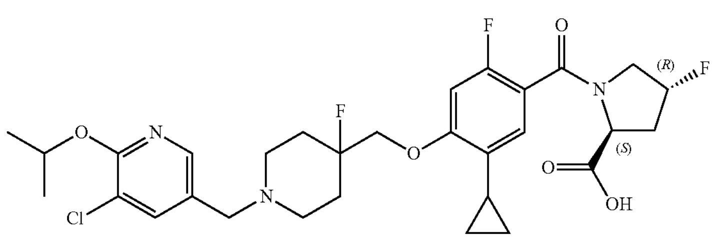 | 0.051 | 0.89 | 30 |
| 110 | 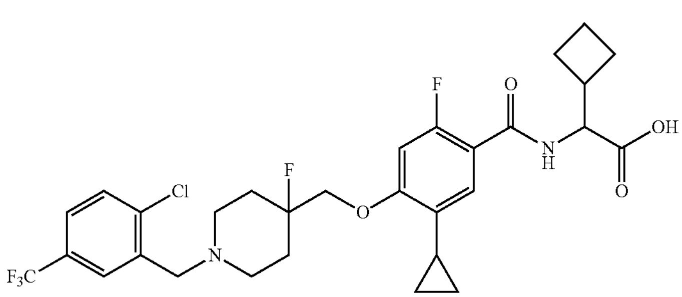 [SMILES: O=C(NC(C(=O)O)C1CCC1)c1cc(C2CC2)c(OCC2(F)CCN(Cc3cc(C(F)(F)F)ccc3Cl)CC2)cc1F] | 0.37 | 10 | 10 |

TABLE 1-continued

| Example | Structure | LBA (μM) | Nav1.7 (μM) | Nav1.5 (μM) |
|---------|-----------|----------|-------------|-------------|
| 111 | 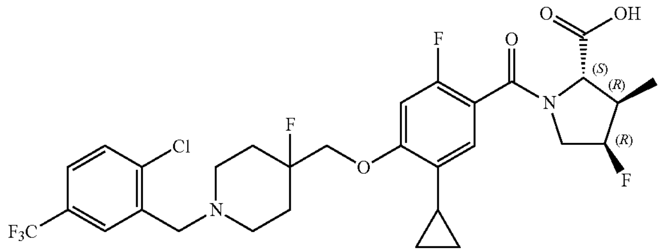 | 0.036 | 0.23 | 14 |
| 112 | 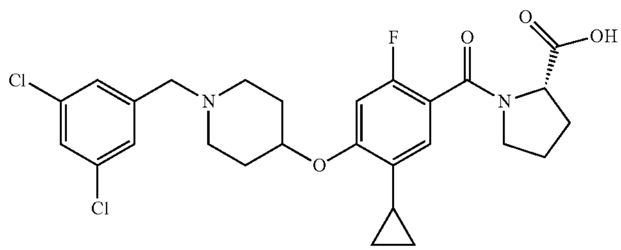 [SMILES: O=C(O)[C@@H]1CCCN1C(=O)c1cc(C2CC2)c(OC2CCN(Cc3cc(Cl)cc(Cl)c3)CC2)cc1F] | 0.52 | 2 | 30 |
| 113 | 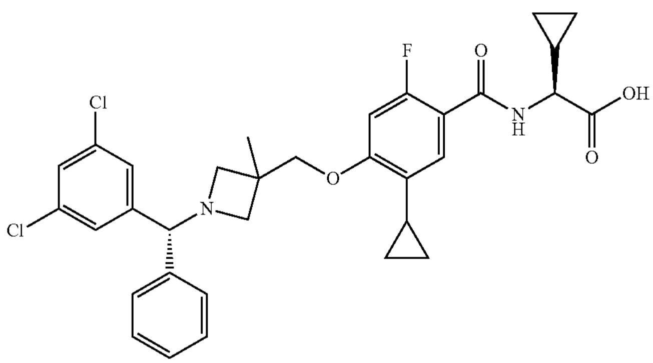 [SMILES: CC1(COc2cc(F)c(C(=O)N[C@H](C(=O)O)C3CC3)cc2C2CC2)CN([C@H](c2ccccc2)c2cc(Cl)cc(Cl)c2)C1] | 0.076 | 0.61 | 15 |
| 114 | 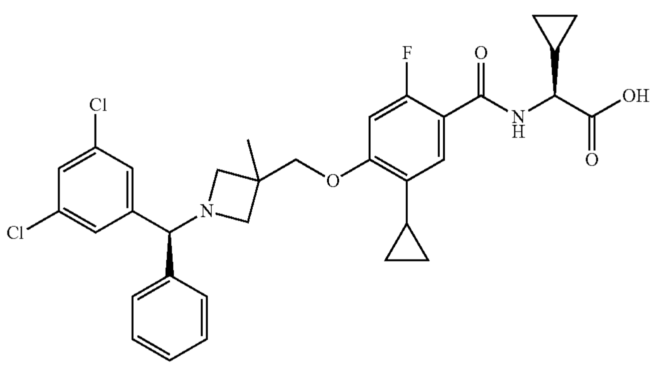 [SMILES: CC1(COc2cc(F)c(C(=O)N[C@H](C(=O)O)C3CC3)cc2C2CC2)CN([C@@H](c2ccccc2)c2cc(Cl)cc(Cl)c2)C1] | 0.02 | 1.7 | 13 |
| 115 | 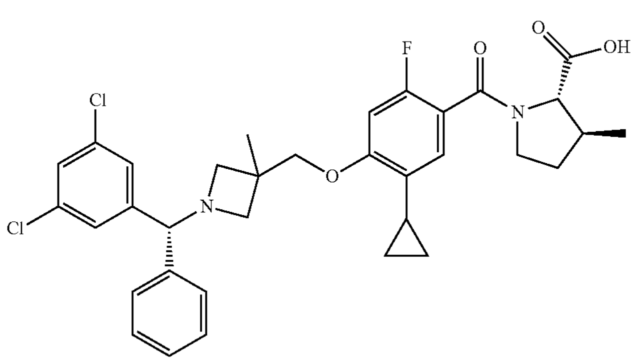 [SMILES: C[C@H]1CCN(C(=O)c2cc(C3CC3)c(OCC3(C)CN([C@H](c4ccccc4)c4cc(Cl)cc(Cl)c4)C3)cc2F)[C@@H]1C(=O)O] | 0.0077 | 0.3 | 11 |

TABLE 1-continued

| Example | Structure | LBA (μM) | Nav1.7 (μM) | Nav1.5 (μM) |
|---|---|---|---|---|
| 116 | 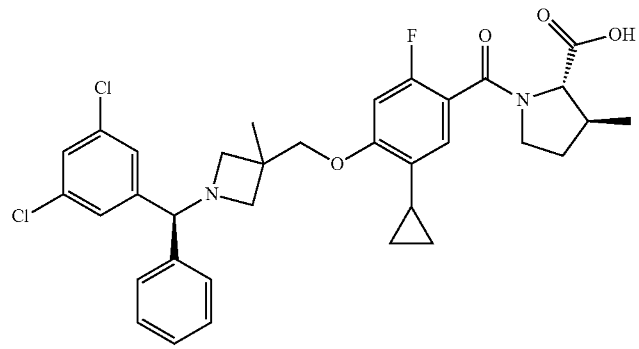 [SMILES: C[C@H]1CCN(C(=O)c2cc(C3CC3)c(OCC3(C)CN([C@@H](c4ccccc4)c4cc(Cl)cc(Cl)c4)C3)cc2F)[C@@H]1C(=O)O] | 0.012 | 0.58 | 15 |
| 117 | 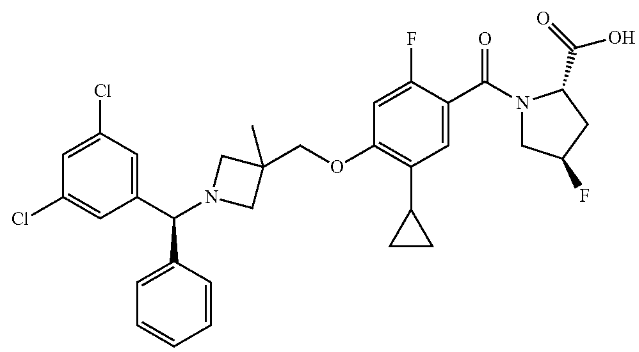 [SMILES: CC1(COc2cc(F)c(C(=O)N3C[C@H](F)C[C@H]3C(=O)O)cc2C2CC2)CN([C@@H](c2ccccc2)c2cc(Cl)cc(Cl)c2)C1] | 0.023 | 0.51 | 8.5 |
| 118 | 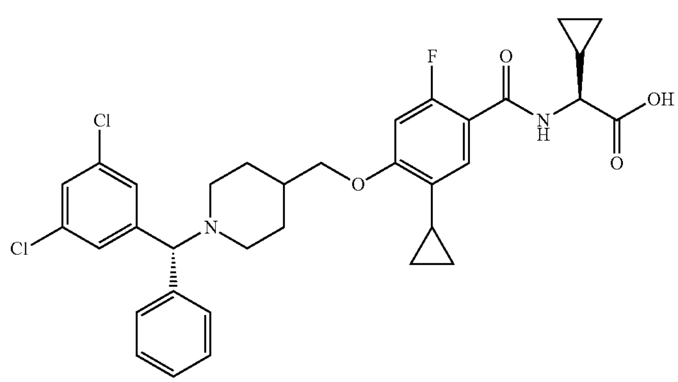 [SMILES: O=C(N[C@H](C(=O)O)C1CC1)c1cc(C2CC2)c(OCC2CCN([C@H](c3ccccc3)c3cc(Cl)cc(Cl)c3)CC2)cc1F] | 0.021 | 0.76 | 15 |
| 119 | 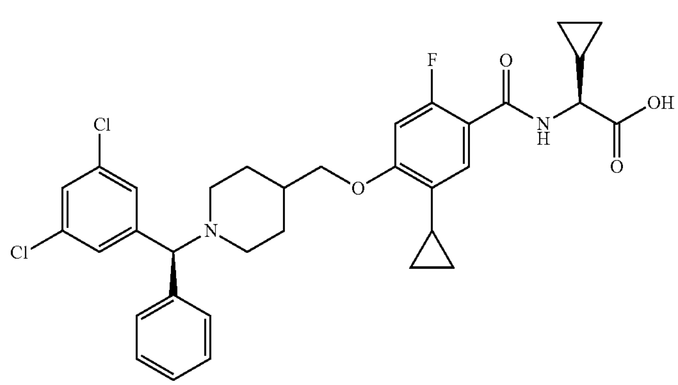 [SMILES: O=C(N[C@H](C(=O)O)C1CC1)c1cc(C2CC2)c(OCC2CCN([C@@H](c3ccccc3)c3cc(Cl)cc(Cl)c3)CC2)cc1F] | 0.015 | 0.85 | 9.4 |

TABLE 1-continued

| Example | Structure | LBA (µM) | Nav1.7 (µM) | Nav1.5 (µM) |
|---|---|---|---|---|
| 120 | 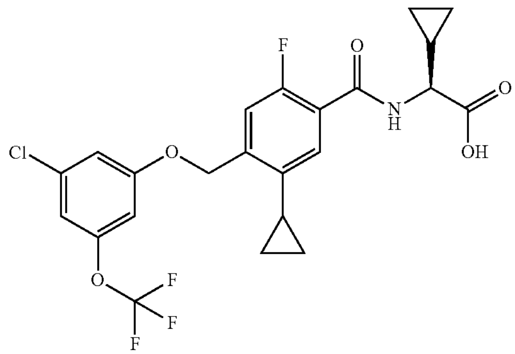 [SMILES: O=C(N[C@H](C(=O)O)C1CC1)c1cc(C2CC2)c(COc2cc(Cl)cc(OC(F)(F)F)c2)cc1F] | 0.027 | 0.29 | 14 |
| 121a | 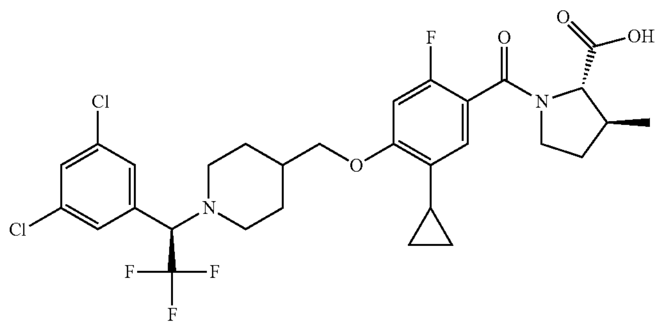 [SMILES: C[C@H]1CCN(C(=O)c2cc(C3CC3)c(OCC3CCN([C@H](c4cc(Cl)cc(Cl)c4)C(F)(F)F)CC3)cc2F)[C@@H]1C(=O)O] | 0.02 | 0.88 | 13 |
| 121b | 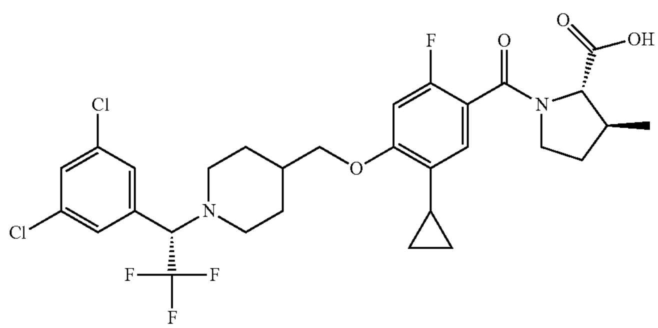 [SMILES: C[C@H]1CCN(C(=O)c2cc(C3CC3)c(OCC3CCN([C@@H](c4cc(Cl)cc(Cl)c4)C(F)(F)F)CC3)cc2F)[C@@H]1C(=O)O] | 0.018 | 0.88 | 17 |
| 122 | 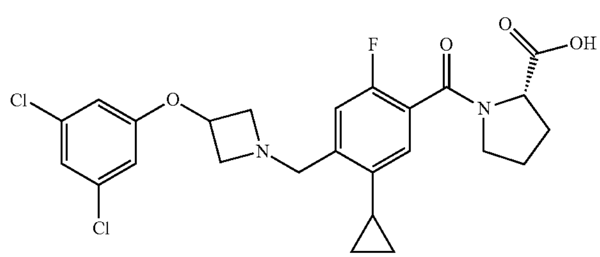 [SMILES: O=C(O)[C@@H]1CCCN1C(=O)c1cc(C2CC2)c(CN2CC(Oc3cc(Cl)cc(Cl)c3)C2)cc1F] | 0.43 | 2 | 30 |
| 123a | 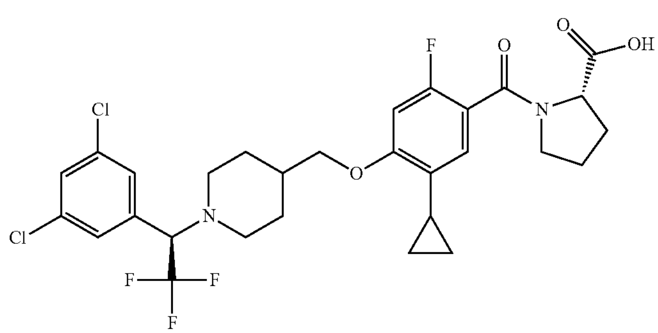 [SMILES: O=C(O)[C@@H]1CCCN1C(=O)c1cc(C2CC2)c(OCC2CCN([C@H](c3cc(Cl)cc(Cl)c3)C(F)(F)F)CC2)cc1F] | 0.048 | 0.49 | 7.1 |

TABLE 1-continued

| Example | Structure | LBA (µM) | Nav1.7 (µM) | Nav1.5 (µM) |
|---------|-----------|----------|-------------|-------------|
| 123b | 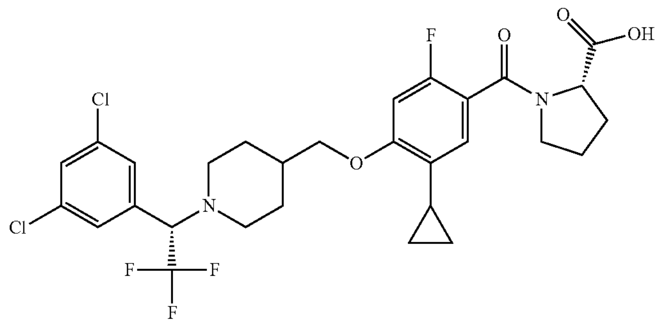 [SMILES: O=C(O)[C@@H]1CCCN1C(=O)c1cc(C2CC2)c(OCC2CCN([C@@H](c3cc(Cl)cc(Cl)c3)C(F)(F)F)CC2)cc1F] | 0.031 | 0.41 | 7.7 |
| 124 | 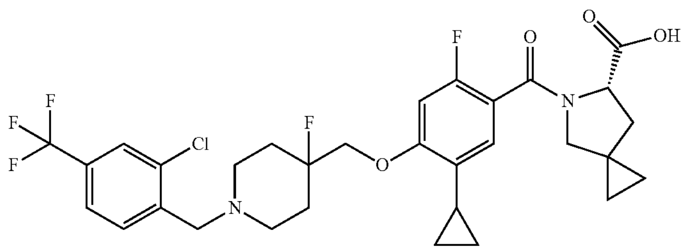 [SMILES: O=C(O)[C@@H]1CC2(CC2)CN1C(=O)c1cc(C2CC2)c(OCC2(F)CCN(Cc3ccc(C(F)(F)F)cc3Cl)CC2)cc1F] | 0.4 | 1.5 | 12 |
| 125 | 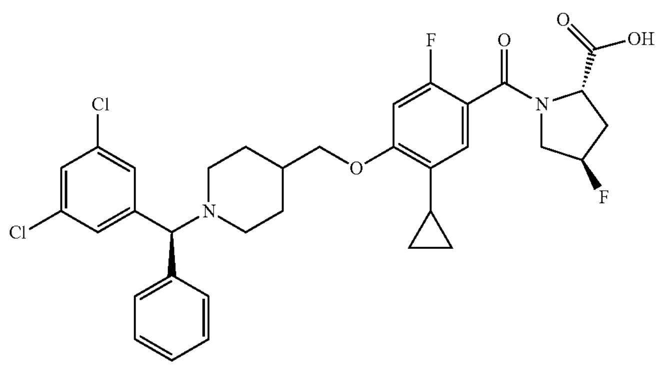 [SMILES: O=C(O)[C@@H]1C[C@@H](F)CN1C(=O)c1cc(C2CC2)c(OCC2CCN([C@@H](c3ccccc3)c3cc(Cl)cc(Cl)c3)CC2)cc1F] | 0.016 | 0.38 | 6.2 |
| 126a | 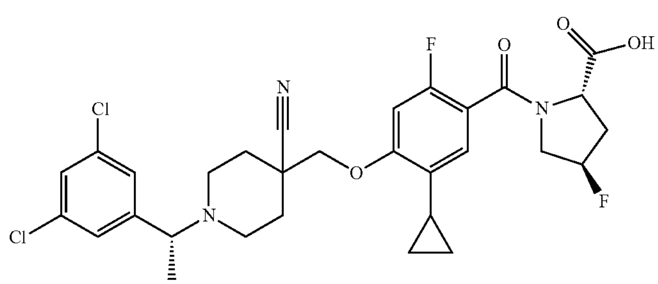 [SMILES: C[C@H](c1cc(Cl)cc(Cl)c1)N1CCC(C#N)(COc2cc(F)c(C(=O)N3C[C@H](F)C[C@H]3C(=O)O)cc2C2CC2)CC1] | 0.12 | 2.3 | 10 |
| 126b | 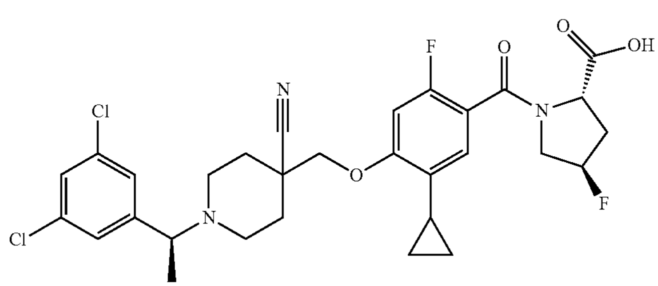 [SMILES: C[C@@H](c1cc(Cl)cc(Cl)c1)N1CCC(C#N)(COc2cc(F)c(C(=O)N3C[C@H](F)C[C@H]3C(=O)O)cc2C2CC2)CC1] | 0.1 | 1.4 | 10 |

TABLE 1-continued
| Example | Structure | LBA (μM) | Nav1.7 (μM) | Nav1.5 (μM) |
|---|---|---|---|---|
| 127 | 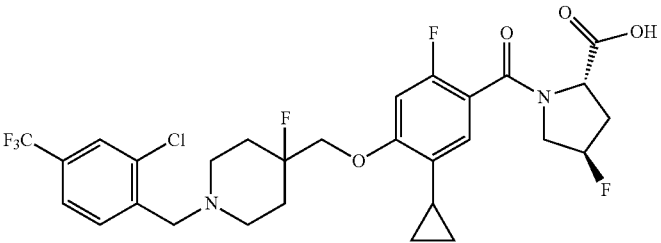 [SMILES: O=C(O)[C@@H]1C[C@@H](F)CN1C(=O)c1cc(C2CC2)c(OCC2(F)CCN(Cc3ccc(C(F)(F)F)cc3Cl)CC2)cc1F] | 0.12 | 0.4 | 13 |
| 128 | 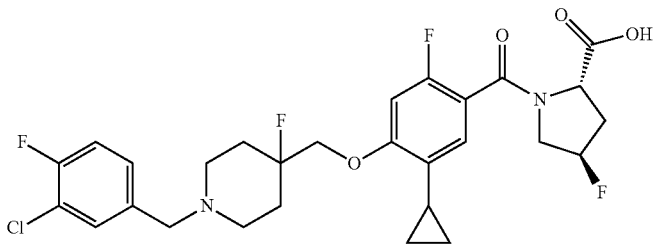 [SMILES: O=C(O)[C@@H]1C[C@@H](F)CN1C(=O)c1cc(C2CC2)c(OCC2(F)CCN(Cc3ccc(F)c(Cl)c3)CC2)cc1F] | 0.087 | 0.71 | 30 |
| 129 | 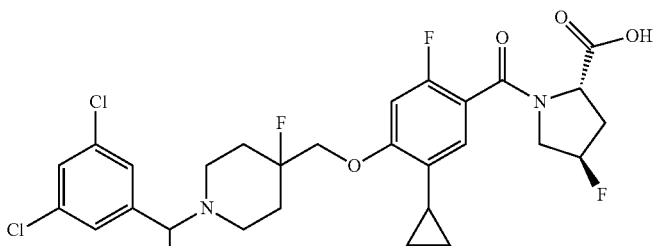 | 0.022 | 0.16 | 9.4 |
| 130 | 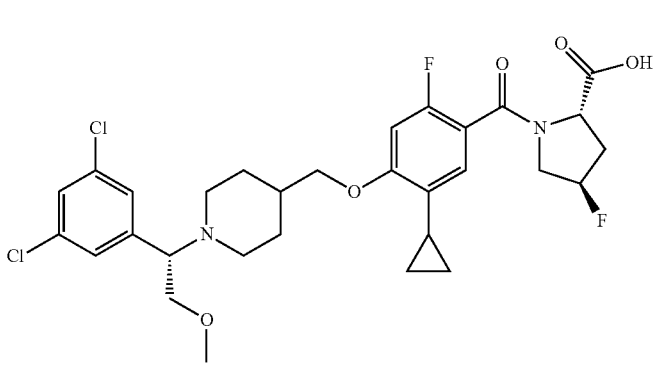 [SMILES: COC[C@H](c1cc(Cl)cc(Cl)c1)N1CCC(COc2cc(F)c(C(=O)N3C[C@H](F)C[C@H]3C(=O)O)cc2C2CC2)CC1] | 0.027 | 0.16 | 14 |
| 131 | 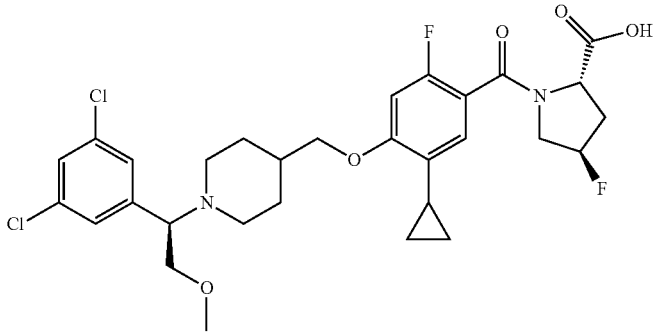 [SMILES: COC[C@@H](c1cc(Cl)cc(Cl)c1)N1CCC(COc2cc(F)c(C(=O)N3C[C@H](F)C[C@H]3C(=O)O)cc2C2CC2)CC1] | 0.028 | 0.25 | 18 |

TABLE 1-continued

| Example | Structure | LBA (μM) | Nav1.7 (μM) | Nav1.5 (μM) |
|---------|-----------|----------|-------------|-------------|
| 132a | 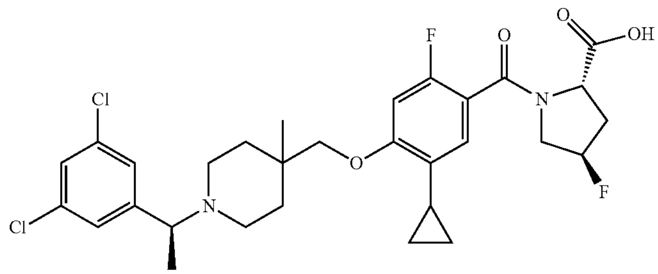 [SMILES: C[C@@H](c1cc(Cl)cc(Cl)c1)N1CCC(C)(COc2cc(F)c(C(=O)N3C[C@H](F)C[C@H]3C(=O)O)cc2C2CC2)CC1] | 0.024 | 0.33 | 17 |
| 132b | 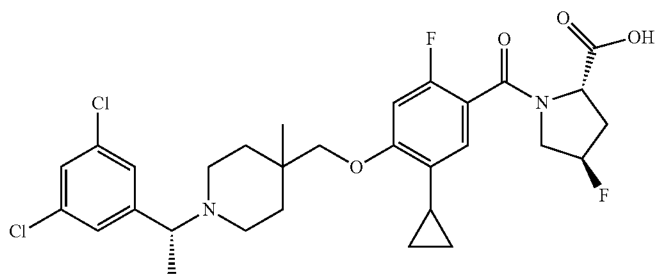 [SMILES: C[C@H](c1cc(Cl)cc(Cl)c1)N1CCC(C)(COc2cc(F)c(C(=O)N3C[C@H](F)C[C@H]3C(=O)O)cc2C2CC2)CC1] | 0.024 | 0.43 | 30 |
| 133 | 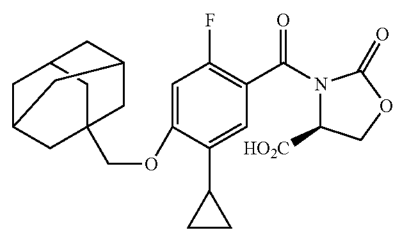 [SMILES: O=C(O)[C@@H]1COC(=O)N1C(=O)c1cc(C2CC2)c(OCC23CC4CC(CC(C4)C2)C3)cc1F] | 1.4 | 18 | 9.4 |
| 134 | 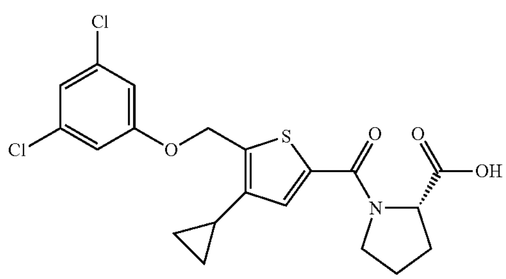 [SMILES: O=C(O)[C@@H]1CCCN1C(=O)c1cc(C2CC2)c(COc2cc(Cl)cc(Cl)c2)s1] | 0.072 | 0.63 | 7.1 |
| 135 | 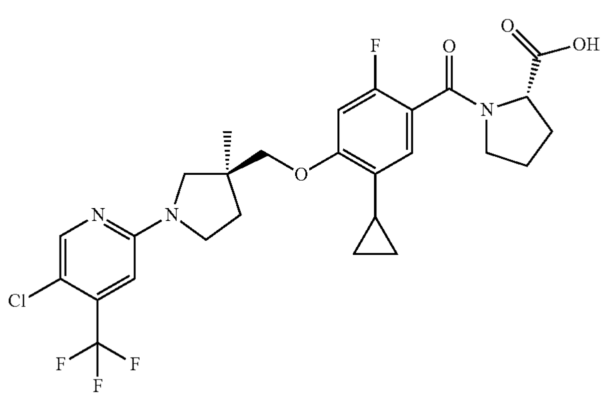 [SMILES: C[C@]1(COc2cc(F)c(C(=O)N3CCC[C@H]3C(=O)O)cc2C2CC2)CCN(c2cc(C(F)(F)F)c(Cl)cn2)C1] | 0.39 | 2.6 | 30 |

TABLE 1-continued
| Example | Structure | LBA (μM) | Nav1.7 (μM) | Nav1.5 (μM) |
|---|---|---|---|---|
| 136 | 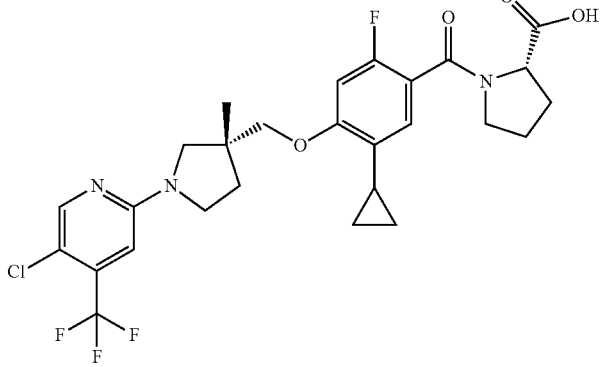 | 0.11 | 1.1 | 30 |
| 137a | 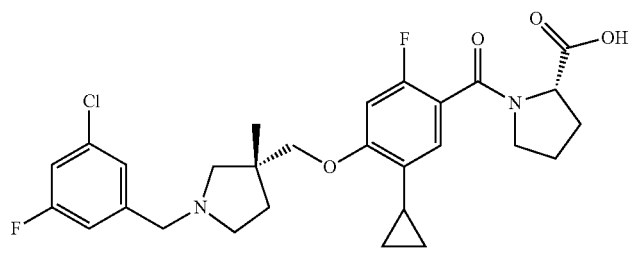 [SMILES: C[C@@]1(COc2cc(F)c(C(=O)N3CCC[C@H]3C(=O)O)cc2C2CC2)CCN(Cc2cc(F)cc(Cl)c2)C1] | 0.57 | 3.7 | 15 |
| 137b | 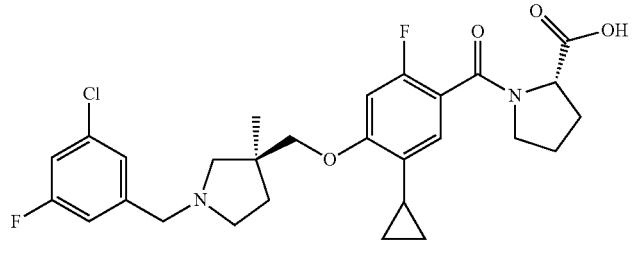 [SMILES: C[C@]1(COc2cc(F)c(C(=O)N3CCC[C@H]3C(=O)O)cc2C2CC2)CCN(Cc2cc(F)cc(Cl)c2)C1] | 0.31 | 2.4 | 30 |
| 138a | 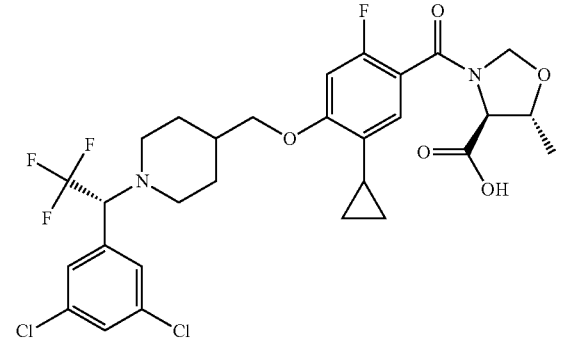 [SMILES: C[C@H]1OCN(C(=O)c2cc(C3CC3)c(OCC3CCN([C@H](c4cc(Cl)cc(Cl)c4)C(F)(F)F)CC3)cc2F)[C@@H]1C(=O)O] | 0.0069 | 0.3 | 13 |
| 138b | 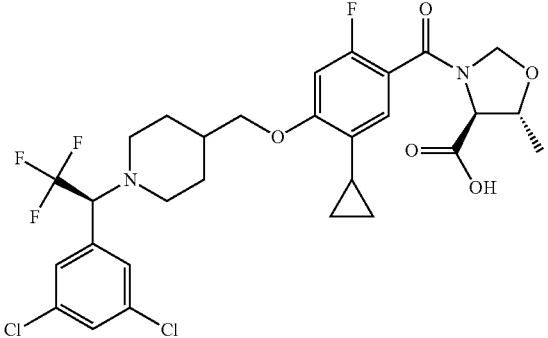 [SMILES: C[C@H]1OCN(C(=O)c2cc(C3CC3)c(OCC3CCN([C@@H](c4cc(Cl)cc(Cl)c4)C(F)(F)F)CC3)cc2F)[C@@H]1C(=O)O] | 0.0076 | 0.32 | 11 |

TABLE 1-continued

| Example | Structure | LBA (µM) | Nav1.7 (µM) | Nav1.5 (µM) |
|---|---|---|---|---|
| 139a | 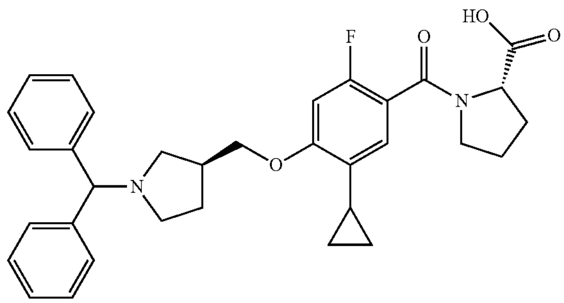 [SMILES: O=C(O)[C@@H]1CCCN1C(=O)c1cc(C2CC2)c(OC[C@H]2CCN(C(c3ccccc3)c3ccccc3)C2)cc1F] | 0.65 | 5 | 25 |
| 139b | 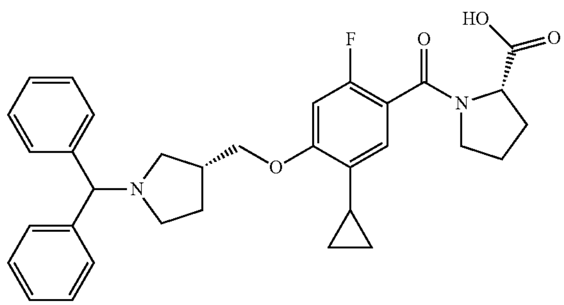 [SMILES: O=C(O)[C@@H]1CCCN1C(=O)c1cc(C2CC2)c(OC[C@@H]2CCN(C(c3ccccc3)c3ccccc3)C2)cc1F] | 0.8 | 7.1 | 22 |
| 140a | 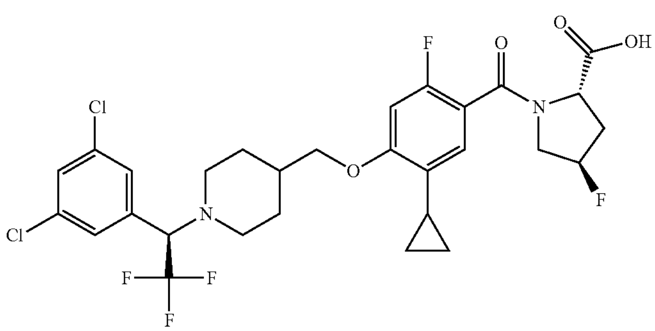 [SMILES: O=C(O)[C@@H]1C[C@@H](F)CN1C(=O)c1cc(C2CC2)c(OCC2CCN([C@H](c3cc(Cl)cc(Cl)c3)C(F)(F)F)CC2)cc1F] | 0.014 | 0.17 | 2.7 |
| 140b | 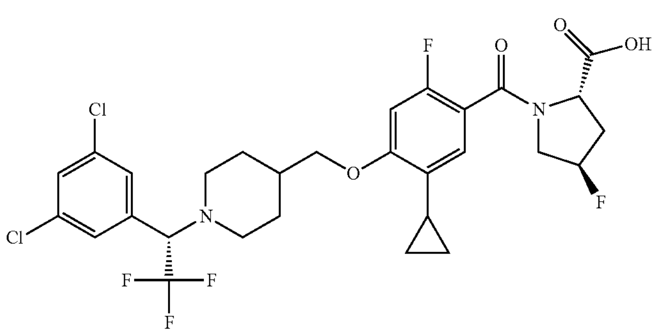 [SMILES: O=C(O)[C@@H]1C[C@@H](F)CN1C(=O)c1cc(C2CC2)c(OCC2CCN([C@@H](c3cc(Cl)cc(Cl)c3)C(F)(F)F)CC2)cc1F] | 0.021 | 0.16 | 3.7 |
| 141 | 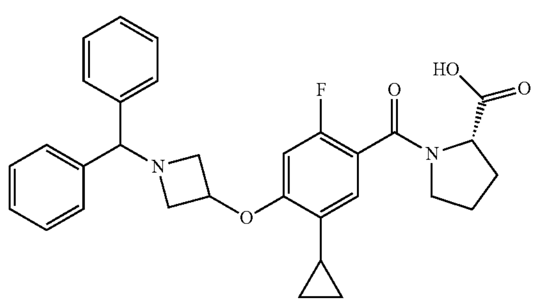 [SMILES: O=C(O)[C@@H]1CCCN1C(=O)c1cc(C2CC2)c(OC2CN(C(c3ccccc3)c3ccccc3)C2)cc1F] | 0.49 | 6.1 | 30 |

TABLE 1-continued

| Example | Structure | LBA (μM) | Nav1.7 (μM) | Nav1.5 (μM) |
| --- | --- | --- | --- | --- |
| 142a | 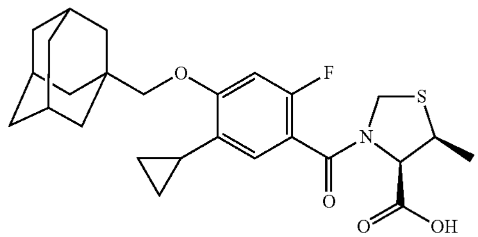 [SMILES: C[C@@H]1SCN(C(=O)c2cc(C3CC3)c(OCC34CC5CC(CC(C5)C3)C4)cc2F)[C@@H]1C(=O)O] | 0.25 | 1.5 | 17 |
| 142b | 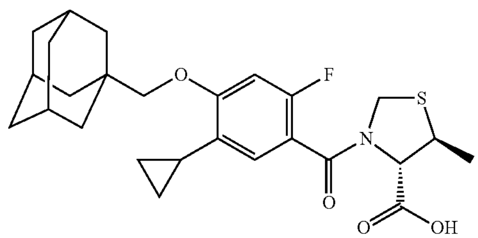 [SMILES: C[C@@H]1SCN(C(=O)c2cc(C3CC3)c(OCC34CC5CC(CC(C5)C3)C4)cc2F)[C@H]1C(=O)O] | 0.76 | 3 | 15 |
| 143 | 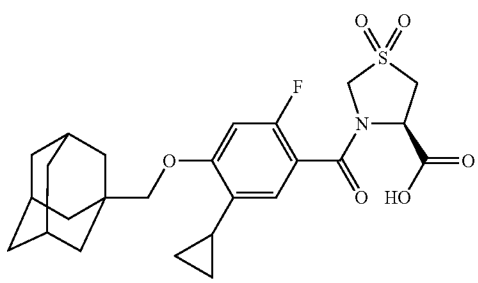 [SMILES: O=C(O)[C@@H]1CS(=O)(=O)CN1C(=O)c1cc(C2CC2)c(OCC23CC4CC(CC(C4)C2)C3)cc1F] | 0.17 | 1.2 | 21 |
| 144 | 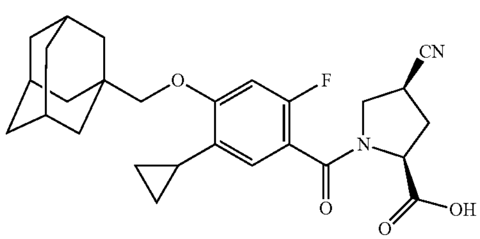 [SMILES: N#C[C@H]1C[C@@H](C(=O)O)N(C(=O)c2cc(C3CC3)c(OCC34CC5CC(CC(C5)C3)C4)cc2F)C1] | 0.87 | 3.5 | 30 |
| 145 | 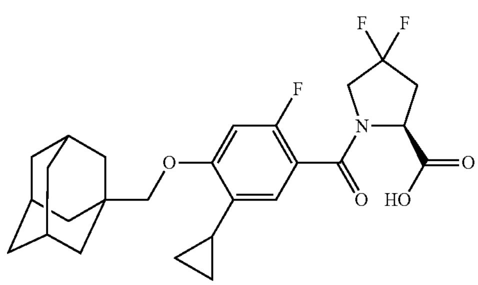 [SMILES: O=C(O)[C@@H]1CC(F)(F)CN1C(=O)c1cc(C2CC2)c(OCC23CC4CC(CC(C4)C2)C3)cc1F] | 0.035 | 0.64 | 16 |
| 146 | 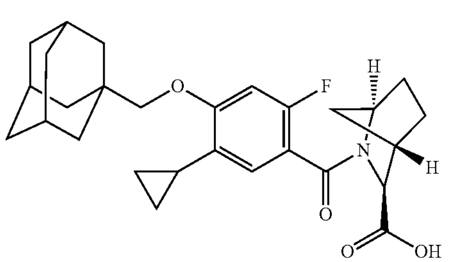 [SMILES: O=C(O)[C@@H]1[C@H]2CC[C@H](C2)N1C(=O)c1cc(C2CC2)c(OCC23CC4CC(CC(C4)C2)C3)cc1F] | 0.18 | 1.5 | 8.4 |

TABLE 1-continued

| Example | Structure | LBA (μM) | Nav1.7 (μM) | Nav1.5 (μM) |
| --- | --- | --- | --- | --- |
| 147 | 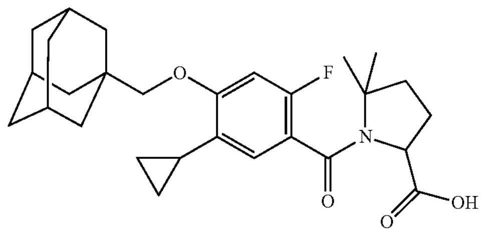 [SMILES: CC1(C)CCC(C(=O)O)N1C(=O)c1cc(C2CC2)c(OCC23CC4CC(CC(C4)C2)C3)cc1F] | 0.26 | 2.1 | 14 |
| 148 | 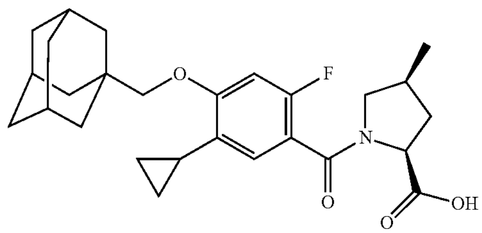 [SMILES: C[C@H]1C[C@@H](C(=O)O)N(C(=O)c2cc(C3CC3)c(OCC34CC5CC(CC(C5)C3)C4)cc2F)C1] | 0.049 | 0.62 | 17 |
| 149 | 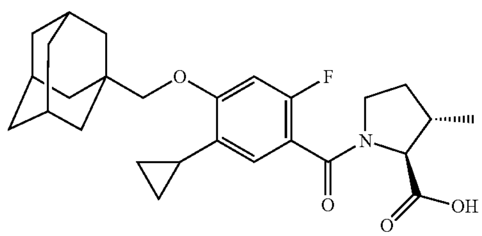 [SMILES: C[C@H]1CCN(C(=O)c2cc(C3CC3)c(OCC34CC5CC(CC(C5)C3)C4)cc2F)[C@@H]1C(=O)O] | 0.01 | 0.3 | 17 |
| 150 | 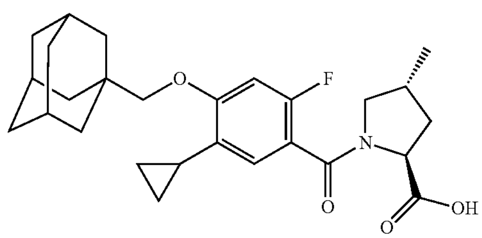 [SMILES: C[C@@H]1C[C@@H](C(=O)O)N(C(=O)c2cc(C3CC3)c(OCC34CC5CC(CC(C5)C3)C4)cc2F)C1] | 0.085 | 1.2 | 19 |
| 151 | 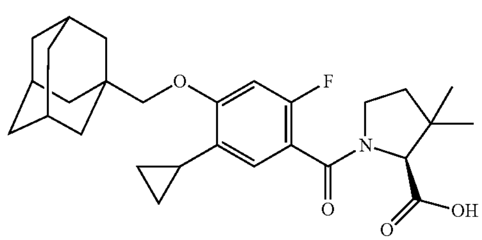 | 0.058 | 0.78 | 5.2 |
| 152 | 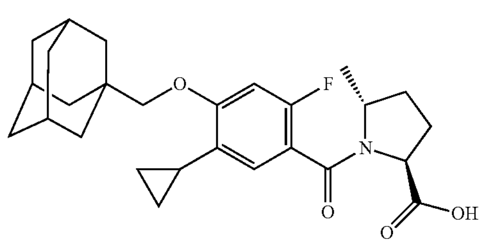 [SMILES: C[C@@H]1CC[C@@H](C(=O)O)N1C(=O)c1cc(C2CC2)c(OCC23CC4CC(CC(C4)C2)C3)cc1F] | 0.093 | 1.3 | 13 |

TABLE 1-continued

| Example | Structure | LBA (μM) | Nav1.7 (μM) | Nav1.5 (μM) |
|---|---|---|---|---|
| 153 | 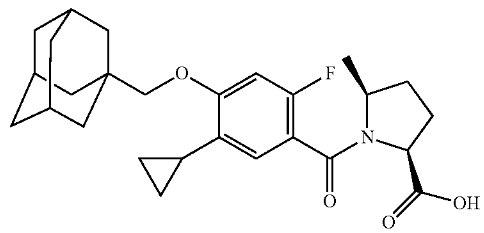 [SMILES: C[C@H]1CC[C@@H](C(=O)O)N1C(=O)c1cc(C2CC2)c(OCC23CC4CC(CC(C4)C2)C3)cc1F] | 0.55 | 1.1 | 19 |
| 154 | 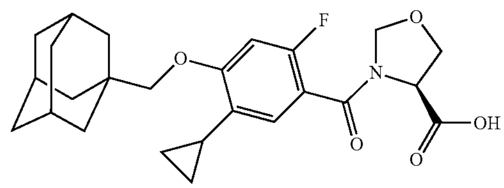 [SMILES: O=C(O)[C@@H]1COCN1C(=O)c1cc(C2CC2)c(OCC23CC4CC(CC(C4)C2)C3)cc1F] | 0.059 | 0.83 | 16 |
| 155 | 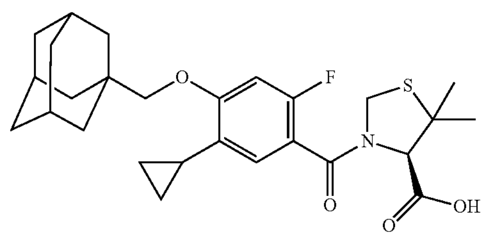 [SMILES: CC1(C)SCN(C(=O)c2cc(C3CC3)c(OCC34CC5CC(CC(C5)C3)C4)cc2F)[C@@H]1C(=O)O] | 0.068 | 0.9 | 9.3 |
| 156 | 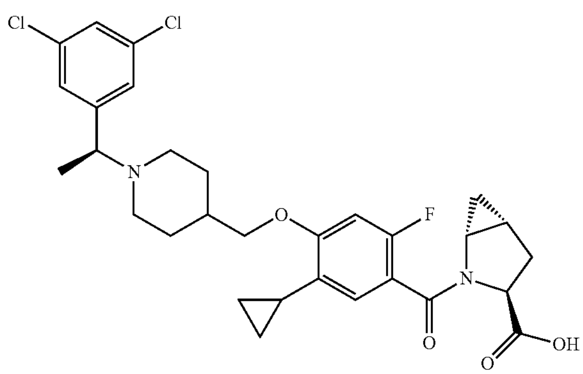 [SMILES: C[C@@H](c1cc(Cl)cc(Cl)c1)N1CCC(COc2cc(F)c(C(=O)N3[C@@H]4C[C@@H]4C[C@H]3C(=O)O)cc2C2CC2)CC1] | 0.83 | 3.1 | 17 |
| 157 | 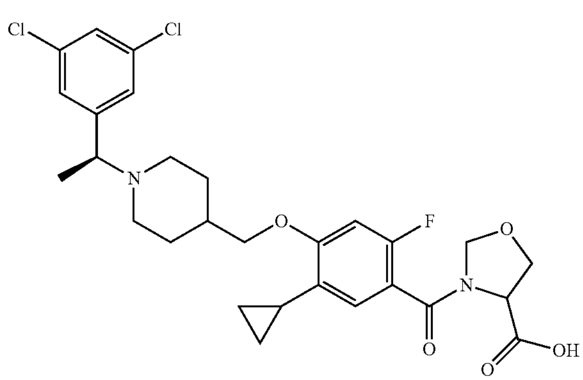 [SMILES: C[C@@H](c1cc(Cl)cc(Cl)c1)N1CCC(COc2cc(F)c(C(=O)N3COCC3C(=O)O)cc2C2CC2)CC1] | 0.48 | 2.2 | 30 |

TABLE 1-continued

| Example | Structure | LBA (µM) | Nav1.7 (µM) | Nav1.5 (µM) |
|---|---|---|---|---|
| 158 | 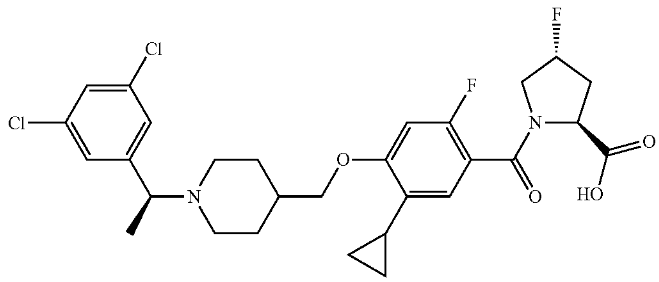 [SMILES: C[C@@H](c1cc(Cl)cc(Cl)c1)N1CCC(COc2cc(F)c(C(=O)N3C[C@H](F)C[C@H]3C(=O)O)cc2C2CC2)CC1] | 0.56 | 1.4 | 30 |
| 159 | 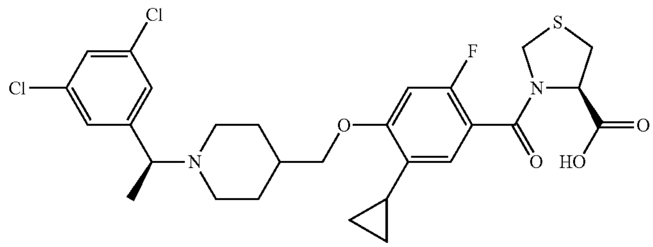 [SMILES: C[C@@H](c1cc(Cl)cc(Cl)c1)N1CCC(COc2cc(F)c(C(=O)N3CSC[C@H]3C(=O)O)cc2C2CC2)CC1] | 0.08 | 1 | 17 |
| 160 | 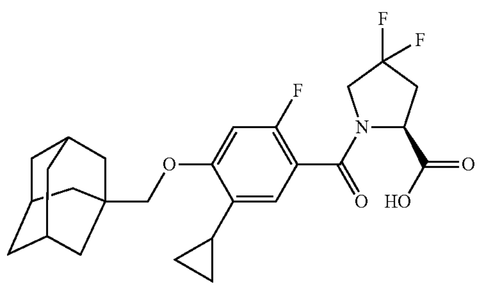 [SMILES: O=C(O)[C@@H]1CC(F)(F)CN1C(=O)c1cc(C2CC2)c(OCC23CC4CC(CC(C4)C2)C3)cc1F] | 0.035 | 0.64 | 16 |
| 161 | 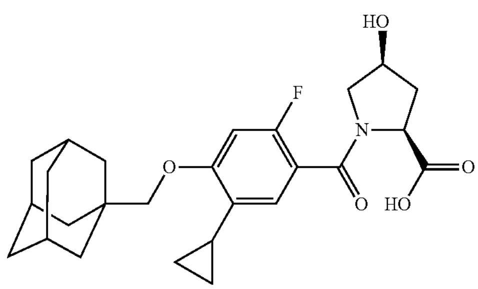 [SMILES: O=C(O)[C@@H]1C[C@H](O)CN1C(=O)c1cc(C2CC2)c(OCC23CC4CC(CC(C4)C2)C3)cc1F] | 0.39 | 0.98 | 30 |
| 162 | 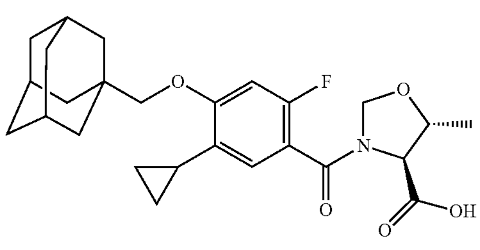 [SMILES: C[C@H]1OCN(C(=O)c2cc(C3CC3)c(OCC34CC5CC(CC(C5)C3)C4)cc2F)[C@@H]1C(=O)O] | 0.0073 | 0.094 | 5.7 |
| 163 | 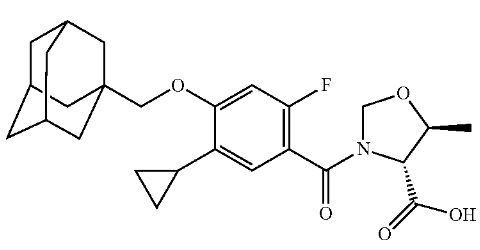 [SMILES: C[C@@H]1OCN(C(=O)c2cc(C3CC3)c(OCC34CC5CC(CC(C5)C3)C4)cc2F)[C@H]1C(=O)O] | 0.12 | 0.82 | 4.7 |

TABLE 1-continued

| Example | Structure | LBA (μM) | Nav1.7 (μM) | Nav1.5 (μM) |
| --- | --- | --- | --- | --- |
| 164 | 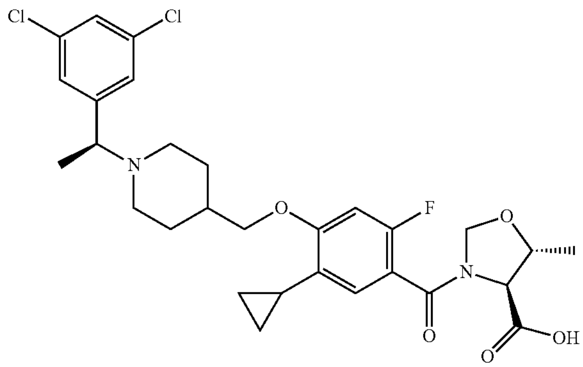 [SMILES: C[C@H]1OCN(C(=O)c2cc(C3CC3)c(OCC3CCN([C@@H](C)c4cc(Cl)cc(Cl)c4)CC3)cc2F)[C@@H]1C(=O)O] | 0.025 | 0.062 | 13 |
| 165 | 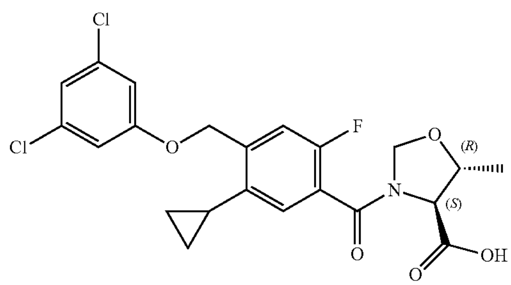 | 0.0092 | 0.02 | 30 |
| 166 | 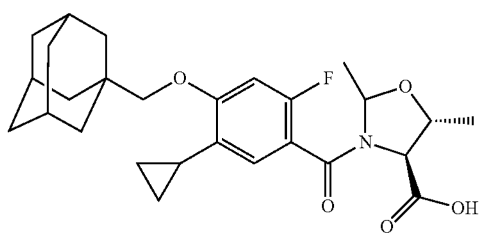 [SMILES: CC1O[C@H](C)[C@@H](C(=O)O)N1C(=O)c1cc(C2CC2)c(OCC23CC4CC(CC(C4)C2)C3)cc1F] | 0.09 | 0.75 | 13 |
| 167 | 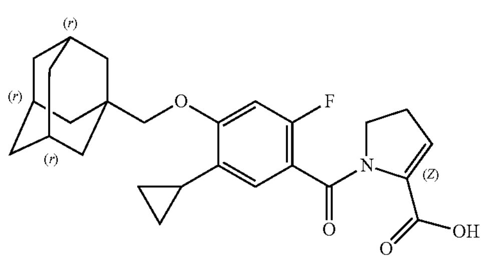 [SMILES: O=C(O)C1=CCCN1C(=O)c1cc(C2CC2)c(OCC23CC4CC(CC(C4)C2)C3)cc1F] | 0.19 | 0.66 | 28 |
| 168a | 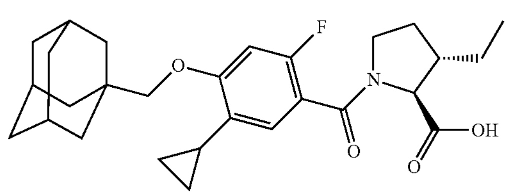 [SMILES: CC[C@H]1CCN(C(=O)c2cc(C3CC3)c(OCC34CC5CC(CC(C5)C3)C4)cc2F)[C@@H]1C(=O)O] | 0.61 | 3.3 | 6.8 |
| 168b | 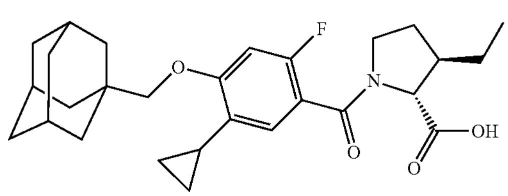 [SMILES: CC[C@@H]1CCN(C(=O)c2cc(C3CC3)c(OCC34CC5CC(CC(C5)C3)C4)cc2F)[C@H]1C(=O)O] | 0.18 | 1.3 | 8.2 |

TABLE 1-continued

| Example | Structure | LBA (μM) | Nav1.7 (μM) | Nav1.5 (μM) |
|---|---|---|---|---|
| 169 | 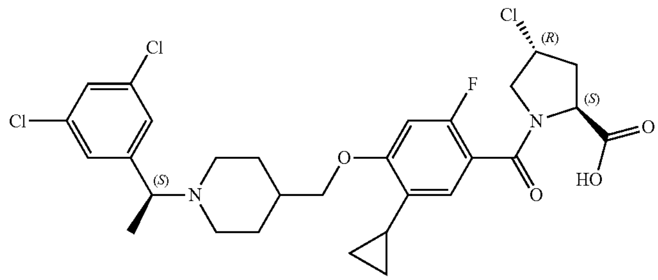 | 0.091 | 0.78 | 13 |
| 170 | 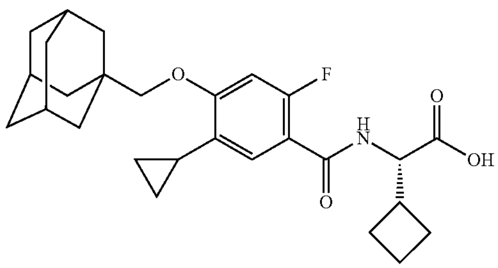 [SMILES: O=C(N[C@H](C(=O)O)C1CCC1)c1cc(C2CC2)c(OCC23CC4CC(CC(C4)C2)C3)cc1F] | 0.26 | 3.8 | 3.7 |
| 171 | 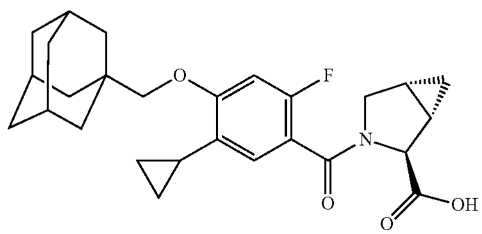 [SMILES: O=C(O)[C@@H]1[C@H]2C[C@H]2CN1C(=O)c1cc(C2CC2)c(OCC23CC4CC(CC(C4)C2)C3)cc1F] | 0.025 | 0.24 | 9 |
| 172 | 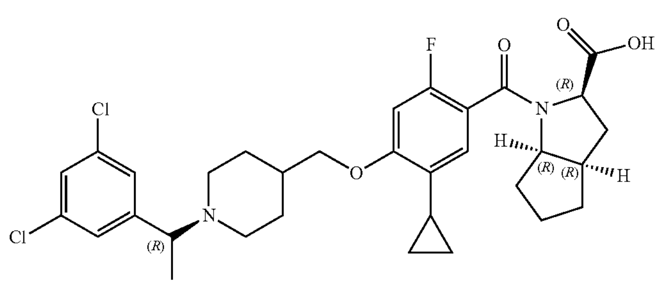 | 1 | 4.2 | 14 |
| 173 | 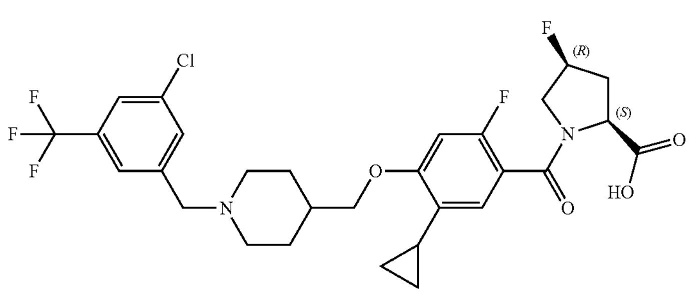 | 0.065 | 0.33 | 23 |

TABLE 1-continued

| Example | Structure | LBA (μM) | Nav1.7 (μM) | Nav1.5 (μM) |
|---------|-----------|----------|-------------|-------------|
| 174 | 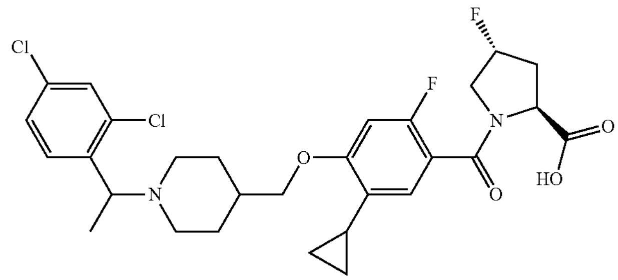 [SMILES: CC(c1ccc(Cl)cc1Cl)N1CCC(COc2cc(F)c(C(=O)N3C[C@H](F)C[C@H]3C(=O)O)cc2C2CC2)CC1] | 0.026 | 0.34 | 30 |
| 175 | 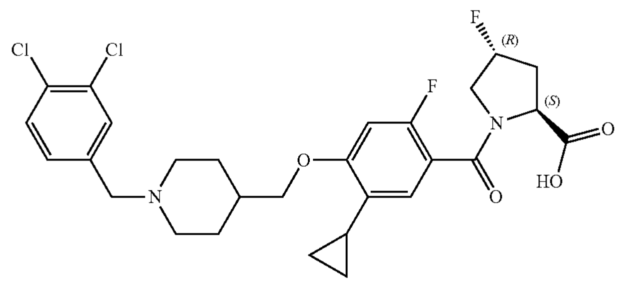 | 0.11 | 1.2 | 30 |
| 176 | 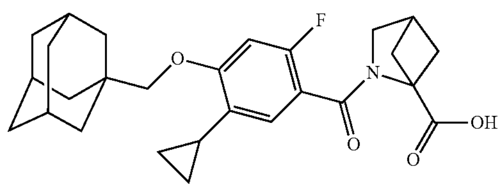 [SMILES: O=C(c1cc(C2CC2)c(OCC23CC4CC(CC(C4)C2)C3)cc1F)N1CC2CC1(C(=O)O)C2] | 0.36 | 1.3 | 7.2 |
| 177 | 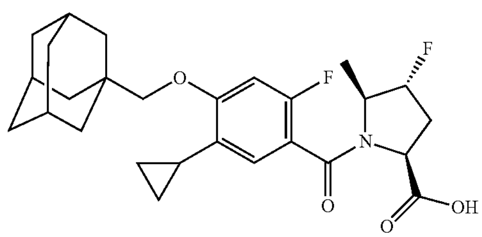 [SMILES: C[C@H]1[C@H](F)C[C@@H](C(=O)O)N1C(=O)c1cc(C2CC2)c(OCC23CC4CC(CC(C4)C2)C3)cc1F] | | | |
| 178 | 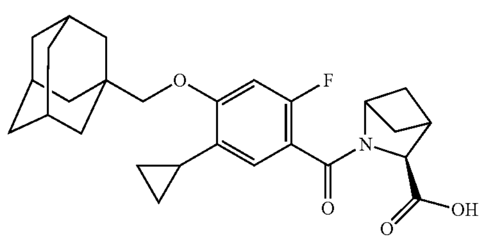 [SMILES: O=C(O)[C@@H]1C2CC(C2)N1C(=O)c1cc(C2CC2)c(OCC23CC4CC(CC(C4)C2)C3)cc1F] | 0.19 | 1.6 | 11 |
| 179 | 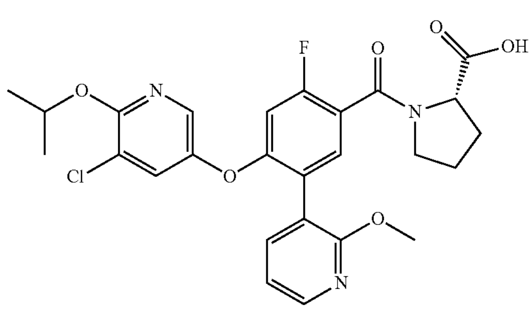 [SMILES: COc1ncccc1-c1cc(C(=O)N2CCC[C@H]2C(=O)O)c(F)cc1Oc1cnc(OC(C)C)c(Cl)c1] | 0.4 | 0.83 | 30 |

TABLE 1-continued

| Example | Structure | LBA (μM) | Nav1.7 (μM) | Nav1.5 (μM) |
|---|---|---|---|---|
| 180 | 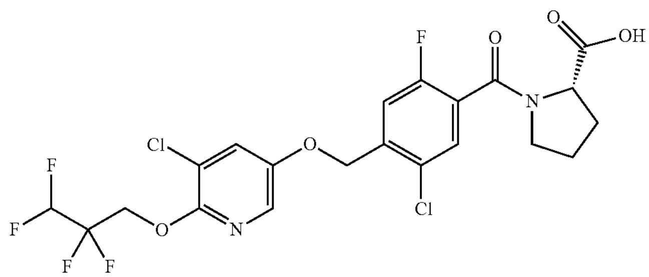 [SMILES: O=C(O)[C@@H]1CCCN1C(=O)c1cc(Cl)c(COc2cnc(OCC(F)(F)C(F)F)c(Cl)c2)cc1F] | 0.83 | 1.4 | 30 |
| 181 | 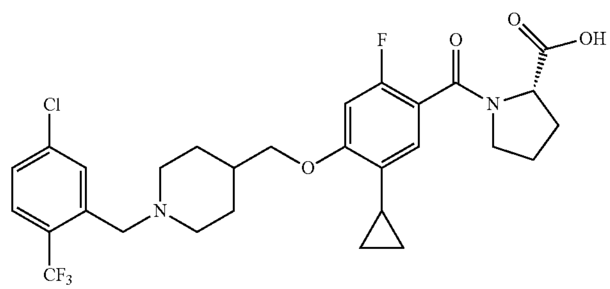 [SMILES: O=C(O)[C@@H]1CCCN1C(=O)c1cc(C2CC2)c(OCC2CCN(Cc3cc(Cl)ccc3C(F)(F)F)CC2)cc1F] | 0.05 | 0.23 | 30 |
| 182 | 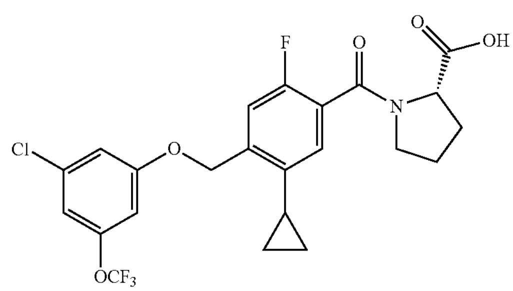 [SMILES: O=C(O)[C@@H]1CCCN1C(=O)c1cc(C2CC2)c(COc2cc(Cl)cc(OC(F)(F)F)c2)cc1F] | 0.032 | 0.22 | 25 |
| 183 | 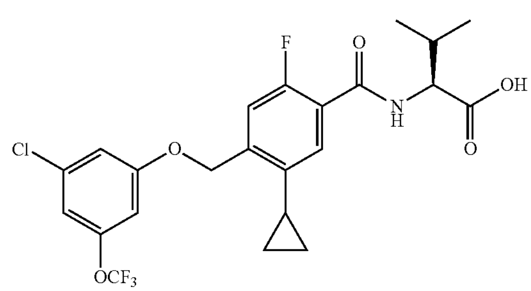 [SMILES: CC(C)[C@H](NC(=O)c1cc(C2CC2)c(COc2cc(Cl)cc(OC(F)(F)F)c2)cc1F)C(=O)O] | 0.031 | 1.9 | 9.2 |
| 184 | 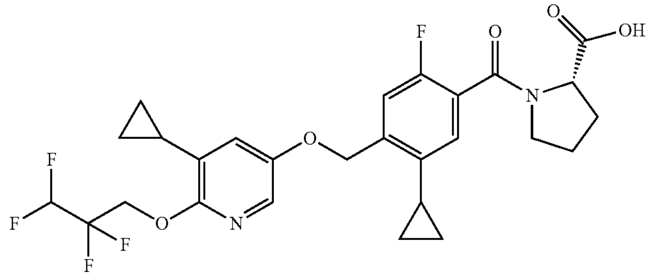 [SMILES: O=C(O)[C@@H]1CCCN1C(=O)c1cc(C2CC2)c(COc2cnc(OCC(F)(F)C(F)F)c(C3CC3)c2)cc1F] | 0.46 | 1.3 | 23 |

TABLE 1-continued

| Example | Structure | LBA (µM) | Nav1.7 (µM) | Nav1.5 (µM) |
|---|---|---|---|---|
| 185 | 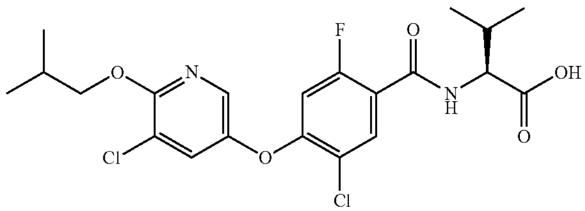 [SMILES: CC(C)COc1ncc(Oc2cc(F)c(C(=O)N[C@H](C(=O)O)C(C)C)cc2Cl)cc1Cl] | 0.1 | 9.6 | 17 |
| 186 | 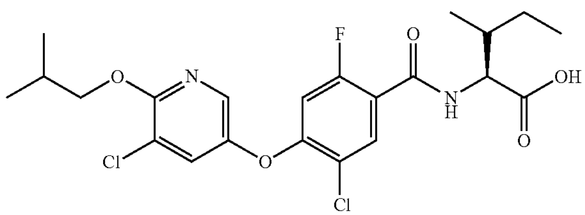 [SMILES: CCC(C)[C@H](NC(=O)c1cc(Cl)c(Oc2cnc(OCC(C)C)c(Cl)c2)cc1F)C(=O)O] | 0.35 | 8.3 | 12 |
| 187 | 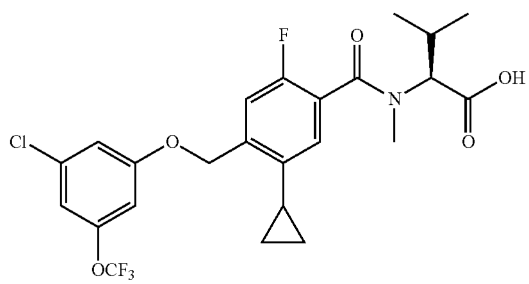 [SMILES: CC(C)[C@@H](C(=O)O)N(C)C(=O)c1cc(C2CC2)c(COc2cc(Cl)cc(OC(F)(F)F)c2)cc1F] | 3.3 | 7.3 | 11 |
| 188 | 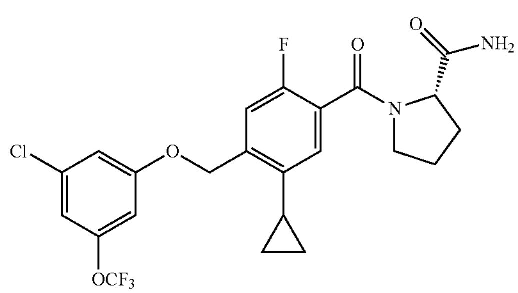 [SMILES: NC(=O)[C@@H]1CCCN1C(=O)c1cc(C2CC2)c(COc2cc(Cl)cc(OC(F)(F)F)c2)cc1F] | 9.1 | 6.6 | 16 |
| 189 | 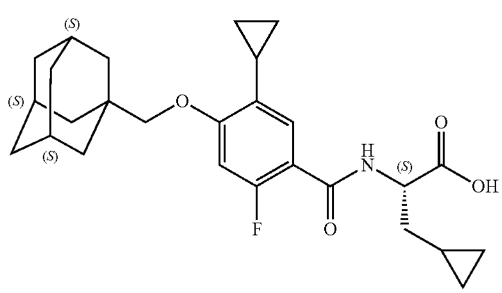 | 0.12 | 4 | 15 |
| 190 | 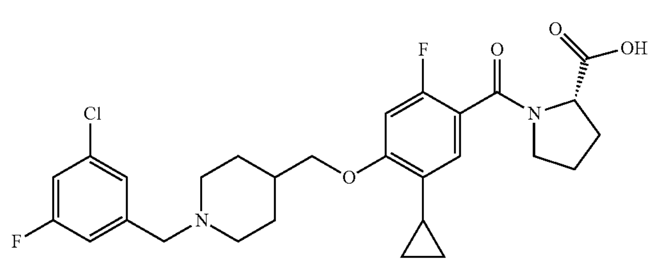 [SMILES: O=C(O)[C@@H]1CCCN1C(=O)c1cc(C2CC2)c(OCC2CCN(Cc3cc(F)cc(Cl)c3)CC2)cc1F] | 0.19 | 2.9 | 30 |

TABLE 1-continued
| Example | Structure | LBA (μM) | Nav1.7 (μM) | Nav1.5 (μM) |
|---|---|---|---|---|
| 191 | 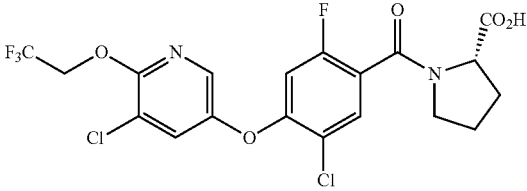 [SMILES: O=C(O)[C@@H]1CCCN1C(=O)c1cc(Cl)c(Oc2cnc(OCC(F)(F)F)c(Cl)c2)cc1F] | 2.7 | 19 | 30 |
| 192 | 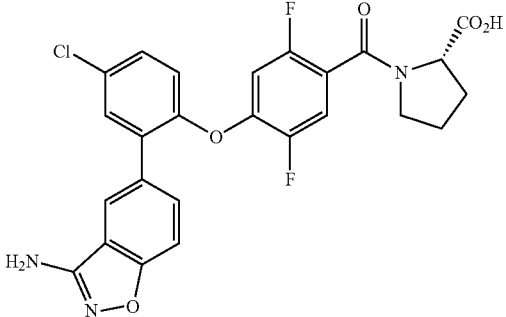 [SMILES: Nc1noc2ccc(-c3cc(Cl)ccc3Oc3cc(F)c(C(=O)N4CCC[C@H]4C(=O)O)cc3F)cc12] | 10 | 30 | 30 |
| 193 | 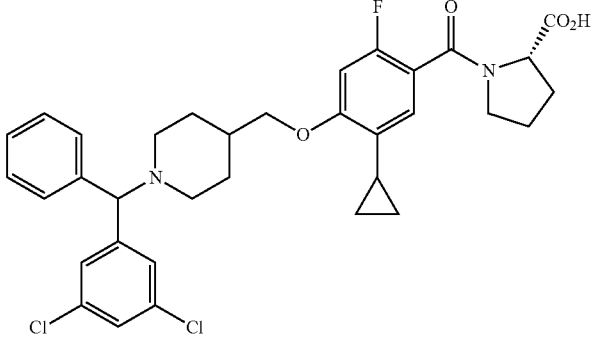 [SMILES: O=C(O)[C@@H]1CCCN1C(=O)c1cc(C2CC2)c(OCC2CCN(C(c3ccccc3)c3cc(Cl)cc(Cl)c3)CC2)cc1F] | 0.02 | 0.99 | 7.6 |
| 194 | 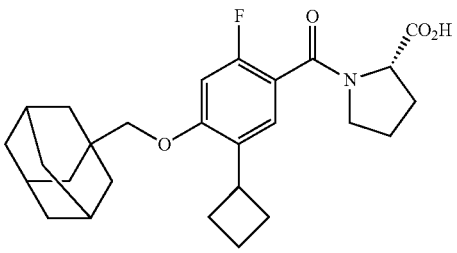 [SMILES: O=C(O)[C@@H]1CCCN1C(=O)c1cc(C2CCC2)c(OCC23CC4CC(CC(C4)C2)C3)cc1F] | 0.022 | 0.64 | 10 |
| 195 | 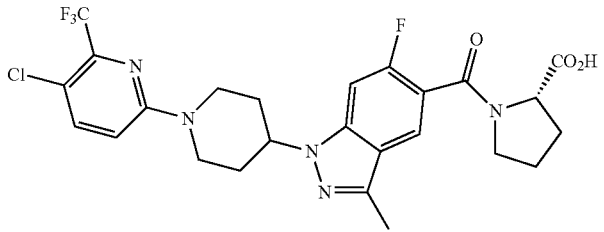 [SMILES: Cc1nn(C2CCN(c3ccc(Cl)c(C(F)(F)F)n3)CC2)c2cc(F)c(C(=O)N3CCC[C@H]3C(=O)O)cc12] | 1.9 | 5.9 | 30 |

TABLE 1-continued

| Example | Structure | LBA (μM) | Nav1.7 (μM) | Nav1.5 (μM) |
|---|---|---|---|---|
| 196 | 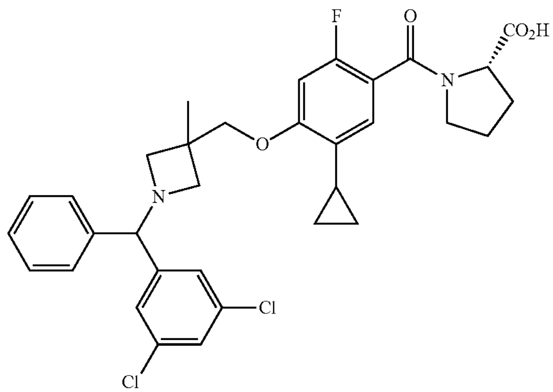 [SMILES: CC1(COc2cc(F)c(C(=O)N3CCC[C@H]3C(=O)O)cc2C2CC2)CN(C(c2ccccc2)c2cc(Cl)cc(Cl)c2)C1] | 0.018 | 1.4 | 13 |
| 197 | 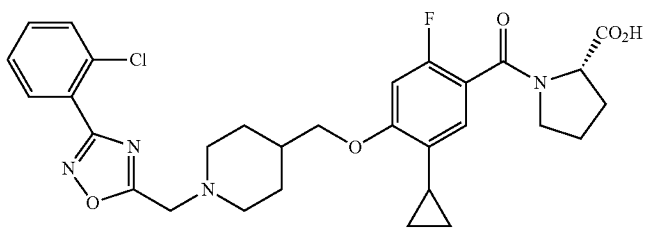 [SMILES: O=C(O)[C@@H]1CCCN1C(=O)c1cc(C2CC2)c(OCC2CCN(Cc3nc(-c4ccccc4Cl)no3)CC2)cc1F] | 0.63 | 3.9 | 30 |
| 198 | 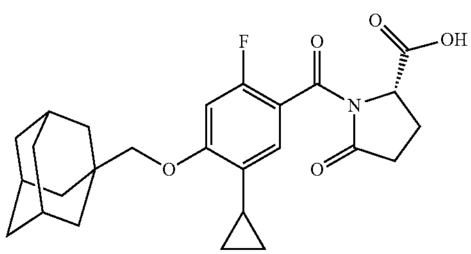 [SMILES: O=C(O)[C@@H]1CCC(=O)N1C(=O)c1cc(C2CC2)c(OCC23CC4CC(CC(C4)C2)C3)cc1F] | 1.1 | 4.5 | 18 |
| 199 | 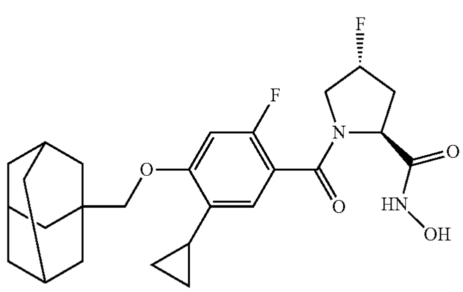 [SMILES: O=C(NO)[C@@H]1C[C@@H](F)CN1C(=O)c1cc(C2CC2)c(OCC23CC4CC(CC(C4)C2)C3)cc1F] | 0.47 | 3.6 | 15 |
| 200 | 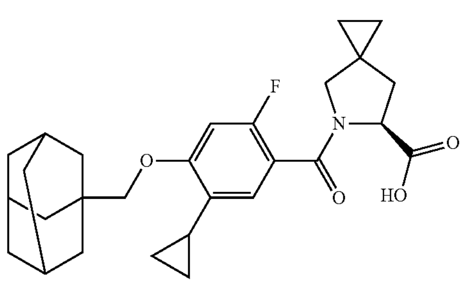 [SMILES: O=C(O)[C@@H]1CC2(CC2)CN1C(=O)c1cc(C2CC2)c(OCC23CC4CC(CC(C4)C2)C3)cc1F] | 0.084 | 0.79 | 12 |

TABLE 1-continued

| Example | Structure | LBA (μM) | Nav1.7 (μM) | Nav1.5 (μM) |
|---------|-----------|----------|-------------|-------------|
| 201 | 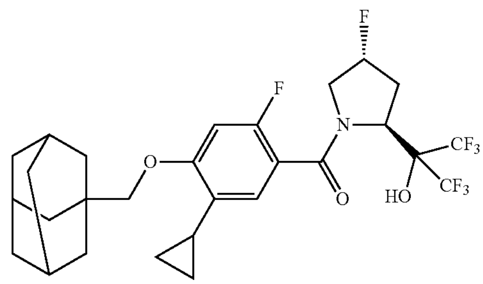 [SMILES: O=C(c1cc(C2CC2)c(OCC23CC4CC(CC(C4)C2)C3)cc1F)N1C[C@H](F)C[C@H]1C(O)(C(F)(F)F)C(F)(F)F] | 10 | 13 | 24 |
| 202 | 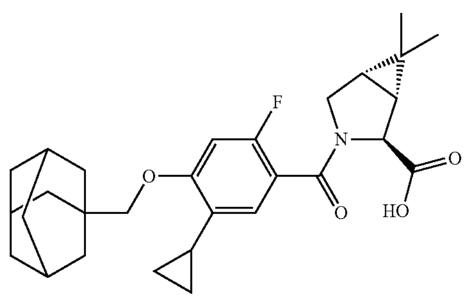 [SMILES: CC1(C)[C@@H]2[C@@H](C(=O)O)N(C(=O)c3cc(C4CC4)c(OCC45CC6CC(CC(C6)C4)C5)cc3F)C[C@@H]21] | 1.9 | 4.4 | 16 |
| 203 | 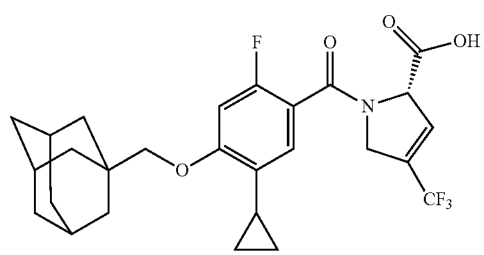 [SMILES: O=C(O)[C@@H]1C=C(C(F)(F)F)CN1C(=O)c1cc(C2CC2)c(OCC23CC4CC(CC(C4)C2)C3)cc1F] | 10 | 10 | 19 |
| 204 | 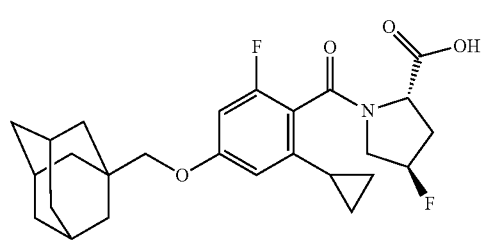 [SMILES: O=C(O)[C@@H]1C[C@@H](F)CN1C(=O)c1c(F)cc(OCC23CC4CC(CC(C4)C2)C3)cc1C1CC1] | 0.56 | 7.8 | 23 |
| 205 | 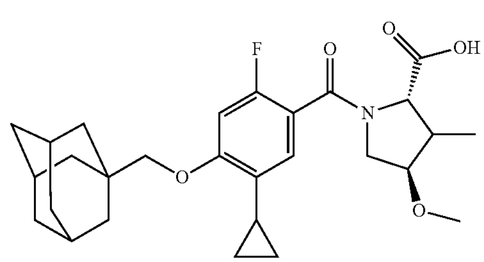 [SMILES: CO[C@H]1CN(C(=O)c2cc(C3CC3)c(OCC34CC5CC(CC(C5)C3)C4)cc2F)[C@H](C(=O)O)C1C] | 0.17 | 2.2 | 25 |

TABLE 1-continued

| Example | Structure | LBA (μM) | Nav1.7 (μM) | Nav1.5 (μM) |
|---------|-----------|----------|-------------|-------------|
| 206 | 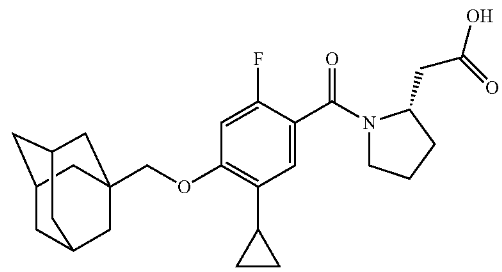 [SMILES: O=C(O)C[C@@H]1CCCN1C(=O)c1cc(C2CC2)c(OCC23CC4CC(CC(C4)C2)C3)cc1F] | 0.26 | 2.6 | 16 |
| 207 | 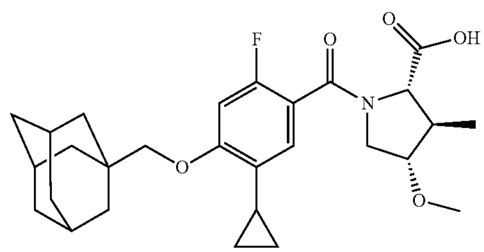 [SMILES: CO[C@@H]1CN(C(=O)c2cc(C3CC3)c(OCC34CC5CC(CC(C5)C3)C4)cc2F)[C@H](C(=O)O)[C@H]1C] | 0.036 | 0.38 | 16 |
| 208 | 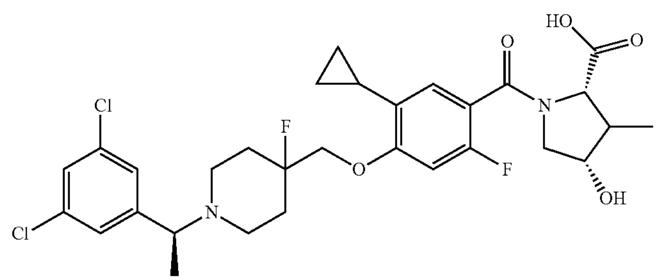 [SMILES: CC1[C@H](O)CN(C(=O)c2cc(C3CC3)c(OCC3(F)CCN([C@@H](C)c4cc(Cl)cc(Cl)c4)CC3)cc2F)[C@@H]1C(=O)O] | 0.082 | 0.21 | 16 |
| 209 | 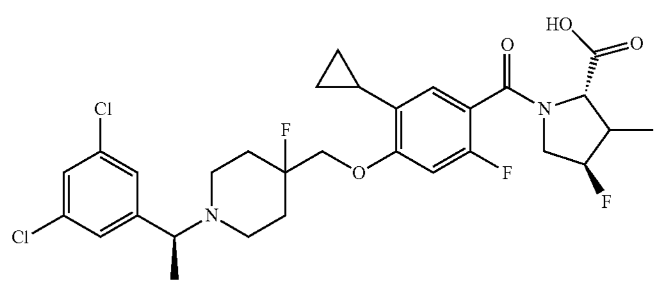 [SMILES: CC1[C@@H](C(=O)O)N(C(=O)c2cc(C3CC3)c(OCC3(F)CCN([C@@H](C)c4cc(Cl)cc(Cl)c4)CC3)cc2F)C[C@@H]1F] | 0.2 | 0.7 | 20 |
| 210a | 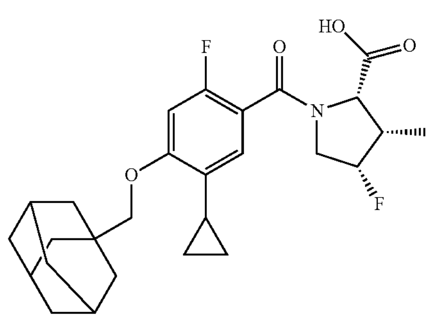 [SMILES: C[C@@H]1[C@H](F)CN(C(=O)c2cc(C3CC3)c(OCC34CC5CC(CC(C5)C3)C4)cc2F)[C@@H]1C(=O)O] | 0.22 | 1.9 | 27 |

TABLE 1-continued

| Example | Structure | LBA (μM) | Nav1.7 (μM) | Nav1.5 (μM) |
|---|---|---|---|---|
| 210b | 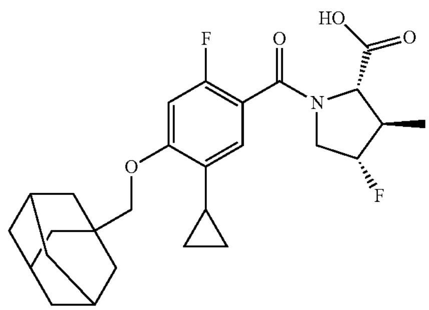 [SMILES: C[C@H]1[C@H](F)CN(C(=O)c2cc(C3CC3)c(OCC34CC5CC(CC(C5)C3)C4)cc2F)[C@@H]1C(=O)O] | 0.03 | 0.81 | 17 |
| 211 | 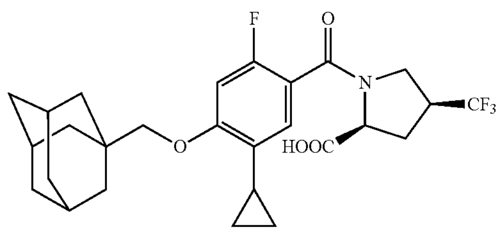 [SMILES: O=C(O)[C@@H]1C[C@H](C(F)(F)F)CN1C(=O)c1cc(C2CC2)c(OCC23CC4CC(CC(C4)C2)C3)cc1F] | 2.3 | 6.7 | 14 |
| 212 | 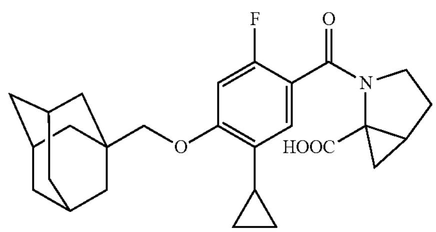 [SMILES: O=C(c1cc(C2CC2)c(OCC23CC4CC(CC(C4)C2)C3)cc1F)N1CCC2CC21C(=O)O] | 0.29 | 3.5 | 17 |
| 213 | 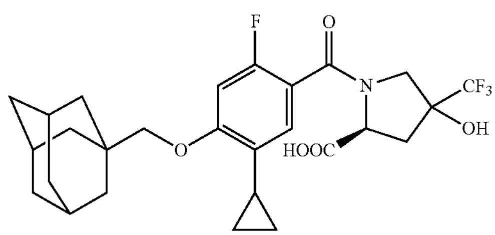 [SMILES: O=C(O)[C@@H]1CC(O)(C(F)(F)F)CN1C(=O)c1cc(C2CC2)c(OCC23CC4CC(CC(C4)C2)C3)cc1F] | 5.3 | 3.4 | 7.6 |
| 214 | 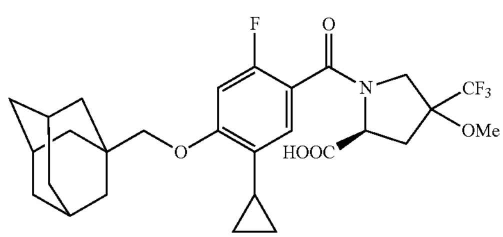 [SMILES: COC1(C(F)(F)F)C[C@@H](C(=O)O)N(C(=O)c2cc(C3CC3)c(OCC34CC5CC(CC(C5)C3)C4)cc2F)C1] | 9.7 | 8.2 | 11 |
| 215 | 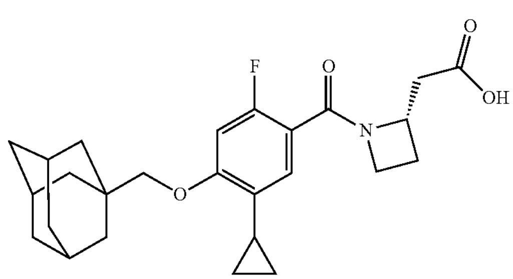 [SMILES: O=C(O)C[C@@H]1CCN1C(=O)c1cc(C2CC2)c(OCC23CC4CC(CC(C4)C2)C3)cc1F] | 1.1 | 5.4 | 30 |

TABLE 1-continued
| Example | Structure | LBA (µM) | Nav1.7 (µM) | Nav1.5 (µM) |
|---------|-----------|----------|-------------|-------------|
| 216 | 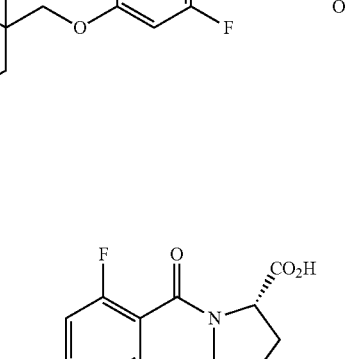 | 0.6 | 8.6 | 30 |
| 217 | 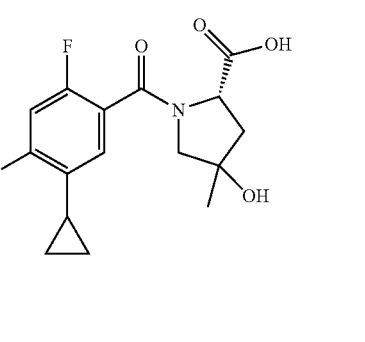 | 2.7 | 19 | 30 |
| 218 | 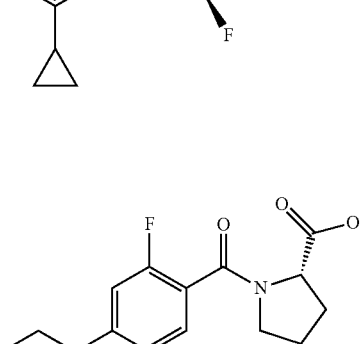 | 0.23 | 1.6 | 24 |
| 219 | 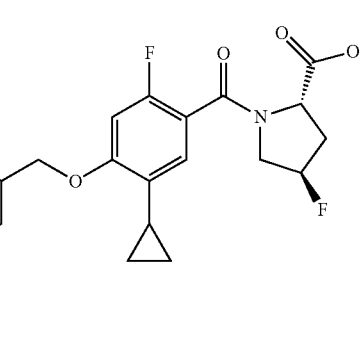 | 0.0064 | 0.26 | 12 |
| 220 | 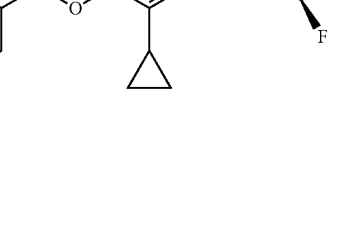 | 0.16 | 0.83 | 30 |

TABLE 1-continued

| Example | Structure | LBA (µM) | Nav1.7 (µM) | Nav1.5 (µM) |
| --- | --- | --- | --- | --- |
| 221 | 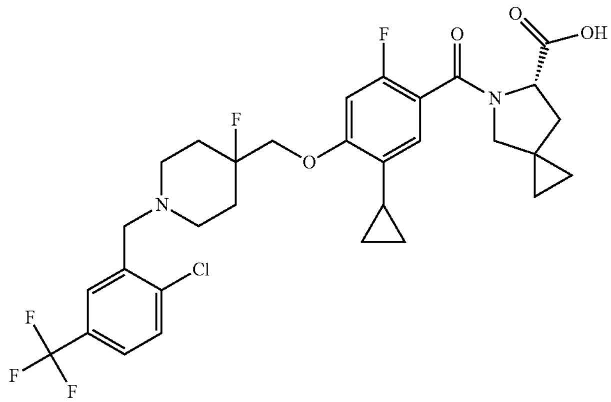 [SMILES: O=C(O)[C@@H]1CC2(CC2)CN1C(=O)c1cc(C2CC2)c(OCC2(F)CCN(Cc3cc(C(F)(F)F)ccc3Cl)CC2)cc1F] | 0.5 | 1.1 | 16 |
| 222 | 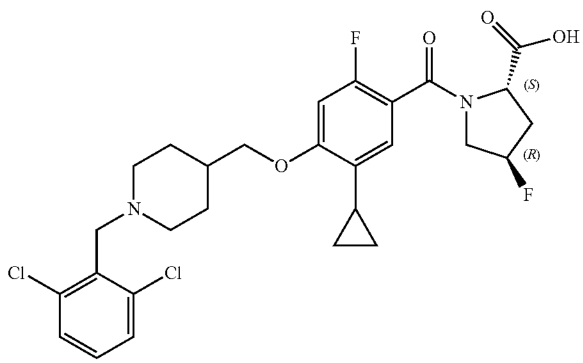 | 0.013 | 0.21 | 30 |
| 223 | 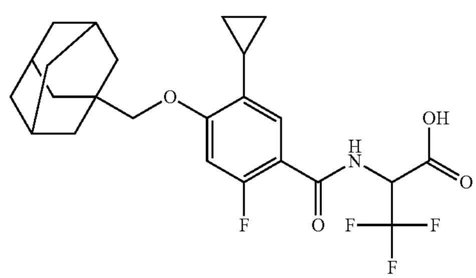 [SMILES: O=C(NC(C(=O)O)C(F)(F)F)c1cc(C2CC2)c(OCC23CC4CC(CC(C4)C2)C3)cc1F] | 0.91 | 2.9 | 3.9 |
| 224 | 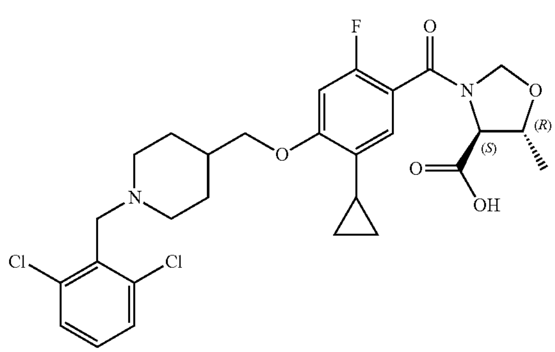 | 0.014 | 0.1 | 22 |

TABLE 1-continued

| Example | Structure | LBA (µM) | Nav1.7 (µM) | Nav1.5 (µM) |
|---|---|---|---|---|
| 225 | 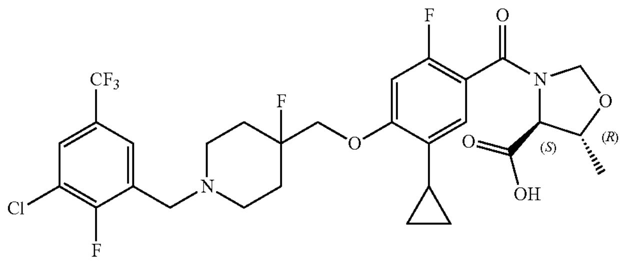 | | | |
| 226 | 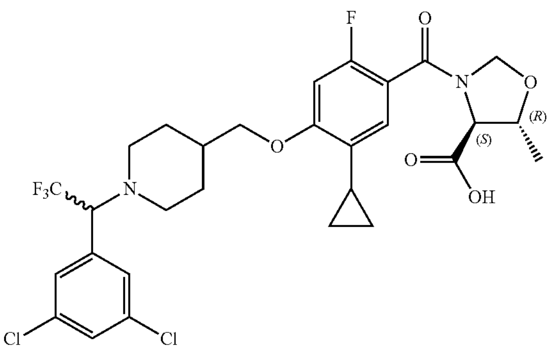 | 0.012 | 0.13 | 6.1 |
| 227 | 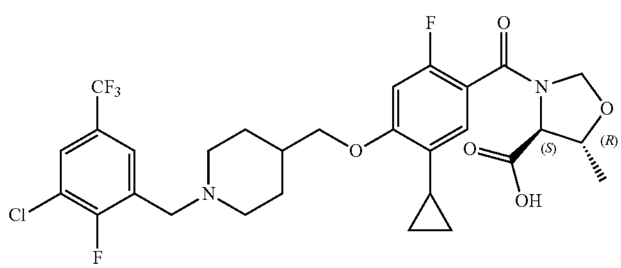 | 0.029 | 0.065 | 16 |
| 228 | 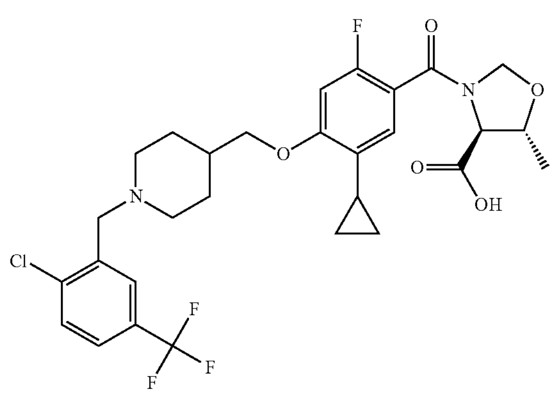 [SMILES: C[C@H]1OCN(C(=O)c2cc(C3CC3)c(OCC3CCN(Cc4cc(C(F)(F)F)ccc4Cl)CC3)cc2F)[C@@H]1C(=O)O] | 0.017 | 0.087 | 25 |

TABLE 1-continued

| Example | Structure | LBA (μM) | Nav1.7 (μM) | Nav1.5 (μM) |
|---|---|---|---|---|
| 229 | 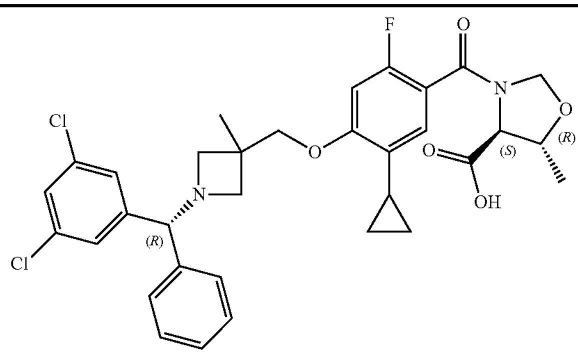 | 0.0069 | 0.27 | 30 |
| 230 | 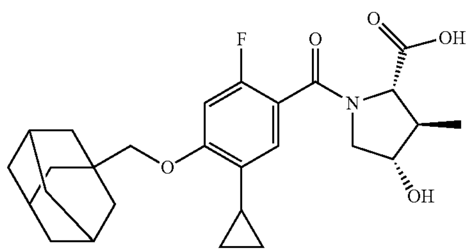 [SMILES: C[C@H]1[C@H](O)CN(C(=O)c2cc(C3CC3)c(OCC34CC5CC(CC(C5)C3)C4)cc2F)[C@@H]1C(=O)O] | 0.021 | 0.032 | 11 |
| 231 | 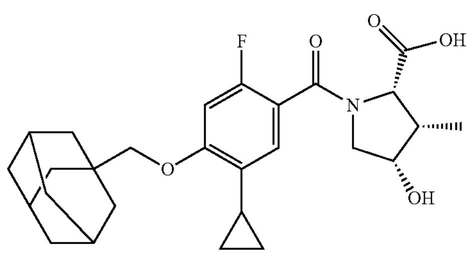 [SMILES: C[C@@H]1[C@H](O)CN(C(=O)c2cc(C3CC3)c(OCC34CC5CC(CC(C5)C3)C4)cc2F)[C@@H]1C(=O)O] | 0.29 | 0.36 | 15 |

Example 234

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \ MPE = \frac{\text{Postdrug latency} - \text{Predrug latency}}{\text{Cut-off time(10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 μL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1, 2, 3) of each animal. A single value for the vehicle group is obtained by averaging all scores within the vehicle treatment group. The following calculation yields the MPIE value for each animal:

MPIE (%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

Pain rating=[0($T_0$)+1($T_1$)+2($T_2$)+3($T_3$)]/($T_0$+$T_1$+$T_2$+$T_3$)

CFA Induced Chronic Inflammatory Pain

In this test, tactile allodynia is assessed with calibrated von Frey filaments. Following a full week of acclimatization to the vivarium facility, 150 μL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic Pain Model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

Ligation of the L5 spinal nerve;
Ligation of the L5 and L6 spinal nerves;
Ligation and transection of the L5 spinal nerve;
Ligation and transection of the L5 and L6 spinal nerves;
or
Mild irritation of the L4 spinal nerve in combination with any one of the above (1)-(4).

While the animals are anaesthetized under 3.5% isoflourane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflourane is readjusted to maintenance levels (1.5%-2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve. The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

A. Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional responses are recorded for a total of six responses. The six responses measured in grams are entered into a formula as described by Chaplan, S. R. et al., J. Neurosci. Methods, 1994 July; 53(1):55-63, and a 50% withdrawal threshold is calculated. This constitutes the mechanical allodynia value.

B. Mechanical Hyperalgesia Method

The response thresholds of animals to tactile stimuli were measured using the Model 2290 Electrovonfrey anesthesiometer (IITC Life Science, Woodland Hills, Calif.). Animals were placed in an elevated Plexiglas enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint. The data were expressed as percent change from baseline threshold measured in grams.

Example 235

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 µL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A compound of Formula (I):

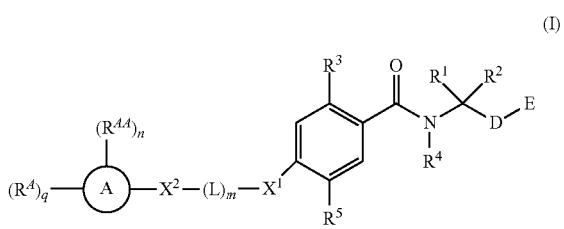

or a pharmaceutically acceptable salt thereof; wherein: the group

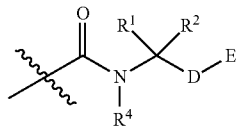

in Formula I is selected from the group consisting of:

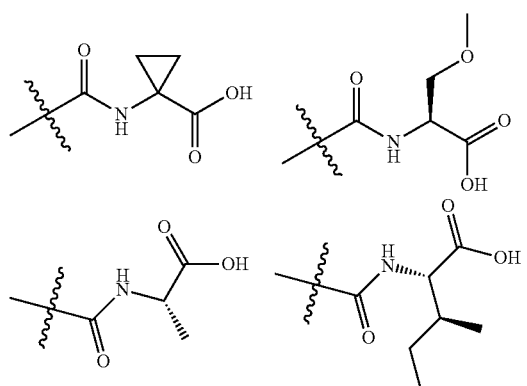

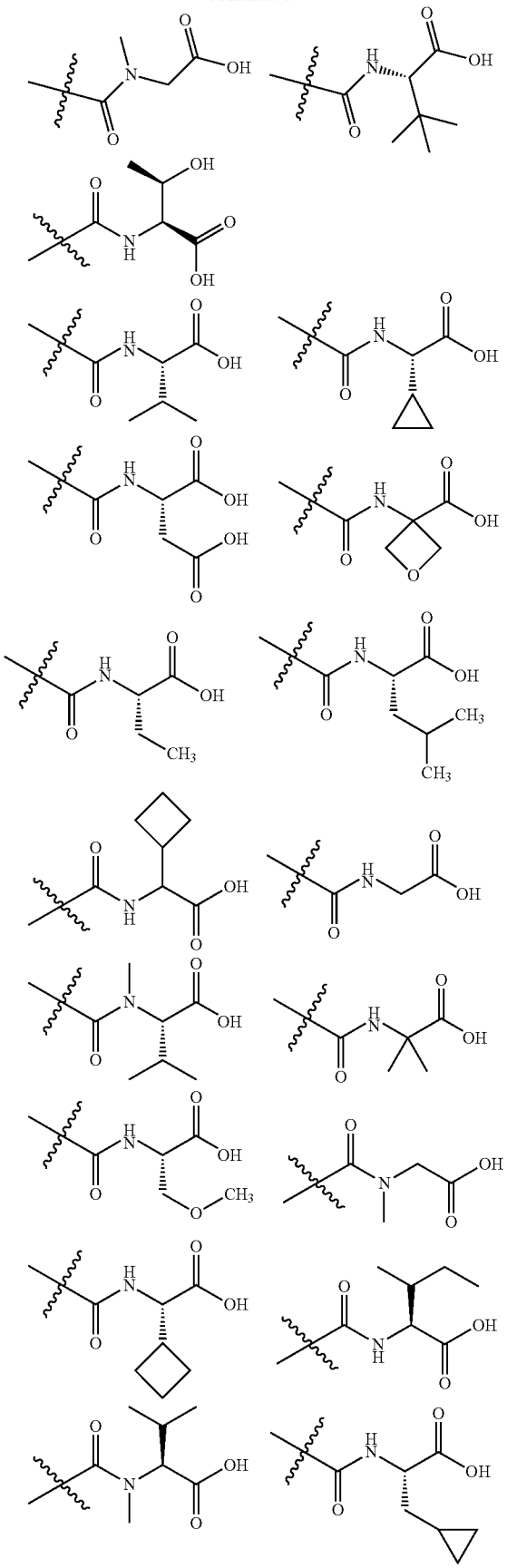

-continued

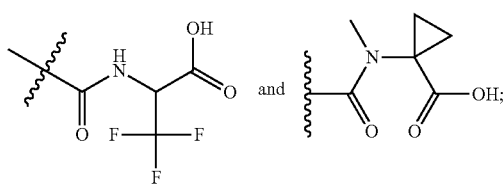

the group

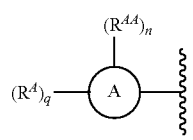

is selected from the group consisting of:

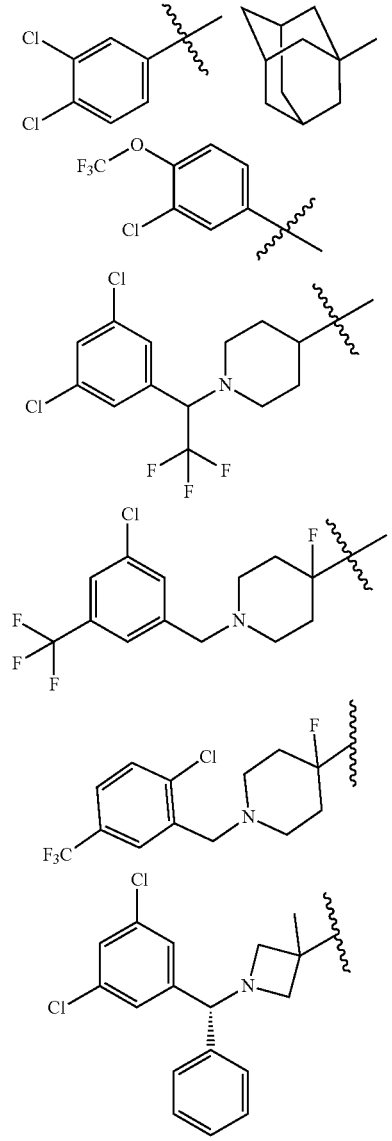

-continued

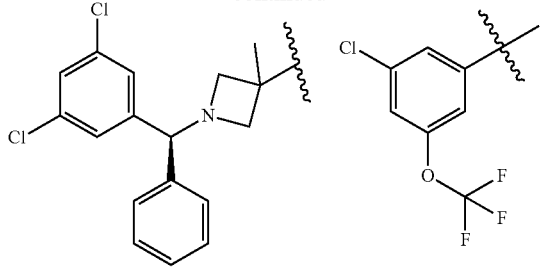

R³ is selected from the group consisting of hydrogen, F, Cl, Br, I, —CN, C$_{1-8}$ alkyl and C$_{1-8}$ haloalkyl;

R⁵ is selected from the group consisting of F, Cl, Br, I, —CN, C$_{1-8}$ alkyl, C$_{1-8}$ haloalkyl, C$_{1-8}$ alkoxy, C$_{3-8}$ cycloalkyl and C$_{2-7}$ heterocyclyl, wherein said C$_{3-8}$ cycloalkyl and C$_{2-7}$ heterocyclyl is optionally substituted with 1-3 substituents selected from F, Cl, Br, I, —OH, —NH$_2$, —NH(C$_{1-4}$ alkyl)-, —N(C$_{1-4}$ dialkyl)-, and C$_{1-4}$ alkyl substituted with 1-3 substituents selected from F, Cl, Br, I, —OH, —NH$_2$, —NH(C$_{1-4}$ alkyl)- and —N(C$_{1-4}$ dialkyl)-;

L is C$_{1-6}$ alkylene, wherein L is optionally substituted with from 1 to 3 substituents selected from the group consisting of C$_{1-4}$ alkyl, C$_{1-4}$ alkoxy, halo, oxo (=O), and C$_{1-4}$ haloalkyl, and wherein any two substituents attached to the same atom on L are optionally combined to form a 3- to 5-membered carbocyclic ring;

the subscript m represents the integer 0 or 1; and

X¹ and X² are each independently selected from the group consisting of absent, —S—, —O— and —N(R$^x$)— wherein R$^x$ is H, C$_{1-8}$ alkyl, or C$_{1-8}$ haloalkyl, wherein if the subscript m is 0 then one of X¹ or X² is absent.

2. A compound selected from the group consisting of:
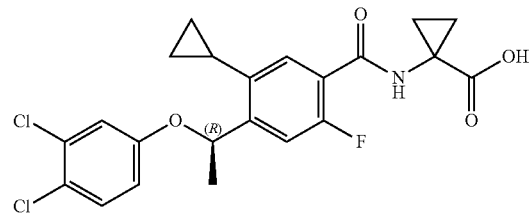
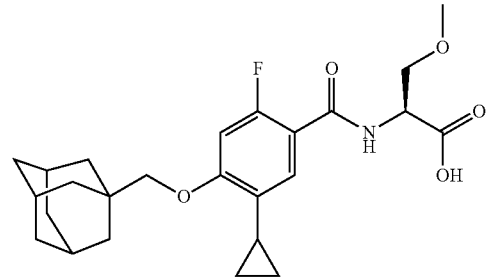
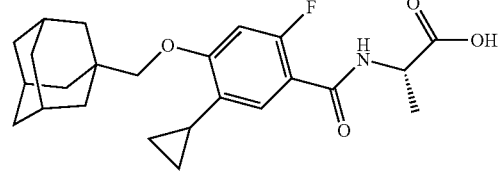
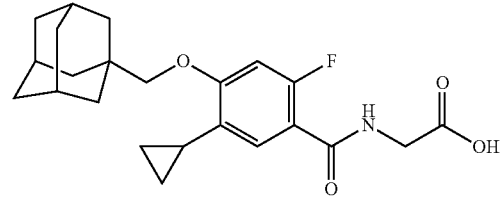
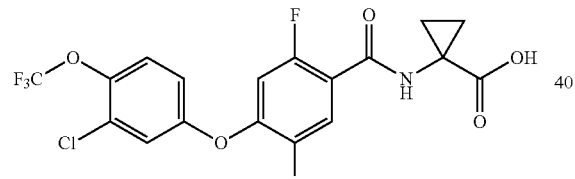
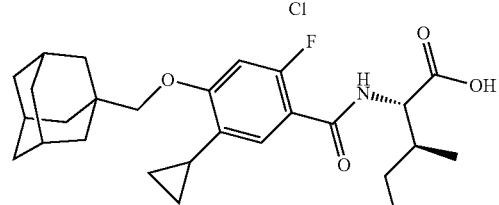
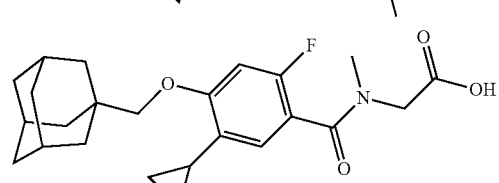
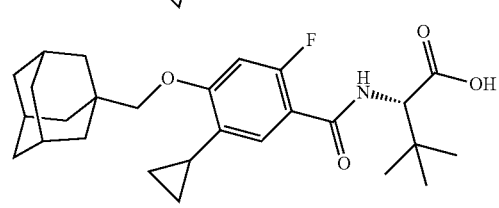
-continued
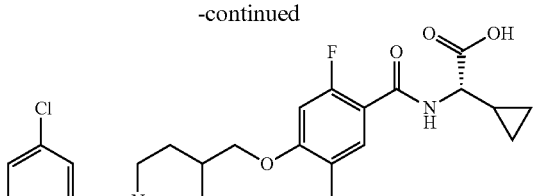
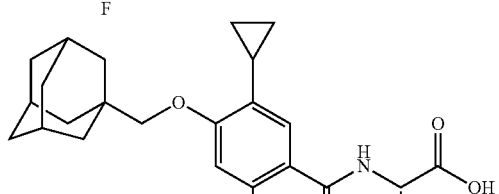
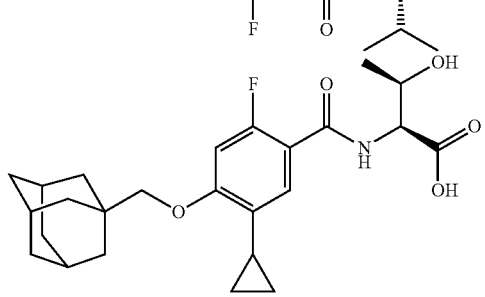
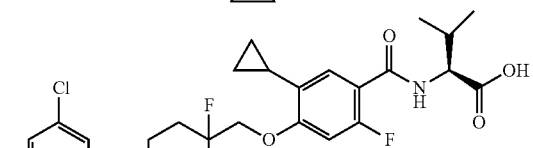
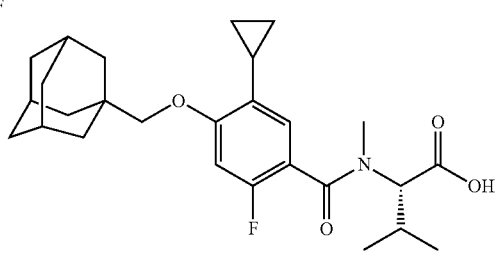
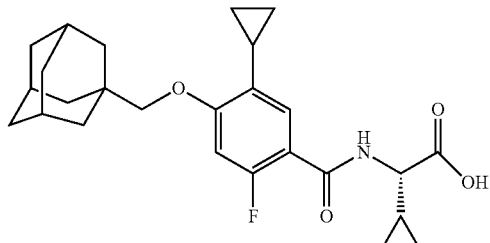
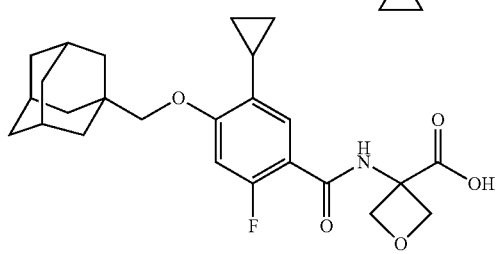

461
-continued
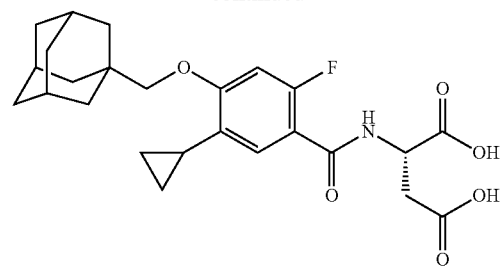
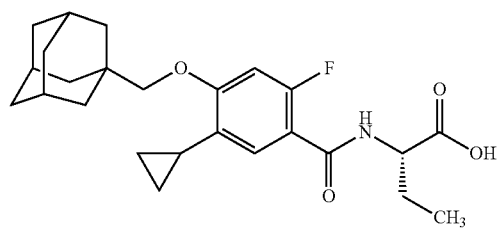
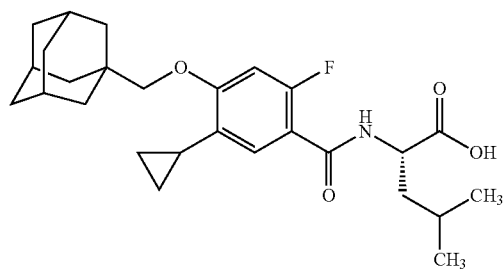
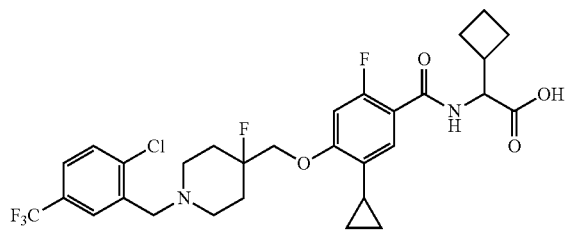
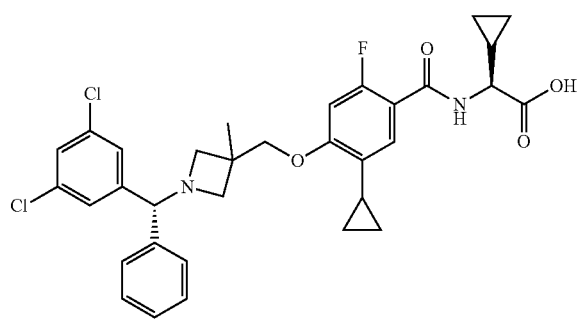
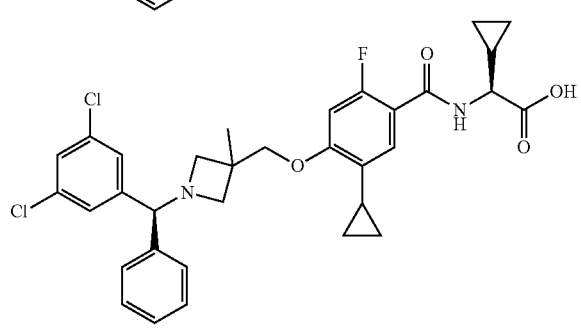
462
-continued
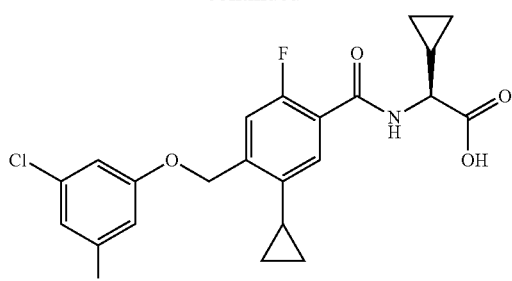
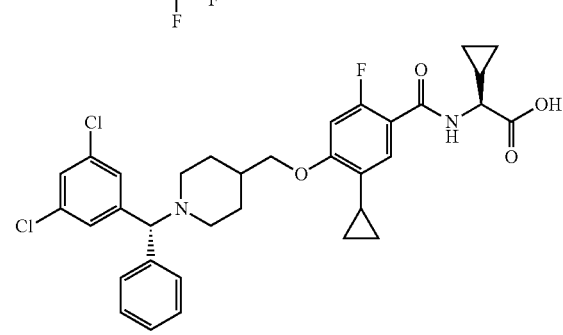
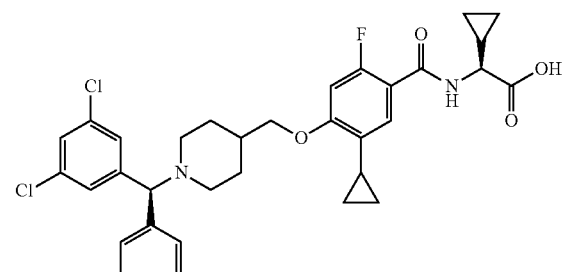
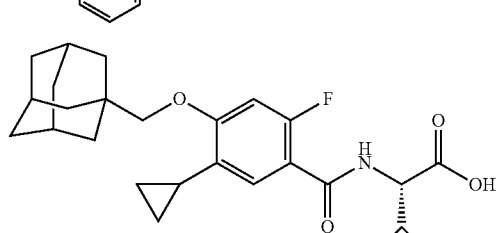
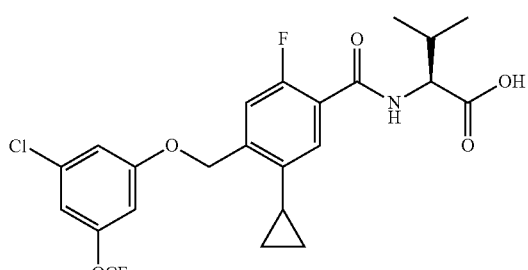
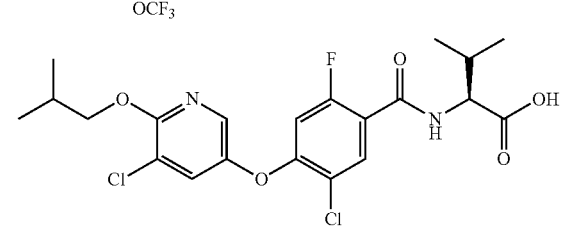

463
-continued
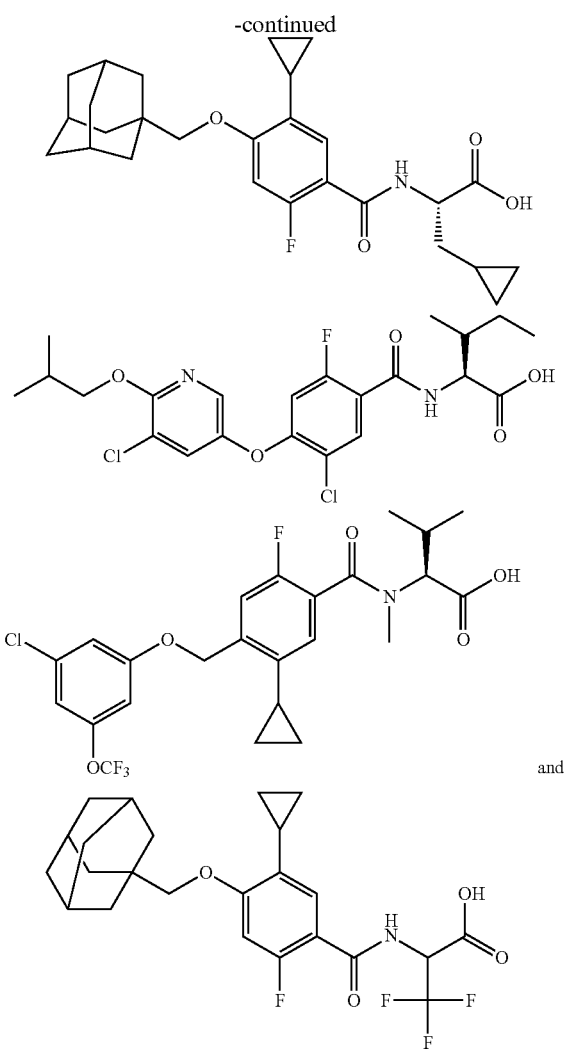
or a pharmaceutically acceptable salt thereof.
3. A compound selected from the group consisting of:
464
-continued
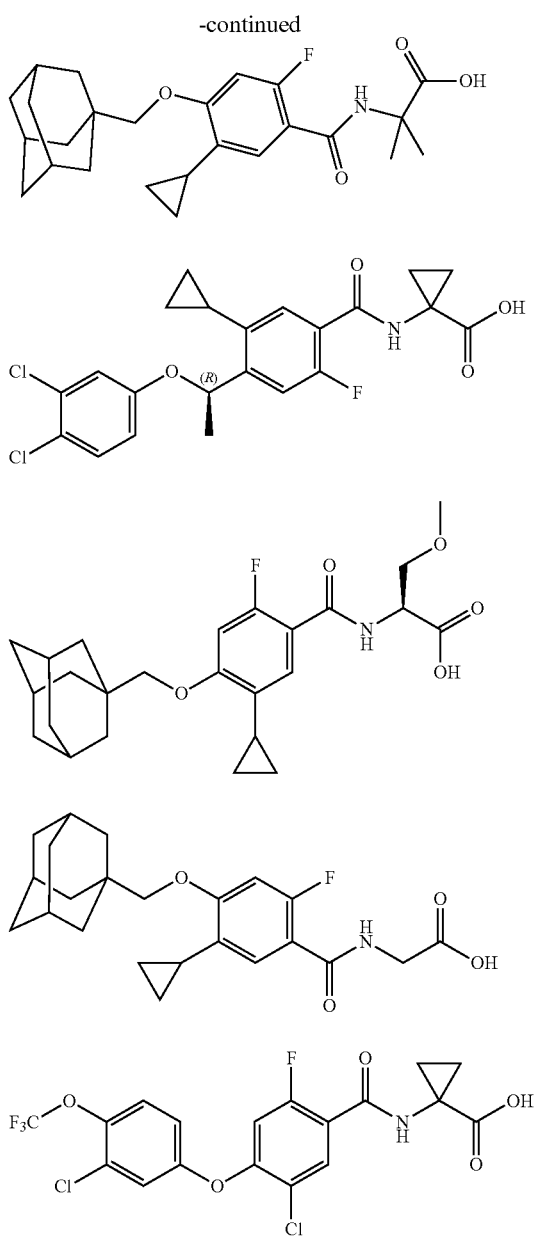
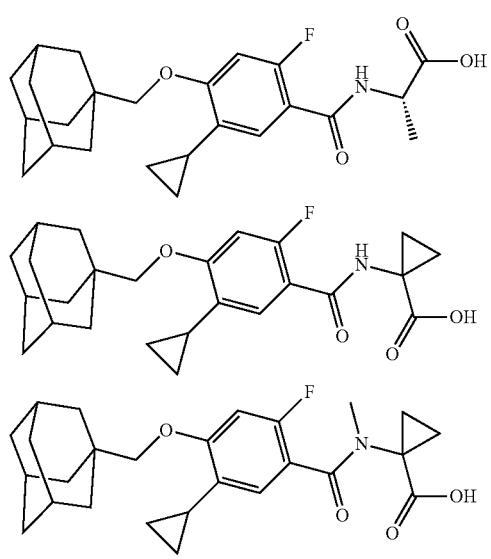

-continued

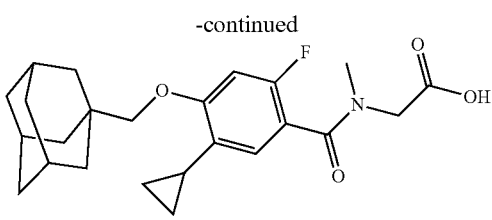

or a pharmaceutically acceptable salt thereof.

4. A pharmaceutical composition comprising a compound of formula (I) as described in claim 1, or a pharmaceutically acceptable salt thereof, and a pharmaceutically acceptable excipient.

5. The compound of claim 1, wherein $R^3$ is F or $C_1$; and $R^5$ is selected from the group consisting of F, Cl, $C_{1-4}$ alkyl, $C_{1-4}$ alkoxy, and $C_{3-8}$ cycloalkyl.

6. The compound of claim 1, wherein $R^3$ is F or $C_1$ and $R^5$ is selected from the group consisting of F, Cl, cyclopropyl, cyclobutyl, and cyclopentyl.

7. The compound of claim 1, wherein $X^1$ is —O— or —N(H)—; $X^2$ is absent; the subscript m is 1; and -(L)- is an optionally substituted $C_{1-4}$ alkylene.

8. The compound of claim 1, wherein $X^1$ is —O— or —N(H)—; $X^2$ is absent; the subscript m is 1; and -(L)- is selected from the group consisting of —CH$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$—, or —CH$_2$CH$_2$CH$_2$CH$_2$—.

9. The compound of claim 1, wherein $X^1$ is —O—; the subscript m is 1 and -(L)- is —CH$_2$—, —C(H)(CH$_3$)—, or —CH$_2$—CH$_2$—.

10. The compound of claim 1, wherein $X^1$ is absent; $X^2$ is —O— or —N(H)—; the subscript m is 1; and -(L)- is selected from the group consisting of —CH$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$—, or —CH$_2$CH$_2$CH$_2$CH$_2$—.

11. The compound of claim 1, wherein $X^1$ and $X^2$ are absent; the subscript m is 1; and -(L)- is selected from the group consisting of —CH$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$—, or —CH$_2$CH$_2$CH$_2$CH$_2$—.

12. The compound of claim 1, wherein $X^1$ and $X^2$ are absent; the subscript m is 1; and -(L)- is selected from the group consisting of —CH$_2$—, —C(=O)—, —C(H)(CH$_3$)—, and —CH$_2$—CH$_2$—.

13. The compound of claim 1, wherein m is 0; $X^1$ is selected from —O— and —N(H)—; and $X^2$ is absent.

14. A pharmaceutical composition comprising a compound as described in claim 2 or a pharmaceutically acceptable salt thereof, and a pharmaceutically acceptable excipient.

15. A pharmaceutical composition comprising a compound as described in claim 3 or a pharmaceutically acceptable salt thereof, and a pharmaceutically acceptable excipient.

16. The compound:

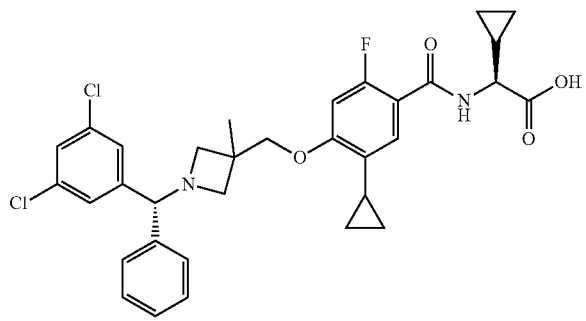 [SMILES: CC1(COc2cc(F)c(C(=O)N[C@H](C(=O)O)C3CC3)cc2C2CC2)CN([C@H](c2ccccc2)c2cc(Cl)cc(Cl)c2)C1]

or a pharmaceutically acceptable salt thereof.

17. A pharmaceutical composition comprising a compound as described in claim 16 or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 10,526,285 B2
APPLICATION NO. : 16/150070
DATED : January 7, 2020
INVENTOR(S) : Jean-Christophe Andrez et al.

Page 1 of 1

It is certified that error appears in the above-identified patent and that said Letters Patent is hereby corrected as shown below:

In the Claims

Column 465, Line 15, Claim 5, please delete "wherein $R^3$ is F or $C_1$; and" and insert -- wherein $R^3$ is F or Cl; and -- therefor.

Signed and Sealed this
Fifth Day of May, 2020

Andrei Iancu
*Director of the United States Patent and Trademark Office*